US012807690B2

(12) United States Patent
Wawersik et al.

(10) Patent No.: US 12,807,690 B2
(45) Date of Patent: Nov. 24, 2026

(54) TGFβ INHIBITORS AND USE THEREOF

(71) Applicant: Scholar Rock, Inc., Cambridge, MA (US)

(72) Inventors: Stefan Wawersik, Westborough, MA (US); Thomas Schurpf, Cambridge, MA (US); Christopher Chapron, Watertown, MA (US); Sandeep Kumar, Lexington, MA (US); Adam Fogel, Watertown, MA (US)

(73) Assignee: Scholar Rock, Inc., Cambridge, MA (US)

( * ) Notice: Subject to any disclaimer, the term of this patent is extended or adjusted under 35 U.S.C. 154(b) by 1098 days.

(21) Appl. No.: 17/791,859

(22) PCT Filed: Jan. 11, 2021

(86) PCT No.: PCT/US2021/012930

§ 371 (c)(1),
(2) Date: Jul. 8, 2022

(87) PCT Pub. No.: WO2021/142427

PCT Pub. Date: Jul. 15, 2021

(65) Prior Publication Data

US 2023/0057012 A1 Feb. 23, 2023

Related U.S. Application Data

(60) Provisional application No. 63/038,413, filed on Jun. 12, 2020, provisional application No. 63/033,904, filed on Jun. 3, 2020, provisional application No. 62/959,925, filed on Jan. 11, 2020.

(51) Int. Cl.

| | |
|---|---|
| ***C07K 16/22*** | (2006.01) |
| ***A61P 1/16*** | (2006.01) |
| ***A61P 11/00*** | (2006.01) |
| ***A61P 35/00*** | (2006.01) |
| ***C07K 16/28*** | (2006.01) |

(52) U.S. Cl.

CPC ................ *C07K 16/22* (2013.01); *A61P 1/16* (2018.01); *A61P 11/00* (2018.01); *A61P 35/00* (2018.01); *C07K 16/2863* (2013.01)

(58) Field of Classification Search

None

See application file for complete search history.

(56) References Cited

U.S. PATENT DOCUMENTS

| | | | | |
|---|---|---|---|---|
| 9,399,676 | B2 | 7/2016 | Schurpf et al. | |
| 9,573,995 | B2 | 2/2017 | Schurpf et al. | |
| 9,580,500 | B2 | 2/2017 | Schurpf et al. | |
| 9,758,576 | B2 | 9/2017 | Schurpf et al. | |
| 9,758,577 | B2 | 9/2017 | Schurpf et al. | |
| 10,597,443 | B2 | 3/2020 | Schurpf et al. | |
| 10,981,981 | B2 | 4/2021 | Schurpf et al. | |
| 11,130,803 | B2 * | 9/2021 | Datta | C07K 16/22 |
| 11,214,614 | B2 | 1/2022 | Schurpf et al. | |
| 11,365,245 | B2 | 6/2022 | Schurpf et al. | |
| 12,122,823 | B2 * | 10/2024 | Datta | A61P 1/16 |
| 2015/0284455 | A1 | 10/2015 | Springer et al. | |
| 2017/0210798 | A1 | 7/2017 | Schurpf et al. | |
| 2018/0016332 | A1 | 1/2018 | Schurpf et al. | |
| 2018/0022798 | A1 | 1/2018 | Schurpf et al. | |
| 2020/0024339 | A1 | 1/2020 | Springer et al. | |
| 2020/0131259 | A1 | 4/2020 | Schurpf et al. | |
| 2020/0231682 | A1 | 7/2020 | Schurpf et al. | |
| 2021/0122814 | A1 | 4/2021 | Datta et al. | |
| 2021/0284722 | A1 | 9/2021 | Schurpf et al. | |
| 2021/0340238 | A1 | 11/2021 | Datta et al. | |
| 2022/0064275 | A1 | 3/2022 | Datta et al. | |
| 2025/0215072 | A1 * | 7/2025 | Datta | A61P 13/12 |

FOREIGN PATENT DOCUMENTS

| | | | | |
|---|---|---|---|---|
| CN | 110049773 A | | 7/2019 | |
| WO | 2017/156500 A1 | | 9/2017 | |
| WO | 2018/129329 A1 | | 7/2018 | |
| WO | 2018/206790 A1 | | 11/2018 | |
| WO | 2019/023661 A1 | | 1/2019 | |
| WO | WO-2020014473 A1 | * | 1/2020 | A61P 35/00 |
| WO | 2020/160291 A2 | | 8/2020 | |

OTHER PUBLICATIONS

Brown et al., Tolerance of single, but not multiple, amino acid replacements in antibody VH CDR 2: a means of minimizing B cell wastage from somatic hypermutation? J Immunol. May 1, 1996;156(9):3285-91.

Rudikoff et al., Single amino acid substitution altering antigen-binding specificity. Proc Natl Acad Sci U S A. Mar. 1982;79(6):1979-83.

U.S. Appl. No. 14/439,284, filed Apr. 29, 2015, 2015-0284455, Abandoned.

U.S. Appl. No. 16/583,799, filed Sep. 26, 2019, 2020-0024339, Abandoned.

U.S. Appl. No. 14/795,007, filed Jul. 9, 2015, U.S. Pat. No. 9,573,995, Issued.

U.S. Appl. No. 14/795,012, filed Jul. 9, 2015, U.S. Pat. No. 9,758,576, Issued.

U.S. Appl. No. 14/795,022, filed Jul. 9, 2015, U.S. Pat. No. 9,580,500, Issued.

U.S. Appl. No. 14/795,033, filed Jul. 9, 2015, U.S. Pat. No. 9,399,676, Issued.

(Continued)

*Primary Examiner* — Patricia Duffy

(74) *Attorney, Agent, or Firm* — McCarter & English, LLP; Marcie B. Clarke

(57) ABSTRACT

Disclosed herein are novel inhibitors of TGFβ1 activation with durable inhibitory effects. Methods directed to the selection of a suitable TGFβ inhibitor for various disease conditions and patient populations are also provided.

5 Claims, 49 Drawing Sheets

Specification includes a Sequence Listing.

(56) References Cited

OTHER PUBLICATIONS

U.S. Appl. No. 15/401,386, filed Jan. 9, 2017, 2017-0210798, Abandoned.
U.S. Appl. No. 15/404,663, filed Jan. 12, 2017, U.S. Pat. No. 10,597,443, Issued.
U.S. Appl. No. 15/187,278, filed Jun. 20, 2016, U.S. Pat. No. 9,758,577, Issued.
U.S. Appl. No. 15/659,974, filed Jul. 26, 2017, 2018-0016332, Abandoned.
U.S. Appl. No. 15/671,217, filed Aug. 8, 2017, 2018-0022798, Abandoned.
U.S. Appl. No. 16/209,078, filed Dec. 4, 2018, U.S. Pat. No. 10,981,981, Issued.
U.S. Appl. No. 16/736,207, filed Jan. 7, 2020, 2020-0131259, Published.
U.S. Appl. No. 17/196,256, filed Mar. 9, 2021, 2021-0284722, Published.
U.S. Appl. No. 16/634,336, filed Jan. 27, 2020, 2020-0231682, Published.
U.S. Appl. No. 17/258,908, filed Jan. 8, 2021, 2021-0340238, Abandoned.
U.S. Appl. No. 16/997,438, filed Aug. 19, 2020, U.S. Pat. No. 11,214,614, Issued.
U.S. Appl. No. 17/530,786, filed Nov. 19, 2021, U.S. Pat. No. 11,365,245, Issued.
U.S. Appl. No. 17/746,325, filed May 17, 2022, Pending.
U.S. Appl. No. 17/258,771, filed Jan. 8, 2021, 2021-0122814, Published.
U.S. Appl. No. 16/509,068, filed Jul. 11, 2019, U.S. Pat. No. 11,130,803, Published.
U.S. Appl. No. 17/406,400, filed Aug. 19, 2021, 2022-0064275, Published.
International Search Report and Written Opinion for Application No. PCT/US2021/012930, dated Apr. 21, 2021, 14 pages.

* cited by examiner

Ab2 specifically binds TGFb1 small latent complexes, but not mature growth factors, in isoform-selective manner Octet® binding curves with Ab2 at 10 µg/ml Ab46 Fab has higher affinity and slower dissociation rate than reference Ab Fab by SPR

Binding to Human LTBP1-ProTGFβ1 (Biacore)

| Antibody (Fab) | $k_{on}$ ($M^{-1}/s^{-1}$) | $k_{off}$ ($s^{-1}$) | $t_{1/2}$ (min) | $K_D$ |
|---|---|---|---|---|
| Ref Ab | 7.18e+5 | 4.83e-3 | 2.4 | 6.73 nM |
| Ab46 | 1.75e+6 | 8.81e-5 | 131 | 50.2 pM |
| *Fold-difference* | 2.4 | 55 | 55 | 134 |

Antigen binding by ELISA: Purified Abs (hIgG4)

Antigen binding by ELISA: Purified Abs (hIgG4)

Inhibition of collagen gene expression by TGFβ1 isoform-specific antibodies in a UUO mouse model Inhibition of fibronectin and Loxl2 gene expression by TGFβ1 isoform-specific antibodies in a UUO mouse model Statistical significance of changes in gene expression vs. IgG alone in a UUO mouse model Single dose (10 mg/kg, 48h post-dose) of Ab2 inhibits pSmad2/3 in kidneys from 9 week old Col4a3 KO mice Effect of TGFβ1 isoform-specific antibodies on pSmad2/3 in a genetic model of Alport syndrome Effect of TGFβ1 isoform-specific antibodies on fibrotic gene expression in a genetic model of Alport syndrome Ab2 Serum Exposure in CDHFD Model of Mouse NASH To allow direct comparison of data from Ab2 and Ab3 samples, data were normalized by the following equation:

$$\frac{sample - AVE_{chow+IgG}}{AVE_{CDHFD+IgG} - AVE_{chow+IgG}} * 100$$

*anti-TGFβ1 Treatment Reduces PS-Red+ Area in the $CCl_4$ Model of Liver Fibrosis*

HDX-MS heatmap for Ab3 Fab-proTGFb1 C4S complex

[ProTGFb1 C4S] - [ProTGFb1 C4S + Ab3 Fab (1:3)]

Ab3 shows H/DX protection within the latency lasso as well as in the growth factor region of ProTGFb1

The protected regions of Ab3 show high sequence diversity within in the latency lasso

| | Region 1 | Region 2 | Region 3 |
|---|---|---|---|
| TGFB1_HUMAN | ...SQGEVPPGPLPEAVLALYNST... | ...LREAVPE... | ...YHANFCLG... |
| TGFB2_HUMAN | ...EDY-PEPEEVPPEVISIYNST... | ...ME---KN... | ...YNANFCAG... |
| TGFB3_HUMAN | ...EPT-V-MTHVPYQVLALYNST... | ...VE---KN... | ...YYANFCSG... |

The protected regions of Ab2 show high sequence diversity

| | Region 1 | Region 2 | Region 3 |
|---|---|---|---|
| TGFB1_HUMAN | ...SPPSQGEVPPGPLPEAVLALYNST... | ...LREAVPE... | ...WKWIHEPKGYHANFCLG... |
| TGFB2_HUMAN | ...SPPEDY-PEPEEVPPEVISIYNST... | ...ME---KN... | ...WKWIHEPKGYNANFCAG... |
| TGFB3_HUMAN | ...SPPEPT-V-MTHVPYQVLALYNST... | ...VE---KN... | ...WKWvHEPKGYYANFCSG... |

Crystal Structure of the Complex of Ab2-Fab/ProTGFb

| | |
|---|---|
| proTGFb1_HUMAN | 27 KLRLASPPSQGEVPPGPLPEAVL 49 |
| proTGFb2_HUMAN | 27 KLKLTSPPEDY-PEPEEVPPEVI 48 |
| proTGFb3_HUMAN | 27 KLRLTSPPEPT-V-MTHVPYQVL 47 |

Pan-TGFβ Antibody Data from 1-Week Safety Study in Fisher_344 Rats

Data from 4-Week Rat Toxicology Safety Study in Sprague Dawley Rats

Dosing of antibodies was qw x 4; IV
Phase II animals were evaluated
after 28 days "One animal administered 30 mg/kg/dose [Ab2] was found dead immediately postdose on Day 8 of Phase II. This death was related to dosing procedure and not test article related. No other mortality occurred during the duration of Phase II."

TGFβ isoform expression in individual tumor samples, by human cancer type

TGFb3 isoform expression in mouse syngeneic cancer cell model lines

TGFb3 isoform expression in mouse syngeneic cancer cell model lines

Differential of TGFB1 Expression

*minΔTGFB1 = smaller value of TGFB1 - TGFB2 or TGFB1 - TGFB3*

Inhibition of MBT2 tumor growth in mice treated with TGFβ1 isoform-specific antibodies in combination with an anti-PD1 antibody Combination effect on S91 tumor growth observed with context-independent TGFβ1 inhibitors and anti-PD-1

Inhibition of TGFβ1 activation triggers CD8+ T cell infiltration into S91 tumors Treated with anti-PD-1;
stained with a CD8+ marker Treated with anti-PD-1 + context-indep TGFβ1 inhibitor;
Stained with a CD8+ marker Infiltration of macrophages into S91 tumors observed after combination treatment Treated with anti-PD-1;
stained with a macrophage marker
(F4/80)

Treated with anti-PD-1 + context-indep TGFβ1 inhibitor;
Stained with a macrophage marker (F4/80)

TGFβ1 inhibition reduces fibrosis in CDHFD-induced mouse liver fibrosis model

Anti-fibrotic effect of TGFβ1 inhibition in CDHFD-induced mouse liver fibrosis model by liver hydroxyproline content

TGFβ1 inhibition reduces Col1+area in CDHFD-induced mouse liver fibrosis model

TGFβ1 inhibition reduces fibrosis in adenine-induced rat kidney fibrosis model

TGFβ3-selective inhibitor exacerbates fibrosis and suppresses anti-fibrotic effects of TGFβ1-selective inhibitor in mouse CDHFD model TGFβ1 and TGFβ3 are expressed in distinct cells
in mouse liver fibrosis Ab46 Fab is more potent than Ab2 Fab
by cell-based potency assays Ab46 suppresses Smad2/3 phosphorylation at all doses tested in mouse CDHFD liver fibrosis model

TGFβ INHIBITORS AND USE THEREOF

RELATED APPLICATIONS

This application is a U.S. national stage filing, under 35 U.S.C. § 371 (c), of International Application No. PCT/US2021/012930, filed Jan. 11, 2021, which claims priority to and benefit under 35 U.S.C. § 119 (e) of U.S. Provisional Application No. 62/959,925, filed Jan. 11, 2020, U.S. Provisional Application No. 63/033,904, filed Jun. 3, 2020, and U.S. Provisional Application No. 63/038,413, filed Jun. 12, 2020. The contents of each of the aforementioned applications are expressly incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 6, 2021 is named 127036-03920_SL.txt and is 209,944 bytes in size.

BACKGROUND OF THE INVENTION

Transforming growth factor beta 1 (TGFβ1) is a member of the TGFβ superfamily of growth factors, along with two other structurally related isoforms, namely, TGFβ2 and TGFβ3, each of which is encoded by a separate gene. TGFβs function as pleiotropic cytokines that regulate cell proliferation, differentiation, immunomodulation (e.g., adaptive immune response), and other diverse biological processes both in homeostasis and in disease contexts. The three TGFβ isoforms signal through the same cell-surface receptors and trigger similar canonical downstream signal transduction events that include the SMAD2/3 pathway.

TGFβ has been implicated in the pathogenesis and progression of a number of disease conditions, such as fibrosis, cancer and immune disorders. In many cases, such conditions are associated with dysregulation of the extracellular matrix (ECM). For these and other reasons, TGFβ has been an attractive therapeutic target for the treatment of fibrotic conditions as well as various proliferative disorders such as cancer. However, observations from preclinical studies, including in rats and dogs, have revealed serious toxicities associated with antagonizing TGFβ signaling in vivo, and to date, there are no TGFβ therapeutics available in the market which are deemed both safe and efficacious.

Previously, Applicant described a class of monoclonal antibodies that functions with a novel mechanism of action to modulate growth factor signaling (see, for example, WO 2014/182676). These antibodies were designed to exploit the fact that TGFβ1 is expressed as latent pro-protein complex comprised of prodomain and growth factor, which requires an activation step that releases the growth factor from the latent complex. Rather than taking the traditional approach of directly targeting the soluble growth factor itself post-activation (such as neutralizing antibodies), the novel class of inhibitory antibodies specifically targets the inactive pro-proprotein complex itself so as to preemptively block the activation step, upstream of ligand-receptor interaction. Without being bound by theory, this unique mechanism of action may provide advantages for achieving both spatial and temporal benefits in that they act at the source, that is, by targeting the latent proTGFβ1 complex within a disease microenvironment before activation takes place. Indeed, advantages of locally targeting tissue/cell-tethered complex at the source, as opposed to soluble active species (i.e., mature growth factors after being released from the source), are further supported by a recent study. Ishihara et al., (Sci. Transl. Med. 11, eaau3259 (2019) "Targeted antibody and cytokine cancer immunotherapies through collagen affinity") reported that when systemically administered drugs are targeted to the affected tissue by conjugating with a collagen-binding moiety, they were able to enhance anti-tumor immunity and reduce treatment-related toxicities, as compared to non-targeted counterparts.

Accordingly, monoclonal antibodies that specifically bind and inhibit the activation step of TGFβ1 (that is, release of mature growth factor from the latent complex) (so-called "activation inhibitors") in an isoform-selective manner were generated; disclosed, for example, in: WO 2017/156500, WO 2018/129329, PCT/US2019/041373, and PCT/US2019/041390, the contents of each of which are herein incorporated by reference in their entirety. These isoform-specific inhibitory agents demonstrated both efficacy and safety in vivo.

While the earlier work described above demonstrated utility of antibodies capable of binding each of known proTGFβ1-presenting molecule complexes and inhibitory activities both in vitro and in vivo, the inventors of the present application set out to generate improved inhibitors of TGFβ1 activation having increased affinity, potency, durability and therapeutic efficacy.

SUMMARY OF THE INVENTION

Disclosed herein are isoform-selective inhibitors of TGFβ1 activation with advantageous features. More specifically, the TGFβ1 inhibitors include monoclonal antibodies (including immunoglobulins and antigen-binding fragments or portions thereof) that exhibit slow dissociation rates (i.e., off-rates, $k_{OFF}$). Thus, the invention is based at least on the recognition that treatment of chronic and progressive disease such as fibrosis may require inhibitors with superior durability, which may be reflected on the dissociation rate of such antibody.

The affinity of an antibody to its antigen is typically measured as the equilibrium dissociation constant, or $K_D$. The ratio of the experimentally measured off- and on-rates ($k_{OFF}/k_{ON}$) can be used to calculate the $K_D$ value. The $k_{OFF}$ value represents the antibody dissociation rate, which indicates how quickly it dissociates from its bound antigen, whilst the $k_{ON}$ value represents the antibody association rate which provides how quickly it binds to its antigen. The latter is typically concentration-dependent, while the former is concentration-independent. The $K_D$ value relates to the concentration of antibody (the amount of antibody needed for a particular experiment) and so the lower the Ko value (lower concentration) and thus the higher the affinity of the antibody. With respect to a reference antibody, a higher affinity antibody may have a lower $k_{OFF}$ rate, a higher $k_{ON}$ rate, or both.

Both the $k_{OFF}$ and $k_{ON}$ rates contribute to the overall affinity of a particular antibody to its antigen, and relative importance or impact of each component may depend on the mechanism of action of the antibody. For example, neutralizing antibodies, which bind mature growth factors (e.g., soluble, transient TGFβ1 ligand liberated from a latent complex), must compete with the endogenous high-affinity receptors for ligand binding in vivo. Because the ligand-receptor interaction is a local event and because the ligand is short-lived, such antibodies must be capable of rapidly targeting and sequestering the soluble growth factor before the ligand finds its cellular receptor-thereby activating the TGFβ1 signaling pathway—in the tissue. Therefore, for ligand-targeting neutralizing antibodies to be potent, the ability to bind the target growth factor fast, i.e., high association rates (KON), may be especially important.

By contrast, Applicant reasoned that antibodies that inhibit the TGFβ1 signaling by preventing the release of mature growth factor from the latent complex ("activation inhibitors") may preferentially benefit from having slow dissociation rates once the antibody is engaged with the target antigen (e.g., proTGFβ1 complexes). Unlike neutralizing antibodies, such antibodies do not directly compete with cellular receptors; rather, they work upstream of the signaling by targeting inactive precursor forms (e.g., latent proTGFβ1 complexes) that remain dormant within a tissue environment thereby preemptively preventing the activation of TGFβ1. Such antibodies may exert their inhibitory activity by preventing mature growth factor from being liberated from the latent complex. For example, such antibodies may function like a "clamp" to lock the active growth factor in the prodomain cage structure to keep it in an inactive (e.g., "latent") state. Indeed, structural analyses, including epitope mapping, provided insight into the molecular mechanism underlining the ability of these antibodies to block TGFβ1 activation. In this regard, the Latency Lasso region of the prodomain may be a particularly useful target.

Upon target engagement, antibodies that are able to remain bound to the target (e.g., dissociate very slowly from the latent complex) are expected to be advantageous in achieving superior in vivo potency, due to enhanced durability of effects and/or avidity. Based on this recognition, Applicant of the present disclosure sought to identify isoform-selective activation inhibitors of TGFβ1 with particularly low $k_{OFF}$ values as compared to previously described antibodies. Thus, according to the invention, preferred antibodies have high affinities (e.g., a Ko of sub-nanomolar to picomolar range) primarily attributable to a slow dissociation rate ($k_{OFF}$), as opposed to fast association rate ($k_{ON}$). In some embodiments, such antibodies bind an epitope that comprises at least a portion of Latency Lasso.

Accordingly, the present disclosure provides an isoform-selective inhibitor of TGFβ1 activation, wherein the inhibitor is a monoclonal antibody or an antigen-binding fragment thereof, which selectively inhibits TGFβ1 activation; wherein the monoclonal antibody binds human LTBP1-proTGFβ1 and/or human LTBP3-proTGFβ1 with a monovalent dissociation rate of 10.0e-04 or less, as measured by a surface plasmon resonance (SPR)-based technique, and optionally with a $K_D$ value of <1.0 nM; and, wherein the antibody or the antigen-binding fragment comprises the following six CDRs: an H-CDR1 comprising GFTFADYA (SEQ ID NO: 276); an H-CDR2 comprising ISGSG ($X_1$) AT, wherein optionally the $X_1$ is A or K (SEQ ID NO: 277); an H-CDR3 comprising VSSG ($X_1$) WD ($X_2$) D, wherein optionally $X_1$ is H, D or Q; and wherein further optionally $X_2$ is F or Y (SEQ ID NO: 278); an L-CDR1 comprising QSISSY (SEQ ID NO: 279); an L-CDR2 comprising AAS ($X_1$) ($X_2$) ($X_3$) ($X_4$), wherein optionally $X_1$ is N, G or V; wherein further optionally $X_2$ is L, N or E; wherein further optionally $X_3$ is Q or E; and wherein further optionally $X_4$ is S or T (SEQ ID NO: 280); and, an L-CDR3 comprising QQTY ($X_1$) VPLT, wherein optionally $X_1$ is T or G (SEQ ID NO: 281).

In preferred embodiments, the antibody comprises an H-CDR1 comprising GFTFADYA (SEQ ID NO: 276); an H-CDR2 comprising ISGSGAAT (SEQ ID NO: 282); an H-CDR3 comprising VSSG ($X_1$) WD ($X_2$) D wherein optionally $X_1$=H or Q and further optionally $X_2$=Y or F (SEQ ID NO: 283); an L-CDR1 comprising QSISSY (SEQ ID NO: 279); an L-CDR2 comprising AASGLES (SEQ ID NO: 284); and, an L-CDR3 comprising QQTYGVPLT (SEQ ID NO: 285).

In particularly preferred embodiments, the antibody comprises the six CDR sequences of Ab42, Ab46 or Ab50.

The invention includes compositions, such as pharmaceutical compositions (e.g., formulations, medicament) that are suitable for administration to human patients, comprising at least one of the antibodies or fragment thereof in accordance with the present disclosure, and an excipient. Thus, the antibodies or fragment thereof in accordance with the present disclosure can be used in the manufacture of such medicament.

The invention further provides therapeutic use of such antibodies. Thus, the TGFβ1-selective inhibitors (e.g., monoclonal antibodies or antigen-binding fragments thereof) of the present disclosure may be used in the treatment of TGFβ1-related indications in a subject. The TGFβ1-selective inhibitors may be particularly advantageous for treating such disease or disorders involving dysregulation of the extracellular matrix (ECM), including, for example, fibrotic disorders (such as organ fibrosis, and fibrosis involving chronic inflammation), proliferative disorders (such as cancer, e.g., solid tumors and myelofibrosis), disease involving endothelial-to-mesenchymal transition (EndMT), disease involving epithelial-to-mesenchymal transition (EMT), disease involving proteases, disease with aberrant gene expression of certain markers described herein. The TGFβ1-selective inhibitors may be used in conjunction with another therapy as combination therapies (e.g., add-on therapies). Methods for treating such disease or disorders comprising administration of the TGFβ1-selective inhibitor in a subject, either as monotherapy or combination therapy, are encompassed by the invention.

The present invention includes selection of subjects or patients who are likely to respond to or benefit from a TGFβ1 inhibition therapy. Related diagnostic methods, as well as methods for monitoring or determining therapeutic response to the TGFβ1 inhibition therapy, are encompassed herein.

Processes and methods for identifying or selecting TGFβ1-selective inhibitors suitable for therapeutic use are encompassed by the invention. In preferred embodiments, selection includes one or more antibodies or antigen-binding fragments with particularly advantageous kinetics criteria characterized by: i) sub-nanomolar affinities to each of human LTBP1/3-proTGFβ1 complexes (e.g., $K_D$<1 nM), and, ii) low dissociation rates ($k_{OFF}$), e.g., ≤5.00E-4, as measured by a suitable in vitro binding/kinetics assay, such as by surface plasmon resonance (SPR), e.g., BIACORE®-based systems. The selected antibody or the plurality of antibodies are evaluated in preclinical studies comprising an efficacy study and a toxicology/safety study, employing suitable preclinical models. Effective amounts of the antibody or the antibodies determined in the efficacy study are below the level that results in undesirable toxicities determined in the toxicology/safety study. Preferably, the antibody or antibodies are selected which has/have at least 3-fold, 6-fold, and more preferably 10-fold therapeutic window. Effective amounts of the antibodies according to the present disclosure may be between about 0.1 mg/kg and about 30 mg/kg when administered weekly. In preferred embodiments, the maximally tolerated dose (MTD) of the antibodies according to the present disclosure is >100 mg/kg when dosed weekly for at least 4 weeks.

The present disclosure includes a surprising finding that, contrary to the general belief that inhibition of multiple isoforms is needed for antifibrotic effects, concurrent inhibition of TGFβ3 produced pro-fibrotic effects in mice. This observation raises the possibility that non-selective TGFβ inhibitors (such as pan-inhibitors and TGFβ1/3 inhibitors) may in fact exacerbate fibrosis. Advantageously, the antibodies disclosed herein are isoform-selective in that they specifically target the latent TGFβ1 complex and do so with low dissociation rates. Thus, the invention includes the recognition that when selecting a particular TGFβ inhibitor for patients with a fibrotic condition (e.g., disease involving ECM dysregulation, such as cardiovascular diseases), isoform selectivity should be carefully considered so as to avoid risk of exacerbating ECM dysregulation. Accordingly, the present disclosure includes therapeutic methods comprising selecting a TGFβ inhibitor that does not inhibit TGFβ3 to treat a subject with a fibrotic condition, wherein optionally the subject has organ fibrosis or cancer, wherein further optionally the cancer is myelofibrosis. In some embodiments, the subject has, or is at risk of developing a cardiovascular disease. In some embodiments, the TGFβ inhibitor is TGFβ1-selective in that it does not inhibit TGFβ2 and TGFβ3. In some embodiments, the organ fibrosis is liver fibrosis, kidney fibrosis or lung fibrosis (e.g., IPF). In some embodiments, the liver fibrosis is associated with NASH. Patients at risk of developing fibrosis or a condition with ECM dysregulation may include those suffering from a metabolic condition, such as diabetes, obesity and NASH.

BRIEF DESCRIPTION OF THE FIGURES

FIG. 10A discloses SEQ ID NO: 25.

FIG. 10B discloses SEQ ID NOS 258-260 and 304-309, respectively, in order of appearance.

FIG. 10C discloses SEQ ID NO: 25.

FIG. 10D discloses SEQ ID NOS 261, 259, 262, 310, 305, 311-312, 308, and 313, respectively, in order of appearance.

FIG. 11 discloses SEQ ID NOS 314-316, respectively, in order of appearance.

FIG. 13A shows TGFβ isoform expression vs. normal comparator (by cancer type).

FIG. 13B shows frequency of TGFβ Isoform Expression by Human Cancer Type.

FIG. 13C shows TGFβ isoform expression in individual tumor samples, by cancer type.

FIG. 13D shows TGFβ isoform expression in mouse syngeneic cancer cell model lines.

FIG. 17A is a tumor section from an animal treated with anti-PD-1 alone. FIG. 17B is a tumor section from an animal treated with both anti-PD-1 and a representative context-independent TGFβ1 inhibitor.

FIG. 18A is a tumor section from an animal treated with anti-PD-1 alone.

FIG. 18B is a tumor section from an animal treated with both anti-PD-1 and a representative context-independent TGFβ1 inhibitor.

DETAILED DESCRIPTION OF THE INVENTION

Definitions

Figure 1:
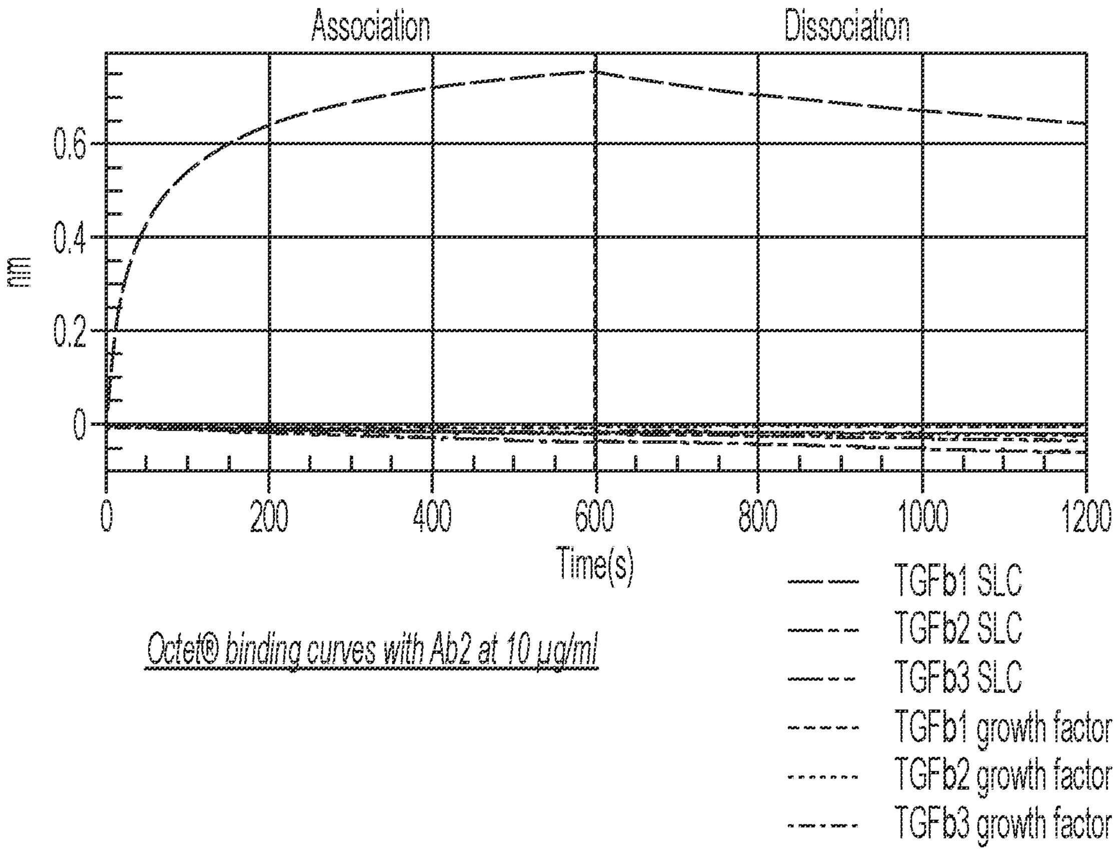
FIG. 1 shows representative OCTET® binding curves showing association and dissociation of Ab2 to six different antigen complexes. Ab2 specifically binds TGFβ1 small latent complexes (SLCs), but not mature growth factors, in isoform-selective manner.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Advanced cancer, advanced malignancy: The term "advanced cancer" or "advanced malignancy" as used herein has the meaning understood in the pertinent art, e.g., as understood by oncologists in the context of diagnosing or treating subjects/patients with cancer. Advanced malignancy with a solid tumor can be locally advanced or metastatic. The term "locally advanced cancer" is used to describe a cancer (e.g., tumor) that has grown outside the organ it started in but has not yet spread to distant parts of the body. Thus, the term includes cancer that has spread from where it started to nearby tissue or lymph nodes. By contrast, "metastatic cancer" is a cancer that has spread from the part of the body where it started (the primary site) to other parts (e.g., distant parts) of the body.

Affinity: Affinity is the strength of binding of a molecule (such as an antibody) to its ligand (such as an antigen). It is typically measured and reported by the equilibrium dissociation constant (KD). In the context of antibody-antigen interactions, KD is the ratio of the antibody dissociation rate ("off rate" or Koff or Kdis), how quickly it dissociates from its antigen, to the antibody association rate ("on rate" or Kon) of the antibody, how quickly it binds to its antigen. For example, an antibody with an affinity of ≤5 nM has a $K_D$ value that is 5 nM or lower (i.e., 5 nM or higher affinity) determined by a suitable in vitro binding assay. Suitable in vitro assays can be used to measure KD values of an antibody for its antigen, such as Biolayer Interferometry (BLI) and Solution Equilibrium Titration (e.g., MSD-SET).

Antibody: The term "antibody" encompasses any naturally-occurring, recombinant, modified or engineered immunoglobulin or immunoglobulin-like structure or antigen-binding fragment or portion thereof, or derivative thereof, as further described elsewhere herein. Unless specified to the contrary, the term "antigen" as used herein shall encompass antigen-binding fragments and functional variants thereof. Thus, the term refers to an immunoglobulin molecule that specifically binds to a target antigen, and includes, for instance, chimeric, humanized, fully human, and bispecific antibodies. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen-binding portions thereof, can be produced in hybridomas, by recombinant DNA techniques, or by enzymatic or chemical cleavage of intact antibodies. The term antibodies, as used herein, includes monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), respectively. In some embodiments, the term also encompasses peptibodies.

Antigen: The term "antigen" broadly includes any molecules comprising an antigenic determinant within a binding region(s) to which an antibody or a binding-fragment specifically binds. An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen-binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen-binding proteins, e.g., antibodies. In the context of the present disclosure, a suitable antigen is a complex (e.g., multimeric complex comprised of multiple components in association) containing a proTGF dimer in association with a presenting molecule. Each monomer of the proTGF dimer comprises a prodomain and a growth factor domain, separated by a furin cleavage sequence. Two such monomers form the proTGF dimer complex. This in turn is covalently associated with a presenting molecule via disulfide bonds, which involve a cysteine residue present near the N-terminus of each of the proTGF monomer. This multi-complex formed by a proTGF dimer bound to a presenting molecule is generally referred to as a large latent complex. An antigen complex suitable for screening antibodies or antigen-binding fragments, for example, includes a presenting molecule component of a large latent complex. Such presenting molecule component may be a full-length presenting molecule or a fragment(s) thereof. Minimum required portions of the presenting molecule typically contain at least 50 amino acids, but more preferably at least 100 amino acids of the presenting molecule polypeptide, which comprises two cysteine residues capable of forming covalent bonds with the proTGFβ1 dimer.

Antigen-binding portion/fragment: The terms "antigen-binding portion" or "antigen-binding fragment" of an antibody, as used herein, refers to one or more fragments of an antibody that retain the ability to specifically bind to an antigen (e.g., TGFβ1). Antigen-binding portions include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments, a monovalent fragment consisting of the VL, VH, CL and CH1 domains; (ii) F(ab')2 fragments, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules (see, e.g., Bird et al., (1988) Science 242:423-426; and Huston et al., (1988) Proc. Nat'l. Acad. Sci. USA 85:5879-5883); (vi) dAb fragments (see, e.g., Ward et al., (1989) Nature 341:544-546); and (vii) minimal recognition units consisting of the amino acid residues that mimic the hypervariable region of an antibody (e.g., an isolated complementarity determining region (CDR)). Other forms of single chain antibodies, such as diabodies are also encompassed. The term antigen-binding portion of an antibody includes a "single chain Fab fragment" otherwise known as an "scFab," comprising an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids.

Bias: In the context of the present disclosure, the term "bias" refers to skewed or uneven affinity towards or against a subset of antigens to which an antibody is capable of specifically binding. For example, an antibody is said to have bias when the affinity for one antigen complex and the affinity for another antigen complex are not equivalent (e.g., more than five-fold difference in affinity). Preferred antibodies of the present disclosure include "matrix-biased" (or "LTBP-biased") antibodies, which preferentially bind EMC-associated complexes (LTBP1-proTGFβ1 and LTBP3-proTGFβ), such that relative affinities between at least one of the matrix-associated complexes and at least one of the cell-associated complexes (GARP-proTGFβ1 and/or LRRC33-proTGFβ1 complexes) is greater than five-fold. By comparison, antibodies characterized as "unbiased" have approximately equivalent affinities towards such antigen complexes (e.g., less than five-fold difference in affinity).

Binding region: As used herein, a "binding region" is a portion of an antigen (e.g., an antigen complex) that, when bound to an antibody or a fragment thereof, can form an interface of the antibody-antigen interaction. Upon antibody binding, a binding region becomes "protected" from surface exposure, which can be detected by suitable techniques, such as HDX-MS. Antibody-antigen interaction may be mediated via multiple (e.g., two or more) binding regions. A binding region can comprise an antigenic determinant, or epitope.

Cancer: The term "cancer" as used herein refers to the physiological condition in multicellular eukaryotes that is typically characterized by unregulated cell proliferation and malignancy. The term broadly encompasses, solid and liquid malignancies, including tumors, blood cancers (e.g., leukemias, lymphomas and myelomas), as well as myelofibrosis.

Cell-associated TGFβ1/proTGFβ1: The term refers to TGFβ1 or its signaling complex (e.g., pro/latent TGFβ1) that is membrane-bound (e.g., tethered to cell surface). Typically, such cell is an immune cell. TGFβ1 that is presented by GARP or LRRC33 is a cell-associated TGFβ1. GARP and LRRC33 are transmembrane presenting molecules that are expressed on cell surface of certain cells. GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 activation/signaling. The term also includes recombinant, purified GARP-proTGFβ1 and LRRC33-proTGFβ1 complexes in solution (e.g., in vitro assays) which are not physically attached to cell membranes. Average $K_D$ values of an antibody (or its fragment) to a GARP-proTGFβ1 complex and an LRRC33-proTGFβ1 complex may be calculated to collectively represent affinities for cell-associated (e.g., immune cell-associated) proTGFβ1 complexes. See, for example, Table, column (G). Human counterpart of a presenting molecule or presenting molecule complex may be indicated by an "h" preceding the protein or protein complex, e.g., "hGARP," "hGARP-proTGFβ1," hLRRC33" and "hLRRC33-proTGFβ1."

Checkpoint inhibitor: In the context of this disclosure, checkpoint inhibitors refer to immune checkpoint inhibitors and carries the meaning as understood in the art. Typically, target is a receptor molecule on T cells or NK cells, or corresponding cell surface ligand on antigen-presenting cells (APCs) or tumor cells. Immune checkpoints are activated in immune cells to prevent inflammatory immunity developing against the "self". Therefore, changing the balance of the immune system via checkpoint inhibition should allow it to be fully activated to detect and eliminate the cancer. The best known inhibitory receptors implicated in control of the immune response are cytotoxic T-lymphocyte antigen-4 (CTLA-4), programmed cell death protein 1 (PD-1), PD-L1, T-cell immunoglobulin domain and mucin domain-3 (TIM3), lymphocyte-activation gene 3 (LAG3), killer cell immunoglobulin-like receptor (KIR), glucocorticoid-induced tumor necrosis factor receptor (GITR) and V-domain immunoglobulin (lg)-containing suppressor of T-cell activation (VISTA). Non-limiting examples of checkpoint inhibitors include: nivolumab, pembrolizumab, BMS-936559, atezolizumab, avelumab, durvalumab, ipilimumab, tremelimumab, IMP-321, BMS-986016, and lirilumab. Keytruda® is one example of PD-1 inhibitors. Therapies or therapeutic regimens that employ one or more of immune checkpoint inhibitors may be referred to as checkpoint blockade therapy (CBT).

Clinical benefit: As used herein, the term "clinical benefits" is intended to include both efficacy and safety of a therapy. Thus, therapeutic treatment that achieves a desirable clinical benefit is both efficacious and safe (e.g., with tolerable or acceptable toxicities or adverse events).

Combination therapy: "Combination therapy" refers to treatment regimens for a clinical indication that comprise two or more therapeutic agents. Thus, the term refers to a therapeutic regimen in which a first therapy comprising a first composition (e.g., active ingredient) is administered in conjunction with a second therapy comprising a second composition (active ingredient) to a patient, intended to treat the same or overlapping disease or clinical condition. The first and second compositions may both act on the same cellular target, or discrete cellular targets. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies. When a subject who has been treated with a first therapy for the treatment of a disease is administered with a second therapy to treat the same disease, the second therapy may be referred to as an "add-on therapy" or "adjunct therapy."

Combinatory or combinatorial epitope: A combinatorial epitope is an epitope that is recognized and bound by a combinatorial antibody at a site (i.e., antigenic determinant) formed by non-contiguous portions of a component or components of an antigen, which, in a three-dimensional structure, come together in close proximity to form the epitope. Thus, antibodies of the invention may bind an epitope formed by two or more components (e.g., portions or segments) of a pro/latent TGFβ1 complex. A combinatory epitope may comprise amino acid residue(s) from a first component of the complex, and amino acid residue(s) from a second component of the complex, and so on. Each component may be of a single protein or of two or more proteins of an antigenic complex. A combinatory epitope is formed with structural contributions from two or more components (e.g., portions or segments, such as amino acid residues) of an antigen or antigen complex.

Compete or cross-compete: The term "compete" when used in the context of antigen-binding proteins (e.g., an antibody or antigen-binding portion thereof) that compete for the same epitope means competition between antigen-binding proteins as determined by an assay in which the antigen-binding protein being tested prevents or inhibits (e.g., reduces) specific binding of a reference antigen-binding protein to a common antigen (e.g., TGFβ1 or a fragment thereof). Numerous types of competitive binding assays can be used to determine if one antigen-binding protein competes with another, for example: solid phase direct or indirect radioimmunoassay (RIA), solid phase direct or indirect enzyme immunoassay (EIA), sandwich competition assay; solid phase direct biotin-avidin EIA; solid phase direct labeled assay, and solid phase direct labeled sandwich assay. Usually, when a competing antigen-binding protein is present in excess, it will inhibit (e.g., reduce) specific binding of a reference antigen-binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more. In some instances, binding is inhibited by at least 80-90%, at least 85%-95%, at least 95-99%. In some instances, binding is inhibited by at least 90%, 91%, 92%, 93%, 94%, 95%, 96%, 97%, 98%, 99% or more. In some embodiments, a first antibody or antigen-binding portion thereof and a second antibody or antigen-binding portion thereof cross-block with each other with respect to the same antigen, for example, as assayed by BLI (such as BIACORE® or OCTET®), using standard test conditions, e.g., according to the manufacturer's instructions (e.g., binding assayed at room temperature, ~20-25 °C). In some embodiments, the first antibody or fragment thereof and the second antibody or fragment thereof may have the same epitope. In other embodiments, the first antibody or fragment thereof and the second antibody or fragment thereof may have non-identical but overlapping epitopes. In yet further embodiments, the first antibody or fragment thereof and the second antibody or fragment thereof may have separate (different) epitopes which are in close proximity in a three-dimensional space, such that antibody binding is cross-blocked via steric hindrance. "Cross-block" means that binding of the first antibody to an antigen prevents binding of the second antibody to the same antigen, and similarly, binding of the second antibody to an antigen prevents binding of the first antibody to the same antigen.

Complementary determining region (CDR): As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region that can bind the antigen. The exact boundaries of these CDRs have been defined differently according to different systems. The system described by Kabat (Kabat et al., (1987; 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk (1987) J. Mol. Biol. 196:901-917; and Chothia et al., (1989) Nature 342:877-883) found that certain sub-portions within Kabat CDRs adopt nearly identical peptide backbone conformations, despite having great diversity at the level of amino acid sequence. These sub-portions were designated as L-CDR1, L-CDR2 and L-CDR3 or H-CDR1, H-CDR2 and H-CDR3, where the "L" and the "H" designate the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262 (5): 732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen-binding (see, for example: Lu X et al., MAbs. 2019 January; 11 (1): 45-57). The methods used herein may utilize CDRs defined according to any of these systems, although certain embodiments use Kabat- or Chothia-defined CDRs.

Conformational epitope: A conformational epitope is an epitope that is recognized and bound by a conformational antibody in a three-dimensional conformation, but not in an unfolded peptide of the same amino acid sequence. A conformational epitope may be referred to as a conformation-specific epitope, conformation-dependent epitope, or conformation-sensitive epitope. A corresponding antibody or fragment thereof that specifically binds such an epitope may be referred to as conformation-specific antibody, conformation-selective antibody, or conformation-dependent antibody. Binding of an antigen to a conformational epitope depends on the three-dimensional structure (conformation) of the antigen or antigen complex.

Constant region/domain: An immunoglobulin constant domain refers to a heavy or light chain constant domain. Human IgG heavy chain and light chain constant domain amino acid sequences are known in the art.

Context-biased: As used herein, "context-biased antibodies" refer to a type of conformational antibodies that binds an antigen with differential affinities when the antigen is associated with (i.e., bound to or attached to) an interacting protein or a fragment thereof. Thus, a context-biased antibody that specifically binds an epitope within proTGFβ1 may bind LTBP1-proTGFβ1, LTBP3-proTGFβ1, GARP-proTGFβ1 and LRRC33-proTGFβ1 with different affinities. For example, an antibody is said to be "matrix-biased" if it has higher affinities for matrix-associated proTGFβ1 complexes (e.g., LTBP1-proTGFβ1 and LTBP3-proTGFβ1) than for cell-associated proTGFβ1 complexes (e.g., GARP-proTGFβ1 and LRRC33-proTGFβ1). Relative affinities of [matrix-associated complexes]: [cell-associated complexes] may be obtained by taking average $K_D$ values of the former, taking average $K_D$ values of the latter, and calculating the ratio of the two, as exemplified herein. A context-biased antibody may also be biased for or against one presenting molecule-proTGFβ1 complex relative to the other presenting molecule-proTGFβ1 complexes, such that the affinity (as measured by $K_D$) for the former is more than 10-fold weaker or greater than the average of the latter, respectively.

Context-independent: According to the present disclosure, "a context-independent antibody" that binds proTGFβ1 has equivalent affinities across the four known presenting molecule-proTGFβ1 complexes, namely, LTBP1-proTGFβ1, LTBP3-proTGFβ1, GARP-proTGFβ1 and LRRC33-proTGFβ1. Context-independent antibodies may also be characterized as "unbiased" or "balanced." Typically, context-independent antibodies show no more than five-fold bias in affinities, such that relative ratios of measured $K_D$ values between matrix-associated complexes and cell-associated complexes are no greater than 5 as measured by a suitable in vitro binding assay, such as surface plasmon resonance, Biolayer Interferometry (BLI), and/or solution equilibrium titration (e.g., MSD-SET).

Dissociation rate: The term dissociation rate as used herein has the meaning understood by the skilled artisan in the pertinent art (e.g., antibody technology) as refers to a kinetics parameter measured by how fast/slow a ligand (e.g., antibody or fragment) dissociates from its binding target (e.g., antigen). Dissociation rate is also referred to as the "off" rate ("$k_{OFF}$"). Relative on/off rates between an antibody and its antigen (i.e., $k_{ON}$ and $k_{OFF}$) determine the overall strength of the interaction, or affinity, typically expressed as a dissociation constant, or $K_D$. Therefore, equivalent affinities (e.g., $K_D$ values) may be achieved by having fast association (high $k_{ON}$), slow dissociation (low $k_{OFF}$), or contribution from both factors. Monovalent interactions may be measured by the use of monovalent antigen-binding molecules/fragments, such as fAb (Fab), whilst divalent interactions may be measured by the use of divalent antigen-binding molecules such as whole immunoglobulins (e.g., IgGs).

ECM-associated TGFβ1/proTGFβ1: The term refers to TGFβ1 or its signaling complex (e.g., pro/latent TGFβ1) that is a component of (e.g., deposited into) the extracellular matrix. TGFβ1 that is presented by LTBP1 or LTBP3 is an ECM-associated TGFβ1. LTBPs are critical for correct deposition and subsequent bioavailability of TGFβ in the ECM, where fibrillin (Fbn) and fibronectin (FN) are believed to be the main matrix proteins responsible for the association of LTBPs with the ECM. Average KD values of an antibody (or its fragment) to an LTBP1-proTGFβ1 complex and an LTBP3-proTGFβ1 complex may be calculated to collectively represent affinities for ECM-associated (or matrix-associated) proTGFβ1 complexes. See, for example, Table, column (D). Human counterpart of a presenting molecule or presenting molecule complex may be indicated by an "h" preceding the protein or protein complex, e.g., "hLTBP1," "hLTBP1-proTGFβ1," hLTBP3" and "hLTBP3-proTGFβ1."

Effective amount: The terms "effective" and "therapeutically effective" refer to the ability or an amount to sufficiently produce a detectable change in a parameter of a disease, e.g., a slowing, pausing, reversing, diminution, or amelioration in a symptom or downstream effect of the disease. The term encompasses but does not require the use of an amount that completely cures a disease. According to some embodiments, an “effective amount” (or therapeutically effective amount, or therapeutic dose) is a dosage, concentration, or dosing regimen that achieves statistically significant clinical benefits (e.g., efficacy) in a patient population. For example, for an antibody that has been shown to be efficacious at doses between 3 mg/kg and 30 mg/kg in preclinical models, the effective amount can be said to be between about 3-30 mg/kg.

Effective tumor control: The term “effective tumor control” may be used to refer to a degree of tumor regression achieved in response to treatment, where, for example, the tumor is regressed by a defined fraction (such as <25%) of an endpoint tumor volume. For instance, in a particular model, if the endpoint tumor volume is set at 2,000 $mm^3$, effective tumor control is achieved if the tumor is reduced to less than 500 $mm^3$ assuming the threshold of <25%. Therefore, effective tumor control encompasses complete regression. Clinically, effective tumor control includes partial response (PR) and complete response (CR) based on art-recognized criteria, such as RECIST 1.1 and corresponding iRECIST. In some embodiments, effective tumor control in clinical settings also includes stable disease, where tumors that are typically expected to grow at certain rates are prevented from such growth by the treatment, even though shrinkage is not achieved.

Effector T cells: Effector T cells, as used herein, are T lymphocytes that actively respond immediately to a stimulus, such as co-stimulation and include, but are not limited to, CD4+ T cells (also referred to as T helper or Th cells) and CD8+ T cells (also referred to as cytotoxic T cells). Th cells assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including Th1, Th2, Th3, Th17, Th9, or TFh, which secrete different cytokines to facilitate different types of immune responses. Signaling from the APC directs T cells into particular subtypes. Cytotoxic (Killer). Cytotoxic T cells (TC cells, CTLs, T-killer cells, killer T cells), on the other hand, destroy virus-infected cells and cancer cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Cytotoxic effector cell (e.g., CD8+ cells) include, e.g., perforin and granzyme B.

Epitope: The term “epitope” may be also referred to as an antigenic determinant, is a molecular determinant (e.g., polypeptide determinant) that can be specifically bound by a binding agent, immunoglobulin or T-cell receptor. Epitope determinants include chemically active surface groupings of molecules, such as amino acids, sugar side chains, phosphoryl, or sulfonyl, and, in certain embodiments, may have specific three-dimensional structural characteristics, and/or specific charge characteristics. An epitope recognized by an antibody or an antigen-binding fragment of an antibody is a structural element of an antigen that interacts with CDRs (e.g., the complementary site) of the antibody or the fragment. An epitope may be formed by contributions from several amino acid residues, which interact with the CDRs of the antibody to produce specificity. An antigenic fragment can contain more than one epitope. In certain embodiments, an antibody specifically binds an antigen when it recognizes its target antigen in a complex mixture of proteins and/or macromolecules.

Fibrosis: The term “fibrosis” or “fibrotic condition/disorder” refers to the process or manifestation characterized by the pathological accumulation of extracellular matrix (ECM) components, such as collagens, within a tissue or organ.

Fibrotic microenvironment: The term “fibrotic microenvironment” refers to a local disease niche within a tissue, in which fibrosis occurs in vivo. The fibrotic microenvironment may comprise disease-associated molecular signature (a set of chemokines, cytokines, etc.), disease-associated cell populations (such as activated macrophages, MDSCs, etc.) as well as disease-associated ECM environments (alterations in ECM components and/or structure). Fibrotic microenvironment is thought to support the transition of fibroblast to α-smooth muscle actin-positive myofibroblast in a TGFβ-dependent manner. Fibrotic microenvironment may be further characterized by the infiltration of certain immune cells (such as macrophages and MDSCs).

GARP-TGFβ1 complex: As used herein, the term “GARP-TGFβ1 complex” (or “GARP-proTGFβ1 complex”) refers to a protein complex comprising a pro-protein form or latent form of a transforming growth factor-β1 (TGFβ1) protein and a glycoprotein-A repetitions predominant protein (GARP) or fragment or variant thereof. In some embodiments, a pro-protein form or latent form of TGFβ1 protein may be referred to as “pro/latent TGFβ1 protein”. In some embodiments, a GARP-TGFβ1 complex comprises GARP covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a GARP-TGFβ1 complex comprises GARP non-covalently linked with pro/latent TGFβ1. In some embodiments, a GARP-TGFβ1 complex is a naturally-occurring complex, for example a GARP-TGFβ1 complex in a cell. The term “hGARP” denotes human GARP.

Human antibody: The term “human antibody,” as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term “human antibody,” as used herein, is not intended to include antibodies in which CDR sequences derived from the germline of another mammalian species, such as a mouse, have been grafted onto human framework sequences.

Humanized antibody: The term “humanized antibody” refers to antibodies, which comprise heavy and light chain variable region sequences from a non-human species (e.g., a mouse) but in which at least a portion of the VH and/or VL sequence has been altered to be more “human-like,” i.e., more similar to human germline variable sequences. One type of humanized antibody is a CDR-grafted antibody, in which human CDR sequences are introduced into nonhuman VH and VL sequences to replace the corresponding nonhuman CDR sequences. Also "humanized antibody" is an antibody, or a variant, derivative, analog or fragment thereof, which immunospecifically binds to an antigen of interest and which comprises an FR region having substantially the amino acid sequence of a human antibody and a CDR region having substantially the amino acid sequence of a non-human antibody. As used herein, the term "substantially" in the context of a CDR refers to a CDR having an amino acid sequence at least 80%, at least 85%, at least 90%, at least 95%, at least 96%, at least 97%, at least 98% or at least 99% identical to the amino acid sequence of a non-human antibody CDR. A humanized antibody comprises substantially all of at least one, and typically two, variable domains (Fab, Fab', F (ab') 2, FabC, Fv) in which all or substantially all of the CDR regions correspond to those of a non-human immunoglobulin (i.e., donor antibody) and all or substantially all of the FR regions are those of a human immunoglobulin consensus sequence. In an embodiment a humanized antibody also comprises at least a portion of an immunoglobulin Fc region, typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

Hydrogen/deuterium exchange mass spectrometry (HDX-MS): HDX-MS is a well-known technique employed to interrogate protein confirmation and protein-protein interactions in solution by measuring the degree of solvent accessibility. See, for example, Wei et al., (2014) Drug Discov Today 19 (1): 95-102. "Hydrogen/deuterium exchange mass spectrometry for probing higher order structure of protein therapeutics: methodology and applications." The HDX-MS technique may be employed to determine a region or regions of an antigen bound by an antibody (i.e., "binding region(s)"). Thus, such binding region(s) may contain or form an epitope.

Immunosuppression, immunosuppressive: The terms refer to the ability to suppress immune cells, such as T cells, NK cells and B cells. The gold standard for evaluating immunosuppressive function is the inhibition of T cell activity, which may include antigen-specific suppression and non-specific suppression. Regulatory T cells (Tregs) and MDSCs may be considered immunosuppressive cells. M2-polarized macrophages (e.g., TAMs) may also be characterized as immunosuppressive.

Isoform-specific/selective: The term "isoform specificity" or "isoform selectivity" refers to an agent's ability to discriminate one isoform over other structurally related isoforms (i.e., selectivity). An isoform-specific TGFβ inhibitor exerts its inhibitory activity towards one isoform of TGFβ but not the other isoforms of TGFβ at a given concentration. For example, an isoform-specific TGFβ1 antibody selectively binds TGFβ1. A TGFβ1-specific inhibitor (antibody) preferentially targets (binds thereby inhibits) the TGFβ1 isoform over TGFβ2 or TGFβ3 with substantially greater affinity. For example, the selectivity in this context may refer to at least a 500-1000-fold difference in respective affinities as measured by an in vitro binding assay such as OCTET® and BIACORER. In some embodiments, the selectivity is such that the inhibitor when used at a dosage effective to inhibit TGFβ1 in vivo does not inhibit TGFβ2 and TGFβ3. For instance, an antibody may preferentially bind TGFβ1 at affinity of ~1 pM, while the same antibody may bind TGFβ2 and/or TGFβ3 at ~0.5-50 nM. For such an inhibitor to be useful as a therapeutic, dosage to achieve desirable effects (e.g., therapeutically effective amounts) must fall within the window within which the inhibitor can effectively inhibit the TGFβ1 isoform without inhibiting TGFβ2 or TGFβ3. The terms "isoform-specific" and "isoform-selective" are used interchangeably herein.

Isolated: An "isolated" antibody as used herein, refers to an antibody that is substantially free of other antibodies having different antigenic specificities. In some embodiments, an isolated antibody is substantially free of other unintended cellular material and/or chemicals.

Large Latent Complex: The term "large latent complex" ("LLC") in the context of the present disclosure refers to a complex comprised of a proTGFβ1 dimer bound to so-called a presenting molecule. Thus, a large latent complex is a presenting molecule-proTGFβ1 complex, such as LTBP1-proTGFβ1, LTBP3-proTGFβ1, GARP-proTGFβ1 and LRRC33-proTGFβ1. Such complexes may be formed in vitro using recombinant, purified components capable of forming the complex. For screening purposes, presenting molecules used for forming such LLCs need not be full length polypeptides; however, the portion of the protein capable of forming disulfide bonds with the proTGFβ1 dimer complex via the cysteine residues near its N-terminal regions is typically required.

Latency associated peptide (LAP): LAP is so-called the "prodomain" of proTGFβ1. As described in more detail herein, LAP is comprised of the "Straight Jacket" domain and the "Arm" domain. Straight Jacket itself is further divided into the Alpha-1 Helix and Latency Lasso domains.

Latency Lasso: As used herein, "Latency Lasso," sometimes also referred to as Latency Loop, is a domain flanked by Alpha-1 Helix and the Arm within the prodomain of proTGFb1. In its unmutated form, Latency Lasso of human proTGFβ1 comprises the amino acid sequence: LASPPSQGEVPPGPL (SEQ ID NO: 270). As used herein, the term Extended Latency Lasso region" refers to the Latency Lasso together with its immediate C-terminal motif referred to as Alpha-2 Helix (α2-Helix) of the prodomain. The proline residue that is at the C-terminus of the Latency Lasso provides the perpendicular "turn" like an "elbow" that connects the lasso loop to the α2-Helix. Certain high affinity TGFβ1 activation inhibitors bind at least in part to Latency Lasso or a portion thereof to confer the inhibitory potency (e.g., the ability to block activation), wherein optionally the portion of the Latency Lasso is ASPPSQGEVPPGPL (SEQ ID NO: 286). In some embodiments, the antibodies of the present disclosure bind a proTGFβ1 complex at ASPPSQGEVPPGPL (SEQ ID NO: 286) or a portion thereof. Certain high affinity TGFβ1 activation inhibitors bind at least in part to Extended Latency Lasso or a portion thereof to confer the inhibitory potency (e.g., the ability to block activation), wherein optionally the portion of the Extended Latency Lasso is LASPPSQGEVPPGPLPEAVLALYNSTR (SEQ ID NO: 271).

Localized: In the context of the present disclosure, the term "localized" (as in "localized tumor") refers to anatomically isolated or isolatable abnormalities, such as solid malignancies, as opposed to systemic disease. Certain leukemia, for example, may have both a localized component (for instance the bone marrow) and a systemic component (for instance circulating blood cells) to the disease.

LRRC33-TGFβ1 complex: As used herein, the term "LRRC33-TGFβ1 complex" (or "LRRC33-proTGFβ1 complex") refers to a complex between a pro-protein form or latent form of transforming growth factor-1 (TGFβ1) protein and a Leucine-Rich Repeat-Containing Protein 33 (LRRC33; also known as Negative Regulator Of Reactive Oxygen Species or NRROS) or fragment or variant thereof. In some embodiments, a LRRC33-TGFβ1 complex comprises LRRC33 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LRRC33-TGFβ1 complex comprises LRRC33 non-covalently linked with pro/latent TGFβ1. In some embodiments, a LRRC33-TGFβ1 complex is a naturally-occurring complex, for example a LRRC33-TGFβ1 complex in a cell. The term "hLRRC33" denotes human LRRC33.

LTBP1-TGFβ1 complex: As used herein, the term "LTBP1-TGFβ1 complex" (or "LTBP1-proTGFβ1 complex") refers to a protein complex comprising a pro-protein form or latent form of transforming growth factor-β1 (TGFβ1) protein and a latent TGF-beta binding protein 1 (LTBP1) or fragment or variant thereof. In some embodiments, a LTBP1-TGFβ1 complex comprises LTBP1 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LTBP1-TGFβ1 complex comprises LTBP1 non-covalently linked with pro/latent TGFβ1. In some embodiments, a LTBP1-TGFβ1 complex is a naturally-occurring complex, for example a LTBP1-TGFβ1 complex in a cell. The term "hLTBP1" denotes human LTBP1.

LTBP3-TGFβ1 complex: As used herein, the term "LTBP3-TGFβ1 complex" (or "LTBP3-proTGFβ1 complex") refers to a protein complex comprising a pro-protein form or latent form of transforming growth factor-β1 (TGFβ1) protein and a latent TGF-beta binding protein 3 (LTBP3) or fragment or variant thereof. In some embodiments, a LTBP3-TGFβ1 complex comprises LTBP3 covalently linked with pro/latent TGFβ1 via one or more disulfide bonds. In nature, such covalent bonds are formed with cysteine residues present near the N-terminus (e.g., amino acid position 4) of a proTGFβ1 dimer complex. In other embodiments, a LTBP3-TGFβ1 complex comprises LTBP1 non-covalently linked with pro/latent TGFβ1. In some embodiments, a LTBP3-TGFβ1 complex is a naturally-occurring complex, for example a LTBP3-TGFβ1 complex in a cell. The term "hLTBP3" denotes human LTBP3.

M2 or M2-like macrophage: M2 macrophages represent a subset of activated or polarized macrophages and include disease-associated macrophages in both fibrotic and tumor microenvironments. Cell-surface markers for M2-polarized macrophages typically include CD206 and CD163 (i.e., CD206+/CD163+). Applicant recently discovered that the M2-polarized macrophages may also express cell-surface LRRC33. The activation of M2 macrophages is promoted mainly by IL-4, IL-13, IL-10 and TGFβ; they secrete the same cytokines that activate them (IL-4, IL-13, IL-10 and TGFβ). These cells have high phagocytic capacity and produce ECM components, angiogenic and chemotactic factors. The release of TGFβ by macrophages may perpetuate the myofibroblast activation, EMT and EndMT induction in the fibrotic tissue. For example, M2 macrophages are essential for TGFβ-driven lung fibrosis and are also enriched in a number of tumors.

Matrix-associated proTGFβ1: LTBP1 and LTBP3 are presenting molecules that are components of the extracellular matrix (ECM). LTBP1-proTGFβ1 and LTBP3-proTGFβ1 may be collectively referred to as "ECM-associated" (or "matrix-associated") proTGFβ1 complexes, which mediate ECM-associated TGFβ1 activation/signaling. The term also includes recombinant, purified LTBP1-proTGFβ1 and LTBP3-proTGFβ1 complexes in solution (e.g., in vitro assays) which are not physically attached to a matrix or substrate.

Maximally tolerated dose (MTD): The term MTD generally refers to, in the context of safety/toxicology considerations, the highest amount of a test article (such as a TGFβ1 inhibitor) evaluated with no observed adverse effect level (NOAEL). For example, the NOAEL for Ab2 in rats was the highest dose evaluated (100 mg/kg), suggesting that the MTD for Ab2 is >100 mg/kg, based on a four-week toxicology study.

Meso-Scale Discovery: "Meso-Scale Discovery" or "MSD" is a type of immunoassay that employs high binding carbon electrodes to capture proteins (e.g., antibodies). The antibodies can be incubated with particular antigens, which binding can be detected with secondary antibodies that are conjugated to electrochemiluminescent labels. Upon an electrical signal, light intensity can be measured to quantify analytes in the sample.

Myelofibrosis: "Myelofibrosis," also known as osteomyelofibrosis, is a relatively rare bone marrow proliferative disorder (e.g., cancer), which belongs to a group of diseases called myeloproliferative disorders and includes primary myelofibrosis and secondary myelofibrosis. Myelofibrosis characterized by the proliferation of an abnormal clone of hematopoietic stem cells in the bone marrow and other sites results in fibrosis, or the replacement of the marrow with scar tissue. Myelofibrosis is characterized by mutations that cause upregulation or overactivation of the downstream JAK pathway.

Myeloid-derived suppressor cell: Myeloid-derived suppressor cells (MDSCs) are a heterogeneous population of cells generated during various pathologic conditions and thought to represent a pathologic state of activation of monocytes and relatively immature neutrophils. MDSCs include at least two categories of cells termed i) "granulocytic" (G-MDSC) or polymorphonuclear (PMN-MDSC), which are phenotypically and morphologically similar to neutrophils; and ii) monocytic (M-MDSC) which are phenotypically and morphologically similar to monocytes. MDSCs are characterized by a distinct set of genomic and biochemical features, and can be distinguished by specific surface molecules. For example, human G-MDSCs/PMN-MDSCs typically express the cell-surface markers CD11b, CD33, CD15 and CD66. In addition, human G-MDSCs/PMN-MDSCs may also express HLA-DR and/or Arginase. By comparison, human M-MDSCs typically express the cell surface markers CD11b, CD33 and CD14. The MDSCs may also express CD39 and CD73 to mediate adenosine signaling involved in organ fibrosis (such as liver fibrosis, and lung fibrosis), cancer and myelofibrosis). In addition, human M-MDSCs may also express HLA-DR. In addition to such cell-surface markers, MDSCs are characterized by the ability to suppress immune cells, such as T cells, NK cells and B cells. Immune suppressive functions of MDSCs may include inhibition of antigen-non-specific function and inhibition of antigen-specific function. MDSCs can express cell surface LRRC33 and/or LRRC33-proTGFβ1.

Myofibroblast: Myofibroblasts are cells with certain phenotypes of fibroblasts and smooth muscle cells and generally express vimentin, alpha-smooth muscle actin (α-SMA; human gene ACTA2) and paladin. In many disease conditions involving extracellular matrix dysregulations (such as increased matrix stiffness), normal fibroblast cells become de-differentiated into myofibroblasts in a TGFβ-dependent manner. Aberrant overexpression of TGFβ is common among myofibroblast-driven pathologies. TGFβ is known to promote myofibroblast differentiation, cell proliferation, and matrix production. Myofibroblasts or myofibroblast-like cells within the fibrotic microenvironment may be referred to as fibrosis-associated fibroblasts (or "FAFs"), and myofibroblasts or myofibroblast-like cells within the tumor microenvironment may be referred to as cancer-associated fibroblasts (or "CAFs").

Off rate ($k_{OFF}$): The off rate is a kinetic parameter of how fast or how slowly an antibody (such as mAb) or antigen-binding fragment (such as fAb) dissociates from its antigen and may be also referred to as the dissociation rate. Dissociation rates can be experimentally measured in suitable in vitro binding assays, such as OCTET®- and BIACORE®-based systems.

Pan-TGFβ inhibitor/pan-inhibition of TGFβ: The term "pan-TGFβ inhibitor" or "pan inhibitor of TGFβ" refers to any agent that is capable of inhibiting or antagonizing all three isoforms of TGFβ. Such an inhibitor may be a small molecule inhibitor of TGFβ isoforms. The term includes pan-TGFβ antibody which refers to any antibody capable of binding to each of TGFβ isoforms, i.e., TGFβ1, TGFβ2, and TGFβ3. In some embodiments, a pan-TGFβ antibody binds and neutralizes activities of all three isoforms, i.e., TGFβ1, TGFβ2, and TGFβ3 activities. The antibody 1D11 (or the human analog fresolimumab (GC1008)) is a well-known example of a pan-TGFβ antibody that neutralizes all three isoforms of TGFβ. Examples of small molecule pan-TGFβ inhibitors include galunisertib (LY2157299 monohydrate, CAS No. 700874-72-2), which is an antagonist for the TGFβ receptor I kinase/ALK5 that mediates signaling of all three TGFβ isoforms.

Potency: The term "potency" as used herein refers to activity of a drug, such as an inhibitory antibody (or fragment) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured in cell-based assays, such as TGFβ activation/inhibition assays, whereby the degree of TGFβ activation, such as activation triggered by integrin binding, can be measured in the presence or absence of test article (e.g., inhibitory antibodies) in a cell-based system. Typically, among those capable of binding to the same or overlapping binding regions of an antigen (e.g., cross-blocking antibodies), antibodies with higher affinities (lower $K_D$ values) tend to show higher potency than antibodies with lower affinities (greater $K_D$ values).

Predictive biomarker: Predictive biomarkers provide information on the probability or likelihood of response to a particular therapy. Typically, a predictive biomarker is measured before and after treatment, and the changes or relative levels of the marker in samples collected from the subject indicates or predicts therapeutic benefit.

Presenting molecule: Presenting molecules in the context of the present disclosure refer to anchoring proteins that can form covalent bonds with latent pro-proteins (e.g., proTGFβ1) and "present" the inactive complex in an extracellular niche (such as ECM or immune cell surface) thereby maintaining its latency until an activation event occurs. Known presenting molecules for proTGFβ1 include: LTBP1, LTBP3, GARP (also known as LRRC32) and LRRC33, which can form presenting molecule-proTGFβ1 complexes (LLCs), namely, LTBP1-proTGFβ1, LTBP3-proTGFβ1, GARP-proTGFβ1 and LRRC33-proTGFβ1, respectively. In nature, LTBP1 and LTBP3 are components of the extracellular matrix (ECM); therefore, LTBP1-proTGFβ1 and LTBP3-proTGFβ1 may be collectively referred to as "ECM-associated" (or "matrix-associated") proTGFβ1 complexes that mediate ECM-associated TGFβ1 signaling/activities. GARP and LRRC33, on the other hand, are transmembrane proteins expressed on cell surface of certain cells; therefore, GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 signaling/activities.

Protection (from solvent exposure): In the context of HDX-MS-based assessment of protein-protein interactions, such as antibody-antigen binding, the degree by which a protein (e.g., a region of a protein containing an epitope) is exposed to a solvent, thereby allowing proton exchange to occur, inversely correlates with the degree of binding/interaction. Therefore, when an antibody described herein binds to a region of an antigen, the binding region is "protected" from being exposed to the solvent because the protein-protein interaction precludes the binding region from being accessible by the surrounding solvent. Thus, the protected region is indicative of a site of interaction. Typically, suitable solvents are physiological buffers.

ProTGFβ1: The term "proTGFβ1" as used herein is intended to encompass precursor forms of inactive TGFβ1 dimer complex that comprises a prodomain sequence of TGFβ1 within the complex. Thus, the term can include the pro-, as well as the latent-forms of TGFβ1. The expression "pro/latent TGFβ1" may be used interchangeably. The "pro" form of TGFβ1 exists prior to proteolytic cleavage at the furin site. Once cleaved, the resulting form is said to be the "latent" form of TGFβ1. The "latent" complex remains associated until further activation trigger, such as integrin-driven activation event. The proTGFβ1 complex is comprised of dimeric TGFβ1 pro-protein polypeptides, linked with disulfide bonds. The latent dimer complex is covalently linked to a single presenting molecule via the cysteine residue at position 4 (Cys4) of each of the proTGFβ1 polypeptides. The adjective "latent" may be used generally to describe the "inactive" state of TGFβ1, prior to integrin-mediated or other activation events. The proTGFβ1 polypeptide contains a prodomain (LAP) and a growth factor domain (SEQ ID NO: 24).

Regression: Regression of tumor or tumor growth can be used as an in vivo efficacy measure. In preclinical settings, median tumor volume (MTV) and Criteria for Regression Responses Treatment efficacy may be determined from the tumor volumes of animals remaining in the study on the last day. Treatment efficacy may also be determined from the incidence and magnitude of regression responses observed during the study. Treatment may cause partial regression (PR) or complete regression (CR) of the tumor in an animal. Complete regression achieved in response to therapy (e.g., administration of a drug) may be referred to as "complete response" and the subject that achieves complete response may be referred to as a "complete responder". In some embodiments of preclinical tumor models, a PR response is defined as the tumor volume that is 50% or less of its Day 1 volume for three consecutive measurements during the course of the study, and equal to or greater than 13.5 $mm^3$ for one or more of these three measurements. In some embodiments, a CR response is defined as the tumor volume that is less than 13.5 $mm^3$ for three consecutive measurements during the course of the study. In preclinical model, an animal with a CR response at the termination of a study may be additionally classified as a tumor-free survivor (TFS). The term "effective tumor control" may be used to refer to a degree of tumor regression achieved in response to treatment, where, for example, the tumor volume is reduced to <25% of the endpoint tumor volume. For instance, in a particular model, if the endpoint tumor volume is 2,000 $mm^3$, effective tumor control is achieved if the tumor is reduced to less than 500 $mm^3$. Therefore, effective tumor control encompasses complete regression, as well as partial regression that reaches the threshold reduction. Similarly, regression of fibrosis can be used as an in vivo efficacy measure of a therapy such as a TGFβ1 inhibitor. The regression of fibrotic conditions may be determined based on the standard criteria to assess the severity of fibrotic manifestation by disease stage.

Regulatory T cells: "Regulatory T cells," or Tregs, are a type of immune cells characterized by the expression of the biomarkers CD4, FOXP3, and CD25. Tregs are sometimes referred to as suppressor T cells and represent a subpopulation of T cells that modulate the immune system, maintain tolerance to self-antigens, and prevent autoimmune disease. Tregs are immunosuppressive and generally suppress or downregulate induction and proliferation of effector T (Teff) cells. Tregs can develop in the thymus (so-called CD4+ Foxp3+ "natural" Tregs) or differentiate from naïve CD4+ T cells in the periphery, for example, following exposure to TGFβ or retinoic acid. Tregs can express cell surface GARP-proTGFβ1.

Resistance (to therapy): Resistance to a particular therapy (such as CBT) may be due to the innate characteristics of the disease such as cancer ("primary resistance"), or due to acquired phenotypes that develop over time following the treatment ("acquired resistance"). Patients who do not show therapeutic response to a therapy (e.g., those who are non-responders or poorly responsive to the therapy) are said to have primary resistance to the therapy and may be characterized as primary non-responders. Patients who initially show therapeutic response to a therapy but later lose effects (e.g., progression or recurrence despite continued therapy) are said to have acquired resistance to the therapy.

Response Evaluation Criteria in Solid Tumors (RECIST) and iRECIST: RECIST is a set of published rules that define when tumors in cancer patients improve ("respond"), stay the same ("stabilize"), or worsen ("progress") during treatment. The criteria were published in February 2000 by an international collaboration including the European Organisation for Research and Treatment of Cancer (EORTC), National Cancer Institute of the United States, and the National Cancer Institute of Canada Clinical Trials Group. Subsequently, a revised version of the RECIST guideline (RECIST v 1.1) has been widely adapted (see: Eisenhauera et al., (2009), "New response evaluation criteria in solid tumours: Revised RECIST guideline (version 1.1)" *Eur J Cancer* 45:228-247, incorporated herein). Response criteria are as follows: Complete response (CR): Disappearance of all target lesions; Partial response (PR): At least a 30% decrease in the sum of the LD of target lesions, taking as reference the baseline sum LD; Stable disease (SD): Neither sufficient shrinkage to qualify for PR nor sufficient increase to qualify for PD, taking as reference the smallest sum LD since the treatment started; Progressive disease (PD): At least a 20% increase in the sum of the LD of target lesions, taking as reference the smallest sum LD recorded since the treatment started or the appearance of one or more new lesions. On the other hand, iRECIST provides a modified set of criteria that takes into account immune-related response. See: www.ncbi.nlm.nih.gov/pmc/articles/PMC5648544/. The RECIST and iRECIST criteria are standardized, may be revised from time to time as more data become available, and are well understood in the art.

Solid tumor: The term "solid tumor" refers to proliferative disorders resulting in an abnormal growth or mass of tissue that usually does not contain cysts or liquid areas. Solid tumors may be benign (non-cancerous), or malignant (cancerous). Solid tumors are typically comprised of multiple cell types, including, without limitation, cancerous (malignant) cells, stromal cells such as CAFs, and infiltrating leukocytes, such as macrophages and lymphocytes. Solid tumors to be treated with an isoform-selective inhibitor of TGFβ1, such as those described herein, are typically TGFβ1-positive (TGFβ1+) tumors.

Solution Equilibrium Titration (SET): The SET is an assay whereby binding between two molecules (such as an antigen and an antibody that binds the antigen) can be measured at equilibrium in a solution. For example, Meso-Scale Discovery ("MSD")-based SET, or MSD-SET, is a useful mode of determining dissociation constants for particularly high-affinity protein-protein interactions at equilibrium, such as picomolar-affinity antibodies binding to their antigens (see, for example: Ducata et al., (2015) J Biomolecular Screening 20 (10): 1256-1267). The SET-based assays are particularly useful for determining $K_D$ values of antibodies with sub-nanomolar (e.g., picomolar) affinities.

Specific binding: As used herein, the term "specific binding" or "specifically binds" means that the interaction of the antibody, or antigen-binding portion thereof, with an antigen or amino acid residue is dependent upon the presence of a particular structure (e.g., an antigenic determinant or epitope). For example, the antibody, or antigen-binding portion thereof, binds to a specific protein rather than to proteins generally. In some embodiments, an antibody, or antigen-binding portion thereof, specifically binds to a target, e.g., TGFβ1, if the antibody has a KD for the target of at least about $10^{-9}$ M, $10^{-10}$ M, $10^{-11}$ M, $10^{-12}$ M, or less. In some embodiments, the term "specific binding to an epitope of proTGFβ1", "specifically binds to an epitope of proTGFβ1", "specific binding to proTGFβ1", or "specifically binds to proTGFβ1" as used herein, refers to an antibody, or antigen-binding portion thereof, that binds to proTGFβ1 and has a dissociation constant (KD) of $1.0\times10^{-8}$ M or less, as determined by suitable in vitro binding assays. In one embodiment, an antibody, or antigen-binding portion thereof, can specifically bind to both human and a non-human (e.g., mouse) orthologues of proTGFβ1.

Subject: The term "subject" in the context of therapeutic applications refers to an individual who receives clinical care or intervention, such as treatment, diagnosis, etc. Suitable subjects include vertebrates, including but not limited to mammals (e.g., human and non-human mammals). Where the subject is a human subject, the term "patient" may be used interchangeably. In a clinical context, the term "a patient population" or "patient subpopulation" is used to refer to a group of individuals that falls within a set of criteria, such as clinical criteria (e.g., disease presentations, disease stages, susceptibility to certain conditions, responsiveness to therapy, etc.), medical history, health status, gender, age group, genetic criteria (e.g., carrier of certain mutation, polymorphism, gene duplications, DNA sequence repeats, etc.) and lifestyle factors (e.g., diet, smoking, alcohol consumption, exercise, etc.).

Target engagement: As used herein, the term target engagement refers to the ability of a molecule (e.g., TGFβ inhibitor) to bind to its intended target in vivo (e.g., endogenous TGFβ). In case of activation inhibitors, the intended target can be a large latent complex.

TGFβ1-related indication: A "TGFβ1-related indication" means any disease, disorder and/or condition related to expression, activity and/or metabolism of a TGFβ1 or any disease, disorder and/or condition that may benefit from inhibition of the activity and/or levels TGFβ1. Certain TGFβ1-related indications are driven predominantly by the TGFβ1 isoform. TGFβ1-related indications include, but are not limited to: fibrotic conditions (such as organ fibrosis, and fibrosis of tissues involving chronic inflammation), proliferative disorders (such as cancer, e.g., solid tumors and myelofibrosis), disease associated with ECM dysregulation (such as conditions involving matrix stiffening and remodeling), disease involving endothelial-to-mesenchymal transition (EndMT), disease involving epithelial-to-mesenchymal transition (EMT), disease involving proteases, disease with aberrant gene expression of certain markers described herein. These disease categories are not intended to be mutually exclusive.

TGFβ inhibitor: The term "TGFβ inhibitor" refers broadly to any agent capable of antagonizing biological activities, signaling or function of TGFβ growth factor (e.g., TGFβ1, TGFβ2 and/or TGFβ3).

The term is not intended to limit its mechanism of action and includes, for example, neutralizing antibodies, receptor antagonists (e.g., kinase inhibitors), soluble ligand traps, and activation inhibitors of TGFβ. Non-selective TGFβ inhibitors are commonly referred to as "pan-inhibitors" of TGFβ. TGFβ inhibitors also include antibodies that are capable of reducing the availability of latent proTGFβ which can be activated in the niche, for example, by inducing antibody-dependent cell mediated cytotoxicity (ADCC), and/or antibody-dependent cellular phagocytosis (ADPC), as well as antibodies that result in internalization of cell-surface complex comprising latent proTGFβ, thereby removing the precursor from the plasma membrane without depleting the cells themselves. Internalization may be a suitable mechanism of action for LRRC33-containing protein complexes (such as human LRRC33-proTGFβ1) which results in reduced levels of cells expressing LRRC33-containing protein complexes on cell surface.

The "TGFβ family" is a class within the TGFβ superfamily and contains three members in human: TGFβ1, TGFβ2, and TGFβ3, which are structurally similar and are encoded by separate genes. The three growth factors are known to signal via the same receptors.

Therapeutic window. The term "therapeutic window" refers to a range of doses/concentrations that produces therapeutic response without causing significant/observable/unacceptable adverse effect (e.g., within adverse effects that are acceptable or tolerable) in subjects. Therapeutic window may be calculated as a ratio between minimum effective concentrations (MEC) to the minimum toxic concentrations (MTC). To illustrate, a TGFβ1 inhibitor that achieves in vivo efficacy at 10 mg/kg and shows tolerability or acceptable toxicities at 100 mg/kg provides at least a 10-fold (e.g., 10×) therapeutic window. By contrast, a pan-inhibitor of TGFβ that is efficacious at 10 mg/kg but causes adverse effects at 5 mg/kg is said to have "dose-limiting toxicities." For example, Ab2 has been shown to be efficacious at dosage ranging between about <3 and 30 mg/kg/week and was also shown to be free of observable toxicities associated with pan-inhibition of TGFβ at least 100 mg/kg/week for 4 weeks in preclinical models such as rats. Based on this, Ab2 shows at minimum a 3.3-fold and up to 33-fold therapeutic window.

Toxicity: As used herein, the term "toxicity" or "toxicities" refers to unwanted in vivo effects in subjects (e.g., patients) associated with a therapy administered to the subjects (e.g., patients), such as undesirable side effects and adverse events. "Tolerability" refers to a level of toxicities associated with a therapy or therapeutic regimen, which can be reasonably tolerated by patients, without discontinuing the therapy due to the toxicities. Typically, toxicity/toxicology studies are carried out in one or more preclinical models prior to clinical development to assess safety profiles of a drug candidate (e.g., monoclonal antibody therapy). Toxicity/toxicology studies may help determine the "no observed adverse effect level (NOAEL)" and the "maximally tolerated dose (MTD)" of a test article, based on which a therapeutic window may be deduced. Preferably, a species that is shown to be sensitive to the particular intervention should be chosen as a preclinical animal model in which safety/toxicity study is to be carried out. In case of TGFβ inhibition, suitable species include rats, dogs, and cynos. Mice are reported to be less sensitive to pharmacological inhibition of TGFβ and may not reveal toxicities that are potentially dangerous in other species, including human, although certain studies report toxicities observed with pan-inhibition of TGFβ in mice. To illustrate in the context of the present disclosure, the NOAEL for Ab2 in rats was the highest dose evaluated (100 mg/kg), suggesting that the MTD is >100 mg/kg, based on a four-week toxicology study.

Treat/treatment: The term "treat" or "treatment" includes therapeutic treatments, prophylactic treatments, and applications in which one reduces the risk that a subject will develop a disorder or other risk factor. Thus the term is intended to broadly mean: causing therapeutic benefits in a patient by, for example, slowing disease progression, reversing certain disease features, normalizing gene expression, enhancing or boosting the body's immunity; reducing or reversing immune suppression; reducing, removing or eradicating harmful cells or substances from the body; reducing disease burden (e.g., fibrosis and tumor burden); preventing recurrence or relapse; prolonging a refractory period, and/or otherwise improving survival. The term includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In the context of combination therapy, the term may also refer to: i) the ability of a second therapeutic to reduce the effective dosage of a first therapeutic so as to reduce side effects and increase tolerability; ii) the ability of a second therapy to render the patient more responsive to a first therapy; and/or iii) the ability to effectuate additive or synergistic clinical benefits.

Tumor-associated macrophage (TAM): TAMs are polarized/activated macrophages with pro-tumor phenotypes (M2-like macrophages). TAMs can be either marrow-originated monocytes/macrophages recruited to the tumor site or tissue-resident macrophages which are derived from erythro-myeloid progenitors. Differentiation of monocytes/macrophages into TAMs is influenced by a number of factors, including local chemical signals such as cytokines, chemokines, growth factors and other molecules that act as ligands, as well as cell-cell interactions between the monocytes/macrophages that are present in the niche (tumor microenvironment). Generally, monocytes/macrophages can be polarized into so-called "M1" or "M2" subtypes, the latter being associated with more pro-tumor phenotype. In a solid tumor, up to 50% of the tumor mass may correspond to macrophages, which are preferentially M2-polarized. Among tumor-associated monocytes and myeloid cell populations, M1 macrophages typically express cell surface HLA-DR, CD68 and CD86, while M2 macrophages typically express cell surface HLA-DR, CD68, CD163 and CD206. Tumor-associated, M2-like macrophages (such as M2c and M2d subtypes) can express cell surface LRRC33 and/or LRRC33-proTGFβ1. M2-like macrophages may be also enriched in fibrotic microenvironment.

Tumor microenvironment: The term "tumor microenvironment (TME)" refers to a local disease niche, in which a tumor (e.g., solid tumor) resides in vivo. The TME may comprise disease-associated molecular signature (a set of chemokines, cytokines, etc.), disease-associated cell populations (such as TAMs, CAFs, MDSCs, etc.) as well as disease-associated ECM environments (alterations in ECM components and/or structure).

Variable region: The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

Other than in the operating examples, or where otherwise indicated, all numbers expressing quantities of ingredients or reaction conditions used herein should be understood as modified in all instances by the term "about." The term "about" when used in connection with percentages can mean±1%.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, e.g., 10-20, 1-10, 30-40, etc.

Transforming Growth Factor-beta (TGFβ)

The Transforming Growth Factor-beta (TGFβ) activities and subsequent partial purification of the soluble growth factors were first described in the late 1970's to early 1980's, with which the TGFβ field began some 40 years ago. To date, 33 gene products have been identified that make up the large TGFβ superfamily. The TGFβ superfamily can be categorized into at least three subclasses by structural similarities: TGFβs, Growth-Differentiation Factors (GDFs) and Bone-Morphogenetic Proteins (BMPs). The TGFβ subclass is comprised of three highly conserved isoforms, namely, TGFβ1, TGFβ2 and TGFβ3, which are encoded by three separate genes in human.

The TGFβs are thought to play key roles in diverse processes, such as inhibition of cell proliferation, extracellular matrix (ECM) remodeling, and immune homeostasis. The importance of TGFβ1 for T cell homeostasis is demonstrated by the observation that TGFβ1−/− mice survive only 3-4 weeks, succumbing to multiorgan failure due to massive immune activation (Kulkarni, A. B., et al., *Proc Natl Acad Sci USA,* 1993. 90 (2): p. 770-4; Shull, M. M., et al., Nature, 1992. 359 (6397): p. 693-9). The roles of TGFβ2 and TGFβ3 are less clear. Whilst the three TGFβ isoforms have distinct temporal and spatial expression patterns, they signal through the same receptors, TGFβRI and TGFβRII, although in some cases, for example for TGFβ2 signaling, type III receptors such as betaglycan are also required (Feng, X. H. and R. Derynck, *Annu Rev Cell Dev Biol,* 2005. 21: p. 659-93; Massague, J., *Annu Rev Biochem,* 1998. 67: p. 753-91). Ligand-induced oligomerization of TGFβRI/II triggers the phosphorylation of SMAD transcription factors, resulting in the transcription of target genes, such as Col1a1, Col3a1, ACTA2, and SERPINE1 (Massague, J., J. Seoane, and D. Wotton, *Genes Dev,* 2005. 19 (23): p. 2783-810). SMAD-independent TGFβ signaling pathways have also been described, for example in cancer or in the aortic lesions of Marfan mice (Derynck, R. and Y. E. Zhang, *Nature,* 2003. 425 (6958): p. 577-84; Holm, T. M., et al., *Science,* 2011. 332 (6027): p. 358-61).

The biological importance of the TGFβ pathway in humans has been validated by genetic diseases. Camurati-Engelman disease results in bone dysplasia due to an autosomal dominant mutation in the TGFβ1 gene, leading to constitutive activation of TGFβ1 signaling (Janssens, K., et al., *J Med Genet,* 2006. 43 (1): p. 1-11). Patients with Loeys/Dietz syndrome carry autosomal dominant mutations in components of the TGFβ signaling pathway, which cause aortic aneurism, hypertelorism, and bifid uvula (Van Laer, L., H. Dietz, and B. Loeys, *Adv Exp Med Biol,* 2014. 802: p. 95-105). As TGFβ pathway dysregulation has been implicated in multiple diseases, several drugs that target the TGFβ pathway have been developed and tested in patients, but with limited success.

Dysregulation of the TGFβ signaling has been associated with a wide range of human diseases. Indeed, in a number of disease conditions, such dysregulation may involve multiple facets of TGFβ function. Diseased tissue, such as fibrotic and/or inflamed tissues and tumors, may create a local environment in which TGFβ activation can cause exacerbation or progression of the disease, which may be at least in part mediated by interactions between multiple TGFβ-responsive cells, which are activated in an autocrine and/or paracrine fashion, together with a number of other cytokines, chemokines and growth factors that play a role in a particular disease setting This invention is further illustrated by the following examples which should not be construed as limiting. The examples refer to the following figures: FIG. 1-FIG. 31.

wherein further optionally the $X_3$ is a Q or E; and wherein further optionally the $X_4$ is an S or T (SEQ ID NO: 280); and, the L-CDR3 comprises a sequence represented by the formula QQTY$X_1$VPLT, wherein optionally the $X_1$ is a T or G (SEQ ID NO: 281). In preferred embodiments, the H-CDR2 comprises ISGSGAAT (SEQ ID NO: 282); the H-CDR3 comprises VSSGHWDYD (SEQ ID NO: 287); the L-CDR2 comprises AASGLES (SEQ ID NO: 284); and, the L-CDR3 comprises QQTYGVPLT (SEQ ID NO: 285). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309. In some embodiments, the H-CDR1 may comprise the sequence GFTFADYA (SEQ ID NO: 276); the H-CDR2 may comprise the sequence ISGSGAAT (SEQ ID NO: 282); the H-CDR3 may comprise a sequence represented by the formula VSSG$X_1$WD$X_2$D, wherein optionally the $X_1$ is an H or Q, and wherein further optionally the $X_2$ is a Y or F (SEQ ID NO: 283); the L-CDR1 may comprise the sequence QSISSY (SEQ ID NO: 279); the L-CDR2 may comprise the sequence AASGLES (SEQ ID NO: 284); and, the L-CDR3 may comprise the sequence QQTYGVPLT (SEQ ID NO: 285). In preferred embodiments, the H-CDR3 is VSSGHWDYD (SEQ ID NO: 287). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309.

The table below provides CDR sequences of useful variants.

TABLE 1

| CDR sequences of exemplary antibody | | | | | |
|---|---|---|---|---|---|
| H-CDR1 | H-CDR2 | H-CDR3 | L-CDR1 | L-CDR2 | L-CDR3 |
| GFTFADYA (SEQ ID NO: 276) | ISGSGAAT (SEQ ID NO: 282) | VSSG$X_1$WD$X_2$D $X_1$ = H or Q $X_2$ = Y or F (SEQ ID NO: 283) | QSISSY (SEQ ID NO: 279) | AASGLES (SEQ ID NO: 284) | QQTYGVPLT (SEQ ID NO: 285) |

Novel, Highly Potent TGFβ1-Selective Inhibitors

The present disclosure provides novel monoclonal antibodies and antigen-binding fragments thereof capable of binding each of the four known human LLCs (hLTBP1-proTGFβ1, hLTBP3-proTGFβ1, hGARP-proTGFβ1 and hLRRC33-proTGFβ1) with high affinity (e.g., below 1 nM $K_D$) and with slow dissociation rates (i.e., low $k_{OFF}$ values), as measured for example by surface plasmon resonance (SPR). The novel antibodies and the fragments are isoform-selective inhibitors of TGFβ1. Such antibody or the antigen-binding fragment thereof comprises an H-CDR1, an H-CDR2, and H-CDR3, an L-CDR1, an L-CDR2 and an L-CFR3, wherein: the H-CDR1 comprises GFTFADYA (SEQ ID NO: 276); the H-CDR2 comprises a sequence represented by the formula ISGSG$X_1$AT, wherein optionally the $X_1$ is an A or K (SEQ ID NO: 277); the H-CDR3 comprises a sequence represented by the formula VSSG$X_1$WD$X_2$D, wherein optionally the $X_1$ is an H, D or Q, and wherein further optionally the $X_2$ is an F or Y (SEQ ID NO: 278); the L-CDR1 comprises QSISSY (SEQ ID NO: 279); the L-CDR2 comprises a sequence represented by the formula AAS$X_1X_2X_3X_4$ wherein optionally the $X_1$ is an N, G or V; wherein further optionally the $X_2$ is an L, N or E;

Optionally, one or more of the six CDRs may include one or more (e.g., 1 or 2) amino acid change.

In some embodiments, an antibody or an antigen-binding fragment thereof selected for use or manufacture according to the present disclosure comprises an H-CDR1, an H-CDR2, and H-CDR3, an L-CDR1, an L-CDR2 and an L-CFR3, wherein: the H-CDR1 comprises GFTFADYA (SEQ ID NO: 276); the H-CDR2 comprises a sequence represented by the formula ISGSG$X_1$AT, wherein optionally the $X_1$ is an A or K (SEQ ID NO: 277); the H-CDR3 comprises a sequence represented by the formula VSSG$X_1$WD$X_2$D, wherein optionally the $X_1$ is an H, D or Q, and wherein further optionally the $X_2$ is an F or Y (SEQ ID NO: 278); the L-CDR1 comprises QSISSY (SEQ ID NO: 279); the L-CDR2 comprises a sequence represented by the formula AAS$X_1X_2X_3X_4$ wherein optionally the $X_1$ is an N, G or V; wherein further optionally the $X_2$ is an L, N or E; wherein further optionally the $X_3$ is a Q or E; and wherein further optionally the $X_4$ is an S or T (SEQ ID NO: 280); and, the L-CDR3 comprises a sequence represented by the formula QQTY$X_1$VPLT, wherein optionally the $X_1$ is a T or G (SEQ ID NO: 281). In preferred embodiments, the H-CDR2 comprises ISGSGAAT (SEQ ID NO: 282); the H-CDR3 comprises VSSGHWDYD (SEQ ID NO: 287); the L-CDR2 comprises AASGLES (SEQ ID NO: 284); and, the L-CDR3 comprises QQTYGVPLT (SEQ ID NO: 285). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309.

The table below further provides CDR sequences of useful variants.

TABLE 2

| CDR variants | | | | | |
|---|---|---|---|---|---|
| H-CDR1 | H-CDR2 | H-CDR3 | L-CDR1 | L-CDR2 | L-CDR3 |
| GFTFADYA (SEQ ID NO: 276) | ISGSGX$_1$AT wherein optionally the $X_1$ is A or K (SEQ ID NO: 277) | VSSGX$_1$WDX$_2$D wherein optionally $X_1$ is H, D or Q; and wherein further optionally $X_2$ is F or Y (SEQ ID NO: 278) | QSISSY (SEQ ID NO: 279) | AASX$_1$X$_2$X$_3$X$_4$ wherein optionally $X_1$ is N, G or V; wherein further optionally $X_2$ is L, N or E; wherein further optionally $X_3$ is Q or E; and wherein further optionally $X_4$ is S or T (SEQ ID NO: 280) | QQTYX$_1$VPLT wherein optionally $X_1$ is T or G (SEQ ID NO: 281) |

In some embodiments, one or more of the six CDRs may include one or more (e.g., 1 or 2) amino acid change.

Non-limiting examples of preferred activation inhibitors of TGFβ1 are provided in the table below, herein referred to as: Ab37, Ab38, Ab39, Ab40, Ab41, Ab42, Ab43, Ab44, Ab45, Ab46, Ab47, Ab48, Ab49, Ab50, Ab51 and Ab52. Each of these antibodies may be in the form of whole immunoglobulin (such as IgG) or an antigen-binding fragment thereof, such as the Fab fragment. The antigen-binding fragment may be used to make an engineered construct that comprises the fragment or a derivative thereof, such as bispecific antibodies and other fusion proteins that functions as a TGFβ1 inhibitor. The six CDRs of each of the exemplary antibodies are listed in the table below.

TABLE 3

| Exemplary CDR sequences | | | | | | | | | | | | |
|---|---|---|---|---|---|---|---|---|---|---|---|---|
| | H-CDR1 | SEQ ID NO: | H-CDR2 | SEQ ID NO: | H-CDR3 | SEQ ID NO: | L-CDR1 | SEQ ID NO: | L-CDR2 | SEQ ID NO: | L-CDR3 | SEQ ID NO: |
| Ab37 | GFTFADYA | 276 | ISGSGAAT | 282 | VSGHWDFD | 289 | QSISSY | 279 | AASNLES | 292 | QQTYTVPLT | 296 |
| Ab38 | GFTFADYA | 276 | ISGSGAAT | 282 | VSGHWDFD | 289 | QSISSY | 279 | AASGLES | 284 | QQTYTVPLT | 296 |
| Ab39 | GFTFADYA | 276 | ISGSGAAT | 282 | VSGHWDFD | 289 | QSISSY | 279 | AASVNES | 293 | QQTYTVPLT | 296 |
| Ab40 | GFTFADYA | 276 | ISGSGAAT | 282 | VSGHWDFD | 289 | QSISSY | 279 | AASNEET | 294 | QQTYTVPLT | 296 |
| Ab41 | GFTFADYA | 276 | ISGSGAAT | 282 | VSGHWDFD | 289 | QSISSY | 279 | AASNLES | 292 | QQTYGVPLT | 285 |
| Ab42 | **GFTFADYA** | 276 | **ISGSGAAT** | 282 | **VSGHWDFD** | 289 | **QSISSY** | 279 | **AASGLES** | 284 | **QQTYGVPLT** | 285 |
| Ab43 | GFTFADYA | 276 | ISGSGAAT | 282 | VSGHWDYD | 287 | QSISSY | 279 | AASNLES | 292 | QQTYTVPLT | 296 |
| Ab44 | GFTFADYA | 276 | ISGSGAAT | 282 | VSGHWDYD | 287 | QSISSY | 279 | AASGLES | 284 | QQTYTVPLT | 296 |
| Ab45 | GFTFADYA | 276 | ISGSGAAT | 282 | VSGHWDYD | 287 | QSISSY | 279 | AASNLES | 292 | QQTYGVPLT | 285 |
| Ab46 | **GFTFADYA** | 276 | **ISGSGAAT** | 282 | **VSGHWDYD** | 287 | **QSISSY** | 279 | **AASGLES** | 284 | **QQTYGVPLT** | 285 |
| Ab47 | GFTFADYA | 276 | ISGSGAAT | 282 | VSGDWDYD | 290 | QSISSY | 279 | AASNLES | 292 | QQTYGVPLT | 285 |
| Ab48 | GFTFADYA | 276 | ISGSGAAT | 282 | VSGDWDYD | 290 | QSISSY | 279 | AASGLES | 284 | QQTYGVPLT | 285 |

TABLE 3-continued

| Exemplary CDR sequences | | | | | | | | | | | | | |
|---|---|---|---|---|---|---|---|---|---|---|---|---|---|
| | H-CDR1 | SEQ ID NO: | H-CDR2 | SEQ ID NO: | H-CDR3 | SEQ ID NO: | L-CDR1 | SEQ ID NO: | L-CDR2 | SEQ ID NO: | L-CDR3 | SEQ ID NO: |
| Ab49 | GFTFADYA | 276 | ISGSGAAT | 282 | VSGQWDYD | 291 | QSISSY | 279 | AASNLES | 292 | QQTYGVPLT | 285 |
| Ab50 | **GFTFADYA** | 276 | **ISGSGAAT** | 282 | **VSGQWDYD** | 291 | **QSISSY** | 279 | **AASGLES** | 284 | QQTYGVPLT | 285 |
| Ab51 | GFTFADYA | 276 | ISGSGKAT | 288 | VSGDWDYD | 290 | QSISSY | 279 | AASNLQS | 295 | QQTYTVPLT | 296 |
| Ab52 | GFTFADYA | 276 | ISGSGKAT | 288 | VSGDWDYD | 290 | QSISSY | 279 | AASGLES | 284 | QQTYGVPLT | 285 |

In some embodiments, the antibody or an antigen-binding fragment thereof comprises a heavy chain variable domain (VH) and a light chain variable domain (VL), wherein, the VH comprises an amino acid sequence having at least 90% (e.g., 90%, 91%, 92%, 93%, 94%, 95%, 96%, 97%, 98%, 99% and 100%) sequence identity to: EVQLLESGG-GLVQPGGSLRLSCAASGFTFADYAMTWVRQAPGK-GLEWVSAISGSGAATYFADSVK GRFTISRDNSKNT-LYLQMNSLRAEDTAVYYCARVSSGHWDYDYWGQ-GTLVTVSS (SEQ ID NO: 297) and wherein the VL comprises an amino acid sequence having at least 90% (e.g., 90%, 91%, 92%, 93%, 94%, 95%, 96%, 97%, 98%, 99% and 100%) sequence identity to: DIQLTQSPSSL-SASVGDRVTITCRASQSISSYLNWYQQKPGKAPKLLI-YAASGLESGVPSRFSGSGSG TDFTLTISSLOPEDFA-TYYCQQTYGVPLTFGGGTKVEIK (SEQ ID NO: 298). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309.

In some embodiments, the antibody or the antigen-binding fragment comprises a heavy chain variable domain (VH) and a light chain variable domain (VL), wherein, the VH comprises EVQLLESGGGLVQPGGSLRLSCAASGF-TFADYAMTWVRQAPGKGLEWVSAISGSGAATY-FADSVK GRFTISRDNSKNTLYLQMNSLRAEDTAVYY-CARVSSGHWDYDYWGQGTLVTVSS (SEQ ID NO: 297) and wherein the VL comprises DIQLTQSPSSL-SASVGDRVTITCRASQSISSYLNWYQQKPGKAPKLLI-YAASGLESGVPSRFSGSGSG TDFTLTISSLQPEDFA-TYYCQQTYGVPLTFGGGTKVEIK (SEQ ID NO: 298).

In some embodiments, the antibody or the antigen-binding fragment comprises a heavy chain variable domain (VH) and a light chain variable domain (VL), wherein, the VH comprises EVQLLESGGGLVQPGGSLRLSCAASGFT-FADYAMTWVRQAPGKGLEWVSAISGSGAATY-FADSVK GRFTISRDNSKNTLYLQMNSLRAEDTAVYY-CARVSSGHWDFDYWGQGTLVTVSS (SEQ ID NO: 299) and wherein the VL comprises DIQLTQSPSSL-SASVGDRVTITCRASQSISSYLNWYQQKPGKAPKLLI-YAASNLQSGVPSRFSGSGSG TDFTLTISS LQPEDFA-TYYCQQTYTVPLTFGGGTKVEIK (SEQ ID NO: 300).

The invention includes nucleic acid sequences that encode any one of the amino acid sequences provided above. Encompassed herein are vectors (e.g., DNA plasmids, such as mammalian expression vectors, and related nucleic acid preparations) comprising the nucleic acid sequence; cells transfected with the vector(s); a cell line with stable expression of the nucleic acids; a cell culture comprising the cell, wherein optionally the cell culture comprises mammalian cells capable of large-scale production of the antibody or a protein construct comprising an antigen-binding fragment of the antibody.

In some embodiments, the monoclonal antibody or an antigen-binding fragment thereof, which selectively inhibits TGFβ1 activation, comprises a heavy chain complementary determining region 1 (CDRH1) having an amino acid sequence at least 95% identical to the sequence set forth in GFTFADYA (SEQ ID NO: 276); a heavy chain complementary determining region 2 (CDRH2) having an amino acid sequence at least 95% identical to the sequence set forth in ISGSGAAT (SEQ ID NO: 282); a heavy chain complementary determining region 3 (CDRH3) having an amino acid sequence at least 95% identical to the sequence set forth in VSSGHWDYD (SEQ ID NO: 287); a light chain complementary determining region 1 (CDRL1) having an amino acid sequence at least 95% identical to the sequence set forth in QSISSY (SEQ ID NO: 279); a light chain complementary determining region 2 (CDRL2) having an amino acid sequence at least 95% identical to the sequence set forth in AASGLES (SEQ ID NO: 284); and, a light chain complementary determining region 3 (CDRL3) having an amino acid sequence at least 95% identical to the sequence set forth in QQTYGVPLT (SEQ ID NO: 285).

In some embodiments, the monoclonal antibody or an antigen-binding fragment thereof, which selectively inhibits TGFβ1 activation, comprises a heavy chain complementary determining region 1 (CDRH1) having an amino acid sequence at least 96% identical to the sequence set forth in GFTFADYA (SEQ ID NO: 276); a heavy chain complementary determining region 2 (CDRH2) having an amino acid sequence at least 96% identical to the sequence set forth in ISGSGAAT (SEQ ID NO: 282); a heavy chain complementary determining region 3 (CDRH3) having an amino acid sequence at least 96% identical to the sequence set forth in VSSGHWDYD (SEQ ID NO: 287); a light chain complementary determining region 1 (CDRL1) having an amino acid sequence at least 96% identical to the sequence set forth in QSISSY (SEQ ID NO: 279); a light chain complementary determining region 2 (CDRL2) having an amino acid sequence at least 96% identical to the sequence set forth in AASGLES (SEQ ID NO: 284); and, a light chain complementary determining region 3 (CDRL3) having an amino acid sequence at least 96% identical to the sequence set forth in QQTYGVPLT (SEQ ID NO: 285).

In some embodiments, the monoclonal antibody or an antigen-binding fragment thereof, which selectively inhibits TGFβ1 activation, comprises a heavy chain complementary determining region 1 (CDRH1) having an amino acid sequence at least 98% identical to the sequence set forth in GFTFADYA (SEQ ID NO: 276); a heavy chain complementary determining region 2 (CDRH2) having an amino acid sequence at least 98% identical to the sequence set forth in ISGSGAAT (SEQ ID NO: 282); a heavy chain complementary determining region 3 (CDRH3) having an amino acid sequence at least 98% identical to the sequence set forth in VSSGHWDYD (SEQ ID NO: 287); a light chain complementary determining region 1 (CDRL1) having an amino acid sequence at least 98% identical to the sequence set forth in QSISSY (SEQ ID NO: 279); a light chain complementary determining region 2 (CDRL2) having an amino acid sequence at least 98% identical to the sequence set forth in AASGLES (SEQ ID NO: 284); and, a light chain complementary determining region 3 (CDRL3) having an amino acid sequence at least 98% identical to the sequence set forth in QQTYGVPLT (SEQ ID NO: 285).

In some embodiments, the monoclonal antibody or an antigen-binding fragment thereof, which selectively inhibits TGFβ1 activation, comprises a heavy chain complementary determining region 1 (CDRH1) having an amino acid sequence at least 99% identical to the sequence set forth in GFTFADYA (SEQ ID NO: 276); a heavy chain complementary determining region 2 (CDRH2) having an amino acid sequence at least 99% identical to the sequence set forth in ISGSGAAT (SEQ ID NO: 282); a heavy chain complementary determining region 3 (CDRH3) having an amino acid sequence at least 99% identical to the sequence set forth in VSSGHWDYD (SEQ ID NO: 287); a light chain complementary determining region 1 (CDRL1) having an amino acid sequence at least 99% identical to the sequence set forth in QSISSY (SEQ ID NO: 279); a light chain complementary determining region 2 (CDRL2) having an amino acid sequence at least 99% identical to the sequence set forth in AASGLES (SEQ ID NO: 284); and, a light chain complementary determining region 3 (CDRL3) having an amino acid sequence at least 99% identical to the sequence set forth in QQTYGVPLT (SEQ ID NO: 285).

In some embodiments, the monoclonal antibody or an antigen-binding fragment thereof, which selectively inhibits TGFβ1 activation, comprises a heavy chain complementary determining region 1 (CDRH1) having an amino acid sequence set forth in GFTFADYA (SEQ ID NO: 276); a heavy chain complementary determining region 2 (CDRH2) having an amino acid sequence set forth in ISGSGAAT (SEQ ID NO: 282); a heavy chain complementary determining region 3 (CDRH3) having an amino acid sequence set forth in VSSGHWDYD (SEQ ID NO: 287); a light chain complementary determining region 1 (CDRL1) having an amino acid sequence set forth in QSISSY (SEQ ID NO: 279); a light chain complementary determining region 2 (CDRL2) having an amino acid sequence set forth in AASGLES (SEQ ID NO: 284); and, a light chain complementary determining region 3 (CDRL3) having an amino acid sequence set forth in QQTYGVPLT (SEQ ID NO: 285). In one embodiment, the antibody or antigen-binding fragment thereof, comprises a a heavy chain variable domain (VH) comprising a sequence having at least 95% identity, 96% identity, 97% identity, 98% identity, 99% identity to, comprises, or consists of SEQ ID NO:297; and a light chain variable domain (VL) comprising a sequence having at least 95% identity, 96% identity, 97% identity, 98% identity, 99% identity to, comprises, or consists of SEQ ID NO:298.

Binding Kinetics of Novel Antibodies

The novel antibodies and antigen-binding fragments thereof (e.g., Fabs) disclosed herein are characterized by enhanced binding properties. The antibodies and the fragments are capable of specifically binding to each of the presenting molecule-proTGFβ1 complexes (sometimes referred to as "Large Latency Complex" or LLC, which is a ternary complex comprised of a proTGFβ1 dimer coupled to a single presenting molecule), namely, LTBP1-proTGFβ1, LTBP3-proTGFβ1, GARP-proTGFβ1 and LRRC33-proTGFβ1. Recombinantly produced, purified protein complexes may be used as antigens (e.g., antigen complexes) to screen, evaluate or confirm the ability of an antibody to bind the antigen complexes in suitable in vitro binding assays. Such assays are well known in the art and include but are not limited to: Bio-Layer Interferometry (BLI)-based assays (such as OCTET®) and surface plasmon resonance (SPR)-based assays (such as BIACORE®).

Previously, antibodies and fragments that exhibited high affinities (e.g., sub-nanomolar $K_D$) to the LLCs were identified. Here, advantageously, antibodies and fragments with particularly slow dissociation rates were specifically selected, aimed to achieve particularly durable inhibitory effects.

Figure 2:
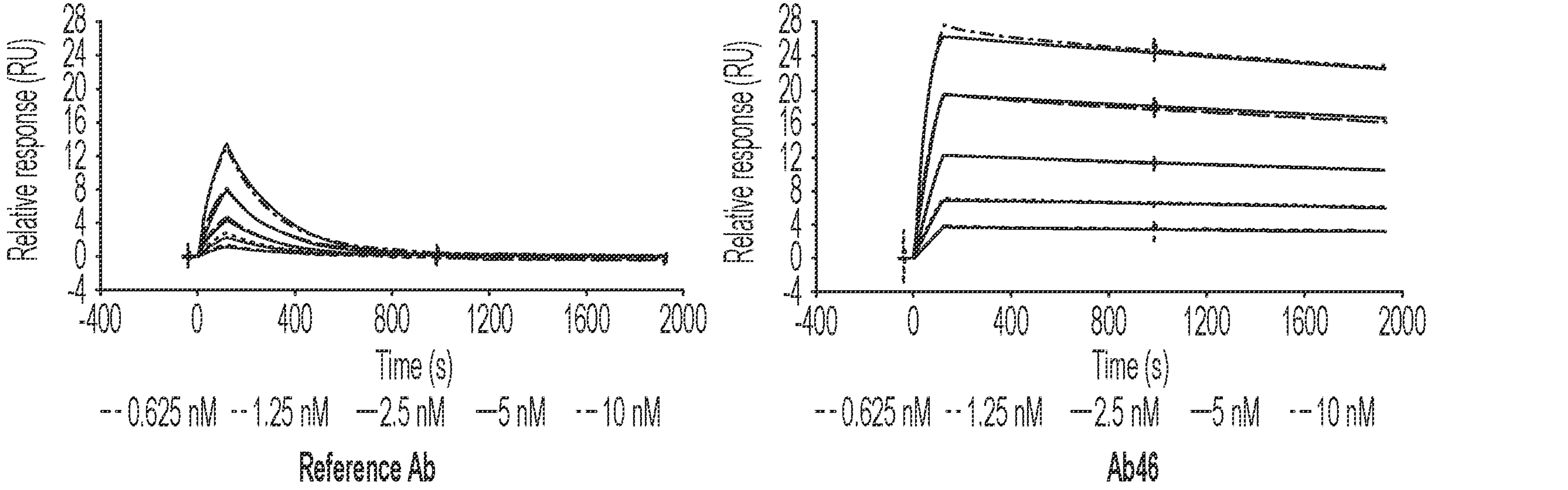
FIG. 2 shows representative Biacore binding curves showing association and dissociation of Ab46 and reference antibody. Summary of binding kinetics is provided.

Accordingly, selection of suitable TGFβ inhibitors for carrying out the methods and therapeutic use in accordance with the present disclosure may include carrying out in vitro binding assays to measure binding kinetics. In preferred embodiments, the antibody or the antigen-binding fragment binds each of the following large latent complexes with a sub-nanomolar affinity, e.g., with $K_D$ of 1.0 nM or less, and with $k_{OFF}$ of 10E-4 (1/s) or lower: hLTBP1-proTc, hLTBP3-proTGFβ1, hGARP-proTGFβ1 and hLRRC33-proTGFβ1. Preferably, the antibody or the fragment further binds each of the murine LLC counterparts, namely, mLTBP1-proTGFβ1, mLTBP3-proTGFβ1, mGARP-proTGFβ1 and mLRRC33-proTGFβ1, with equivalent affinities as human LLCs. In vitro binding kinetics may be readily determined by measuring interactions of test antibodies (such as antigen-binding fragments) and suitable antigen, such as large latent complexes (LLCs) and small latent complexes (SLCs). Suitable methods for in vitro binding assays to determine the parameters of binding kinetics include BLI-based assays such as OCTET®, and surface plasmon resonance-based assays, such as BIACORE® systems. An example of an Octet-based in vitro binding assays is provided in FIG. 1. An example of SPR-based in vitro binding assays is provided in FIG. 2. Fab fragments of Ab46 and a reference antibody, which are both activation inhibitors of TGFβ1, were used in this experiment. As illustrated in FIG. 2, the two Fabs have similar "ON" rates ($k_{ON}$) indicating that they engage (i.e., associate) with antigen at similar rates. However, their "OFF" rates ($k_{OFF}$) are markedly different, in that $t_{1/2}$ of Ab46 is over 130 minutes, whereas the reference antibody has a $t_{1/2}$ value of only 2.4 minutes, showing that even though the binding/association phase of the interaction occurs at similar kinetics, Ab46 is able to remain bound to the antigen for a much longer duration of time (e.g., greater $t_{1/2}$) than the reference antibody, which "falls off" (e.g., dissociates from) the antigen relatively quickly. Thus, the difference in the dissociation kinetics predominantly attributes to the notable difference in their overall affinities ($K_D$), which may result in enhanced potency (see below). Therefore, characterization of binding kinetics provides useful information as to potential durability of effects and resulting in vivo potency.

Accordingly, the invention includes a method of selecting a TGFβ activation inhibitor for therapeutic use, wherein the method comprises selection of an antibody or antigen-binding fragment thereof that has a dissociation rate of 10.0e-4 ($s^{-1}$) or less as measured by SPR. In some embodiments, the antibody or the fragment binds antigen with an affinity of less than 1 nM (i.e., sub-nanomolar), e.g., less than 500 pM, 400 pM, 300 pM, 200 pM, 100 pM, or 50 pM.

The table below exemplifies binding kinetics of the listed antibodies (e.g., Fabs) obtained by OCTET®-based binding assays. The experiments were conducted with immobilized, biotinylated antigen and Fab fragments (e.g., test antibodies) in solution.

TABLE 4

Octet binding kinetics of exemplary antibodies

| | hLTBP1-proTGFβ1 | | hLTBP3-proTGFβ1 | | hGARP-proTGFβ1 | |
|---|---|---|---|---|---|---|
| Ab | $K_{ON}$ ($M^{-1}/s^{-1}$) | $K_{OFF}$ ($s^{-1}$) | $K_{ON}$ ($M^{-1}/s^{-1}$) | $K_{OFF}$ ($s^{-1}$) | $K_{ON}$ ($M^{-1}/s^{-1}$) | $K_{OFF}$ ($s^{-1}$) |
| Ref | 7.14E+05 | 3.47E−03 | 8.09E+05 | 4.63E−03 | 7.14E+06 | 2.24E−03 |
| Ab37 | 7.04E+05 | 2.21E−04 | 6.77E+05 | 8.81E−04 | 7.04E+05 | 3.11E−04 |
| Ab38 | 7.45E+05 | 1.00E−05 | 6.74E+05 | 5.55E−04 | 7.45E+06 | 2.72E−04 |
| Ab39 | 6.30E+05 | 2.86E−04 | 1.16E+06 | 1.89E−03 | 6.30E+05 | 9.61E−04 |
| Ab40 | 6.80E+05 | 5.26E−04 | 7.01E+05 | 9.64E−04 | 6.80E+06 | 7.63E−04 |
| Ab41 | 5.23E+05 | 1.79E−04 | 5.39E+05 | 4.35E−04 | 5.23E+05 | 3.48E−04 |
| Ab42 | 7.00E+05 | 2.21E−05 | 6.20E+05 | 2.96E−04 | 7.00E+05 | 3.01E−04 |
| Ab43 | 7.38E+05 | 4.57E−04 | 6.54E+05 | 6.36E−04 | 7.38E+06 | 4.92E−04 |
| Ab44 | 6.78E+05 | 3.39E−04 | 7.04E+05 | 6.66E−04 | 6.78E+05 | 6.82E−04 |
| Ab45 | 5.24E+05 | 2.26E−04 | 5.54E+05 | 5.21E−04 | 5.24E+05 | 2.44E−04 |
| Ab46 | 7.03E+05 | 4.98E−05 | 6.19E+05 | 4.38E−04 | 7.03E+05 | 2.90E−04 |
| Ab47 | 6.55E+05 | 1.13E−04 | 5.17E+05 | 5.78E−04 | 6.55E+05 | 8.63E−04 |
| Ab48 | 4.37E+05 | 1.00E−05 | 6.71E+05 | 5.20E−05 | 4.37E+05 | 3.23E−04 |
| Ab49 | 6.30E+05 | 2.00E−04 | 5.81E+05 | 8.13E−04 | 6.30E+05 | 6.43E−04 |
| Ab50 | 6.70E+05 | 5.55E−05 | 4.61E+05 | 4.48E−04 | 6.70E+05 | 3.21E−04 |
| Ab51 | 8.13E+05 | 1.92E−03 | 6.50E+05 | 2.50E−03 | 8.13E+06 | 1.37E−03 |
| Ab52 | 6.65E+05 | 2.69E−04 | 5.70E+05 | 5.57E−04 | 6.65E+05 | 5.42E−04 |

Among these antibodies, Ab42, Ab46 and Ab50 were selected for further evaluation. Surface plasmon resonance (SPR) was used to measure binding kinetics using a BIACORE® system. Association and dissociation kinetics of Fab fragments of Ab42, Ab46, Ab50 and a reference antibody (shown as "Ref"), to antigen complexes were measured, and resulting equilibrium dissociation constants ($K_D$) are provided below. Experiments were carried out with eight types of LLCs, namely, hLTBP1-proTGFβ1, mLTBP1-proTGFβ1, hLTBP3-proTGFβ1, mLTBP3-proTGFβ1, hGARP-proTGFβ1, mGARP-proTGFβ1, hLRRC33-proTGFβ1 and mLRRC33-proTGFβ1.

TABLE 5 hLTBP1-proTGFβ1

| Ab (Fab) | $K_{ON}$ ($M^{-1}/s^{-1}$) | $K_{OFF}$ ($s^{-1}$) | $K_D$ (M) | Fold difference |
|---|---|---|---|---|
| Ref | 7.18E+05 | 4.83E−03 | 6.73E−9 | |
| Ab42 | 1.54E+06 | 9.34E−05 | 6.06E−11 | 111 |
| Ab46 | 1.75E+06 | 8.81E−05 | 5.02E−11 | 134 |
| Ab50 | 1.55E+06 | 1.40E−04 | 9.03E−11 | 75 |

TABLE 6 mLTBP1-proTGFβ1

| Ab (Fab) | $K_{ON}$ ($M^{-1}/s^{-1}$) | $K_{OFF}$($s^{-1}$) | $K_D$ (M) | Fold difference |
|---|---|---|---|---|
| Ref | 8.53E+05 | 5.61E−03 | 6.58E−9 | |
| Ab42 | 1.66E+06 | 1.01E−04 | 6.05E−11 | 109 |
| Ab46 | 1.85E+06 | 9.87E−05 | 5.34E−11 | 123 |
| Ab50 | 1.70E+06 | 1.77E−04 | 1.05E−10 | 63 |

TABLE 7 hLTBP3-proTGFβ1

| Ab (Fab) | $K_{ON}$ ($M^{-1}/s^{-1}$) | $K_{OFF}$($s^{-1}$) | $K_D$ (M) | Fold difference |
|---|---|---|---|---|
| Ref | 1.35E+06 | 1.24E−02 | 9.20E−9 | |
| Ab42 | 8.44E+05 | 1.21E−04 | 1.44E−10 | 64 |
| Ab46 | 1.00E+06 | 1.28E−04 | 1.27E−10 | 72 |
| Ab50 | 9.05E+05 | 1.74E−04 | 1.93E−10 | 48 |

TABLE 8 mLTBP3-proTGFβ1

| Ab (Fab) | $K_{ON}$ ($M^{-1}/s^{-1}$) | $K_{OFF}$($s^{-1}$) | $K_D$ (M) | Fold difference |
|---|---|---|---|---|
| Ref | 4.66E+05 | 4.08E−03 | 8.74E−9 | |
| Ab42 | 1.20E+06 | 1.17E−04 | 9.71E−11 | 90 |
| Ab46 | 1.20E+06 | 1.15E−04 | 9.56E−11 | 91 |
| Ab50 | 1.08E+06 | 1.73E−04 | 1.61E−10 | 54 |

TABLE 9 hGARP-proTGFβ1

| Ab (Fab) | $K_{ON}$ ($M^{-1}/s^{-1}$) | $K_{OFF}$($s^{-1}$) | $K_D$ (M) | Fold difference |
|---|---|---|---|---|
| Ref | 3.07E+05 | 3.77E−03 | 1.23E−8 | |
| Ab42 | 8.46E+05 | 2.47E−04 | 2.91E−10 | 42 |
| Ab46 | 9.65E+05 | 2.22E−04 | 2.30E−10 | 53 |
| Ab50 | 8.76E+05 | 3.08E−04 | 3.51E−10 | 35 |

TABLE 10

| mGARP-proTGFβ1 | | | | |
|---|---|---|---|---|
| Ab (Fab) | $K_{ON}$ ($M^{-1}/s^{-1}$) | $K_{OFF}$($s^{-1}$) | $K_D$ (M) | Fold difference |
| Ref | 2.76E+05 | 5.24E−03 | 1.90E−8 | |
| Ab42 | 9.46E+05 | 3.46E−04 | 3.65E−10 | 52 |
| Ab46 | 1.02E+06 | 2.78E−04 | 2.74E−10 | 69 |
| Ab50 | 9.15E+05 | 4.21E−04 | 4.60E−10 | 41 |

TABLE 11

| hLRRC33-proTGFβ1 | | | | |
|---|---|---|---|---|
| Ab (Fab) | $K_{ON}$ ($M^{-1}/s^{-1}$) | $K_{OFF}$($s^{-1}$) | $K_D$ (M) | Fold difference |
| Ref | 4.72E+05 | 4.70E−03 | 9.95E−9 | |
| Ab42 | 10.00E+05 | 1.23E−04 | 1.23E−10 | 81 |
| Ab46 | 1.52E+06 | 1.28E−04 | 8.41E−11 | 118 |
| Ab50 | 9.47E+05 | 1.80E−04 | 1.90E−10 | 52 |

TABLE 12

| mLRRC33-proTGFβ1 | | | | |
|---|---|---|---|---|
| Ab (Fab) | $K_{ON}$ ($M^{-1}/s^{-1}$) | $K_{OFF}$($s^{-1}$) | $K_D$ (M) | Fold difference |
| Ref | 5.77E+05 | 4.89E−03 | 8.48E−9 | |
| Ab42 | 1.08E+06 | 1.23E−04 | 1.14E−10 | 74 |
| Ab46 | 1.26E+06 | 1.12E−04 | 8.92E−11 | 95 |
| Ab50 | 1.07E+06 | 1.87E−04 | 1.76E−10 | 48 |

Potency; Inhibitory Activity

Antibodies disclosed herein may be broadly characterized as "functional antibodies" for their ability to inhibit TGFβ1 signaling. As used herein, "a functional antibody" confers one or more biological activities by virtue of its ability to bind an antigen (e.g., antigen complexes). Functional antibodies therefore broadly include those capable of modulating the activity/function of target molecules (i.e., antigen). Such modulating antibodies include inhibiting antibodies (or inhibitory antibodies) and activating antibodies. The present disclosure is drawn to antibodies which can inhibit a biological process mediated by TGFβ1 signaling associated with multiple contexts of TGFβ1. Inhibitory agents used to carry out the present invention, such as the antibodies described herein, are intended to be TGFβ1-selective and not to target or interfere with TGFβ2 and TGFβ3 when administered at a therapeutically effective dose (dose at which sufficient efficacy is achieved within acceptable toxicity levels). The novel antibodies of the present disclosure have enhanced inhibitory activities (potency) as compared to previously identified activation inhibitors of TGFβ1.

Pharmacodynamics (PD) effects may be measured to determine relative potencies of inhibitory antibodies. Commonly used PD measures for the TGFβ signaling pathway include, without limitation, phosphorylation of SMAD2/3 and expression of downstream effector genes, the transcription of which is sensitive to TGFβ activation, such as those with a TGFβ-responsive promoter element (e.g., SMAD-binding elements). In some embodiments, the antibodies of the present disclosure are capable of completely blocking disease-induced SMAD2/3 phosphorylation in preclinical fibrosis models when the animals are administered at a dose of 3 mg/kg or less. In some embodiments, the antibodies of the present disclosure are capable of reducing and/or completely blocking disease-induced SMAD2/3 phosphorylation. In some embodiments, the antibodies of the present disclosure are capable of reducing and/or completely blocking disease-induced SMAD2 phosphorylation (e.g., regardless of any change in SMAD3). In some embodiments, reduction is measured as a ratio of phosphorylated SMAD2/3 over total SMAD2/3. In some embodiments, reduction is measured as a ratio of phosphorylated SMAD2 over total SMAD2. In some embodiments, the antibodies of the present disclosure are capable of reducing nuclear localization of phosphorylated SMAD2, as measured, for example, by IHC. Without being bound by theory, in some embodiments, measuring SMAD2 phosphorylation (without measuring SMAD3) may improve the accurate detection of a treatment-related effect. Denis et al., *Development* 143: 3481-90 (2016); Liu et al., *J. Biol. Chem.* 278:11721-8 (2003); David et al., *Oncoimmunology* 6: e1349589 (2017). In some embodiments, the antibodies of the present disclosure are capable of significantly suppressing fibrosis-induced expression of a panel of marker genes including Acta2, Col1a1, Col3a1, Fn1, Itga11, Lox, Loxl2, when the animals are administered at a dose of 10 mg/kg or less in the UUO model of kidney fibrosis.

In some embodiments, potency of an inhibitory antibody may be measured in suitable cell-based assays, such as CAGA reporter assays described herein. Generally, cultured cells, such as heterologous cells and primary cells, may be used for carrying out cell-based potency assays. Cells that express endogenous TGFβ1 and/or a presenting molecule of interest, such as LTBP1, LTBP3, GARP and LRRC33, may be used. Alternatively, exogenous nucleic acids encoding protein(s) of interest, such as TGFβ1 and/or a presenting molecule of interest, such as LTBP1, LTBP3, GARP and LRRC33, may be introduced into such cells, for example by transfection (e.g., stable transfection or transient transfection) or by viral vector-based infection. In some embodiments, LN229 cells are employed for such assays. The cells expressing TGFβ1 and a presenting molecule of interest (e.g., LTBP1, LTBP3, GARP or LRRC33) are grown in culture, which "present" the large latent complex either on cell surface (when associated with GARP or LRRC33) or deposit into the ECM (when associated with an LTBP). Activation of TGFβ1 may be triggered by integrin, expressed on another cell surface. The integrin-expressing cells may be the same cells co-expressing the large latent complex or a separate cell type. Reporter cells are added to the assay system, which incorporates a TGFβ-responsive element. In this way, the degree of TGFβ activation may be measured by detecting the signal from the reporter cells (e.g., TGFβ-responsive reporter genes, such as luciferase coupled to a TGFβ-responsive promoter element) upon TGFβ activation. Using such cell-based assay systems, inhibitory activities of the antibodies can be determined by measuring the change (reduction) or difference in the reporter signal (e.g., luciferase activities as measured by fluorescence readouts) either in the presence or absence of test antibodies.

Results from cell-based potency studies are exemplified below. In these studies, human LM229 cells were employed to measure the potency of test antibodies in their ability to inhibit TGFβ signaling. These cells express endogenous LTBP-proTGFβ1. Assays were carried out using i) monoclonal antibodies (hIgG4 immunoglobulin), and ii) Fab fragments of the same panel of test antibodies, as shown.

TABLE 13

In vitro potency of full-length IgG and Fab fragments of novel activation inhibitors

| Ab | mAb IC50 (nM) | fAb IC50 (nM) |
|---|---|---|
| Reference Ab | 1.201 | 4.967 |
| Ab37 | 7.825 | 1.006 |
| Ab38 | 8.46 | 0.5946 |
| Ab39 | 1.289 | 3.449 |
| Ab40 | 0.6699 | 0.7588 |
| Ab41 | 1.314; 1.007 | 2.018 |
| Ab42 | 1.169 | 1.113 |
| Ab43 | 1.267 | 0.9992 |
| Ab44 | 1.483 | 2.633 |
| Ab45 | 0.6719 | 0.5937 |
| Ab46 | 0.9501 | 0.7226 |
| Ab47 | 0.8328 | 0.5517 |
| Ab48 | 0.8912 | 0.7448 |
| Ab49 | 1.028 | 3.374 |
| Ab50 | 1.063 | 0.8716 |
| Ab51 | 1.252 | 2.051 |
| Ab52 | 0.4739 | 0.9549 |

While the reference antibody used as a benchmark ("Reference Ab") was shown to have similar association kinetics as many of the novel antibodies examined, the overall potency was markedly improved in the novel antibodies presumably by having much slower dissociation rates, as compared to the reference antibody.

In some embodiments, the inhibitory potency (e.g., $IC_{50}$) of the novel antibodies of the present disclosure calculated based on cell-based assays (such as LN229 cell assays described elsewhere herein) may be less than 10 nM measured against each of the hLTBP1-proTGFβ1 and hLTBP3-proTGFβ1 complexes. In some embodiments, the antibodies have an $IC_{50}$ of 5 nM or less (i.e., ≤5 nM) measured against each of the hLTBP1-proTGFβ1 and hLTBP3-proTGFβ1 complexes. In preferred embodiments, the $IC_{50}$ of the antibody measured against at least one of the hLTBP1-proTGFβ1 and hLTBP3-proTGFβ1 complexes is less than 1 nM. In some embodiments, the antibody has an $IC_{50}$ of less than 1 nM against at least one of the hLTBP1-proTGFβ1 and hLTBP3-proTGFβ1 complexes and further at least one of the mLTBP1-proTGFβ1 and mLTBP3-proTGFβ1 complexes. In some embodiments, the antibody of the present disclosure has an $IC_{50}$ of 10 nM or less (i.e., ≤10 nM) for each of the hLTBP1-proTGFβ1, hLTBP3-proTGFβ1, hGARP-proTGFβ1 and hLRRC33-proTGFβ1 complexes. In some embodiments, the antibody of the present disclosure has an $IC_{50}$ of 5 nM or less (i.e., ≤5 nM) (e.g., 1 nM or less) for each of the hLTBP1-proTGFβ1, hLTBP3-proTGFβ1, hGARP-proTGFβ1 and hLRRC33-proTGFβ1 complexes.

In some embodiments, potency may be evaluated in suitable in vivo models as a measure of efficacy and/or pharmacodynamics effects. For example, if the first antibody is efficacious in an in vivo model at a certain concentration, and the second antibody is equally efficacious at a lower concentration than the first in the same in vivo model, then, the second antibody can be said to me more potent than the first antibody. Any suitable disease models known in the art may be used to assess relative potencies of TGFβ1 inhibitors, depending on the particular indication of interest, e.g., cancer models and fibrosis models. Preferably, multiple doses or concentrations of each test antibody are included in such studies.

Similarly, pharmacodynamics (PD) effects may be measured to determine relative potencies of inhibitory antibodies. Commonly used PD measures for the TGFβ signaling pathway include, without limitation, phosphorylation of SMAD2/3 and expression of downstream effector genes, the transcription of which is sensitive to TGFβ activation, such as those with a TGFβ-responsive promoter element (e.g., SMAD-binding elements). In some embodiments, the antibodies of the present disclosure are capable of completely blocking disease-induced SMAD2/3 phosphorylation in preclinical fibrosis models when the animals are administered at a dose of 3 mg/kg or less. In some embodiments, the antibodies of the present disclosure are capable of significantly suppressing fibrosis-induced expression of a panel of marker genes including Acta2, Col1a1, Col3a1, Fn1, Itga11, Lox, Loxl2, when the animals are administered at a dose of 10 mg/kg or less in the UUO model of kidney fibrosis.

Binding Regions

In the context of the present disclosure, the "binding region" of an antigen provides a structural basis for the antibody-antigen interaction. As used herein, a "binding region" refers to the areas of interface between the antibody and the antigen, such that, when bound to the proTGFβ1 complex ("antigen") in a physiological solution, the antibody or the fragment protects the binding region from solvent exposure, as determined by suitable techniques, such as hydrogen-deuterium exchange mass spectrometry (HDX-MS).

The art is familiar with HDX-MS, which is a widely used technique for exploring protein conformation or protein-protein interactions in solution. This method relies on the exchange of hydrogens in the protein backbone amide with deuterium present in the solution. By measuring hydrogen-deuterium exchange rates, one can obtain information on protein dynamics and conformation (reviewed in: Wei et al., (2014) "Hydrogen/deuterium exchange mass spectrometry for probing higher order structure of protein therapeutics: methodology and applications." *Drug Disc Today.* 19 (1): 95-102; incorporated by reference). The application of this technique is based on the premise that when an antibody-antigen complex forms, the interface between the binding partners may occlude solvent, thereby reducing or preventing the exchange rate due to steric exclusion of solvent.

Using this technique, binding (hence the protected) regions of proTGFβ1 can be determined. In some embodiments, a portion on proTGFβ1 identified to be important in binding of any one of Ab37, Ab38, Ab39, Ab40, Ab41, Ab42, Ab43, Ab44, Ab45, Ab46, Ab47, Ab48, Ab49, Ab50, Ab51, Ab52 and variants thereof (e.g., having VH sequence with at least 90% sequence identity (e.g., at least 90%, 91%, 92%, 93%, 94%, 95%, 96%, 97%, 98% or 99% sequence identity) and VL sequence with at least 90% sequence identity e.g., at least 90%, 91%, 92%, 93%, 94%, 95%, 96%, 97%, 98% or 99% sequence identity)) the includes at least a portion of amino acid stretch SPPSQGEVPPGPLPEAVLALYNST (SEQ ID NO: 261) ("first binding region"), which largely overlaps with the protein domain within the LAP commonly referred to as Latency Lasso. In some embodiments, the antibody binds (hence protects) at least portions of the amino acid sequence LREAVPE (SEQ ID NO: 259) ("second binding region") within the Arm domain of the LAP. In some embodiments, antibody binds (hence protects) at least portion of the amino acid sequence WKWIHEPKGYHANFCLG (SEQ ID NO: 262) ("third binding region"), which largely overlaps with so-called Finger-1 within the growth factor domain. In some embodiments, the antibody binds to an epitope of a proTGFβ1 complex comprising one or more amino acid residues of SPPSQGEVPPGPLPEAVLALYNST (SEQ ID NO: 261) ("first binding region"), LREAVPE (SEQ ID NO: 259) ("second binding region"), and/or one or more amino acid residues of WKWIHEPKGYHANFCLG (SEQ ID NO: 262) ("third binding region").

In some embodiments, additional residue(s), for example residues outside of the three identified binding regions protected by HD-X, may further contribute to achieve the enhanced antibody-antigen binding of the novel antibodies disclosed herein. In some embodiments, the Lysine (Lys) residue at position 309 (i.e., K309) within the growth factor domain of the proTGFβ1 polypeptide sequence may be involved in mediating a strong interaction with one or more of: Ab37, Ab38, Ab39, Ab40, Ab41, Ab42, Ab43, Ab44, Ab45, Ab46, Ab47, Ab48, Ab49, Ab50, Ab51, Ab52 and variants thereof (e.g., having VH sequence with at least 90% sequence identity (e.g., at least 90%, 91%, 92%, 93%, 94%, 95%, 96%, 97%, 98% or 99% sequence identity) and $V_L$ sequence with at least 90% sequence identity (e.g., at least 90%, 91%, 92%, 93%, 94%, 95%, 96%, 97%, 98% or 99% sequence identity). In some embodiments, the Proline (Pro) residue at position 43 (i.e., P43) within the prodomain of the proTGFβ1 polypeptide sequence may be involved in mediating a strong interaction with one or more of: Ab37, Ab38, Ab39, Ab40, Ab41, Ab42, Ab43, Ab44, Ab45, Ab46, Ab47, Ab48, Ab49, Ab50, Ab51, Ab52 and variants thereof (e.g., having VH sequence with at least 90% sequence identity (e.g., at least 90%, 91%, 92%, 93%, 94%, 95%, 96%, 97%, 98% or 99% sequence identity) and VL sequence with at least 90% sequence identity (e.g., at least 90%, 91%, 92%, 93%, 94%, 95%, 96%, 97%, 98% or 99% sequence identity). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309. In some embodiments, the epitope is a combinatorial epitope (see below) that comprises P43 and K309.

In some embodiments, the first binding region and/or the second binding region confers the isoform selectivity of the antibody or the fragment.

Advantageously, preferred inhibitory antibodies of the present disclosure are capable of inhibiting the release of mature growth factor from a latent complex, thereby reducing growth factor signaling. Such antibodies may target any epitope that results in a reduction of growth factor release or activity when associated with such antibodies. In some embodiments, the antibodies of the present disclosure specifically bind a combinatorial epitope, i.e., an epitope formed by two or more components/portions of an antigen or antigen complex. For example, a combinatorial epitope may be formed by contributions from multiple portions of a single protein, i.e., amino acid residues from more than one non-contiguous segments of the same protein. Alternatively, a combinatorial epitope may be formed by contributions from multiple protein components of an antigen complex. In some embodiments, the antibodies of the present disclosure specifically bind a conformational epitope (or conformation-specific epitope), e.g., an epitope that is sensitive to the three-dimensional structure (i.e., conformation) of an antigen or antigen complex. In preferred embodiments, the combinatorial epitope comprises an amino acid residue within Latency Lasso and an amino acid residue within the growth factor domain.

TABLE 14

Select protein domains/modules of human TGFβ1 polypeptide

| Human TGFβ1 domain/module | Amino Acid Sequence | SEQ ID NO |
|---|---|---|
| Latency Associated Peptide (LAP) (prodomain) | LSTCKTIDMELVKRKRIEAIRGQILSKLRLASPPSQGEVPPGPLP EAVLALYNSTRDRVAGESAEPEPEPEADYYAKEVTRVLMVETH NEIYDKFKQSTHSIYMFFNTSELREAVPEPVLLSRAELRLLRLKL KVEQHVELYQKYSNNSWRYLSNRLLAPSDSPEWLSFDVTGVV RQVVLSRGGEIEGFRLSAHCSCDSRDNTLQVDINGFTTGRRGD LATIHGMNRPFLLLMATPLERAQHLQSSRHRR ("First binding region" as determined by HD-X is underlined) | 263 |
| Straight Jacket | LSTCKTIDMELVKRKRIEAIRGQILSKLRLASPPSQGEVPPGPLP | 264 |
| Growth Factor Domain | ALDTNYCFSSTEKNCCVRQLYIDFRKDLGWKWIHEPKGYHANF CLGPCPYIWSLDTQYSKVLALYNQHNPGASAAPCCVPQALEPL PIVYYVGRKPKVEQLSNMIVRSCKCS | 265 |
| Fastener | residues 74-76, YYA | n/a |
| Furin cleavage site | RHRR | 266 |
| Arm | EAVLALYNSTRDRVAGESAEPEPEPEADYYAKEVTRVLMVETH NEIYDKFKQSTHSIYMFFNTSELREAVPEPVLLSRAELRLLRLKL KVEQHVELYQKYSNNSWRYLSNRLLAPSDSPEVVLSFDVTGVV RQVVLSRGGEIEGFRLSAHCSCDSRDNTLQVDINGFTTGRRGD LATIHGMNRPFLLLMATPLERAQHLQSSRHRR ("Second binding region" as determined by HD-X is underlined) | 267 |
| Finger-1 | CVRQLYIDFRKDLGWKWIHEPKGYHANFC ("Third binding region" as determined by HD-X is underlined) | 268 |
| Finger-2 | CVPQALEPLPIVYYVGRKPKVEQLSNMIVRSCKCS | 269 |

TABLE 14-continued

| Select protein domains/modules of human TGFβ1 polypeptide | | |
|---|---|---|
| Human TGFβ1 domain/module | Amino Acid Sequence | SEQ ID NO |
| Residue for presenting molecule association | Cys 4 | n/a |
| Latency Lasso | LASPPSQGEVPPGPL | 270 |
| Extended Latency Lasso | LASPPSQGEVPPGPLPEAVLALYNSTR | 271 |
| Alpha-1 Helix | LSTCKTIDMELVKRKRIEAIRGQILSKLR | 272 |
| Alpha-2 Helix | AVLALYNSTR | 273 |
| Trigger Loop | NGFTTGRRGDLATIHGMNRP | 274 |
| Integrin binding | residue 215-217, RGD | n/a |
| Bowtie | CSCDSRDNTLQVD | 275 |

Antigen Complexes and Components

The novel antibodies of the present disclosure specifically bind each of the four known human large latency complexes (e.g., hLTBP1-proTGFβ1, hLTBP3-proTGFβ1, hGARP-proTGFβ1 and hLRRC33-proTGFβ1), with low dissociation rates, selectively inhibits TGFβ1 activation, and, satisfy safety criteria discussed herein. Screening (e.g., identification and selection) of such antibodies involves the use of suitable antigen complexes, which are typically recombinantly produced. Useful protein components that may comprise such antigen complexes are provided, including TGFβ isoforms and related polypeptides, fragments and variants, presenting molecules (e.g., LTBPs, GARP, LRRC33) and related polypeptides, fragments and variants. These components may be expressed, purified, and allowed to form a protein complex (such as large latent complexes), which can be used in the process of antibody screening. The screening may include positive selection, in which desirable binders are selected from a pool or library of binders and non-binders, and negative selection, in which undesirable binders are removed from the pool.

In some embodiments, the TGFβ1 comprises a naturally occurring mammalian amino acid sequence. In some embodiment, the TGFβ1 comprises a naturally occurring human amino acid sequence. In some embodiments, the TGFβ1 comprises a human, a monkey, a rat or a mouse amino acid sequence. In some embodiments, an antibody, or antigen-binding portion thereof, described herein does not specifically bind to TGFβ2. In some embodiments, an antibody, or antigen-binding portion thereof, described herein does not specifically bind to TGFβ3. In some embodiments, an antibody, or antigen-binding portion thereof, described herein does not specifically bind to TGFβ2 or TGFβ3. In some embodiments, an antibody, or antigen-binding portion thereof, described herein does not specifically bind to TGFβ2 and TGFβ3. In some embodiments, an antibody, or antigen-binding portion thereof, described herein specifically binds to a TGFβ1 comprising the amino acid sequence set forth in SEQ ID NO: 24. The amino acid sequences of TGFβ2 and TGFβ3 amino acid sequence are set forth in SEQ ID NOs: 28 and 32, respectively. In some embodiments, an antibody, or antigen-binding portion thereof, described herein specifically binds to a TGFβ1 comprising a non-naturally-occurring amino acid sequence (otherwise referred to herein as a non-naturally-occurring TGFβ1). For example, a non-naturally-occurring TGFβ1 may comprise one or more recombinantly generated mutations relative to a naturally-occurring TGFβ1 amino acid sequence. In some embodiments, a TGFβ1, TGFβ2, or TGFβ3 amino acid sequence comprises the amino acid sequence as set forth in SEQ ID NOs: 24-35, as shown in Table 10. In some embodiments, a TGFβ1, TGFβ2, or TGFβ3 amino acid sequence comprises the amino acid sequence as set forth in SEQ ID NOs: 36-43, as shown in Table 11.

TGFβ1 (prodomain + growth factor domain)
(SEQ ID NO: 24)

```
LSTCKTIDMELVKRKRIEAIRGQILSKLRLASPPSQGEVPPGPLPEAVL

ALYNSTRDRVAGESAEPEPEPEADYYAKEVTRVLMVETHNEIYDKFKQS

THSIYMFFNTSELREAVPEPVLLSRAELRLLRLKLKVEQHVELYQKYSN

NSWRYLSNRLLAPSDSPEWLSFDVTGVVRQWLSRGGEIEGFRLSAHCSC

DSRDNTLQVDINGFTTGRRGDLATIHGMNRPFLLLMATPLERAQHLQSS

RHRRALDTNYCFSSTEKNCCVRQLYIDFRKDLGWKWIHEPKGYHANFCL

GPCPYIWSLDTQYSKVLALYNQHNPGASAAPCCVPQALEPLPIVYYVGR

KPKVEQLSNMIVRSCKCS
```

TGFβ2 (prodomain + growth factor domain)
(SEQ ID NO: 28)

```
SLSTCSTLDMDQFMRKRIEAIRGQILSKLKLTSPPEDYPEPEEVPPEVI

SIYNSTRDLLQEKASRRAAACERERSDEEYYAKEVYKIDMPPFFPSENA

IPPTFYRPYFRIVRFDVSAMEKNASNLVKAEFRVFRLQNPKARVPEQRI

ELYQILKSKDLTSPTQRYIDSKVVKTRAEGEWLSFDVTDAVHEWLHHKD

RNLGFKISLHCPCCTFVPSNNYIIPNKSEELEARFAGIDGTSTYTSGDQ

KTIKSTRKKNSGKTPHLLLMLLPSYRLESQQTNRRKKRALDAAYCFRNV

QDNCCLRPLYIDFKRDLGVVKWIHEPKGYNANFCAGACPYLWSSDTQHS

RVLSLYNTINPEASASPCCVSQDLEPLTILYYIGKTPKIEQLSNMIVKS

CKCS
```

-continued

TGFβ3 (prodomain + growth factor domain)

(SEQ ID NO: 32)

SLSLSTCTTLDFGHIKKKRVEAIRGQILSKLRLTSPPEPTVMTHVPYQV

LALYNSTRELLEEMHGEREEGCTQENTESEYYAKEIHKFDMIQGLAEHN

ELAVCPKGITSKVFRFNVSSVEKNRTNLFRAEFRVLRVPNPSSKRNEQR

-continued

IELFQILRPDEHIAKQRYIGGKNLPTRGTAEWLSFDVTDTVREWLLRRE

SNLGLEISIHCPCHTFQPNGDILENIHEVMEIKFKGVDNEDDHGRGDLG

RLKKQKDHHNPHLILMMIPPHRLDNPGQGGQRKKRALDTNYCFRNLEEN

CCVRPLYIDFRQDLGWKWVHEPKGYYANFCSGPCPYLRSADTTHSTVLG

LYNTLNPEASASPCCVPQDLEPLTILYYVGRTPKVEQLSNMVVKSCKCS

TABLE 15

Exemplary TGFβ1, TGFβ2, and TGFβ3 amino acid sequences

| Protein | Sequence | SEQ ID NO |
|---|---|---|
| proTGFβ1 | LSTCKTIDMELVKRKRIEAIRGQILSKLRLASPPSQGEVPPGPLPE AVLALYNSTRDRVAGESAEPEPEPEADYYAKEVTRVLMVETHN EIYDKFKQSTHSIYMFFNTSELREAVPEPVLLSRAELRLLRLKLKV EQHVELYQKYSNNSWRYLSNRLLAPSDSPEWLSFDVTGVVRQ WLSRGGEIEGFRLSAHCSCDSRDNTLQVDINGFTTGRRGDLATI HGMNRPFLLLMATPLERAQHLQSSRHRRALDTNYCFSSTEKNC CVRQLYIDFRKDLGWKWIHEPKGYHANFCLGPCPYIWSLDTQY SKVLALYNQHNPGASAAPCCVPQALEPLPIVYYVGRKPKVEQLS NMIVRSCKCS | 24 |
| proTGFβ1 C4S | LSTSKTIDMELVKRKRIEAIRGQILSKLRLASPPSQGEVPPGPLPE AVLALYNSTRDRVAGESAEPEPEPEADYYAKEVTRVLMVETHN EIYDKFKQSTHSIYMFFNTSELREAVPEPVLLSRAELRLLRLKLKV EQHVELYQKYSNNSWRYLSNRLLAPSDSPEWLSFDVTGVVRQ WLSRGGEIEGFRLSAHCSCDSRDNTLQVDINGFTTGRRGDLATI HGMNRPFLLLMATPLERAQHLQSSRHRRALDTNYCFSSTEKNC CVRQLYIDFRKDLGWKWIHEPKGYHANFCLGPCPYIWSLDTQY SKVLALYNQHNPGASAAPCCVPQALEPLPIVYYVGRKPKVEQLS NMIVRSCKCS | 25 |
| proTGFβ1 D2G | LSTCKTIDMELVKRKRIEAIRGQILSKLRLASPPSQGEVPPGPLPE AVLALYNSTRDRVAGESAEPEPEPEADYYAKEVTRVLMVETHN EIYDKFKQSTHSIYMFFNTSELREAVPEPVLLSRAELRLLRLKLKV EQHVELYQKYSNNSWRYLSNRLLAPSDSPEWLSFDVTGVVRQ WLSRGGEIEGFRLSAHCSCDSRDNTLQVDINGFTTGRRGDLATI HGMNRPFLLLMATPLERAQHLQSSRHGALDTNYCFSSTEKNCC VRQLYIDFRKDLGWKWIHEPKGYHANFCLGPCPYIWSLDTQYSK VLALYNQHNPGASAAPCCVPQALEPLPIVYYVGRKPKVEQLSNM IVRSCKCS | 26 |
| proTGFβ1 C4S D2G | LSTSKTIDMELVKRKRIEAIRGQILSKLRLASPPSQGEVPPGPLPE AVLALYNSTRDRVAGESAEPEPEPEADYYAKEVTRVLMVETHN EIYDKFKQSTHSIYMFFNTSELREAVPEPVLLSRAELRLLRLKLKV EQHVELYQKYSNNSWRYLSNRLLAPSDSPEWLSFDVTGVVRQ WLSRGGEIEGFRLSAHCSCDSRDNTLQVDINGFTTGRRGDLATI HGMNRPFLLLMATPLERAQHLQSSRHGALDTNYCFSSTEKNCC VRQLYIDFRKDLGWKWIHEPKGYHANFCLGPCPYIWSLDTQYSK VLALYNQHNPGASAAPCCVPQALEPLPIVYYVGRKPKVEQLSNM IVRSCKCS | 27 |
| proTGFβ2 | SLSTCSTLDMDQFMRKRIEAIRGQILSKLKLTSPPEDYPEPEEVP PEVISIYNSTRDLLQEKASRRAAACERERSDEEYYAKEVYKIDMP PFFPSENAIPPTFYRPYFRIVRFDVSAMEKNASNLVKAEFRVFRL QNPKARVPEQRIELYQILKSKDLTSPTQRYIDSKVVKTRAEGEWL SFDVTDAVHEWLHHKDRNLGFKISLHCPCCTFVPSNNYIIPNKSE ELEARFAGIDGTSTYTSGDQKTIKSTRKKNSGKTPHLLLMLLPSY RLESQQTNRRKKRALDAAYCFRNVQDNCCLRPLYIDFKRDLGW KWIHEPKGYNANFCAGACPYLWSSDTQHSRVLSLYNTINPEASA SPCCVSQDLEPLTILYYIGKTPKIEQLSNMIVKSCKCS | 28 |
| proTGFβ2 C5S | SLSTSSTLDMDQFMRKRIEAIRGQILSKLKLTSPPEDYPEPEEVP PEVISIYNSTRDLLQEKASRRAAACERERSDEEYYAKEVYKIDMP PFFPSENAIPPTFYRPYFRIVRFDVSAMEKNASNLVKAEFRVFRL QNPKARVPEQRIELYQILKSKDLTSPTQRYIDSKVVKTRAEGEWL SFDVTDAVHEWLHHKDRNLGFKISLHCPCCTFVPSNNYIIPNKSE ELEARFAGIDGTSTYTSGDQKTIKSTRKKNSGKTPHLLLMLLPSY RLESQQTNRRKKRALDAAYCFRNVQDNCCLRPLYIDFKRDLGW KWIHEPKGYNANFCAGACPYLWSSDTQHSRVLSLYNTINPEASA SPCCVSQDLEPLTILYYIGKTPKIEQLSNMIVKSCKCS | 29 |

TABLE 15-continued

| Exemplary TGFβ1, TGFβ2, and TGFβ3 amino acid sequences | | |
|---|---|---|
| Protein | Sequence | SEQ ID NO |
| proTGFβ2 C5S D2G | SLSTSSTLDMDQFMRKRIEAIRGQILSKLKLTSPPEDYPEPEEVP<br>PEVISIYNSTRDLLQEKASRRAAACERERSDEEYYAKEVYKIDMP<br>PFFPSENAIPPTFYRPYFRIVRFDVSAMEKNASNLVKAEFRVFRL<br>QNPKARVPEQRIELYQILKSKDLTSPTQRYIDSKVVKTRAEGEWL<br>SFDVTDAVHEWLHHKDRNLGFKISLHCPCCTFVPSNNYIIPNKSE<br>ELEARFAGIDGTSTYTSGDQKTIKSTRKKNSGKTPHLLLMLLPSY<br>RLESQQTNRRKGALDAAYCFRNVQDNCCLRPLYIDFKRDLGWK<br>WIHEPKGYNANFCAGACPYLWSSDTQHSRVLSLYNTINPEASAS<br>PCCVSQDLEPLTILYYIGKTPKIEQLSNMIVKSCKCS | 30 |
| proTGFβ2 D2G | SLSTCSTLDMDQFMRKRIEAIRGQILSKLKLTSPPEDYPEPEEVP<br>PEVISIYNSTRDLLQEKASRRAAACERERSDEEYYAKEVYKIDMP<br>PFFPSENAIPPTFYRPYFRIVRFDVSAMEKNASNLVKAEFRVFRL<br>QNPKARVPEQRIELYQILKSKDLTSPTQRYIDSKVVKTRAEGEWL<br>SFDVTDAVHEWLHHKDRNLGFKISLHCPCCTFVPSNNYIIPNKSE<br>ELEARFAGIDGTSTYTSGDQKTIKSTRKKNSGKTPHLLLMLLPSY<br>RLESQQTNRRKGALDAAYCFRNVQDNCCLRPLYIDFKRDLGWK<br>WIHEPKGYNANFCAGACPYLWSSDTQHSRVLSLYNTINPEASAS<br>PCCVSQDLEPLTILYYIGKTPKIEQLSNMIVKSCKCS | 31 |
| proTGFβ3 | SLSLSTCTTLDFGHIKKKRVEAIRGQILSKLRLTSPPEPTVMTHVP<br>YQVLALYNSTRELLEEMHGEREEGCTQENTESEYYAKEIHKFDM<br>IQGLAEHNELAVCPKGITSKVFRFNVSSVEKNRTNLFRAEFRVLR<br>VPNPSSKRNEQRIELFQILRPDEHIAKQRYIGGKNLPTRGTAEWL<br>SFDVTDTVREWLLRRESNLGLEISIHCPCHTFQPNGDILENIHEV<br>MEIKFKGVDNEDDHGRGDLGRLKKQKDHHNPHLILMMIPPHRLD<br>NPGQGGQRKKRALDTNYCFRNLEENCCVRPLYIDFRQDLGWK<br>WVHEPKGYYANFCSGPCPYLRSADTTHSTVLGLYNTLNPEASA<br>SPCCVPQDLEPLTILYYVGRTPKVEQLSNMVVKSCKCS | 32 |
| proTGFβ3 C7S | SLSLSTSTTLDFGHIKKKRVEAIRGQILSKLRLTSPPEPTVMTHVP<br>YQVLALYNSTRELLEEMHGEREEGCTQENTESEYYAKEIHKFDM<br>IQGLAEHNELAVCPKGITSKVFRFNVSSVEKNRTNLFRAEFRVLR<br>VPNPSSKRNEQRIELFQILRPDEHIAKQRYIGGKNLPTRGTAEWL<br>SFDVTDTVREWLLRRESNLGLEISIHCPCHTFQPNGDILENIHEV<br>MEIKFKGVDNEDDHGRGDLGRLKKQKDHHNPHLILMMIPPHRLD<br>NPGQGGQRKKRALDTNYCFRNLEENCCVRPLYIDFRQDLGWK<br>WVHEPKGYYANFCSGPCPYLRSADTTHSTVLGLYNTLNPEASA<br>SPCCVPQDLEPLTILYYVGRTPKVEQLSNMVVKSCKCS | 33 |
| proTGFβ3 C7S D2G | SLSLSTSTTLDFGHIKKKRVEAIRGQILSKLRLTSPPEPTVMTHVP<br>YQVLALYNSTRELLEEMHGEREEGCTQENTESEYYAKEIHKFDM<br>IQGLAEHNELAVCPKGITSKVFRFNVSSVEKNRTNLFRAEFRVLR<br>VPNPSSKRNEQRIELFQILRPDEHIAKQRYIGGKNLPTRGTAEWL<br>SFDVTDTVREWLLRRESNLGLEISIHCPCHTFQPNGDILENIHEV<br>MEIKFKGVDNEDDHGRGDLGRLKKQKDHHNPHLILMMIPPHRLD<br>NPGQGGQRKGALDTNYCFRNLEENCCVRPLYIDFRQDLGWKW<br>VHEPKGYYANFCSGPCPYLRSADTTHSTVLGLYNTLNPEASASP<br>CCVPQDLEPLTILYYVGRTPKVEQLSNMVVKSCKCS | 34 |
| proTGFβ3 D2G | SLSLSTCTTLDFGHIKKKRVEAIRGQILSKLRLTSPPEPTVMTHVP<br>YQVLALYNSTRELLEEMHGEREEGCTQENTESEYYAKEIHKFDM<br>IQGLAEHNELAVCPKGITSKVFRFNVSSVEKNRTNLFRAEFRVLR<br>VPNPSSKRNEQRIELFQILRPDEHIAKQRYIGGKNLPTRGTAEWL<br>SFDVTDTVREWLLRRESNLGLEISIHCPCHTFQPNGDILENIHEV<br>MEIKFKGVDNEDDHGRGDLGRLKKQKDHHNPHLILMMIPPHRLD<br>NPGQGGQRKGALDTNYCFRNLEENCCVRPLYIDFRQDLGWKW<br>VHEPKGYYANFCSGPCPYLRSADTTHSTVLGLYNTLNPEASASP<br>CCVPQDLEPLTILYYVGRTPKVEQLSNMVVKSCKCS | 35 |

TABLE 16

| Exemplary non-human amino acid sequences | | | |
|---|---|---|---|
| Protein | Species | Sequence | SEQ ID NO |
| proTGFβ1 | Mouse | LSTCKTIDMELVKRKRIEAIRGQILSKLRLASPPSQGEVPPGPL<br>PEAVLALYNSTRDRVAGESADPEPEPEADYYAKEVTRVLMV<br>DRNNAIYEKTKDISHSIYMFFNTSDIREAVPEPPLLSRAELRLQ<br>RLKSSVEQHVELYQKYSNNSWRYLGNRLLTPTDTPEWLSFD | 36 |

TABLE 16-continued

Exemplary non-human amino acid sequences

| Protein | Species | Sequence | SEQ ID NO |
|---|---|---|---|
| | | VTGVVRQWLNQGDGIQGFRFSAHCSCDSKDNKLHVEINGIS PKRRGDLGTIHDMNRPFLLLMATPLERAQHLHSSRHRRALDT NYCFSSTEKNCCVRQLYIDFRKDLGWKWIHEPKGYHANFCL GPCPYIWSLDTQYSKVLALYNQHNPGASASPCCVPQALEPL PIVYYVGRKPKVEQLSNMIVRSCKCS | |
| proTGFβ1 | Cyno | LSTCKTIDMELVKRKRIEAIRGQILSKLRLASPPSQGEVPPGPL PEAVLALYNSTRDRVAGESAEPEPEPEADYYAKEVTRVLMV ETHNEIYDKFKQSTHSIYMFFNTSELREAVPEPVLLSRAELRL LRLKLKVEQHVELYQKYSNNSWRYLSNRLLAPSDSPEWLSF DVTGVVRQWLSRGGEIEGFRLSAHCSCDSKDNTLQVDINGF TTGRRGDLATIHGMNRPFLLLMATPLERAQHLQSSRHRRAL DTNYCFSSTEKNCCVRQLYIDFRKDLGWKWIHEPKGYHANF CLGPCPYIWSLDTQYSKVLALYNQHNPGASAAPCCVPQALE PLPIVYYVGRKPKVEQLSNMIVRSCKCS | 37 |
| TGFβ1 LAP C4S | Mouse | LSTSKTIDMELVKRKRIEAIRGQILSKLRLASPPSQGEVPPGPL PEAVLALYNSTRDRVAGESADPEPEPEADYYAKEVTRVLMV DRNNAIYEKTKDISHSIYMFFNTSDIREAVPEPPLLSRAELRLQ RLKSSVEQHVELYQKYSNNSWRYLGNRLLTPTDTPEWLSFD VTGVVRQWLNQGDGIQGFRFSAHCSCDSKDNKLHVEINGIS PKRRGDLGTIHDMNRPFLLLMATPLERAQHLHSSRHRR | 38 |
| TGFβ1 LAP C4S | Cyno | LSTSKTIDMELVKRKRIEAIRGQILSKLRLASPPSQGEVPPGPL PEAVLALYNSTRDRVAGESAEPEPEPEADYYAKEVTRVLMV ETHNEIYDKFKQSTHSIYMFFNTSELREAVPEPVLLSRAELRL LRLKLKVEQHVELYQKYSNNSWRYLSNRLLAPSDSPEWLSF DVTGVVRQWLSRGGEIEGFRLSAHCSCDSKDNTLQVDINGF TTGRRGDLATIHGMNRPFLLLMATPLERAQHLQSSRHRR | 39 |
| proTGFβ1 C4S D2G | Mouse | LSTSKTIDMELVKRKRIEAIRGQILSKLRLASPPSQGEVPPGPL PEAVLALYNSTRDRVAGESADPEPEPEADYYAKEVTRVLMV DRNNAIYEKTKDISHSIYMFFNTSDIREAVPEPPLLSRAELRLQ RLKSSVEQHVELYQKYSNNSWRYLGNRLLTPTDTPEWLSFD VTGVVRQWLNQGDGIQGFRFSAHCSCDSKDNKLHVEINGIS PKRRGDLGTIHDMNRPFLLLMATPLERAQHLHSSRHGALDT NYCFSSTEKNCCVRQLYIDFRKDLGWKWIHEPKGYHANFCL GPCPYIWSLDTQYSKVLALYNQHNPGASASPCCVPQALEPL PIVYYVGRKPKVEQLSNMIVRSCKCS | 40 |
| proTGFβ1 C4S | Mouse | LSTSKTIDMELVKRKRIEAIRGQILSKLRLASPPSQGEVPPGPL PEAVLALYNSTRDRVAGESADPEPEPEADYYAKEVTRVLMV DRNNAIYEKTKDISHSIYMFFNTSDIREAVPEPPLLSRAELRLQ RLKSSVEQHVELYQKYSNNSWRYLGNRLLTPTDTPEWLSFD VTGVVRQWLNQGDGIQGFRFSAHCSCDSKDNKLHVEINGIS PKRRGDLGTIHDMNRPFLLLMATPLERAQHLHSSRHRRALDT NYCFSSTEKNCCVRQLYIDFRKDLGWKWIHEPKGYHANFCL GPCPYIWSLDTQYSKVLALYNQHNPGASASPCCVPQALEPL PIVYYVGRKPKVEQLSNMIVRSCKCS | 41 |
| proTGFβ1 C4S | Cyno | LSTSKTIDMELVKRKRIEAIRGQILSKLRLASPPSQGEVPPGPL PEAVLALYNSTRDRVAGESAEPEPEPEADYYAKEVTRVLMV ETHNEIYDKFKQSTHSIYMFFNTSELREAVPEPVLLSRAELRL LRLKLKVEQHVELYQKYSNNSWRYLSNRLLAPSDSPEWLSF DVTGVVRQWLSRGGEIEGFRLSAHCSCDSKDNTLQVDINGF TTGRRGDLATIHGMNRPFLLLMATPLERAQHLQSSRHRRAL DTNYCFSSTEKNCCVRQLYIDFRKDLGWKWIHEPKGYHANF CLGPCPYIWSLDTQYSKVLALYNQHNPGASAAPCCVPQALE PLPIVYYVGRKPKVEQLSNMIVRSCKCS | 42 |
| proTGFβ1 C4S D2G | Cyno | LSTSKTIDMELVKRKRIEAIRGQILSKLRLASPPSQGEVPPGPL PEAVLALYNSTRDRVAGESAEPEPEPEADYYAKEVTRVLMV ETHNEIYDKFKQSTHSIYMFFNTSELREAVPEPVLLSRAELRL LRLKLKVEQHVELYQKYSNNSWRYLSNRLLAPSDSPEWLSF DVTGVVRQWLSRGGEIEGFRLSAHCSCDSKDNTLQVDINGF TTGRRGDLATIHGMNRPFLLLMATPLERAQHLQSSRHGALDT NYCFSSTEKNCCVRQLYIDFRKDLGWKWIHEPKGYHANFCL GPCPYIWSLDTQYSKVLALYNQHNPGASAAPCCVPQALEPL PIVYYVGRKPKVEQLSNMIVRSCKCS | 43 |
| LTBP3 | CYNO | GPAGERGAGGGGALARERFKVVFAPVICKRTCLKGQCRDSC QQGSNMTLIGENGHSTDTLTGSGFRVVVCPLPCMNGGQCS SRNQCLCPPDFTGRFCQVPAGGAGGGTGGSGPGLSRAGAL STGALPPLAPEGDSVASKHAIYAVQVIADPPGPGEGPPAQHA AFLVPLGPGQISAEVQAPPPVVNVRVHHPPEASVQVHRIESS | 44 |

TABLE 16-continued

| Exemplary non-human amino acid sequences | | | |
|---|---|---|---|
| Protein | Species | Sequence | SEQ ID NO |
| | | NAEGAAPSQHLLPHPKPSHPRPPTQKPLGRCFQDTLPKQPC<br>GSNPLPGLTKQEDCCGSIGTAWGQSKCHKCPQLQYTGVQK<br>PGPVRGEVGADCPQGYKRLNSTHCQDINECAMPGVCRHGD<br>CLNNPGSYRCVCPPGHSLGPSRTQCIADKPEEKSLCFRLVS<br>PEHQCQHPLTTRLTRQLCCCSVGKAWGARCQRCPADGTAA<br>FKEICPAGKGYHILTSHQTLTIQGESDFSLFLHPDGPPKPQQL<br>PESPSQAPPPEDTEEERGVTTDSPVSEERSVQQSHPTATTS<br>PARPYPELISRPSPPTMRVVFLPDLPPSRSAVEIAPTQVTETD<br>ECRLNQNICGHGECVPGPPDYSCHCNPGYRSHPQHRYCVD<br>VNECEAEPCGPGRGICMNTGGSYNCHCNRGYRLHVGAGGR<br>SCVDLNECAKPHLCGDGGFCINFPGHYKCNCYPGYRLKASR<br>PPVCEDIDECRDPSSCPDGKCENKPGSFKCIACQPGYRSQG<br>GGACRDVNECAEGSPCSPGWCENLPGSFRCTCAQGYAPAP<br>DGRSCVDVDECEAGDVCDNGICTNTPGSFQCQCLSGYHLS<br>RDRSHCEDIDECDFPAACIGGDCINTNGSYRCLCPQGHRLV<br>GGRKCQDIDECTQDPGLCLPHGACKNLQGSYVCVCDEGFT<br>PTQDQHGCEEVEQPHHKKECYLNFDDTVFCDSVLATNVTQQ<br>ECCCSLGAGWGDHCEIYPCPVYSSAEFHSLCPDGKGYTQD<br>NNIVNYGIPAHRDIDECMLFGAEICKEGKCVNTQPGYECYCK<br>QGFYYDGNLLECVDVDECLDESNCRNGVCENTRGGYRCAC<br>TPPAEYSPAQRQCLSPEEMDVDECQDPAACRPGRCVNLPG<br>SYRCECRPPWVPGPSGRDCQLPESPAERAPERRDVCWSQ<br>RGEDGMCAGPQAGPALTFDDCCCRQGRGWGAQCRPCPPR<br>GAGSQCPTSQSESNSFWDTSPLLLGKPRRDEDSSEEDSDE<br>CRCVSGRCVPRPGGAVCECPGGFQLDASRARCVDIDECRE<br>LNQRGLLCKSERCVNTSGSFRCVCKAGFARSRPHGACVPQ<br>RRR | |
| LTBP3 | Mouse | GPAGERGTGGGGALARERFKVVFAPVICKRTCLKGQCRDSC<br>QQGSNMTLIGENGHSTDTLTGSAFRVVVCPLPCMNGGQCS<br>SRNQCLCPPDFTGRFCQVPAAGTGAGTGSSGPGLARTGAM<br>STGPLPPLAPEGESVASKHAIYAVQVIADPPGPGEGPPAQHA<br>AFLVPLGPGQISAEVQAPPPVVNVRVHHPPEASVQVHRIEGP<br>NAEGPASSQHLLPHPKPPHPRPPTQKPLGRCFQDTLPKQPC<br>GSNPLPGLTKQEDCCGSIGTAWGQSKCHKCPQLQYTGVQK<br>PVPVRGEVGADCPQGYKRLNSTHCQDINECAMPGNVCHGD<br>CLNNPGSYRCVCPPGHSLGPLAAQCIADKPEEKSLCFRLVST<br>EHQCQHPLTTRLTRQLCCCSVGKAWGARCQRCPADGTAAF<br>KEICPGKGYHILTSHQTLTIQGESDFSLFLHPDGPPKPQQLPE<br>SPSRAPPLEDTEEERGVTMDPPVSEERSVQQSHPTTTTSPP<br>RPYPELISRPSPPTFHRFLPDLPPSRSAVEIAPTQVTETDECR<br>LNQNICGHGQCVPGPSDYSCHCNAGYRSHPQHRYCVDVNE<br>CEAEPCGPGKGICMNTGGSYNCHCNRGYRLHVGAGGRSCV<br>DLNECAKPHLCGDGGFCINFPGHYKCNCYPGYRLKASRPPI<br>CEDIDECRDPSTCPDGKCENKPGSFKCIACQPGYRSQGGGA<br>CRDVNECSEGTPCSPGWCENLPGSYRCTCAQYEPAQDGLS<br>CIDVDECEAGKVCQDGICTNTPGSFQCQCLSGYHLSRDRSR<br>CEDIDECDFPAACIGGDCINTNGSYRCLCPLGHRLVGGRKCK<br>KDIDECSQDPGLCLPHACENLQGSYVCVCDEGFTLTQDQHG<br>CEEVEQPHHKKECYLNFDDTVFCDSVLATNVTQQECCCSLG<br>AGWGDHCEIYPCPVYSSAEFHSLVPDGKRLHSGQQHCELCI<br>PAHRDIDECILFGAEICKEGKCVNTQPGYECYCKQGFYYDGN<br>LLECVDVDECLDESNCRNGVCENTRGGYRCACTPPAEYSPA<br>QAQCLIPERWSTPQRDVKCAGASEERTACVWGPWAGPALT<br>FDDCCCRQPRLGTQCRPCPPRGTGSQCPTSQSESNSFWDT<br>SPLLLGKSPRDEDSSEEDSDECRCVSGRCVPRPGGAVCEC<br>PGGFQLDASRARCVDIDECRELNQRGLLCKSERCVNTSGSF<br>RCVCKAGFTRSRPHGPACLSAAADDAAIAHTSVIDHRGYFH | 45 |
| LTBP1S | Cyno | NHTGRIKVVFTPSICKVTCTKGSCQNSCEKGNTTTLISENGHA<br>ADTLTATNFRVVLCHLPCMNGGQCSSRDKCQCPPNFTGKLC<br>QIPVHGASVPKLYQHSQQPGKALGTHVIHSTHTLPLTVTSQQ<br>GVKVKFPPNIVNIHVKHPPEASVQIHQVSRIDGPTGQKTKEAQ<br>PGQSQVSYQGLPVQKTQTIHSTYSHQQVIPHVYPVAAKTQL<br>GRCFQETIGSQCGKALPGLSKQEDCCGTVGTSWGFNKCQK<br>CPKKPSYHGYNQMMECLPGYKRVNNTFCQDINECQLQGVC<br>PNGECLNTMGSYRCTCKIGFGPDPTFSSCVPDPPVISEEKGP<br>CYRLVSSGRQCMHPLSVHLTKQLCCCSVGKAWGPHCEKCP<br>LPGTAAFKEICPGGMGYTVSGVHRRRPIHHHVGKGPVFVKP<br>KNTQPVAKSTHPPPLPAKEEPVEALTFSREHGPGVAEPEVAT<br>APPEKEIPSLDQEKTKLEPGQPQLSPGISTIHLHPQFPVVIEKT<br>SPPVPVEVAPEASTSSASQVIAPTQVTEINECTVNPDICGAGH<br>CINLPVRYTCICYEGYKFSEQQRKCVDIDECTQVQHLCSQGR<br>CENTEGSFLCICPAGFMASEEGTNCIDVDECLRPDVCGEGH<br>CVNTVGAFRCEYCDSGYRMTQRGRCEDIDECLNPSTCPDE | 46 |

TABLE 16-continued

| Exemplary non-human amino acid sequences | | | |
|---|---|---|---|
| Protein | Species | Sequence | SEQ ID NO |
| | | QCVNSPGSYQCVPCTEGFRGVVNGQCLDVDECLEPNVCTN<br>GDCSNLEGSYMCSCHKGYTRTPDHKHCKDIDECQQGNLCV<br>NGQCKNTEGSFRCTCGQGYQLSAAKDQCEDIDECQHHHLC<br>AHGQCRNTEGSFQCVCDQGYRASGLGDHCEDINECLEDKS<br>VCQRGDCINTAGSYDCTCPDGFQLDDNKTCQDINECEHPGL<br>CGPQGECLNTEGSFHCVCQQGFSISADGRTCEDIDECVNNT<br>VCDSHGFCDNTAGSFRCLCYQGFQAPQDGQGCVDVNECEL<br>LSGVCGEAFCENVEGSFLCVCADENQEYSPMTGQCRSRTS<br>TDLDVEQPKEEKKECYYNLNDASLCDNVLAPNVTKQECCCT<br>SGAGWGDNCEIFPCPVLGTAEFTEMCPKGKGFVPAGESSSE<br>AGGENYKDADECLLFGQEICKNGFCLNTRPGYECYCKQGTY<br>YDPVKLQCFDMDECQDPSSCIDGQCVNTEGSYNCFCTHPM<br>VLDASEKRCIRPAESNEQIEETDVYQDLCVVEHLSDEYVCSRP<br>LVGKQTTYTECCCLYGEAWGMQCALCPMKDSDDYAQLCNI<br>PVTGRRQPYGRDALVDFSEQYAPEADPYFIQDRFLNSFEEL<br>QAEECGILNGCENGRCVRVQEGYTCDCFDGYHLDTAKMTC<br>VDVNECDELNNRMSLCKNAKCINTEGSYKCLCLPGYVPSDK<br>PNYCTPLNTALNLEKDSDLE | |
| LTBP1S | mouse | NHTGRIKVVFTPSICKVTCTKGNCQNSCQKGNTTTLISENGH<br>AADTLTATNFRVVICHLPCMNGGQCSSRDKCQCPPNFTGKL<br>CQIPVLGASMPKLYQHAQQQGKALGSHVIHSTHTLPLTMTSQ<br>QGVKVKFPPNIVNIHVKHPPEASVQIHQVSRIDSPGGQKVKE<br>AQPGQSQVSYQGLPVQKTQTVHSTYSHQQLIPHVYPVAAKT<br>QLGRCFQETIGSQCGKALPGLSKQEDCCGTVGTSWGFNKC<br>QKCPKKQSYHGYTQMMECLQGYKRVNNTFCQDINECQLQG<br>VCPNGECLNTMGSYRCSCKMGFGPDPTFSSCVPDPPVISEE<br>KGPCYRLVSPGRHCMHPLSVHLTKQICCCSVGKAWGPHCE<br>KCPLPGTAAFKEICPGGMGYTVSGVHRRRPIHQHIGKEAVYV<br>KPKNTQPVAKSTHPPPLPAKEEPVEALTSSVVEHGPRGAEPE<br>VVTAPPEKEIPSLDQEKTRLEPGQPQLSPGVSTIHLHPQFPVV<br>VEKTSPPVPVEVAPEASTSSASQVIAPTQVTEINECTVNPDIC<br>GAGHCINLPVRYTCICYEGYKFSEQLRKCVDIDECAQVRHLC<br>SQGRCENTEGSFLCVCPAGFMASEEGTNCIDVDECLRPDMC<br>RDGRCINTAGAFRCEYCDSGYRMSRRGYCEDIDECLKPSTC<br>PEEQCVNTPGSYQCVPCTEGFRGVVNGQCLDVDECLQPKVC<br>TNGSCTNLEGSYMCSCHRGYSPTPDHRHCQDIDECQQGNL<br>CMNGQCRNTDGSFRCTCGQGYQLSAAKDQCEDIDECEHHH<br>LCSHGQCRNTEGSFQCVCNQGYRASVLGDHCEDINECLED<br>SSVCQGGDCINTAGSYDCTCPDGFQLNDNKGCQDINECAQP<br>GLCGSHGECLNTQGSFHCVCEQGFSISADGRTCEDIDECVN<br>NTVCDSHGFCDNTAGSFRCLCYQGFQAPQDGQGCVDVNEC<br>ELLSGVCGEAFCENVEGSFLCVCADENQEYSPMTGQCRSR<br>VTEDSGVDRQPREEKKECYYNLNDASLCDNVLAPNVTKQEC<br>CCTSGAGWGDNCEIFPCPVQGTAEFTEMCPRGKGLVPAGE<br>SSYDTGGENYKDADECLLFGEEICKNGYCLNTQPGYECYCK<br>QGTYYDPVKLQCFDMDECQDPNSCIDGQCVNTEGSYNCFC<br>THPMVLDASEKRCVQPTESNEQIEETDVYQDLCVVEHLSEEY<br>VCSRPLVGKQTTYTECCCLYGEAWGMQCALCPMKDSDDYA<br>QLCNIPVTGRRRPYGRDALVDFSEQYGPETDPYFIQDRFLNS<br>FEELQAEECGILNGCENGRCVRVQEGYTCDCFDGYHLDMAK<br>MTCVDVNECSELNNRMSLCKNAKCINTEGSYKCLCLPGYIPS<br>DKPNYCTPLNSALNLDKESDLE | 47 |
| GARP | mouse | ISQRREQVPCRTVNKEALCHGLGLLQVPSVLSLDIQALYLSG<br>NQLQSILVSPLGFYTALRHLDLSDNQISFLQAGVFQALPYLEH<br>LNLAHNRLATGMALNSGGLGRLPLLVSLDLSGNSLHGNLVER<br>LLGETPRLRTLSLAENSLTRLARHTFWGMPAVEQLDLHSNVL<br>MDIEDGAFEALPHLTHLNLSRNSLTCISDFSLQQLQVLDLSCN<br>SIEAFQTAPEPQAQFQLAWLDLRENKLLHFPDLAVFPRLIYLN<br>VSNNLIQLPAGLPRGSEDLHAPSEGWSASPLSNPSRNASTH<br>PLSQLLNLDLSYNEIELVPASFLEHLTSLRFLNLSRNCLRSFEA<br>RQVDSLPCLVLLDLSHNVLEALELGTKVLGSLQTLLLQDNALQ<br>ELPPYTFASLASLQRLNLQGNQVSPCGGPAEPGPPGCVDFS<br>GIPTLHVLNMAGNSMGMLRAGSFLHTPLTELDLSTNPGLDVA<br>TGALVGLEASLEVLELQGNGLTVLRVDLPCFLRLKRLNLAEN<br>QLSHLPAWTRAVSLEVLDLRNNSFSLLPGNAMGGLETSLRRL<br>YLQGNPLSCCGNGVVLAAQLHQGRVDVDATQDLICRFGSQE<br>ELSLSLVRPEDCEKGGLKNVNLILLLSFTLVSAIVLTTLATICFL<br>RRQKLSQQYKA | 48 |
| sGARP | mouse | ISQRREQVPCRTVNKEALCHGLGLLQVPSVLSLDIQALYLSG<br>NQLQSILVSPLGFYTALRHLDLSDNQISFLQAGVFQALPYLEH<br>LNLAHNRLATGMALNSGGLGRLPLLVSLDLSGNSLHGNLVER<br>LLGETPRLRTLSLAENSLTRLARHTFWGMPAVEQLDLHSNVL | 49 |

TABLE 16-continued

Exemplary non-human amino acid sequences

| Protein | Species | Sequence | SEQ ID NO |
|---|---|---|---|
| | | MDIEDGAFEALPHLTHLNLSRNSLTCISDFSLQQLQVLDLSCN SIEAFQTAPEPQAQFQLAWLDLRENKLLHFPDLAVFPRLIYLN VSNNLIQLPAGLPRGSEDLHAPSEGWSASPLSNPSRNASTH PLSQLLNLDLSYNEIELVPASFLEHLTSLRFLNLSRNCLRSFEA RQVDSLPCLVLLDLSHNVLEALELGTKVLGSLQTLLLQDNALQ ELPPYTFASLASLQRLNLQGNQVSPCGGPAEPGPPGCVDFS GIPTLHVLNMAGNSMGMLRAGSFLHTPLTELDLSTNPGLDVA TGALVGLEASLEVLELQGNGLTVLRVDLPCFLRLKRLNLAEN QLSHLPAWTRAVSLEVLDLRNNSFSLLPGNAMGGLETSLRRL YLQGNPLSCCGNGVVLAAQLHQGRVDVDATQDLICRFGSQE ELSLSLVRPEDCEKGGLKNVN | |

In some embodiments, antigenic protein complexes may be so-called a small latent complex (or SLC), comprised of a dimeric complex of the LAP (or prodomain) and a growth factor domain. In other embodiments, antigenic protein complexes may be so-called a large latent complex (or LLC) which further comprises a presenting molecule bound to a SLC. Presenting molecules include LTBP proteins (e.g., LTBP1, LTBP2, LTBP3, and LTBP4), GARP proteins, LRRC33 proteins, or fragment(s) thereof. When LLCs are used as antigenic protein complexes, typically, a minimum required fragment suitable for carrying out the embodiments disclosed herein includes at least 50 amino acids, preferably at least 100 amino acids, of a presenting molecule protein, comprising at least two cysteine residues capable of forming disulfide bonds with a proTGFβ1 complex. Specifically, these Cys residues form covalent bonds with Cysteine resides present near the N-terminus of each monomer of the proTGFβ1 complex.

An antibody, or antigen-binding portion thereof, as described herein, is capable of binding to a latent LTBP1-TGFβ1 complex. In some embodiments, the LTBP1 protein is a naturally-occurring protein or fragment thereof. In some embodiments, the LTBP1 protein is a non-naturally occurring protein or fragment thereof. In some embodiments, the LTBP1 protein is a recombinant protein. Such recombinant LTBP1 protein may comprise LTBP1, alternatively spliced variants thereof and/or fragments thereof. Recombinant LTBP1 proteins may also be modified to comprise one or more detectable labels. In some embodiments, the LTBP1 protein comprises a leader sequence (e.g., a native or non-native leader sequence). In some embodiments, the LTBP1 protein does not comprise a leader sequence (i.e., the leader sequence has been processed or cleaved). Such detectable labels may include, but are not limited to biotin labels, polyhistidine tags, myc tags, HA tags and/or fluorescent tags. In some embodiments, the LTBP1 protein is a mammalian LTBP1 protein. In some embodiments, the LTBP1 protein is a human, a monkey, a mouse, or a rat LTBP1 protein. In some embodiments, the LTBP1 protein comprises an amino acid sequence as set forth in SEQ ID NOs: 46 and 47 in Table 11. In some embodiments, the LTBP1 protein comprises an amino acid sequence as set forth in SEQ ID NO: 50 in Table 12.

The antibody, or antigen-binding portion thereof, as described herein, is capable of binding to a latent LTBP3-TGFβ1 complex. In some embodiments, the LTBP3 protein is a naturally-occurring protein or fragment thereof. In some embodiments, the LTBP3 protein is a non-naturally occurring protein or fragment thereof. In some embodiments, the LTBP3 protein is a recombinant protein. Such recombinant LTBP3 protein may comprise LTBP3, alternatively spliced variants thereof and/or fragments thereof. In some embodiments, the LTBP3 protein comprises a leader sequence (e.g., a native or non-native leader sequence). In some embodiments, the LTBP3 protein does not comprise a leader sequence (i.e., the leader sequence has been processed or cleaved). Recombinant LTBP3 proteins may also be modified to comprise one or more detectable labels. Such detectable labels may include, but are not limited to biotin labels, polyhistidine tags, myc tags, HA tags and/or fluorescent tags. In some embodiments, the LTBP3 protein is a mammalian LTBP3 protein. In some embodiments, the LTBP3 protein is a human, a monkey, a mouse, or a rat LTBP3 protein. In some embodiments, the LTBP3 protein comprises an amino acid sequence as set forth in SEQ ID NOs: 44 and 45 in Table 11. In some embodiments, the LTBP1 protein comprises an amino acid sequence as set forth in SEQ ID NO: 51 in Table 12.

The antibody, or antigen-binding portion thereof, as described herein, is capable of binding to a latent GARP-TGFβ1 complex. In some embodiments, the GARP protein is a naturally-occurring protein or fragment thereof. In some embodiments, the GARP protein is a non-naturally occurring protein or fragment thereof. In some embodiments, the GARP protein is a recombinant protein. Such a GARP may be recombinant, referred to herein as recombinant GARP. Some recombinant GARPs may comprise one or more modifications, truncations and/or mutations as compared to wild type GARP. Recombinant GARPs may be modified to be soluble. In some embodiments, the GARP protein comprises a leader sequence (e.g., a native or non-native leader sequence). In some embodiments, the GARP protein does not comprise a leader sequence (i.e., the leader sequence has been processed or cleaved). In other embodiments, recombinant GARPs are modified to comprise one or more detectable labels. In further embodiments, such detectable labels may include, but are not limited to biotin labels, polyhistidine tags, flag tags, myc tags, HA tags and/or fluorescent tags. In some embodiments, the GARP protein is a mammalian GARP protein. In some embodiments, the GARP protein is a human, a monkey, a mouse, or a rat GARP protein. In some embodiments, the GARP protein comprises an amino acid sequence as set forth in SEQ ID NOS: 48-49 in Table 11. In some embodiments, the GARP protein comprises an amino acid sequence as set forth in SEQ ID NOs: 52 and 53 in Table 13. In some embodiments, the antibodies, or antigen-binding portions thereof, described herein do not bind to TGFβ1 in a context-dependent manner, for example binding to TGFβ1 would only occur when the TGFβ1 molecule was complexed with a specific presenting molecule, such as GARP. Instead, the antibodies, and antigen-binding portions thereof, bind to TGFβ1 in a context-independent manner. In other words, the antibodies, or antigen-binding portions thereof, bind to TGFβ1 when bound to any presenting molecule: GARP, LTBP1, LTBP3, and/or LRCC33.

The antibody, or antigen-binding portion thereof, as described herein, is capable of binding to a latent LRRC33-TGFβ1 complex. In some embodiments, the LRRC33 protein is a naturally-occurring protein or fragment thereof. In some embodiments, the LRRC33 protein is a non-naturally occurring protein or fragment thereof. In some embodiments, the LRRC33 protein is a recombinant protein. Such a LRRC33 may be recombinant, referred to herein as recombinant LRRC33. Some recombinant LRRC33 proteins may comprise one or more modifications, truncations and/or mutations as compared to wild type LRRC33. Recombinant LRRC33 proteins may be modified to be soluble. For example, in some embodiments, the ectodomain of LRRC33 may be expressed with a C-terminal His-tag in order to express soluble LRRC33 protein (sLRRC33; see, e.g., SEQ ID NO: 84). In some embodiments, the LRRC33 protein comprises a leader sequence (e.g., a native or non-native leader sequence). In some embodiments, the LRRC33 protein does not comprise a leader sequence (i.e., the leader sequence has been processed or cleaved). In other embodiments, recombinant LRRC33 proteins are modified to comprise one or more detectable labels. In further embodiments, such detectable labels may include, but are not limited to biotin labels, polyhistidine tags, flag tags, myc tags, HA tags and/or fluorescent tags. In some embodiments, the LRRC33 protein is a mammalian LRRC33 protein. In some embodiments, the LRRC33 protein is a human, a monkey, a mouse, or a rat LRRC33 protein. In some embodiments, the LRRC33 protein comprises an amino acid sequence as set forth in SEQ ID NOs: 83, 84, and 101 in Table 13.

TABLE 17

Exemplary LTBP amino acid sequences

| Protein | Sequence | SEQ ID NO |
|---|---|---|
| LTBP1S | NHTGRIKVVFTPSICKVTCTKGSCQNSCEKGNTTTLISENGHA<br>ADTLTATNFRVVICHLPCMNGGQCSSRDKCQCPPNFTGKLCQ<br>IPVHGASVPKLYQHSQQPGKALGTHVIHSTHTLPLTVTSQQGV<br>KVKFPPNIVNIHVKHPPEASVQIHQVSRIDGPTGQKTKEAQPG<br>QSQVSYQGLPVQKTQTIHSTYSHQQVIPHVYPVAAKTQLGRC<br>FQETIGSQCGKALPGLSKQEDCCGTVGTSWGFNKCQKCPKK<br>PSYHGYNQMMECLPGYKRVNNTFCQDINECQLQGVCPNGEC<br>LNTMGSYRCTCKIGFGPDPTFSSCVPDPPVISEEKGPCYRLVS<br>SGRQCMHPLSVHLTKQLCCCSVGKAWGPHCEKCPLPGTAAF<br>KEICPGGMGYTVSGVHRRRPIHHHVGKGPVFVKPKNTQPVAK<br>STHPPPLPAKEEPVEALTFSREHGPGVAEPEVATAPPEKEIPS<br>LDQEKTKLEPGQPQLSPGISTIHLHPQFPVVIEKTSPPVPVEVA<br>PEASTSSASQVIAPTQVTEINECTVNPDICGAGHCINLPVRYTC<br>ICYEGYRFSEQQRKCVDIDECTQVQHLCSQGRCENTEGSFLC<br>ICPAGFMASEEGTNCIDVDECLRPDVCGEGHCVNTVGAFRCE<br>YCDSGYRMTQRGRCEDIDECLNPSTCPDEQCVNSPGSYQCV<br>PCTEGFRGVVNGQCLDVDECLEPNVCANGDCSNLEGSYMCS<br>CHKGYTRTPDHKHCRDIDECQQGNLCVNGQCKNTEGSFRCT<br>CGQGYQLSAAKDQCEDIDECQHRHLCAHGQCRNTEGSFQCV<br>CDQGYRASGLGDHCEDINECLEDKSVCQRGDCINTAGSYDCT<br>CPDGFQLDDNKTCQDINECEHPGLCGPQGECLNTEGSFHCV<br>CQQGFSISADGRTCEDIDECVNNTVCDSHGFCDNTAGSFRCL<br>CYQGFQAPQDGQGCVDVNECELLSGVCGEAFCENVEGSFLC<br>VCADENQEYSPMTGQCRSRTSTDLDVDVDQPKEEKKECYYN<br>LNDASLCDNVLAPNVTKQECCCTSGVGWGDNCEIFPCPVLGT<br>AEFTEMCPKGKGFVPAGESSSEAGGENYKDADECLLFGQEIC<br>KNGFCLNTRPGYECYCKQGTYYDPVKLQCFDMDECQDPSSC<br>IDGQCVNTEGSYNCFCTHPMVLDASEKRCIRPAESNEQIEETD<br>VYQDLCWEHLSDEYVCSRPLVGKQTTYTECCCLYGEAWGMQ<br>CALCPLKDSDDYAQLCNIPVTGRRQPYGRDALVDFSEQYTPE<br>ADPYFIQDRFLNSFEELQAEECGILNGCENGRCVRVQEGYTC<br>DCFDGYHLDTAKMTCVDVNECDELNNRMSLCKNAKCINTDGS<br>YKCLCLPGYVPSDKPNYCTPLNTALNLEKDSDLE | 50 |
| LTBP3 | GPAGERGAGGGGALARERFKVVFAPVICKRTCLKGQCRDSC<br>QQGSNMTLIGENGHSTDTLTGSGFRVVVCPLPCMNGGQCSS<br>RNQCLCPPDFTGRFCQVPAGGAGGGTGGSGPGLSRTGALST<br>GALPPLAPEGDSVASKHAIYAVQVIADPPGPGEGPPAQHAAFL<br>VPLGPGQISAEVQAPPPVVNVRVHHPPEASVQVHRIESSNAE<br>SAAPSQHLLPHPKPSHPRPPTQKPLGRCFQDTLPKQPCGSNP<br>LPGLTKQEDCCGSIGTAWGQSKCHKCPQLQYTGVQKPGPVR<br>GEVGADCPQGYKRLNSTHCQDINECAMPGVCRHGDCLNNPG<br>SYRCVCPPGHSLGPSRTQCIADKPEEKSLCFRLVSPEHQCQH<br>PLTTRLTRQLCCCSVGKAWGARCQRCPTDGTAAFKEICPAGK<br>GYHILTSHQTLTIQGESDFSLFLHPDGPPKPQQLPESPSQAPP<br>PEDTEEERGVTTDSPVSEERSVQQSHPTATTTPARPYPELISR<br>PSPPTMRWFLPDLPPSRSAVEIAPTQVTETDECRLNQNICGH<br>GECVPGPPDYSCHCNPGYRSHPQHRYCVDVNECEAEPCGP<br>GRGICMNTGGSYNCHCNRGYRLHVGAGGRSCVDLNECAKP<br>HLCGDGGFCINFPGHYKCNCYPGYRLKASRPPVCEDIDECRD<br>PSSCPDGKCENKPGSFKCIACQPGYRSQGGGACRDVNECAE<br>GSPCSPGWCENLPGSFRCTCAQGYAPAPDGRSCLDVDECEA | 51 |

TABLE 17-continued

| Exemplary LTBP amino acid sequences | | |
|---|---|---|
| Protein | Sequence | SEQ ID NO |
| | GDVCDNGICSNTPGSFQCQCLSGYHLSRDRSHCEDIDECDFP AACIGGDCINTNGSYRCLCPQGHRLVGGRKCQDIDECSQDPS LCLPHGACKNLQGSYVCVCDEGFTPTQDQHGCEEVEQPHHK KECYLNFDDTVFCDSVLATNVTQQECCCSLGAGWGDHCEIYP CPVYSSAEFHSLCPDGKGYTQDNNIVNYGIPAHRDIDECMLFG SEICKEGKCVNTQPGYECYCKQGFYYDGNLLECVDVDECLDE SNCRNGVCENTRGGYRCACTPPAEYSPAQRQCLSPEEMDVD ECQDPAACRPGRCVNLPGSYRCECRPPVVVPGPSGRDCQLP ESPAERAPERRDVCWSQRGEDGMCAGPLAGPALTFDDCCC RQGRGWGAQCRPCPPRGAGSHCPTSQSESNSFVVDTSPLLL GKPPRDEDSSEEDSDECRCVSGRCVPRPGGAVCECPGGFQ LDASRARCVDIDECRELNQRGLLCKSERCVNTSGSFRCVCKA GFARSRPHGACVPQRRR | |

TABLE 18

| Exemplary GARP and LRRC33 amino acid sequences | | |
|---|---|---|
| Protein | Sequence | SEQ ID NO |
| GARP | AQHQDKVPCKMVDKKVSCQVLGLLQVPSVLPPDTETLDLSGNQ LRSILASPLGFYTALRHLDLSTNEISFLQPGAFQALTHLEHLSLAH NRLAMATALSAGGLGPLPRVTSLDLSGNSLYSGLLERLLGEAPS LHTLSLAENSLTRLTRHTFRDMPALEQLDLHSNVLMDIEDGAFE GLPRLTHLNLSRNSLTCISDFSLQQLRVLDLSCNSIEAFQTASQP QAEFQLTWLDLRENKLLHFPDLAALPRLIYLNLSNNLIRLPTGPP QDSKGIHAPSEGWSALPLSAPSGNASGRPLSQLLNLDLSYNEIE LIPDSFLEHLTSLCFLNLSRNCLRTFEARRLGSLPCLMLLDLSHN ALETLELGARALGSLRTLLLQGNALRDLPPYTFANLASLQRLNLQ GNRVSPCGGPDEPGPSGCVAFSGITSLRSLSLVDNEIELLRAGA FLHTPLTELDLSSNPGLEVATGALGGLEASLEVLALQGNGLMVL QVDLPCFICLKRLNLAENRLSHLPAVVTQAVSLEVLDLRNNSFSLL PGSAMGGLETSLRRLYLQGNPLSCCGNGVVLAAQLHQGRVDVD ATQDLICRFSSQEEVSLSHVRPEDCEKGGLKNINLIIILTFILVSAIL LTTLAACCCVRRQKFNQQYKA | 52 |
| sGARP | AQHQDKVPCKMVDKKVSCQVLGLLQVPSVLPPDTETLDLSGNQ LRSILASPLGFYTALRHLDLSTNEISFLQPGAFQALTHLEHLSLAH NRLAMATALSAGGLGPLPRVTSLDLSGNSLYSGLLERLLGEAPS LHTLSLAENSLTRLTRHTFRDMPALEQLDLHSNVLMDIEDGAFE GLPRLTHLNLSRNSLTCISDFSLQQLRVLDLSCNSIEAFQTASQP QAEFQLTWLDLRENKLLHFPDLAALPRLIYLNLSNNLIRLPTGPP QDSKGIHAPSEGWSALPLSAPSGNASGRPLSQLLNLDLSYNEIE LIPDSFLEHLTSLCFLNLSRNCLRTFEARRLGSLPCLMLLDLSHN ALETLELGARALGSLRTLLLQGNALRDLPPYTFANLASLQRLNLQ GNRVSPCGGPDEPGPSGCVAFSGITSLRSLSLVDNEIELLRAGA FLHTPLTELDLSSNPGLEVATGALGGLEASLEVLALQGNGLMVL QVDLPCFICLKRLNLAENRLSHLPAVVTQAVSLEVLDLRNNSFSLL PGSAMGGLETSLRRLYLQGNPLSCCGNGVVLAAQLHQGRVDVD ATQDLICRFSSQEEVSLSHVRPEDCEKGGLKNIN | 53 |
| LRRC33 (also known as NRROS; Uniprot Accession No. Q86YC3) | **MELLPLWLCLGFHFLTVG**WRNRSGTATAASQGVCKLVGGAAD CRGQSLASVPSSLPPHARMLTLDANPLKTLVVNHSLQPYPLLESL SLHSCHLERISRGAFQEQGHLRSLVLGDNCLSENYEETAAALHA LPGLRRLDLSGNALTEDMAALMLQNLSSLRSVSLAGNTIMRLDD SVFEGLERLRELDLQRNYIFEIEGGAFDGLAELRHLNLAFNNLPCI VDFGLTRLRVLNVSYNVLEWFLATGGEAAFELETLDLSHNQLLF FPLLPQYSKLRTLLLRDNNMGFYRDLYNTSSPREMVAQFLLVDG NVTNITTVSLVVEEFSSSDLADLRFLDMSQNQFQYLPDGFLRKMP SLSHLNLHQNCLMTLHIREHEPPGALTELDLSHNQLSELHLAPGL ASCLGSLRLFNLSSNQLLGVPPGLFANARNITTLDMSHNQISLCP LPAASDRVGPPSCVDFRNMASLRSLSLEGCGLGALPDCPFQGT SLTYLDLSSNWGVLNGSLAPLQDVAPMLQVLSLRNMGLHSSFM ALDFSGFGNLRDLDLSGNCLTTFPRFGGSLALETLDLRRNSLTA LPQKAVSEQLSRGLRTIYLSQNPYDCCGVDGWGALQHGQTVAD WAMVTCNLSSKIIRVTELPGGVPRDCKWERLDLGLLYLVLILPSC LTLLVACTVIVLTFKKPLLQVIKSRCHWSSVY *Native signal peptide is depicted in bold font. | 83 |

TABLE 18-continued

| Exemplary GARP and LRRC33 amino acid sequences | | |
|---|---|---|
| Protein | Sequence | SEQ ID NO |
| soluble LRRC33 (sLRRC33) | **MDMRVPAQLLGLLLLWFSGVLG**VVWRNRSGTATAASQGVCKLVG<br>GAADCRGQSLASVPSSLPPHARMLTLDANPLKTLWNHSLQPYP<br>LLESLSLHSCHLERISRGAFQEQGHLRSLVLGDNCLSENYEETA<br>AALHALPGLRRLDLSGNALTEDMAALMLQNLSSLRSVSLAGNTI<br>MRLDDSVFEGLERLRELDLQRNYIFEIEGGAFDGLAELRHLNLAF<br>NNLPCIVDFGLTRLRVLNVSYNVLEWFLATGGEAAFELETLDLSH<br>NQLLFFPLLPQYSKLRTLLLRDNNMGFYRDLYNTSSPREMVAQF<br>LLVDGNVTNITTVSLWEEFSSSDLADLRFLDMSQNQFQYLPDGF<br>LRKMPSLSHLNLHQNCLMTLHIREHEPPGALTELDLSHNQLSEL<br>HLAPGLASCLGSLRLFNLSSNQLLGVPPGLFANARNITTLDMSH<br>NQISLCPLPAASDRVGPPSCVDFRNMASLRSLSLEGCGLGALPD<br>CPFQGTSLTYLDLSSNWGVLNGSLAPLQDVAPMLQVLSLRNMG<br>LHSSFMALDFSGFGNLRDLDLSGNCLTTFPRFGGSLALETLDLR<br>RNSLTALPQKAVSEQLSRGLRTIYLSQNPYDCCGVDGWGALQH<br>GQTVADWAMVTCNLSSKIIRVTELPGGVPRDCKWERLDLGLHH<br>HHHH<br>*Modified human kappa light chain signal peptide is depicted in bold font.<br>**Histidine tag is underlined. | 84 |
| Human LRRC33-GARP chimera | **MDMRVPAQLLGLLLLWFSGVLG**WRNRSGTATAASQGVCKLVG<br>GAADCRGQSLASVPSSLPPHARMLTLDANPLKTLWNHSLQPYP<br>LLESLSLHSCHLERISRGAFQEQGHLRSLVLGDNCLSENYEETA<br>AALHALPGLRRLDLSGNALTEDMAALMLQNLSSLRSVSLAGNTI<br>MRLDDSVFEGLERLRELDLQRNYIFEIEGGAFDGLAELRHLNLAF<br>NNLPCIVDFGLTRLRVLNVSYNVLEWFLATGGEAAFELETLDLSH<br>NQLLFFPLLPQYSKLRTLLLRDNNMGFYRDLYNTSSPREMVAQF<br>LLVDGNVTNITTVSLWEEFSSSDLADLRFLDMSQNQFQYLPDGF<br>LRKMPSLSHLNLHQNCLMTLHIREHEPPGALTELDLSHNQLSEL<br>HLAPGLASCLGSLRLFNLSSNQLLGVPPGLFANARNITTLDMSH<br>NQISLCPLPAASDRVGPPSCVDFRNMASLRSLSLEGCGLGALPD<br>CPFQGTSLTYLDLSSNWGVLNGSLAPLQDVAPMLQVLSLRNMG<br>LHSSFMALDFSGFGNLRDLDLSGNCLTTFPRFGGSLALETLDLR<br>RNSLTALPQKAVSEQLSRGLRTIYLSQNPYDCCGVDGWGALQH<br>GQTVADWAMVTCNLSSKIIRVTELPGGVPRDCKWERLDLGL*LIII*<br>*LTFILVSAILLTTLAACC*CVRRQKFNQQYKA<br>*Modified human kappa light chain signal peptide is depicted in bold font.<br>**LRRC33 ectodomain is underlined.<br>#GARP transmembrane domain is italicized.<br>##GARP intracellular tail is double underlined. | 101 |

Safety/Toxicity Considerations

Histopathology, Toxicology

As mentioned above, known pan-inhibitors that antagonize all TGFβ isoforms, namely, TGFβ1, TGFβ2 and TGFβ3, have been documented to cause various toxicities across multiple mammalian species. Most notable known toxicities include cardiovascular toxicities (such as valvulopathy) and epithelial hyperplasia, skin lesions, inflammation and bleeding. More specifically, some of the observed toxicities associated with pan-TGFβ inhibitors (e.g., small molecule antagonists of the TGFβR and non-selective neutralizing antibodies) reported in the literature include the following.

Cardiovascular toxicities associated with TGFβ inhibition include, hyperplasia in aortic valve, right AV valve, and left AV valve; inflammation in aortic valve, left AV valve, and ascending aorta; hemorrhage in ascending aorta, aortic valve and left AV valve; connective tissue degeneration in ascending aorta (see for example, Strauber et al., (2014) "Non-clinical safety evaluation of a Transforming Growth Factor β receptor I kinase inhibitor in Fischer 344 rats and beagle dogs" *J. Clin. Pract* 4 (3): 1000196).

In addition, neutralizing antibodies that bind all three TGFβ isoforms have been associated with certain epithelial toxicities, which are summarized in the table below.

TABLE 19

| Epithelial and other toxicities across species for 1D11 and GC1008 | | | |
|---|---|---|---|
| | Mice | Cyno | Human |
| Toxicities | Hyperplasia and inflammation of tongue, gingiva, and esophagus.<br>Findings not reversible (12 wk recovery) | Hyperplasia of gingiva, nasal epithelium, and bladder<br>Anemia lead to cessation of treatment<br>Changes were reversible (except bladder) | Gingival bleeding<br>Epistaxis<br>Headache<br>Fatigue<br>Various skin disorders, including keratoacanthomas (KA), hyperkeratosis, |

TABLE 19-continued

Epithelial and other toxicities across species for 1D11 and GC1008

| | Mice | Cyno | Human |
|---|---|---|---|
| | | | cutaneous SCC, and basal cell carcinoma |
| Drug/Dose/ Duration | 1D11 Dosing: 50 mg/kg (3x/week) Duration: 9-12 weeks | GC1008 Dosing: 10 and 50 mg/kg Duration: 6 months | GC1008 Dose: 0.1, 0.3, 1, 3, 10, 15 mg/kg Duration: 4 monthly doses |
| Exposure | Serum conc. = 1-2 mg/mL (over 4-12 weeks) | Not disclosed | Half-life: 21.7 d DN Cmax ~(350 ng/mL) mg |

*Vitsky et al., *Am. J Pathology* vol. 174, 2009; and Lonning et al., *Current Pharmaceutical Biotech*, 12, 2176-2189. 2011

Applicant of the present disclosure previously demonstrated the improved safety profiles of monoclonal antibodies that selectively block the activation step of TGFβ1 by targeting latent proTGFβ1 complex (see, for example, WO 2017/156500 and WO 2018/129329). In rat toxicology studies described therein, there were no observable test article-related toxicities when the animals were dosed with the inhibitors up to 100 mg/kg per week for 4 weeks.

Building upon the earlier recognition by the applicant of the present disclosure (see, e.g., WO 2017/156500) that lack of isoform-specificity of conventional TGFβ antagonists may underlie the source of toxicities associated with TGFβ inhibition, the present inventors sought to further achieve broad-spectrum TGFβ1 inhibition for treating various diseases that manifest multifaceted TGFβ1 dysregulation, while maintaining the safety/tolerability aspect of isoform-selective inhibitors. One of the aims of the work presented herein was therefore to maintain at least the same or equivalent level of safety profiles while increasing potency of such inhibitors by specifically selecting, among high-affinity inhibitors, a subset of antibodies with particularly low dissociation rates ($k_{OFF}$) in order to improve durability. Indeed, data presented herein show that the objective has been achieved.

Thus, in some embodiments, the novel antibody according to the present disclosure has the maximally tolerated dose (MTD) of >100 mg/kg when dosed weekly for at least 4 weeks (e.g., 4, 6, 8, 10, 12 weeks). In some embodiments, the novel antibody according to the present disclosure has the no observed adverse effect level (NOAEL) of up to 100 mg/kg when dosed weekly for at least 4 weeks in rats. In some embodiments, the antibody has a NOAEL of at least 100 mg/kg/week when dosed for 4 weeks or 12 weeks in mice. Suitable animal models to be used for conducting safety/toxicology studies for TGFβ inhibitors and TGFβ1 inhibitors include, but are not limited to: rats, dogs, cynos, and mice. In preferred embodiments, the minimum effective amount of the antibody based on a suitable preclinical efficacy study is below the NOAEL. More preferably, the minimum effective amount of the antibody is about one-third or less of the NOAEL. In particularly preferred embodiments, the minimum effective amount of the antibody is about one-sixth or less of the NOAEL. In some embodiments, the minimum effective amount of the antibody is about one-tenth or less of the NOAEL.

In some embodiments, the invention encompasses an isoform-selective antibody capable of inhibiting TGFβ1 signaling, which, when administered to a subject, does not cause cardiovascular or known epithelial toxicities at a dose effective to treat a TGFβ1-related indication. In some embodiments, the TGFβ inhibitor is TGFβ1-isoform selective in that it does not inhibit TGFβ2. In some embodiments, the TGFβ inhibitor is TGFβ1-isoform selective in that it does not inhibit TGFβ3. In some embodiments, the TGFβ inhibitor is TGFβ1-isoform selective in that it does not inhibit TGFβ2 and TGFβ3. In some embodiments, the antibody has a minimum effective amount of about 3-10 mg/kg administered weekly, biweekly or monthly. Preferably, the antibody causes no to minimum toxicities at a dose that is at least six-times the minimum effective amount (e.g., a six-fold therapeutic window). More preferably, the antibody causes no to minimum toxicities at a dose that is at least ten-times the minimum effective amount (e.g., a ten-fold therapeutic window). Even more preferably, the antibody causes no to minimum toxicities at a dose that is at least fifteen-times the minimum effective amount (e.g., a fifteen-fold therapeutic window).

Thus, selection of an antibody or an antigen-binding fragment thereof for therapeutic use may include: selecting an antibody or antigen-binding fragment that meets the criteria of one or more of TGFβ inhibitors (such as monoclonal antibodies and antigen-binding fragments selected for example for having slow dissociation rates, e.g., $k_{OFF}$ of 10.0E-4 or less); carrying out an in vivo efficacy study in a suitable preclinical model to determine an effective amount of the antibody or the fragment; carrying out an in vivo safety/toxicology study in a suitable model to determine an amount of the antibody that is safe or toxic (e.g., MTD, NOAEL, or any art-recognized parameters for evaluating safety/toxicity); and, selecting the antibody or the fragment that provides at least a three-fold therapeutic window (preferably 6-fold, more preferably a 10-fold therapeutic window, even more preferably a 15-fold therapeutic window). The selected antibody or the fragment may be used in the manufacture of a pharmaceutical composition comprising the antibody or the fragment. Such pharmaceutical composition may be used in the treatment of a TGFβ1 indication in a subject as described herein. For example, the TGFβ1 indication may be a fibrotic disorder and/or a proliferative disorder. Preferably, a TGFβ inhibitor to be selected for therapeutic use or large-scale manufacture, does not produce observable adverse effects in the treated animals after at least 4 week, e.g., 8 weeks, and 12 weeks, of sustained exposure. In some embodiments, certain toxicities observed in histopathological analyses are considered non-adverse.

Immune Safety Assessment

Cytokines play an important role in normal immune responses, but when the immune system is triggered to become hyperactive, the positive feedback loop of cytokine production can lead to a "cytokine storm" or hypercytokinemia, a situation in which excessive cytokine production causes an immune response that can damage organs, especially the lungs and kidneys, and even lead to death. Such condition is characterized by markedly elevated proinflammatory cytokines in the serum.

Historically, a Phase 1 Trial of the anti-CD28 monoclonal antibody TGN1412 in healthy volunteers led to a life-threatening "cytokine storm" response resulted from an unexpected systemic and rapid induction of proinflammatory cytokines (Suntharalingam G et al., *N Engl J Med.* 2006 Sep. 7;355 (10): 1018-28). This incident prompted heightened awareness of the potential danger associated with pharmacologic stimulation of T cells.

Whilst TGFβ-directed therapies do not target a specific T cell receptor or its ligand, it is contemplated that it is prudent to carry out immune safety assessment, including, for example, in vitro cytokine release assays, in vivo cytokine measurements from plasma samples of non-human primate treated with a TGFβ inhibitor, and platelet assays using human platelets.

In some embodiments, selection of a TGFβ inhibitor for therapeutic use and/or large-scale production thereof includes an assessment of the ability for the TGFβ inhibitor to trigger cytokine release from cytokine-producing cells. In such an assessment, one or more of the cytokines (e.g., inflammatory cytokines) IL-2, TNFα, IFNγ, IL-1B, CCL2 (MCP-1), and IL-6 may be assayed. In some embodiments, the cytokine-producing cells may include peripheral blood mononuclear cell (PBMC) constituents from heathy donors. Cytokine response after exposure to the TGFβ inhibitor (such as an antibody disclosed) herein may be compared to release after exposure to a control, e.g., an IgG isotype negative control, or any other suitable control depending on the TGFβ inhibitor being tested. Cytokine activation may be assessed in plate-bound (e.g., immobilized) and/or soluble assay formats. Levels of IFNγ, IL-2, IL-1β, TNFα, IL-6, and CCL2 (MCP-1) should not exceed 10-fold, e.g., 8—, 6—, 4—, or 2-fold the activation in the negative control. In some embodiments, a positive control may also be used to confirm cytokine activation in the sample, e.g., in the PBMCs. In some embodiments, these in vitro cytokine release results may be further confirmed in vivo, e.g., in an animal model such as a monkey toxicology study, e.g., a 4-week GLP or non-GLP repeat-dose monkey study.

Human platelets have been reported to express GARP, which can form TGFβ1 LLCs (Tran et al., 2009. *Proc. Nat'l. Acad. Sci. USA.* 106 (32): 13445-13450). In some embodiments, an antibody disclosed herein does not significantly bind GARP expressed on platelets. In some embodiments, platelet activation is evaluated in vitro. In some embodiments, platelet aggregation, binding, and activation may be assessed in human whole blood or platelet-rich plasma from healthy donors. Platelet aggregation and binding after exposure to an antibody disclosed herein, may be compared to exposure to a negative control, e.g., saline solution, or a reference article in a vehicle, e.g., a buffered solution. In selecting a suitable TGFβ inhibitor for therapeutic use, the candidate drug should be evaluated to ensure that it does not trigger spontaneous or agonist-induced activation. In addition, the drug should not interfere with the normal function of platelets (e.g., aggregation or clotting).

In certain embodiments, platelet aggregation and binding do not exceed 10% above the aggregation in the negative control. In some embodiments, platelet activation following exposure to an antibody disclosed herein, may be compared to exposure to a positive control, e.g., adenosine diphosphate (ADP). The activation status of platelets may be determined by surface expression of activation markers e.g., CD62P (P-Selectin) and GARP detectable by flow cytometry. Platelet activation should not exceed 10% above the activation in the negative control. In some embodiments, in vitro platelet response results may be further confirmed in vivo, e.g., in an animal model such as an immune-directed safety study in non-human primates.

In some embodiments, selection of an antibody or an antigen-binding fragment thereof for therapeutic use may include: identifying an antibody or antigen-binding fragment that meets the criteria of one or more of those described herein; carrying out an in vivo efficacy study in a suitable preclinical model to determine an effective amount of the antibody or the fragment; carrying out an in vivo safety/toxicology study in a suitable model to determine an amount of the antibody that is safe or toxic (e.g., MTD, NOAEL, or any art-recognized parameters for evaluating safety/toxicity); and, selecting the antibody or the fragment that provides at least a three-fold therapeutic window (preferably 6-fold, more preferably a 10-fold therapeutic window, even more preferably a 15-fold therapeutic window). In certain embodiments, the in vivo efficacy study is carried out in two or more suitable preclinical models that recapitulate human conditions. In some embodiments, such preclinical models comprise TGFβ1-positive fibrosis. In some embodiments, the preclinical models are selected from liver fibrosis model, kidney fibrosis model, lung fibrosis model, heart (cardiac) fibrosis model, skin fibrosis model.

Identification of an antibody or antigen-binding fragment thereof for therapeutic use may further include carrying out an immune safety assay, which may include, but is not limited to, measuring cytokine release and/or determining the impact of the antibody or antigen-binding fragment on platelet binding, activation, and/or aggregation. In certain embodiments, cytokine release may be measured in vitro using PBMCs or in vivo using a preclinical model such as non-human primates. In certain embodiments, the antibody or antigen-binding fragment thereof does not induce a greater than 10-fold release in IL-6, IFNγ, and/or TNFα levels as compared to levels in an IgG control sample in the immune safety assessment. In certain embodiments, assessment of platelet binding, activation, and aggregation may be carried out in vitro using PBMCs. In some embodiments, the antibody or antigen-binding fragment thereof does not induce a more than 10% increase in platelet binding, activation, and/or aggregation as compared to buffer or isotype control in the immune safety assessment.

The selected antibody or the fragment may be used in the manufacture of a pharmaceutical composition comprising the antibody or the fragment. Such pharmaceutical composition may be used in the treatment of a TGFβ indication in a subject as described herein. For example, the TGFβ indication may be a fibrotic disorder, such as organ fibrosis, e.g., liver fibrosis. Thus, the invention includes a method for manufacturing a pharmaceutical composition comprising a TGFβ inhibitor, wherein the method includes the step of selecting a TGFβ inhibitor which is tested for immune safety as assessed by immune safety assessment comprising a cytokine release assay and optionally further comprising a platelet assay. The TGFβ inhibitor selected by the method does not trigger unacceptable levels of cytokine release, as compared to control (such as IgG control). Similarly, the TGFβ inhibitor selected by the method does not cause unacceptable levels of platelet aggregation, platelet activation and/or platelet binding. Such TGFβ inhibitor is then manufactured at large-scale, for example 250L or greater, e.g., 1000L, 2000L, 3000L, 4000L or greater, for commercial production of the pharmaceutical composition comprising the TGFβ inhibitor.

Isoform Selectivity and Mechanisms of Action of TGFβ Inhibitors

TGFβ inhibitors useful for carrying out various embodiments of the invention are aimed to pharmacologically interfere with one or more aspects of TGFβ1 function in vivo. The TGFβ inhibitor may be a TGFβ1 inhibitor, such as a TGFβ1-isoform selective inhibitor, or an isoform-non-selective inhibitor. Isoform-non-selective inhibitors include, without limitation, low molecular weight ALK5 antagonists, neutralizing antibodies that bind two or more of TGFβ1/2/3, e.g., GC1008 and variants, antibodies that bind TGFβ1/3, and ligand traps, e.g., TGFβ1/3 inhibitors.

From a safety standpoint, there has been an increasing recognition that broad inhibition of TGFβ across isoforms may be a cause of observed toxicities, which underscores the fact that no TGFβ inhibitors have been successfully developed to this day. To circumvent potentially dangerous adverse effects, a number of groups have recently turned to identifying inhibitors that target a subset-but not all—of the isoforms and still retain efficacy. From an efficacy standpoint, however, the prevailing view of the field remains to be that it is advantageous to inhibit multiple isoforms of TGFβ to achieve therapeutic effects, and to accommodate this, toxicity management by "careful dosing regimen" is suggested as a solution (Brennan et al., (2018) mAbs, 10:1, 1-17). Consistent with this premise, numerous groups are developing TGFβ inhibitors that target more than one isoform. These include low molecular weight antagonists of TGFβ receptors, e.g., ALK5 antagonists, such as Galunisertib (LY2157299 monohydrate, Eli Lilly); monoclonal antibodies (such as neutralizing antibodies) that inhibit all three isoforms ("pan-inhibitor" antibodies) (see, for example, WO 2018/134681); monoclonal antibodies that preferentially inhibit two of the three isoforms (e.g., antibodies against TGFβ1/2 (for example, WO 2016/161410) and TGFβ1/3 (for example, WO 2006/116002 and WO 2020/051333); integrin inhibitors such as antibodies that bind to αvβ3, αvβ5, αvβ6, αvβ8, $\alpha_5\beta_1$, $\alpha_{IIb}\beta_3$, or $\alpha_8\beta_1$ integrins and inhibit downstream activation of TGFβ, e.g., selective inhibition of TGFβ1 and/or TGFβ3 (e.g., PLN-74809, a small-molecule, dual selective inhibitor of αvβ1/αvβ6, Pliant Therapeutics, San Francisco, CA), and engineered molecules (e.g., fusion proteins) such as ligand traps (for example, see Internation Publication Nos. WO 2018/029367; WO 2018/129331 and WO 2018/158727). Similarly, inhibitors of integrins such as αvβ6 also block integrin-dependent activation of both TGFβ1 and TGFβ3 and therefore may be considered as isoform-non-selective inhibitors of TGFβ signaling.

Previously, Applicant demonstrated that inhibition of TGFβ1 alone was sufficient to sensitize immunosuppressive tumors to a checkpoint inhibitor therapy even in tumors where both TGFβ1/3 are co-expressed (see International Publication No. WO/2020/014460). Similarly, TGFβ1-selective inhibitors are shown to mitigate fibrosis in preclinical models, including mouse liver fibrosis model where both of the TGFβ1/3 isoforms are co-expressed in the fibrotic tissue, albeit in discrete cell types (herein). Surprisingly, inhibition of TGFβ3 promoted pro-fibrotic phenotypes. The exacerbation of fibrosis is observed when the TGFβ3 inhibitor is used alone. In addition, when used in combination with a TGFβ1-selective inhibitor, the TGFβ3 inhibitor attenuated the anti-fibrotic effect of the TGFβ1-selective inhibitor, as evidenced by increased collagen accumulation in the fibrotic liver. These results raise the possibility that inhibitory potency against TGFβ3 may be an undesirable feature of TGFβ inhibitors to be used as therapy in situations where fibrosis is a concern.

Beyond the fibrosis context, there is a broader implication to this unexpected finding since the pro-fibrotic phenotype (e.g., increased collagen deposit into the ECM) is associated not only with fibrosis, but also with aspects of cancer progression, such as tumor invasion and metastasis. See, for example, Chakravarthy et al., (*Nature Communications*, (2018) 9:4692. "TGF-β-associated extracellular matrix genes link cancer-associated fibroblasts to immune evasion and immunotherapy failure"). Diseased tissues with dysregulated ECM, including fibrotic tissues and stroma of various tumor types, can express both TGFβ1 and TGFβ3. As of today, multiple groups are making effort to develop TGFβ inhibitors that target both of these isoforms, such as ligand traps, neutralizing antibodies and integrin inhibitors. However, the finding presented herein suggests that such approach may in fact exacerbate the disease.

Accordingly, the present disclosure provides the teaching that for the treatment of a disorder involving ECM dysregulation, such as fibrosis and cancer, a TGFβ inhibitor that does not specifically target TGFβ3 should be selected. Preferably, such inhibitor is an isoform-selective inhibitor of TGFβ1. Related methods include a method for selecting a TGFβ inhibitor for use in the treatment of a fibrotic disorder in a subject, wherein the method includes the steps of: testing potency of one or more candidate inhibitors for the ability to inhibit TGFβ1, TGFβ2 and TGFβ3, and selecting an inhibitor that inhibits TGFβ1 but does not inhibit TGFβ3, for therapeutic use. Related treatment methods can further comprise a step of administering to the subject the inhibitor that inhibits TGFβ1 but does not inhibit TGFβ3 in an amount sufficient to treat the fibrotic disorder or treat a subject having or at risk of developing a fibrotic disorder and/or a cardiovascular disease. In some embodiments, subjects at risk of developing a fibrotic disorder may suffer from a metabolic disorder, such as diabetes, obesity and NASH. The proposed exclusion of the subpopulation of patients is aimed to reduce risk of triggering, facilitating or exacerbating a pro-fibrotic effect.

In preferred embodiments, a TGFβ inhibitor for use in the treatment of a fibrotic disorder is an isoform-selective activation inhibitor of TGFβ1 (such as the novel antibodies with low $k_{OFF}$ disclosed herein) capable of targeting TGFβ1-containing latent complexes in vivo. In some embodiments, the inhibitor is selected from the group consisting of: Ab37, Ab38, Ab39, Ab40, Ab41, Ab42, Ab43, Ab44, Ab45, Ab46, Ab47, Ab48, Ab49, Ab50, Ab51 and Ab52. In preferred embodiments, the isoform-selective activation inhibitor of TGFβ1 is Ab2, Ab42, Ab46, Ab50, or derivatives thereof. Preferably, the isoform-selective activation inhibitor of TGFβ1 is Ab46 or an engineered molecule comprising an antigen-binding fragment thereof.

Thus, the antibody of the invention is aimed to target the following complexes in a disease site (e.g., TME or fibrotic tissue) where it preemptively binds the latent complex thereby preventing the growth factor from being released: i) proTGFβ1 presented by GARP; ii) proTGFβ1 presented by LRRC33; iii) proTGFβ1 presented by LTBP1; and iv) proTGFβ1 presented by LTBP3. Typically, complexes (i) and (ii) above are present on cell surface because both GARP and LRRC33 are transmembrane proteins capable of presenting or tethering latent proTGFβ1 on the extracellular face of the cell expressing GARP or LRRC33, whilst complexes (iii) and (iv) are components of the extracellular matrix. In this way, the inhibitors embodied herein do away with having to complete binding with endogenous high affinity receptors for exerting inhibitory effects. Moreover, targeting upstream of the ligand/receptor interaction may enable more durable effects since the window of target accessibility is longer and more localized to relevant tissues than conventional inhibitors that target active, soluble growth factors only after it has been released from the latent complex.

A number of studies have shed light on the mechanisms of TGFβ1 activation. Three integrins, αVβ6, αvβ8, and αvβ1 have been demonstrated to be key activators of latent TGFβ1 (Reed, N. I., et al., *Sci Transl Med,* 2015. 7 (288): p. 288ra79; Travis, M. A. and D. Sheppard, *Annu Rev Immunol,* 2014. 32: p. 51-82; Munger, J. S., et al., *Cell,* 1999. 96 (3): p. 319-28). αV integrins bind the RGD sequence present in TGFβ1 and TGFβ1 LAPs with high affinity (Dong, X., et al., *Nat Struct Mol Biol,* 2014. 21 (12): p. 1091-6). Transgenic mice with a mutation in the TGFβ1 RGD site that prevents integrin binding, but not secretion, phenocopy the TGFβ1−/− mouse (Yang, Z. et al., *J Cell Biol,* 2007. 176 (6): p. 787-93). Mice that lack both β6 and β8 integrins recapitulate all essential phenotypes of TGFβ1 and TGFβ3 knockout mice, including multiorgan inflammation and cleft palate, confirming the essential role of these two integrins for TGFβ1/3 activation in development and homeostasis (Aluwihare, P., et al., *J Cell Sci,* 2009. 122 (Pt 2): p. 227-32). Key for integrin-dependent activation of latent TGFβ1 is the covalent tether to presenting molecules; disruption of the disulfide bonds between GARP and TGFβ1 LAP by mutagenesis does not impair complex formation, but completely abolishes TGFβ1 activation by αvβ6 (Wang, R., et al., *Mol Biol Cell,* 2012. 23 (6): p. 1129-39). The recent structure of latent TGFβ1 illuminates how integrins enable release of active TGFβ1 from the latent complex: the covalent link of latent TGFβ1 to its presenting molecule anchors latent TGFβ1, either to the ECM through LTBPs, or to the cytoskeleton through GARP or LRRC33. Integrin binding to the RGD sequence results in a force-dependent change in the structure of LAP, allowing active TGFβ1 to be released and bind nearby receptors (Shi, M., et al., *Nature,* 2011. 474 (7351): p. 343-9). The importance of integrin-dependent TGFβ1 activation in disease has also been well validated. A small molecular inhibitor of αVβ1 protects against bleomycin-induced lung fibrosis and carbon tetrachloride-induced liver fibrosis (Reed, N. I., et al., *Sci Transl Med,* 2015. 7 (288): p. 288ra79), and αvβ6 blockade with an antibody or loss of integrin 36 expression suppresses bleomycin-induced lung fibrosis and radiation-induced fibrosis (Munger, J. S., et al., *Cell,* 1999. 96 (3): p. 319-28); Horan, G. S., et al., *Am J Respir Crit Care Med,* 2008. 177 (1): p. 56-65). In addition to integrins, other mechanisms of TGFβ1 activation have been implicated, including thrombospondin-1 and activation by proteases such as thrombin, Plasmin, matrix metalloproteinases (MMPs, e.g., MMP2, MMP9 and MMP12), cathepsin D and kallikrein. Knockout of thrombospondin-1 recapitulates some aspects of the TGFβ1−/− phenotype in some tissues, but is not protective in bleomycin-induced lung fibrosis, known to be TGFβ-dependent (Ezzie, M. E., et al., *Am J Respir Cell Mol Biol,* 2011. 44 (4): p. 556-61). Additionally, knockout of candidate proteases did not result in a TGFβ1 phenotype (Worthington, J. J., J. E. Klementowicz, and M. A. Travis, *Trends Biochem Sci,* 2011. 36 (1): p. 47-54). This could be explained by redundancies or by these mechanisms being critical in specific diseases rather than development and homeostasis.

The antibodies of the present disclosure work by preventing the step of TGFβ1 activation. In some embodiments, such inhibitors can inhibit integrin-dependent (e.g., mechanical or force-driven) activation of TGFβ1. In some embodiments, such inhibitors can inhibit protease-dependent or protease-induced activation of TGFβ1. The latter includes inhibitors that inhibit the TGFβ1 activation step in an integrin-independent manner. In some embodiments, such inhibitors can inhibit TGFβ1 activation irrespective of the mode of activation, e.g., inhibit both integrin-dependent activation and protease-dependent activation of TGFβ1. Non-limiting examples of proteases which may activate TGFβ1 include serine proteases, such as Kallikreins, Chemotrypsin, Trypsin, Elastases, Plasmin, thrombin, as well as zinc metalloproteases (MMP family) such as MMP-2, MMP-9, MMP-12, MMP-13 and ADAM proteases (e.g., ADAM10 and ADAM17). Kallikreins include plasma-Kallikreins and tissue Kallikreins, such as KLK1, KLK2, KLK3, KLK4, KLK5, KLK6, KLK7, KLK8, KLK9, KLK10, KLK11, KLK12, KLK13, KLK14 and KLK15. Data presented herein demonstrate examples of an isoform-specific TGFβ1 inhibitors, capable of inhibiting Kallikrein-dependent activation of TGFβ1 in vitro. In some embodiments, inhibitors of the present invention prevent release or dissociation of active (mature) TGFβ1 growth factor from the latent complex.

In some embodiments, the antibodies according to the present disclosure may induce internalization of the complex comprising proTGFβ1 bound to LRRC33 or GARP on cell surface. In some embodiments, the antibodies are inhibitors of cell-associated TGFβ1 (e.g., GARP-presented proTGFβ1 and LRRC33-presented proTGFβ1). The invention includes antibodies or fragments thereof that specifically bind such complex (e.g., GARP-pro/latent TGFβ1 and LRRC33-pro/latent TGFβ1), thereby triggering internalization of the complex (e.g., endocytosis). This mode of action causes removal or depletion of the inactive TGFβ1 complexes from the cell surface (e.g., Treg, macrophages, MDSCs, etc.), hence reducing latent TGFβ1 available for activation.

TGFβ Inhibitors Suitable for Therapeutic Use

A body of evidence supports the notion that many diseases manifest complex perturbations of TGFβ signaling, which likely involve participation of heterogeneous cell types that confer different effects of TGFβ function, which are mediated by its interactions with so-called presenting molecules. At least four such presenting molecules have been identified, which can "present" TGFβ in various extracellular niches to enable its activation in response to local stimuli. In one category, TGFβ is deposited into the ECM in association with ECM-associated presenting molecules, such as LTBP1 and LTBP3, which mediate ECM-associated TGFβ activities. In another category, TGFβ is tethered onto the surface of cells (e.g., immune cells), via presenting molecules such as GARP and LRRC33, which mediate certain immune function. These presenting molecules show differential expression, localization and/or function in different tissues and cell types, indicating that triggering events and outcome of TGFβ activation will vary, depending on the biological or pathological microenvironment. Based on the notion that many TGFβ effects may interact and contribute to disease progression, therapeutic agents that can antagonize multiple facets of TGFβ function may provide greater efficacy.

In preferred embodiments, a TGFβ inhibitor for use in the treatment of a fibrotic disorder is an isoform-selective activation inhibitor of TGFβ1 (such as the novel antibodies with low $k_{OFF}$ disclosed herein) capable of targeting TGFβ1-containing latent complexes in vivo. In most preferred embodiments, the isoform-selective activation inhibitor of TGFβ1 is Ab2, Ab42, Ab46, Ab50, or derivatives thereof. Preferably, the isoform-selective activation inhibitor of TGFβ1 is Ab46 or an engineered molecule comprising an antigen-binding fragment thereof.

It has been recognized that various diseases involve heterogeneous populations of cells as multiple sources of TGFβ1 that collectively contribute to the pathogenesis and/or progression of the disease. More than one type of TGFβ1-containing complexes ("contexts") likely coexist within the same disease microenvironment. Therefore, the ability to inhibit TGFβ1 in different biological contexts may be important.

However, in certain situations, so-called context-biased antibodies that still specifically bind to all four antigen complexes but with stronger affinities for matrix-associated complexes over cell-associated complexes may be advantageous. The feature, i.e., differential binding affinities of these antibodies for the ECM complexes relative to immune cell complexes may raise the possibility that such inhibitors may be particularly suited as therapeutics to treat fibrotic conditions, such as organ fibrosis, in which affected patients receive a long-term therapeutic regimen to treat chronic conditions. In these circumstances, it is desirable to minimize unwanted inflammation triggered by immune stimulation.

In some embodiments, the antibodies of the present disclosure have greater affinities towards EMC-complexes, e.g., hLTBP1-proTGFβ1 and hLTBP3-proTGFβ1 ($K_D$ of <1 nM) over cell-associated complexes, as determined by, for example, solution equilibrium titration. It is envisaged that the EMC-biased antibodies are capable of preferentially targeting and inhibiting EMC-associated TGFβ1 in vivo. Such antibodies may be advantageous for use in the treatment of conditions with ECM dysregulation, such as abnormal remodeling and/or stiffness of the ECM. Typically, the ECM dysregulation may be accompanied by an increased number of myofibroblasts or myofibroblast-like cells in the disease environment, such as tumor microenvironment and fibrotic microenvironment. Many of the abnormal features of the ECM are often manifested in a wide range of pathological conditions, including fibrosis and proliferative disorders are at least in part driven by the TGFβ1 pathway.

The context-biased antibodies with weaker binding to a GARP-associated TGFβ complex (e.g., human GARP-proTGFβ1) may be used in the treatment of a condition where it is undesirable to stimulate the subject's immune response and/or in situations where the subject is expected to benefit from a long-term TGFβ inhibition therapy to manage a chronic condition, such as many types of fibrosis. Rationale for the therapeutic use of a TGFβ1 inhibitor with a weaker binding affinity for GARP-proTGFβ1 is at least threefold:

First, GARP is predominantly expressed on regulatory T cells, which play a crucial role in maintaining immune tolerance to self-antigens and in preventing autoimmune disease. Since Tregs generally suppress, dampen or down-regulate induction and proliferation of effector T cells, systemic inhibition of this function may lead to overactive or exaggerated immune responses in the host by disabling the "break" that is normally provided by Treg cells. Thus, the approach taken here (e.g., TGFβ1 inhibition without fully disabling Treg function) is aimed to avoid the risk of eliciting autoimmunity. Furthermore, patients who already have a propensity for developing over-sensitive immune responses or autoimmunity may be particularly at risk of triggering or exacerbating such conditions, without the availability of functional Tregs; and therefore, the inhibitors that at least partially preserve GARP-mediated TGFβ1 function may advantageously minimize such risk.

Second, evidence suggests that an alteration in the Th17/Treg ratio leads to an imbalance in pro-fibrotic Th17 cytokines, which correlate with severity of fibrosis, such as liver fibrosis (see, for example, Shoukry et al., (2017) J Immunol 198 (1 Supplement): 197.12). The present inventors reasoned that disabling perturbation of the GARP arm of TGFβ1 function may directly or indirectly exacerbate fibrotic conditions.

Third, regulatory T cells are indispensable for immune homeostasis and the prevention of autoimmunity. It was reasoned that, particularly for a TGFβ1 inhibition therapy intended for a long-term or chronic administration, it would be desirable to spare at least part of GARP-mediated TGFβ1 and avoid potential side effects stemming from complete perturbation of normal Treg function in maintaining immune homeostasis (reviewed in, for example, Richert-Spuhler and Lund (2015) Prog Mol Biol Transl Sci. 136:217-243). This strategy is at least in part aimed to preserve normal immune function, which is required, inter alia, for combatting infections.

TGFβ1-Related Indications

The isoform-specific TGFβ1 inhibitors described herein may be used to treat a TGFβ1-related indication in subjects. Various disease conditions have been suggested to involve dysregulation of TGFβ signaling as a contributing factor. Indeed, the pathogenesis and/or progression of certain human conditions appear to be predominantly driven by or dependent on TGFβ1 activities. Moreover, it is contemplated that there is crosstalk among TGFβ1-responsive cells. In some cases, interplays between multifaceted activities of the TGFβ1 axis may trigger a cascade of events that lead to disease progression, aggravation, and/or suppression of the host's ability to combat disease. For example, certain disease microenvironments, such as tumor microenvironment (TME), may be associated with TGFβ1 presented by multiple different presenting molecules, e.g., LTBP1-proTGFβ1, LTBP3-proTGFβ1, GARP-proTGFβ1, LRRC33-proTGFβ1, and any combinations thereof. TGFβ1 activities of one context may in turn regulate or influence TGFβ1 activities of another context, raising the possibility that when dysregulated, this may result in exacerbation of disease conditions. Therefore, it is desirable to broadly inhibit across multiple modes of TGFβ1 function (i.e., multiple contexts) while selectively limiting such inhibitory effects to the TGFβ1 isoform. The aim is not to perturb homeostatic TGFβ signaling mediated by the other isoforms, including TGFβ3, which plays an important role in would healing.

Moreover, recent observations in murine fibrosis models suggest detrimental effects of TGFβ3 inhibition (see Example 17) in tissues with dysregulated ECM, raising the possibility that role of TGFβ3 expands beyond homeostasis. Ample evidence suggests that dysregulation of the ECM is found in a number of disease conditions, including fibrosis and cancer. Indeed, many of the key profibrotic genes are also recognized among markers of various cancers. These markers include, for example, col1A1, col3A1, PAI-1, CCL2, ACTA2, FN-1, CTGF and TGFβ1. Therefore, the finding that concurrent blockade of TGFβ3 appears harmful in fibrosis may be applicable to a broader scope of conditions associated with ECM dysregulation.

In addition to the possible concerns of inhibiting TGFβ3 addressed above, Takahashi et al., (Nat Metab. 2019, 1 (2): 291-303) recently reported a beneficial role of TGFβ2 in regulating metabolism. The authors identified TGFβ2 as an exercise-induced adipokine, which stimulated glucose and fatty acid uptake in vitro, as well as tissue glucose uptake in vivo; which improved metabolism in obese mice; and, which reduced high fat diet-induced inflammation. Moreover, the authors obesrved that lactate, a metabolite released from muscle during exercise, stimulated TGFβ2 expression in human adipocytes and that a lactate-lowering agent reduced circulating TGFβ2 levels and reduced exercise-stimulated improvements in glucose tolerance. These observations suggest that therapeutic use of a TGFβ inhibitor with inhibitory activity towards the TGFβ2 isoform may be harmful, at least in the metabolic aspect.

Accordingly, the present disclosure provides a TGFβ inhibitor for use in the treatment of a TGFβ-related indication (e.g., fibrosis) in a subject, wherein, the TGFβ inhibitor inhibits TGFβ1 but does not inhibit TGFβ2. In some embodiments, the subject benefits from improved metabolism, wherein optionally, the subject has or is at risk of developing a metabolic disease, such as obesity, high fat diet-induced inflammation, glucose dysregulation (e.g., diabetes). In some embodiments, the TGFβ-related indication is cancer, wherein optionally the cancer comprises a solid tumor, such as locally advanced cancer and metastatic cancer. In some embodiments, the TGFβ-related indication is myelofibrosis. In some embodiments, the TGFβ-related indication is an immune disorder. In some embodiments, the TGFβ-related indication is fibrosis.

In some embodiments, the TGFβ inhibitor is TGFβ1-selective in that it does not inhibit TGFβ2. In some embodiments, the TGFβ inhibitor is TGFβ1-selective in that it does not inhibit TGFβ3. In preferred embodiments, the TGFβ inhibitor is TGFβ1-selective in that it does not inhibit TGFβ2 and TGFβ3.

Related methods for selecting a TGFβ inhibitor for therapeutic use are also encompassed herein. According to some embodiments, the TGFβ inhibitor is TGFβ-1 selective.

According to preferred embodiments, TGFβ1-selective inhibitors are selected for use in treating patients with a fatty liver (e.g., non-alcoholic fatty liver disease (NAFLD)) or fibrosis associated with non-alcoholic steatohepatitis (NASH). This is at least based on the rationale that i) avoiding TGFβ3 inhibition may reduce the risk of exacerbating ECM dysregulation (which may increase fibrosis), and ii) avoiding TGFβ2 inhibition may reduce the risk of increasing metabolic burden in the patients. The present invention extends the notion of selecting "the right TGFβ1 inhibitor" for "the right patient population" to treat a disease condition with certain criteria and/or clinical features. At least two inquiries may be made as to the identification/selection of suitable indications and/or patient populations for which the inhibitors of TGFβ1 described herein, are likely to have advantageous effects (e.g., clinical benefits): i) whether the disease is driven by or dependent predominantly on the TGFβ1 isoform over the other isoforms in human (or at least co-dominant); and ii) whether the disease involves both matrix-associated and/or immune cell-associated TGFβ1 function.

Differential expressions of the three known TGFβ isoforms, namely, TGFβ1, TGFβ2, and TGFβ3, have been observed under normal (healthy; homeostatic) as well as disease conditions in various tissues (note that "TGFβ" is sometimes used to refer to the gene as opposed to protein). Nevertheless, the concept of isoform selectivity has neither been fully exploited nor achieved with conventional approaches that favor pan-inhibition of TGFβ across multiple isoforms. Moreover, expression patterns of the isoforms may be differentially regulated, not only in normal (homeostatic) vs, abnormal (pathologic) conditions, but also in different subpopulations of patients. Because most preclinical studies are conducted in a limited number of animal models, data obtained with the use of such models may be biased, resulting in misinterpretations of data or misleading conclusions as to the applicability to human conditions (i.e., translatability).

Accordingly, the present invention includes the recognition that differential expression of TGFβ isoforms in preclinical animal models should be taken into account in predicting effectiveness of particular inhibitors, as well as in the meaningful interpretation of preclinical data as to the translatability into human clinical conditions. As exemplified herein, TGFβ1 and TGFβ3 are co-dominant in certain murine syngeneic cancer models (e.g., EMT-6 and 4T1) that are widely used in preclinical studies (see FIG. 13D). By contrast, numerous other cancer models (e.g., S91, B16 and MBT-2) express almost exclusively TGFβ1, similar to that observed in many human tumors, in which TGFβ1 appears to be more frequently the dominant isoform over TGFβ2/3 (see FIGS. 13B and 13C). Furthermore, the TGFβ isoform(s) predominantly expressed under homeostatic conditions may not be the disease-associated isoform(s). For example, in normal lung tissues in healthy rats, tonic TGFβ signaling appears to be mediated mainly by TGFβ3. However, TGFβ1 appears to become markedly upregulated in disease conditions, such as lung fibrosis. Taken together, it is beneficial to test or confirm relative expression of TGFβ isoforms in clinical samples so as to select suitable therapeutics to which the patient is likely to respond.

As described herein, the isoform-selective TGFβ1 inhibitors are particularly advantageous for the treatment of diseases in which the TGFβ1 isoform is predominantly expressed relative to the other isoforms (e.g., referred to as TGFβ1-dominant). As an example, a non-limiting list of human cancer clinical samples with relative expression levels of TGFβ1 (left), TGFβ2 (center) and TGFβ3 (right) is provided in FIG. 13C. Each horizontal lime across the three isoforms represents a single patient. As can be seen, overall TGFβ1 expression (TGFβ1) is significantly higher in most of these human tumors/cancers than the other two isoforms across many tumor/cancer types, suggesting that TGFβ1-selective inhibition may be beneficial in these disease types. More recent bioinformatic analyses also support the notion that TGFβ1 is the primary driver in a number of disease conditions.

In some embodiments, the TGFβ1-selective inhibitors disclosed herein are sufficient to treat a disease (e.g., fibrosis, solid tumors, etc.) despite co-expression of TGFβ1 and TGFβ3. In some embodiments, the antibody is selected from the group: Ab37, Ab38, Ab39, Ab40, Ab41, Ab42, Ab43, Ab44, Ab45, Ab46, Ab47, Ab48, Ab49, Ab50, Ab51 and Ab52. In preferred embodiments, the isoform-selective inhibitor of TGFβ1 is Ab2, Ab42, Ab46, Ab50, or derivatives thereof. Preferably, the isoform-selective activation inhibitor of TGFβ1 is Ab46 or an engineered molecule comprising an antigen-binding fragment thereof.

In certain instances, it is beneficial to test or confirm relative expression levels of the three TGFβ isoforms (i.e., TGFβ1/TGFβ1, TGFβ2/TGFβ2 and TGFβ3/TGFβ3) in clinical samples collected from individual patients. Such information may provide better prediction as to the effectiveness of a particular therapy in individual patients or patient populations, which can help ensure selection of appropriate treatment regimen (e.g., individualized/personalized treatment) in order to increase the likelihood of a clinical response.

Accordingly, the invention includes a method for selecting a patient population or a subject who is likely to respond to a therapy comprising an isoform-specific TGFβ1 inhibitor according to the present disclosure. Such method comprises the steps of: providing a biological sample (e.g., a clinical sample) collected from a subject, determining (e.g., measuring or assaying) relative levels of TGFβ1, TGFβ2 and TGFβ3 in the sample, and, administering to the subject a composition comprising the TGFβ1 inhibitor, if TGFβ1 is the dominant isoform over TGFβ2 and TGFβ3; and/or, if TGFβ1 is significantly overexpressed or upregulated as compared to control. In some embodiments, such method comprises the steps of: obtaining information on the relative expression levels of TGFβ1, TGFβ2 and TGFβ3 which was previously determined; identifying a subject to have TGFβ1-positive, preferably TGFβ1-dominant disease; and, administering to the subject the TGFβ1 inhibitor. In some embodiments, such subject has a disease (such as cancer) that is resistant to a therapy (such as cancer therapy). In some embodiments, such subject shows intolerance to the therapy and therefore has or is likely to discontinue the therapy. Addition of the TGFβ1 inhibitor to the therapeutic regimen may enable reducing the dosage of the first therapy and still achieve clinical benefits in combination. Preferably, the isoform-selective activation inhibitor of TGFβ1 is Ab46 or an engineered molecule comprising an antigen-binding fragment thereof.

Relative levels of the isoforms may be determined by RNA-based assays and/or protein-based assays, which are well-known in the art. In some embodiments, the step of administration may also include another therapy, such as immune checkpoint inhibitors, or other agents provided elsewhere herein. Such methods may optionally include a step of evaluating a therapeutic response by monitoring changes in relative levels of TGFβ1/TGFβ1, TGFβ2/TGFβ2 and TGFβ3/TGFβ3 at two or more time points. In some embodiments, clinical samples (such as biopsies) are collected both prior to and following administration. In some embodiments, clinical samples (such as biopsies) are collected multiple times following treatment to assess in vivo effects over time.

In addition to the first inquiry drawn to the aspect of isoform specificity, the second inquiry interrogates the breadth of TGFβ1 function involved in a particular disease. This may be represented by the number of TGFβ1 contexts, namely, which presenting molecule(s) mediate disease-associated TGFβ1 function. TGFβ1-specific, broad-context inhibitors, such as context-independent inhibitors, are advantageous for the treatment of diseases that involve both an ECM component and an immune component of TGFβ1 function. Such disease may be associated with dysregulation in the ECM as well as perturbation in immune cell function or immune response.

Whether or not a particular condition of a patient involves or is driven by multiple aspects of TGFβ1 function may be assessed by evaluating expression profiles of the presenting molecules, in a clinical sample collected from the patient. Various assays are known in the art, including RNA-based assays and protein-based assays, which may be performed to obtain expression profiles. Relative expression levels (and/or changes/alterations thereof) of LTBP1, LTBP3, GARP, and LRRC33 in the sample(s) may indicate the source and/or context of TGFβ1 activities associated with the condition. For instance, a biopsy sample taken from a solid tumor may exhibit high expression of all four presenting molecules. For example, LTBP1 and LTBP3 may be highly expressed in CAFs within the tumor stroma, while GARP and LRRC33 may be highly expressed by disease-associated immune cells, such as Tregs, MDSCs and leukocyte infiltrate, respectively. Similarly, LTBP1 and LTBP3 may be highly expressed in FAFs (e.g., myofibroblasts) within the fibrotic microenvironment, while LRRC33 may be highly expressed by fibrosis-associated immune cells, such as M2 macrophages and MDSCs.

Accordingly, the invention includes a method for determining (e.g., testing or confirming) the involvement of TGFβ1 in the disease, relative to TGFβ2 and TGFβ3. In some embodiments, the method further comprises a step of: identifying a source (or context) of disease-associated TGFβ1. In some embodiments, the source/context is assessed by determining the expression of TGFβ presenting molecules, e.g., LTBP1, LTBP3, GARP and LRRC33 in a clinical sample collected from patients. In some embodiments, tissue biopsies are used. In some embodiments, histopathological analyses may include digital pathology.

Isoform-selective TGFβ1 inhibitors, such as those described herein, may be used to treat a wide variety of diseases, disorders and/or conditions that are associated with TGFβ1 dysregulation (i.e., TGFβ1-related indications) in human subjects, As used herein, "disease (disorder or condition) associated with TGFβ1 dysregulation" or "TGFβ1-related indication" means any disease, disorder and/or condition related to expression, activity and/or metabolism of a TGFβ1 or any disease, disorder and/or condition that may benefit from inhibition of the activity and/or levels TGFβ1. Preferably, the isoform-selective activation inhibitor of TGFβ1 is Ab46 or an engineered molecule comprising an antigen-binding fragment thereof.

The present invention includes the use of such isoform-specific TGFβ1 inhibitor in a method for treating a disease associated with TGFβ1 dysregulation in a human subject. Such inhibitor is typically formulated into a pharmaceutical composition that further comprises a pharmaceutically acceptable excipient. TGFβ is a key regulator of ECM components, structure and function. Advantageously, the inhibitor targets both ECM-associated TGFβ1 signaling and immune cell-associated TGFβ1 signaling but does not target TGFβ2 and/or TGFβ3 signaling in vivo. In some embodiments, the inhibitor preferentially binds ECM-associated proTGFβ1 complexes thereby blocking TGFβ1 signaling in the matrix niche. The disease may involve dysregulation or impairment of ECM components or function and comprises increased collagen deposition. In some embodiments, the dysregulation or impairment of ECM components or function may further comprise increased stiffness and/or ECM reorganization. In some embodiments, the dysregulation or impairment of ECM components or function includes increased myofibroblast cells within the disease site. In some embodiments, the dysregulation of the ECM includes increased stiffness of the matrix. In some embodiments, the dysregulation of the ECM involves fibronectin and/or fibrillin. Preferably, the isoform-selective activation inhibitor of TGFβ1 is Ab46 or an engineered molecule comprising an antigen-binding fragment thereof.

In some embodiments, the disease is characterized by dysregulation or impairment of myeloid cell proliferation or differentiation; wherein optionally the dysregulation or impairment of myeloid cells comprises monocyte recruitment to the disease site or differentiation into polarized M2 cells, and/or, abnormal macrophage function. In some embodiments, the dysregulation of myeloid cells comprises increased levels of MDSCs. Elevated MDSCs may comprise an increased number/frequency of circulating MDSCs, e.g., in peripheral blood. Elevated MDSCs may be observed at the site of the disease, such as fibrotic tissues and solid tumors. The terms circulating and circulatory (as in "circulating MDSCs" and "circulatory MDSCs") may be used interchangeably.

In some embodiments, disease is a fibrotic disorder or disease (such as organ fibrosis). In some embodiments, the disclosure provides methods of using measurements of circulating MDSCs in treating fibrosis in subjects administered a TGFβ inhibitor. In some embodiments, the TGFβ inhibitor is TGFβ1-isoform selective in that it does not inhibit TGFβ2. In some embodiments, the TGFβ inhibitor is TGFβ1-isoform selective in that it does not inhibit TGFβ3. Preferably, the TGFβ inhibitor is TGFβ1-isoform selective in that it does not inhibit TGFβ2 and TGFβ3. Furthermore, in some embodiments, the circulating MDSC population can be used as an early predictive biomarker of efficacy of treatment of the fibrotic disorder, e.g., at a time point before other markers of treatment efficacy can be detected.

In some embodiments, the disease is characterized by abnormal cell differentiation involving epithelial-to-mesenchymal transition (EMT) and/or endothelial-to-mesenchymal transition (EndMT). In some embodiments, these processes occurring at the disease sites (such as TME and fibrotic microenvironment) result in increased myofibroblasts or myofibroblast-like cells at the site. These include, for example, CAFs and FAFs.

In some embodiments, the disease is characterized by abnormal gene expression in one or more of marker genes selected from the group consisting of: PAI-1, ACTA2, CCL2, Col1a1, Col3a1, FN-1, CTGF, and TGFβ1.

A therapeutically effective amount of such inhibitor is administered to the subject suffering from or diagnosed with the disease.

In some embodiments, the dysregulation or impairment of fibroblast differentiation comprises increased myofibroblasts or myofibroblast-like cells. In some embodiments, the myofibroblasts or myofibroblast-like cells are cancer-associated fibroblasts (CAFs). In some embodiments, the CAFs are associated with a tumor stroma and may produce CCL2/MCP-1 and/or CXCL12/SDF-1. In some embodiments, the myofibroblasts or myofibroblast-like cells are localized to a fibrotic tissue.

In some embodiments, the dysregulation or impairment of regulatory T cells comprises increased Treg activity.

In some embodiments, the dysregulation or impairment of effector T cell (Teff) proliferation or function comprises suppressed CD4+/CD8+ cell proliferation.

In some embodiments, the dysregulation or impairment of myeloid cell proliferation or differentiation comprises increased proliferation of myeloid progenitor cells. The increased proliferation of myeloid cells may occur in a bone marrow, In some embodiments, the dysregulation or impairment of monocyte differentiation comprises increased differentiation of bone marrow-derived and/or tissue resident monocytes into macrophages at a disease site, such as a fibrotic tissue and/or a solid tumor.

In some embodiments, the dysregulation or impairment of monocyte recruitment comprises increased bone marrow-derived monocyte recruitment into a disease site such as TME, leading to increased macrophage differentiation and M2 polarization, followed by increased TAMs.

In some embodiments, the dysregulation or impairment of macrophage function comprises increased polarization of the macrophages into M2 phenotypes.

In some embodiments, the dysregulation or impairment of myeloid cell proliferation or differentiation comprises an increased number of Tregs, MDSCs and/or TANs.

TGFβ-related indications may include conditions comprising an immune-excluded disease microenvironment, such as tumor or cancerous tissue that suppresses the body's normal defense mechanism/immunity in part by excluding effector immune cells (e.g., CD4+ and/or CD8+ T cells). In some embodiments, such immune-excluding conditions are associated with poor responsiveness to treatment (e.g., cancer therapy). Non-limiting examples of the cancer therapies, to which patients are poorly responsive, include but are not limited to: checkpoint inhibitor therapy, cancer vaccines, chemotherapy, and radiation therapy. Without intending to be bound by particular theory, it is contemplated that TGFβ inhibitors, such as those described herein, may help counter the tumor's ability to evade or exclude anti-cancer immunity by restoring T cell (e.g., CD8+ cells) access by promoting T cell expansion and/or infiltration into tumor.

Thus, TGFβ inhibition may overcome treatment resistance (e.g., immune checkpoint resistance, cancer vaccine resistance, CAR-T resistance, chemotherapy resistance, radiation therapy resistance, etc.) in immune-excluded disease environment (such as TME) by unblocking and restoring effector T cell access and cytotoxic effector functions. Such effects of TGFβ inhibition may further provide long-lasting immunological memory mediated, for example, by CD8+ T cells.

Non-limiting examples of TGFβ-related indications include: fibrosis, including organ fibrosis (e.g., kidney fibrosis, liver fibrosis, cardiac/cardiovascular fibrosis, muscle fibrosis, skin fibrosis, uterine fibrosis/endometriosis and lung fibrosis), scleroderma, Alport syndrome, cancer (including, but not limited to: blood cancers such as leukemia, myelofibrosis, multiple myeloma, colon cancer, renal cancer, breast cancer, malignant melanoma, glioblastoma), fibrosis associated with solid tumors (e.g., cancer desmoplasia, such as desmoplastic melanoma, pancreatic cancer-associated desmoplasia and breast carcinoma desmoplasia), stromal fibrosis (e.g., stromal fibrosis of the breast), radiation-induced fibrosis (e.g., radiation fibrosis syndrome), facilitation of rapid hematopoiesis following chemotherapy, bone healing, wound healing, dementia, myelofibrosis, myelodysplasia (e.g., myelodysplasic syndromes or MDS), a renal disease (e.g., end-stage renal disease or ESRD), unilateral ureteral obstruction (UUO), tooth loss and/or degeneration, endothelial proliferation syndromes, asthma and allergy, gastrointestinal disorders, anemia of the aging, aortic aneurysm, orphan indications (such as Marfan's syndrome and Camurati-Engelmann disease), obesity, diabetes, arthritis, multiple sclerosis, muscular dystrophy (e.g., Myotonic muscular dystrophy, Duchenne muscular dystrophy, Becker muscular dystrophy, Limb-girdle muscular dystrophy, Facioscapulohumeral muscular dystrophy, Congenital muscular dystrophy, Oculopharyngeal muscular dystrophy, Distal muscular dystrophy and Emery-Dreifuss muscular dystrophy), amyotrophic lateral sclerosis (ALS), Parkinson's disease, osteoporosis, osteoarthritis, osteopenia, metabolic syndromes, nutritional disorders, organ atrophy, chronic obstructive pulmonary disease (COPD), and anorexia.

TGFβ-related indications may also include conditions in which major histocompatibility complex (MHC) class I is deleted or deficient (e.g., downregulated). Such conditions include genetic disorders in which one or more components of the MHC-mediated signaling is impaired, as well as conditions in which MHC expression is altered by other factors, such as cancer, infections, fibrosis, and medications.

For example, MHC I downregulation in tumor is associated with tumor escape from immune surveillance. Indeed, immune escape strategies aimed to avoid T-cell recognition, including the loss of tumor MHC class I expression, are commonly found in malignant cells. Tumor immune escape has been observed to have a negative effect on the clinical outcome of cancer immunotherapy, including treatment with antibodies blocking immune checkpoint molecules (reviewed in, for example: Garrido et al., (2017) *Curr Opin Immunol* 39:44-51. "The urgent need to recover MHC class I in cancers for effective immunotherapy", incorporated by reference herein). Thus, the isoform-selective, TGFβ1 inhibitors encompassed by the present disclosure may be administered either as a monotherapy or in conjunction with another therapy (such as checkpoint inhibitor, chemotherapy, radiation therapy, etc.) to unleash or boost anti-cancer immunity and/or enhance responsiveness to or effectiveness of another therapy.

Downregulation of MHC class I proteins are also associated with certain infectious diseases, including viral infections such as HIV. See for example, Cohen et al., (1999) *Immunity* 10 (6): 661-671. "The selective downregulation of class I major histocompatibility complex proteins by HIV-1 protects HIV-infected cells from NK Cells", incorporated herein by reference. Thus, the isoform-selective, TGFβ1 inhibitors encompassed by the present disclosure may be administered either as a monotherapy or in conjunction with another therapy (such as anti-viral therapy, protease inhibitor therapy, etc.) to unleash or boost host immunity and/or enhance responsiveness to or effectiveness of another therapy.

Fibrotic Conditions

In response to tissue injury due physical damage/trauma, toxic substances, and/or infection, a natural reparative process begins which involves several cell types including fibroblasts, several different types of immune cells, and resident epithelial and endothelial cells. However, if left unchecked, this process can lead to excessive accumulation of extracellular matrix (ECM) and fibrosis, which in turn can lead to progressive loss of tissue function and organ failure (Caja et al., *Int. J. Mol. Sci.* 2018, 19, 1294).

Fibrosis can occur in several different organs, including lung, kidney, liver, heart, and skin. Independent of the organ, the fibrotic response is characterized by inflammation, altered epithelial-mesenchymal interactions, and proliferation of fibroblasts. One of the hallmarks of fibrosis is the differentiation of fibroblasts into myofibroblasts, which greatly contribute to the dysregulation of the ECM. However, myofibroblasts have also been proposed to come from other cellular sources (e.g., endothelial cells, epithelial cells, and mesenchymal stem cells (Kim, K. K. et al., *Cold Spring Harb. Perspect. Biol.,* 2017; Okabe, H. *Histol. Histophathol.,* 2016, 31, 141-148; and Li, C et al., *Nat Commun.,* 2016, 7, 11455). Moreover, immune cells play an important role in the process by secreting cytokines and chemokines which promote differentiation of myofibroblasts, stimulate ECM deposition, and recruit additional immune cells to the damaged tissue (Caja et al., *Int. J. Mol. Sci.* 2018, 19, 1294).

Similar to activation of fibroblasts in fibrotic tissue, activation of cancer-associated fibroblasts (CAFs) can occur in the tumor milieu, which produces excessive amounts of ECM. The ECM provides a scaffold for the infiltration of other cells (e.g., pro-tumorigenic immune cells) and a substrate for cell migration. In other cases, excessive ECM may act as a barrier against anti-tumorigenic immune cells.

TGFβ is recognized as the central orchestrator of the fibrotic response. TGFβ can promote myofibroblast differentiation, recruit immune cells, and affect epithelial and endothelial cell differentiation. Particularly, TGFβ upregulates the production of ECM and basement membrane proteins, such as fibronectin, collagen, laminin, osteopontin, tenascin, elastin, decorin. TGFβ-induced myofibroblast differentiation can lead to additional deposition of ECM proteins, secretion of matrix metalloproteinase (MMPs), and myofibroblast proliferation (Fabregat et al., *FEBS J.* 2016, 283, 2219-2232; Meng et al., *Nat. Rev. Nephrol.* 2016, 12, 325-338; and Kulkarni et al., *Am. J. Respir. Cell Mol. Biol.,* 2016, 54, 751-760). Additionally, TGFβ mediates phenotypic changes affecting contractile proteins and collagen I in vascular smooth muscle cells (VSCM) and can activate myofibroblasts and other stromal cells to enhance the synthesis of collagen cross-linking proteins, such as lysyl oxidase (LOX) family of matrix-remodeling enzymes (Busnadiego et al., *Mol. Cell. Biol.* 2013, 33, 2388-2401). Moreover, TGFβ has been shown to regulate both EMT and EndMT, which contributes to the differentiation of pro-fibrotic cell types, such as myofibroblasts and CAFs. Moreover, TGFβ has been shown to induce epithelial apoptosis, which can promote lung and liver fibrosis among other tissues (Barbas-Filho et al., *J. Clin. Pathol.* 2001, 54, 132-138; and Wang et al., *Dev. Dyn.* 2017, 247, 492-508).

Whether innate or recruited, macrophages play an important role in responding to tissue damage and repair. However, upon certain signals they can become pro-fibrotic. TGFβ, among other cytokines, has also been shown to activate M2 macrophages, which are pro-inflammatory. Upon activation, these macrophages secrete their own cytokines, including TGFβ, ECM components, angiogenic factors, and chemotactic factors. M2 macrophages have been shown to be essential for TGFβ-driven lung fibrosis (Murray et al., *Int. J. Biochem. Cell Biol.* 2011, 43, 154-162).

Thus, according to the invention, isoform-specific, inhibitors TGFβ1 such as those described herein are used in the treatment of fibrosis (e.g., fibrotic indications, fibrotic conditions) in a subject. Suitable inhibitors to carry out the present invention include antibodies and/or compositions according to the present disclosure which may be useful for altering or ameliorating fibrosis. More specifically, such antibodies and/or compositions are selective antagonists of TGFβ1 that are capable of targeting TGFβ1 presented by various types of presenting molecules.

Antibodies targeting TGFβ decrease fibrosis in numerous preclinical models. Such antibodies and/or antibody-based compounds include LY2382770 (Eli Lilly, Indianapolis, IN, available e.g., from Creative Biolabs, CAT #: TAB-605CL). Also included are those described in U.S. Patent Numbers U.S. Pat. Nos. 6,492,497, 7,151,169, 7,723,486 and 8,383,780, the contents of each of which are herein incorporated by reference in their entirety. Prior art TGFβ antagonists include, for example, agents that target and block integrin-dependent activation of TGFβ.

However, evidence suggests that such prior art agents may not mediate isoform-specific inhibition and may cause unwanted effects by inadvertently blocking normal function of TGFβ2 and/or TGFβ3. Indeed, data presented herein support this notion. Normal (undiseased) lung tissues contain relatively low but measurable levels of TGFβ2 and TGFβ3, but notably less TGFβ1. In comparison, in certain disease conditions such as fibrosis, TGFβ1 becomes preferentially upregulated relative to the other isoforms. Preferably, TGFβ antagonists for use in the treatment of such conditions exert their inhibitory activities only towards the disease-induced or disease-associated isoform, while preserving the function of the other isoforms that are normally expressed to mediate tonic signaling in the tissue. Prior art inhibitors (LY2109761 (CAS No. 700874-71-1, Eli Lilly)), a small molecule TGFβ receptor antagonist, and a monoclonal antibody that targets αvβ6 integrin) both are shown to inhibit TGFβ downstream tonic signaling in non-diseased rat BAL, raising the possibility that these inhibitors may cause unwanted side effects. Alternatively or additionally, agents that target and block integrin-dependent activation of TGFβ may be capable of blocking only a subset of integrins responsible for disease-associated TGFβ1 activation, among numerous integrin types that are expressed by various cell types and play a role in the pathogenesis. Furthermore, even where such antagonists may selectively block integrin-mediated activation of the TGFβ1 isoform, it may be ineffective in blocking TGFβ1 activation triggered by other modes, such as protease-dependent activation. By contrast, the isoform-specific, inhibitors of TGFβ1 such as those described herein are aimed to prevent the activation step of TGFβ1 regardless of the particular mode of activation, while maintaining isoform selectivity. Preferably, the isoform-selective activation inhibitor of TGFβ1 is Ab46 or an engineered molecule comprising an antigen-binding fragment thereof.

It is further contemplated that isoform-specific TGFβ1 inhibitors that preferentially inhibit matrix-associated over cell-associated antigen complexes (i.e., display context-bias) may offer a therapeutic advantage in certain clinical situations. For example, TGFβ1 inhibitors (which target all four antigen complexes), may increase immune activation through the targeting of cell-associated TGFβ1 (e.g., GARP-TGFβ1 which is expressed on regulatory T cells). Immune activation may be disadvantageous for certain patients, e.g., patients with autoimmune disease or who are at risk of sepsis. Accordingly, context-bias antibodies may be useful for treating diseases associate with matrix-associated TGFβ1 complexes (e.g., fibrosis), while minimizing immune activation.

As discussed above, inhibitory potency against TGFβ3 may be an undesirable feature of TGFβ inhibitors to be used as therapy in situations where fibrosis is a concern. Accordingly, in some embodiments, the TGFβ inhibitor is TGFβ1-isoform selective in that it does not inhibit TGFβ3. In some embodiments, the TGFβ inhibitor is TGFβ1-isoform selective in that it does not inhibit TGFβ2. In some embodiments, the TGFβ inhibitor is TGFβ1-isoform selective in that it does not inhibit TGFβ2 and TGFβ3.

It is further contemplated that isoform-specific TGFβ3 inhibitors may offer a therapeutic benefit in particular disease states. For example, certain fibrotic diseases to be treated with a TGFβ1 inhibitor may also be TGFβ3-positive (i.e., TGFβ1+/TGFβ3+fibrotic tissue) characterized in that the disease tissue (e.g., fibrotic tissue) expresses both the isoforms. Accordingly, the invention includes the use of isoform-selective TGFβ1 inhibitor in conjunction with an isoform-selective TGFβ3 inhibitor in the treatment of such conditions (i.e., TGFβ1+/TGFβ3+fibrotic tissue). Such TGFβ3 inhibitors may be context-independent or context-bias.

Fibrotic indications for which antibodies and/or compositions of the present disclosure may be used therapeutically include, but are not limited to lung indications (e.g., idiopathic pulmonary fibrosis (IPF), chronic obstructive pulmonary disorder (COPD), allergic asthma, acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease (CKD), fibrosis associated with kidney transplantation and chronic rejection, IgA nephropathy, diabetic kidney disease (DKD), and hemolytic uremic syndrome), liver fibrosis (e.g., associated with or caused by non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g., skin fibrosis in systemic sclerosis, diffuse cutaneous systemic sclerosis, scleroderma, pathological skin scarring, keloid, post-surgical scarring, scar revision surgery, radiation-induced scarring and chronic wounds), eye-related conditions such as subretinal fibrosis, uveitis syndrome, uveitis associated with idiopathic retroperitoneal fibrosis, extraocular muscle fibrosis, eye diseases associated with the major histocompatibility complex (MHC class I) or histocompatibility antigens, subretinal fibrosis in macular degeneration (e.g., age-related macular degeneration), and cancers or secondary fibrosis (e.g., myelofibrosis, head and neck cancer, M7 acute megakaryoblastic leukemia and mucositis). Other diseases, disorders or conditions related to fibrosis (including degenerative disorders) that may be treated using compounds and/or compositions of the present disclosure, include, but are not limited to adenomyosis, endometriosis, Marfan's syndrome, stiff skin syndrome, scleroderma, rheumatoid arthritis, bone marrow fibrosis, Crohn's disease, ulcerative colitis, systemic lupus erythematosus, muscular dystrophy (such as DMD), Parkinson's disease, ALS, Dupuytren's contracture, Camurati-Engelmann disease, neural scarring, dementia, proliferative vitreoretinopathy, corneal injury, complications after glaucoma drainage surgery, and multiple sclerosis (MS). Many such fibrotic indications are also associated with inflammation of the affected tissue(s), indicating involvement of an immune component. Such inflammation may be accompanied by aberrant immune cell populations, such as increased numbers of Th17 cells, reduced numbers of Treg cells, and/or both. In each case, the affected patient may exhibit increased Th17/Treg cell ratios.

In some embodiments, fibrotic indications that may be treated with the compositions and/or methods described herein include organ fibrosis, such as fibrosis of the lung (e.g., IPF), fibrosis of the kidney (e.g., fibrosis associated with CKD), fibrosis of the liver (e.g., associated with or due to NASH), fibrosis of the heart or cardiac tissues, fibrosis of the skin (e.g., scleroderma), fibrosis of the uterus (e.g., endometrium, myometrium), fibrosis of muscle (e.g., skeletal muscle), and fibrosis of the bone marrow. In some embodiments, such therapy may reduce or delay the need for organ transplantation in patients. In some embodiments, such therapy may prolong the survival of the patients.

In some embodiments, the TGFβ1 inhibitors such as those disclosed herein may delay or reduce the need for organ transplantation. In some embodiments, the organ transplantation is a lung transplant, a liver transplant or a kidney transplant.

To treat IPF, patients who may benefit from the treatment include those with familial IPF and those with sporadic IPF. Administration of a therapeutically effective amount of an isoform-specific, inhibitor of TGFβ1 may reduce myofibroblast accumulation in the lung tissues, reduce collagen deposits, reduce IPF symptoms, improve or maintain lung function, and prolong survival. In some embodiments, the inhibitor blocks activation of ECM-associated TGFβ1 (e.g., pro/latent TGFβ1 presented by LTBP1/3) within the fibrotic environment of IPF. The inhibitor may optionally further block activation of macrophage-associated TGFβ1 (e.g., pro/latent TGFβ1 presented by LRRC33), for example, alveolar macrophages. As a result, the inhibitor may suppress fibronectin release and other fibrosis-associated factors. In some embodiments, the inhibitor blocks hepatic stellate cell activation.

According to some embodiments, a patient with IPF who may benefit from treatment with the compositions described herein (e.g., a therapeutically effective amount of an isoform-specific, inhibitor of TGFβ1) is a subject who is a candidate for a lung transplant. According to some embodiments, a subject with IPF who may benefit from treatment with the compositions described herein (e.g., a therapeutically effective amount of an isoform-specific, inhibitor of TGFβ1) is a subject who is not a candidate for a lung transplant.

According to some embodiments, a patient with IPF is administered a composition described herein in combination with a second agent. According to some embodiments, the second agent is one or more of pirfenidone, nintedanib, and/or N-acetylcysteine. According to some embodiments, a patient with IPF is administered a therapeutically effective amount of an isoform-specific, inhibitor of TGFβ1 in combination with one or more of pirfenidone, nintedanib, and/or N-acetylcysteine.

It is well-established that the activation of hepatic stellate cells (HSCs) are the central drivers of fibrosis in liver injury. In this process, quiescent, vitamin-A-storing cells, transdifferentiated into proliferative, fibrogenic myofibroblasts (the principal source of extracellular matrix (ECM) protein accumulation). However, this process has been shown to be mediated by many different pathways, including autophagy, endoplasmic reticulum stress, oxidative stress, retinol and cholesterol metabolism, epigenetics, and receptor-mediated signals. Moreover, inflammatory cells including macrophages, hepatocytes, liver sinusoidal endothelial cells, natural killer cells, natural killer T cells, platelets and B cells have also been shown to modulate HSC activation (Tsuchida and Friedman, *Nature Reviews Gastroenterology & Hepatology* volume 14, pages 397-411 (2017)). In just one particular example, Seki et al. demonstrated that TLR4 (which recognizes LPS presented by bacteria) activation leads to upregulation of chemokine secretion and induces chemotaxis of Kupffer cells, and also sensitizes HSCs to TGFβ-induced signals and allows for unrestricted activation of Kupffer cells (Seki et al., Nature Medicine volume 13, pages 1324-1332 (2007)).

It is well known that inflammation plays a key role in liver fibrosis development and progression. Specifically, liver injury leads to inflammation and the recruitment of monocytes/macrophages (as well as lymphocytes, eosinophils, and plasma cells) which produce pro-fibrotic factors, including TGFβ. Moreover, the research indicates that both hepatic tissue-resident macrophages (Kupffer cells) and bone marrow-derived recruited macrophages play important roles in the progression of liver fibrosis, and that the TGFβ pathway can promote the polarization and pro-fibrotic functions of macrophages during liver fibrosis. Indeed, it has been shown that both Kupffer cells and recruited macrophages can activate HSCs and induce their transdifferentiation into myofibroblasts by paracrine mechanisms, including TGFβ. The myofibroblasts in turn produce and deposit ECM components leading to fibrosis (Fabregat and Caballero-Diaz, *Front Oncol.* 2018; 8:357).

However, myofibroblasts may come from other sources as well, including portal and resident fibroblasts, bone marrow-derived fibrocytes, liver epithelial cells that undergo EMT, endothelial cells that undergo EndMT, and vascular smooth muscle cells and pericytes. Indeed, TGFβ has also been shown to regulate both EndMT and EMT resulting in increased myofibroblasts, which drive liver fibrosis. (Pardali et al., *Int J Mol Sci.* 2017 October; 18 (10): 2157). Accordingly, targeting TGFβ has been an attractive therapeutic target for the treatment of fibrotic conditions.

TGFβ has been shown to play many roles in liver fibrosis and disease progression. For example, TGFβ has been shown to be responsible for the activation HSCs to myofibroblasts. TGFβ also has been shown to mediate epithelial-mesenchymal transition (EMT) in hepatocytes that may contribute to increase the myofibroblast population. Moreover, TGFβ has been shown to induce changes in tumor cell plasticity (Fabregat and Caballero-Diaz, Front Oncol. 2018; 8:357).

Although TGFβ can be found on many different cellular sources in the fibrotic and/or tumor microenvironment, thus suggesting TGFb presentation by multiple different presenting molecules (e.g., LTBP1, LTBP3, GARP, and/or LRRC33), it may be beneficial in certain situations to target particular sources of TGFβ over others. For example, Henderson et al. showed that deleting av integrin in HSCs, protected mice form CCL4-induced liver fibrosis (Henderson et al., Nat. Med. 2013, 19, 1617-16-24). Because integrins are the main activators of LTBP-presented TGFβ, this result suggests that targeting LTBP-presented TGFβ may be sufficient to treat fibrosis in certain situations. However, because immune cells play an important role in the fibrotic response, TGFβ inhibitors that target TGFβ presented by most or all of the presenting-molecule TGFβ complexes may be beneficial.

In recent years, the treatment of liver fibrosis has become an area interest due to its increasing prevalence around the world. For example, non-alcoholic fatty liver disease (NAFLD) is associated with metabolic abnormalities such as obesity, insulin resistance, fasting hyperglycemia, dyslipidaemia, and altered adipokine profiles. NAFLD is characterized by excessive lipid accumulation in hepatocytes and is a spectrum of diseases progressing from liver steatosis (lipid/fat droplet accumulation in hepatocytes) to non-alcoholic steatohepatitis (NASH), liver fibrosis, and eventually cirrhosis in the most severe cases. NASH with fibrosis or cirrhosis increases the risk of developing hepatocellular carcinoma (HCC) (Starley B Q, et al., *Hepatology* 2010; 51:1820-1832). The progression from steatosis to NASH has been proposed to be regulated by a 'multiple-hit' model, wherein the first hit is insulin resistance and metabolic disturbance, which leads to liver steatosis, followed by oxidative stress, proinflammatory cytokine-mediated hepatocyte injury, altered lipid partitioning and hepatoxicity mediated by free fatty acids, abnormal intrahepatic cholesterol loading, hyperinsulinaemia, hyperleptinaemia, and hypoadiponectinaemia (Tilg H, Moschen A R, Hepatology 2010; 52:1836-1846; and Yilmaz Y., *Aliment Pharmacol Ther* 2012; 36:815-823).

There are many animal models that have been develop to study liver fibrosis. For example, a high fat diet in mice has been shown to mimic both the histopathology and pathogenesis of human NAFLD. Moreover, some genetic models also display features of human metabolic syndrome and NAFLD, such as db/db and ob/ob mouse models. There are also animal models for the study of NASH, which mainly consist of various diet-induced models, including, but not limited to, methionine and choline-deficient diet (MCD), high-cholesterol diet (HCD), choline-deficient high fat diet (CDHFD), choline-deficient L-amino acid-deficient diet, choline-deficient L-amino acid-deficient diet+carbon tetrachloride, high-fat diet+streptozotocin, high fat+high cholesterol diet (HFHC), high-fructose diet (HFD), and high-fructose high fat diet (HFHF). Genetic mouse models for the study of NASH include, but are not limited to foz/foz mice, Hepatocyte-specific PTEN-deficient mice, Db/db mice+diethylnitrosamine (DEN), and db/db mice+MCD. The details of all of these models, including the pluses and minus of each, are outlined in Jennie Ka Ching Lau et al., *J Pathol* 2017; 241:36-44; the contents of which are incorporated herein by reference.

Another model useful for testing the efficacy of isoform-specific TGFβ inhibitors in liver fibrosis include the carbon tetrachloride ($CCL_4$) model and choline deficient high fat diet (CDHFD) liver fibrosis model. Another model useful for testing the efficacy of isoform-specific TGFβ inhibitors in liver fibrosis include the bile duct ligation (BDL) model (see, e.g., Tag et al., *J Vis Exp*. 2015; (96): 52438).

As discussed herein, based on the lines of evidence suggesting the possibility of harmful effects of TGFβ2/3 inhibition, inhibitory potency against TGFβ2 and/or TGFβ3 may be an undesirable feature of TGFβ inhibitors to be used as therapy in situations where fibrosis is a concern. According to some embodiments, preferred inhibitors for use in the treatment of liver conditions such as NAFLD and NASH are TGFβ1-isoform selective. In some embodiments, the TGFβ inhibitor is TGFβ1-isoform selective in that it does not inhibit TGFβ3. In some embodiments, the TGFβ inhibitor is TGFβ1-isoform selective in that it does not inhibit TGFβ2. In some embodiments, the TGFβ inhibitor is TGFβ1-isoform selective in that it does not inhibit TGFβ2 and TGFβ3.

The isoform-specific, TGFβ1 inhibitors such as those provided herein may be used to treat fibrotic conditions of the liver, such as fatty liver (e.g., non-alcoholic fatty liver disease (NAFLD) and non-alcoholic steatohepatitis (NASH). The fatty liver may or may not be inflamed. Inflammation of the liver due to fatty liver (i.e., steatohepatitis) may develop into scarring (fibrosis), which then often progresses to cirrhosis (scarring that distorts the structure of the liver and impairs its function). The inhibitor may therefore be used to treat such conditions. In some embodiments, the inhibitor blocks activation of ECM-associated TGFβ1 (e.g., pro/latent TGFβ1 presented by LTBP1/3) within the fibrotic environment of the liver. The inhibitor may optionally further block activation of macrophage-associated TGFβ1 (e.g., pro/latent TGFβ1 presented by LRRC33), for example, Kupffer cells (also known as stellate macrophages) as well as infiltrating monocyte-derived macrophages and MDSCs. As a result, the inhibitor may suppress fibrosis-associated factors (e.g., fibrotic markers described herein). Administration of the inhibitor in a subject with such conditions may reduce one or more symptoms, prevent or retard progression of the disease, reduce or stabilize fat accumulations in the liver, reduce disease-associated biomarkers (such as serum collagen fragments), reduce liver scarring, reduce liver stiffness, and/or otherwise produce clinically meaningful outcome in a patient population treated with the inhibitor, as compared to a control population not treated with the inhibitor. In some embodiments, an effective amount of the inhibitor may achieve both reduced liver fat and reduced fibrosis (e.g., scarring) in NASH patients. In some embodiments, an effective amount of the inhibitor may achieve improvement in fibrosis by at least one stage with no worsening steatohepatitis in NASH patients. In some embodiments, an effective amount of the inhibitor may reduce the rate of occurrence of liver failure and/or liver cancer in NASH patients.

In some embodiments, an effective amount of the inhibitor may normalize, as compared to control, the levels of multiple inflammatory or fibrotic serum biomarkers as assessed following the start of the therapy, at, for example, 12-36 weeks. In some embodiments, inflammatory or fibrotic biomarkers may be used to assess severity of NAFLD (by measure levels of hepatic steatosis), select patients for treatment, and/or monitor disease progression or treatment response. For example, blood biomarkers and panels may include, but are not limited to:

i) the Fatty liver index (BMI, waist circumference, serum triglycerides, and gamma-glutamyltransferase (GGT);
ii) the Hepatic steatosis index (serum aspartate aminotransferase (AST): alanine aminotransferase (ALT) ratio, BMI, gender, and presence of diabetes mellitus);
i) the NAFLD liver fat score (serum ALT, HDL cholesterol, trigliceridеs, haemoglobin $A_{1c}$ and leukocyte count);
ii) the SteatoTest (BioPredictive) (serum levels of total bilirubin, GGT, α2-macroglobin, haptoglobin, ALT, apolipoprotein Al, total cholesterol, triglycerides, glucose (adjusted for age and gender) and BMI); and
iii) the NAFLD ridge score (serum levels of ALT, HDL cholesterol, triglycerides, haemoglobin $A_{1c}$, leukocyte count, and comorbidity data (and the presence of hypertension)).

In some embodiments, imaging biomarkers can be used to assess levels of hepatic steatosis. For example, imaging biomarkers may include but are not limited to: ultrasonography, controlled attenuation parameter (CAP), MRI-estimated proton density fat fraction (MRI-PDFF), and magnetic resonance spectroscopy (MRS).

Liver biopsies are the current standard for diagnosis NASH, however, variability among pathologists limits the effectiveness of such diagnostic method. Accordingly, use of the Fatty Liver Inhibition of Progression (FLIP) algorithm (comprising histological steatosis, activity and fibrosis scores) may be used to improve the consistency of NASH diagnosis by biopsy. Moreover, many noninvasive biomarkers may also be useful for diagnosing and monitoring disease. Accordingly, in some embodiments, inflammatory or fibrotic biomarkers may be used to assess severity of NASH, select patients for treatment, and/or monitor disease progression or treatment response. Blood biomarkers may include:

i) apoptosis markers, such as CK18 fragments, total cytokeratin and sFAS;
ii) inflammatory markers, such as CRP, TNF, IL-8, and CXCL10;
iii) lipid oxidation products, such as 11-HETE, 9-HODE, 13-HODE, 12-oxo-ODE, LA-13-HODE (oxNASH-score), and 11,12-diHETrE;
iv) lysosomal enzymes, such as cathepsin D; and
v) combination panels, such as NASHTest (BioPredictive) and NASH Diagnostics Panel (comprising, presence of diabetes mellitus, sex, BMI, and serum levels of triglyceride, CK18 fragments, and total CK18).

In some embodiments, biomarkers and related panels may be useful in diagnosis levels of fibrosis and/or cirrhosis, select patients for treatment, and/or monitor disease progression or treatment response. For example, noninvasive tests of liver fibrosis and cirrhosis include, but are not limited to: AST: ALT ratio, AST: platelet ratio index, fibrosis-4 index (age, AST, ALT, and platelet count), NAFLD fibrosis score (age, BMI, impaired fasting glucose and/or diabetes, AST ALT, platelet count, and albumin), BARD score (AST, ALT, BMI, and diabetes).

Specific fibrosis markers and panels may also be useful, and include, but are not limited to: hyaluronic acid; PIIPNP; Pro-C3; TIMP1; Laminin; enhanced liver fibrosis (ELF) panel (PIINP, hyaluronic acid, TIMP1); FibroTest (GGT, total bilirubin, $\alpha_2$m, apolipoprotein Al, and haptoglobin); and FibroMeter NAFLD (body weight, prothrombin index, ALT, AST, ferritin, and fasting glucose). Imaging biomarkers for liver fibrosis may include, but are not limited to: FibroScan (TE), point shear wave elastography (pSWE) (aka acoustic radiation force impulse (ARFI)), 2D-3D SWE, magnetic resonance elastography (MRE), and multiparameteric MRI.

In some embodiments, serum levels of liver enzymes such as alkaline phosphatase (ALP), alanine aminotransferase (ALT), aspartate tramsaminase (AST), or G-glutamyl transferase (GGT) may be measured as indicators of fibrosis in the liver.

In some embodiments, genetic and genomic biomarkers may be useful in assessing NAFLD risk and severity, which include the assessment of various SNPs, cell-free ncRNAs, and miRNAs. A comprehensive review of known genetic and genomic biomarkers, as well as the above-discussed blood biomarkers, panels, imaging biomarkers, and tests are summarized in VWS Wong et al., Nat Rev Gastroenterol Hepatol. 2018 August;15 (8): 461-478; the contents of which are incorporated herein by reference.

In some embodiments in NASH patients, the isoform-specific, TGFβ1 inhibitors may be administered in patients who receive one or more additional therapies, including, but are not limited to myostatin inhibitors, which may generally enhance metabolic regulation in patients with clinical manifestation of metabolic syndrome, including NASH and NAFLD. In preferred embodiments, the isoform-selective activation inhibitor of TGFβ1 is Ab42, Ab46, Ab50, a derivative thereof, or an engineered molecule comprising an antigen-binding fragment thereof.

In some embodiments, in NASH patients, the isoform-specific, TGFβ1 inhibitors may be administered in patients who receive an Acetyl COA Carboxylase inhibitor (ACCi) (e.g., firsocostat (aka GS-0976) or PF-05221304). Other therapeutics which may be useful in combination with the improved isoform-specific TGFβ1 inhibitors described herein, include, but are not limited to: GLP-1 receptor agonists or analgues (e.g., semaglutide), farnesoid X receptor (FXR) agonists (e.g., GS-9674; aka Cilofexor), ASK1 inhibitors (e.g., selonsertib); obeticholic acid, PPAR agonists (e.g., GFT505; aka elafibranor); nitazoxanide, ketohexokinase (KHK) inhibitors (e.g., PF-06835919); and/or Diacylglycerol O-Acyltransferase 2 (DGAT2) inhibitors (e.g., PF-06865571). In some embodiments, any one or more of the above-mentioned therapeutics can be used in combination with an isoform specific TGFβ1 inhibitor of the present disclosure, for example, an isoform-specific TGFβ1 inhibitor in combination with a FXR agonist, an ACC inhibitor, and/or a GLP-1 analogue.

In some embodiments, treatment with the isoform specific TGFβ1 inhibitors alone or in combination with one or more additional therapeutics reduces hepatic fat as measured by MRI-PDFF. In some embodiments, the reduction of hepatic fat is at least 20%, e.g., ≥20%, ≥25%, ≥30%, ≥35%, >40%, >45%, or >50%. In some embodiments, treatment with the isoform specific TGFβ1 inhibitors alone or in combination with one or more additional therapeutics reduces serum ALT and/or GGT by at least 20%, e.g., ≥20%, ≥25%, ≥30%, ≥35%, ≥40%, ≥45%, or ≥50%. In some embodiments, treatment with the isoform specific TGFβ1 inhibitors alone or in combination with one or more additional therapeutics reduces bile acid synthesis.

In some embodiments, the NASH patients may have advanced liver fibrosis (stage F3/F4). In some embodiments, such patients have stage F3 advanced liver fibrosis. In some embodiments, such patients have stage F4 liver fibrosis characterized by cirrhosis. In some embodiments, the NASH patients develop or at risk of developing hepatocellular carcinoma and/or esophageal varices.

Fibrosis staging in non-alcoholic fatty liver disease according to the classification derived by the Nonalcoholic Steatohepatitis Clinical Research Network Pathology Committee is provided below:

TABLE 20

Stages of fibrosis

| Fibrotic manifestation | Fibrosis Stage |
|---|---|
| Perisinusoidal or periportal fibrosis | 1 |
| Mild perisinusoidal fibrosis (zone 3) | 1A |
| Moderate perisinusoidal fibrosis (zone 3) | 1B |
| Portal/periportal fibrosis | 1C |
| Perisinusoidal and portal/periportal fibrosis | 2 |
| Bridging fibrosis | 3 |
| Cirrhosis | 4 |

To enable assessment of the various histologic features during therapy and encompass the whole spectrum of NAFLD, the NASH Clinical Research Network (CRN) Pathology Committee performed a thorough univariate and multivariate analysis on the associations between the different histologic features observed in NASH and the diagnosis of NASH according to the Pathology Committee. The result was a scoring system of both NASH activity (Grade), and collagen deposition plus architectural remodeling (Stage). The grading system, the NASH Activity Score (NAS), was the unweighted sum of three histological components: steatosis (0-3), lobular inflammation (0-3) and ballooning degeneration (0-2). It ranged from 0 to 8. NAS includes the features of active injury that are potentially reversible. Additionally, the fibrosis staging system of Brunt et al., was further developed. In the NASH CRN system, the fibrosis score for stage 1 was subdivided into delicate (1A) and dense (1B) peri-sinusoidal fibrosis, whereas stage 1C was defined as portal fibrosis without concomitant peri-sinusoidal fibrosis (reviewed by Stål, *World J. Gastroenterol.* 2015 Oct. 21; 21 (39): 11077-11087, incorporated by reference herein).

The isoform-specific, TGFβ1 inhibitors such as those provided herein may be used to treat fibrotic conditions of the kidney, e.g., diseases characterized by extracellular matrix accumulation (IgA nephropathy, focal and segmental glomerulosclerosis, crescentic glomerulonephritis, lupus nephritis and diabetic nephropathy) in which significantly increased expression of TGFβ in glomeruli and the tubulointerstitium has been observed. While glomerular and tubulointerstitial deposition of two matrix components induced by TGFβ, fibronectin EDA+ and PAI-1, was significantly elevated in all diseases with matrix accumulation, correlation analysis has revealed a close relationship primarily with the TGFβ1 isoform. Accordingly, the isoform-specific, TGFβ1 inhibitors are useful as therapeutic for a spectrum of human glomerular disorders, in which TGFβ is associated with pathological accumulation of extracellular matrix. In preferred embodiments, the isoform-selective activation inhibitor of TGFβ1 is Ab42, Ab46, Ab50, a derivative thereof, or an engineered molecule comprising an antigen-binding fragment thereof.

In some embodiments, the fibrotic condition of the kidney is associated with chronic kidney disease (CKD). CKD is caused primarily by high blood pressure or diabetes and claims more than one million lives each year. CKD patients require lifetime medical care that ranges from strict diets and medications to dialysis and transplants. In some embodiments, the TGFβ1 inhibitor therapy described herein may reduce or delay the need for dialysis and/or transplantation. In some embodiments, such therapy may reduce the need (e.g., dosage, frequency) for other treatments. In some embodiments, the isoform-specific, TGFβ1 inhibitors may be administered in patients who receive one or more additional therapies, including, but are not limited to myostatin inhibitors, which may generally enhance metabolic regulation in patients with CKD.

Fibrotic conditions that may be treated with the TGFβ1 inhibitor of the present disclosure include conditions involving fibrosis and/or chronic inflammation. Such conditions may be neuromuscular disorders, including but are not limited to Duchenne muscular dystrophy (DMD), and other genetic disorders such as multiple sclerosis (MS) and cystic fibrosis (CF). Through the inhibition of both the ECM- and immune cell-associated TGFβ1 arms, the TGFβ1 inhibitor such as those described herein is thought to suppress fibrotic progression and restore M1/M2 macrophage polarization. In preferred embodiments, the isoform-selective activation inhibitor of TGFβ1 is Ab42, Ab46, Ab50, a derivative thereof, or an engineered molecule comprising an antigen-binding fragment thereof.

Models useful for studying CKD and kidney fibrosis include but are not limited to, NZB/W, MRL//pr and BXSB mouse strains, anti-GBM models, anti-Thyl models, 5/6 nephrectomy, Radiation nephropathy, puromycin aminonucleoside nephrosis (PAN) and adriamycin nephropathy, Folic acid nephropathy, CyA nephropathy, DOCA-salt nephropathy, HIV-associated nephropathy (HIVAN) transgenic mouse model, Spontaneously hypertensive rats (SHR), Buffalo/mna rats, Munich Wistar Fromter (MWF) rat, unilateral ureteral obstruction (UUO), Col4A knock-out mice (Alport Syndrome) (see Yang et al., *Drug Discov Today Dis Models.* 2010; 7 (1-2): 13-19; the contents of which are incorporated herein by reference).

The organ fibrosis which may be treated with the methods provided herein includes cardiac (e.g., cardiovascular) fibrosis. In some embodiments, the cardiac fibrosis is associated with heart failure, e.g., chronic heart failure (CHF). In some embodiments, the heart failure may be associated with myocardial diseases and/or metabolic diseases. In some embodiments, the isoform-specific, TGFβ1 inhibitors may be administered in patients who receive one or more additional therapies, including, but are not limited to myostatin inhibitors in patients with cardiac dysfunction that involves heart fibrosis and metabolic disorder. In preferred embodiments, the isoform-selective activation inhibitor of TGFβ1 is Ab42, Ab46, Ab50, a derivative thereof, or an engineered molecule comprising an antigen-binding fragment thereof.

Genetic models useful for studying cardiac fibrosis include but are not limited to, cardiac myocyte-specific FAK-KO mouse, genetically modified SR-BI/apoE double KO (dKO) mice, syndecan-1 null mice, EC-SOD-overexpressing mice, PKC-δ knockout mice. Surgical mouse models useful for studying cardiac fibrosis include but are not limited to, coronary artery ligation, ischemic-reperfusion model (open and closed chest), Chronic ischemia model, ischemia-reperfusion with ischemic preconditioning model, Langendorff model, traverse aortic constriction (TAC), ascending aortic constriction, abdominal aorta constriction, pulmonary artery banding, TAC with distal left anterior coronary ligation, aortocaval fistula (ACF) model, and aortic insufficiency model (see Rai et al., *Mol Cell Biochem.* 2017 January; 424 (1-2): 123-145; the contents of which are incorporated herein by reference).

In some embodiments, fibrotic conditions that may be treated with the compositions and/or methods described herein include desmoplasia. Desmoplasia may occur around a neoplasm, causing dense fibrosis around the tumor (e.g., desmoplastic stroma), or scar tissue within the abdomen after abdominal surgery. In some embodiments, desmoplasia is associated with malignant tumor. Due to its dense formation surrounding the malignancy, conventional anti-cancer therapeutics (e.g., chemotherapy) may not effectively penetrate to reach cancerous cells for clinical effects. Isoform-specific, inhibitors of TGFβ1 such as those described herein may be used to disrupt the desmoplasia, such that the fibrotic formation can be loosened to aid effects of anti-cancer therapy. In some embodiments, the isoform-specific, inhibitors of TGFβ1 can be used as monotherapy (more below).

In some embodiments, a patient has a fibrotic solid tumor (e.g., desmoplasia) and is or has been excluded from a surgical candidate pool, such that the fibrotic solid tumor is considered to be non-resectable or non-operative. Such patient may be a candidate for receiving a TGFβ1 inhibition therapy of the present disclosure. The TGFβ1 inhibitor of the present invention may render the tumor become resectable or operable after administration so that the patient may become a candidate for surgical resection.

To treat patients with fibrotic conditions, TGFβ1 isoform-specific, inhibitors are administered to a subject in an amount effective to treat the fibrosis. In preferred embodiments, the isoform-selective activation inhibitor of TGFβ1 is Ab42, Ab46, Ab50, a derivative thereof, or an engineered molecule comprising an antigen-binding fragment thereof. The effective amount of such an antibody is an amount effective to achieve both therapeutic efficacy and clinical safety in the subject. In some embodiments, the inhibitor is an antibody that can block activation of an LTBP-mediated TGFβ1 localized (e.g., tethered) in the ECM and GARP-mediated TGFβ1 localized in (e.g., tethered on) immune cells. In some embodiments, antibody is an antibody that can block activation of an LTBP-mediated TGFβ1 localized in the ECM and LRRC33-mediated TGFβ1 localized in (e.g., tethered on) monocytes/macrophages. In some embodiments, the LTBP is LTBP1 and/or LTBP3. In some embodiments, targeting and inhibiting TGFβ1 presented by LRRC33 on profibrotic, M2-like macrophages in the fibrotic microenvironment may be beneficial.

Assays useful in determining the efficacy of the antibodies and/or compositions of the present disclosure for the alteration of fibrosis include, but are not limited to, histological assays for counting fibroblasts and basic immunohistochemical analyses known in the art.

In some embodiments, circulating LAP fragment(s) may be used as a serum marker of fibrogenesis. See for example, U.S. Pat. No. 8,198,412, the contents of which are incorporated herein by reference.

Disease Involving ECM Dysregulation

The extracellular matrix is a cell-secreted network that surrounds cells and is primarily composed of proteoglycans and fibrous proteins, the most abundant of which is collagen. The novel antibodies disclosed herein may be used in the treatment of diseases associated with extracellular matrix dysregulation. The diseases associated with extracellular matrix dysregulation are typically myofibroblast-driven pathologies and include cancer, fibrosis, and cardiovascular disease (reviewed, for example, in: Lampi and Reinhart-King (2018) "Targeting extracellular matrix stiffness to attenuate disease: From molecular mechanisms to clinical trials" *Sci Transl Med* 10 (422): eaao0475). Progression of fibrotic conditions involves increased levels of matrix components deposited into the ECM and/or maintenance/remodeling of the ECM. TGFβ1 at least in part contributes to this process. This is supported, for example, by the observation that increased deposition of ECM components such as collagens can alter the mechanophysical properties of the ECM (e.g., the stiffness of the matrix/substrate) and this phenomenon is associated with TGFβ1 signaling. The inhibitors of TGFβ1, such as those described herein may be used to block this process to counter disease progression involving ECM alterations, such as fibrosis, tumor growth, invasion, metastasis and desmoplasia. The LTBP-arm of such inhibitors can directly block ECM-associated pro/latent TGFβ complexes which are presented by LTBP1 and/or LTBP3, thereby preventing activation/release of the growth factor from the complex in the disease niche. In some embodiments, the isoform-specific TGFβ1 inhibitors such as those described herein may normalize ECM stiffness to treat a disease that involves integrin-dependent signaling. In some embodiments, the integrin comprises an α11 chain, β1 chain, or both.

Thus, the antibody may be administered to a subject diagnosed with a disease with extracellular matrix dysregulation in an amount effective to treat the disease. Therapeutically effective amount of the antibody may be an amount sufficient to reduce expression of one or more markers of myofibroblasts, such as α-SMA. The amount may be an amount sufficient to reduce the stiffness of the extracellular matrix of an affected tissue (e.g., fibrotic tissues). The amount may be an amount sufficient to reduce TGFβ1 downstream effectors, such as phosphorylation of SMAD2 and/or SMAD3. In preferred embodiments, the isoform-selective activation inhibitor of TGFβ1 is Ab42, Ab46, Ab50, a derivative thereof, or an engineered molecule comprising an antigen-binding fragment thereof.

Disease Involving Endothelial-to-Mesenchymal Transition (EndMT)

Similarly, TGFβ is also a key regulator of the endothelial-mesenchymal transition (EndMT) observed in normal development, such as heart formation. However, the same or similar phenomenon is also seen in many diseases, such as cancer stroma. In some disease processes, endothelial markers such as CD31 become downregulated upon TGFβ1 exposure and instead the expression of mesenchymal markers such as FSP-1, α-SMA and fibronectin becomes induced. Indeed, stromal CAFs may be derived from vascular endothelial cells. Thus, isoform-specific inhibitors of TGFβ1, such as those described herein, may be used to treat a disease that is initiated or driven by EndMT. In preferred embodiments, the isoform-selective activation inhibitor of TGFβ1 is Ab42, Ab46, Ab50, a derivative thereof, or an engineered molecule comprising an antigen-binding fragment thereof.

Disease Involving Epithelial-to-Mesenchymal Transition (EMT)

EMT (epithelial mesenchymal transition) is the process by which epithelial cells with tight junctions switch to mesenchymal properties (phenotypes) such as loose cell-cell contacts. The process is observed in a number of normal biological processes as well as pathological situations, including embryogenesis, wound healing, cancer metastasis and fibrosis (reviewed in, for example, Shiga et al., (2015) "Cancer-Associated Fibroblasts: Their Characteristics and Their Roles in Tumor Growth." *Cancers,* 7:2443-2458). Generally, it is believed that EMT signals are induced mainly by TGFβ. In preferred embodiments, the isoform-selective activation inhibitor of TGFβ1 is Ab42, Ab46, Ab50, a derivative thereof, or an engineered molecule comprising an antigen-binding fragment thereof.

Epithelial cells have also been proposed to give rise to myofibroblasts by undergoing the process of EMT in several fibrotic tissues such as kidney, lung and in the liver. EMT takes place when epithelial cells lose their cuboidal shape, lose the expression of adherence and tight junction proteins, which leads to weak cell-cell contacts and reorganization of their actin cytoskeleton; while the cells acquire the expression of mesenchymal proteins (fibronectin, vimentin, N-cadherin), they adopt a fibroblast-like architecture favoring cell migration and invasion. EMT is induced by many growth factors, among them TGFβ being a very potent inducer, which regulate the expression and activity of several transcription factors known as EMT-TFs (Snail1/Snail, Snail2/Slug, ZEB1, ZEB2, Twist1/Twist and more) that are the responsible actors to execute the change in cell differentiation that is EMT. The gene and protein markers used to identify the generation of mesenchymal cells after EMT in the context of fibrosis are FSP1 (Fibroblast-specific protein 1), α-SMA and collagen I along with vimentin and desmin, whose expression increases concomitant with a reduction in levels of expression of epithelial markers (E-cadherin and certain cytokeratins). Cells that co-express epithelial and mesenchymal markers represent an intermediate stage of EMT (reviewed by, for example: Caja et al., *Int. J. Mol. Sci.* 2018, 19 (5), 1294).

Many types of cancer, for example, appear to involve transdifferentiation of cells towards mesenchymal phenotype (such as CAFs) which correlate with poorer prognosis. Thus, isoform-specific inhibitors of TGFβ1, such as those described herein, may be used to treat a disease that is initiated or driven by EMT. Indeed, data exemplified herein (e.g., FIGS. 12 and 13) show that such inhibitors have the ability to suppress expression of CAF markers in vivo, such as α-SMA, Col1 (Type I collagen), and FN (fibronectin). In preferred embodiments, the isoform-selective activation inhibitor of TGFβ1 is Ab42, Ab46, Ab50, a derivative thereof, or an engineered molecule comprising an antigen-binding fragment thereof.

Disease Involving Proteases

Activation of TGFβ from its latent complex may be triggered by integrin in a force-dependent manner, and/or by proteases. Evidence suggests that certain classes of proteases may be involved in the process, including but are not limited to Ser/Thr proteases such as Kallikreins, chemotrypsin, elastases, plasmin, thrombin, as well as zinc metalloproteases of ADAM family such as ADAM 10 and ADAM 17, as well as MMP family, such as MMP-2, MMP-9 and MMP-13. MMP-2 degrades the most abundant component of the basement membrane, Collagen IV, raising the possibility that it may play a role in ECM-associated TGFβ1 regulation. MMP-9 has been implicated to play a central role in tumor progression, angiogenesis, stromal remodeling and metastasis. Thus, protease-dependent activation of TGFβ1 in the ECM may be important for treating cancer.

Kallikreins (KLKs) are trypsin- or chymotrypsin-like serine proteases that include plasma Kallikreins and tissue Kallikreins. The ECM plays a role in tissue homeostasis acting as a structural and signaling scaffold and barrier to suppress malignant outgrowth. KLKs may play a role in degrading ECM proteins and other components which may facilitate tumor expansion and invasion. For example, KLK1 is highly upregulated in certain breast cancers and can activate pro-MMP-2 and pro-MMP-9. KLK2 activates latent TGFβ1, rendering prostate cancer adjacent to fibroblasts permissive to cancer growth. KLK3 has been widely studied as a diagnostic marker for prostate cancer (PSA). KLK3 may directly activate TGFβ1 by processing plasminogen into plasmin, which proteolytically cleaves LAP. KLK6 may be a potential marker for Alzheimer's disease.

Known activators of TGFβ1, such as plasmin, TSP-1 and αVβ6 integrin, all interact directly with LAP. It is postulated that proteolytic cleavage of LAP may destabilize the LAP-TGFβ interaction, thereby releasing active TGFβ1. It has been suggested that the region containing 54-LSKLRL-59 (SEQ ID NO: 301) is important for maintaining TGFβ1 latency. Thus, agents (e.g., antibodies) that stabilize the interaction, or block the proteolytic cleavage of LAP may prevent TGFβ activation.

Many of these proteases associated with pathological conditions (e.g., cancer) function through distinct mechanisms of action. Thus, targeted inhibition of particular proteases, or combinations of proteases, may provide therapeutic benefits for the treatment of conditions involving the protease-TGFβ axis. Accordingly, it is contemplated that inhibitors (e.g., TGFβ1 antibodies) that selectively inhibit protease-induced activation of TGFβ1 may be advantageous in the treatment of such diseases (e.g., fibrosis and cancer). Similarly, selective inhibition of TGFβ1 activation by one protease over another protease may also be preferred, depending on the condition being treated. In preferred embodiments, the isoform-selective activation inhibitor of TGFβ1 is Ab42, Ab46, Ab50, a derivative thereof, or an engineered molecule comprising an antigen-binding fragment thereof.

Plasmin is a serine protease produced as a precursor form called Plasminogen. Upon release, Plasmin enters circulation and therefore is detected in serum. Elevated levels of Plasmin appear to correlate with cancer progression, possibly through mechanisms involving disruption of the extracellular matrix (e.g., basement membrane and stromal barriers) which facilitates tumor cell motility, invasion, and metastasis. Plasmin may also affect adhesion, proliferation, apoptosis, cancer nutrition, oxygen supply, formation of blood vessels, and activation of VEGF (Didiasova et al., *Int. J. Mol. Sci,* 2014, 15, 21229-21252). In addition, Plasmin may promote the migration of macrophages into the tumor microenvironment (Philips et al., *Cancer Res.* 2011 Nov. 1;71 (21): 6676-83 and Choong et al., *Clin. Orthop. Relat. Res.* 2003, 415S, S46-S58). Indeed, tumor-associated macrophages (TAMs) are well characterized drivers of tumorigenesis through their ability to promote tumor growth, invasion, metastasis, and angiogenesis.

Plasmin activities have been primarily tied to the disruption of the ECM. However, there is mounting evidence that Plasmin also regulate downstream MMP and TGF beta activation. Specifically, Plasmin has been suggested to cause activation of TGF beta through proteolytic cleavage of the Latency Associated Peptide (LAP), which is derived from the N-terminal region of the TGF beta gene product (Horiguchi et al., *J Biochem.* 2012 October; 152 (4): 321-9), resulting in the release of active growth factor. Since TGFβ1 may promote cancer progression, this raises the possibility that plasmin-induced activation of TGFb may at least in part mediate this process. In preferred embodiments, the isoform-selective activation inhibitor of TGFβ1 is Ab42, Ab46, Ab50, a derivative thereof, or an engineered molecule comprising an antigen-binding fragment thereof.

TGFβ1 has also been shown to regulate expression of uPA, which is a critical player in the conversion of Plasminogen into Plasmin (Santibanez, Juan F., ISRN Dermatology, 2013:597927). uPA has independently been shown to promote cancer progression (e.g., adhesion, proliferation, and migration) by binding to its cell surface receptor (uPAR) and promoting conversion of Plasminogen into Plasmin. Moreover, studies have shown that expression of uPA and/or plasminogen activator inhibitor-1 (PAI-1) are predictors of poor prognosis in colorectal cancer (D. Q. Seetoo, et al., *Journal of Surgical Oncology*, vol. 82, no. 3, pp. 184-193, 2003), breast cancer (N. Harbeck et al., *Clinical Breast Cancer*, vol. 5, no. 5, pp. 348-352, 2004), and skin cancer (Santibanez, Juan F., ISRN Dermatology, 2013:597927). Thus, without wishing to be bound by a particular theory, the interplay between Plasmin, TGFβ1, and uPA may create a positive feedback loop towards promoting cancer progression. Accordingly, inhibitors that selectively inhibit Plasmin-dependent TGFβ1 activation may be particularly suitable for the treatment of cancers reliant on the Plasmin/TGFβ1 signaling axis.

Thrombin may be involved in the activation of GARP-associated TGFβ1. Platelets are reported to express GARP-proTGFβ1. Therefore, thrombin may mediate TGFβ1 activation by targeting this axis in an integrin-independent manner.

In one aspect of the invention, the isoform-specific inhibitors of TGFβ1 described herein include inhibitors that can inhibit protease-dependent activation of TGFβ1. In some embodiments, the inhibitors can inhibit protease-dependent TGFβ1 activation in an integrin-independent manner. In some embodiments, such inhibitors can inhibit TGFβ1 activation irrespective of the mode of activation, e.g., inhibit both integrin-dependent activation and protease-dependent activation of TGFβ1. In some embodiments, the protease is selected from the group consisting of: serine proteases, such as Kallikreins, Chemotrypsin, Trypsin, Elastases, Plasmin, thrombin, as well as zinc metalloproteases (MMP family) such as MMP-2, MMP-9 and MMP-13.

In some embodiments, the inhibitors can inhibit Plasmin-induced activation of TGFβ1. In some embodiments, the inhibitors can inhibit Plasmin- and integrin-induced TGFβ1 activation. In some embodiments, the inhibitors are monoclonal antibodies that specifically bind TGFβ1. In some embodiments, the antibody is a monoclonal antibody that specifically binds proTGFβ1. In some embodiments, the antibody binds latent proTGFβ1 thereby inhibiting release of mature growth factor from the latent complex. In some embodiments, the inhibitor of TGFβ1 activation suitable for use in the method of inhibiting Plasmin-dependent activation of TGFβ1 is any one of the isoform-specific inhibitors disclosed herein. In preferred embodiments, the isoform-selective activation inhibitor of TGFβ1 is Ab42, Ab46, Ab50, a derivative thereof, or an engineered molecule comprising an antigen-binding fragment thereof.

In some embodiments, the inhibitor (e.g., TGFβ1 antibody) inhibits cancer cell migration. In some embodiments, the inhibitor inhibits monocyte/macrophage migration. In some embodiments, the inhibitor inhibits accumulation of TAMs.

In another aspect, provided herein is a method for treating cancer in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby treating cancer in the subject.

In another aspect, provided herein is a method of reducing tumor growth in a subject in need thereof, the method comprising administering to the subject an effective amount of an TGFβ1 inhibitor (e.g., TGFβ1 antibody), wherein the inhibitor inhibits protease-induced activation of TGFβ1 (e.g., Plasmin), thereby reducing tumor growth in the subject.

Disease Involving Aberrant Gene Expression

It has been observed that abnormal activation of the TGFβ1 signal transduction pathway in various disease conditions is associated with altered gene expression of a number of markers. These gene expression markers (e.g., as measured by mRNA) include, but are not limited to: Serpine 1 (encoding PAI-1), MCP-1 (also known as CCL2), Col1a1, Col3a1, FN1, TGFβ1, CTGF, ACTA2 (encoding α-SMA), SNAI1 (drives EMT in fibrosis and metastasis by downregulating E-cadherin (Cdh1), MMP2 (matrix metalloprotease associated with EMT), MMP9 (matrix metalloprotease associated with EMT), TIMP1 (matrix metalloprotease associated with EMT), FOXP3 (marker of Treg induction), CDH1 (E cadherin (marker of epithelial cells) which is downregulated by TGFβ), and, CDH2 (N cadherin (marker of mesenchymal cells) which is upregulated by TGFβ). Interestingly, many of these genes are implicated to play a role in a diverse set of disease conditions, including various types of organ fibrosis, as well as in many cancers, which include myelofibrosis. Indeed, pathophysiological link between fibrotic conditions and abnormal cell proliferation, tumorigenesis and metastasis has been suggested. See for example, Cox and Erler (2014) Clinical Cancer Research 20 (14): 3637-43 "Molecular pathways: connecting fibrosis and solid tumor metastasis"; Shiga et al., (2015) *Cancers* 7:2443-2458 "Cancer-associated fibroblasts: their characteristics and their roles in tumor growth"; Wynn and Barron (2010) *Semin. Liver Dis.* 30 (3): 245-257 "Macrophages: master regulators of inflammation and fibrosis", contents of which are incorporated herein by reference. Without wishing to be bound by a particular theory, the inventors of the present disclosure contemplate that the TGFβ1 signaling pathway may in fact be a key link between these broad pathologies.

The ability of chemotactic cytokines (or chemokines) to mediate leukocyte recruitment (e.g., monocytes/macrophages) to injured or disease tissues has crucial consequences in disease progression. Members of the C-C chemokine family, such as monocyte chemoattractant protein 1 (MCP-1), also known as CCL2, macrophage inflammatory protein 1-alpha (MIP-1a), also known as CCL3, and MIP-1B, also known as $CCL_4$, have been implicated in this process.

For example, MCP-1/CCL2 is thought to play a role in both fibrosis and cancer. MCP-1/CCL2 is characterized as a profibrotic chemokine and is a monocyte chemoattractant, and evidence suggests that it may be involved in both initiation and progression of cancer. In fibrosis, MCP-1/CCL2 has been shown to play an important role in the inflammatory phase of fibrosis. For example, neutralization of MCP-1 resulted in a dramatic decrease in glomerular crescent formation and deposition of type I collagen. Similarly, passive immunotherapy with either anti-MCP-1 or anti-MIP-1 alpha antibodies is shown to significantly reduce mononuclear phagocyte accumulation in bleomycin-challenged mice, suggesting that MIP-1 alpha and MCP-1 contribute to the recruitment of leukocytes during the pulmonary inflammatory response (Smith, *Biol Signals.* 1996 July-Aug;5 (4): 223-31, "Chemotactic cytokines mediate leukocyte recruitment in fibrotic lung disease"). Elevated levels of MIP-1alpha in patients with cystic fibrosis and multiple myeloma have been reported (see, for example: Mrugacz et al., *J Interferon Cytokine Res.* 2007 June;27 (6): 491-5), supporting the notion that MIP-1a is associated with localized or systemic inflammatory responses.

Lines of evidence point to the involvement of C-C chemokines in tumor progression. For example, tumor-derived MCP-1/CCL2 can promote "pro-cancer" phenotypes in macrophages. For example, in lung cancer, MCP-1/CCL2 has been shown to be produced by stromal cells and promote metastasis. In human pancreatic cancer, tumors secrete CCL2, and immunosuppressive CCR2-positive macrophages infiltrate these tumors. Patients with tumors that exhibit high CCL2 expression/low CD8 T-cell infiltrate have significantly decreased survival. It is contemplated that monocytes that are recruited to an injured or diseased tissue environment may subsequently become polarized in response to local cues (such as in response to tumor-derived cytokines), thereby further contributing to disease progression. These M2-like macrophages are likely to contribute to immune evasion by suppressing effector cells, such as CD4+ and CD8+ T cells. In some embodiments, this process is in part mediated by LRRC33-TGFβ1 expressed by activated macrophages. In some embodiments, the process is in part mediated by GARP-TGFβ1 expressed by Tregs.

Similarly, involvement of PAI-1/Serpine1 has been implicated in a variety of cancers, angiogenesis, inflammation, neurodegenerative diseases (e.g., Alzheimer's Disease). Elevated expression of PAI-1 in tumor and/or serum is correlated with poor prognosis (e.g., shorter survival, increased metastasis) in various cancers, such as breast cancer and bladder cancer (e.g., transitional cell carcinoma) as well as myelofibrosis. In the context of fibrotic conditions, PAI-1 has been recognized as an important downstream effector of TGFβ1-induced fibrosis, and increased PAI-1 expression has been observed in various forms of tissue fibrosis, including lung fibrosis (such as Idiopathic Pulmonary Fibrosis (IPF)), kidney fibrosis, liver fibrosis and scleroderma. In some embodiments, the process is in part mediated by ECM-associated TGFβ1, e.g., via LTBP1 and/or LTBP3.

In some embodiments, in vivo effects of the TGFβ1 inhibitor therapy may be assessed by measuring changes in gene markers. Suitable markers include TGFβ (e.g., TGFβ1, TGFβ2, and TGFβ3). Suitable markers may also include one or more presenting molecules for TGFβ (e.g., TGFβ1, TGFβ2, and TGFβ3), such as LTBP1, LTBP3, GARP (or LRRC32) and LRRC33. In some embodiments, suitable markers include mesenchymal transition genes (e.g., fibronectin, vimentin, N-cadherin, AXL, ROR2, WNT5A, LOXL2, TWIST2, TAGLN, and/or FAP), immunosuppressive genes (e.g., IL10, VEGFA, VEGFC), monocyte and macrophage chemotactic genes (e.g., CCL2, CCL3, $CCL_4$, CCL7, CCL8 and CCL13), and/or various fibrotic markers discussed herein. Preferred markers are plasma markers.

As shown in the Examples herein, isoform-specific inhibitors of TGFβ1 described herein can reduce expression levels of many of these markers in a mechanistic animal model, such as UUO, which has been shown to be TGFβ1-dependent. Therefore, such inhibitors may be used to treat a disease or disorder characterized by abnormal expression (e.g., overexpression/upregulation or underexpression/downregulation) of one or more of the gene expression markers.

Thus, in some embodiments, an isoform-specific inhibitor of TGFβ1 is used in the treatment of a disease associated with overexpression of one or more of the following: PAI-1 (encoded by Serpine1), MMP2, MMP9, MCP-1 (also known as CCL2), Col1a1, Col3a1, FN1, TGFβ1, CTGF, α-SMA, ITGA11, and ACTA2, wherein the treatment comprises administration of the inhibitor to a subject suffering from the disease in an amount effective to treat the disease. In some embodiments, the inhibitor is used to treat a disease associated with overexpression of PAI-1, MCP-1/CCL2, CTGF, and/or α-SMA. In some embodiments, the disease is myelofibrosis. In some embodiments, the disease is cancer, for example, cancer comprising a solid tumor. In some embodiments, the disease is organ fibrosis, e.g., fibrosis of the liver, the kidney, the lung, the muscle, the skin and/or the cardiac or cardiovascular tissue. In some embodiments, the disease is Alport Syndrome. In some embodiments, the inhibitor reduces expression of one or more of the following: PAI-1 (encoded by Serpine1), MMP2, MMP9, MCP-1 (also known as CCL2), Col1a1, Col3a1, FN1, TGFβ1, CTGF, α-SMA, ITGA11, and ACTA2. In preferred embodiments, the TGFβ1-selective inhibitor is Ab42, Ab46, Ab50, a derivative thereof, or an engineered molecule comprising an antigen-binding fragment thereof.

Another biomarker which may be used to assess the in vivo effects of the TGFβ1 inhibitor therapy is blood urea nitrogen (BUN). Urea is naturally formed in the body as a by-product of protein breakdown. The urea travels from the liver to the kidneys where it is filtered/removed from the blood. Accordingly, BUN levels may increase in situations when a patient's kidneys are not functioning properly. For example, patients having kidney fibrosis may display increased BUN. Accordingly, in some embodiments, BUN is measured to assess the in vivo effects of the isoform-specific inhibitors of TGFβ1 as described herein. In other embodiments, an isoform-specific inhibitor of TGFβ1 is used in the treatment of a disease associated with increased BUN (e.g., kidney fibrosis and/or acute or chronic kidney disease, damage, or failure). In a particular embodiment, the disease associated with increased BUN is Alport Syndrome.

Accordingly, the present disclosure includes a method of selecting a candidate patient or patient population likely to respond to a TGFβ1 inhibition therapy. Such method may comprise a step of testing a biological sample collected from the patient (or patient population), such as biopsy samples, for the expression of one or more of the markers discussed herein. Similarly, such genetic marker(s) may be used for purposes of monitoring the patient's responsiveness to a therapy. Monitoring may include testing two or more biological samples collected from the patient, for example, before and after administration of a therapy, and during the course of a therapeutic regimen over time, to evaluate changes in gene expression levels of one or more of the markers, indicative of therapeutic response or effectiveness.

In some embodiments, a method of selecting a candidate patient or patient population likely to respond to a TGFβ1 inhibition therapy may comprise a step of identifying a patient or patient population previously tested for the genetic marker(s), such as those described herein, which showed aberrant expression thereof. In some embodiments, the aberrant marker expression includes elevated levels of at least one of the following: TGFβ1, LRRC33, GARP, LTBP1, LTBP3, CCL2, CCL3, PAI-1/Serpine1, MMP2, MMP9, Col1a1, Col3a1, FN1, CTGF, α-SMA, ITGA11, and ACTA2. In some embodiments, the patient or patient population (e.g., biological samples collected therefrom) shows elevated TGFβ1 activation, phospho-SMAD2/3, or combination thereof. In some embodiments, the patient or patient population shows elevated BUN.

Circulating/Circulatory MDSCs as a Biomarker

MDSCs are a heterogeneous population of cells named for their myeloid origin and their main immune suppressive function (Gabrilovich. Cancer *Immunol* Res. 2017 January; 5 (1): 3-8). MDSCs generally exhibit high plasticity and strong capacity to reduce cytotoxic functions of T cells and natural killer (NK) cells, including their ability to promote T regulatory cell (Treg) expansion and in turn suppress T effector cell function (Gabrilovich et al., *Nat Rev Immunol.* (2012) 12:253-68). MDSCs are typically classified into two subsets, monocytic (m-MDSCs) and granulocytic (G-MDSCs or PMN-MDSCs), based on their expression of surface markers (Consonni et al., *Front Immunol.* 2019 May 3; 10:949). Suppressive G-MDSCs can be characterized by their production of reactive oxygen species (ROS) as the major mechanism of immune suppression. In contrast, M-MDSCs mediate immune suppression primarily by upregulating the inducible nitric oxide synthase gene (iNOS) and produce nitric oxide (NO) as well as an array of immune suppressive cytokines (Youn and Garilovich, *Eur J Immunol.* 2010 November; 40 (11): 2969-2975).

In some embodiments, the patient or patient population (e.g., biological samples collected therefrom) shows elevated MDSCs. In some embodiments, the sample is a whole blood sample or a blood component (e.g., plasma or serum). In some embodiments, the sample is fresh whole blood or a blood component (e.g., of a sample that has not been previously frozen).

In some embodiments, the patient or patient population has a fibrotic disorder or disease (such as organ fibrosis). In some embodiments, the patient has NASH.

In certain embodiments, a TGFβ inhibitor described herein, e.g., an isoform-selective activation inhibitor of TGFβ1 such as Ab2, Ab42, Ab46, Ab50, or derivatives thereof, an isoform-non-selective inhibitor, e.g., low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors, and/or an integrin inhibitor (e.g., an antibody that binds to αVβ3, αVβ5, αVβ6, αVβ8, $\alpha_5\beta_1$, $\alpha_{IIb}\beta_3$, or a8B1 integrins, and inhibits downstream activation of TGFβ. e.g., selective inhibition of TGFβ1 and/or TGFβ3) is administered such that the amount (e.g., dose) of TGFβ1 inhibition administered is sufficient to reduce circulating MDSC levels by at least 10%, at least 15%, at least 20%, at least 25%, or more, as compared to baseline MDSC levels. Circulating MDSC levels may be measured prior to or after each treatment or each dose of the TGFβ inhibitor such that a decrease of at least 10%, at least 15%, at least 20%, at least 25%, or more in circulating MDSC levels may be indicative or predictive of treatment efficacy. In some embodiments, the level of circulating MDSCs may be used to determine disease burden (e.g., as measured by a change in fibrosis before and after a treatment regimen). In certain embodiments, a decrease in circulating MDSC levels may be indicative of a decrease in disease burden (e.g., a decrease in fibrosis). For instance, circulating MDSC levels may be measured prior to and after the administration of a dose of a TGFβ inhibitor described herein, e.g., an isoform-selective activation inhibitor of TGFβ1 such as Ab2, Ab42, Ab46, Ab50, or derivatives thereof, isoform-non-selective TGFβ inhibitors, e.g., low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors, and/or an integrin inhibitor (e.g., an antibody that binds to αVβ3, αVβ5, αVβ6, αVβ8, $\alpha_5\beta_1$, $\alpha_{IIb}\beta_3$, or a8B1 integrins, and inhibits downstream activation of TGFβ. e.g., selective inhibition of TGFβ1 and/or TGFβ3) and a reduction in circulating MDSC levels may be indicative or predictive of pharmacological effects, e.g., of a reduction in disease burden (e.g., a reduction in fibrosis). In certain embodiments, circulating MDSC levels may be measured prior to and following administration of a first dose of a TGFβ inhibitor, such as a TGFβ inhibitor described herein, e.g., an isoform-selective activation inhibitor of TGFβ1 such as Ab2, Ab42, Ab46, Ab50, or derivatives thereof, an isoform-non-selective inhibitor, e.g., low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors, and/or an integrin inhibitor (e.g., an antibody that binds to αVβ3, αVβ5, αVβ6, αVβ8, a531, $\alpha_{IIb}\beta_3$, or a8B1 integrins, and inhibits downstream activation of TGFβ. e.g., selective inhibition of TGFβ1 and/or TGFβ3). In some embodiments, reduction in circulating MDSC levels is indicative or predictive of pharmacological effects and further warrants administration of a second or more dose(s) of the TGFβ inhibitor. In some embodiments, the first dose of the TGFβ inhibitor is the very first dose of TGFβ inhibitor received by the patient. In some embodiments, the first dose of the TGFβ inhibitor is the first dose of a given treatment regimen comprising more than one dose of TGFβ inhibitor. In another embodiment, circulating MDSC levels may be measured prior to and after combination treatment comprising a TGFβ inhibitor described herein, e.g., an isoform-selective activation inhibitor of TGFβ1 such as Ab2, Ab42, Ab46, Ab50, or derivatives thereof. In some embodiments, the reduction of circulating MDSC levels following the treatment of a TGFβ inhibitor described herein, e.g., an isoform-selective activation inhibitor of TGFβ1 such as Ab2, Ab42, Ab46, Ab50, or derivatives thereof, an isoform-non-selective inhibitor, e.g., low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors, and/or an integrin inhibitor (e.g., an antibody that binds to αVβ3, αVβ5, αVβ6, αVβ8, $\alpha_5\beta_1$, $\alpha_{IIb}\beta_3$, or a8B1 integrins, and inhibits downstream activation of TGFβ. e.g., selective inhibition of TGFβ1 and/or TGFβ3), may warrant continuation of treatment.

In some aspects, the disclosure provides a method of treating fibrosis in a subject, the method comprising steps of selecting a TGFβ inhibitor that inhibits TGFβ1 but does not inhibit one or both of TGFβ2 and TGFβ3; administering to a subject having a fibrotic condition the TGFβ inhibitor in an amount sufficient to reduce circulating MDSC levels. In some embodiments, the circulating MDSC levels are determined from whole blood or a blood component collected from the subject. In some embodiments, the circulating MDSC levels are reduced by at least 10%, optionally by at least 15%, 20%, 25%, or more.

In some embodiments, the isoform-selective inhibitor of TGFβ1 as described herein is used in a method of reducing circulating MDSC levels in a subject. In some embodiments, the circulating MDSC levels are determined from whole blood or a blood component collected from the subject. In some embodiments, the circulating MDSC levels are reduced by at least 10%, optionally by at least 15%, 20%, 25%, or more. In some embodiments, the TGFβ inhibitor is administered in an amount sufficient to reduce circulating MDSC levels.

In certain embodiments of the present disclosure, levels of circulating MDSCs may be used to predict, determine, and monitor pharmacological effects of treatment comprising a dose of TGFβ inhibitor, such as a TGFβ inhibitor described herein, e.g., an isoform-selective activation inhibitor of TGFβ1 such as Ab2, Ab42, Ab46, Ab50, or derivatives thereof, an isoform-non-selective inhibitor, e.g., low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors, and/or an integrin inhibitor (e.g., an antibody that binds to αVβ3, αVβ5, αVβ6, αVβ8, a51, αIIbβ3, or α8β1 integrins, and inhibits downstream activation of TGFβ. e.g., selective inhibition of TGFβ1 and/or TGFβ3) administered alone or in conjunction with another therapy. In certain embodiments, circulating MDSCs may be measured within six weeks following administration of the initial treatment (e.g., the (first) dose of TGFβ inhibitor). In certain embodiments, circulating MDSC levels may be measured within thirty days following administration of the initial dose of TGFβ inhibitor. In some embodiments, MDSC levels may be measured within or at about three weeks following administration of the initial dose of TGFβ inhibitor. In some embodiments, MDSC levels may be measured within or at about two weeks following administration of the initial dose of TGFβ inhibitor. In some embodiments, MDSC levels may be measured within or at about ten days following administration of the initial dose of TGFβ inhibitor.

In some embodiments, such patient or patient population has cancer, which may comprise a solid tumor. The solid tumor may be a TGFβ1-dominant tumor, in which TGFβ1 is the predominant isoform expressed in the tumor, relative to the other isoforms. In some embodiments, such patient or patient population exhibits resistance to a cancer therapy, such as chemotherapy, radiation therapy and/or immune checkpoint therapy, e.g., anti-PD-1 (e.g., pembrolizumab and nivolumab), anti-PD-L1 (e.g., atezolizumab), anti-CTLA4 (e.g., ipilimumab), engineered immune cell therapy (e.g., CAR-T), and cancer vaccines, etc. According to the invention, the isoform-specific TGFβ1 inhibitor, such as those disclosed herein, overcomes the resistance by unblocking immunosuppression so as to allow effector cells to gain access to cancer cells thereby achieving anti-tumor effects.

Proliferative Disorders (e.g., Myeloproliferative Disorder)

In some embodiments, the antibodies described herein, may be used to treat a proliferative disorder. In some embodiments, the isoform-selective inhibitor of TGFβ1 described herein is for use in the treatment of a myeloproliferative disorder in a subject. In some embodiments, the proliferative disorder is a cancer or a myeloproliferative disorder. In some embodiments, the myeloproliferative disorder is myelofibrosis.

Myelofibrosis, also known as osteomyelofibrosis, is a relatively rare bone marrow proliferative disorder (cancer), which belongs to a group of diseases called myeloproliferative disorders. Myelofibrosis is classified into the Philadelphia chromosome-negative (−) branch of myeloproliferative neoplasms. Myelofibrosis is characterized by clonal myeloproliferation, aberrant cytokine production, extramedullary hematopoiesis, and bone marrow fibrosis. The proliferation of an abnormal clone of hematopoietic stem cells in the bone marrow and other sites results in fibrosis, or the replacement of the marrow with scar tissue. The term myelofibrosis, unless otherwise specified, refers to primary myelofibrosis (PMF). This may also be referred to as chronic idiopathic myelofibrosis (cIMF) (the terms idiopathic and primary mean that in these cases the disease is of unknown or spontaneous origin). This is in contrast with myelofibrosis that develops secondary to polycythemia vera or essential thrombocythaemia. Myelofibrosis is a form of myeloid metaplasia, which refers to a change in cell type in the blood-forming tissue of the bone marrow, and often the two terms are used synonymously. The terms agnogenic myeloid metaplasia and myelofibrosis with myeloid metaplasia (MMM) are also used to refer to primary myelofibrosis. In some embodiments, the hematologic proliferative disorders which may be treated in accordance with the present invention include myeloproliferative disorders, such as myelofibrosis. So-called "classical" group of BCR-ABL (Ph) negative chronic myeloproliferative disorders includes essential thrombocythemia (ET), polycythemia vera (PV) and primary myelofibrosis (PMF).

Myelofibrosis disrupts the body's normal production of blood cells. The result is extensive scarring in the bone marrow, leading to severe anemia, weakness, fatigue and often an enlarged spleen. Production of cytokines such as fibroblast growth factor by the abnormal hematopoietic cell clone (particularly by megakaryocytes) leads to replacement of the hematopoietic tissue of the bone marrow by connective tissue via collagen fibrosis. The decrease in hematopoietic tissue impairs the patient's ability to generate new blood cells, resulting in progressive pancytopenia, a shortage of all blood cell types. However, the proliferation of fibroblasts and deposition of collagen is thought to be a secondary phenomenon, and the fibroblasts themselves may not be part of the abnormal cell clone.

Myelofibrosis may be caused by abnormal blood stem cells in the bone marrow. The abnormal stem cells produce mature and poorly differentiated cells that grow quickly and take over the bone marrow, causing both fibrosis (scar tissue formation) and chronic inflammation.

Primary myelofibrosis is associated with mutations in Janus kinase 2 (JAK2), thrombopoietin receptor (MPL) and calreticulin (CALR), which can lead to constitutive activation of the JAK-STAT pathway, progressive scarring, or fibrosis, of the bone marrow occurs. Patients may develop extramedullary hematopoiesis, i.e., blood cell formation occurring in sites other than the bone marrow, as the haemopoetic cells are forced to migrate to other areas, particularly the liver and spleen. This causes an enlargement of these organs. In the liver, the abnormal size is called hepatomegaly. Enlargement of the spleen is called splenomegaly, which also contributes to causing pancytopenia, particularly thrombocytopenia and anemia. Another complication of extramedullary hematopoiesis is poikilocytosis, or the presence of abnormally shaped red blood cells.

The principal site of extramedullary hematopoiesis in myelofibrosis is the spleen, which is usually markedly enlarged in patients suffering from myelofibrosis. As a result of massive enlargement of the spleen, multiple subcapsular infarcts often occur in the spleen, meaning that due to interrupted oxygen supply to the spleen partial or complete tissue death happens. On the cellular level, the spleen contains red blood cell precursors, granulocyte precursors and megakaryocytes, with the megakaryocytes prominent in their number and in their abnormal shapes. Megakaryocytes may be involved in causing the secondary fibrosis seen in this condition.

It has been suggested that TGFβ may be involved in the fibrotic aspect of the pathogenesis of myelofibrosis (see, for example, Agarwal et al., "Bone marrow fibrosis in primary myelofibrosis: pathogenic mechanisms and the role of TGFβ" (2016) Stem Cell Investig 3:5). Bone marrow pathology in primary myelofibrosis is characterized by fibrosis, neoangeogenesis and osteosclerosis, and the fibrosis is associated with an increase in production of collagens deposited in the ECM.

A number of biomarkers have been described, alternations of which are indicative of or correlate with the disease. In some embodiments, the biomarkers are cellular markers. Such disease-associated biomarkers are useful for the diagnosis and/or monitoring of the disease progression as well as effectiveness of therapy (e.g., patients' responsiveness to the therapy). These biomarkers include a number of fibrotic markers, as well as cellular markers. In lung cancer, for example, TGFβ1 concentrations in the bronchoalveolar lavages (BAL) fluid are reported to be significantly higher in patients with lung cancer compared with patients with benign diseases (~2+fold increase), which may also serve as a biomarker for diagnosing and/or monitoring the progression or treatment effects of lung cancer.

Because primary myelofibrosis is associated with abnormal megakaryocyte development, certain cellular markers of megakaryocytes as well as their progenitors of the stem cell lineage may serve as markers to diagnose and/or monitor the disease progression as well as effectiveness of therapy. In some embodiments, useful markers include, but are not limited to: cellular markers of differentiated megakaryocytes (e.g., CD41, CD42 and Tpo R), cellular markers of megakaryocyte-erythroid progenitor cells (e.g., CD34, CD38, and CD45RA-), cellular markers of common myeloid progenitor cells (e.g., IL-3a/CD127, CD34, SCF R/c-kit and Flt-3/Flk-2), and cellular markers of hematopoietic stem cells (e.g., CD34, CD38-, Flt-3/Flk-2). In some embodiments, useful biomarkers include fibrotic markers. These include, without limitation: TGFβ1, PAI-1 (also known as Serpine1), MCP-1 (also known as CCL2), Col1a1, Col3a1, FN1, CTGF, α-SMA, ACTA2, Timp1, Mmp8, and Mmp9. In some embodiments, useful biomarkers are serum markers (e.g., proteins or fragments found and detected in serum samples).

Based on the finding that TGFβ is a component of the leukemic bone marrow niche, it is contemplated that targeting the bone marrow microenvironment with TGFβ inhibitors may be a promising approach to reduce leukemic cells expressing presenting molecules that regulate local TGFβ availability in the effected tissue.

Indeed, due to the multifaceted nature of the pathology which manifests TGFβ-dependent dysregulation in both myelo-proliferative and fibrotic aspects (as the term "myelofibrosis" itself suggests), isoform-specific, inhibitors of TGFβ1, which target matrix- and cell-associated TGFβ1 complexes, such as those described herein, may provide particularly advantageous therapeutic effects for patients suffering from myelofibrosis. It is contemplated that the LTBP-arm of such inhibitor can target ECM-associated TGFβ1 complex in the bone marrow, whilst the LRRC33-arm of the inhibitor can block myeloid cell-associated TGFβ1. In addition, abnormal megakaryocyte biology associated with myelofibrosis may involve both GARP- and LTBP-mediated TGFβ1 activities. The isoform-specific inhibitor of TGFβ1 is capable of targeting such complexes thereby inhibiting release of active TGFβ1 in the niche.

Thus, such TGFβ1 inhibitors are useful for treatment of patients with polycythemia vera who have had an inadequate response to or are intolerant of other (or standard-of-care)

treatments, such as hydroxyurea and JAK inhibitors. Such inhibitors are also useful for treatment of patients with intermediate or high-risk myelofibrosis (MF), including primary MF, post-polycythemia vera MF and post-essential thrombocythemia MF. In preferred embodiments, the isoform-selective inhibitor of TGFβ1 is Ab42, Ab46, Ab50, a derivative thereof, or an engineered molecule comprising an antigen-binding fragment thereof.

Accordingly, one aspect of the invention relates to methods for treating primary myelofibrosis. The method comprises administering to a patient suffering from primary myelofibrosis a therapeutically effective amount of a composition comprising a TGFβ inhibitor that causes reduced TGFβ availability. In some embodiments, an inhibitor of TGFβ1 activation is administered to patients with myelofibrosis. Such antibody may be administered at dosages ranging between 0.1 and 100 mg/kg, such as between 1 and 30 mg, e.g., 1 mg/kg, 3 mg/kg, 5 mg/kg, 10 mg/kg, 15 mg/kg, 20 mg/kg, etc. For example, suitable dosing regimens include between 1-20 mg/kg administered weekly. Preferred routes of administration of a pharmaceutical composition comprising the antibody is intravenous or subcutaneous administration. When the composition is administered intravenously, the patient may be given the therapeutic over a suitable duration of time, e.g., approximately 30-120 minutes (e.g., 30 min, 60 min, 75 min, 90 min, and 120 min), per treatment, and then repeated every several weeks, e.g., 3 weeks, 4 weeks, 6 weeks, etc., for a total of several cycles, e.g., 4 cycles, 6, cycles, 8 cycles, 10 cycles, 12 cycles, etc. In some embodiments, patients are treated with a composition comprising the inhibitory antibody at dose level of 1-10 mg/kg (e.g., 1, 2, 3, 4, 5, 6, 7, 8, 9, or 10 mg/kg per dosing) via intravenous administration every 28 days (4 weeks) for 6 cycles or 12 cycles. In some embodiments, such treatment is administered as a chronic (long-term) therapy (e.g., to be continued indefinitely, as long as deemed beneficial) in lieu of discontinuing following a set number of cycles of administration.

While myelofibrosis is considered a type of leukemia, it is also characterized by the manifestation of fibrosis. Because TGFβ is known to regulate aspects of ECM homeostasis, the dysregulation of which can lead to tissue fibrosis, it is desirable to inhibit TGFβ activities associated with the ECM. Accordingly, the antibodies or fragments described herein inhibit proTGFβ presented by LTBPs (such as LTBP1 and LTBP3), as well as inhibit proTGFβ presented by GARP and LRRC33.

Early in vivo data indicate that an isoform-selective inhibitor of TGFβ1, such as those described herein, can be used to treat myelofibrosis in a translatable murine model of primary myelofibrosis. Unlike the current standard of care JAK2 inhibitor, which only provides symptomatic relief but does not provide clinical or survival benefits, the isoform-selective inhibitor of TGFβ1 achieves significant anti-fibrotic effects in the bone marrow of the diseased mice and may also prolong survival, supporting the notion that the TGFβ1 inhibitor may be effective to treat myeloproliferative disorders in human patients.

Suitable patient populations of myeloproliferative neoplasms who may be treated with the compositions and methods described herein may include, but are not limited to: a) a patient population that is Philadelphia (+); b) a patient population that is Philadelphia (−); c) a patient population that is categorized "classical" (PV, ET and PMF); d) a patient population carrying the mutation JAK2V617F (+); e) a patient population carrying JAK2V617F (−); f) a patient population with JAK2 exon 12 (+); g) a patient population with MPL (+); and h) a patient population with CALR (+).

In some embodiments, the patient population includes patients with intermediate-2 or high-risk myelofibrosis. In some embodiments, the patient population comprises subjects with myelofibrosis who are refractory to or not candidates for available therapy. In some embodiments, the subject has platelet counts between 100-200×$10^9$/L. In some embodiments, the subject has platelet counts>200×$10^9$/L prior to receiving the treatment.

In some embodiments, a subject to receive (and who may benefit from receiving) an isoform-specific, TGFβ1 inhibitor therapy is diagnosed with intermediate-1 or higher primary myelofibrosis (PMF), or post-polycythemmia vera/essential thrombocythemia myelofibrosis (post-PV/ET MF). In some embodiments, the subject has documented bone marrow fibrosis prior to the treatment. In some embodiments, the subject has MF-2 or higher as assessed by the European consensus grading score and grade 3 or higher by modified Bauermeister scale prior to the treatment. In some embodiments, the subject has the ECOG performance status of 1 prior to the treatment. In some embodiments, the subject has white blood cell count ($10^9$/L) ranging between 5 and 120 prior to the treatment. In some embodiments, the subject has the JAK2V617F allele burden that ranges between 10-100%.

In some embodiments, a subject to receive (and who may benefit from receiving) an isoform-specific, TGFβ1 inhibitor therapy is transfusion-dependent (prior to the treatment) characterized in that the subject has a history of at least two units of red blood cell transfusions in the last month for a hemoglobin level of less than 8.5 g/dL that is not associated with clinically overt bleeding.

In some embodiments, a subject to receive (and who may benefit from receiving) an isoform-specific, TGFβ1 inhibitor therapy previously received a therapy to treat myelofibrosis. In some embodiments, the subject has been treated with one or more of therapies, including but are not limited to: AZD1480, panobinostat, EPO, IFNα, hydroxyurea, pegylated interferon, thalidomide, prednisone, and JAK2 inhibitor (e.g., Lestaurtinib, CEP-701).

In some embodiments, the patient has extramedullary hematopoiesis. In some embodiments, the extramedullary hematopoiesis is in the liver, lung, spleen, and/or lymph nodes. In some embodiments, the pharmaceutical composition of the present invention is administered locally to one or more of the localized sites of disease manifestation.

According to some embodiments, the isoform-selective inhibitor of TGFβ1 is for use in the treatment of a myeloproliferative disorder in a subject. The isoform-specific, TGFβ1 inhibitor is administered to patients in an amount effective to treat myelofibrosis.

The therapeutically effective amount is an amount sufficient to relieve one or more symptoms and/or complications of myelofibrosis in patients, including but are not limited to: excessive deposition of ECM in bone marrow stroma, neoangiogenesis, osteosclerosis, splenomegaly, hematomegaly, anemia, bleeding, bone pain and other bone-related morbidity, extramedullary hematopoiesis, thrombocytosis, leukopenia, cachexia, infections, thrombosis and death. In preferred embodiments, the inhibitor is Ab42, Ab46, Ab50, a derivative thereof, or an engineered molecule comprising an antigen-binding fragment thereof.

In some embodiments, the amount is effective to reduce TGFβ1 expression and/or secretion (such as of megakaryocytic cells) in patients. Such inhibitor may therefore reduce TGFβ1 mRNA levels in treated patients. In some embodiments, such inhibitor reduces TGFβ1 mRNA levels in bone marrow, such as in mononuclear cells. PMF patients typically show elevated plasma TGFβ1 levels of above ~2,500 μg/mL, e.g., above 3,000, 3,500, 4,000, 4,500, 5,000, 6,000, 7,000, 8,000, 9,000, and 10,000 μg/mL (contrast to normal ranges of ~600-2,000 μg/mL as measured by ELISA) (see, for example, Mascaremhas et al., (*Leukemia & Lymphoma,* 2014, 55 (2): 450-452)). Zingariello (Blood, 2013, 121 (17): 3345-3363) quantified bioactive and total TGFβ1 contents in the plasma of PMF patients and control individuals. According to this reference, the median bioactive TGFβ1 in PMF patients was 43 ng/mL (ranging between 4-218 ng/ml) and total TGFβ1 was 153 ng/ml (32-1000 ng/ml), while in control counterparts, the values were 18 (0.05-144) and 52 (8-860), respectively. Thus, based on these reports, plasma TGFβ1 contents in PMF patients are elevated by several fold, e.g., 2-fold, 3-fold, 4-fold, 5-fold, etc., as compared to control or healthy plasma samples. Treatment with the inhibitor, e.g., following 4-12 cycles of administration (e.g., 2, 4, 6, 8, 10, 12 cycles) or chronic or long-term treatment, for example every 4 weeks, at dosage of 0.1-100 mg/kg, for example, 1-30 mg/kg monoclonal antibody) described herein may reduce the plasma TGFβ1 levels by at least 10% relative to the corresponding baseline (pre-treatment), e.g., at least 15%, 20%, 25%, 30%, 35%, 40%, 45%, and 50%.

Some of the therapeutic effects may be observed relatively rapidly following the commencement of the treatment, for example, after 1 week, 2 weeks, 3 weeks, 4 weeks, 5 weeks or 6 weeks. For example, the inhibitor may effectively increase the number of stem cells and/or precursor cells within the bone marrow of patients treated with the inhibitor within 1-8 weeks. These include hematopoietic stem cells and blood precursor cells. A bone marrow biopsy may be performed to assess changes in the frequencies/number of marrow cells. Correspondingly, the patient may show improved symptoms such as bone pain and fatigue.

One of the morphological hallmarks of myelofibrosis is fibrosis in the bone marrow (e.g., marrow stroma), characterized in part by aberrant ECM. In some embodiments, the amount is effective to reduce excessive collagen deposition, e.g., by mesenchymal stromal cells. In some embodiments, the inhibitor is effective to reduce the number of CD41-positive cells, e.g., megakaryocytes, in treated subjects, as compared to control subjects that do not receive the treatment. In some embodiments, baseline frequencies of megakaryocytes in PMF bone marrow may range between 200-700 cells per square millimeters ($mm_2$), and between 40-300 megakaryocites per square-millimeters ($mm_2$) in PMF spleen, as determined with randomly chosen sections. In contrast, megakaryocyte frequencies in bone marrow and spleen of normal donors are fewer than 140 and fewer than 10, respectively. Treatment with the inhibitor may reduce the number (e.g., frequencies) of megakaryocytes in bone marrow and/or spleen. In some embodiments, treatments with the inhibitor can cause reduced levels of downstream effector signaling, such as phosphorylation of SMAD2/3.

Patients with myelofibrosis may suffer from enlarged spleen. Thus, clinical effects of a therapeutic may be evaluated by monitoring changes in spleen size. Spleen size may be examined by known techniques, such as assessment of the spleen length by palpation and/or assessment of the spleen volume by ultrasound. In some embodiments, the subject to be treated with an isoform-specific, inhibitor of TGFβ1 has a baseline spleen length (prior to the treatment) of 5 cm or greater, e.g., ranging between 5 and 30 cm as assessed by palpation. In some embodiments, the subject to be treated with an isoform-specific, \inhibitor of TGFβ1 has a baseline spleen volume (prior to the treatment) of 300 ml or greater, e.g., ranging between 300-1500 mL, as assessed by ultrasound. Treatment with the inhibitor, e.g., following 4-12 cycles of administration (e.g., 2, 4, 6, 8, 10, 12 cycles), for example every 4 weeks, at dosage of 0.1-30 mg/kg monoclonal antibody) described herein may reduce spleen size in the subject. In some embodiments, the effective amount of the inhibitor is sufficient to reduce spleen size in a patient population that receives the inhibitor treatment by at least 10%, 20%, 30%, 35%, 40%, 50%, and 60%, relative to corresponding baseline values. For example, the treatment is effective to achieve a>35% reduction in spleen volume from baseline in 12-24 weeks as measured by MRI or CT scan, as compared to placebo control. In some embodiments, the treatment is effective to achieve a≥35% reduction in spleen volume from baseline in 24-48 weeks as measured by MRI or CT scan, as compare to best available therapy control. Best available therapy may include hydroxyurea, glucocorticoids, as well as no medication, anagrelide, epoetin alfa, thalidomide, lenalidomide, mercaptopurine, thioguanine, danazol, peginterferon alfa-2a, interferon-α, melphalan, acetylsalicylic acid, cytarabine, and colchicine.

In some embodiments, a patient population treated with an isoform-specific, TGFβ1 inhibitor such as those described herein, shows a statistically improved treatment response as assessed by, for example, International Working Group for Myelofibrosis Research and Treatment (IWG-MRT) criteria, degree of change in bone marrow fibrosis grade measured by the modified Bauermeister scale and European consensus grading system after treatment (e.g., 4, 6, 8, or 12 cycles), symptom response using the Myeloproliferative Neoplasm Symptom Assessment Form (MPN-SAF).

In some embodiments, the treatment with an isoform-specific, TGFβ1 inhibitor such as those described herein, achieves a statistically improved treatment response as assessed by, for example, modified Myelofibrosis Symptom Assessment Form (MFSAF), in which symptoms are measured by the MFSAF tool (such as v2.0), a daukt diary capturing the debilitating symptoms of myelofibrosis (abdominal discomfort, early satiety, pain under left ribs, pruritus, night sweats, and bone/muscle pain) using a scale of 0 to 10, where 0 is absent and 10 is the worst imaginable. In some embodiments, the treatment is effective to achieve a 50%>reduction in total MFSAF score from the baseline in, for example, 12-24 weeks. In some embodiments, a significant fraction of patients who receive the therapy achieves a>50% improvement in Total Symptom Score, as compared to patients taking placebo. For example, the fraction of the patient pool to achieve>50% improvement may be over 40%, 50%, 55%, 60%, 65%, 70%, 75% or 80%.

In some embodiments, the therapeutically effective amount of the inhibitor is an amount sufficient to attain clinical improvement as assessed by an anemia response. For example, an improved anemia response may include longer durations of transfusion-independence, e.g., 8 weeks or longer, following the treatment of 4-12 cycles, e.g., 6 cycles.

In some embodiments, the therapeutically effective amount of the inhibitor is an amount sufficient to maintain stable disease for a duration of time, e.g., 6 weeks, 8 weeks, 12 weeks, six months, etc. In some embodiments, progression of the disease may be evaluated by changes in overall bone marrow cellularity, the degree of reticulin or collagen fibrosis, and/or a change in JAK2V617F allele burden.

In some embodiments, a patient population treated with an isoform-specific, TGFβ1 inhibitor such as those described herein, shows statistically improved survival, as compared to a control population that does not receive the treatment. For example, in control groups, median survival of PMF patients is approximately six years (approximately 16 months in high-risk patients), and fewer than 20% of the patients are expected to survive 10 years or longer post-diagnosis. Treatment with the isoform-specific TGFβ1 inhibitor such as those described herein, may prolong the survival time by, at least 6 months, 12 months, 18 months, 24 months, 30 months, 36 months, or 48 months. In some embodiments, the treatment is effective to achieve improved overall survival at 26 weeks, 52 weeks, 78 weeks, 104 weeks, 130 weeks, 144 weeks, or 156 weeks, as compared to patients who receive placebo.

Clinical benefits of the therapy, such as those exemplified above, may be seen in patients with or without new onset anemia.

One of the advantageous features of the isoform-specific, TGFβ1 inhibitors is that they maintain improved safety profiles enabled by isoform selectivity, as compared to conventional TGFβ antagonists that lack the selectivity. Therefore, it is anticipated that treatment with an isoform-specific, inhibitor of TGFβ1, such as those described herein, may reduce adverse events in a patient population, in comparison to equivalent patient populations treated with conventional TGFβ antagonists, with respect to the frequency and/or severity of such events. Thus, the isoform-specific, TGFβ1 inhibitors may provide a greater therapeutic window as to dosage and/or duration of treatment. In preferred embodiments, the isoform-selective activation inhibitor of TGFβ1 is Ab42, Ab46, Ab50, a derivative thereof, or an engineered molecule comprising an antigen-binding fragment thereof.

Adverse events may be graded by art-recognized suitable methods, such as Common Terminology Criteria for Adverse Events (CTCAE) version 4. Previously reported adverse events in human patients who received TGFβ antagonists, such as GC1008, include: leukocytosis (grade 3), fatigue (grade 3), hypoxia (grade 3), asystole (grade 5), leukopenia (grade 1), recurrent, transient, tender erythematous, nodular skin lesions, suppurative dermatitis, and herpes zoster.

The isoform-specific, TGFβ1 inhibitor therapy may cause less frequent and/or less severe adverse events (side effects) as compared to JAK inhibitor therapy in myelofibrosis patients, with respect to, for example, anemia, thrombocytopenia, neutropenia, hypercholesterolemia, elevated alanine transaminase (ALT), elevated aspartate transaminase (AST), bruising, dizziness, and headache, thus offering a safer treatment option.

It is contemplated that inhibitors of TGFβ1 signaling may be used in conjunction with one or more therapeutics for the treatment of myelofibrosis as a combination therapy. In some embodiments, an inhibitor of TGFβ1 activation described herein is administered to patients suffering from myelofibrosis, who have received a JAK1 inhibitor, JAK2 inhibitor or JAK1/JAK2 inhibitor. In some embodiments, such patients are responsive to the JAK1 inhibitor, JAK2 inhibitor or JAK1/JAK2 inhibitor therapy, while in other embodiments such patients are poorly responsive or not responsive to the JAK1 inhibitor, JAK2 inhibitor or JAK1/JAK2 inhibitor therapy. In some embodiments, use of an isoform-specific inhibitor of TGFβ1 described herein may render those who are poorly responsive or not responsive to the JAK1 inhibitor, JAK2 inhibitor or JAK1/JAK2 inhibitor therapy more responsive. In some embodiments, use of an isoform-specific inhibitor of TGFβ1 described herein may allow reduced dosage of the JAK1 inhibitor, JAK2 inhibitor or JAK1/JAK2 inhibitor which still produces equivalent clinical efficacy in patients but fewer or lesser degrees of drug-related toxicities or adverse events (such as those listed above). In some embodiments, treatment with the inhibitor of TGFβ1 activation described herein used in conjunction with JAK1 inhibitor, JAK2 inhibitor or JAK1/JAK2 inhibitor therapy may produce synergistic or additive therapeutic effects in patients. In some embodiments, treatment with the inhibitor of TGFβ1 activation described herein may boost the benefits of JAK1 inhibitor, JAK2 inhibitor or JAK1/JAK2 inhibitor or other therapy given to treat myelofibrosis. In some embodiments, patients may additionally receive a therapeutic to address anemia associated with myelofibrosis. In some embodiments, the combination therapy comprises a checkpoint inhibitor, such as a PD-(L) 1 antibody.

TGFβ1-Positive Cancer:

Various cancers involve TGFβ1 activities and may be treated with antibodies and/or compositions of the present disclosure. As used herein, the term "cancer" refers to any of various TGFβ1-positive malignant neoplasms characterized by the proliferation of anaplastic cells that tend to invade surrounding tissue and metastasize to new body sites and also refers to the pathological condition characterized by such malignant neoplastic growths. Cancers may be localized (e.g., solid tumors) or systemic. In the context of the present disclosure, the term "localized" (as in "localized tumor") refers to anatomically isolated or isolatable abnormalities/lesions, such as solid malignancies, as opposed to systemic disease (e.g., so-called liquid tumors or blood cancers). Certain cancers, such as certain leukemia (e.g., myelofibrosis) and multiple myeloma, for example, may have both a localized component (for instance the bone marrow) and a systemic component (for instance circulating blood cells) to the disease. In some embodiments, cancers may be systemic, such as hematological malignancies. Cancers that may be treated according to the present disclosure are TGFβ1-positive and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. In cancer, TGFβ (e.g., TGFβ1) may be either growth promoting or growth inhibitory. As an example, in pancreatic cancers, SMAD4 wild type tumors may experience inhibited growth in response to TGFβ, but as the disease progresses, constitutively activated type II receptor is typically present. Additionally, there are SMAD4-null pancreatic cancers. In some embodiments, antibodies, antigen-binding portions thereof, and/or compositions of the present disclosure are designed to selectively target components of TGFβ signaling pathways that function uniquely in one or more forms of cancer. Leukemias, or cancers of the blood or bone marrow that are characterized by an abnormal proliferation of white blood cells, i.e., leukocytes, can be divided into four major classifications including acute lymphoblastic leukemia (ALL), chronic lymphocytic leukemia (CLL), acute myelogenous leukemia or acute myeloid leukemia (AML) (AML with translocations between chromosome 10 and 11 [t (10, 11)], chromosome 8 and 21 [t (8;21)], chromosome 15 and 17 [t (15;17)], and inversions in chromosome 16 [inv (16)]; AML with multilineage dysplasia, which includes patients who have had a prior myelodysplastic syndrome (MDS) or myeloproliferative disease that transforms into AML; AML and myelodysplastic syndrome (MDS), therapy-related, which category includes patients who have had prior chemotherapy and/or radiation and subsequently develop AML or MDS; d) AML not otherwise categorized, which includes subtypes of AML that do not fall into the above categories; and e) acute leukemias of ambiguous lineage, which occur when the leukemic cells cannot be classified as either myeloid or lymphoid cells, or where both types of cells are present); and chronic myelogenous leukemia (CML).

The isoform-selective TGFβ1 inhibitors of the invention may be used to treat patients suffering from chronic myeloid leukemia, which is a stem cell disease, in which the BCR/ABL oncoprotein is considered essential for abnormal growth and accumulation of neoplastic cells. Imatinib is an approved therapy to treat this condition; however, a significant fraction of myeloid leukemia patients show Imatinib-resistance. TGFβ1 inhibition achieved by the inhibitor such as those described herein may potentiate repopulation/expansion to counter BCR/ABL-driven abnormal growth and accumulation of neoplastic cells, thereby providing clinical benefit.

Isoform-specific, inhibitors of TGFβ1, such as those described herein, may be used to treat multiple myeloma. Multiple myeloma is a cancer of B lymphocytes (e.g., plasma cells, plasmablasts, memory B cells) that develops and expands in the bone marrow, causing destructive bone lesions (i.e., osteolytic lesion). Typically, the disease manifests enhanced osteoclastic bone resorption, suppressed osteoblast differentiation (e.g., differentiation arrest) and impaired bone formation, characterized in part, by osteolytic lesions, osteopenia, osteoporosis, hypercalcemia, as well as plasmacytoma, thrombocytopenia, neutropenia and neuropathy. The TGFβ1-selective, inhibitor therapy described herein may be effective to ameliorate one or more such clinical manifestations or symptoms in patients. The TGFβ1 inhibitor may be administered to patients who receive additional therapy or therapies to treat multiple myeloma, including those listed elsewhere herein. In some embodiments, multiple myeloma may be treated with a TGFβ1 inhibitor in combination with a myostatin inhibitor or an IL-6 inhibitor. In some embodiments, the TGFβ1 inhibitor may be used in conjunction with traditional multiple myeloma therapies, such as bortezomib, lenalidomide, carfilzomib, pomalidomide, thalidomide, doxorubicin, corticosteroids (e.g., dexamethasone and prednisone), chemotherapy (e.g., melphalan), radiation therapy, stem cell transplantation, plitidepsin, Elotuzumab, Ixazomib, Masitinib, and/or Panobinostat.

The types of carcinomas which may be treated by the methods of the present invention include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

The types of sarcomas include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

Isoform-selective, inhibitors of TGFβ1 activation, such as those described herein, may be suited for treating malignancies involving cells of neural crest origin. Cancers of the neural crest lineage (i.e., neural crest-derived tumors) include, but are not limited to: melanoma (cancer of melanocytes), neuroblastoma (cancer of sympathoadrenal precursors), ganglioneuroma (cancer of peripheral nervous system ganglia), medullary thyroid carcinoma (cancer of thyroid C cells), pheochromocytoma (cancer of chromaffin cells of the adrenal medulla), and MPNST (cancer of Schwann cells). In some embodiments, antibodies and methods of the disclosure may be used to treat one or more types of cancer or cancer-related conditions that may include, but are not limited to colon cancer, renal cancer, breast cancer, malignant melanoma and glioblastomas (Schlingensiepen et al., 2008. *Cancer Res.* 177:137-50; Ouhtit et al., 2013. *J Cancer.* 4 (7): 566-572).

While Tregs play an important role in dampening immune responses in healthy individuals, an elevated number of Tregs in cancer has been associated with poor prognosis. For example, human ovarian cancer ascites are infiltrated with Foxp3+GARP+Tregs (Downs-Canner et al., *Nat Commun.* 2017, 8:14649). Similarly, Tregs positively correlated with a more immunosuppressive and more aggressive phenotype in advanced hepatocellular carcinoma (Kalathil et al., *Cancer Res.* 2013, 73 (8): 2435-44). Tregs can suppress the proliferation of effector T cells. In addition, Tregs exert contact-dependent inhibition of immune cells (e.g., naïve CD4+ T cells) through the production of TGFβ1. To combat a tumor, therefore, it is advantageous to inhibit Tregs so sufficient effector T cells can be available to exert anti-tumor activities.

Increasing lines of evidence suggest the role of macrophages in tumor/cancer progression. The present invention encompasses the notion that this is in part mediated by TGFβ1 activation in the disease environment, such as TME. Bone marrow-derived monocytes (e.g., CD11b+) are recruited to tumor sites in response to tumor-derived cytokines/chemokines (such as CCL2, CCL3, and $CCL_4$), where monocytes undergo differentiation and polarization to acquire pro-cancer phenotype (e.g., M2-biased, TAMs or TAM-like cells). A majority of TAMs in many tumors are M2-biased. Among the M2-like macrophages, M2c and M2d subtypes, but not M1, are found to express elevated LRRC33 on the cell surface. Moreover, macrophages can be further skewed or activated by an M-CSF exposure, resulting in a marked increase in LRRC33 expression, which coincides with TGFβ1 expression. Increased circulating M-CSF (i.e., serum M-CSF concentrations) in patients with myeloproliferative disease (e.g., myelofibrosis) has also been observed. Generally, tumors with high macrophage (TAM) and/or MDSC infiltrate are associated with poor prognosis. Similarly, elevated levels of M-CSF are also indicative of poor prognosis.

On the other hand, macrophage infiltration into a tumor may also signify effectiveness of a therapy. As exemplified in FIGS. 17A-17B and 18A-18B, tumors that are effectively penetrated by effector T cells (e.g., CD8+ T cells) following the treatment with a combination of a checkpoint inhibitor and a context-independent (or context biased) TGFβ1 inhibitor may lead to recruitment of phagocytic monocytes/macrophages that clean up cell debris. As clear from FIG. 17B, the combination of anti-PD-1 and a TGFβ1 inhibitor resulted in robust CD8 T cell influx throughout the tumor, as compared to anti-PD-1 treatment alone. Concurrently, extensive infiltration of the tumor by F4/80-positive macrophages is observed (see FIG. 18B). This may be indicative of macrophages clearing cancer cell debris generated by cytotoxic cells and is presumably a direct consequence of TGFβ1 inhibition.

As mentioned above, inhibitors of TGFβ1 activation may be used in the treatment of Melanoma. The types of melanoma that may be treated with such inhibitors include, but are not limited to: Lentigo maligna; Lentigo maligna melanoma; Superficial spreading melanoma; Acral lentiginous melanoma; Mucosal melanoma; Nodular melanoma; Polypoid melanoma and Desmoplastic melanoma. In some embodiments, the melanoma is a metastatic melanoma.

More recently, immune checkpoint inhibitors have been used to effectively treat advanced melanoma patients. In particular, anti-programmed death (PD)-1 antibodies (e.g., nivolumab and pembrolizumab) have now become the standard of care for certain types of cancer such as advanced melanoma, which have demonstrated significant activity and durable response with a manageable toxicity profile. However, effective clinical application of PD-1 antagonists is encumbered by a high rate of innate resistance (~60-70%) (see Hugo et al., (2016) *Cell* 165:35-44), illustrating that ongoing challenges continue to include the questions of patient selection and predictors of response and resistance as well as optimizing combination strategies (Perrot et al., (2013) *Ann Dermatol* 25 (2): 135-144). Moreover, studies have suggested that approximately 25% of melanoma patients who initially responded to an anti-PD-1 therapy eventually developed acquired resistance (Ribas et al., (2016) JAMA 315:1600-9).

The number of tumor-infiltrating CD8+ T cells expressing PD-1 and/or CTLA-4 appears to be a key indicator of success with checkpoint inhibition, and both PD-1 and CTLA-4 blockade may increase the infiltrating T cells. In patients with higher presence of tumor-associated macrophages, however, anti-cancer effects of the CD8 cells may be suppressed.

It is contemplated that LRRC33-expressing cells, such as myeloid cells, including myeloid precursors, MDSCs and TAMs, may create or support an immunosuppressive environment (such as TME and myelofibrotic bone marrow) by inhibiting T cells (e.g., T cell depletion), such as CD4 and/or CD8 T cells, which may at least in part underline the observed anti-PD-1 resistance in certain patient populations. Indeed, evidence suggests that resistance to anti-PD-1 monotherapy was marked by failure to accumulate CD8+ cytotoxic T cells and reduced Teff/Treg ratio. Notably, the present inventors have recognized that there is a bifurcation among certain cancer patients, such as a melanoma patient population, with respect to LRRC33 expression levels: one group exhibits high LRRC33 expression (LRRC33high), while the other group exhibits relatively low LRRC33 expression (LRRC33low). Thus, the invention includes the notion that the LRRC33high patient population may represent those who are poorly responsive to or resistant to immuno checkpoint inhibitor therapy. Accordingly, agents that inhibit LRRC33, such as those described herein, may be particularly beneficial for the treatment of cancer, such as melanoma, lymphoma, and myeloproliferative disorders, that is resistant to checkpoint inhibitor therapy (e.g., anti-PD-1).

In some embodiments, cancer/tumor is intrinsically resistant to or unresponsive to an immune checkpoint inhibitor. To give but one example, certain lymphomas appear poorly responsive to immune checkpoint inhibition such as anti-PD-1 therapy. Similarly, a subset of melanoma patient population is known to show resistance to immune checkpoint inhibitors. Without intending to be bound by particular theory, the inventors of the present disclosure contemplate that this may be at least partly due to upregulation of TGFβ1 signaling pathways, which may create an immunosuppressive microenvironment where checkpoint inhibitors fail to exert their effects. TGFβ1 inhibition may render such cancer more responsive to checkpoint inhibitor therapy. Non-limiting examples of cancer types which may benefit from a combination of an immune checkpoint inhibitor and a TGFβ1 inhibitor include: myelofibrosis, melanoma, renal cell carcinoma, bladder cancer, colon cancer, hematologic malignancies, non-small cell carcinoma, non-small cell lung cancer (NSCLC), lymphoma (classical Hodgkin's and non-Hodgkin's), head and neck cancer, urothelial cancer, cancer with high microsatellite instability, cancer with mismatch repair deficiency, gastric cancer, renal cancer, and hepatocellular cancer. However, any cancer (e.g., patients with such cancer) in which TGFβ1 is overexpressed or is the dominant isoform over TGFβ2/3, as determined by, for example biopsy, may be treated with an isoform-selective inhibitor of TGFβ1 in accordance with the present disclosure.

In some embodiments, a cancer/tumor becomes resistant over time. This phenomenon is referred to as acquired resistance or adaptive resistance. Like intrinsic resistance, in some embodiments, acquired resistance is at least in part mediated by TGFβ1-dependent pathways, Isoform-specific TGFβ1 inhibitors described herein may be effective in restoring anti-cancer immunity in these cases.

In some embodiments, combination therapy comprising an immune checkpoint inhibitor and an isoform-specific inhibitor of TGFβ1 which targets an LRRC33-proTGFβ1 complex (such as those described herein) may be effective to treat such cancer. In addition, high LRRC33-positive cell infiltrate in tumors, or otherwise sites/tissues with abnormal cell proliferation, may serve as a biomarker for host immunosuppression and immune checkpoint resistance. Similarly, effector T cells may be precluded from the immunosuppressive niche which limits the body's ability to combat cancer. Moreover, as demonstrated in the Example section below, Tregs that express GARP-presented TGFβ1 suppress effector T cell proliferation. Together, TGFβ1 is likely a key driver in the generation and maintenance of an immune inhibitory disease microenvironment (such as TME), and multiple TGFβ1 presentation contexts are relevant for tumors. In some embodiments, the combination therapy may achieve more favorable Teff/Treg ratios.

In some embodiments, the antibodies, or antigen-binding portions thereof, that specifically bind a GARP-TGFβ1 complex, a LTBP1-TGFβ1 complex, a LTBP3-TGFβ1 complex, and/or a LRRC33-TGFβ1 complex, as described herein, may be used in methods for treating cancer in a subject in need thereof, said method comprising administering the antibody, or antigen-binding portion thereof, to the subject such that the cancer is treated. In certain embodiments, the cancer is colon cancer.

In some embodiments, the antibodies, or antigen-binding portions thereof, as described herein, may be used in methods for treating solid tumors. In some embodiments, solid tumors may be desmoplastic tumors, which are typically dense and hard for therapeutic molecules to penetrate. By targeting the ECM component of such tumors, such antibodies may "loosen" the dense tumor tissue to disintegrate, facilitating therapeutic access to exert its anti-cancer effects.

Thus, additional therapeutics, such as any known anti-tumor drugs, may be used in combination. In preferred embodiments, the isoform-selective activation inhibitor of TGFβ1 is Ab42, Ab46, Ab50, a derivative thereof, or an engineered molecule comprising an antigen-binding fragment thereof.

Additionally or alternatively, isoform-specific, antibodies for fragments thereof that are capable of inhibiting TGFβ1 activation, such as those disclosed herein, may be used in conjunction with the chimeric antigen receptor T-cell ("CAR-T") technology as cell-based immunotherapy, such as cancer immunotherapy for combatting cancer.

In some embodiments, the antibodies, or antigen-binding portions thereof, as described herein, may be used in methods for inhibiting or decreasing solid tumor growth in a subject having a solid tumor, said method comprising administering the antibody, or antigen-binding portion thereof, to the subject such that the solid tumor growth is inhibited or decreased. In certain embodiments, the solid tumor is a colon carcinoma tumor. In some embodiments, the antibodies, or antigen-binding portions thereof useful for treating a cancer is an isoform-specific, inhibitor of TGFβ1 activation.

The invention includes the use of isoform-specific inhibitors of TGFβ1, as described herein, in the treatment of cancer comprising a solid tumor in a subject. In some embodiments, such isoform-specific inhibitor may inhibit the activation of TGFβ1. In some embodiments, the solid tumor is characterized by having stroma enriched with CD8+ T cells making direct contact with CAFs and collagen fibers. Such a tumor may create an immuno-suppressive environment that prevents anti-tumor immune cells (e.g., effector T cells) from effectively infiltrating the tumor, limiting the body's ability to fight cancer. Instead, such cells may accumulate within or near the tumor stroma. These features may render such tumors poorly responsive to an immune checkpoint inhibitor therapy. As discussed in more detail below, TGFβ1 inhibitors disclosed herein may unblock the suppression so as to allow effector cells to reach and kill cancer cells, for example, used in conjunction with an immune checkpoint inhibitor. In preferred embodiments, the isoform-selective activation inhibitor of TGFβ1 is Ab42, Ab46, Ab50, a derivative thereof, or an engineered molecule comprising an antigen-binding fragment thereof.

TGFβ1 is contemplated to play multifaceted roles in a tumor microenvironment, including tumor growth, host immune suppression, malignant cell proliferation, vascularity, angiogenesis, migration, invasion, metastasis, and chemo-resistance. Each "context" of TGFβ1 presentation in the environment may therefore participate in the regulation (or dysregulation) of disease progression. For example, the GARP axis is particularly important in Treg response that regulates effector T cell response for mediating host immune response to combat cancer cells. The LTBP1/3 axis may regulate the ECM, including the stroma, where cancer-associated fibroblasts (CAFs) play a role in the pathogenesis and progression of cancer. The LRRC33 axis may play a crucial role in recruitment of circulating monocytes to the tumor microenvironment, subsequent differentiation into tumor-associated macrophages (TAMs), infiltration into the tumor tissue and exacerbation of the disease.

The tumor microenvironment (TME) contains multiple cell types expressing TGFβ1, such as activated myofibroblast-like fibroblasts, stromal cells, infiltrating macrophages, MDSCs and other immune cells, in addition to cancer (i.e., malignant) cells. Thus, the TME represents a heterogeneous population of cells expressing and/or responsive to TGFβ1 but in association with more than one types of presenting molecules, e.g., LTBP1, LTBP3, LRRC33 and GARP, within the niche.

More recently, a phenomenon referred to as "immune exclusion" was coined to describe a tumor environment from which anti-tumor effector T cells (e.g., CD8+ T cells) are kept away (hence "excluded") by immunosuppressive local cues, and TGFβ is thought to at least in part mediate this process. In an immune-excluded tumor, effector cells, which would otherwise be capable of attacking cancer cells by recognizing cell-surface tumor antigens, are prevented from gaining access to the site of cancer cells. In this way, cancer cells evade host immunity and immuno-oncologic therapeutics, such as checkpoint inhibitors, that exploit and rely on such immunity. Indeed, such tumors show resistance to checkpoint inhibition, such as anti-PD-1 and anti-PD-L1 antibodies, presumably because target T cells are blocked from entering the tumor hence failing to exert anti-cancer effects.

Increasing evidence suggests that TGFβ may be a primary player in creating and/or maintaining immunosuppression in disease tissues, including the immune-excluded tumor environment. Therefore, TGFβ inhibition may unblock the immunosuppression and enable effector T cells (particularly cytotoxic CD8+ T cells) to access and kill target cancer cells. In addition to tumor infiltration, TGFβ inhibition may also promote CD8+ T cell expansion. While the exact mechanism underlining this process has yet to be elucidated, it is contemplated that immunosuppression is at least in part mediated by immune cell-associated TGFβ1 activation involving regulatory T cells and activated macrophages. It has been reported that TGFβ directly promotes Foxp3 expression in CD4+ T cells, thereby converting them into a regulatory phenotype (i.e., Treg). Moreover, Tregs suppress effector T cell proliferation (see, for example, FIG. 26), thereby reducing immune responses. This process is shown to be TGFβ1-dependent and likely involves GARP-associated TGFβ1 signaling. Observations in both humans and animal models have indicated that an increase in Tregs in TME is associated with poor prognosis in multiple types of cancer. In addition, Applicant has previously shown that M2-polarized macrophages exposed to tumor-derived factors such as M-CSF dramatically upregulate cell-surface expression of LRRC33, which is a presenting molecule for TGFβ1 (see, for example: PCT/US2018/031759). These so-called tumor-associated macrophages (or TAMs) are thought to contribute to the observed TGFβ1-dependent immunosuppression in TMEs and promote tumor growth.

A number of solid tumors are characterized by having tumor stroma enriched with myofibroblasts or myofibroblast-like cells. These cells produce collagenous matrix that surrounds or encases the tumor (such as desmoplasia), which at least in part may be caused by overactive TGFβ1 signaling. It is contemplated that the TGFβ1 activation is mediated via ECM-associated presenting molecules, e.g., LTBP1 and LTBP3 in the tumor stroma.

In some embodiments, TGFβ1-expressing cells infiltrate the tumor, creating an immunosuppressive local environment. The degree by which such infiltration is observed may correlate with worse prognosis. In some embodiments, higher infiltration is indicative of poorer treatment response to another cancer therapy, such as immune checkpoint inhibitors. In some embodiments, TGFβ1-expressing cells in the tumor microenvironment comprise Tregs and/or myeloid cells. In some embodiments, the myeloid cells include, but are not limited to: macrophages, monocytes (tissue resident or bone marrow-derived), and MDSCs.

In some embodiments, LRRC33-expressing cells in the TME are myeloid-derived suppressor cells (MDSCs). MDSC infiltration (e.g., solid tumor infiltrate) may underline at least one mechanism of immune escape, by creating an immunosuppressive niche from which host's anti-tumor immune cells become excluded. Evidence suggest that MDSCs are mobilized by inflammation-associated signals, such as tumor-associated inflammatory factors, Opon mobilization, MDSCs can influence immunosuppressive effects by impairing disease-combating cells, such as CD8+ T cells and NK cells. In addition, MDSCs may induce differentiation of Tregs by secreting TGFβ and IL-10. Thus, an isoform-specific TGFβ1 inhibitor, such as those described herein, may be administered to patients with immune evasion (e.g., compromised immune surveillance) to restore or boost the body's ability to fight the disease (such as tumor). As described in more detail herein, this may further enhance (e.g., restore or potentiate) the body's responsiveness or sensitivity to another therapy, such as cancer therapy.

In some embodiments, elevated frequencies (e.g., number) of circulating MDSCs in patients are predictive of poor responsiveness to checkpoint blockade therapies, such as PD-1 antagonists and PD-L1 antagonists. For example, biomarker studies showed that circulating pre-treatment HLA-DR lo/CD14+/CD11b+ myeloid-derived suppressor cells (MDSC) were associated with progression and worse OS (p=0.0001 and 0.0009). In addition, resistance to PD-1 checkpoint blockade in inflamed head and neck carcinoma (HNC) associates with expression of GM-CSF and Myeloid Derived Suppressor Cell (MDSC) markers. This observation suggested that strategies to deplete MDSCs, such as chemotherapy, should be considered in combination or sequentially with anti-PD-1. LRRC33 or LRRC33-TGFβ complexes represent a novel target for cancer immunotherapy due to selective expression on immunosuppressive myeloid cells. Therefore, without intending to be bound by particular theory, targeting this complex may enhance the effectiveness of standard-of-care checkpoint inhibitor therapies in the patient population.

The invention therefore provides the use of an isoform-specific, TGFβ1 inhibitor described herein for the treatment of cancer that comprises a solid tumor. Such treatment comprises administration of the isoform-specific, TGFβ1 inhibitor to a subject diagnosed with cancer that includes at least one localized tumor (solid tumor) in an amount effective to treat the cancer. In preferred embodiments, the isoform-selective activation inhibitor of TGFβ1 is Ab42, Ab46, Ab50, a derivative thereof, or an engineered molecule comprising an antigen-binding fragment thereof.

Evidence suggests that cancer progression (e.g., tumor proliferation/growth, invasion, angiogenesis and metastasis) may be at least in part driven by tumor-stroma interaction. In particular, CAFs may contribute to this process by secretion of various cytokines and growth factors and ECM remodeling. Factors involved in the process include but are not limited to stromal-cell-derived factor 1 (SCD-1), MMP2, MMP9, MMP3, MMP-13, TNF-α, TGFβ1, VEGF, IL-6, M-CSF. In addition, CAFs may recruit TAMs by secreting factors such as CCL2/MCP-1 and SDF-1/CXCL12 to a tumor site; subsequently, a pro-TAM niche (e.g., hyaluronan-enriched stromal areas) is created where TAMs preferentially attach. Since TGFβ1 has been suggested to promote activation of normal fibroblasts into myofibroblast-like CAFs, administration of an isoform-specific, TGFβ1 inhibitor such as those described herein may be effective to counter cancer-promoting activities of CAFs. Indeed, data presented herein suggest that an isoform-specific antibody that blocks activation of TGFβ1 can inhibit UUO-induced upregulation of maker genes such as CCL2/MCP-1, α-SMA. FN1 and Col1, which are also implicated in many cancers.

In certain embodiments, the antibodies, or antigen-binding portions thereof, as described herein, are administered to a subject having cancer or a tumor, either alone or in combination with an additional agent, e.g., an anti-PD-1 antibody (e.g., an anti-PD-1 antagonist). Other combination therapies which are included in the invention are the administration of an antibody, or antigen-binding portion thereof, described herein, with radiation, or a chemotherapeutic agent. Exemplary additional agents include, but are not limited to, a PD-1 antagonist, a PD-L1 antagonist, a PD-L1 or PD-L2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an anti-CD20 antibody, an oncolytic virus, and a PARP inhibitor.

In some embodiments, determination or selection of therapeutic approach for combination therapy that suits particular cancer types or patient population may involve the following: a) considerations regarding cancer types for which a standard-of-care therapy is available (e.g., immunotherapy-approved indications); b) considerations regarding treatment-resistant subpopulations; and c) considerations regarding cancers/tumors that are "TGFβ1 pathway-active" or otherwise at least in part TGFβ1-dependent (e.g., TGFβ1 inhibition-sensitive). For example, many cancer samples show that TGFβ1 is the predominant isoform by, for instance, TCGA RNAseq analysis. In some embodiments, over 50% (e.g., over 50%, 60%, 70%, 80% and 90%) of samples from each tumor type are positive for TGFβ1 isoform expression. In some embodiments, the cancers/tumors that are "TGFβ1 pathway-active" or otherwise at least in part TGFβ1-dependent (e.g., TGFβ1 inhibition-sensitive) contain at least one Ras mutation, such as mutations in K-ras, N-ras and/or H-ras. In some embodiments, the cancer/tumor comprises at least one K-ras mutation.

In some embodiments, the isoform-specific, TGFβ1 inhibitor is administered in conjunction with checkpoint inhibitory therapy to patients diagnosed with cancer for which one or more checkpoint inhibitor therapies are approved or shown effect. These include, but are not limited to: bladder urothelial carcinoma, squamous cell carcinoma (such as head & neck), kidney clear cell carcinoma, kidney papillary cell carcinoma, liver hepatocellular carcinoma, lung adenocarcinoma, skin cutaneous melanoma, and stomach adenocarcinoma. In preferred embodiments, such patients are poorly responsive or non-responsive to the checkpoint inhibitor therapy. In some embodiments, the poor responsiveness is due to primary resistance. In some embodiments, the cancer that is resistant to checkpoint blockade shows downregulation of TCF7 expression. In some embodiments, TCF7 downregulation in checkpoint inhibition-resistant tumor may be correlated with a low number of intratumoral CD8+ T cells. In preferred embodiments, the isoform-selective activation inhibitor of TGFβ1 is Ab42, Ab46, Ab50, a derivative thereof, or an engineered molecule comprising an antigen-binding fragment thereof.

The isoform-specific, TGFβ1 inhibitor may be used in the treatment of chemotherapy- or radiotherapy-resistant cancers. Thus, in some embodiments, the isoform-specific, TGFβ1 inhibitor is administered to patients diagnosed with cancer for which they receive or have received chemotherapy and/or radiation therapy. In particular, the use of the TGFβ1 inhibitor is advantageous where the cancer (patient) is resistant to such therapy. In some embodiments, such cancer comprises quiescent tumor propagating cancer cells (TPCs), in which TGFβ signaling controls their reversible entry into a growth arrested state, which protects TPCs from chemotherapy or radiation therapy. It is contemplated that upon pharmacological inhibition of TGFβ1, TPCs with compromised fail to enter quiescence and thus rendered susceptible to chemotherapy and/or radiation therapy. Such cancer includes various carcinomas, e.g., squamous cell carcinomas. See, for example, Brown et al., (2017) "TGF—B-Induced Quiescence Mediates Chemoresistance of Tumor-Propagating Cells in Squamous Cell Carcinoma." Cell Stem Cell. 21 (5): 650-664.

Conditions that Benefit from Tissue Regeneration and Stem Cell Repopulation

Evidence suggests that TGFβ1 plays a role in regulating the homeostasis of various stem cell populations and their differentiation/repopulation within a tissue. During homeostasis, tissue-specific stem cells are held predominantly quiescent but are triggered to enter cell cycle upon certain stress. TGFβ1 is thought to function as a "break" during the process that tightly regulates stem cell differentiation and reconstitution, and the stress that triggers cell cycle entry coincides with TGFβ1 inhibition that removes the "break." Thus, it is contemplated that isoform-selective inhibitors of TGFβ1, such as those described herein, may be used to skew or correct cell cycle and GO entry decision of stem cells/progenitor cells within a particular tissue.

Accordingly, the inventors of the present disclosure contemplate the use of isoform-selective TGFβ1 inhibitors in conditions in which: i) stem cell/progenitor cell differentiation/reconstitution is halted or perturbed due to a disease or induced as a side effect of a therapy/mediation; ii) patients are on a therapy or mediation that causes healthy cells to be killed or depleted; iii) patients may benefit from increased stem cell/progenitor cell differentiation/reconstitution; iv) disease is associated with abnormal stem cell differentiation or reconstitution.

For example, mesenchymal stromal/stem cells (MSCs) are a small population of stromal cells present in most adult connective tissues, such as bone marrow, fat tissue, and umbilical cord blood. MSCs are maintained in a relative state of quiescence in vivo but, in response to a variety of physiological and pathological stimuli, are capable of proliferating then differentiating into osteoblasts, chondrocytes, adipocytes, or other mesoderm-type lineages like smooth muscle cells (SMCs) and cardiomyocytes. Multiple signaling networks orchestrate MSCs differentiating into functional mesenchymal lineages, among which TGF-$\beta_1$ has emerged as a key player (reviewed for example by Zhao & Hantash (2011). *Vitam Horm* 87:127-41).

Similarly, hematopoietic stem cells are required for lifelong blood cell production; to prevent exhaustion, the majority of hematopoietic stem cells remain quiescent during steady-state hematopoiesis. During hematologic stress, however, these cells are rapidly recruited into cell cycle and undergo extensive self-renewal and differentiation to meet increased hematopoietic demands. TGFβ1 may work as the "switch" to control the quiescence-repopulation transition/balance.

Thus, the isoform-selective inhibitors of TGFβ1 can be used in the treatment of conditions involving hematopoietic stem cell defects and bone marrow failure. In some embodiments, depletion or impairment of the hematopoietic stem cell reservoir leads to hematopoietic failure or hematologic malignancies. In some embodiments, such conditions are DNA repair disorder characterized by progressive bone marrow failure. In some embodiments, such condition is caused by stem and progenitor cell attrition. In some embodiments, such conditions are associated with anemia. In preferred embodiments, the isoform-selective activation inhibitor of TGFβ1 is Ab42, Ab46, Ab50, a derivative thereof, or an engineered molecule comprising an antigen-binding fragment thereof.

Conditions Involving Treatment-Induced Hematopoietic Dysregulation

It is recognized that certain drugs which are designed to treat various disease conditions, often induce or exacerbate anemia in the patient being treated (e.g., treatment- or drug-induced anemia, such as chemotherapy-induced anemia and radiation therapy-induced anemia). In some embodiments, the patient is treated with a myelosuppressive drug that may cause side effects that include anemia. Such patient may benefit from pharmacological TGFβ1 inhibition in order to boost hematopoiesis. In some embodiments, the TGFβ1 inhibitor may promote hematopoiesis in patients by preventing entry into a quiescent state. In some embodiments, the patient may receive a G-CSF therapy (e.g., Filgrastim).

Accordingly, the invention includes the use of an isoform-selective inhibitor of TGFβ1, such as those disclosed herein, to be administered to patients who receive myelosuppressive therapy (e.g., therapy with side effects including myelosuppressive effects). Examples of myelosuppressive therapies include but are not limited to: peginterferon alfa-2a, interferon alfa-n3, peginterferon alfa-2b, aldesleukin, gemtuzumab ozogamicin, interferon alfacon-1, rituximab, ibritumomab tiuxetan, tositumomab, alemtuzumab, bevacizumab, L-Phenylalanine, bortezomib, cladribine, carmustine, amsacrine, chlorambucil, raltitrexed, mitomycin, bexarotene, vindesine, floxuridine, tioguanine, vinorelbine, dexrazoxane, sorafenib, streptozocin, gemcitabine, teniposide, epirubicin, chloramphenicol, lenalidomide, altretamine, zidovudine, cisplatin, oxaliplatin, cyclophosphamide, fluorouracil, propylthiouracil, pentostatin, methotrexate, carbamazepine, vinblastine, linezolid, imatinib, clofarabine, pemetrexed, daunorubicin, irinotecan, methimazole, etoposide, dacarbazine, temozolomide, tacrolimus, sirolimus, mechlorethamine, azacitidine, carboplatin, dactinomycin, cytarabine, doxorubicin, hydroxyurea, busulfan, topotecan, mercaptopurine, thalidomide, melphalan, fludarabine, flucytosine, capecitabine, procarbazine, arsenic trioxide, idarubicin, ifosfamide, mitoxantrone, lomustine, paclitaxel, docetaxel, dasatinib, decitabine, nelarabine, everolimus, vorinostat, thiotepa, ixabepilone, nilotinib, belinostat, trabectedin, trastuzumab emtansine, temsirolimus, bosutinib, bendamustine, cabazitaxel, eribulin, ruxolitinib, carfilzomib, tofacitinib, ponatinib, pomalidomide, obinutuzumab, tedizolid phosphate, blinatumomab, ibrutinib, palbociclib, olaparib, dinutuximab, and colchicine.

Additional indications may include any of those disclosed in U.S. Pat. Nos. 8,871,209, 8,415,459, or International Pub. No. WO 2011/151432, the contents of each of which are herein incorporated by reference in their entirety.

In preferred embodiments, antibodies, antigen-binding portions thereof, and compositions of the disclosure may be used to treat a wide variety of diseases, disorders and/or conditions associated with TGFβ1 signaling. In some embodiment, target tissues/cells preferentially express the TGFβ1 isoform over the other isoforms. Thus, the invention includes methods for treating such a condition associated with TGFβ1 expression (e.g., dysregulation of TGFβ1 signaling and/or upregulation of TGFβ1 expression) using a pharmaceutical composition that comprises an antibody or antigen-binding portion thereof described herein.

In some embodiments, the disease involves TGFβ1 associated with (e.g., presented on or deposited from) multiple cellular sources. In some embodiments, such disease involves both an immune component and an ECM component of TGFβ1 function. In some embodiments, such disease involves: i) dysregulation of the ECM (e.g., overproduction/deposition of ECM components such as collagens and proteases; altered stiffness of the ECM substrate; abnormal or pathological activation or differentiation of fibroblasts, such as myofibroblasts and CAFs); ii) immune suppression due to increased Tregs and/or suppressed effector T cells (Teff), e.g., elevated ratios of Treg/Teff; increased leukocyte infiltrate (e.g., macrophage and MDSCs) that causes suppression of CD4 and/or CD8 T cells; and/or iii) abnormal or pathological activation, differentiation, and/or recruitment of myeloid cells, such as macrophages (e.g., bone marrow-derived monocytic/macrophages and tissue resident macrophages), monocytes, myeloid-derived suppresser cells (MDSCs), neutrophils, dendritic cells, and NK cells.

In some embodiments, the condition involves TGFβ1 presented by more than one types of presenting molecules (e.g., two or more of: GARP, LRRC33, LTBP1 and/or LTBP3). In some embodiments, an affected tissues/organs/cells that include TGFβ1 from multiple cellular sources. To give but one example, a solid tumor (which may also include a proliferative disease involving the bone marrow, e.g., myelofibrosis and multiple myeloma) may include TGFβ1 from multiple sources, such as the cancer cells, stromal cells, surrounding healthy cells, and/or infiltrating immune cells (e.g., CD45+ leukocytes), involving different types of presenting molecules. Relevant immune cells include but are not limited to myeloid cells and lymphoid cells, for example, neutrophils, eosinophils, basophils, lymphocytes (e.g., B cells, T cells, and NK cells), and monocytes.

Treatment Regimen and Administration

To practice the methods disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies, or antigen-binding portions thereof, that specifically bind a GARP-TGFβ1 complex, a LTBP1-TGFβ1 complex, a LTBP3-TGFβ1 complex, and/or a LRRC33-TGFβ1 complex can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a TGFβ-related indication, such as those noted above. A subject having a TGFβ-related indication can be identified by routine medical examination, e.g., laboratory tests, organ functional tests, CT scans, MRI, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the intended purpose may be to inhibit TGFβ-1 activation in vivo, to achieve clinically meaningful outcome associated with the TGFβ-1 inhibition. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a TGFβ-related indication. Alternatively, sustained continuous release formulations of an antibody that specifically binds a GARP-TGFβ1 complex, a LTBP1-TGFβ1 complex, a LTBP3-TGFβ1 complex, and/or a LRRC33-TGFβ1 complex may be appropriate. Various formulations and devices for achieving sustained release would be apparent to the skilled artisan and are within the scope of this disclosure.

In one example, dosages for an antibody that specifically binds a GARP-TGFβ1 complex, a LTBP1-TGFβ1 complex, a LTBP3-TGFβ1 complex, and/or a LRRC33-TGFβ1 complex as described herein may be determined empirically in individuals who have been given one or more administration(s) of the antibody. Individuals are given incremental dosages of the antagonist. To assess efficacy, an indicator of the TGFβ-related indication can be followed. For example, methods for measuring for myofiber damage, myofiber repair, inflammation levels in muscle, and/or fibrosis levels in muscle are well known to one of ordinary skill in the art.

The present invention encompasses the recognition that agents capable of modulating the activation step of TGFβs in an isoform-specific manner may provide improved safety profiles when used as a medicament. Accordingly, the invention includes antibodies and antigen-binding fragments thereof that specifically bind with low dissociation rates and inhibit activation of TGFβ1, but not TGFβ2 or TGFβ3, thereby conferring specific inhibition of the TGFβ1 signaling in vivo while minimizing unwanted side effects from affecting TGFβ2 and/or TGFβ3 signaling. In preferred embodiments, the isoform-selective activation inhibitor of TGFβ1 is Ab42, Ab46, Ab50, a derivative thereof, or an engineered molecule comprising an antigen-binding fragment thereof.

In some embodiments, the antibodies, or antigen-binding portions thereof, as described herein, are not toxic when administered to a subject. In some embodiments, the antibodies, or antigen-binding portions thereof, as described herein, exhibit reduced toxicity when administered to a subject as compared to an antibody that specifically binds to both TGFβ1 and TGFβ2. In some embodiments, the antibodies, or antigen-binding portions thereof, as described herein, exhibit reduced toxicity when administered to a subject as compared to an antibody that specifically binds to both TGFβ1 and TGFβ3. In some embodiments, the antibodies, or antigen-binding portions thereof, as described herein, exhibit reduced toxicity when administered to a subject as compared to an antibody that specifically binds to TGFβ1, TGFβ2 and TGFβ3.

Generally, for administration of any of the antibodies described herein, an initial candidate dosage can be about 1-20 mg/kg per administration, e.g., weekly, every 2 weeks, every 3 weeks, monthly, etc. For example, patients may receive an injection of about 1-10 mg/kg per 1 week, per 2 weeks, per 3 weeks, or per 4 weeks, etc., in an amount effective to treat a disease (e.g., fibrosis or cancer) wherein the amount is well-tolerated (within acceptable toxicities or adverse events).

For the purpose of the present disclosure, a typical dosage (per administration, such as an injection and infusion) might range from about any of 0.1 mg/kg to 1 mg/kg to 2 mg/kg to 3 mg/kg, to 5 mg/kg to 10 mg/kg to 20 mg/kg to 30 mg/kg to 100 mg/kg or more, depending on the factors mentioned above. In some embodiments, suitable dosage include between about 10-3000 mg per dose, e.g., about 10 mg, 30 mg, 40 mg, 50 mg, 60 mg, 70 mg, 80 mg, 90 mg, 100 mg, 120 mg, 150 mg, 180 mg, 200 mg, 240 mg, 300 mg, 400 mg, 500 mg, 800 mg, 1000 mg, 1600 mg, 2000 mg, 2400 mg, etc.). For repeated administrations over several days or longer, depending on the condition, the treatment is sustained until a desired suppression of symptoms occurs or until sufficient therapeutic levels are achieved to alleviate a TGFβ-related indication, or a symptom thereof. An exemplary dosing regimen comprises administering an initial, followed by one or more maintenance doses. However, other dosage regimens may be useful, depending on the pattern of pharmacokinetic decay that the practitioner wishes to achieve. Pharmacokinetics experiments may be readily carried out to assess the serum concentration of an antibody disclosed herein. This stability post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an antibody disclosed herein will depend on the specific antibody (or compositions thereof) employed, the type and severity of the indication, whether the antibody is administered for preventive or therapeutic purposes, previous therapy, the patient's clinical history and response to the antagonist, and the discretion of the attending physician. In some embodiments, a clinician will administer an antibody until a dosage is reached that achieves the desired result. Administration of an antibody can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a TGFβ-related indication.

Serum concentrations of the TGFβ1 antibody that are therapeutically effective to treat a TGFβ1-related indication in accordance with the present disclosure may be at least about 10 μg/mL, e.g., between about 10 μg/mL and 1.0 mg/mL. In some embodiments, effective amounts of the antibody as measured by serum concentrations are about 20-400 μg/mL. In some embodiments, effective amounts of the antibody as measured by serum concentrations are about 100-800 μg/mL. In some embodiments, effective amounts of the antibody as measured by serum concentrations are at least about 20 μg/mL, e.g., at least about 50 μg/mL, 100 μg/mL, 150 μg/mL or 200 μg/mL.

In some instances, intermittent dosing regimen is considered. Intermittent dosing regimen may be particularly appropriate where patients receive a therapy comprising a TGFβ inhibitor that is not selective for TGFβ1, because there may be a greater risk of toxicity. To mitigate or manage such risk, the non-selective TGFβ inhibitor may be administered infrequently or intermittently, for example on an "as-needed" basis.

Based on the observation that inhibiting TGFβ3 can increase collagen deposition or accumulation in fibrosis, add-on therapy comprising a TGFβ1-selective inhibitor (such as the novel antibodies disclosed herein) may be considered for patients who are treated with a TGFβ inhibitor with TGFβ3-inhibiting activity, e.g., inhibitors of TGFβ1/2/3, TGFβ1/3 and TGFβ3. Examples of TGFβ inhibitors with TGFβ3-inhibiting activity include but are not limited to: low molecular weight antagonists of TGFβ receptors, e.g., ALK5 antagonists, such as Galunisertib (LY2157299 monohydrate); monoclonal antibodies (such as neutralizing antibodies) that inhibit all three isoforms ("pan-inhibitor" antibodies) (see, for example, WO 2018/134681); monoclonal antibodies that preferentially inhibit two of the three isoforms (e.g., TGFβ1/3 (for example WO 2006/116002); and engineered molecules (e.g., fusion proteins) such as ligand traps (for example, WO 2018/029367; WO 2018/129331 and WO 2018/158727). In some embodiments, the ligand trap comprises the structure in accordance with the disclosure of WO/2018/15872. In some embodiments, the ligand trap comprises the structure in accordance with the disclosure of WO 2018/029367; WO 2018/129331. In some embodiments, the ligand trap is a construct known as M7824. In some embodiments, the ligand trap is a construct known as AVID200. In some embodiments, the neutralizing pan-TGFβ antibody is GC1008 or a derivative thereof. In some embodiments, such antibody comprises the sequence in accordance with the disclosure of WO/2018/134681.

In some embodiments, the antibody is a neutralizing antibody that specifically binds both TGFβ1 and TGFβ3. In some embodiments such antibody preferentially binds TGFβ1 over TGFβ3. For example, the antibody comprises the sequence in accordance with the disclosure of WO/2006/116002. In some embodiments, the antibody is 21D1.

The add-on therapy is aimed to counter or overcome the pro-fibrotic effect of TGFβ3 inhibition. In some embodiments, the patient has a fibrotic disorder or is at risk of developing a fibrotic disorder and/or a cardiovascular disease. For example, the patient may suffer from a metabolic condition that is associated with higher risk of developing liver fibrosis. The metabolic conditions linked to such risk include obesity, type 2 diabetes and NASH. Accordingly, the invention includes a TGFβ1-selective inhibitor for use in an add-on therapy of a subject treated with a TGFβ3 inhibitor, in an amount sufficient to reduce pro-fibrotic effects of the TGFβ3 inhibitor. In some embodiments, the subject has fibrosis. In some embodiments, the subject has myelofibrosis. In some embodiments, the subject has advanced cancer, e.g., metastatic or locally advanced tumor. In some embodiments, the TGFβ1-selective inhibitor is Ab2, Ab46, Ab42, Ab50, or a derivative thereof. In preferred embodiments, the TGFβ1-selective inhibitor is Ab46.

Without being bound by theory, in some embodiments, sparing of TGFβ inhibitors with anti-TGFβ3 activities may be especially useful for treating patients who are diagnosed with a type of cancer known to be highly metastatic, myelofibrotic, and/or those having or are at risk of developing a fibrotic condition and/or a cardiovascular disease. Accordingly, the disclosure herein includes a TGFβ inhibitor for use in the treatment of cancer wherein the inhibitor does not inhibit TGFβ3 and wherein the patient has a metastatic cancer or myelofibrosis, or the patient has or is at risk of developing a fibrotic condition and/or a cardiovascular disease, wherein optionally the fibrotic condition is non-alcoholic steatohepatitis (NASH).

As used herein, the term "treating" refers to the application or administration of a composition including one or more active agents to a subject, who has a TGFβ-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a TGFβ-related indication with an antibody disclosed herein includes delaying the development or progression of the indication, or reducing indication's severity. Alleviating the indication does not necessarily require curative results. As used therein, "delaying" the development of an indication associated with a TGFβ-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

Combination Therapy

The disclosure further encompasses pharmaceutical compositions and related methods used as combination therapies for treating subjects who may benefit from TGFβ inhibition in vivo. In any of these embodiments, such subjects may receive combination therapies that include a first composition comprising at least one TGFβ inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition associated with TGFβ signaling, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the reduction of TGFβ1 protein activation and the treatment or prevention of diseases or conditions associated with TGFβ1 signaling, as described herein. Accordingly, the methods or the pharmaceutical compositions further comprise a second therapy. In some embodiments, the second therapy may be useful in treating or preventing diseases or conditions associated with TGFβ1 signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more anti-TGFβ antibodies, or antigen-binding portions thereof, of the invention may be used in combination with one or more of additional therapeutic agents. Examples of the additional therapeutic agents which can be used with an anti-TGFβ antibody of the invention include, but are not limited to: cancer vaccines, engineered immune cell therapies, chemotherapies, radiation therapies, a modulator of a member of the TGFβ superfamily, such as a myostatin inhibitor and a GDF11 inhibitor; a VEGF agonist; an IGF1 agonist; an FXR agonist; a CCR2 inhibitor; a CCR5 inhibitor; a dual CCR2/CCR5 inhibitor; a lysyl oxidase-like-2 inhibitor; an ASK1 inhibitor; an Acetyl-CoA Carboxylase (ACC) inhibitor; a p38 kinase inhibitor; Pirfenidone; Nintedanib; an M-CSF inhibitor (e.g., M-CSF receptor antagonist and M-CSF neutralizing agents); a MAPK inhibitor (e.g., Erk inhibitor), an immune checkpoint agonist or antagonist; an IL-11 antagonist; and IL-6 antagonist, and the like. Other examples of the additional therapeutic agents which can be used with the TGFβ inhibitors include, but are not limited to, an indoleamine 2,3-dioxygenase (IDO) inhibitor, a tyrosine kinase inhibitor, Ser/Thr kinase inhibitor, a dual-specific kinase inhibitor. In some embodiments, such an agent may be a PI3K inhibitor, a PKC inhibitor, or a JAK inhibitor. In some embodiments, such an agent may be a TGFβ3-selective inhibitor. In preferred embodiments, the isoform-selective activation inhibitor of TGFβ1 is Ab42, Ab46, Ab50, a derivative thereof, or an engineered molecule comprising an antigen-binding fragment thereof.

In some embodiments, the additional agent is a checkpoint inhibitor. In some embodiments, the additional agent is selected from the group consisting of a PD-1 antagonist, a PD-L1 antagonist, a PD-L1 or PD-L2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor. In some embodiments, the isoform-specific inhibitor of TGFβ1 activation disclosed herein is used in A treatment of cancer in a subject who is a poor responder or non-responder of a checkpoint inhibition therapy, such as those listed herein.

In some embodiments, the additional agent binds a T-cell costimulation molecule, such as inhibitory costimulation molecules and activating costimulation molecules. In some embodiments, the additional agent is selected from the group consisting of an anti-CD40 antibody, an anti-CD38 antibody, an anti-KIR antibody, an anti-CD33 antibody, an anti-CD137 antibody, and an anti-CD74 antibody.

In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that specifically binds a pro/latent myostatin complex and blocks activation of myostatin. In some embodiments, the monoclonal antibody that specifically binds a pro/latent myostatin complex and blocks activation of myostatin does not bind free, mature myostatin.

In some embodiments, an additional therapy comprises cell therapy, such as CAR-T therapy or CAR-NK therapy.

In some embodiments, an additional therapy is a cancer vaccine. Numerous clinical trials that tested peptide-based cancer vaccines have targeted hematological malignancies (cancers of the blood), melanoma (skin cancer), breast cancer, head and neck cancer, gastroesophageal cancer, lung cancer, pancreatic cancer, prostate cancer, ovarian cancer, and colorectal cancers. The antigens included peptides from HER2, telomerase (TERT), survivin (BIRC5), and Wilms' tumor 1 (WT1). Several trials also used "personalized" mixtures of 12-15 distinct peptides. That is, they contain a mixture of peptides from the patient's tumor that the patient exhibits an immune response against. Some trials are targeting solid tumors, glioma, glioblastoma, melanoma, and breast, cervical, ovarian, colorectal, and non-small lung cell cancers and include antigens from MUC1, IDO1 (Indoleamine 2,3-dioxygenase), CTAG1B, and two VEGF receptors, FLT1 and KDR. Notably, the IDO1 vaccine is tested in patients with melanoma in combination with the immune checkpoint inhibitor ipilimumab and the BRAF (gene) inhibitor vemurafenib.

Non-limiting examples of tumor antigens useful as cancer vaccines include: NY-ESO-1, HER2, HPV16 E7 (Papillomaviridae #E7), CEA (Carcinoembryonic antigen), WT1, MART-1, gp100, tyrosinase, URLC10, VEGFR1, VEGFR2, surviving, MUC1 and MUC2.

Activated immune cells primed by such cancer vaccine may, however, be excluded from the TME in part through TGFβ1-dependent mechanisms. To overcome the immunosuppression, use of isoform-specific TGFβ1 inhibitors, as described herein, may be considered so as to unleash the potential of the vaccine.

Combination therapies contemplated herein may advantageously utilize lower dosages of the administered therapeutic agents, thus avoiding possible toxicities or complications associated with the various monotherapies. In some embodiments, use of an isoform-specific inhibitor of TGFβ1 described herein may render those who are poorly responsive or not responsive to a therapy (e.g., standard of care) more responsive. In some embodiments, use of an isoform-specific inhibitor of TGFβ1 described herein may allow reduced dosage of the therapy (e.g., standard of care) which still produces equivalent clinical efficacy in patients but fewer or lesser degrees of drug-related toxicities or adverse events.

In some embodiments, the isoform-selective inhibitors of TGFβ1 contemplated herein may be used in conjunction with (e.g., combination therapy, add-on therapy, etc.) a TGFβ3 inhibitor. Such use may further comprise additional therapy, such as therapy intended to treat fibrosis, cancer therapy, e.g., immune checkpoint inhibitor, cancer vaccine, radiation therapy, and/or chemotherapy.

In some embodiments, the isoform-selective inhibitors of TGFβ1 contemplated herein may be used in conjunction with (e.g., combination therapy, add-on therapy, etc.) a selective inhibitor of myostatin (GDF8).

In any of the embodiments contemplated herein for combination therapy, the antibodies disclosed herein, e.g., Ab37, Ab38, Ab39, Ab40, Ab41, Ab42, Ab43, Ab44, Ab45, Ab46, Ab47, Ab48, Ab49, Ab50, Ab51 and Ab52, may be used. In some embodiments, the preferred TGFβ1 inhibitor is Ab2, Ab42, Ab46, Ab50, a derivative thereof, or an engineered molecule comprising an antigen-binding fragment thereof.

Diagnostics, Patient Selection, Monitoring

Therapeutic methods that include TGFβ1 inhibition therapy may comprise diagnosis of a TGFβ1 indication and/or selection of patients likely to respond to such therapy. Additionally, patients who receive the TGFβ1 inhibitor may be monitored for therapeutic effects of the treatment, which typically involves measuring one or more suitable parameters which are indicative of the condition and which can be measured (e.g., assayed) before and after the treatment and evaluating treatment-related changes in the parameters. For example, such parameters may include levels of biomarkers present in biological samples collected from the patients. Biomarkers may be RNA-based, protein-based, cell-based and/or tissue-based. For example, genes that are overexpressed in certain disease conditions may serve as the biomarkers to diagnose and/or monitor the disease or response to the therapy. Cell-surface proteins of disease-associated cell populations may serve as biomarkers. Such methods may include the direct measurements of disease parameters indicative of the extent of the particular disease, such as tumor size/volume. Any suitable sampling methods may be employed, such as serum/blood samples, biopsies, and imaging. The biopsy may include tissue biopsies (such as tumor) and liquid biopsies. In some embodiments, the liquid biopsies involve measuring or detecting immune cells in blood (e.g., in a serum, and/or plasma sample), e.g., circulating lymphocytes, such as circulating MDSCs. In some embodiments, circulating MDSC levels serve as a predictive biomarker.

Circulating MDSC levels may be determined in a sample such as a whole blood sample or a blood component (e.g., plasma or serum). In some embodiments, the sample is fresh whole blood or a blood component of a sample that has not been previously frozen. In certain embodiments, circulating MDSCs may be collected by drawing peripheral blood into heparinized tubes. From peripheral blood, peripheral blood mononuclear cells may be isolated using, e.g., elutriation, magnetic beads separation, or density gradient centrifugation methods (e.g., Ficoll-PaqueR) known in the art. In some embodiments, MDSCs may be separated from peripheral blood mononuclear cells by CD11b+ marker selection (e.g., using CD11b+ microbeads or antibodies). G-MDSCs and M-MDSCs may be further distinguished from CD11b+ cells via e.g., flow cytometry/FACS analysis based on surface marker expression. For example, human G-MDSCs may be identified by expression of the cell-surface markers CD11b, CD33, CD15 and CD66b. In some embodiments, human G-MDSCs may also express LOX-1, Arginase, and/or low levels of HLA-DR. Human M-MDSCs may be identified by expression of the cell surface markers CD11b, CD33 and CD14, as well as low levels of HLA-DR in some embodiments. Quantification of circulating MDSCs may be represented as percentage of total CD45+ cells.

While biopsies have traditionally been the standard for diagnosing and monitoring various diseases, such as fibrosis (e.g., organ fibrosis) and proliferative disorders (e.g., cancer), less invasive alternatives may be preferred. For example, many non-invasive in vivo imaging techniques may be used to diagnose, monitor, and select patients for treatment. Thus, the invention includes the use of in vivo imaging techniques to diagnose and/or monitor disease in a patient or subject. In some embodiments, the patient or subject is receiving an isoform-specific TGFβ1 inhibitor as described herein. In other embodiments, an in vivo imaging technique may be used to select patients for treatment with an isoform-specific TGFβ1 inhibitor. In some embodiments, such techniques may be used to determine if or how patients respond to a therapy, e.g., TGFβ1 inhibition therapy.

Exemplary in vivo imaging techniques used for the methods include, but are not limited to X-ray radiography, magnetic resonance imaging (MRI), medical ultrasonography or ultrasound, endoscopy, elastography, tactile imaging, thermography, medical photography. Other imaging techniques include nuclear medicine functional imaging, e.g., positron emission tomography (PET) and Single-photon emission computed tomography (SPECT). Methods for conducting these techniques and analyzing the results are known in the art.

Non-invasive imaging techniques commonly used to diagnose and monitor cancer include, but are not limited to: magnetic resonance imaging (MRI), computed tomography (CT), ultrasound, positron emission tomography (PET), single-photon emission computed tomography (SPECT), fluorescence reflectance imaging (FRI), and fluorescence mediated tomography (FMT). Hybrid imaging platforms may also be used to diagnose and monitor cancer. For example, hybrid techniques include, but are not limited to: PET-CT, FMT-CT, FMT-MRI, and PET-MRI. Dynamic contrast enhanced MRI (DCE-MRI) is another imaging technique commonly used to detect breast cancers. Methods for conducting these techniques and analyzing the results are known in the art.

Non-invasive imaging techniques commonly used to diagnosis and monitor fibrosis include, but are not limited to: ultrasound (e.g., conventional or contrast-enhanced ultrasound), ultrasound elastography (e.g., transient elastography, point shear wave elastography and 2D-shear wave elastography), CT scan (e.g., conventional CT or CT perfusion imaging), magnetic resonance imaging (MRI) (e.g., conventional MRI, Magnetic resonance elastography, diffusion weighted magnetic resonance imaging, gadoxetic acid disodium, and magnetic resonance perfusion imaging).

In some embodiments, non-invasive imaging techniques are used to assess levels of liver fibrosis or hepatic steatosis. For example, imaging techniques particularly useful to assess liver fibrosis may include but are not limited to: FibroScan (transient elastography; TE), point shear wave elastography (pSWE; a.k.a. acoustic radiation force impulse (ARFI)), 2D-3D SWE, magnetic resonance elastography (MRE), and multiparameteric MRI. Imaging techniques particularly useful to assess hepatic steatosis may include but are not limited to: ultrasonography, controlled attenuation parameter (CAP) elastography, MRI-estimated proton density fat fraction (MRI-PDFF), and magnetic resonance spectroscopy (MRS). In some embodiments, the in vivo imaging technique is used to assess liver stiffness. In some embodiments, the in vivo imaging technique is used to detect and assess intrahepatic triglyceride levels. In some embodiments, in vivo imaging technique is used to assess liver surface nodularity (LSN; a.k.a. "liver score"), liver stiffness, and/or liver segmental volume ratio (LSVR), which are all beneficial in the staging of hepatic fibrosis and sub-staging cirrhosis. Methods for conducting these techniques and analyzing the results are known in the art.

More recently, non-invasive imaging methods are being developed which will allow the detection of cells of interest (e.g., cytotoxic T cells, macrophages, and cancer cells) in vivo. See for example, www.imaginab.com/technology/; Tavare et al., (2014) PNAS, 111 (3): 1108-1113; Tavare et al., (2015) *J Nucl Med* 56 (8): 1258-1264; Rashidian et al., (2017) *J Exp Med* 214 (8): 2243-2255; Beckford Vera et al., (2018) *PLOS ONE* 13 (3): e0193832; and Tavare et al., (2015) *Cancer Res* 76 (1): 73-82, each of which is incorporated herein by reference. So-called "T-cell tracking" is aimed to detect and localize anti-tumor effector T-cells in vivo. This may provide useful insights into understanding the immunosuppressive phenotype of solid tumors. Tumors that are well-infiltrated with cytotoxic T cells ("inflammed" or "hot" tumors) are likely to respond to cancer therapies such as checkpoint blockade therapy (CBT). On the other hand, tumors with immunosuppressive phenotypes tend to have poor T-cell infiltration even when there is an anti-tumor immune response. These so-called "immune excluded" tumors likely fail to respond to cancer therapies such as CBT. T-cell tracking techniques may reveal these different phenotypes and provide information to guide in therapeutic approach that would likely benefit the patients. For example, patients with an "immune excluded" tumor are likely benefit from a TGFβ1 inhibitor therapy to help reverse the immunosuppressive phenotype. It is contemplated that similar techniques may be used to diagnose and monitor other diseases, for example, fibrosis. Typically, antibodies or antibody-like molecules engineered with a detection moiety (e.g., radiolabel, fluorescence, etc.) can be infused into a patient, which then will distribute and localize to sites of the particular marker (for instance CD8+ and M2 macrophages).

Non-invasive in vivo imaging techniques may be applied in a variety of suitable methods for purposes of diagnosing patients; selecting or identifying patients who are likely to benefit from TGFβ1 inhibitor therapy; and/or, monitoring patients for therapeutic response upon treatment. Any cells with a known cell-surface marker may be detected/localized by virtue of employing an antibody or similar molecules that specifically bind to the cell marker. Typically, cells to be detected by the use of such techniques are immune cells, such as cytotoxic T lymphocytes, regulatory T cells, MDSCs, disease-associated macrophages, (M2 macrophages such as TAMs and FAMs), NK cells, dendritic cells, and neutrophils.

Non-limiting examples of suitable immune cell markers include monocyte markers, macrophage markers (e.g., M1 and/or M2 macrophage markers), CTL markers, suppressive immune cell markers, MDSC markers (e.g., markers for G-and/or M-MDSCs), including but are not limited to: CD8, CD3, CD4, CD11b, CD163, CD206, CD68, CD14, CD15, CD66, CD34, CD25, and CD47.

In vivo imaging techniques described above may be employed to detect, localize and/or track certain MDSCs in a patient diagnosed with a TGFβ1-associated disease, such as cancer and fibrosis. Healthy individuals have no or low frequency of MDSCs in circulation. With the onset of or progression of such a disease, elevated levels of circulating and/or disease-associated MDSCs may be detected. For example, CCR2-positive M-MDSCs have been reported to accumulate to tissues with inflammation and may cause progression of fibrosis in the tissue (such as pulmonary fibrosis), and this is shown to correlate with TGFβ1 expression. Similarly, MDSCs are enriched in a number of solid tumors (including triple-negative breast cancer) and in part contribute to the immunosuppressive phenotype of the TME. Therefore, treatment response to TGFβ1 inhibition therapy according to the present disclosure may be monitored by localizing, tracking or measuring MDSCs. Reduction of or low frequency of detectable MDSCs is typically indicative of therapeutic benefits or better prognosis.

In some embodiments, the present disclosure provides methods of treating fibrosis, predicting, or determining efficacy, and/or confirming pharmacological response by monitoring the levels of circulating MDSCs in a sample obtained from a patient (e.g., in the blood, (e.g., in serum, and/or plasma of a patient) receiving a TGFβ inhibitor, e.g., a TGFβ1-selective inhibitor (such as a selective pro- or latent-TGFβ1 inhibitor as described herein), isoform-non-selective TGFβ inhibitors (such as low molecular weight ALK5 antagonists, neutralizing antibodies that bind two or more of TGFβ1/2/3, e.g., GC1008 and variants, antibodies that bind TGFβ1/3, ligand traps, e.g., TGFβ1/3 inhibitors), and/or an integrin inhibitor (and integrin inhibitors (e.g., antibodies that bind to αVβ3, αVβ5, αVβ6, αVβ8, a5β1, $\alpha_{IIb}\beta_3$, or α8β1 integrins, and inhibit downstream activation of TGFβ. e.g., selective inhibition of TGFβ1 and/or TGFβ3). Exemplary integrin inhibitors include the anti-αVβ8 integrin antibodies provided in WO2020051333, the disclosure of which is incorporated by reference. In various embodiments disclosed herein, the circulating MDSCs may be measured within 1, 2, 3, 4, 5, 6, or 7 days, or within 1, 2, 3, 4, 5, 6, 7, 8, 9, or 10 weeks (e.g., preferably less than 6 weeks) following administration of a treatment to a subject, e.g., administration of a therapeutic dose of a TGFβ inhibitor.

Many human cancers are known to cause elevated levels of MDSCs in patients, as compared to healthy control (reviewed, for example, in Elliott et al., (2017) "Human tumor-infiltrating myeloid cells: phenotypic and functional diversity" Frontiers in Immunology, Vol. 8, Article 86). These human cancers include but are not limited to: bladder cancer, colorectal cancer, prostate cancer, breast cancer, glioblastoma, hepatocellular carcinoma, head and neck squamous cell carcinoma, lung cancer, melanoma, NSCL, ovarian cancer, pancreatic cancer, and renal cell carcinoma. Elevated levels of MDSCs may be detected in biological samples such as peripheral blood mononuclear cell (PBMC) and tissue samples (e.g., tumor biopsy). For example, frequency of or changes in the number of MDSCs may be measured as: percent (%) of total PBMCs, percent (%) of CD14+ cells, percent (%) of CD45+ cells; percent (%) of mononuclear cells, percent (%) of total cells, percent (%) of CD11b+ cells, percent (%) of monocytes, percent (%) of non-lymphocytic MNCs, percent (%) of KLA-DR cells, using suitable cell surface markers (phenotype).

Additionally, using immune cell markers, in the case of cancer, it is possible to determine whether the tumor has an immune-excluded phenotype. If the tumor is determined to have an immune-excluded phenotype, cancer therapy (such as CBT) alone may not be efficacious because the tumor lacks sufficient cytotoxic cells within the tumor environment. Thus, an add-on therapy with a TGFβ1 inhibitor such as those described herein may reduce immune-suppression thereby rendering the cancer therapy-resistant tumor more responsive to a cancer therapy. It is contemplated, that immune markers could also be used to track immune cells in the fibrotic context, and/or determine the immune cell composition of fibrotic tissue (e.g., to track the presence of macrophages and/or myofibroblasts).

Accordingly, the invention also includes a method for treating a TGFβ1-related disease or condition which may comprise the following steps: i) selecting a patient diagnosed with a TGFβ1-related disease or condition; and, ii) administering to the patient an antibody or the fragment encompassed herein in an amount effective to treat the disease or condition. In some embodiments, the selection step (i) comprises detection of disease markers (e.g., fibrosis or cancer markers as described herein), wherein optionally the detection comprises a biopsy analysis, serum marker analysis, and/or in vivo imaging. In some embodiments, the selection step (i) comprises an in vivo imaging technique as described herein.

In some embodiments, the TGFβ1-related disease or condition is a fibrotic condition. In some embodiments, the selection step (i) comprises detection of myofibroblasts cells, or one or more markers thereof. In some embodiments, the selection step (i) comprises detection of hepatic steatosis, hepatic triglycerides, immune cells, and/or myofibroblasts. In some embodiments, the detection comprises a biopsy analysis, serum marker analysis, and/or in vivo imaging. In some embodiments, the in vivo imaging comprises ultrasound, ultrasound elastography, CT scan, MRI, PET-SPECT, optical fluorescence/bioluminescence FibroScan (TE), pSWE, 2D-3D SWE, MRE, ultrasonography, CAP, MRI-PDFF, and/or MRS. In some embodiments, in vivo imaging comprises direct or indirect labeling of immune cells or antibody that binds a cell-surface marker of immune cells. In some embodiments, the in vivo imaging comprises the use of a tracer.

In some embodiments, the in vivo imaging technique measures hepatic steatosis, hepatic triglycerides, immune cells (e.g., as described below), and/or myofibroblasts. In some embodiments, the treatment reduces triglycerides, steatosis, liver surface nodules, inflammation, and/or macrophages, in the diseased tissue. In some embodiments, the selected patient has an intrahepatic triglyceride content of >5.5% of liver volume, optionally wherein the intrahepatic triglyceride content is >10% of liver volume. In some embodiments, the treatment reduces intrahepatic triglyceride content to ≤5.5% of liver volume. In some embodiments, the treatment reduces MDSCs in the diseased tissue. In some embodiments, the treatment reduces macrophages in the diseased tissue. In some embodiments, the effective amount is from 0.1 mg/kg to 30 mg/kg, optionally 3 mg/kg to 30 mg/kg. In some embodiments, the method further comprises monitoring the subject for a therapeutic response as described herein (e.g., reduced triglycerides, reduced steatosis, reduced liver surface nodules, reduced inflammation, reduced macrophages, and/or reduced liver score).

The invention also includes a method for treating cancer which may comprise the following steps: i) selecting a patient diagnosed with cancer comprising a solid tumor, wherein the solid tumor is or is suspected to be an immune excluded tumor; and, ii) administering to the patient an antibody or the fragment encompassed herein in an amount effective to treat the cancer. Preferably, the patient has received, or is a candidate for receiving a cancer therapy such as immune checkpoint inhibition therapies (e.g., PD-(L) 1 antibodies), chemotherapies, radiation therapies, engineered immune cell therapies, and cancer vaccine therapies. In some embodiments, the selection step (i) comprises detection of immune cells or one or more markers thereof, wherein optionally the detection comprises a tumor biopsy analysis, serum marker analysis, and/or in vivo imaging. In some embodiments, the selection step (i) comprises an in vivo imaging technique as described here. In some embodiments, the method further comprises monitoring for a therapeutic response as described herein.

In some embodiments, in vivo imaging is performed for monitoring a therapeutic response to the TGFβ1 inhibition therapy in the subject. The in vivo imaging can comprise any one of the imaging techniques described herein and measure any one of the markers and/or parameters described herein. For example, in the case of liver fibrosis, the therapeutic response may comprise reduced liver steatosis, reduced triglyceride content, reduced ECM deposition/fibrosis, reduced cirrhosis, and/or reduced disease progression. In some embodiments, treatment with an isoform-specific TGFβ1 inhibitor as described herein reduces intrahepatic triglyceride content to levels of ≤5.5% as measured by MRI. In the case of cancer, the therapeutic response may comprise conversion of an immune excluded tumor into an inflamed tumor (which correlates with increased immune cell infiltration into a tumor), reduced tumor size, and/or reduced disease progression. Increased immune cell infiltration may be visualized by increased intratumoral immune cell frequency or degree of detection signals, such as radiolabeling and fluorescence.

In some embodiments, the in vivo imaging used for diagnosing, selecting, treating, or monitoring patients, comprises MDSC tracking, such as G-MDSCs (also known as PMN-MDSCs) and M-MDSCs. For example, MDSCs may be enriched at a disease site (such as fibrotic tissues and solid tumors) at the baseline. Upon therapy (e.g., TGFβ1 inhibitor therapy), fewer MDSCs may be observed, as measured by reduced intensity of the label (such as radioisotope and fluorescence), indicative of therapeutic effects.

In some embodiments, the in vivo imaging comprises tracking or localization of LRRC33-positive cells. LRRC33-positive cells include, for example, MDSCs and activated M2-like macrophages (e.g., TAMs and activated macrophages associated with fibrotic tissues). For example, LRRC33-positive cells may be enriched at a disease site (such as fibrotic tissues and solid tumors) at the baseline. Upon therapy (e.g., TGFβ1 inhibitor therapy), fewer cells expressing cell surface LRRC33 may be observed, as measured by reduced intensity of the label (such as radioisotope and fluorescence), indicative of therapeutic effects.

In some embodiments, the in vivo imaging techniques described herein may comprise the use of PET-SPECT, MRI and/or optical fluorescence/bioluminescence in order to detect cells of interest.

In some embodiments, labeling of antibodies or antibody-like molecules with a detection moiety may comprise direct labeling or indirect labeling.

In some embodiments, the detection moiety may be a tracer. In some embodiments, the tracer may be a radioisotope, wherein optionally the radioisotope may be a positron-emitting isotope. In some embodiments, the radioisotope is selected from the group consisting of: 18F, 11C, 13N, 150, 68Ga, 177Lu, and 89Zr.

Thus, such methods may be employed to carry out in vivo imaging with the use of labeled antibodies in immune-PET.

Accordingly, the invention also includes a method for treating a TGFβ1 indication in a subject, which incorporates a step of diagnosis, patient selection, and/or monitoring therapeutic effects, which employs an imaging technique. In some embodiments, a high-affinity, isoform-selective TGFβ1 inhibitor according to the present disclosure is used in the treatment of a TGFβ1 indication, wherein the treatment comprises administration of an effective amount of the TGFβ1 inhibitor to treat the indication, and further comprising a step of monitoring therapeutic effects in the subject by in vivo imaging. Optionally, the subject may be selected as a candidate for receiving the TGFβ1 inhibitor therapy, using a diagnostic or selection step that comprises in vivo imaging. In some embodiments, the TGFβ1 indication is a proliferative disorder (such as cancer with a solid tumor and myelofibrosis). In some embodiments, the TGFβ1 indication is a fibrotic disorder (such as organ fibrosis).

Circulating/circulatory latent-TGFβ

According to the present disclosure, circulating latent TGFβ may serve as a target engagement biomarker. Where an activation inhibitor is selected as a therapeutic candidate, for example, such biomarker may be employed to evaluate or confirm in vivo target engagement by monitoring the levels of circulating latent TGFβ before and after administration. In various embodiments, the present disclosure provides methods of treating a TGFβ-related disorder, comprising monitoring the level of circulating latent TGFβ (e.g., TGFβ1) in a sample obtained from a patient (e.g., in the blood, e.g., plasma and/or serum, of a patient) receiving a TGFβ inhibitor. The level of circulating latent TGFβ may be monitored alone or in conjunction with one or more of the biomarkers disclosed herein (e.g., MDSCs). In certain embodiments, the TGFβ inhibitor may be administered alone or in conjunction with an additional therapy. In some embodiments, the treatment may be administered to a subject afflicted with a fibrotic disorder (e.g., organ fibrosis). In some embodiments, the TGFβ inhibitor is a TGFβ1-selective antibody or antigen-binding fragment thereof described herein. In some embodiments, the TGFβ inhibitor is an isoform-non-selective TGFβ inhibitor (such as low molecular weight ALK5 antagonists, neutralizing antibodies that bind two or more of TGFβ1/2/3, e.g., GC1008 and variants, antibodies that bind TGFβ1/3, and ligand traps, e.g., TGFβ1/3 inhibitors). In some embodiments, the TGFβ inhibitor is an integrin inhibitor (e.g., an antibody that binds to αVβ3, αVβ5, αVβ6, αVβ8, a531, $\alpha_{IIb}\beta_3$, or α8β1 integrins, and inhibits downstream activation of TGFβ. e.g., selective inhibition of TGFβ1 and/or TGFβ3).

In various embodiments, circulating latent TGFβ (e.g., latent TGFβ1) may be measured in a sample obtained from a subject (e.g., whole blood or a blood component). In various embodiments, the circulating latent TGFβ levels (e.g., latent TGFβ1) may be measured within 1, 2, 3, 4, 5, 6, 7, 8, 10, 12, 14, 16, 18, 21, 25, 28, 30, 35, 40, 45, 48, 50, or 56 days following administration of the TGFβ inhibitor to a subject, e.g., up to 7 days after administration of a therapeutic dose of a TGFβ inhibitor. In some embodiments, the circulating latent TGFβ levels (e.g., latent TGFβ1) may be measured by any method known in the art (e.g., ELISA).

In various embodiments, a method of treating a fibrotic disorder or other TGF-related disorder comprises administering a TGFβ inhibitor (e.g., an anti-TGFβ1 antibody, e.g., an isoform-selective activation inhibitor of TGFβ1 such as Ab2, Ab42, Ab46, Ab50, or derivatives thereof,) to a patient in need thereof and confirming the level of target engagement by the inhibitor. In some embodiments, determining the level of target engagement comprises determining the levels of circulating latent TGFβ (e.g., TGFβ1) in a sample obtained from a patient (e.g., in the blood or a blood component of a patient) receiving the TGFβ inhibitor. In some embodiments, an increase in circulating latent TGFβ (e.g., TGFβ1) after administration of the TGF inhibitor indicates target engagement. In some embodiments, an increase in circulating latent TGFβ (e.g., TGFβ1) of at least 2-fold, at least 3-fold, at least 4-fold, at least 5-fold, at least 6-fold, at least 7-fold, at least 8-fold, at least 9-fold, at least 10-fold, or more, after administration of the TGF inhibitor indicates target engagement. In various embodiments, the present disclosure also provides methods of using circulating latent TGFβ levels (e.g., TGFβ1 levels) as a predictive biomarker, i.e., to predict therapeutic response, as well as for informing further treatment decisions (e.g., by continuing treatment if an increase is observed).

In one aspect of the current disclosure, levels of circulating latent TGFβ are determined to inform treatment and predict therapeutic efficacy in subjects administered a TGFβ inhibitor such as a TGFβ1-selective inhibitor described herein (e.g., Ab2, Ab42, Ab46, Ab50, or derivatives thereof). In certain embodiments, a TGFβ inhibitor (e.g., an isoform-selective activation inhibitor of TGFβ1 such as Ab2, Ab42, Ab46, Ab50, or derivatives thereof) is administered alone or concurrently (e.g., simultaneously), separately, or sequentially with an additional therapy, such that the amount of TGFβ1 inhibition administered is sufficient to increase the levels of circulating latent-TGFβ (e.g., latent TGFβ1) as compared to baseline circulating latent-TGFβ levels. Circulating latent-TGFβ levels may be measured prior to or after each treatment such that an increase in circulating latent-TGFβ levels (e.g., latent TGFβ1) following the treatment indicates therapeutic efficacy. For instance, circulating latent-TGFβ levels (e.g., latent TGFβ1) may be measured prior to and after the administration of a TGFβ inhibitor and an increase in circulating latent-TGFβ levels (e.g., latent TGFβ1) following the treatment predicts therapeutic efficacy. In some embodiments, treatment is continued if an increase is detected. In certain embodiments, circulating latent-TGFβ levels may be measured prior to and following administration of a first dose of a TGFβ inhibitor such as a TGFβ1 inhibitor described herein (e.g., an isoform-selective activation inhibitor of TGFβ1 such as Ab2, Ab42, Ab46, Ab50, or derivatives thereof), and an increase in circulating latent-TGFβ levels (e.g., latent TGFβ1) following the administration predicts therapeutic efficacy and further warrants administration of a second or more dose(s) of the TGFβ inhibitor. In some embodiments, circulating latent-TGFβ levels (e.g., latent TGFβ1) may be measured prior to and after a combination treatment of TGFβ inhibitor such as a TGFβ1-selective inhibitor (e.g., an isoform-selective activation inhibitor of TGFβ1 such as Ab2, Ab42, Ab46, Ab50, or derivatives thereof, and an additional therapy, administered concurrently (e.g., simultaneously), separately, or sequentially, and a change in circulating latent-TGFβ levels following the treatment predicts therapeutic efficacy. In some embodiments, treatment is continued if an increase is detected. In some embodiments, the increase in circulating latent-TGFβ levels following a combination treatment may warrant continuation of treatment.

In various embodiments, the current disclosure encompasses a method of treating a TGFβ-related disorder, e.g., a fibrotic disorder, comprising administering a therapeutically effective amount of a TGFβ inhibitor (e.g., an isoform-selective activation inhibitor of TGFβ1 such as Ab2, Ab42, Ab46, Ab50, or derivatives thereof), to a subject having a TGFβ-related disorder, wherein the therapeutically effective amount is an amount sufficient to increase the level of circulating latent TGFβ (e.g., latent TGFβ1). In certain embodiments, the TGFβ inhibitor is a TGFβ activation inhibitor. In certain embodiments, the TGFβ inhibitor is a TGFβ1 inhibitor. In some embodiments, the TGFβ inhibitor is an isoform-selective activation inhibitor of TGFβ1 such as Ab2, Ab42, Ab46, Ab50, or derivatives thereof. In certain embodiments, the circulating latent TGFβ is latent TGFβ1. In some embodiments, the therapeutically effective amount of the TGFβ inhibitor (e.g., an isoform-selective activation inhibitor of TGFβ1 such as Ab2, Ab42, Ab46, Ab50, or derivatives thereof,) is between 0.1-30 mg/kg per dose. In some embodiments, the TGFβ inhibitor is dosed weekly, every 2 weeks, every 3 weeks, every 4 weeks, monthly, every 6 weeks, every 8 weeks, bi-monthly, every 10 weeks, every 12 weeks, every 3 months, every 4 months, every 6 months, every 8 months, every 10 months, or once a year.

In various embodiments, circulating latent TGFβ (e.g., latent TGFβ1) may be measured in a sample obtained from a subject (e.g., whole blood or a blood component). In some embodiments, circulating latent TGFβ1 may be measured using an enzyme-linked immunosorbent assay (ELISA) that measures total free TGFβ1 after acid treatment. Analysis of latent TGF-31 by TGF-31 ELISA first requires dissociation of TGF-$\beta_1$ from the latent complex, e.g. by acidification of samples. The ELISA then measures total TGF-31, equivalent to dissociated latent TGF-$\beta_1$, in addition to any free TGF-β1 present prior to acidification, which is known to be only a small fraction of circulating TGFβ1. In certain embodiments, the level of circulating latent TGFβ (e.g., latent TGFβ1) following administration of a TGFβ inhibitor is increased by at least two-fold (e.g., at least 2-fold, 3-fold, 4-fold, 5-fold, 6-fold, 7-fold, 8-fold, 9-fold and 10-fold) as compared to circulating latent TGFβ levels prior to the administration.

In certain embodiments, circulating total TGFβ levels (e.g., latent and mature TGFβ1) may be used to monitor target engagement and pharmacological activity of a TGFβ inhibitor in a subject receiving a TGFβ inhibitor therapy (e.g., an isoform-selective activation inhibitor of TGFβ1 such as Ab2, Ab42, Ab46, Ab50, or derivatives thereof). In certain embodiments, circulating total TGFβ levels (e.g., latent and mature TGFβ1 levels) may be measured prior to and after administration of a first dose of TGFβ inhibitor such that an increase in circulating TGFβ levels of at least two-fold (e.g. at least 2-fold, 3-fold, 4-fold, 5-fold, 6-fold, 7-fold, 8-fold, 9-fold, 10-fold, or more) in following the administration indicates target engagement (e.g., binding of the TGFβ inhibitor to human large latent proTGFb1 complex). In certain embodiments, circulating latent TGFβ levels (e.g., latent TGFβ1) may be measured prior to and after administration of a first dose of TGFβ inhibitor such that an increase in circulating latent TGFβ levels (e.g., latent TGFβ1) following the administration indicates therapeutic efficacy. In certain embodiments, treatment is continued if an increase in circulating latent-TGFβ levels (e.g., latent TGFβ1) following administration of a TGFβ inhibitor is detected. In some embodiments, total TGFβ1 in a blood sample (e.g., serum) comprises both latent and mature forms, the former of which representing vast majority of circulatory TGFβ1. Acid treatment of the sample releases mature growth factor from the latent complex. Well-known assays such as ELISA can then used to measure the amount of free TGFβ1. Alternatively, reagents such as antibodies that specifically bind the latent form of TGFβ1 may be employed to specifically measure circulatory latent TGFβ1. In some embodiments, circulating latent-TGFβ levels (e.g., latent TGFβ1) may be measured prior to and after administration of a first dose of a TGFβ inhibitor, and an increase in circulating latent-TGFβ levels (e.g., latent TGFβ1) after the administration indicates target engagement and/or treatment response, and/or further warrants administration of a second or more dose(s) of the TGFβ inhibitor. In another embodiment, circulating latent-TGFβ levels may be measured prior to and after administration of a first dose of a TGFβ inhibitor such as a TGFβ1-selective inhibitor, and an increase in circulating latent-TGFβ levels after the administration indicates target engagement and/or treatment response, and/or further warrants continuation of treatment. In various embodiments, a TGFβ inhibitor such as a TGFβ1-selective inhibitor, an isoform-non-selective inhibitor (e.g., low molecular weight ALK5 antagonists), neutralizing antibodies that bind two or more of TGFβ1/2/3 (e.g., GC1008 and variants), antibodies that bind TGFβ1/3, and/or an integrin inhibitor (e.g., an antibody that binds to αVβ3, αVβ5, αVβ6, αVβ8, $\alpha_5\beta_1$, $\alpha_{IIb}\beta_3$, or α8β1 integrins, and inhibits downstream activation of TGFβ. e.g., selective inhibition of TGFβ1 and/or TGFβ3).

In some embodiments, the processing of blood to serum activates platelets and leads to release of large pools of latent TGFβ1, which confounds the measurements. Therefore, according to some embodiments, it is preferable to measure circulating levels of TGFβ1 in plasma instead of in serum. Accordingly, in preferred embodiments, circulating TGFβ (e.g., circulating latent-TGFβ levels (e.g., latent TGFβ1)) is measured in plasma samples collected from the subject.

Various Modifications and Variants

Non-limiting variations, modifications, and features of any of the antibodies or antigen-binding fragments thereof encompassed by the present disclosure are briefly discussed below. Embodiments of related analytical methods are also provided.

Naturally-occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human antibody light chains are typically classified as kappa and lambda light chains. Heavy chains are typically classified as mu, delta, gamma, alpha, or epsilon, and define the isotype of the antibody. An antibody can be of any type (e.g., IgM, IgD, IgG, IgA, IgY, and IgE) and class (e.g., $IgG_1$, $IgG_2$, $IgG_3$, $IgG_4$, $IgM_1$, $IgM_2$, $IgA_1$, and $IgA_2$). Within full-length light and heavy chains, typically, the variable and constant regions are joined by a "J" region of about 12 or more amino acids, with the heavy chain also including a "D" region of about 10 more amino acids (see, e.g., Fundamental Immunology, Ch. 7 (Paul, W., ed., $2^{nd}$ ed. Raven Press, N.Y. (1989)) (incorporated by reference in its entirety)). The variable regions of each light/heavy chain pair typically form the antigen-binding site.

In some embodiments, the "percent identity" of two amino acid sequences is determined using the algorithm of Karlin and Altschul *Proc. Natl. Acad. Sci. USA* 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al., *J. Mol. Biol.* 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., *Nucleic Acids Res.* 25 (17): 3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a GARP-TGFβ1 complex, a LTBP1-TGFβ1 complex, a LTBP3-TGFβ1 complex, and a LRRC33-TGFβ1 complex as determined based on the crystal structure. In some embodiments, likely interface (e.g., residues involved in an antigen-antibody interaction) may be deduced from known structural information on another antigen sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk (1987) *J. Mol. Biol.* 196:901-917; Chothia et al., (1989) *Nature* 342:878-883. The CDRs of a light chain can also be referred to as L-CDR1, L-CDR2, and L-CDR3, and the CDRs of a heavy chain can also be referred to as H-CDR1, H-CDR2, and H-CDR3. In some embodiments, an antibody can comprise a small number of amino acid deletions from the carboxy end of the heavy chain(s). In some embodiments, an antibody comprises a heavy chain having 1-5 amino acid deletions in the carboxy end of the heavy chain. In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In some embodiments, various methods of analysis can be employed to identify or approximate the CDR regions. Examples of such methods include, but are not limited to, the Kabat definition, the Chothia definition, the AbM definition, and the contact definition.

An "affinity matured" antibody is an antibody with one or more alterations in one or more CDRs thereof, which result an improvement in the affinity of the antibody for antigen compared to a parent antibody, which does not possess those alteration(s). Exemplary affinity matured antibodies will have nanomolar or even picomolar affinities for the target antigen. Affinity matured antibodies are produced by procedures known in the art. Marks et al., (1992) *Bio/Technology* 10:779-783 describes affinity maturation by VH and VL domain shuffling. Random mutagenesis of CDR and/or framework residues is described by Barbas, et al., (1994) *Proc Nat. Acad. Sci. USA* 91:3809-3813; Schier et al., (1995) *Gene* 169:147-155; Yelton et al., (1995) *J. Immunol.* 155:1994-2004; Jackson et al., (1995) *J. Immunol.* 154 (7): 3310-9; and Hawkins et al., (1992) *J. Mol. Biol.* 226:889-896; and selective mutation at selective mutagenesis positions, contact or hypermutation positions with an activity enhancing amino acid residue is described in U.S. Pat. No. 6,914,128.

The term "CDR-grafted antibody" refers to antibodies, which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "chimeric antibody" refers to antibodies, which comprise heavy and light chain variable region sequences from one species and constant region sequences from another species, such as antibodies having murine heavy and light chain variable regions linked to human constant regions.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (L-CDR1, L-CDR2, and L-CDR3 of light chain and H-CDR1, H-CDR2, and H-CDR3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

In some embodiments, the antibody, or antigen-binding portion thereof, comprises a heavy chain immunoglobulin constant domain of a human IgM constant domain, a human IgG constant domain, a human IgG1 constant domain, a human IgG2 constant domain, a human IgG2A constant domain, a human IgG2B constant domain, a human IgG2 constant domain, a human IgG3 constant domain, a human IgG3 constant domain, a human IgG4 constant domain, a human IgA constant domain, a human IgA1 constant domain, a human IgA2 constant domain, a human IgD constant domain, or a human IgE constant domain. In some embodiments, the antibody, or antigen-binding portion thereof, comprises a heavy chain immunoglobulin constant domain of a human IgG1 constant domain or a human IgG4 constant domain. In some embodiments, the antibody, or antigen-binding portion thereof, comprises a heavy chain immunoglobulin constant domain of a human IgG4 constant domain. In some embodiments, the antibody, or antigen-binding portion thereof, comprises a heavy chain immunoglobulin constant domain of a human IgG4 constant domain having a backbone substitution of Ser to Pro that produces an IgG1-like hinge and permits formation of inter-chain disulfide bonds.

In some embodiments, the antibodies provided herein comprise mutations that confer desirable properties to the antibodies. For example, to avoid potential complications due to Fab-arm exchange, which is known to occur with native $IgG_4$ mAbs, the antibodies provided herein may comprise a stabilizing 'Adair' mutation (Angal et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like (CPPCP (SEQ ID NO: 54)) hinge sequence. Accordingly, any of the antibodies may include a stabilizing 'Adair' mutation or the amino acid sequence CPPCP (SEQ ID NO: 54).

In some embodiments, the antibody or antigen-binding portion thereof, further comprises a light chain immunoglobulin constant domain comprising a human Ig lambda constant domain or a human lg kappa constant domain.

In some embodiments, the antibody is an IgG having four polypeptide chains which are two heavy chains and two light chains.

In some embodiments, wherein the antibody is a humanized antibody, a diabody, or a chimeric antibody. In some embodiments, the antibody is a humanized antibody. In some embodiments, the antibody is a human antibody. In some embodiments, the antibody comprises a framework having a human germline amino acid sequence.

In some embodiments, the antigen-binding portion is a Fab fragment, a F(ab')2 fragment, a scFab fragment, or an scFv fragment.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin (see, e.g., Shapiro et al., (2002) *Crit. Rev. Immunol.* 22 (3): 183-200; Marchalonis et al., (2001) *Adv. Exp. Med. Biol.* 484:13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "neutralizing" refers to counteracting the biological activity of an antigen when a binding protein specifically binds to the antigen. In an embodiment, the neutralizing binding protein binds to the antigen/target, e.g., cytokine, kinase, growth factor, cell surface protein, soluble protein, phosphatase, or receptor ligand, and reduces its biologically activity by at least about 20%, 40%, 60%, 80%, 85%, 90%, 95%, 96%, 97%, 98%, 99% or more.

The term "binding protein" as used herein includes any polypeptide that specifically binds to an antigen (e.g., TGFβ1), including, but not limited to, an antibody, or antigen-binding portions thereof, a DVD-Ig™, a TVD-Ig, a RAb-Ig, a bispecific antibody and a dual specific antibody.

The term "monoclonal antibody" or "mAb" when used in a context of a composition comprising the same may refer to an antibody preparation obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "recombinant human antibody," as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom, H. R. (1997) *TIB Tech.* 15:62-70; Azzazy, H. and Highsmith, W. E. (2002) *Clin. Biochem.* 35:425-445; Gavilondo, J. V. and Larrick, J. W. (2002) *BioTechniques* 29:128-145; Hoogenboom, H. and Chames, P. (2000) *Immunol. Today* 21:371-378, incorporated herein by reference), antibodies isolated from an animal (e.g., a mouse) that is transgenic for human immunoglobulin genes (see, Taylor, L. D. et al., (1992) *Nucl. Acids Res.* 20:6287-6295; Kellermann, S-A. and Green, L. L. (2002) *Cur. Opin. In Biotechnol.* 13:593-597; Little, M. et al., (2000) *Immunol. Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In some embodiments, the antibody or antigen-binding portion, is an antibody fragment, e.g., (i) Fab fragments, a monovalent fragment consisting of the VL, VH, CL and CH1 domains; (ii) F(ab')2 fragment, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules; (vi) dAb fragments; or (vii) minimal recognition units consisting of the amino acid residues that mimic the hypervariable region of an antibody (e.g., an isolated complementarity determining region (CDR)). In some embodiments, the antibody or antigen-binding portion, is (i) a "Dual Variable Domain Immunoglobulin" or "DVD-Ig™," (ii) a "Triple Variable Domain Immunoglobulin" or "TVD-Ig", (iii) a "Receptor-Antibody Immunoglobulin" or "RAb-Ig," (iv) a "bispecific antibody," or (v) a "dual-specific antibody,"

As used herein, "Dual Variable Domain Immunoglobulin" or "DVD-Ig™" and the like include binding proteins comprising a paired heavy chain DVD polypeptide and a light chain DVD polypeptide with each paired heavy and light chain providing two antigen-binding sites. Each binding site includes a total of 6 CDRs involved in antigen-binding per antigen-binding site. A DVD-Ig™ is typically has two arms bound to each other at least in part by dimerization of the CH3 domains, with each arm of the DVD being bispecific, providing an immunoglobulin with four binding sites. DVD-Ig™ are provided in US Patent Publication No. 2010/0260668 and U.S. Pat. No. 9,109,026, each of which is incorporated herein by reference including sequence listings.

As used herein, "Triple Variable Domain Immunoglobulin" or "TVD-Ig" and the like are binding proteins comprising a paired heavy chain TVD binding protein polypeptide and a light chain TVD binding protein polypeptide with each paired heavy and light chain providing three antigen-binding sites. Each binding site includes a total of 6 CDRs involved in antigen-binding per antigen-binding site. A TVD binding protein may have two arms bound to each other at least in part by dimerization of the CH3 domains, with each arm of the TVD binding protein being trispecific, providing a binding protein with six binding sites.

As used herein, "Receptor-Antibody Immunoglobulin" or "RAb-Ig" and the like are binding proteins comprising a heavy chain RAb polypeptide, and a light chain RAb polypeptide, which together form three antigen-binding sites in total. One antigen-binding site is formed by the pairing of the heavy and light antibody variable domains present in each of the heavy chain RAb polypeptide and the light chain RAb polypeptide to form a single binding site with a total of 6 CDRs providing a first antigen-binding site. Each the heavy chain RAb polypeptide and the light chain RAb polypeptide include a receptor sequence that independently binds a ligand providing the second and third "antigen" binding sites. A RAb-Ig is typically has two arms bound to each other at least in part by dimerization of the CH3 domains, with each arm of the RAb-Ig being trispecific, providing an immunoglobulin with six binding sites. RAb-Igs are described in US Patent Application Publication No. 2002/0127231, the entire contents of which including sequence listings are incorporated herein by reference).

The term "bispecific antibody," as used herein, and as differentiated from a "bispecific half-lg binding protein" or "bispecific (half-Ig) binding protein", refers to full-length antibodies that are generated by quadroma technology (see Milstein, C. and Cuello, A. C. (1983) Nature 305 (5934): p. 537-540), by chemical conjugation of two different monoclonal antibodies (see Staerz, U. D. et al., (1985) *Nature* 314 (6012): 628-631), or by knob-into-hole or similar approaches, which introduce mutations in the Fc region that do not inhibit CH3-CH3 dimerization (see Holliger, P. et al., (1993) *Proc. Natl. Acad. Sci USA* 90 (14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences) and is monovalent for each antigen it binds to.

The term "dual-specific antibody," as used herein, and as differentiated from a bispecific half-lg binding protein or bispecific binding protein, refers to full-length antibodies that can bind two different antigens (or epitopes) in each of its two binding arms (a pair of HC/LC) (see PCT Publication No. WO 02/02773). Accordingly, a dual-specific binding protein has two identical antigen-binding arms, with identical specificity and identical CDR sequences, and is bivalent for each antigen to which it binds.

The term "Kon," as used herein, is intended to refer to the on rate constant for association of a binding protein (e.g., an antibody) to the antigen to form the, e.g., antibody/antigen complex as is known in the art. The "Kon" also is known by the terms "association rate constant," or "ka," as used interchangeably herein. This value indicating the binding rate of an antibody to its target antigen or the rate of complex formation between an antibody and antigen also is shown by the equation: Antibody ("Ab")+Antigen ("Ag")→Ab-Ag.

The term "Koff" as used herein, is intended to refer to the off rate constant for dissociation of a binding protein (e.g., an antibody) from the, e.g., antibody/antigen complex as is known in the art. The "Koff" also is known by the terms "dissociation rate constant" or "kdis" as used interchangeably herein. This value indicates the dissociation rate of an antibody from its target antigen or separation of Ab-Ag complex over time into free antibody and antigen as shown by the equation: Ab+Ag←Ab-Ag.

The terms "equilibrium dissociation constant" or "$K_D$," as used interchangeably herein, refer to the value obtained in a titration measurement at equilibrium, or by dividing the dissociation rate constant (koff) by the association rate constant (kon). The association rate constant, the dissociation rate constant, and the equilibrium dissociation constant are used to represent the binding affinity of a binding protein, e.g., antibody, to an antigen. Methods for determining association and dissociation rate constants are well known in the art. Using fluorescence-based techniques offers high sensitivity and the ability to examine samples in physiological buffers at equilibrium. Other experimental approaches and instruments, such as a BIACORE® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Idaho), can also be used.

The terms "crystal" and "crystallized" as used herein, refer to a binding protein (e.g., an antibody), or antigen-binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, $2^{nd}$ ea., pp. 201-16, Oxford University Press, New York, New York, (1999).

The term "linker" is used to denote polypeptides comprising two or more amino acid residues joined by peptide bonds and are used to link one or more antigen-binding portions. Such linker polypeptides are well known in the art (see, e.g., Holliger, P. et al., (1993) *Proc. Natl. Acad. Sci. USA* 90:6444-6448; Poljak, R. J. et al., (1994) *Structure* 2:1121-1123). Exemplary linkers include, but are not limited to, ASTKGPSVFPLAP (SEQ ID NO: 55), ASTKGP (SEQ ID NO: 56); TVAAPSVFIFPP (SEQ ID NO: 57); TVAAP (SEQ ID NO: 58); AKTTPKLEEGEFSEAR (SEQ ID NO: 59); AKTTPKLEEGEFSEARV (SEQ ID NO: 60); AKTTPKLGG (SEQ ID NO: 61); SAKTTPKLGG (SEQ ID NO: 62); SAKTTP (SEQ ID NO: 63); RADAAP (SEQ ID NO: 64); RADAAPTVS (SEQ ID NO: 65); RADAAAAGGPGS (SEQ ID NO: 66); RADAAAA (G4S) 4 (SEQ ID NO: 67); SAKTTPKLEEGEFSEARV (SEQ ID NO: 68); ADAAP (SEQ ID NO: 69); ADAAPTVSIFPP (SEQ ID NO: 70); QPKAAP (SEQ ID NO: 71);

QPKAAPSVTLFPP (SEQ ID NO: 72); AKTTPP (SEQ ID NO: 73); AKTTPPSVTPLAP (SEQ ID NO: 74); AKTTAP (SEQ ID NO: 75); AKTTAPSVYPLAP (SEQ ID NO: 76); GGGGSGGGGSGGGGS (SEQ ID NO: 77); GENKVEYAPALMALS (SEQ ID NO: 78); GPAKELTPLKEAKVS (SEQ ID NO: 79); GHEAAAVMQVQYPAS (SEQ ID NO: 80); TVAAPSVFIFPPTVAAPSVFIFPP (SEQ ID NO: 81); and ASTKGPSVFPLAPASTKGPSVFPLAP (SEQ ID NO: 82).

"Label" and "detectable label" or "detectable moiety" mean a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$); chromogens; fluorescent labels (e.g., FITC, rhodamine, and lanthanide phosphors); enzymatic labels (e.g., horseradish peroxidase, luciferase, and alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

In some embodiments, the binding affinity of an antibody, or antigen-binding portion thereof, to an antigen (e.g., protein complex), such as presenting molecule-proTGFβ1 complexes, is determined using an Octet assay. In some embodiments, an Octet assay is an assay that determines one or more a kinetic parameters indicative of binding between an antibody and antigen. In some embodiments, an OCTET® system (FORTEBIOR, Menlo Park, CA) is used to determine the binding affinity of an antibody, or antigen-binding portion thereof, to presenting molecule-proTGFβ1 complexes. For example, binding affinities of antibodies may be determined using the FORTEBIOR Octet QKe dip and read label free assay system utilizing bio-layer interferometry. In some embodiments, antigens are immobilized to biosensors (e.g., streptavidin-coated biosensors) and the antibodies and complexes (e.g., biotinylated presenting molecule-proTGFβ1 complexes) are presented in solution at high concentration (50 μg/mL) to measure binding interactions. In some embodiments, the binding affinity of an antibody, or antigen-binding portion thereof, to a presenting molecule-proTGFβ1 complex is determined using the protocol outlined in Table 14.

The antibodies according to the present disclosure include pH-sensitive antibodies. In some embodiments, such antibodies or fragments thereof bind the target complex in a pH-dependent manner such that relatively high affinity binding occurs at a neutral or physiological pH, but the antibody dissociates from its antigen more rapidly at an acidic pH; or, dissociation rates are higher at acidic pH than at neutral pH. Such antibodies or fragments thereof may function as recycling antibodies. Such antibodies may also be referred to as "pH-sensitive" antibodies.

Thus, the invention encompasses pH-sensitive antibodies that selectively bind a proTGFβ1 complex characterized in that the antibodies have lower dissociation rates at a neutral pH (e.g., around pH 7) as compared to at an acidic pH (e.g., around pH 5). Ph-dependent binding profiles of one such antibody are provided in Example 14 herein.

In some embodiments, the antibodies according to the present disclosure may induce internalization of the complex comprising proTGFβ1 bound to LRRC33 or GARP on cell surface. In some embodiments, the antibodies are inhibitors of cell-associated TGFβ1 (e.g., GARP-presented proTGFβ1 and LRRC33-presented proTGFβ1) according to the invention include antibodies or fragments thereof that specifically bind such complex (e.g., GARP-pro/latent TGFβ1 and LRRC33-pro/latent TGFβ1), thereby triggering internalization of the complex (e.g., endocytosis). This mode of action causes removal or depletion of the inactive TGFβ1 complexes from the cell surface (e.g., Treg, macrophages, MDSCs, etc.), hence reducing latent TGFβ1 available for activation. Such antibodies or fragments thereof may function as recycling antibodies. Such antibodies may also be referred to as "pH-sensitive" antibodies.

In some embodiments, such "pH sensitive" antibodies have a $K_{dis}$ (a.k.a. $K_{off}$) of $\geq 5\times10^{-3}$ $s^{-1}$ (e.g., $\geq 5.1\times10^{-3}$, $\geq 5.2\times10^{-3}$, $\geq 5.3\times10^{-3}$, $\geq 5.4\times10^{-3}$, $\geq 5.5\times10^{-3}$, $\geq 5.6\times10^{-3}$, $\geq 5.7\times10^{-3}$, $\geq 5.8\times10^{-3}$, $\geq 5.9\times10^{-3}$, or $>6.0\times10^{3}$) at pH 5, as measured by a suitable affinity assay (e.g., biolayer interferometry, surface plasmon resonance, and/or solution equilibrium titration). In a particular embodiment, such "pH-sensitive" antibodies have a $K_{dis} \geq 5.6\times10^{-3}$ at pH 5.

In some embodiments, such "pH-sensitive" antibodies have a pH 5 $K_{dis}$ to pH 7 $K_{dis}$ ratio (i.e., $K_{dis}$ at pH 5: $K_{dis}$ at pH7) of ≥1.5 (e.g., ≥1.6, ≥1.7, ≥1.8, ≥1.9, or ≥2.0), as measured by a suitable affinity assay (e.g., biolayer interferometry, surface plasmon resonance, and/or solution equilibrium titration). In a particular embodiment, such "pH-sensitive" antibodies have a $K_{dis}$ ratio of ≥2.0, as measured by biolayer interferometry.

Process of Screening; Manufacture

The invention encompasses screening methods, production methods and manufacture processes of antibodies or fragments thereof which bind to and dissociates at slow rates from each of: a hGARP-proTGFβ1 complex, a hLTBP1-proTGFβ1 complex, a hLTBP3-proTGFβ1 complex, and a hLRRC33-proTGFβ1 complex, and pharmaceutical compositions and related kits comprising the same.

Methods for making a pharmaceutical composition comprising the antibody (or an engineered construct comprising an antigen-binding fragment thereof) require identification and selection of such antibodies with desirable attributes. Here, the invention includes the recognition that antibodies with low $k_{OFF}$ values (i.e., off rates) may provide the durability that reflects the mechanism of action of these activation inhibitors, which do not rely on the ability to rapidly compete binding with endogenous receptors, but rather, exert inhibitory effects by latching onto inactive latent forms of TGFβ1 within the tissue. The ability to stay bound to the latent antigen complex (corresponding to low dissociation rates) may achieve durable potency in vivo.

Accordingly, the invention provides a method for manufacturing a pharmaceutical composition comprising a TGFβ1-selective activation inhibitor, wherein the method comprises the steps of: selecting an antibody or antigen-binding fragment thereof that specifically binds a human LLC with a low dissociation rate (e.g., below 10.0E-4 (1/s)) or a long half time (e.g., $t_{1/2}$ of at least 90 minutes), and producing the antibody at large-scale.

The selection of inhibitors with favorable off rates (low dissociation) may be determined with monovalent antibodies (e.g., Fab fragments) or full-length antibodies (e.g., IgGs).

In some embodiments, the step of producing comprises a mammalian cell culture having a volume of 250L or greater, e.g., 1000L, 2000L, 3000L, 4000L. The method may further comprise the step of purifying the antibody from the cell culture, and optionally formulating the purified antibody into a pharmaceutical composition. In some embodiments, the method further comprises the step of testing the selected antibody in a suitable preclinical model for efficacy and safety and confirming that the antibody is efficacious at a NOAEL. The safety assessment may include in vivo toxicology study comprising histopathology and immune-directed safety assessment including, for example, in vitro cytokine release assays and platelet assays.

In order to achieve durable inhibitory effects, antibodies with dissociation rates (e.g., monovalent dissociation rates) of no greater than 10.0E-4 ($s^{-1}$) (e.g., 5.0E-4 or less, 1.0E-4 or less, 5.0E-5 or less) may be selected for therapeutic use and/or large-scale manufacture in accordance with the present disclosure.

In some embodiments, an antibody or an antigen-binding fragment thereof selected for use or manufacture according to the present disclosure comprises the following six CDR sequences: H-CDR1 may comprise the sequence GFTFADYA (SEQ ID NO: 276); H-CDR2 may comprise the sequence ISGSGAAT (SEQ ID NO: 282); H-CDR3 may comprise a sequence represented by the formula VSSGX$_1$WDX$_2$D, wherein optionally the $X_1$ is an H or Q, and wherein further optionally the $X_2$ is a Y or F (SEQ ID NO: 283); L-CDR1 may comprise the sequence QSISSY (SEQ ID NO: 279); L-CDR2 may comprise the sequence AASGLES (SEQ ID NO: 284); and, L-CDR3 may comprise the sequence QQTYGVPLT (SEQ ID NO: 285). In preferred embodiments, the H-CDR3 may comprise the sequence VSSGHWDYD (SEQ ID NO: 287). In some embodiments, the antibody or the fragment binds an epitope that comprises one or more of the following amino acid residues of the proTGFβ1 polypeptide sequence: S35, G37, E38, V39, P40, P41, G42, P43, R274, K280, H283 and K309.

Numerous methods may be used for obtaining antibodies, or antigen-binding fragments thereof, of the disclosure. For example, antibodies can be produced using recombinant DNA methods. Monoclonal antibodies may also be produced by generation of hybridomas (see e.g., Kohler and Milstein (1975) Nature, 256:495-499) in accordance with known methods. Hybridomas formed in this manner are then screened using standard methods, such as enzyme-linked immunosorbent assay (ELISA) and surface plasmon resonance (e.g., OCTET® or BIACORE®) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228: 1315-1317; Clackson et al., (1991) Nature, 352:624-628; Marks et al., (1991) J. Mol. Biol., 222:581-597; WO 92/18619; WO 91/17271; WO 92/20791; WO 92/15679; WO 93/01288; WO 92/01047; WO 92/09690; and WO 90/02809.

In addition to the use of display libraries, the specified antigen (e.g., presenting molecule-TGFβ1 complexes) can be used to immunize a non-human host, e.g., rabbit, guinea pig, rat, mouse, hamster, sheep, goat, chicken, camelid, as well as non-mammalian hosts such as shark. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci.

U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal, or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects, and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen-binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen-binding fragments. Furthermore, transgenic animals, preferably mammals, comprising the aforementioned host cells may be used for the large-scale production of the antibody or antibody fragments. As used herein, "large-scale" production includes a volume of at least 250L. Typically, commercial-scale bioreactors used for producing biologics are in a range of 1000-12000L.

The transformed host cells can be grown in fermenters and cultured using any suitable techniques to achieve optimal cell growth. Once expressed, the whole antibodies, their dimers, individual light and heavy chains, other immunoglobulin forms, or antigen-binding fragments, can be purified according to standard procedures of the art, including ammonium sulfate precipitation, affinity columns, column chromatography, gel electrophoresis and the like; see, Scopes, Protein Purification, Springer Verlag, N.Y. (1982). The antibody or antigen-binding fragments can then be isolated from the growth medium, cellular lysates, or cellular membrane fractions. The isolation and purification of the, e.g., microbially expressed antibodies or antigen-binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen-binding fragment may be undertaken by culturing a modified recombinant host under culture conditions appropriate for the growth of the host cells and the expression of the coding sequences. The antibodies or antigen-binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen-binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation, and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen-binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen-binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain (s) of the immunoglobulin chains encoding sequences and expression control sequences) can be transferred into the host cell by suitable methods, which vary depending on the type of cellular host.

The screening methods may include a step of evaluating or confirming desired activities of the antibody or fragment thereof. In some embodiments, the step comprises selecting for the ability to inhibit target function, e.g., inhibition of release of mature/soluble growth factor (e.g., TGFβ1) from a latent complex. In preferred embodiments, such step comprises a cell-based potency assay, in which inhibitory activities of test antibody or antibodies are assayed by measuring the level of growth factor released in the medium (e.g., assay solution) upon activation, when proTGFβ complex is expressed on cell surface or present in the ECM. The level of growth factor released into the medium/solution can be assayed by, for example, measuring TGFβ activities. Non-limiting examples of useful cell-based potency assays are described in below (see, e.g., "Cell-Based Assays for Measuring TGFβ Activation and/or Inhibitory Potency") and Example 3 herein.

In some embodiments, the screening method comprises the step of removing antibodies that have an $IC_{50}$ of greater than 5 nM (e.g., greater than 10 nM) as measured by a suitable cell-based potency assay. In some embodiments, the screening method comprises the step of removing antibodies that have an $IC_{50}$ of greater than 5 nM (e.g., greater than 10 nM) as measured by a suitable cell-based potency assay against a LTBP1-TGFβ1, LTBP3-TGFβ1, GARP-TGFβ1, and/or LRRC33-TGFβ1.

In some embodiments, the screening method comprises the step of selecting antibodies based on their bias (or non-bias) for one or more presenting molecule-TGFb1 affinities. Accordingly, in some embodiments, the screening method comprises selecting antibodies having a bias for matrix-associated TGFβ1 complexes. In some embodiments, the screening method comprises selecting antibodies having relatively equivalent affinities for a GARP-TGFβ1 complex, a LTBP1-TGFβ1 complex, a LTBP3-TGFβ1 complex, and a LRRC33-TGFβ1 complex.

In some embodiments, the screening method comprises the step of selecting for antibodies or fragments thereof that induce ADCC. In some embodiments, the step comprises selecting for antibodies or fragments thereof that accumulate to a desired site(s) in vivo (e.g., cell type, tissue, or organ). In some embodiments, the step comprises selecting for antibodies or fragments thereof with the ability to cross the blood brain barrier. The methods may optionally include a step of optimizing one or more antibodies or fragments thereof to provide variant counterparts that possess desirable profiles, as determined by criteria such as stability, binding affinity, functionality (e.g., inhibitory activities, Fc function, etc.), immunogenicity, pH sensitivity and developability (e.g., high solubility, low self-association, etc.).

In some embodiments, the screening method comprises the step of selecting antibodies that are pH-sensitive. In some embodiments, the screening method comprises the step of selecting antibodies that have a $K_{dis}$ of $\geq 5\times10^{-3}$ $s^{-1}$ (e.g., $\geq 5.1\times10^{-3}$, $\geq 5.2\times10^{-3}$, $\geq 5.3\times10^{-3}$, $\geq 5.4\times10^{-3}$, $\geq 5.5\times10^{-3}$, $\geq 5.6\times10^{-3}$, $\geq 5.7\times10^{-3}$, $\geq 5.8\times10^{-3}$, $\geq 5.9\times10^{-3}$, or $\geq 6.0\times10^{-3}$) at pH 5, as measured by a suitable affinity assay (e.g., biolayer interferometry, surface plasmon resonance, and/or solution equilibrium titration). In some embodiments, the screening method comprises the step of selecting antibodies that have a pH 5 $K_{dis}$ to pH 7 $K_{dis}$ ratio (i.e., $K_{dis}$ at pH 5: $K_{dis}$ at pH7) of ≥1.5 (e.g., ≥1.6, ≥1.7, ≥1.8, ≥1.9, or ≥2.0), as measured by a suitable affinity assay (e.g., biolayer interferometry, surface plasmon resonance, and/or solution equilibrium titration).

In some embodiments, the screening method comprises the step of selecting antibodies that are cross-reactive with proTGFβ1 from other species (e.g., mouse, rat, and/or cynomolgus).

Modifications

Antibodies, or antigen-binding portions thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and isolation of a GARP-proTGFβ1 complex, a LTBP1-proTGFβ1 complex, a LTBP3-proTGFβ1 complex, and/or a LRRC33-proTGFβ1 complex. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, B-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine (1311, 1251, 1231, 1211), carbon (14C), sulfur (35S), tritium (3H), indium (115mln, 113mln, 112 In, 111 In), and technetium (99Tc, 99mTc), thallium (201Ti), gallium (68Ga, 67Ga), palladium (103Pd), molybdenum (99Mo), xenon (133Xe), fluorine (18F), 153Sm, Lu, 159Gd, 149Pm, 140La, 175Yb, 166Ho, 90Y, 47 Sc, 86R, 188Re, 142Pr, 105Rh, 97Ru, 68Ge, 57Co, 65Zn, 85Sr, 32P, 153Gd, 169Yb, 51Cr, 54Mn, 75Se, zirconium (89Zr) and tin (113Sn, 117Sn). The detectable substance may be coupled or conjugated either directly to the antibodies of the disclosure that bind specifically to a GARP-proTGFβ1 complex, a LTBP1-proTGFβ1 complex, a LTBP3-proTGFβ1 complex, and/or a LRRC33-proTGFβ1 complex, or any components thereof, or indirectly, through an intermediate (such as, for example, a linker) using suitable techniques. Any of the antibodies provided herein that are conjugated to a detectable substance may be used for any suitable diagnostic assays, such as those described herein. Such assays include in vivo imaging, which may be used for monitoring disease progression and/or response to a therapy, such as TGFβ1 inhibition therapy described herein.

In addition, antibodies, or antigen-binding portions thereof, of the disclosure may also be modified with a drug. The drug may be coupled or conjugated either directly to the polypeptides of the disclosure, or indirectly, through an intermediate (such as, for example, a linker (e.g., a cleavable linker)) using suitable techniques.

Pharmaceutical Compositions and Formulations

The invention further provides pharmaceutical compositions used as a medicament suitable for administration in human and non-human subjects. One or more isoform-specific antibodies encompassed by the invention can be formulated or admixed with a pharmaceutically acceptable carrier (excipient), including, for example, a buffer, to form a pharmaceutical composition. Such formulations may be used for the treatment of a disease or disorder that involves TGFβ signaling. In particularly preferred embodiments, such formulations may be used for immune-oncology applications.

The pharmaceutical compositions of the invention may be administered to patients for alleviating a TGFβ-related indication (e.g., fibrosis, immune disorders, and/or cancer). "Acceptable" means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one antibody that specifically binds a GARP-proTGFβ1 complex, a LTBP1-proTGFβ1 complex, a LTBP3-proTGFβ1 complex, and a LRRC33-proTGFβ1 complex where the antibodies recognize different epitopes/residues of the complex.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONIC® or polyethylene glycol (PEG). Pharmaceutically acceptable excipients are further described herein.

The invention also includes pharmaceutical compositions that comprise an antibody or fragment thereof according to the present invention, and a pharmaceutically acceptable excipient.

Thus, the antibody or a molecule comprising an antigen-binding fragment of such antibody can be formulated into a pharmaceutical composition suitable for human administration.

The pharmaceutical formulation may include one or more excipients. In some embodiments, excipient(s) may be selected from the in the following: list provided accessdata.fda.gov/scripts/cder/iig/index.Cfm?event=browseByLetter.page&Letter=A The pharmaceutical composition is typically formulated to a final concentration of the active biologic (e.g., monoclonal antibody, engineered binding molecule comprising an antigen-binding fragment, etc.) to be between about 2 mg/ml and about 200 mg/mL. For example, the final concentration (wt/vol) of the formulations may range between about 2-200, 2-180, 2-160, 2-150, 2-120, 2-100, 2-80, 2-70, 2-60, 2-50, 2-40, 5-200, 5-180, 5-160, 5-150, 5-120, 5-100, 5-80, 5-70, 5-60, 5-50, 5-40, 10-200, 10-180, 10-160, 10-150, 10-120, 10-100, 10-80, 10-70, 10-60, 10-50, 10-40, 20-200, 20-180, 20-160, 20-150, 20-120, 20-100, 20-80, 20-70, 20-60, 20-50, 20-40, 30-200, 30-180, 30-160, 30-150, 30-120, 30-100, 30-80, 30-70, 30-60, 30-50, 30-40, 40-200, 40-180, 40-160, 40-150, 40-120, 40-100, 40-80, 40-70, 40-60, 40-50, 50-200, 50-180, 50-160, 50-150, 50-120, 50-100, 50-80, 50-70, 50-60, 60-200, 60-180, 60-160, 60-150, 60-120, 60-100, 60-80, 60-70, 70-200, 70-180, 70-160, 70-150, 70-120, 70-100, 70-80 mg/mL. In some embodiments, the final concentration of the biologic in the formulation is about 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg/mL.

The pharmaceutical compositions of the present invention are preferably formulated with suitable buffers. Suitable buffers include but are not limited to: phosphate buffer, citric buffer, and histidine buffer.

The final pH of the formulation is typically between pH 5.0 and 8.0. For example, the pH of the pharmaceutical composition may be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7 or 7.8.

The pharmaceutical composition of the present disclosure may comprise a surfactant, such as nonionic detergent, approved for the use in pharmaceutical formulations. Such surfactants include, for example, polysorbates, such as Polysorbate 20 (Tween™-20), Polysorbate 80 (Tween™-80) and NP-40.

The pharmaceutical composition of the present disclosure may comprise a stabilizer. For liquid-protein preparations, stability can be enhanced by selection of pH-buffering salts, and often amino acids can also be used. It is often interactions at the liquid/air interface or liquid/solid interface (with the packaging) that lead to aggregation following adsorption and unfolding of the protein. Suitable stabilizers include but are not limited to: sucrose, maltose, sorbitol, as well as certain amino acids such as histidine, glycine, methionine and arginine.

The pharmaceutical composition of the present disclosure may contain one or any combinations of the following excipients: Sodium Phosphate, Arginine, Sucrose, Sodium Chloride, Tromethamine, Mannitol, Benzyl Alcohol, Histidine, Sucrose, Polysorbate 80, Sodium Citrate, Glycine, Polysorbate 20, Trehalose, Poloxamer 188, Methionine, Trehalose, rhHyaluronidase, Sodium Succinate, Potassium Phosphate, Disodium Edetate, Sodium Chloride, Potassium Chloride, Maltose, Histidine Acetate, Sorbitol, Pentetic Acid, Human Serum Albumin, Pentetic Acid.

In some embodiments, the pharmaceutical composition of the present disclosure may contain a preservative.

The pharmaceutical composition of the present disclosure is typically presented as a liquid or a lyophilized form. Typically, the products can be presented in vial (e.g., glass vial). Products available in syringes, pens, or autoinjectors may be presented as pre-filled liquids in these container/closure systems.

In some examples, the pharmaceutical composition described herein comprises liposomes containing an antibody that specifically binds a GARP-proTGFβ1 complex, a LTBP1-proTGFβ1 complex, a LTBP3-proTGFβ1 complex, and a LRRC33-proTGFβ1 complex, which can be prepared by any suitable method, such as described in Epstein et al., Proc. Natl. Acad. Sci. USA 82:3688 (1985); Hwang et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In some embodiments, liposomes with targeting properties are selected to preferentially deliver or localize the pharmaceutical composition to certain tissues or cell types. For example, certain nanoparticle-based carriers with bone marrow-targeting properties may be employed, e.g., lipid-based nanoparticles or liposomes. See, for example, Sou (2012) “Advanced drug carriers targeting bone marrow”, ResearchGate publication 232725109.

In some embodiments, pharmaceutical compositions of the invention may comprise or may be used in conjunction with an adjuvant. It is contemplated that certain adjuvant can boost the subject’s immune responses to, for example, tumor antigens, and facilitate Teffector function, DC differentiation from monocytes, enhanced antigen uptake and presentation by APCs, etc. Suitable adjuvants include but are not limited to retinoic acid-based adjuvants and derivatives thereof, oil-in-water emulsion-based adjuvants, such as MF59 and other squalene-containing adjuvants, Toll-like receptor (TRL) ligands, α-tocopherol (vitamin E) and derivatives thereof.

The antibodies described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody of the invention with Intralipid™ or the components thereof (soybean oil, egg phospholipids, glycerol and water).

Inhibition of TGFβ1 Activity

Methods of the present disclosure include methods of inhibiting TGFβ1 growth factor activity in one or more biological system. Such methods may include contacting one or more biological system with an antibody and/or composition of the disclosure. In some cases, these methods include modifying the level of free growth factor in a biological system (e.g., in a cell niche or subject). Antibodies and/or compositions according to such methods may include, but are not limited to biomolecules, including, but not limited to recombinant proteins, protein complexes and/or antibodies, or antigen portions thereof, described herein.

In some embodiments, methods of the present disclosure may be used to reduce or eliminate growth factor activity, termed “inhibiting methods” herein. Some such methods may comprise mature growth factor retention in a TGFβ complex (e.g., a TGFβ1 complexed with GARP, LTBP1, LTBP3 and/or LRRC33) and/or promotion of reassociation of growth factor into a TGFβ complex. In some cases, inhibiting methods may comprise the use of an antibody disclosed herein. According to some inhibiting methods, one or more inhibiting antibody is provided.

In some embodiments, antibodies, antigen-binding portions thereof, and compositions of the disclosure may be used for inhibiting TGFβ1 activation. In some embodiments, provided herein is a method for inhibiting TGFβ1 activation comprising exposing a GARP-TGFβ1 complex, a LTBP1-TGFβ1 complex, a LTBP3-TGFβ1 complex, and/or a LRRC33-TGFβ1 complex to an antibody, an antigen-binding portion thereof, or a pharmaceutical composition described herein. In some embodiments, the antibody, antigen-binding portion thereof, or pharmaceutical composition, inhibits the release of mature TGFβ1 from the GARP-TGFβ1 complex, the LTBP1-TGFβ1 complex, a LTBP3-TGFβ1 complex, and/or the LRRC33-TGFβ1 complex. In some embodiments, the method is performed in vitro. In some embodiments, the method is performed in vivo. In some embodiments, the method is performed ex vivo.

In some embodiments, the GARP-TGFβ1 complex or the LRRC33-TGFβ1 complex is present at the outer surface of a cell.

In some embodiments, the cell expressing the GARP-TGFβ1 complex or the LRRC33-TGFβ1 complex is a fibroblast, a myofibroblast, a macrophage, a T-cell, a monocyte, a dendritic cell, an antigen presenting cell, a neutrophil, a myeloid-derived suppressor cell (MDSC), a lymphocyte, a mast cell, or a microglial cell. The myofibroblast may be a fibrosis-associated fibroblast (FAF) of a cancer-associated fibroblasts (CAF). The T-cell may be a regulatory T cell (e.g., immunosuppressive T cell). The neutrophil may be an activated neutrophil. The macrophage may be a resident macrophage (e.g., a liver kupffer cell) or an infiltrating macrophage. The macrophage may be an activated (e.g., polarized) macrophage, including profibrotic and/or tumor-associated macrophages (TAM), e.g., M2c subtype and M2d subtype macrophages. In some embodiments, macrophages are exposed to tumor-derived factors (e.g., cytokines, growth factors, etc.) which may further induce pro-cancer phenotypes in macrophages. In some embodiments, such tumor-derived factor is CSF-1/M-CSF.

In some embodiments, the cell expressing the GARP-TGFβ1 complex or the LRRC33-TGFβ1 complex is a cancer cell, e.g., circulating cancer cells and tumor cells.

In some embodiments, the LTBP1-TGFβ1 complex or the LTBP3-TGFβ1 complex is bound to an extracellular matrix (i.e., components of the ECM). In some embodiments, the extracellular matrix comprises fibrillin and/or fibronectin. In some embodiments, the extracellular matrix comprises a protein comprising an RGD motif.

LRRC33 is expressed in selective cell types, in particular those of myeloid lineage, including monocytes and macrophages. Monocytes originated from progenitors in the bone marrow and circulate in the bloodstream and reach peripheral tissues. Circulating monocytes can then migrate into tissues where they become exposed to the local environment (e.g., tissue-specific, disease-associated, etc.) that includes a panel of various factors, such as cytokines and chemokines, triggering differentiation of monocytes into macrophages, dendritic cells, etc. These include, for example, alveolar macrophages in the lung, osteoclasts in bone marrow, microglia in the CNS, histiocytes in connective tissues, Kupffer cells in the liver, and brown adipose tissue macrophages in brown adipose tissues. In fibrotic tissues, infiltrated myeloid cells may include fibrosis-associated macrophages (FAM) which are typically M2-like macrophages, as well as MDSCs. In a solid tumor, infiltrated macrophages may be tumor-associated macrophages (TAMs), tumor-associated neutrophils (TANs), and myeloid-derived suppressor cells (MDSCs), etc. Such macrophages may activate and/or be associated with activated fibroblasts, such as carcinoma-associated (or cancer-associated) fibroblasts (CAFs) and/or the stroma. Thus, inhibitors of TGFβ1 activation described herein which inhibits release of mature TGFβ1 from LRRC33-containing complexes can target any of these cells expressing LRRC33-proTGFβ1 on cell surface.

In some embodiments, the LRRC33-TGFβ1 complex is present at the outer surface of profibrotic (M2-like) macrophages. In some embodiments, the profibrotic (M2-like) macrophages are present in the fibrotic microenvironment. In some embodiments, targeting of the LRRC33-TGFβ1 complex at the outer surface of profibrotic (M2-like) macrophages provides a superior effect as compared to solely targeting LTBP1-TGFβ1 and/or LTBP1-TGFβ1 complexes. In some embodiments, M2-like macrophages, are further polarized into multiple subtypes with differential phenotypes, such as M2c and M2d TAM-like macrophages. In some embodiments, macrophages may become activated by various factors (e.g., growth factors, chemokines, cytokines and ECM-remodeling molecules) present in the tumor microenvironment, including but are not limited to TGFβ1, CCL2 (MCP-1), CCL22, SDF-1/CXCL12, M-CSF (CSF-1), IL-6, IL-8, IL-10, IL-11, CXCR4, VEGF, PDGF, prostaglandin-regulating agents such as arachidonic acid and cyclooxygenase-2 (COX-2), parathyroid hormone-related protein (PTHrP), RUNX2, HIF1a, and metalloproteinases. Exposures to one or more of such factors may further drive monocytes/macrophages into pro-tumor phenotypes. To give but one example, CCL2 and VEGF co-expression in tumors has been shown to be correlated with increased TAM and poor diagnosis. In turn, these activated tumor-associated cells may also facilitate recruitment and/or differentiation of other cells into pro-tumor cells, e.g., CAFs, TANS, MDSCs, and the like. Stromal cells may also respond to macrophage activation and affect ECM remodeling, and ultimately vascularization, invasion, and metastasis. For example, CCL2 not only functions as a monocyte attractant but also promotes cell adhesion by upregulating MAC-1, which is a receptor for ICAM-1, expressed in activated endothelium. This may lead to CCL2-dependent arteriogenesis and cancer progression. Thus, TGFβ1 inhibitors described herein may be used in a method for inhibiting arteriogenesis by interfering with the CCL2 signaling axis.

In some embodiments, the GARP-TGFβ1 complex, the LTBP1-TGFβ1 complex, the LTBP3-TGFβ1 complex, and/or the LRRC33-TGFβ1 complex is bound to an extracellular matrix. In some embodiments, the extracellular matrix comprises fibrillin. In some embodiments, the extracellular matrix comprises a protein comprising an RGD motif.

In some embodiments, provided herein is a method for reducing TGFβ1 protein activation in a subject comprising administering an antibody, an antigen-binding portion thereof, or a pharmaceutical composition described herein to the subject, thereby reducing TGFβ1 protein activation in the subject. In some embodiments, the subject has or is at risk of having fibrosis. In some embodiments, the subject has or is at risk of having cancer. In some embodiments, the subject has or is at risk of having dementia.

In some embodiments, the antibodies, or the antigen-binding portions thereof, as described herein, reduce the suppressive activity of regulatory T cells (Tregs).

Cell-Based Assays for Measuring TGFβ Activation and/or Inhibitory Potency

Activation of TGFβ (and inhibition thereof by a TGFβ test inhibitor, such as an antibody) may be measured by any suitable method known in the art. For example, integrin-mediated activation of TGFβ can be utilized in a cell-based assay, such as the "CAGA12" luciferase assay, described in more detail herein.

The development of novel context-dependent cell-based assays of TGFβ1 activation is described in U.S. Provisional Patent Application No. 62/538,476 and the corresponding International Application Pub. No. WO 2019/023661, each of which are incorporated by reference in their entirety herein. Previous assay formats could not differentiate between the activation of proTGFβ1 presented by endogenous presenting molecules and the activation of proTGFβ1 presented by exogenous LTBPs. By directly transfecting integrin-expressing cells, the novel assays disclosed in International Application Pub. No. WO 2019/023661, and used herein, establish a window between endogenous presenter-proTGFβ1 activity and exogenous LTBP-proTGFβ1 activity.

As opposed to GARP- or LRRC33-proTGFβ1 complexes, which are presented on the surface of cells, LTBP-proTGFβ1 complexes are embedded in the extracellular matrix. Thus, the assay plate coating is an important component of the assay when assessing activation of proTGFβ1 in complex with LTBP (e.g., LTBP1/3). In this regard, it has been shown, fibronectin andin are two ECM components that appear to be critical for LTBP association with the matrix and activation of latent TGFβ (Robertson et al., Matrix Biol. 2015 September; 47:44-53). For example, LTBP3 ECM-incorporation appears to be dependent on fibrillin expression in both in vitro and in vivo models (Zilberberg et al., J Cell Physiol. 2012; 227 (12): 3828-3836).

On the other hand, LTBP1 has been shown to interact with fibrillin microfibrils and fibronectin via its C- and N-termini, respectively (Dallas et al., J Biol Chem. 2005; 280 (19): 18871-18880; Fontana et al., FASEB J. 2005; 19 (13): 1798-1808; and Kantola et al., Exp Cell Res. 2008; 314 (13): 2488-2500). Moreover, in the absence of fibrillin, LTBP1 still co-localizes with fibronectin fibers (Robertson et al., Matrix Biol. 2015 September; 47:44-53). LTBP1 has also been shown to interact with ADAMTSL2 and 3 (Sengle et al., PloS Genet. 2012; 8 (1): e1002425), IGFBP3 (Gui and Murphy, Mol Cell Biochem. 2003; 250 (1-2): 189-195), fibulin-4 (Massam-Wu et al., J Cell Sci. 2010 Sep. 1;123 (Pt 17): 3006-18), and heparin (Chen et al., J Biol Chem. 2007; 282 (36): 26418-26430).

Beyond traditional ECM components/proteins, tissue transglutaminase (TG2) may also play a critical role in TGFβ localization in the ECM. TG2 is known to catalyze inter- and intramolecular isopeptide bonds which cross-link ECM fibrils, effectively stiffening the ECM and protecting the ECM from proteolytic degradation (Benn et al., Current Opinion in Biomedical Engineering., 2019, https://doi.org/10.1016/j.cobme.2019.06.003). Moreover, TG2 can cross-link LTBP1 to the ECM, thus promoting a matrix reservoir of TGFβ (Nunes et al., J *Cell Biol.* 1997;136 (5): 1151-1163).

Accordingly, the N-terminus of LTBPs may be covalently bound to the ECM via an isopeptide bond, the formation of which may be catalyzed by transglutaminases. The structural integrity of the ECM is believed to be important in mediating LTBP-associated TGFβ1 activity. For example, stiffness of the matrix can significantly affect TGFβ1 activation. In addition, incorporating fibronectin and/or fibrillin in the scaffold may significantly increase the LTBP-mediated TGFβ1 activation. Similarly, presence of fibronectin and/or fibrillin in LTBP assays (e.g., cell-based potency assays) may increase an assay window.

Accordingly, a cell-based assay for measuring TGFβ1 activation may comprise the following components: i) a source of TGFβ (recombinant, endogenous or transfected); ii) a source of activator such as integrin (recombinant, endogenous, or transfected); and iii) a reporter system that responds to TGFβ activation, such as cells expressing TGFβ receptors capable of responding to TGFβ and translating the signal into a readable output (e.g., luciferase activity in CAGA12 cells or other reporter cell lines). In some embodiments, the reporter cell line comprises a reporter gene (e.g., a luciferase gene) under the control of a TGFβ-responsive promoter (e.g., a PAI-1 promoter). In some embodiments, certain promoter elements that confer sensitivity may be incorporated into the reporter system. In some embodiments, such promoter element is the CAGA12 element. Reporter cell lines that may be used in the assay have been described, for example, in Abe et al., (1994) Anal Biochem. 216 (2): 276-84, incorporated herein by reference. In some embodiments, each of the aforementioned assay components are provided from the same source (e.g., the same cell). In some embodiments, two of the aforementioned assay components are provided from the same source, and a third assay component is provided from a different source. In some embodiments, all three assay components are provided from different sources. For example, in some embodiments, the integrin and the latent TGFβ complex (proTGFβ and a presenting molecule) are provided for the assay from the same source (e.g., the same transfected cell line). In some embodiments, the integrin and the TGF are provided for the assay from separate sources (e.g., two different cell lines, a combination of purified integrin and a transfected cell). When cells are used as the source of one or more of the assay components, such components of the assay may be endogenous to the cell, stably expressed in the cell, transiently transfected, or any combination thereof. In some embodiments, the assay is performed in a tissue culture plate or dish. In some embodiments, the tissue culture plate or dish is coated with a component of the extracellular matrix (ECM). In some embodiments, the tissue culture plate or dish is coated with fibronectin and/or fibrillin. In some embodiments, the cell-based assay further comprises a fourth component comprising a source of TG2. In some embodiments, the TG2 component is provided from the same, or different, source as any one of the above-mentioned components. The results from a non-limiting exemplary embodiment of a cell-based assay for measuring TGFβ activation demonstrating the inhibition of LTBP1-proTGFβ1 complex, LTBP3-proTGFβ1 complex, GARP-proTGFβ1 complex, or LRRC33-proTGFβ1 complex are disclosed herein (see, e.g., Example 3).

A skilled artisan could readily adapt such assays to various suitable configurations. For instance, a variety of sources of TGFβ may be considered. In some embodiments, the source of TGFβ is a cell that expresses and deposits TGFβ (e.g., a primary cell, a propagated cell, an immortalized cell or cell line, etc.). In some embodiments, the source of TGFβ is purified and/or recombinant TGFβ immobilized in the assay system using suitable means. In some embodiments, TGFβ immobilized in the assay system is presented within an extracellular matrix (ECM) composition on the assay plate, with or without de-cellularization, which mimics fibroblast-originated TGFβ. In some embodiments, TGFβ is presented on the cell surface of a cell used in the assay. Additionally, a presenting molecule of choice may be included in the assay system to provide suitable latent-TGFβ complex. One of ordinary skill in the art can readily determine which presenting molecule(s) may be present or expressed in certain cells or cell types. Using such assay systems, relative changes in TGFβ activation in the presence or absence of a test agent (such as an antibody) may be readily measured to evaluate the effects of the test agent on TGFβ activation in vitro. Data from exemplary cell-based assays are provided in the Example section below.

Such cell-based assays may be modified or tailored in a number of ways depending on the TGFβ isoform being studied, the type of latent complex (e.g., presenting molecule), and the like. In some embodiments, a cell known to express integrin capable of activating TGFβ may be used as the source of integrin in the assay. Such cells typically include LN229 cells. Other suitable cells include SW480/β6 cells (e.g., clone 1E7). In some embodiments, the cell-line(s) may be modified to reduce or eliminate expression of one or more presenting molecules (e.g., through CRISPR-mediated gene ablation). For example, the cell-line may be a LTBP1 knock-out cell-line (e.g., CRISPR-mediated gene ablation by targeting exon 7). In other embodiments, the cell-line may be a LTBP3 knock-out cell-line. In other embodiments, the cell-line may be a GARP knock-out cell-line. In other embodiments, the cell-line may be a LRRC33 knock-out cell-line.

In some embodiments, integrin-expressing cells may be co-transfected with a plasmid encoding a presenting molecule of interest (such as GARP, LRRC33, LTBP (e.g., LTBP1 or LTBP3), etc.) and a plasmid encoding a pro-form of the TGFβ isoform of interest (such as proTGFβ1). After transfection, the cells are incubated for sufficient time to allow for the expression of the transfected genes (e.g., about 24 hours), cells are washed, and incubated with serial dilutions of a test agent (e.g., an antibody). Then, a reporter cell line (e.g., CAGA12 cells) is added to the assay system, followed by appropriate incubation time to allow TGFβ signaling. After an incubation period (e.g., about 18-20 hours) following the addition of the test agent, signal/read-out (e.g., luciferase activity) is detected using suitable means (e.g., for luciferase-expressing reporter cell lines, the Bright-Glo™ reagent (Promega®) can be used). In some embodiments, Luciferase fluorescence may be detected using a BioTek® (Synergy™ H1) plate reader, with autogain settings.

Data demonstrate that exemplary antibodies of the invention which are capable of selectively inhibiting the activation of TGFβ1 (see, e.g., Example 3 and Table 15).

Nucleic Acids

In some embodiments, antibodies, antigen-binding portions thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure. In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

The present invention is further illustrated by the following examples, which are not intended to be limiting in any way. The entire contents of all references, patents and published patent applications cited throughout this application, as well as the Figures, are hereby incorporated herein by reference.

Kits For Use in Alleviating Diseases/Disorders Associated with a TGFβ-related Indication The present disclosure also provides kits for use in alleviating diseases/disorders associated with a TGFβ-related indication. Such kits can include one or more containers comprising an antibody, or antigen-binding portion thereof, as described herein.

In some embodiments, the kit can comprise instructions for use in accordance with any of the methods described herein. The included instructions can comprise a description of administration of the antibody, or antigen-binding portion thereof, to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen-binding portion thereof, to an individual at risk of the target disease.

The instructions relating to the use of antibodies, or antigen-binding portions thereof, generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with a TGFβ-related indication. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody, or antigen-binding portion thereof, as described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

EXAMPLES

Example 1: Antibody screening and selection methodology

Antigen-binding fragments were screened from libraries using purified, recombinant protein antigen complexes in positive selection and negative selection steps. Antigens for the positive selection included all 4 human LLCs and all 4 murine LLCs each with human proTGFβ1. Antigens for the negative selection included mature growth factors (i.e., human TGFβ1, TGFβ2, TGFβ3). After specific and selective binders were identified by Octet, these were made into full length IgGs for further evaluation. Among the high affinity binders identified, those with slow off rates were selected.

Among the 16 novel antibodies that showed enhanced dissociation rates (slower $k_{OFF}$) and inhibitory activities as measured by cell-based potency assays, three antibodies, namely, Ab42, Ab46 and Ab50, were selected for further evaluation.

Figure 3:
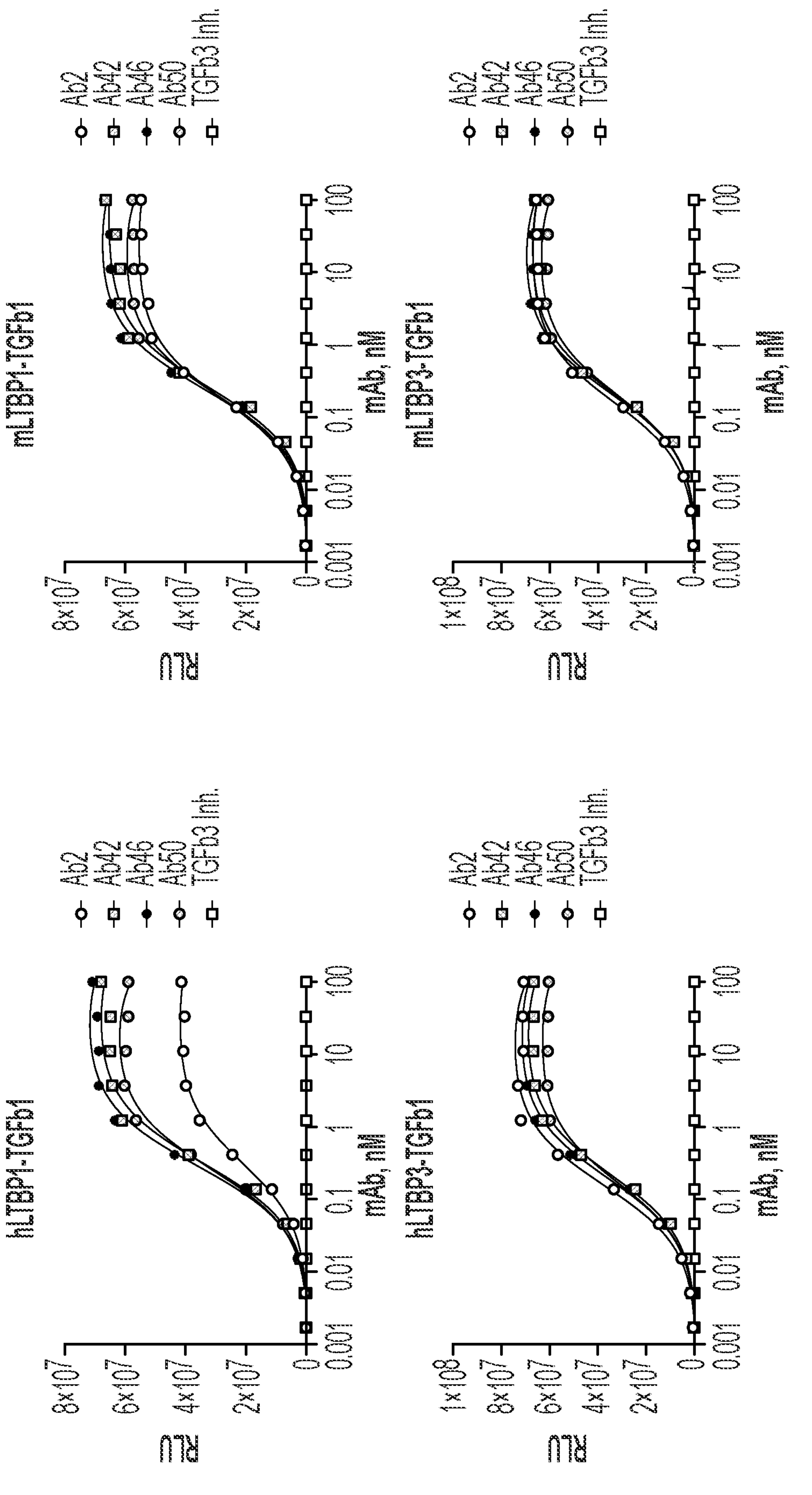
FIG. 3 provides 4 graphs that shows dose-dependent binding by ELISA of 5 antibodies (hIgG4) to the LLCs shown.
Figure 4:
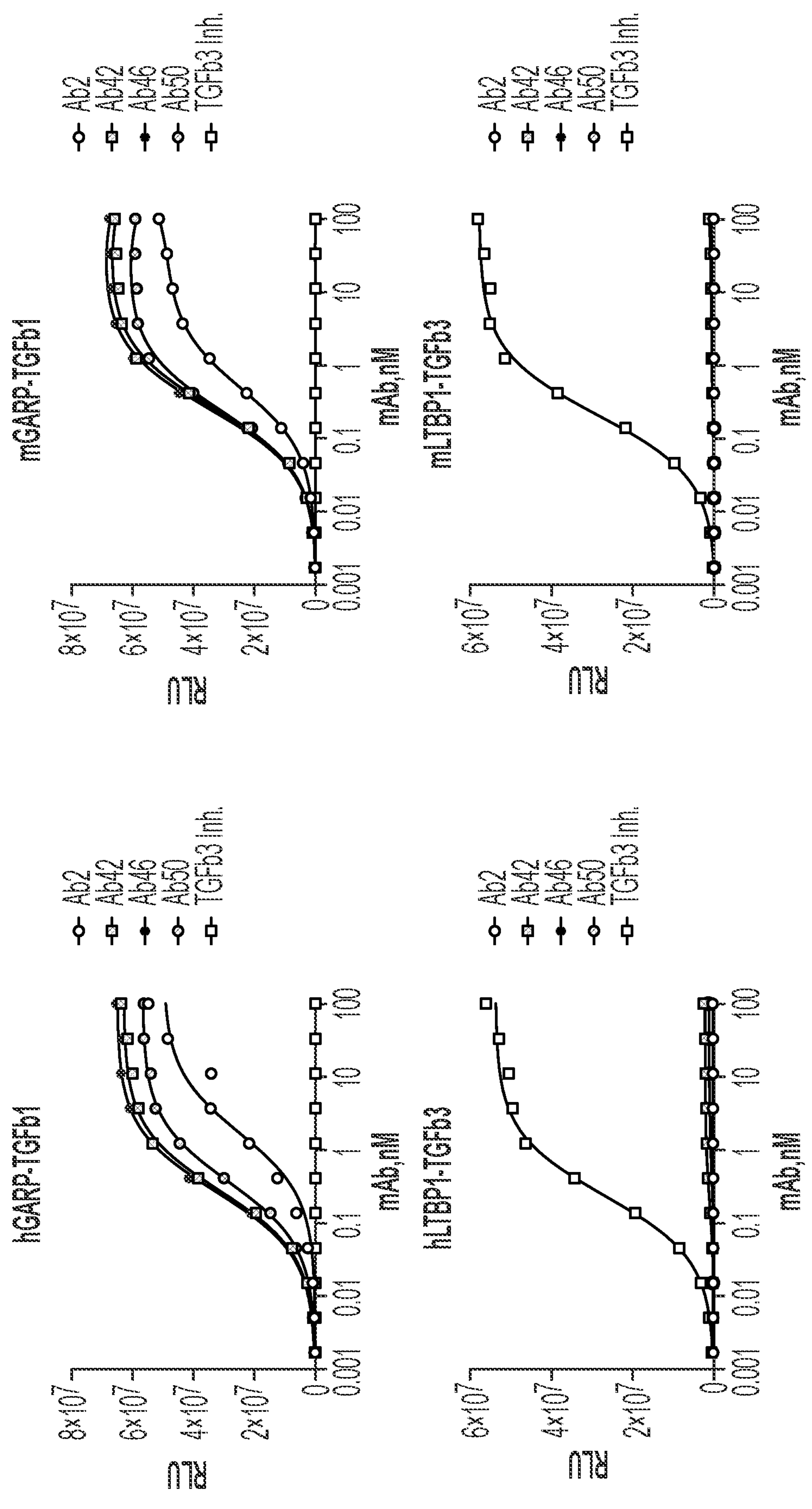
FIG. 4 provides 4 graphs that shows dose-dependent binding by ELISA of 5 antibodies (hIgG4) to the LLCs.

Specific and selective binding of Ab42, Ab46 and Ab50 were confirmed by ELISA (FIGS. 3 and 4). Ab2 was used as positive control because Ab2 has been previously demonstrated to be a selective binder and inhibitor of TGFβ1, as shown in FIG. 1. An isoform-selective activation inhibitor of TGFβ3 was used as negative control to demonstrate isoform-selectivity of the novel antibodies.

In vitro binding kinetics (on/off rates) were measured in Biacore-based assays and affinities were determined against all four known LLCs using both human and murine counterparts for each. Based on the association rate and dissociation rate, $K_D$ was calculated for each. In addition, relative affinities, as compared to the reference antibody as a benchmark, were calculated and expressed as “fold difference” relative to the reference antibody.

Example 2. In vitro Binding/kinetics Profiles

1) BLI-based binding assays

The affinities of Ab1, Ab2 and Ab3 were measured by OCTET® assay on human proTGFβ1 cells, while activity was measured by CAGA12 reporter cells testing human proTGFβ1 inhibition. The protocol used to measure the affinity of the antibodies to the complexes provided herein is summarized in Table 14 below, and a summary list of affinity profiles of exemplary antibodies of the present disclosure is provided in Table 6 herein.

2) SET-based binding assays

The affinities of Ab2, Ab3, Ab11, Ab12, Ab19, Ab20, and Ab35, C1, and C2 were also measured by Meso-Scale Discovery (MSD) Solution Equilibrium Titration (SET). MSD-SET is a well-characterized technique which can be used for the determination of solution-phase equilibrium $K_D$. Solution-based equilibrium assays such as MSD-SET are based on the principle of kinetic exclusion, in which free ligand binding at equilibrium rather than real-time association and dissociation rates is measured to determine affinity.

In brief, standard MSD plates were coated with 20 nM solution of monoclonal antibody of interest (capture antibody) for 30 minutes at room temperature or overnight at 4 °C. On a separate non-binding 96 well plate, the same monoclonal antibody used as the capture antibody is then titrated from μM to fM concentrations and incubated with one set concentration of biotinylated antigen overnight at room temperature without shaking. After 20-24 hours of equilibration, the capture antibody plate is blocked and washed before adding the equilibrated antibody-antigen sample solutions to the plate for exactly 150 seconds. The plate is then washed prior to addition of streptavidin-sulfotag secondary reagent for 3 minutes. Plates are washed prior to reading in MSD read buffer using the MESOR QuickPlex SQ 120. The affinity profiles by MSD-SET as described above are provided in Table 7 herein.

3) Surface plasmon resonance (SPR)-based assays

A BIACORE® system was employed to determine the monovalent binding affinity and the kinetic parameters for

TABLE 21

| Protocol for performing Octet binding assay |
|---|
| Materials: |
| 96 well black polypropylene plates |
| Streptavidin-coated tips for Octet |
| 10× kinetics buffer (diluted 1:10 in PBS) |
| 1. Soak required amount of streptavidin tips in 1X kinetics buffer; place in machine to equilibrate |
| 2. Load sample plate: |
| 200 μl of buffer or antibody dilution to each well |
| a. Column 1-baseline (buffer) |
| b. Column 2-biotinylated protein (e.g., sGARP-proTGFβ1 or LTBP1-proTGFβ1); diluted to 5 μg/mL |
| c. Column 3-baseline 2 (buffer) |
| d. Column 4-antibody association for Ab |
| e. Column 5-antibody association for Ab |
| f. Column 6-dissociation Ab (buffer) |
| g. Column 7-dissociation Ab (buffer) |
| 3. Make dilutions in the 96 well plate: |
| a. Dilute both antibodies to 50 μg/mL in 300 μl of 1× buffer in row A. |
| b. Add 200 μl of buffer to the rest of each column |
| c. Transfer 100 μl down the column to make 3-fold dilutions |
| 4. Place the sample plate in the machine next to the tips plate |
| 5. Set up the software |
| a. Indicate buffer, load, sample (one assay per antibody tested) |
| b. Indicate steps of the protocol (baseline, load, association, dissociation) for set amounts of time: |
| Baseline: 60 seconds |
| Loading: 300 seconds |
| Baseline 2: 60 seconds |
| Association: 300 seconds |
| Dissociation: 600 seconds |
| 6. Analyze data |
| a. Subtract baseline from reference well |
| b. Set normalization to last five seconds of baseline |
| c. Align to dissociation |
| d. Analyze to association and dissociation (1:1 binding model, fit curves) |
| e. Determine the best $R^2$ values; include concentrations with best $R^2$ values |
| f. Select global fit |
| g. Set colors of samples by sensor type |
| h. Analyze |
| i. Save table and export |

antigen binding of test antibodies. The binding kinetics were evaluated by surface plasmon resonance using Biacore 8K (GE Healthcare). A Biotin CAP sensor chip was used to capture the biotinylated antigens. Fabs at various concentrations (0 nM, 0.62 nM, 1.25 nM, 2.5 nM, 5 nM and 10 nM) were injected over the captured antigens. Multi-cycle kinetics was employed where each analyte concentration was injected in a separate cycle and the sensor chip surface was regenerated after each cycle. All the assays were carried out in freshly prepared 1×HBS-EP+buffer (10 mM HEPES, 150 mM NaCl, 3 mM EDTA, 0.05% Tween20, pH 7.4). Data for all the analyte concentrations for each interaction were fit globally to a 1:1 binding model to obtain the kinetic parameters. The Sensorgram for 0 nM analyte concentration was used as reference.

The binding kinetics of antibody interactions with each of the antigen complexes, human LTBP1-ProTGFb1, human LTBP3-ProTGFb1, human GARP-ProTGFb1, and human LRRC33-ProTGFb1, were evaluated by surface plasmon resonance. Binding kinetics was evaluated by surface plasmon resonance using a BIACORER 8K (GE) instrument. Biotinylated antigens were captured on a Biotin CAP chip and the Fab fragments of the antibodies were used as analytes. Sensorgrams for Fab binding at variable concentrations (0.6-10 nM) were globally fit to obtain the kinetic parameters.

Binding kinetics for the Fabs were evaluated against each of the four human antigens, LTBP1-ProTGFb1, LTBP3-ProTGFb1, GARP-ProTGFb1, and LRRC33-ProTGFb1. The data were collected at Fab concentrations 0.62 nM, 1.25 nM, 2.5 nM, 5 nM and 10 nM and were fit globally to a 1:1 binding model to obtain the kinetic parameters and the binding affinity for each interaction. These experiments were repeated.

FIG. 2 shows a representative data set demonstrating markedly improved off rates of Ab46, as compared to a reference antibody used as a benchmark, which is also an activation inhibitor of TGFβ1. The two antibodies in Fab form show similar association kinetics, but Ab46 remain bound to the antigen more than 50 times longer than the reference antibody.

by endogenous presenting molecules and the activation of proTGFβ1 presented by exogenous LTBPs. By directly transfecting integrin-expressing cells, the novel assays disclosed in U.S. Provisional Patent Application No. 62/538,476, and used herein, establish a window between endogenous presenter-proTGFβ1 activity and exogenous LTBP-proTGFβ1 activity. As LTBP-proTGFβ1 complexes are embedded in the extracellular matrix, the assay plate coating is also an important component of the assay. The use of tissue culture plates, coated with the ECM protein Fibronectin, made the LTBP assays more robust.

To determine if any of the isoform-specific antibodies described herein were functional, cell-based assays of aVB integrin activation of TGFβ1 large latent complex (LLC) were developed, which are specific for each known presenting molecule: LTBP1, LTBP3, GARP and LRRC33. Through the process of assay development and optimization, it was determined that fibronectin is a critical ECM protein for the integrin-dependent in vitro activation of LTBP presented TGFβ1 LLCs.

Assay I. Activation of Latent TGFβ1 Deposited in the ECM

For cell-based potency assays, the following protocol was developed. This assay is optimal for extracellular matrix (LTBP presented) activation by integrin cells.

Materials:

- MvLu1-CAGA12 cells (Clone 4A4)
- SW480/86 cells (Clone 1E7) (αV subunit is endogenously expressed at high levels; 36 subunit is stably overexpressed)
- LN229 cell line (high levels of endogenous αVβ8 integrin) ATCC® CRL-2611™
- Costar white walled TC treated 96 well assay plate #3903
- Greiner Bio-One® High Binding white uclear 96 well assay plate #655094
- Human Fibronectin (Corning® #354008)
- P200 multichannel pipet
- P20, P200, and P1000 pipets with sterile filter tips for each
- Sterile microfuge tubes and rack
- Sterile reagent reservoirs
- 0.4% trypan blue

TABLE 22

Fab binding kinetics by Biacore

| Antigen | Fab | $k_{on}$ (1/Ms) | $k_{off}$ (1/s) | $K_D$ (nM) |
|---|---|---|---|---|
| hLTBP1-proTGFβ1 | Reference-1 | 4.25e+6 | 1.04e−2 | 2.44 |
| | Reference-2 | 1.74e+6 | 4.78e−3 | 2.76 |
| | Ab46 | 2.44e+6 | 8.52e−5 | 0.035 |
| hLTBP3-proTGFβ1 | Reference-1 | 3.14e+6 | 9.09e−3 | 2.90 |
| | Reference-2 | 1.36e+6 | 4.64e−3 | 3.42 |
| | Ab46 | 1.78e+6 | 1.95e−4 | 0.109 |
| hGARP-proTGFβ1 | Reference-1 | 4.41e+6 | 1.43e−2 | 3.25 |
| | Reference-2 | 1.52e+6 | 4.08e−3 | 2.67 |
| | Ab46 | 1.89e+6 | 3.59e−4 | 0.190 |
| hLRRC33-proTGFβ1 | Reference-1 | 2.50e+6 | 1.33e−2 | 5.3 |
| | Reference-2 | 1.52e+6 | 6.38e−3 | 4.20 |
| | Ab46 | 1.36e+6 | 1.62e−4 | 0.119 |

Example 3: Functional Assays to Detect Inhibition of Activated Recombinant Latent TGFβ1

The development of novel context-dependent cell-based assays of TGFβ1 activation is described in U.S. Provisional Patent Application No. 62/538,476, incorporated by reference in its entirety herein. Previous assay formats could not differentiate between the activation of proTGFβ1 presented

- 2 mL, 5 mL, 10 mL, and 25 mL sterile pipets
- Tissue culture treated 100 mm or 150 mm plates
- 70% Ethanol
- Opti-MEM reduced serum media (Life Tech #31985-070)
- Lipofectamine® 3000 (Life Tech #L3000015)
- Bright-Glo™ luciferase assay reagent (Promega® #E2620)
- 0.25% Tryspin+0.53 mM EDTA proTGFβ1 expression plasmid, human
LTBP1S expression plasmid, human
LTBP3 expression plasmid, human
LRRC32 (GARP) expression plasmid, human
LRRC33 expression plasmid, human Equipment:

BioTek Synergy H1 plate reader
TC hood
Bench top centrifuge
$CO_2$ incubator 37C 5% CO2
37 °C water/bead bath
Platform shaker
Microscope
Hemocytometer/countess

DEFINITIONS

CAGA12 4A4 cells: Derivative of MvLu1 cells (Mink Lung Epithelial Cells), stably transfected with CAGA12 synthetic promoter, driving luciferase gene expression DMEM-0.1% BSA: Assay media; base media is DMEM (Gibco Cat #11995-065), media also contains BSA diluted to 0.1% w/v, penicillin/streptinomycin, and 4 mM glutamine D10: DMEM 10% FBS, P/S, 4 mM glutamine, 1% NEAA, 1X GlutaMAX (Gibco Cat #35050061)

SW480/β6 Media: D10+1000 μg/mL G-418

CAGA12 (4A4) media: D10+0.75 μg/mL puromycin

Procedure:

On Day 0, cells were seeded for transfection. SW480/36 (clone 1E7) cells were detached with trypsin and pellet (spin 5 min @ 200× g). Cell pellet was resuspended in D10 media and viable cells per ml were counted. Cells were seeded at $5.0\times10^6$ cells/12 ml/100 mm tissue culture dish. For CAGA12 cells, cells were passaged at a density of 1.0 million per T75 flask, to be used for the assay on Day 3. Cultures were incubated at 37 °C and 5% $CO_2$.

On Day 1, integrin-expressing cells were transfected. Manufacturer's protocol for transfection with Lipofectamine® 3000 reagent was followed. The following were diluted into Opti-MEM™ I, for 125 μl per well: 7.5 μg DNA (presenting molecule)+7.5 μg DNA (proTGFβ1), 30 μl P3000, and Up to 125 μl with OptiMEM I. The well was mixed by pipetting DNA together, then Opti-MEM™ was added. P3000 was added, and everything was mixed well by pipetting. A master mix of Lipofectamine® 3000 was made, to be added to DNA mixes: for the LTBP1 assay: 15 μl Lipofectamine® 3000, up to 125 μl in OptiMEM I, per well; for the LTBP3 assay: 45 μl Lipofectamine® 3000, up to 125 μl in Opti-MEM™ I, per well. Diluted Lipofectamine® 3000 was added to DNA, mixed well by pipetting, and incubated at room temp for 15 min. After the incubation, the solution was mixed a few times by pipetting, and then 250 μl of DNA: Lipofectamine® 3000 (2×125 μl) per dish was added dropwise. Each dish was gently swirled to mix and the dish was returned to the tissue culture incubator for ~24 hrs.

On Days 1-2, the assay plates were coated with human fibronectin. Specifically, lyophilized fibronectin was diluted to 1 mg/ml in ultra-pure distilled water (sterile). 1 mg/ml stock solution was diluted to 19.2 μg/ml in PBS (sterile). Added 50 μl/well to assay plate (high binding) and incubated O/N in tissue culture incubator (37 °C and 5% $CO_2$). Final concentration was 3.0 $\mu g/cm^2$.

On Day 2, transfected cells were plated for assay and inhibitor addition. First, the fibronectin coating was washed by adding 200 μl/well PBS to the fibronectin solution already in the assay plate.

Removed wash manually with multichannel pipette. Wash was repeated for two washes total. The plate was allowed to dry at room temperature with lid off prior to cell addition. The cells were then plated by detaching with trypsin and pellet (spin 5 min @ 200× g). The pellet was resuspended in assay media and viable cells were counted per ml. For the LTBP1 assay cells were diluted to $0.10\times10^6$ cells/ml and seed 50 μl per well (5,000 cells per well). For the LTBP3 assay, cells were diluted to $0.05\times10^6$ cells/ml and seed 50 μl per well (2,500 cells per well). To prepare functional antibody dilutions, antibodies were pre-diluted to a consistent working concentration in vehicle. Stock antibodies were serially diluted in vehicle (PBS is optimal, avoid sodium citrate buffer). Each point of serial dilution was diluted into assay media for a 4X final concentration of antibody. Added 25 μl per well of 4X antibody and incubated cultures at 37 °C and 5% $CO_2$ for ~24 hours.

On Day 3, the TGFβ reporter cells were added. CAGA12 (clone 4A4) cells for the assay were detached with trypsin and pellet (spin 5 min @ 200× g.). The pellet was resuspended in assay media and count viable cells per ml. Cells were diluted to $0.4\times10^6$ cell/ml and seed 50 μl per well (20,000 cells per well). Cells were returned to incubator.

On Day 4, the assay was read (16-20 hours after antibody and/or reporter cell addition). Bright-Glo™ reagent and test plate were allowed to come to room temperature before reading. Read settings on Bio-Tek® Synergy™ H1 were set using TMLC_std protocol—this method has an auto-gain setting. Selected positive control wells for autoscale (high). 100 μL of Bright-Glo reagent was added per well. Incubated for 2 min with shaking, at room temperature, protected plate from light. The plate was read on BioTek Synergy H1.

Figure 27:
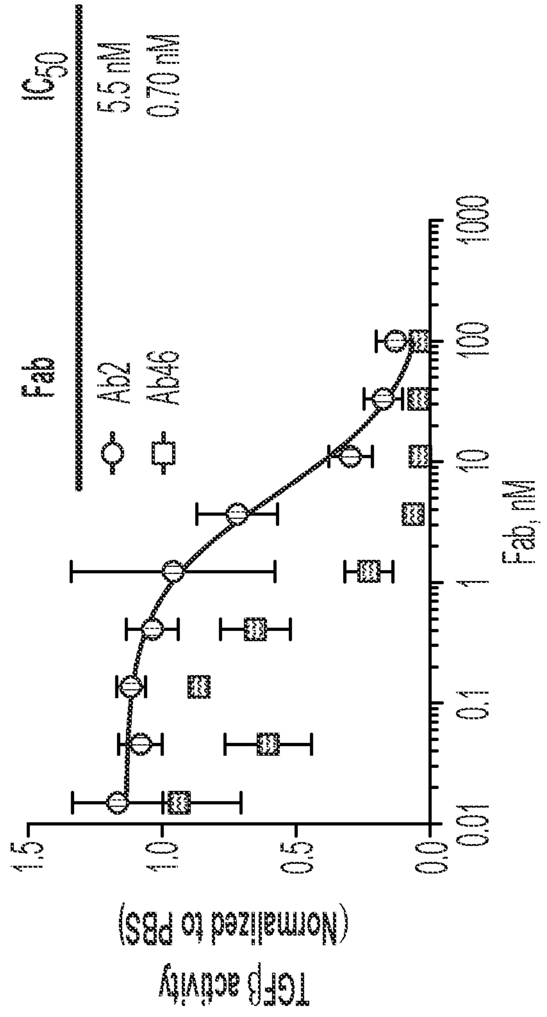
FIG. 27 provides a graph showing cell-based potency assay data by reporter cells. TGFβ activities are inhibited by increasing concentrations of Ab2 or Ab46.

For the assay depicted in FIG. 27, the following protocol was developed. This assay, or "direct-transfection" protocol, is optimal for cell-surface presented TGFβ1 (GARP or LRRC33 presenter) activation by integrin cells.

Materials:

MvLu1-CAGA12 cells (Clone 4A4)
SW480/86 cells (Clone 1E7) (αV subunit is endogenously expressed at high levels; 36 subunit is stably overexpressed)
LN229 cell line (high levels of endogenous αVβ8 integrin)
Costar white walled TC treated 96 well assay plate #3903
Greiner Bio-One® High Binding white uclear 96 well assay plate #655094
Human Fibronectin (Corning #354008) P200 multichannel pipet
P20, P200, and P1000 pipets with sterile filter tips for each
Sterile microfuge tubes and rack
Sterile reagent reservoirs
0.4% trypan blue
2 mL, 5 mL, 10 mL, and 25 mL sterile pipets
Tissue culture treated 100 mm or 150 mm plates
70% Ethanol
Opti-MEM® reduced serum media (Life Tech #31985-070)
Lipofectamine® 3000 (Life Tech #L3000015)
Bright-Glo™ luciferase assay reagent (Promega® #E2620)
0.25% Tryspin+0.53 mM EDTA
proTGFβ1 expression plasmid, human LTBP1S expression plasmid, human
LTBP3 expression plasmid, human
LRRC32 (GARP) expression plasmid, human
LRRC33 expression plasmid, human Equipment:
Bio-Tek® Synergy™ H1 plate reader
Tissue culture hood
Bench top centrifuge
$CO_2$ incubator 37 °C 5% $CO_2$
37 °C water/bead bath
Platform shaker
Microscope
Hemocytometer/countess

DEFINITIONS

CAGA12 4A4 cells: Derivative of MvLu1 cells (Mink Lung Epithelial Cells), stably transfected with CAGA12 synthetic promoter, driving luciferase gene expression DMEM-0.1% BSA: Assay media; base media is DMEM (Gibco Cat #11995-065), media also contains BSA diluted to 0.1% w/v, penicillin/streptinomycin, and 4 mM glutamine D10: DMEM 10% FBS, P/S, 4 mM glutamine, 1% NEAA, 1X GlutaMAX (Gibco Cat #35050061)

SW480/β6 Media: D10+1000 μg/mL G-418

CAGA12 (4A4) media: D10+0.75 μg/mL puromycin

Methods:

On Day 0, integrin expressing cells were seeded for transfection. Cells were detached with trypsin and pelleted (spin 5 min at 200× g). Cell pellet was resuspended in D10 media and count viable cells per ml. Cells were diluted to $0.1\times10^6$ cells/ml and seeded 100 μl per well (10,000 cells per well) in an assay plate. For CAGA12 cells, passaged at a density of 1.5 million per T75 flask, to be used for the assay on Day 2. Cultures were incubated at 37 °C and 5% $CO_2$.

On Day 1, cells were transfected. The manufacturer's protocol was followed for transfection with Lipofectamine® 3000 reagent. The following was diluted into OptiMEM® I, for 5 μl per well: 0.1 μg DNA (presenting molecule)+0.1 μg DNA (proTGFβ1), 0.4 μl P3000, and up to 5 μl with OptiMEM I. The well was mixed by pipetting DNA together, then add OptiMEM®. Add P3000 and mix everything well by pipetting. A master mix was made with Lipofectamine® 3000, to be added to DNA mixes: 0.2 μl Lipofectamine® 3000, up to 5 μl in OptiMEM I, per well. Diluted Lipofectamine® 3000 was added to DNA, mixed well by pipetting, and incubated at room temp for 15 min. After the incubation, the solution was mixed a few times by pipetting, and then 10 μl per well of DNA: Lipofectamine® 3000 (2×5 μl) was added. The cell plate was returned to the tissue culture incubator for ~ 24 hrs.

On Day 2, the antibody and TGFβ reporter cells were added. In order to prepare functional antibody dilutions, stock antibody in vehicle (PBS is optimal) was serially diluted. Then each point was diluted into assay media for 2X final concentration of antibody. After preparing antibodies, the cell plate was wished twice with assay media, by aspirating (vacuum aspirator) followed by the addition of 100 μl per well assay media. After second wash, the assay media was replaced with 50 μl per well of 2× antibody. The cell plate was returned to the incubator for ~ 15-20 min.

In order to prepare the CAGA12 (clone 4A4) cells for the assay, the cells were detached with trypsin and pelleted (spin 5 min @ 200× g.). The pellet was resuspended in assay media and viable cells per ml were counted. Cells were diluted to $0.3\times10^6$ cells/ml and seeded 50 μl per well (15,000 cells per well). Cells were returned to incubator.

On Day 3, the assay was read about 16-20 hours after the antibody and/or reporter cell addition. Bright-Glo™ Luciferase Assay System (Promega®) and test plate were allowed to come to room temperature before reading. The read settings on Bio-Tek® Synergy™ H1 were set to use TMLC_std protocol—this method has an auto-gain setting. Positive control wells were set for autoscale (high). 100 μL of Bright-Glo reagent was added per well. Incubated for 2 min with shaking, at room temperature, protected plate from light. The plate was read on Bio-Tek® Synergy™ H1.

To calculate IC50 values, raw luminescence values were normalized against wells treated with PBS only (vehicle). Normalized values were plotted using PRISM® software, and values were calculated using 3-point non-linear regression.

Table 23 shows calculated IC50 values for isoform-specific antibodies. Reported IC50 values are averaged from duplicate wells of a single dose-response experiment; dose response curves and IC50 values are representative of multiple independent experiments.

TABLE 23

IC50s for isoform-specific antibodies against proTGFβ1-presenting molecule complexes as measured by an in vitro potency assay

| | IC50 (nM) | | | |
|---|---|---|---|---|
| Ab Ref. | hLTBP1-proTGFβ1 | hLTBP3-proTGFβ1 | hGARP-proTGFβ1 | hLRRC33-proTGFβ1 |
| Ab3 | 24.29 | 10.42 | 0.981 | 0.8578 |
| Ab11 | 2.954 | 1.562 | 0.7902 | 1.268 |
| Ab12 | 3.794 | 1.555 | 1.077 | 2.434 |
| Ab2 | 3.394 | 0.8673 | 0.7758 | 1.375 |
| Ab19 | 1.656 | 1.599 | 1.34 | 0.4014 |
| Ab20 | 1.851 | 1.184 | 0.3872 | 1.354 |
| Ab35 | 6.246 | 2.707 | 3.715 | 5.37 |
| Ab1 | 14.47 | 2.707 | 3.715 | 5.37 |

Example 4. Inhibition of Acute Fibrosis by Anti-proTGFβ1 Antibodies in the Unilateral Ureteral Obstruction (UUO) Model of Acute Kidney Fibrosis Inhibition of acute fibrosis by anti-TGFβ1 antibodies was tested in the unilateral ureteral obstruction (UUO) model of acute kidney fibrosis. In this model, fibrosis is induced in male mice by permanent surgical ligation of the left ureter on study day 0. Sham-treated mice, which underwent surgery but did not have their ureters obstructed, were included as a healthy control in these experiments.

Control or test antibodies (Ab3, Ab2) were administered to mice by intraperitoneal (i.p.) injection on study days −1 and 4. Kidneys were collected at the end of study, on day 5 after surgery, and RNA was harvested from these tissues. The degree of fibrosis induction was subsequently assessed by quantitative polymerase chain reaction (qPCR) for a panel of fibrosis-associated genes, including Collagen I (Col1a1), Collagen III (Co/3a1), Fibronectin 1 (Fn1), Lysyl Oxidase (Lox), Lysyl Oxidase-like 2 (Loxl2), Smooth muscle actin (Acta2), Matrix metalloprotease (Mmp2), and Integrin alpha 11 (Itga11) (Rolfe et al., 2007. *Sound Repair Regen.* 15 (6): 897-906) (Tamaki et al., 1994. *Kidney Int.* 45 (2): 525-536) (Bansal et al., 2017. *Exp Mol Med.* 49 (11): e396) (Leaf & Duffield, 2016. *J Clin Invest.* 127 (1): 321-334).

Effect of Ab2 or Ab3 Treatment on Collagen Gene Expression

Figure 5A:
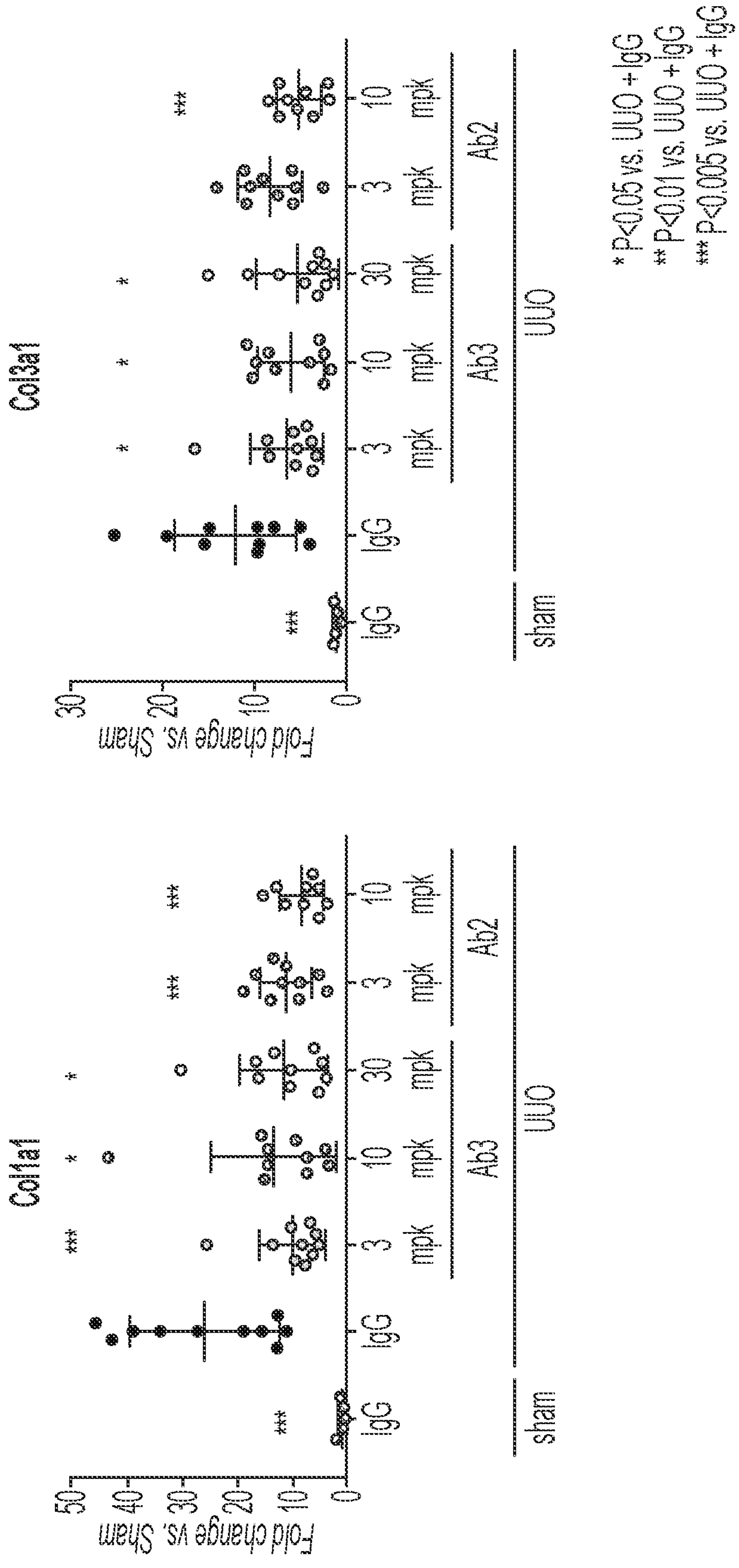
FIG. 5A is a graph that shows effect of Ab2 or Ab3 on expression of collagen genes (Col1a1 and Col3a1) in UUO mice. Mice were treated with 3, 10, or 30 mg/kg/wk of Ab3 or 3 or 10 mg/kg/week of Ab2. IgG alone was used as control.

Col1a1 and Col3a1 are key drivers of fibrosis. As shown in FIG. 5A, Col1a1 is induced 10- to 40-fold in obstructed kidneys and Col3a1 is upregulated 5- to 25-fold (P<0.005, compare sham+IgG treated mice to UUO+IgG group). UUO mice treated with 3, 10, or 30 mg/kg/wk of Ab3 show reduced expression of both collagen genes compared to the UUO+IgG (P<0.05). Treatment with 10 mg/kg/wk of Ab2 also suppressed fibrotic gene induction by UUO (P<0.005 compared to UUO+IgG). Samples from the 3 mg/kg/wk Ab2 group also show a trend towards reduced Col3a1 expression, though this effect does not reach statistical significance. Taken together, these data suggest that TGFβ1 inhibition with either Ab2 or Ab3 potently ameliorates the collagen induction associated with UUO.

Figure 5B:
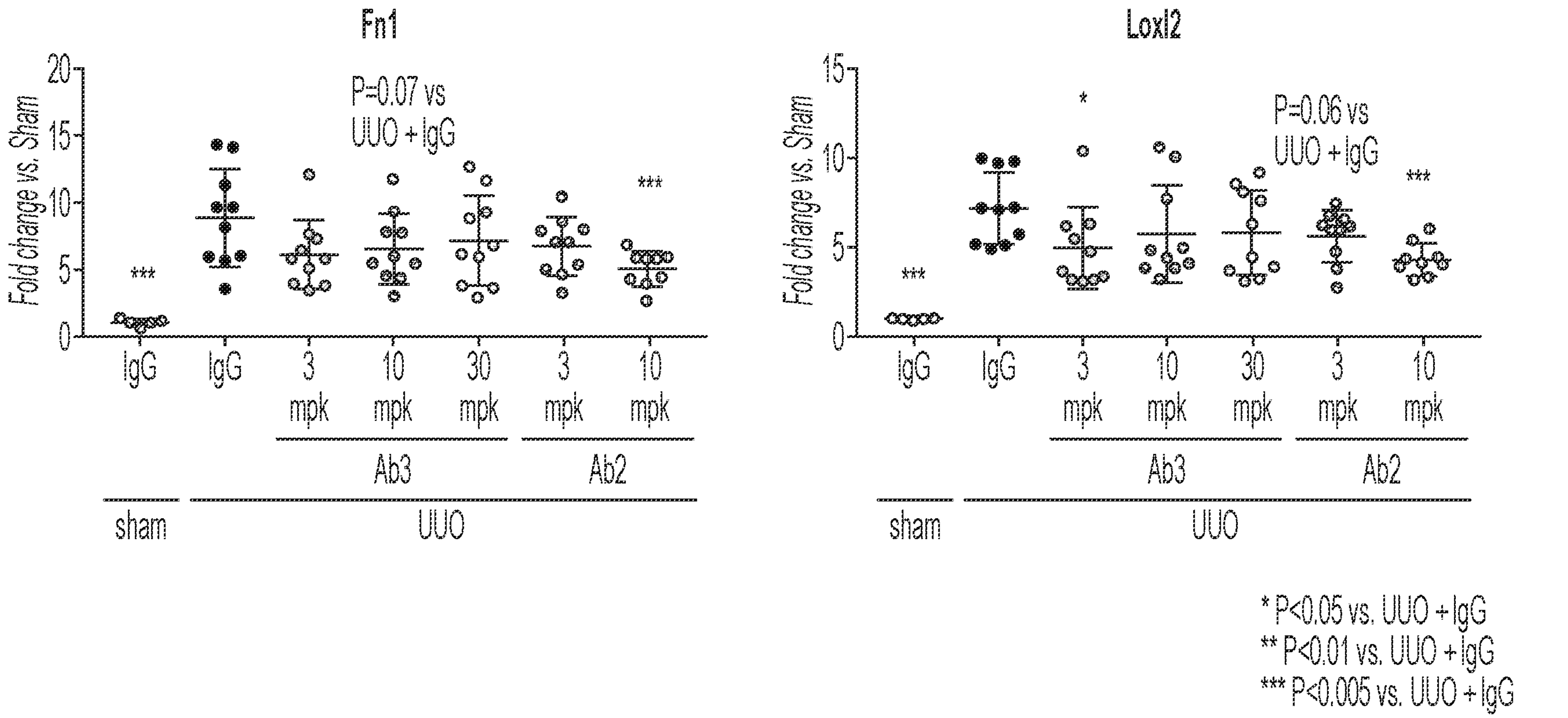
FIG. 5B is a graph that shows effect of Ab3 or Ab2 on expression of Fn1 and Loxl2 genes in UUO mice. Mice were treated with 3, 10, or 30 mg/kg/wk of Ab3 or 3 or 10 mg/kg/week of Ab2. IgG alone was used as control.

Effect of Ab2 or Ab3 Treatment on Fibronectin and Lysyl Oxidase-Like 2 Gene Expression Fn1 and Loxl2 encode proteins that play roles in deposition and stiffness of extracellular matrix in fibrosis. As shown in FIG. 5B, both genes are upregulated in samples from the UUO+IgG group (P<0.005 vs. Sham+IgG), though the fold increase in gene expression for both genes, but particularly for Loxl2, is smaller than for the Collagen genes. In samples treated with 3, 10, or 30 mg/kg/wk of Ab3, a trend towards reduced Fn1 and Loxl2 (vs. UUO+IgG) was noted, but this treatment effect is only statistically significant for Loxl2 expression, and only at the 3 mg/kg/wk dose (Fn1 at the 10 mg/kg/wk dose is approaching statistical significance, with P=0.07). Treatment with 10 mg/kg/wk Ab2, however, leads to a highly significant (P<0.005 vs UUO+IgG) inhibition of both Fn1 and Loxl2. A lower, 3 mg/kg/wk dose of Ab2 leads to a reduction of both Fn1 and, particularly, Loxl2 (P=0.06), though suppression of neither gene is statistically significant.

Figure 6:
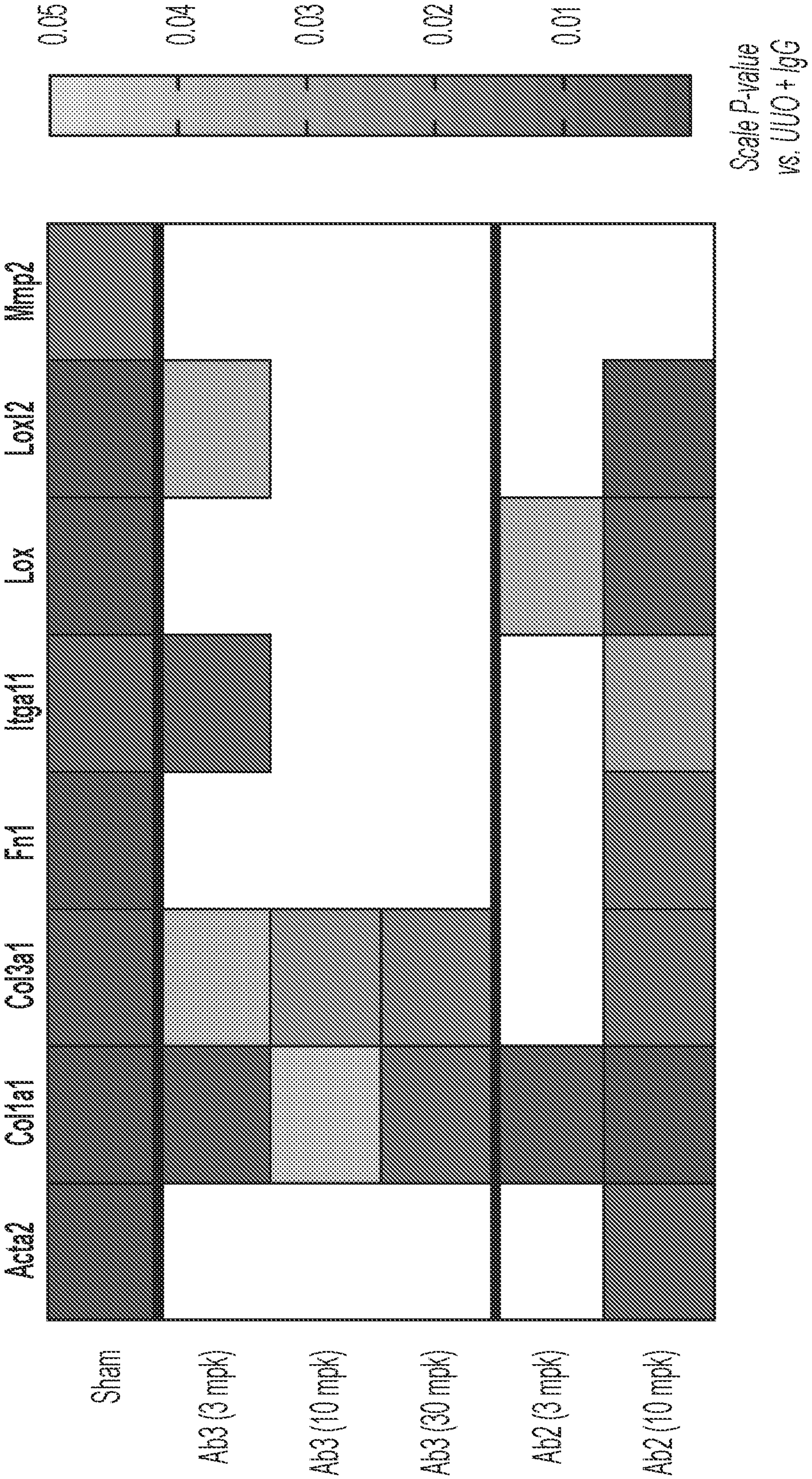
FIG. 6 summarizes the statistical significance of the changes in gene expression (vs. UUO+IgG) after treatment in the UUO model.

FIG. 6 summarizes the statistical significance of changes in gene expression (vs. UUO+IgG) after treatment in the UUO model. Ab3 showed reduction in Col1a1 and Col3a1 at all doses tested. Statistically significant changes were also observed in Itga11 and Loxl2 (both levels were reduced relative to UUO+IgG), but only in the 3 mg/kg/wk dose. In contrast, all genes examined except Mmp2 showed a statistically significant change in expression (all levels reduced relative to UUO+IgG) after treatment with 10 mg/kg/wk Ab2. Col1a1 and Lox expression were also reduced at the 3 mg/kg/wk dose.

Example 5: Inhibition of TGFβ Signaling by Anti-proTGFβ1 Antibodies in a Genetic Model of Alport Syndrome The murine Col4a3−/− model is an established genetic model of autosomal recessive Alport syndrome. Alport mice lack a functional collagen 4A3 gene (Col4A3−/−) and therefore cannot form normal type IV collagen trimers, which require α3, α4, and α5 chains. Col4α3−/− mice develop fibrosis in the kidney consistent with renal fibrosis in human patients, including interstitial fibrosis and tubular atrophy, and Col4α3−/− mice develop end-stage renal disease (ESRD) between 10 and 30 weeks of age, depending on the genetic background of the mouse. The structural and functional manifestation of renal pathology in Col4α3−/− mice, combined with the progression to ESRD make Col4α3−/− mice an ideal model to understand kidney fibrosis. Previous reports point to the importance of the TGFβ signaling pathway in this process, and treatment with either αvβ6 integrin, a known activator of TGFβ, or with a TGFβ ligand trap has been reported to prevent renal fibrosis and inflammation in Alport mice (Hahm et al., (2007) *The American Journal of Pathology,* 170 (1): 110-125).

Ab3 and Ab2, which are isoform-specific, inhibitors of TGFβ1 activation, were tested for their ability to inhibit or mitigate renal fibrosis in Alport mice as follows.

F1 offspring from Col4α3+/−males on a 129/Sv genetic background crossed to Col4α3+/−females on a C57/B16 genetic were employed for the study. These mice typically exhibit proteinuria by 4-5 weeks old and typically progress to ESRD by 14-15 weeks old, providing a good therapeutic window for testing efficacy of treatment.

Figure 7A:
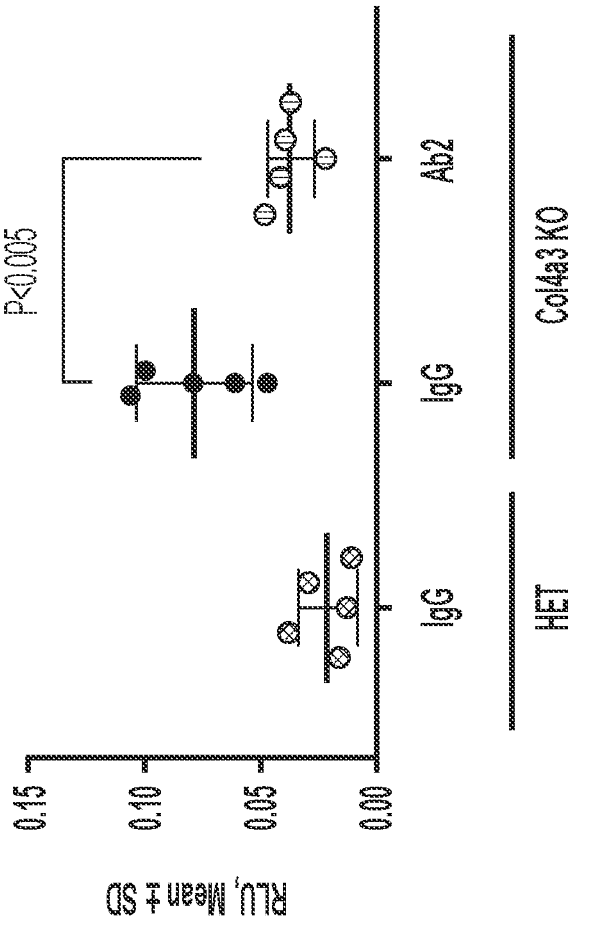
FIG. 7A and FIG. 7B are graphs showing relative ratios of phosphorylated vs. total (phosphorylated and unphosphorylated) SMAD2/3 in kidneys from a genetic model of Alport syndrome treated with and without antibodies Ab2 and Ab3.

It is well documented that TGFβ receptor activation leads to a downstream signaling cascade of intracellular events, including phosphorylation of SMAD2/3. Therefore, the ability of Ab2 antibody treatment to inhibit TGFβ signaling may be assessed in kidney lysate samples by measuring relative phosphorylation levels of SMAD2/3 as assayed by ELISA (Cell Signaling Technologies) according to the manufacturer's instructions. Accordingly, 9 week old Col4α3−/− mice were dosed with 10 mg/kg Ab2 intraperitoneally (i.p.) 48 hours prior to animal sacrifice and tissue collection. FIG. 7A provides a graph showing relative ratios of phosphorylated vs. total (phosphorylated and unphospohrylated) SMAD2/3. A single dose of Ab2 was sufficient to significantly inhibit pSMAD2/3 signaling in whole kidney lysates from 9 week old Col4α3−/− mice, demonstrating efficient target engagement by Ab2 in this model.

In a separate study, Col4α3−/− mice were treated with Ab2 or Ab3 beginning six weeks after birth. Mice were dosed i.p. twice weekly with either 5 mg/kg or 1.5 mg/kg Ab3 or with 1.5 mg/kg Ab2 for a test duration of six weeks. An IgG was used as negative control in both heterozygous (Col4α3+/−; Het) and knock out (Col4α3−/−; KO) mice. Following six weeks of antibody treatment (12 weeks after birth), animals were sacrificed, and the kidneys were collected for analyses.

Figure 7B:
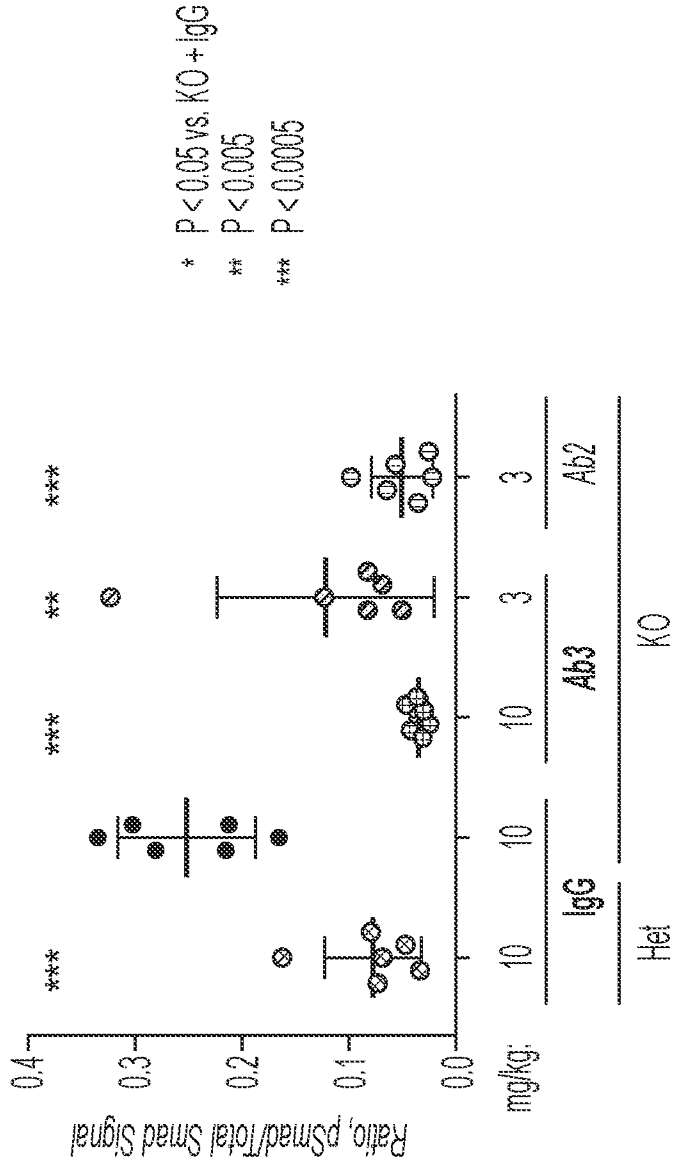

FIG. 7B shows relative ratios of phosphorylated vs. total SMAD2/3 in whole kidney lysates prepared from samples of animals treated with Ab3 or Ab2. Treatment with either antibody showed a significant reduction in relative phosphorylation of SMAD2/3, as compared to IgG treated Col4α3−/− mice. The average SMAD ratios in the treated KO mice were equivalent to those of heterozygous control.

Figure 7C:
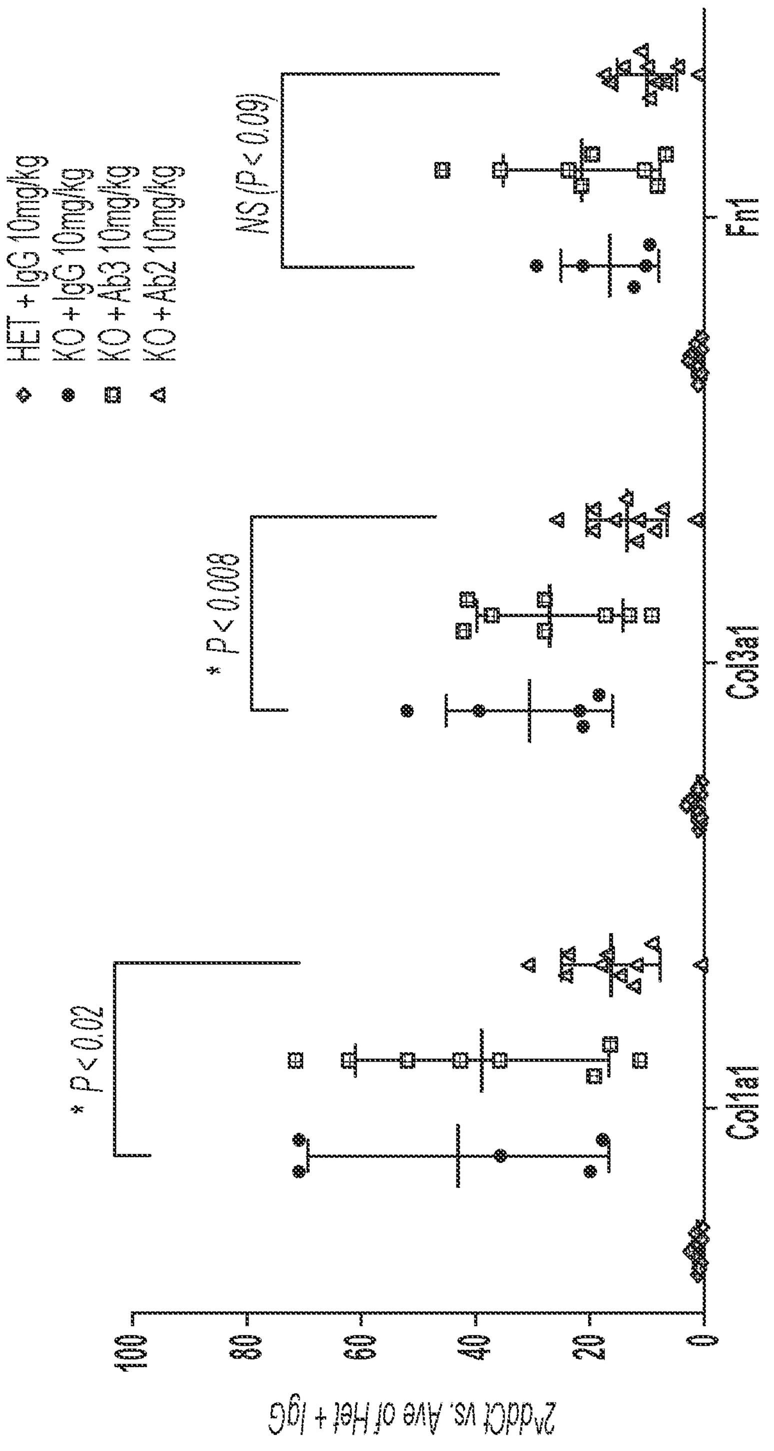
FIG. 7C is a graph showing the effect of Ab3 and Ab2 on gene expression in kidneys from a genetic model of Alport syndrome.

To assess the functional effect of TGFβ inhibition, a third study was carried out in the Col4α3−/− model of kidney fibrosis. In this case, mice were treated i.p. twice a week with a 5 mg/kg dose of Ab3 or Ab2, beginning six weeks after birth and continuing until mice were sacrificed at 14 weeks old. Treatment effect was assessed by gene expression, which was evaluated by quantitative polymerase chain reaction (qPCR) using cDNA generated from the kidneys of mice in this study. FIG. 7C shows expression of genes encoding three proteins commonly associated with fibrosis, Collagen 1 (Col1a1), Collagen 3 (Col3a1), and Fibronectin 1 (Fn1). In Col4α3−/− kidneys from animals treated with IgG control antibody, expression of all three genes is significantly upregulated relative to that in heterozygous Col4α3+/− mice. Treatment with Ab2 significantly reduced the expression of Col1a1 and Col3a1 in Col4α3−/− mice. Expression of Fn1 showed a similar trend in Ab2-treated Col4α3−/− mice, though this effect was not statistically significant ($P<0.09$).

Example 6: Inhibition of TGFβ Signaling by Anti-proTGFβ1 Antibodies in Choline-Deficient High Fat Diet (CDHFD) Model of Mouse NASH The Choline deficient high fat diet (CDHFD) is an established dietary model of Non-Alcoholic steatohepatitis (NASH). In this model, male C57BL/6J mice are fed a choline deficient, 0.1% Methionine, high fat diet for 12 weeks. Three to six weeks after the start of the CDHFD, expression of α-sma protein (a marker for activation of hepatic stellate cells) increases and the development of hepatic fibrosis is accompanied by an increase in the hydroxyproline content accompanied by a rise in intrahepatic collagen synthesis and deposition (Matsumoto et al., *Int J Exp Pathol.* 2013 April;94 (2): 93-103).

Ab3 and Ab2 were tested for their ability to inhibit and/or reduce the extent of liver fibrosis in mice on CDHFD as follows.

Animals in the test cohorts were on the CDHFD for the duration of the study. A separate cohort of mice were administered a regular chow diet as a study control. Antibodies Ab3 and Ab2 were administered to mice by intraperitoneal (i.p.) injection beginning at 4 weeks post start of the CDHFD. Antibody test concentrations were as follows: 15 mg/kg, 5 mg/kg or 1.5 mg/kg twice a week (i.e., 30, 10, or 3 mg/kg/week) for a test duration of 8 weeks (i.e., weeks 4 thru 12). An IgG isotype antibody was used as a negative control at 15 mg/kg twice weekly (30 mg/kg/week). Following 8 weeks of dosing, animals were sacrificed and livers collected for analyses.

Figure 8A:
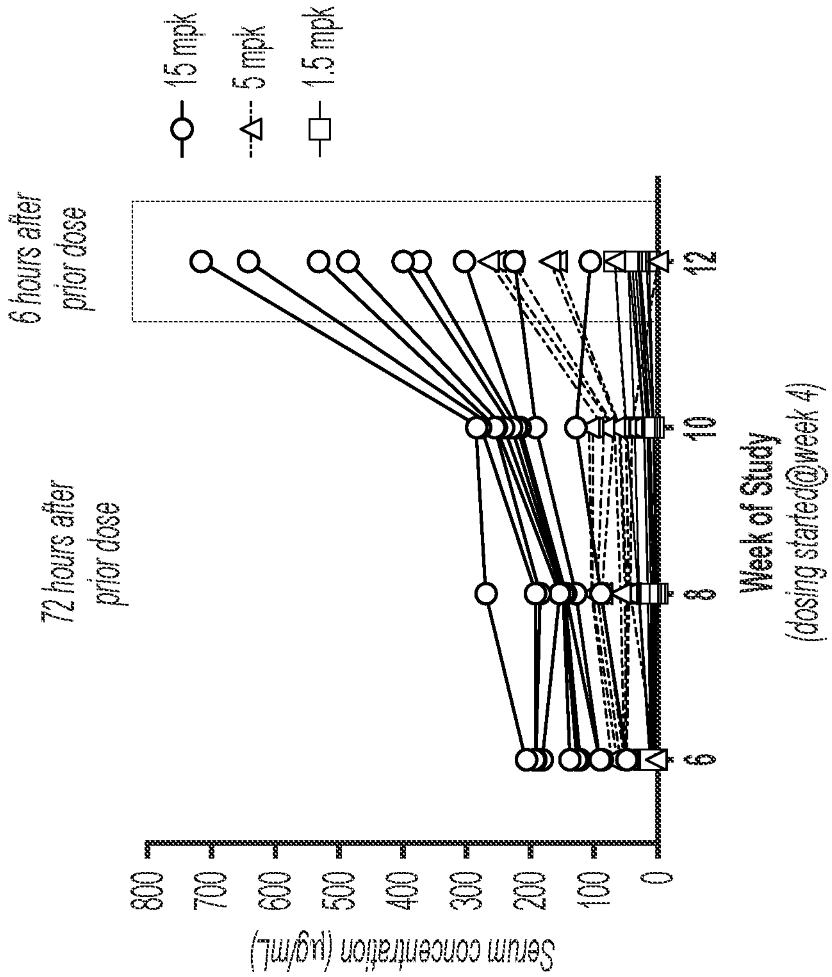
FIG. 8A is a graph that shows the serum exposure of Ab2 in the CDHFD mouse model at 6, 8, 10, and 12 weeks.

Serum measurements were also taken to determine circulating antibody exposure during the study. Serum samples were collected 72 hours after Ab2 dosing at weeks 6, 8, and 10. At week 12, animals were given their final Ab2 injection and serum was taken 6 hrs post injection and at the time of sacrifice. FIG. 8A shows the serum levels of Ab2 during the duration of the study, indicating that we have quantifiable levels of Ab2 exposure in serum throughout the study. The two highest test doses of Ab2 at 15 and 5 mg/kg (2×/week) provide the best coverage throughout the study despite any presumed effect by the rise of anti-drug antibodies throughout the 8 weeks of dosing (van Brummelen et al., The Oncologist. 2016 July;21:1-9)

Figure 8B:
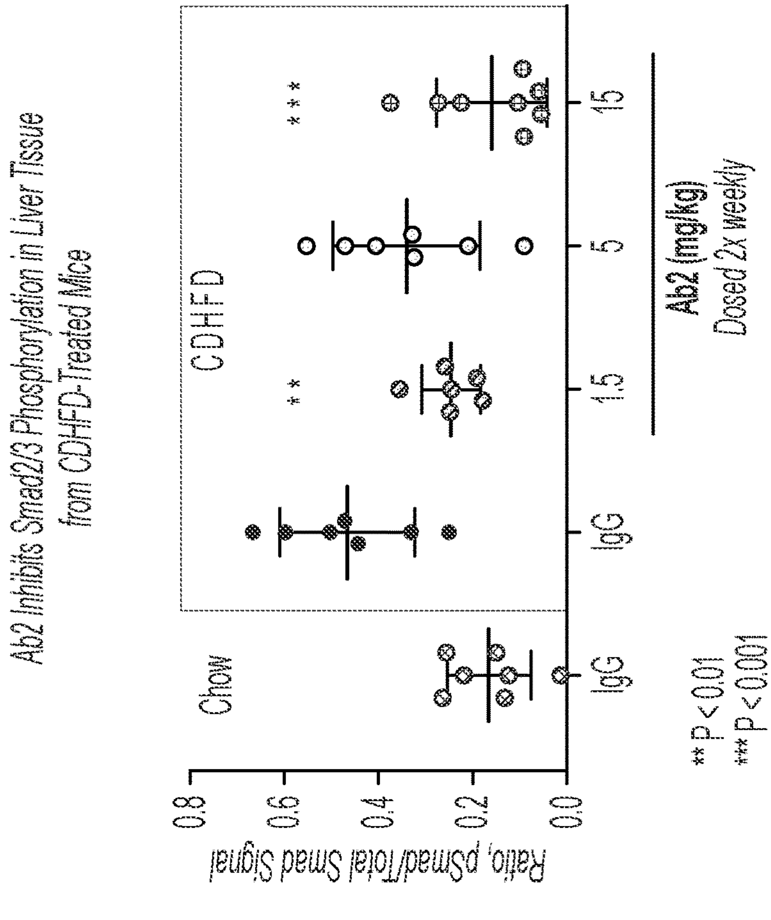
FIG. 8B is a graph that shows the effect of Ab2 on SMAD2/3 phosphorylation in liver tissue from CDHFD-treated mice.
Figure 8C:
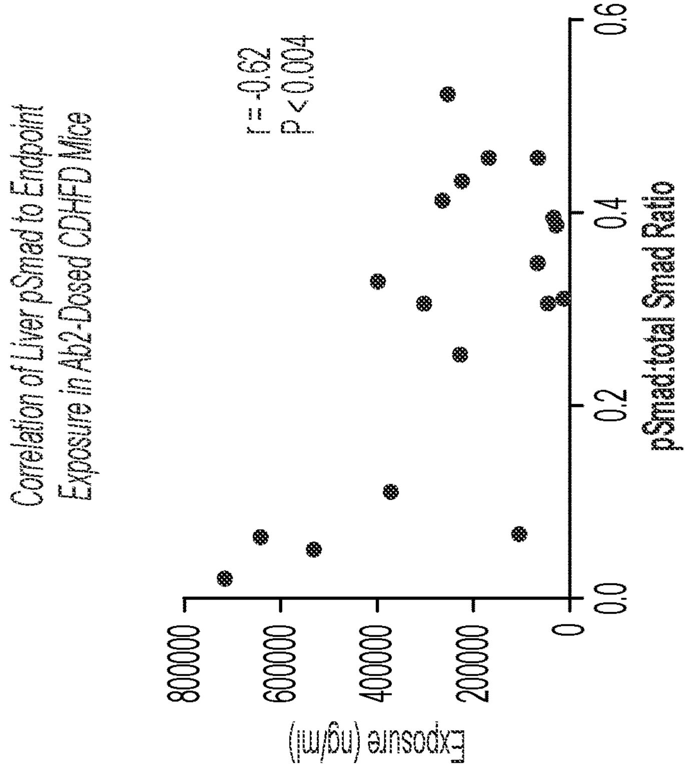
FIG. 8C is a graph that shows a correlation between reduced phosphorylated SMAD2/3 and Ab2 exposure.
Figure 8D:
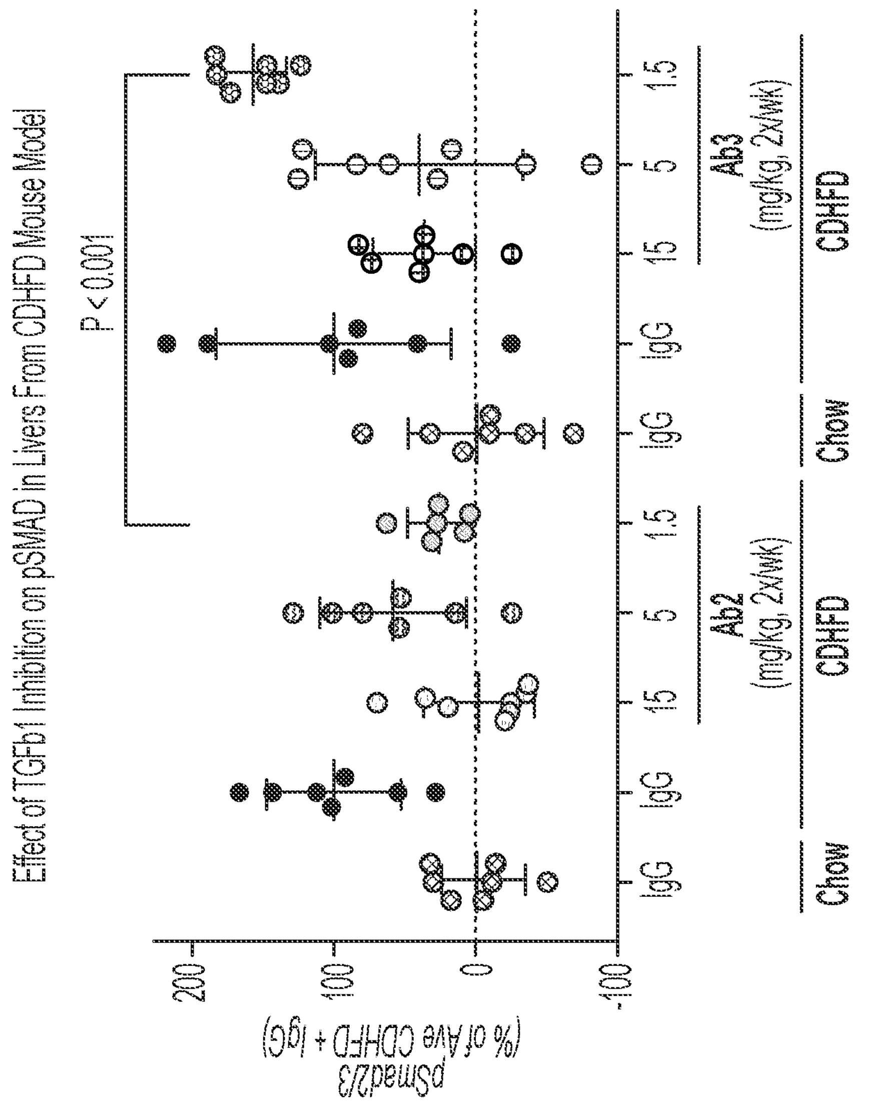
FIG. 8D is a graph that shows a comparison of the effect of Ab3 and Ab2 on SMAD2/3 phosphorylation in liver tissue from CDHFD-treated mice.

TGFβ1 receptor engagement leads to intracellular signaling events including the phosphorylation of SMAD2 and SMAD3. Accordingly, Ab3 and Ab2 were tested for their ability to inhibit SMAD2/3 in liver lysates from CDHFD-treated mice by ELISA (Cell Signaling Technologies) according to manufacturer's protocol. As shown in FIG. 8B, Ab2 significantly reduced the relative ratio of phosphorylated SMAD2/3 compared to IgG control. FIG. 8C demonstrates an inverse correlation between serum levels of Ab2 and phosphorylated SMAD2/3. FIG. 8D shows Ab2 significantly reduces phosphorylation of SMAD2/3 as compared to Ab3 and IgG treated mice on CDHFD (see, e.g., 1.5 mg/kg dose).

Figure 8E:
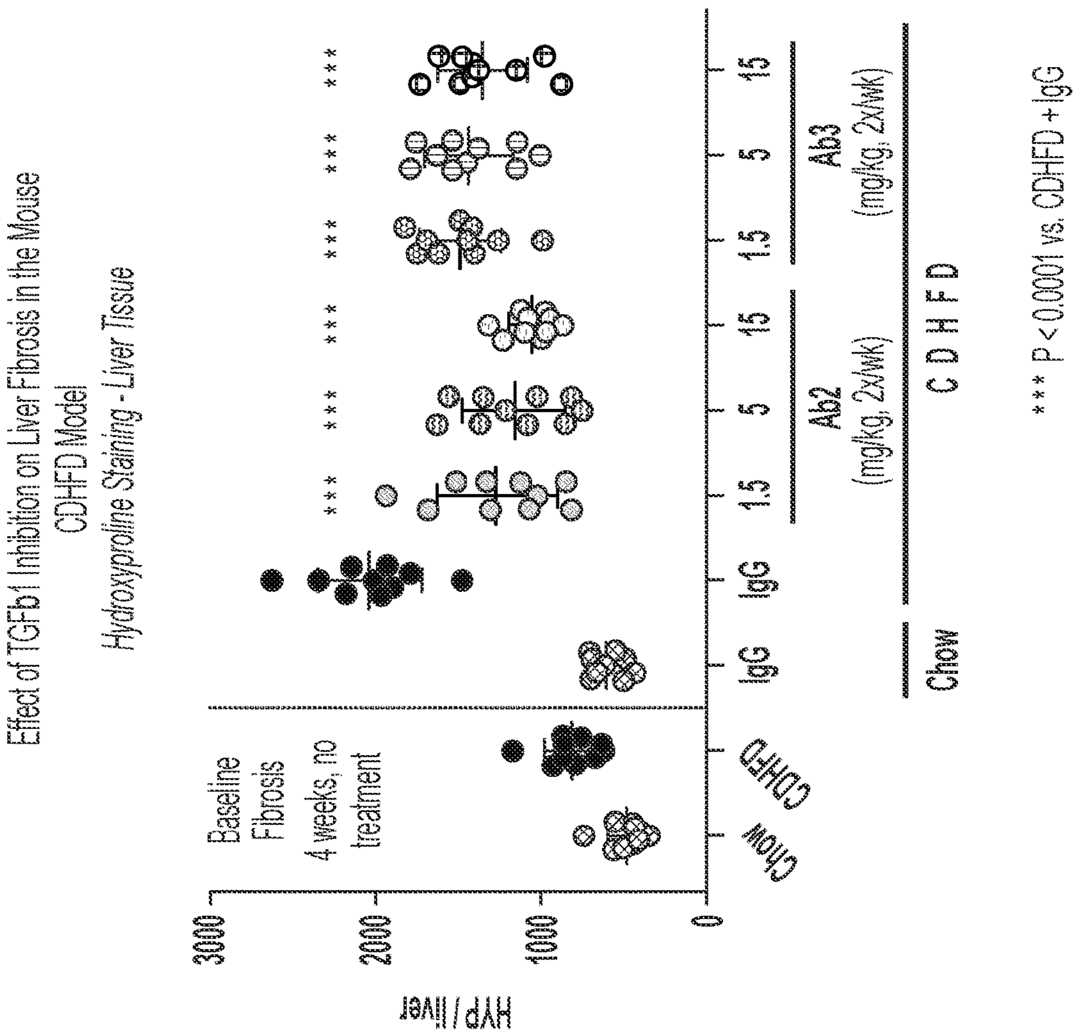
FIG. 8E is a graph that shows the effect of Ab3 and Ab2 on liver fibrosis as measured by hydroxyproline levels.

Hydroxyproline is a signature amino acid for fibrillar collagens and comprises approximately 13.5% of the protein. Fibrosis that occurs in the liver has the capacity to develop into chronic hepatitis, liver sclerosis, liver cancer, pulmonary fibrosis and glomerulonephritis (Qui et al., 2014 *Mol. Med. Reports* 2014 10;1157-1163). Hydroxyproline acts as an important diagnostic indicator of the severity of fibrosis. As shown in FIG. 8E, animals undergoing treatment with Ab3 and Ab2 demonstrated a marked reduction in collagen deposition when compared to the control CDHFD animals administered IgG control Ab, indicating a positive treatment affect.

To assess the levels of type 1 collagen deposition in livers from CDHFD-treated mice, immunohistochemistry (IHC) protocols were developed for anti-mouse type I collagen antibody (rabbit polyclonal; Abcam; ab21286) using the Leica Bond RX staining system. Mouse liver was collected and fixed in 10% neutral buffered formalin (NBF) for 24 hours at room temperature. Fixed livers were then trimmed into 3-5 mm cross sections and stored in 70% ethanol until processed for paraffin infiltration and embedding. Paraffin embedded livers were sectioned at 4 μm and mounted on slides for IHC staining. Type 1 collagen primary antibody was used at a 5 μg/mL final concentration along with a matched isotype primary control (rabbit monoclonal IgG; Cell Signaling Technologies; 3900S). Epitope retrieval was performed with a pH 6 citrate buffer incubated at 100 °C for 20 minutes. Slides were washed in a tris-based buffer, incubated with a peroxide blocking reagent, then washed 3× in buffer, and incubated with a protein blocking reagent for 20 minutes before a 30 minute primary antibody incubation. Slides were again washed with buffer before incubation with a Leica HRP-polymer conjugate for 8 minutes. Slides were then washed 2× in buffer and 1× in deionized (DI) water before incubated with a Leica diaminobenzidine (DAB) chromogen for 10 minutes. Slides were then washed 3× with DI water before counterstaining with hematoxylin for 5 minutes. After final wash steps, stained IHC slides were then dehydrated and coverslipped using a xylene based mounting media.

Figure 8F:
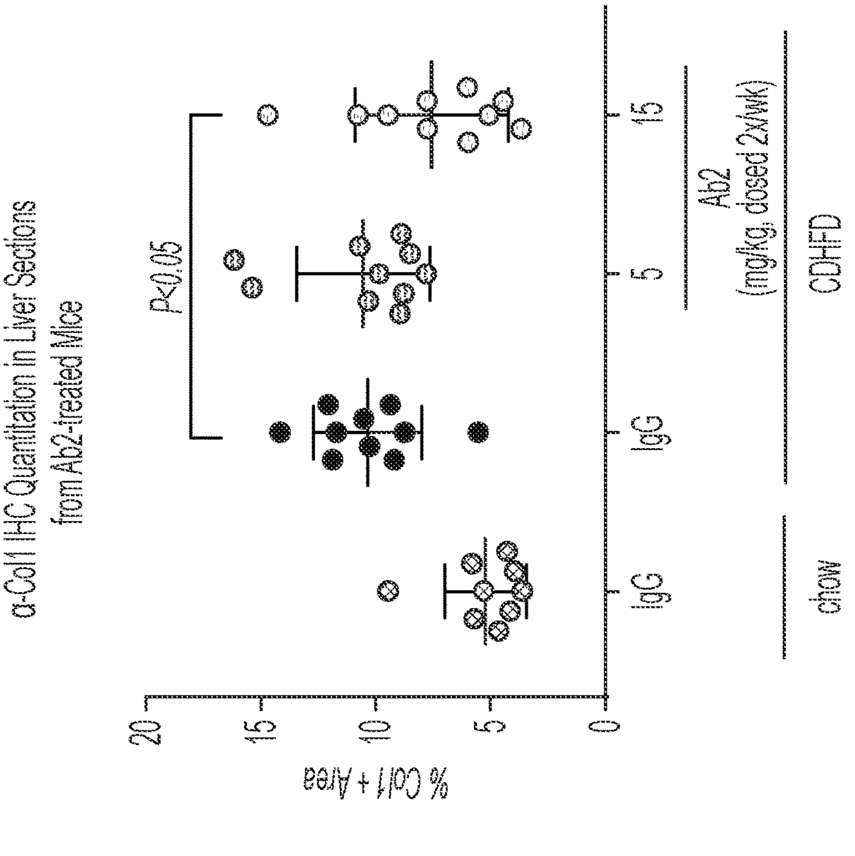
FIG. 8F is a graph that shows the effect of Ab2 on α-Col1 by IHC in CDHFD-treated mice.
Figure 8G:
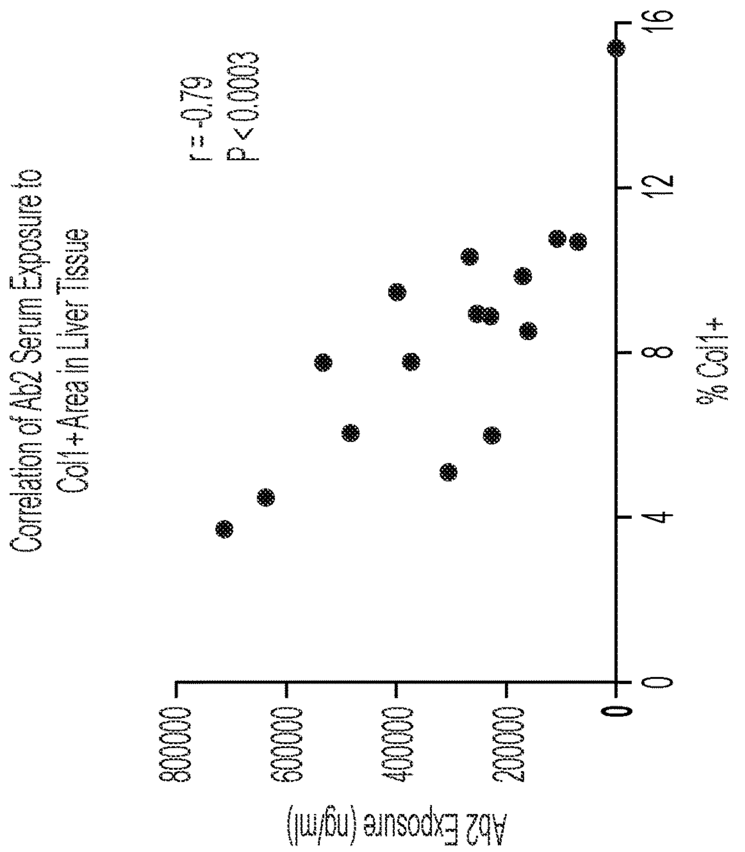
FIG. 8G is a graph that shows a correlation between Ab2 exposure levels and reduced α-Col1 levels.

Stained slides were sent to HistoTox Labs for imaging with an Aperio AT2 whole slide scanner and collagen staining was analyzed using Visiopharm image analysis software. Regions of interest (ROI) were selected by digitally tracing the tissue perimeter, marking each region for analysis. Tissue regions exhibiting folds or tears were excluded from analysis. Total collagen positive area was measured using an intensity-based thresholding algorithm which classified each pixel of the image as high positive, medium positive, low positive, or negative staining area. Total high, medium, and low pixel areas were summed together as a single positive value and divided by the total analyzed area of the tissue, resulting in the percentage of collagen positive area in the tissue. As shown in FIG. 8F, animals undergoing 15 mg/kg treatment with Ab2 had less total collagen I positive area than control CDHFD animals. In FIG. 8G, Ab2 treated animals showed an inverse correlation between their end-of-study exposure levels and their collagen IHC positive area; animals with high exposure showed much less collagen content by IHC, indicating lower levels of fibrosis in the liver.

Example 7: Inhibition of TGFβ Signaling by Anti-proTGFβ1 Antibodies in a $CCl_4$ Model of Liver Fibrosis Carbon tetrachloride ($CCl_4$) treatment of mice is a well-characterized model of liver fibrosis. In this model, Balb/C mice were dosed intraperitoneally (i.p.) twice weekly with 2.5 μl of a 20% $CCl_4$ solution in corn oil per gram body weight. This $CCl_4$ dosing was maintained throughout the duration of the study (6 weeks). After two weeks of $CCl_4$ dosing, dosing with test articles started. Mice were dosed i.p. with either twice weekly doses of 15 mg/kg, 5 mg/kg or 1.5 mg/kg of Ab2 or Ab3 twice a week (i.e., 30, 10, or 3 mg/kg/week), with twice weekly 5 mg/kg (10 mg/kg/week) doses of the pan-TGFβ antibody 1D11, or with twice weekly doses of 15 mg/kg (30 mg/kg/week) of a control IgG antibody. After 6 weeks of $CCl_4$ dosing (4 weeks of antibody treatment), mice were sacrificed and liver tissue was collected.

Figure 9:
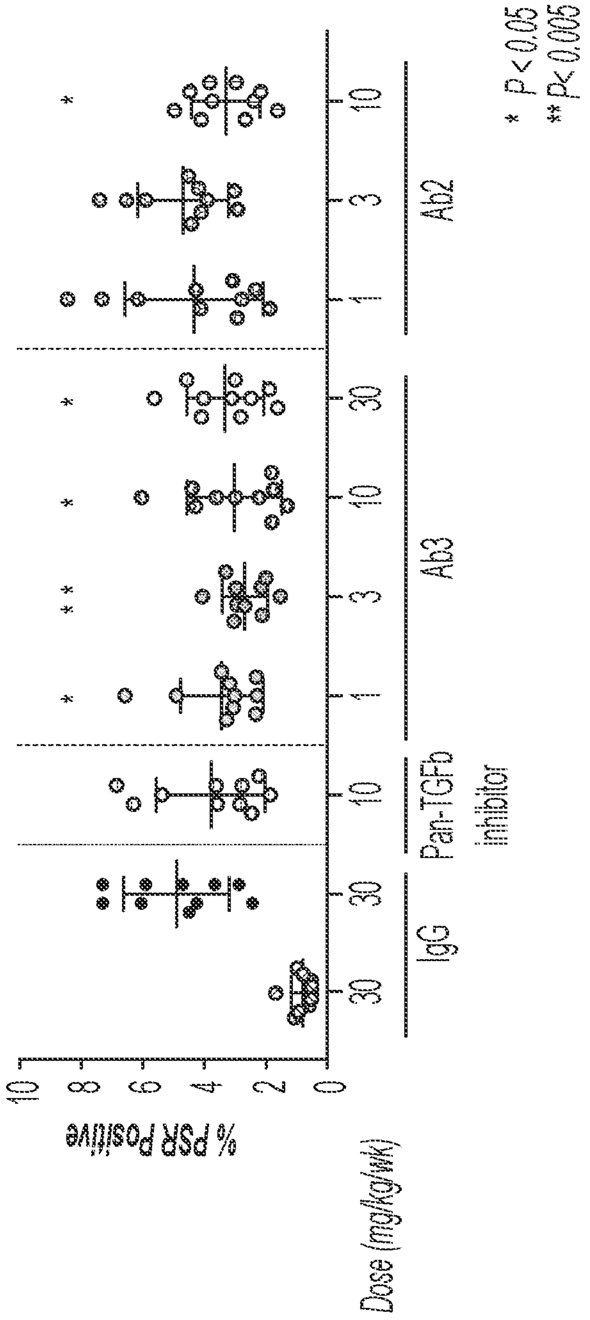
FIG. 9 is a graph that shows the effect of Ab3 and Ab2 on picrosirius red staining (PRS) in a CCL4 mouse model of liver fibrosis.

The hydroxyproline assay (see description above) was used to measure fibrosis in liver lysates from this study. FIG. 9 shows the results of this assay, in which treatment with all doses of Ab3 or with the high (15 mg/kg) dose of Ab2 showed a statistically significant reduction in liver hydroxyproline. Mice treated the lower doses of Ab2 (5 or 1.5 mg/kg) showed a trend towards reduced liver hydroxyproline, but these differences are not statistically significant due to experimental variation in this model. The treatment effect of both TGFβ1-specific antibodies was similar to that of the pan-TGFβ inhibitor 1D11.

Example 8. Determination of Binding Regions for Ab3 and Ab2 by HDX-MS

Hydrogen/Deuterium exchange mass spectrometry (HDX-MS) is a widely used technique for exploring protein conformation in solution. HDX-MS methodology is described, for example, in Wei et al., Drug Discov Today. 2014 January; 19 (1): 95-102; Engen JR. Anal Chem. 2009 Oct. 1;81 (19): 7870-5, incorporated by reference in its entirety herein. HDX-MS relies on the exchange of the protein backbone amide hydrogens with deuterium in solution. The backbone amide hydrogens involved in weak hydrogen bonds or located at the surface of the protein may exchange rapidly while those buried in the interior or those involved in stabilizing hydrogen bonds exchange more slowly. Based on the mass difference between hydrogen (1 Da) and deuterium (2 Da), which can be detected for example by mass spectrometry, the H-D exchange can be monitored over time. Thus, by measuring HDX rates of backbone amide hydrogens, one can obtain information on protein dynamics, conformation and protein-protein interaction such as antibody-antigen-binding.

To gain insights for purposes of epitope mapping, HDX-MS was carried out to determine the binding regions of proTGFβ1 involved in Ab3-antigen-binding (e.g., where in the proTGFβ complex Ab3 was binding). In HDX-MS, the regions of an antigen that are tightly bound by an antibody are protected from proton exchange, due to protein-protein interaction, while regions that are exposed to solvent can readily undergo proton exchange. Based on this, binding regions within the antigen, which are protected by the specific binding of the antibody, were identified.

A modified proTGFβ1 complex (proTGFβ1 C4S) in which the cysteine residue at position 4 of the pro-domain has been substituted with a serine residue (described in WO 2014/182676) was used to assess Ab3 binding by HDX-MS. It is known that the cysteines from a proTGFβ1 homodimer are involved in forming covalent bonds with a presenting molecule, such as an LTBP, GARP and LRRC33. A 1:3 molar ratio of proTGFβ1 to Ab3 Fab was used in the experiment. The result is summarized in FIG. 10A. As shown, there are at least three regions (labeled regions 1, 2 and 3 in FIG. 10A) in proTGFβ1 where H/D exchange was significantly protected upon binding to Ab3 Fab suggesting that these regions or portions thereof may represent binding region(s) of Ab3 to proTGFβ1. Region 1 (SQGEVPPG-PLPEAVLALYNST; SEQ ID NO: 258) resulted in the highest H/D exchange among all peptic peptides resolved in proTGFβ1 and is mapped onto the latency lasso within the prodomain of proTGFβ1. The other two regions that showed significant H/D exchange protections are region 2 (LREAVPE; SEQ ID NO: 259) and region 3 (YHANFCLG; SEQ ID NO: 260) and are mapped onto the α3 helix within the prodomain and part of the growth factor of proTGFβ1, respectively. Amino acid sequence alignment of regions 1 and 2 comparing all three proTGFβ isoforms showed significant sequence diversity in these regions (see FIG. 10B) and thus provides a structural argument for the specificity of Ab3 to proTGFβ1 over the other isoforms.

Figure 10A:
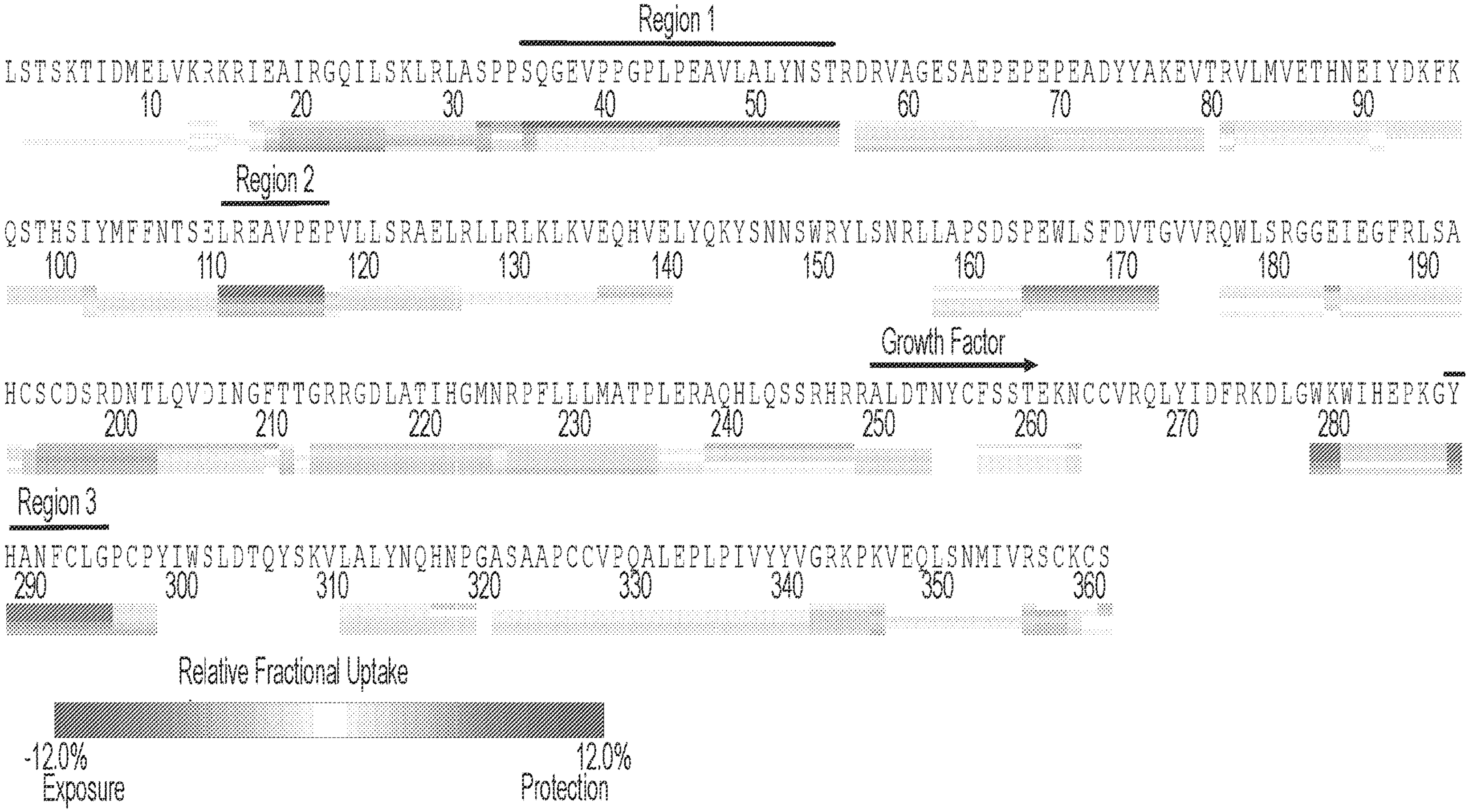
FIG. 10A provides a HDX-MS heatmap for Ab3 Fab-LTBP3: ProTGFβ1 complex.
Figure 10B:
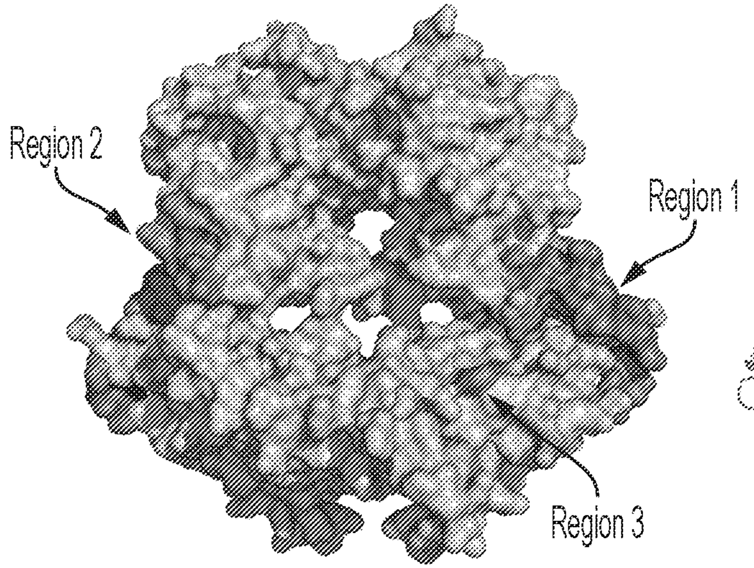
FIG. 10B shows the protected regions by Ab3 on surface and ribbon structures of proTGFβ1.
Figure 10B:
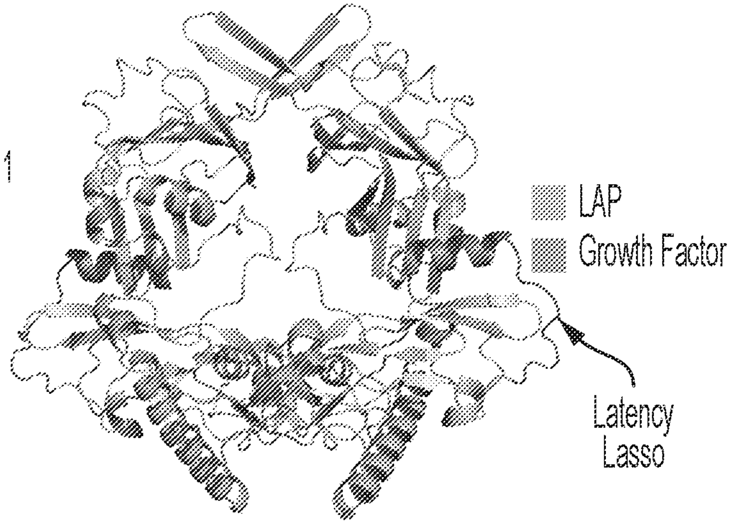
Figure 10C:
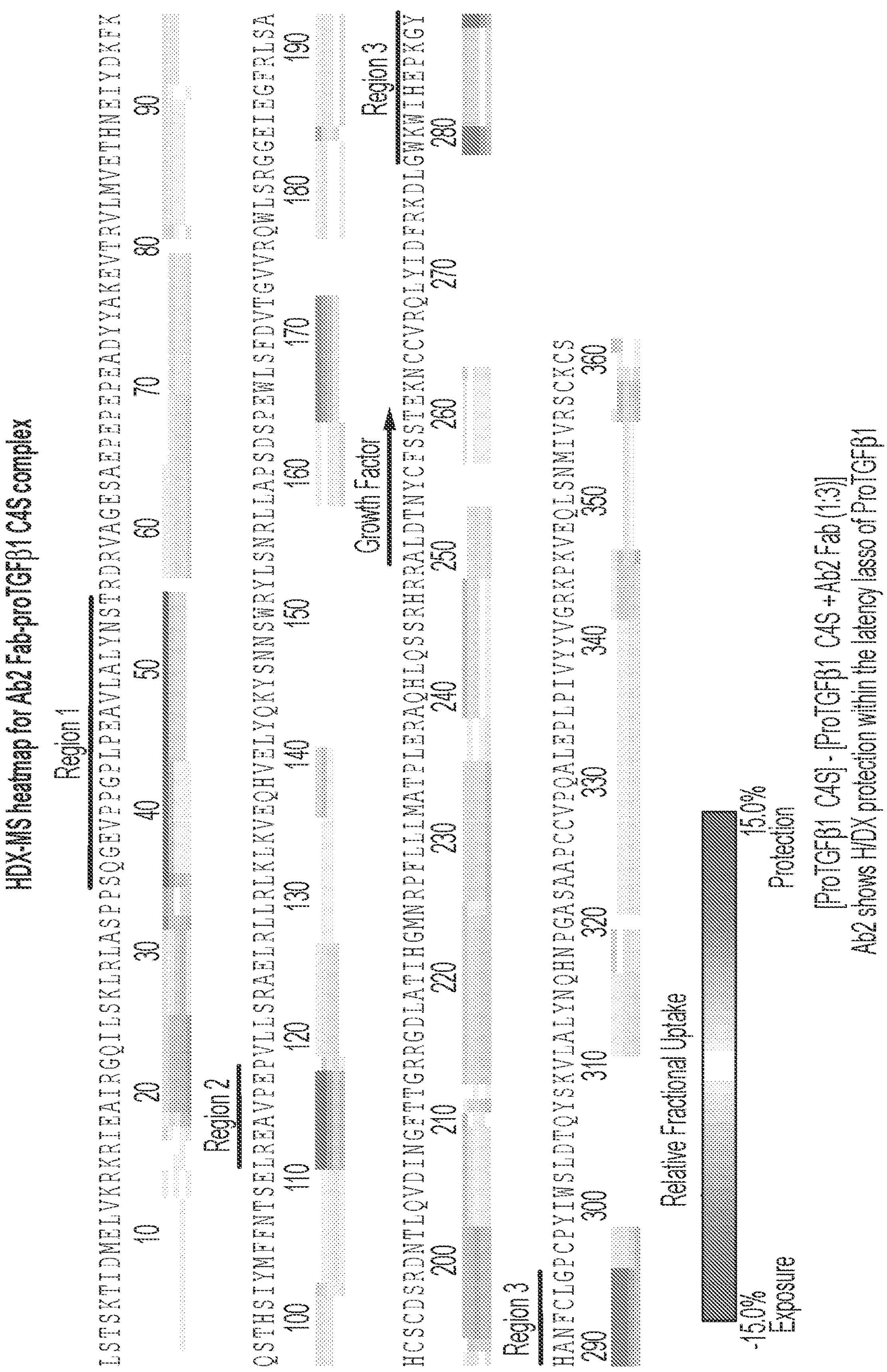
FIG. 10C provides an HDX-MS heatmap for Ab2 Fab-proTGFβ1 C4S complex.
Figure 10D:
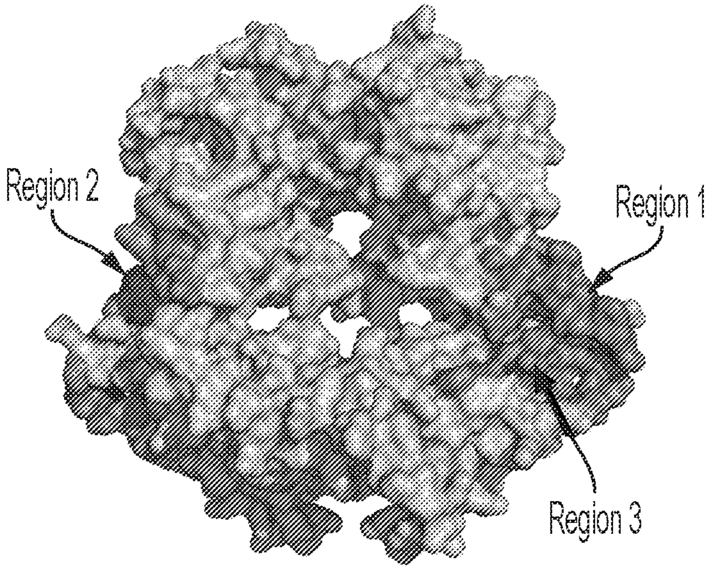
FIG. 10D shows the protected regions by Ab2 on surface and ribbon structures of proTGFβ1. Region 1 overlaps with so-called "Latency Lasso" within the prodomain of proTGFβ1, while Region 3 is within the growth factor domain. Sequence alignment among the three isoforms is also provided.
Figure 10D:
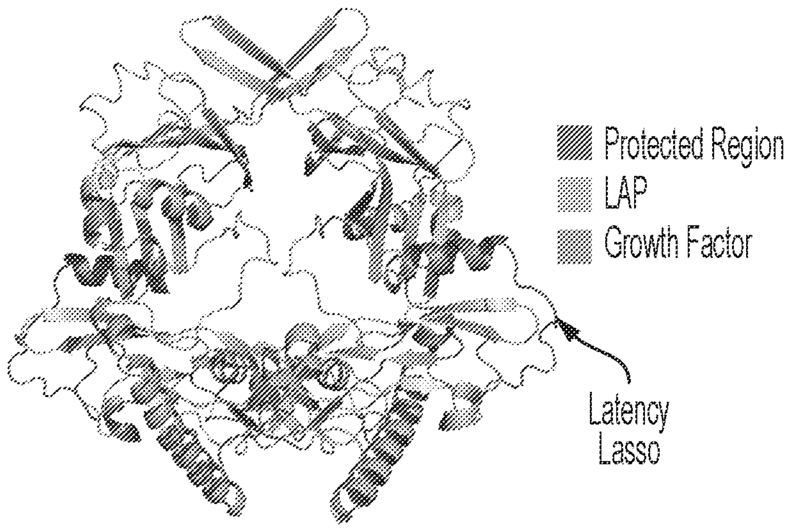

To gain further structural insights into binding mechanism of Ab2 to proTGFβ1, we performed HDX-MS on proTGFβ1 C4S with Ab2 Fab using a 1:3 molar ratio of proTGFβ1 to Ab2 Fab (see FIG. 10C). As shown in FIG. 10C, there are at least three regions in proTGFβ1 that showed significant H/D exchange protection suggesting that these regions or portions thereof may represent the binding region(s) of Ab2 in proTGFβ1. Region 1 (SPPSQGEVPPGPLPEAVLA-LYNST; SEQ ID NO: 261) showed the highest H/D exchange among all peptic peptides resolved in proTGFβ1 and is mapped onto the latency lasso within the prodomain of proTGFβ1. Regions 2 (LREAVPE; SEQ ID NO: 259) and 3 (WKWIHEPKGYHANFCLG; SEQ ID NO: 262) are mapped onto the α3 helix within the prodomain and part of the growth factor of proTGFβ1, respectively. Amino acid sequence alignment of regions 1 and 2 comparing all proTGFβ isoforms −1. −2, and −3 showed sequence diversity in these regions (see FIG. 10D) and may provide the structural argument for the specificity of Ab2 to proTGFβ1 over the other isoforms

Example 9: Determination of proTGFβ1 Binding Regions for Ab2 by X-Ray Crystallography The epitope of Ab2 in proTGFβ1 was further elucidated by solving the crystal structure of the ternary complex of human proTGFβ1: Ab2-Fab: AbX-Fab. In this work, an uncleavable human proTGFβ1 C4S/R249A variant was used that spans residues 30-390 based on the full-length sequence of human proTGFβ1 (Uniprot ID P01137). The numbering system that will be used for the rest of this document will designate position 1 as the first amino acid residue after the removal of the signal sequence for proTGFβ isoforms. The C4S mutation renders proTGFβ1 not capable of covalent crosslinking to any known presenting molecules, e.g., LTBPs and GARP, while the R249A renders proTGFβ1 resistant to proprotein convertase/furin protease cleavage, thus maintaining proTGFβ1 in its uncleaved, proprotein form. ProTGFβ1 C4S/R249A was co-expressed with C-terminally 6×-His tagged (SEQ ID NO: 302) Ab2-Fab in kifunensine-treated expi293 mammalian expression system to reduce N-linked glycosylation events. The proTGFβ1 C4S/R249A: Ab2-Fab was affinity purified, treated with endoglycosidase H and purified by gel filtration. The proTGFβ1 C4S/R249A: Ab2-Fab complex was then incubated with AbX-Fab to generate the ternary complex. The AbX Fab in this context was used as an auxiliary protein, which acts as a crystallization chaperone to increase the probability of obtaining protein crystals.

Crystallization experiments were performed at room temperature in a sitting drop format. Crystals suitable for X-ray analysis were obtained using 18% polyethylene glycol 6000, 0.2 M $MgCl_2$, 0.1 M sodium acetate buffer, pH 5.0. The crystals were cryoprotected by soaking in the mother liquor supplemented with 25% glycerol and flashed frozen in liquid nitrogen. X-ray diffraction data were collected at the SER-CAT beamline 22-ID at the Advanced Photon Source (APS) at the Argonne National Laboratory (ANL) using a Dectris Eiger 16M detector. The diffraction images were processed with X-ray Detector Software (XDS) in space group C2221 with an asymmetric unit containing one half of a 2:2:2 complex. The structure of the ternary complex was solved by molecular replacement using Phaser. Ab2-Fab was modeled using Fab structure of the same human germlines IGKV1-39/IGHV3-23 (PDB ID 5119). The AbX-Fab was modeled using the Fab structure of human germlines IGHV1/IGKV3-11 (PDB ID 5116). The core of the proTGFβ1 monomer was modeled using the previously reported crystal structure of proTGFβ1 (PDB ID 5VQP). The structure was manually rebuilt with Coot and refined using Refmac5 to a final resolution of 3.4 Å with $R_{work}$ and $R_{free}$ values 21% and 29%, respectively.

Figure 11:
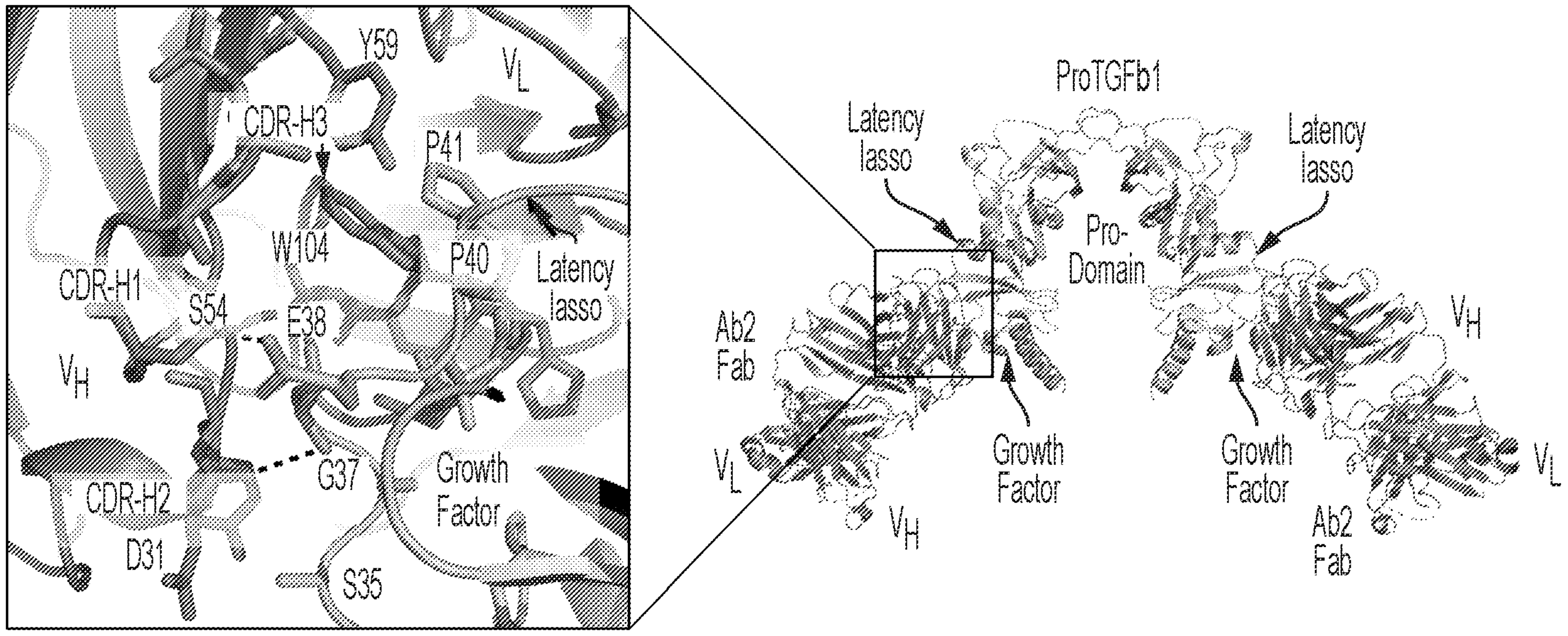
FIG. 11 provides the crystal structure of Ab2 Fab bound to proTGFβ1 and shows contact residues on proTGFβ1 and Ab2.

In the present crystal form, proTGFβ1 exists as a homodimer that sits on the crystallographic two-fold axis so that the asymmetric unit contains one proTGFβ1 monomer and two Fabs, while the entire complex has a 2:2:2 stoichiometry (FIG. 11). Ab2-Fab and AbX-Fab do not compete for binding proTGFβ1. Consistent with this fact, their binding epitopes on proTGFβ1 are spatially distant. Ab2-Fab binds a linear epitope formed by residues 35-43 within the proline-rich loop of proTGFβ1 within the latency lasso. Pro40 and Pro41 of the proTGFβ1 are particularly important for binding as they are engaged in the pi stacking interactions with Trp104 and Tyr59 in the H-CDR3 and H-CDR1, respectively, of the Ab2-Fab. There are also relevant interactions in the growth factor residues (R274, K280, H283) with the heavy (S101, G102 H103) and light (Y49) chain residues of Ab2 Fab. Finally, sequence alignment of the epitope region in the latency lasso across TGFβ family showed significant diversity, which affords the exquisite specificity of Ab2 over other relevant members in the TGFβ family, e.g., TGFβ2, TGFβ3. The epitope and paratope for the interaction between proTGFβ1 and Ab2-Fab are listed in Table 24.

TABLE 24

Epitope and paratope for the interactions between proTGFβ1 and Ab2-Fab. Letters h and l denote heavy and light chains, respectively

| ProTGFβ1 (Epitope) | Ab2 (Paratope) |
|---|---|
| S35 | D31h |
| G37 | D31h, A33h |
| E38 | S54h |
| V39 | G102h |
| P40 | W104h, Y59h |
| P41 | W104h, Y59h |
| G42 | T91l, Y92l, Y32l |
| P43 | Y92l, Y32l |
| R274 | Y49l |
| K280 | S101h, H103h |
| H283 | G102h |

Example 10. Ab3 and Ab2 Exhibit Reduced Toxicity as Compared to the ALK5 Kinase Inhibitor LY2109761 and a Pan-TGFβ antibody To evaluate the potential in vivo toxicity of Ab3 and Ab2, as compared to the small molecule TGF-β type I receptor (ALK5) kinase inhibitor LY2109761 (CAS No. 700874-71-1) and to a pan-TGFβ antibody (hIgG4; neutralizing all three TGFβ growth factors), toxicity studies were performed in rats. The selection of rat as the species for this toxicology study was based on the previous reports that rats are more sensitive to TGFβ inhibition as compared to mice. Similar toxicities observed in rats have been also observed in other mammalian species, such as dogs, non-human primates, as well as humans.

Female Fischer344 rats (FIGS. 12A and 12B) or Sprague Dawley (SD) rats were administered with either Ab3 at 3 mg/kg (1 group, n=5), at 10 mg/kg (1 group, n=5), at 30 mg/kg (1 group, n=5), or at 100 mg/kg (1 group, n=5); Ab2 at 10 mg/kg (1 group, n=5), at 30 mg/kg (1 group, n=5), or at 100 mg/kg (1 group, n=5); pan-TGFβ antibody at 3 mg/kg (1 group, n=5), at 10 mg/kg (1 group, n=5), at 30 mg/kg (1 group, n=5), or at 100 mg/kg (1 group, n=5); LY2109761 at 200 mg/kg (1 group, n=5) or 300 mg/kg (1 group, n=5); or PBS (pH 7.4) vehicle control (1 group, n=5).

Animals receiving pan-TGFβ antibody were dosed once intravenously (at day 1) at a volume of 10 ml/kg and sacrificed at day 8 and necropsies performed. Animals receiving either Ab3 or Ab2 were dosed once weekly for 4 weeks at a volume of 10 ml/kg. Animals receiving LY2109761 were dosed by oral gavage once daily for five or seven days. Animals were sacrificed and necropsies performed.

Figure 12A:
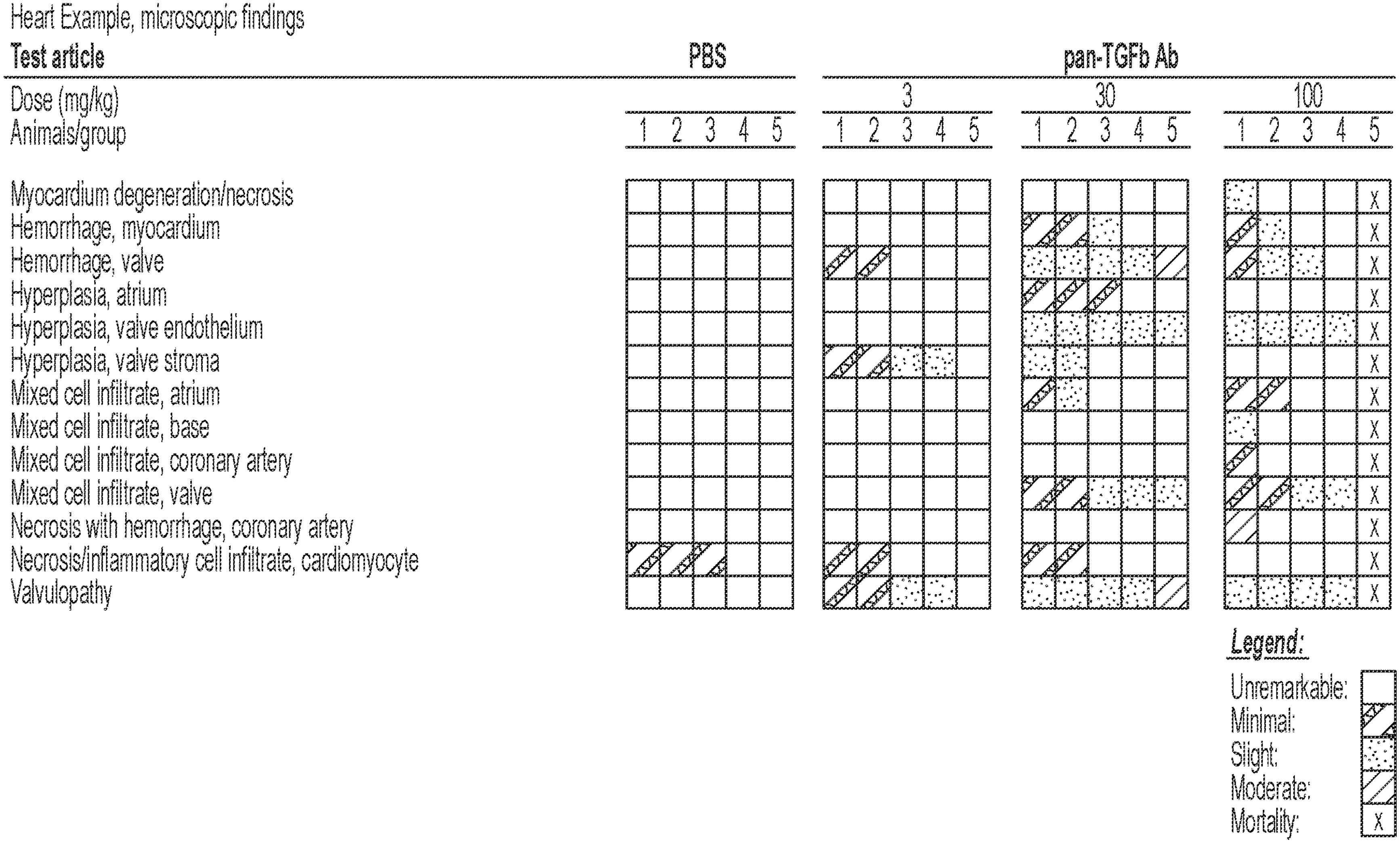
FIG. 12A depicts microscopic heart findings from a pan-TGFβ antibody from a 1-week rat toxicology study.

As shown in FIG. 12A and Table 25, animals administered pan-TGFβ antibody exhibited similar toxicities to those described in animals administered LY2109761 as described in International Pat. Pub. No. WO/2018/129329, which is incorporated herein by reference in its entirety. Specifically, animals administered>3 mg/kg of the pan-TGFβ antibody exhibited heart valve findings (e.g., valvulopathy) similar to those described in the animals administered LY2109761. Animals administered≥30 mg/kg of the pan-TGFβ antibody exhibited atrium findings similar to those described in animals administered LY2109761. Animals administered 100 mg/kg of the pan-TGFβ antibody exhibited myocardium findings similar to those described in animals administered LY2109761, and animals administered 30 mg/kg of pan-TGFβ antibody had hemorrhage in the myocardium. One animal administered 100 mg/kg of the pan-TGFβ antibody had moderate intramural necrosis with hemorrhage in a coronary artery, which was associated with slight perivascular mixed inflammatory cell infiltrates. Bone findings in animals administered the pan-TGFβ antibody and LY2109761 consisted of macroscopic abnormally shaped sternum and microscopic increased thickness of the hypertrophic zone in the endplate of the sternum and physis of the femur and tibia. Subsequent studies in a different rat strain (SD rats) with LY2109761 and pan-TGFβ as shown in FIG. 12C also demonstrated similar toxicities.

TABLE 25

Microscopic Heart Findings in Animals Receiving the Pan-TGFβ Antibody

| | Pan-TGFβ Antibody | | | |
|---|---|---|---|---|
| Dose Level (mg/kg/day) | 0 | 3 | 30 | 100 |
| Heart<br>Heart valves | | | | |
| Valvulopathy | | | | |
| Minimal | 0 | 2 | 0 | 0 |
| Slight | 0 | 2 | 4 | 5 |
| Moderate | 0 | 0 | 1 | 0 |

TABLE 25-continued

Microscopic Heart Findings in Animals Receiving the Pan-TGFβ Antibody

| | Pan-TGFβ Antibody | | | |
|---|---|---|---|---|
| Dose Level (mg/kg/day) | 0 | 3 | 30 | 100 |
| Atrium | | | | |
| Infiltrate, mixed cell | | | | |
| Minimal | 0 | 0 | 1 | 2 |
| Slight | 0 | 0 | 1 | 1 |
| Hyperplasia, endothelium | | | | |
| Minimal | 0 | 0 | 3 | 1 |
| Hemorrhage | | | | |
| Minimal | 0 | 0 | 1 | 0 |
| Myocardium | | | | |
| Degeneration/necrosis | | | | |
| Slight | 0 | 0 | 0 | 2 |
| Hemorrhage | | | | |
| Minimal | 0 | 0 | 2 | 1 |
| Slight | 0 | 0 | 1 | 1 |
| Infiltrate, mixed cell, base | | | | |
| Slight | 0 | 0 | 0 | 1 |
| Coronary artery | | | | |
| Necrosis with hemorrhage | | | | |
| Moderate | 0 | 0 | 0 | 1 |
| Infiltrate, mixed cell, perivascular | | | | |
| Slight | 0 | 0 | 0 | 1 |

Figure 12B:
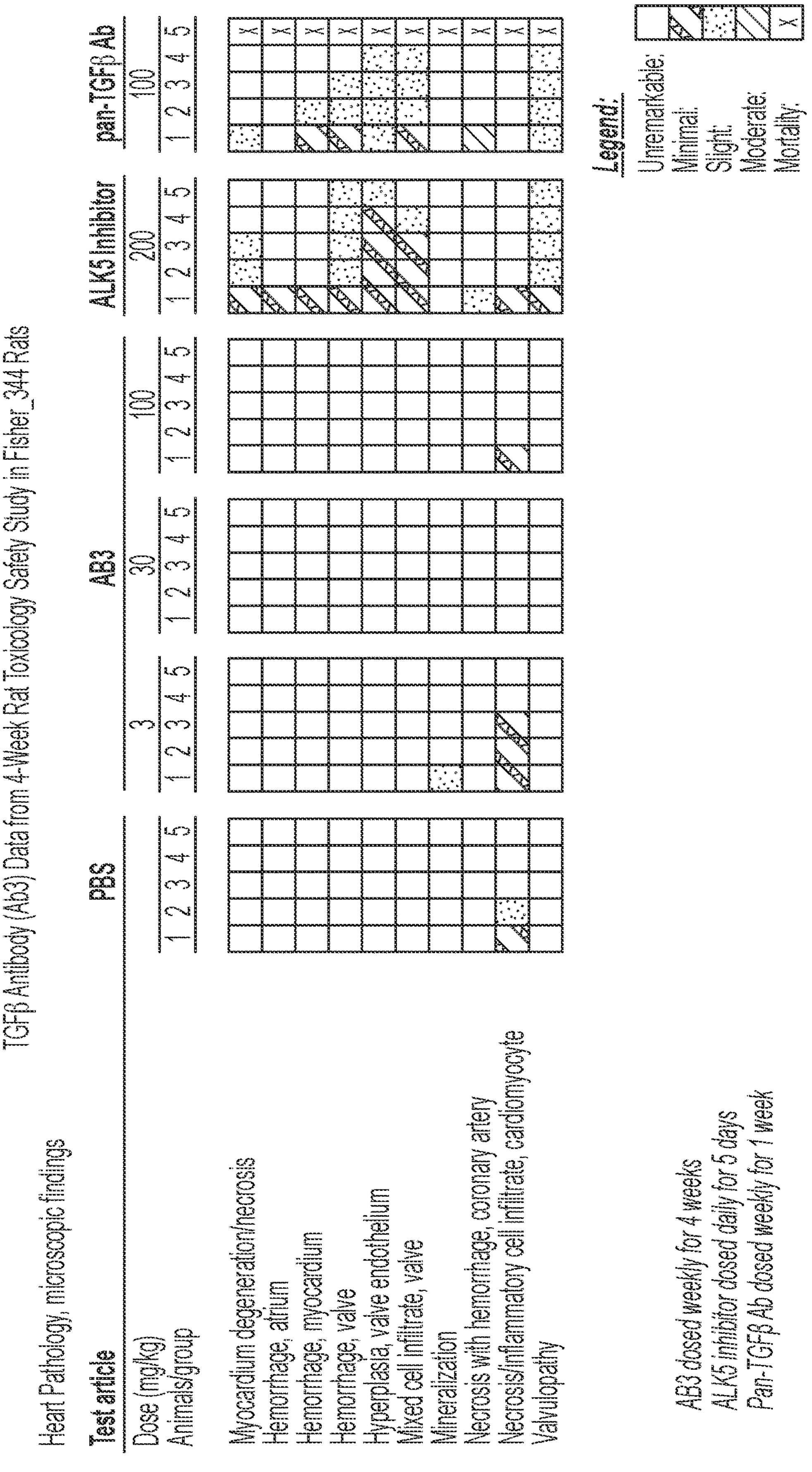
FIG. 12B depicts microscopic heart findings from Ab3 as compared to an ALK5 inhibitor or pan-TGFβ antibody from a 4-week rat toxicology study.
Figure 12C:
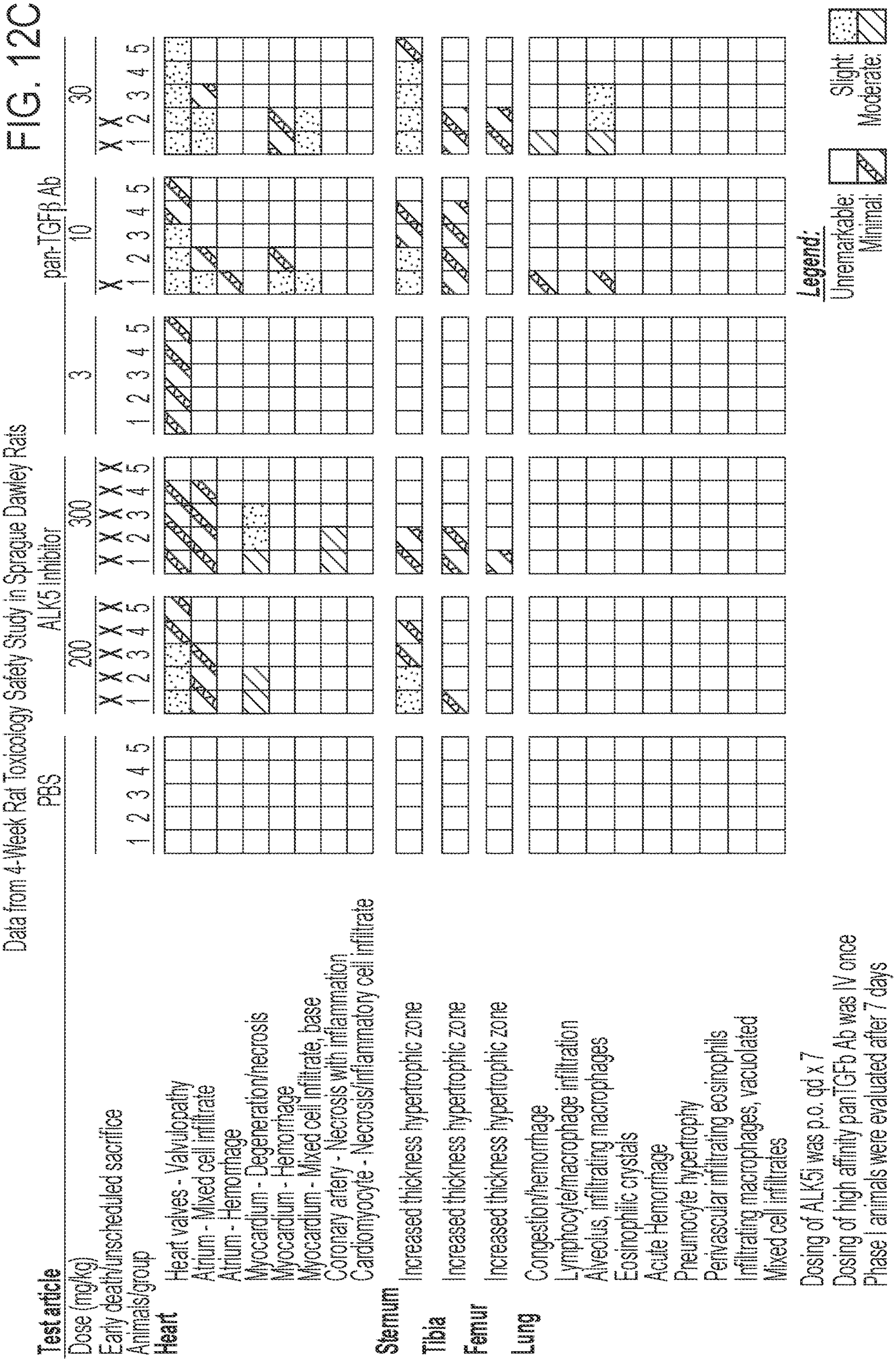
FIGS. 12C and 12D depict microscopic heart, bone, and lung, findings from Ab3 and Ab2 as compared to an ALK5 inhibitor or pan-TGFβ antibody from a 4-week rat toxicology study.
Figures 1, 12D:
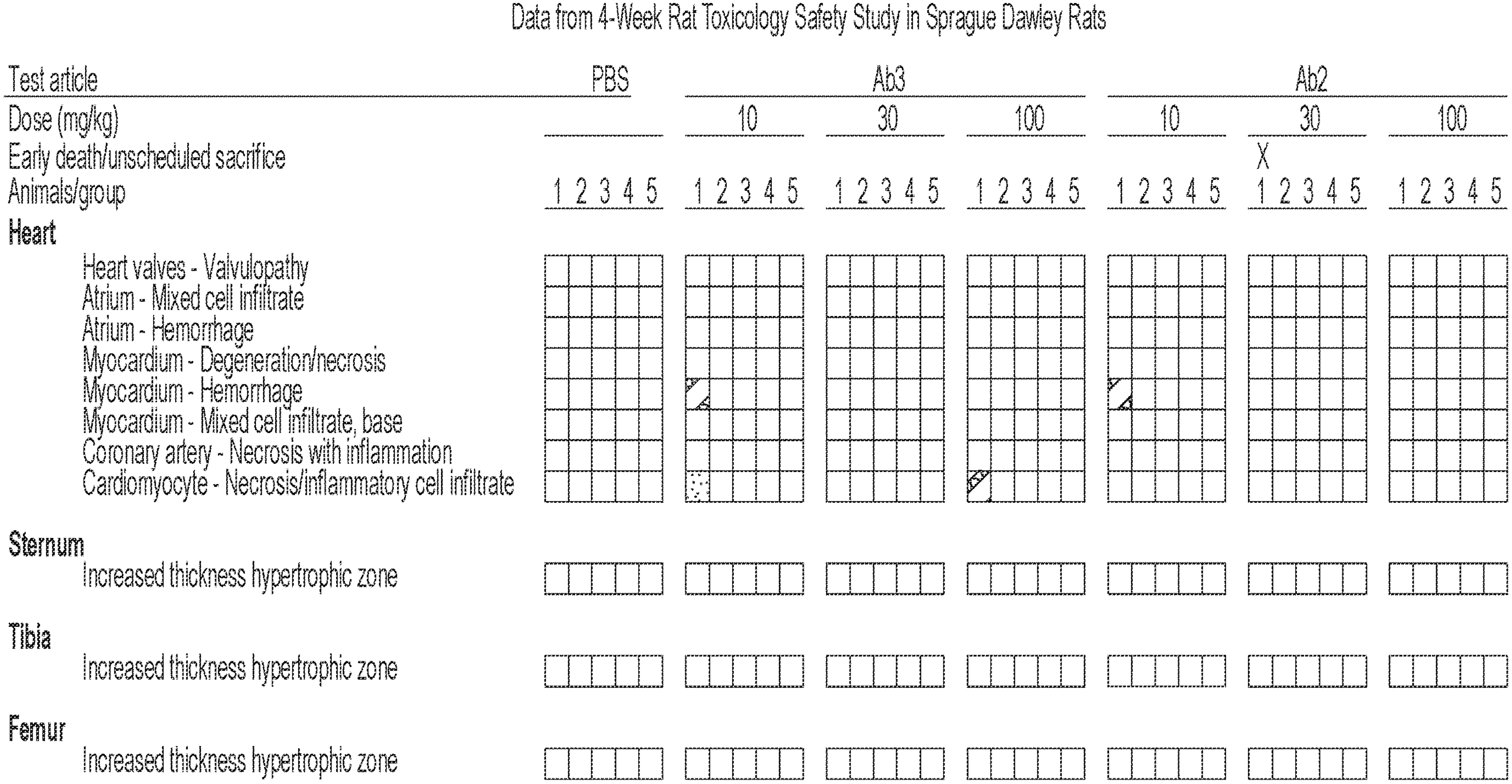
Figures 2, 12D:
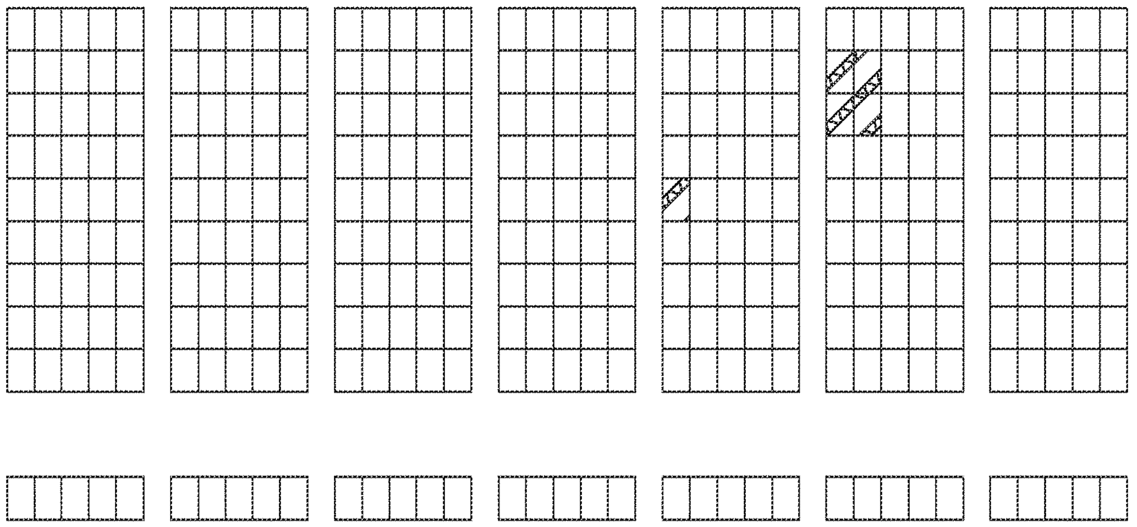

However, unlike pan-TGFβ antibody or LY2109761-treated animals, animals administered Ab3 or Ab2 for 4 weeks showed no observable test article-related toxicity in either rat strain, and the NOAEL for both Ab3 and Ab2 was 100 mg/kg weekly dose, which was the highest dose tested (FIGS. 12B and 12D).

In summary, animals treated with Ab3 or Ab2 at all doses tested (10 mg/kg, 30 mg/kg or 100 mg/kg) over a period of 4 weeks exhibited no toxic effects over background in any of the following parameters: myocardium degeneration or necrosis, atrium hemorrhage, myocardium hemorrhage, valve hemorrhage, valve endothelium hyperplasia, valve stroma hyperplasia, mixed inflammatory cell infiltrates in heart valves, mineralization, necrosis with hemorrhage in coronary artery, necrosis with inflammation in aortic root, necrosis or inflammatory cell infiltrate in cardiomyocyte, and valvulopathy. The NOAEL for both Ab3 (in Fischer rats and in SD rats) and Ab2 (in SD rats) was a weekly dose of 100 mg/kg, the highest dose tested. Thus, treatment with isoform-specific inhibitors of TGFβ1 activation surprisingly resulted in significantly improved safety profiles, e.g., reduced mortality, reduced cardiotoxicity, and reduced bone findings as compared to pan-TGFβ inhibition.

Example 11: Bioinformatic Analysis of Relative Expressions of TGFβ1, TGFβ2 and TGFβ3

Figure 13A:
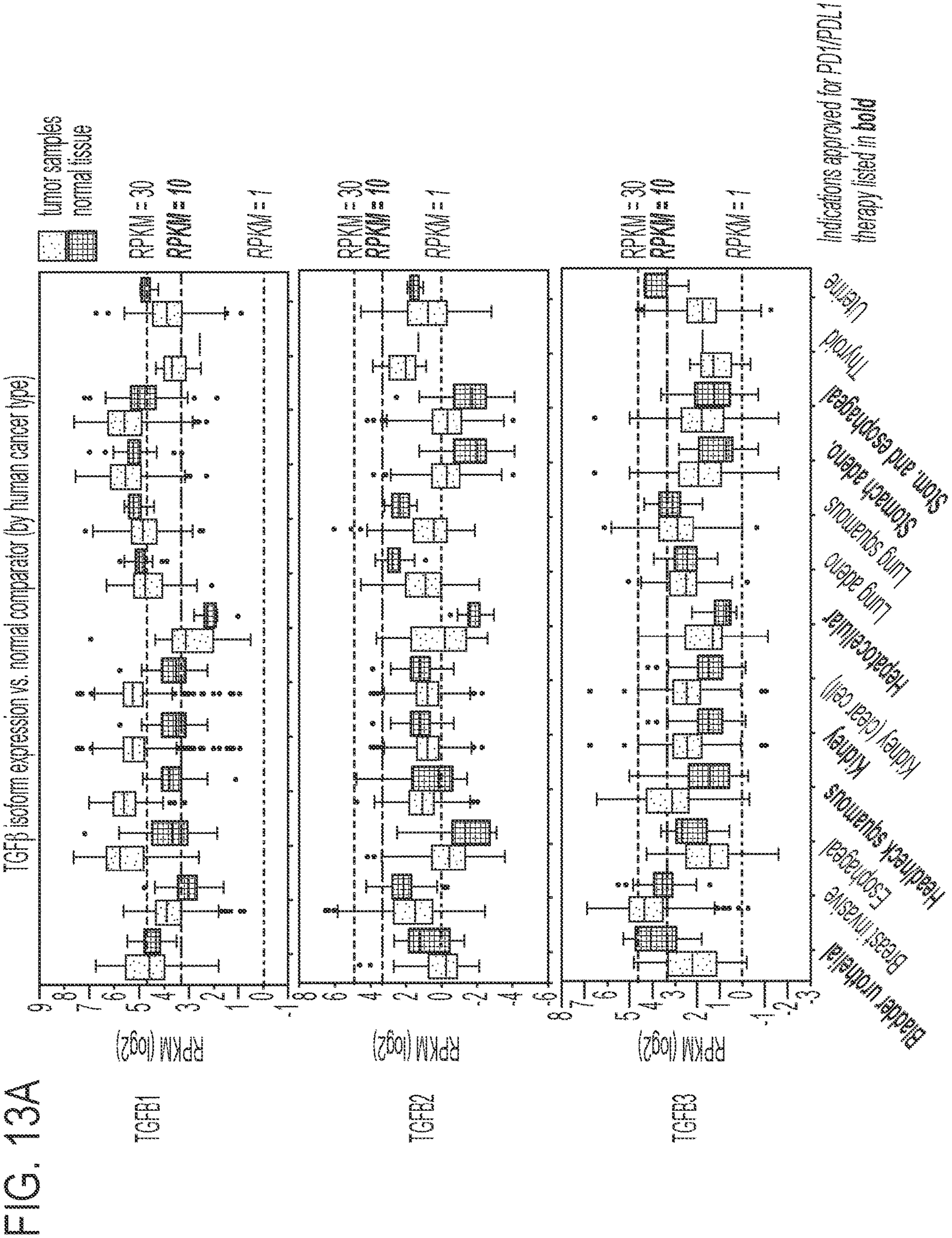
FIGS. 13A-13D provide relative expression of TGFβ isoforms.

To evaluate the expression of TGFβ isoforms in cancerous tumors, gene expression (RNAseq) data from publically available datasets was examined. Using a publically available online interface tool (Firebrowse) to examine expression of TGFβ isoforms in The Cancer Genome Atlas (TCGA), the differential expression of RNA encoding TGFβ isoforms in both normal and cancerous tissue were first examined. All tumor RNAseq datasets in the TCGA database for which there were normal tissue comparators were selected, and expression of the TGFβ1, TGFβ2, and TGFβ3 genes was examined (FIG. 13A). Data from the Firebrowse interface are represented as log 2 of reads per kilobase million (RPKM).

These data suggest that in most tumor types (gray), TGFβ1 is the most abundantly expressed transcript of the TGFβ isoforms, with log 2 (RPKM) values generally in the range of 4-6, vs. 0-2 for TGFβ2 and 2-4 for TGFβ3. We also note that in several tumor types, the average level of both TGFβ1 and TGFβ3 expression are elevated relative to normal comparator samples (black), suggesting that increased expression of these TGFβ isoforms may be associated with cancerous cells. Because of the potential role of TGFβ signaling in suppressing the host immune system in the cancer microenvironment, we were interested to note that TGFβ1 transcripts were elevated in cancer types for which anti-PD-1 or anti-PD-L1 therapies are approved—these indications are labeled in gray on FIG. 13A.

Note that while RPKM>1 is generally considered to be the minimum value associated with biologically relevant gene expression (Hebenstreit et al., *Molecular Systems Biology* (2011) 7:497; Wagner et al., *Theory Biosci.* 2013 September;132 (3): 159-64, however for subsequent analyses, more stringent cutoffs of RPKM (or of the related measure FPKM (see Conesa et al., *Genome Biology* vol. 17:13 (2016)))>10 or >30 to avoid false positives were used. For comparison, all three of those thresholds are indicated on FIG. 13A.

The large interquartile ranges in FIG. 13A indicate significant variability in TGFβ isoform expression among individual patients. To identify cancers where at least a subset of the patient population have tumors that differentially express the TGFβ1 isoform, RNAseq data from individual tumor samples in the TCGA dataset was analyzed, calculating the number of fragments per kilobase million (FPKM). RPKM and FPKM are roughly equivalent, though FPKM corrects for double-counting reads at opposite ends of the same transcript (Conesa et al., Genome Biology vol. 17:13 (2016)). Tumor samples were scored as positive for TGFβ1, TGFβ2, or TGFβ3 expression if the FPKM value the transcript was >30 and the fraction of patients (expressed as %) of each cancer type that expressed each TGFβ isoform were calculated (FIG. 13B).

Figure 13B:
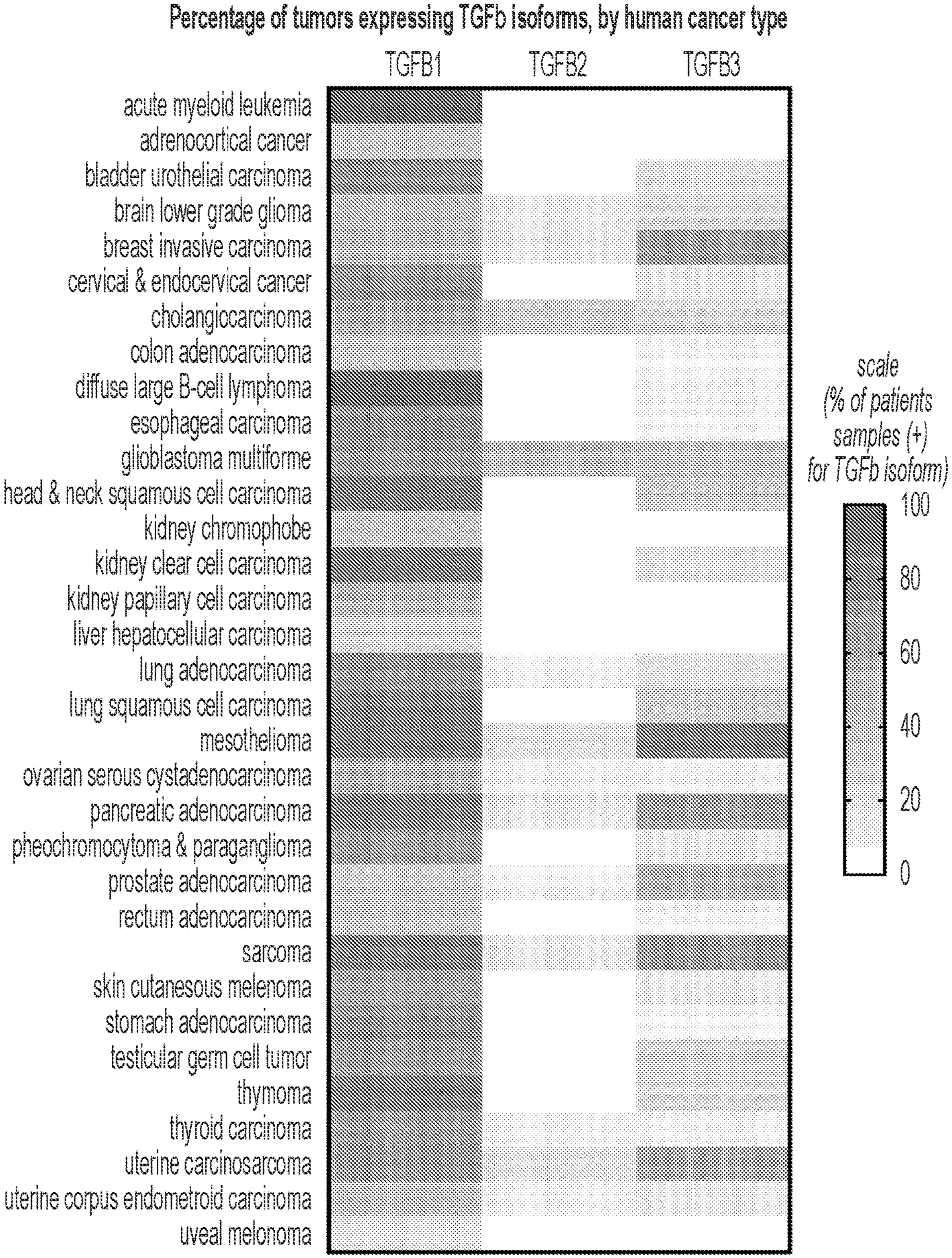
Figure 13C:
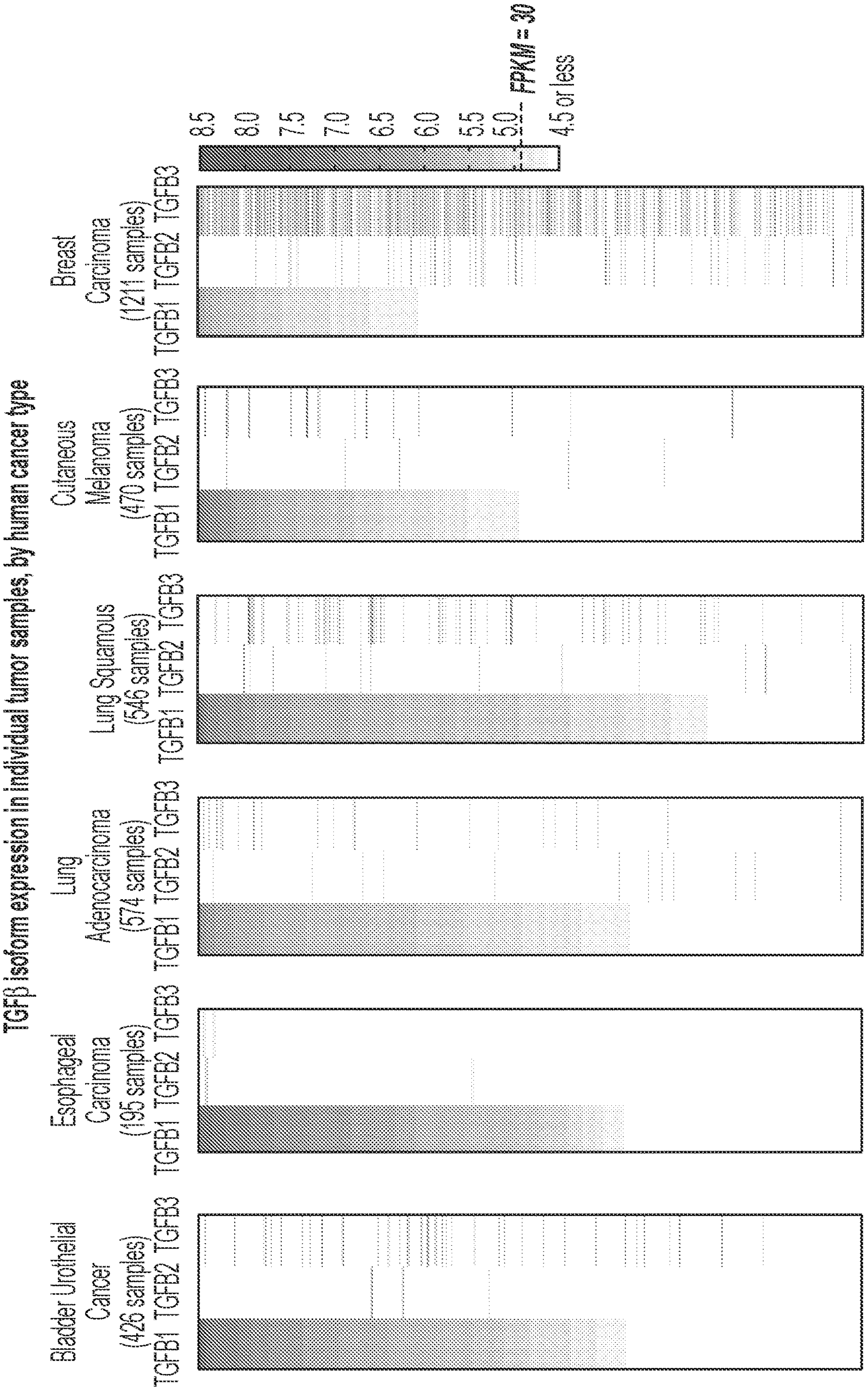

As shown in FIG. 13B, a majority of tumor types in the TGCA dataset show a significant percentage of individual samples that are TGFβ1 positive, with some cancer types, including acute myeloid leukemia, diffuse large B-cell lymphoma, and head and neck squamous cell carcinoma, expressing TGFβ1 in more than 80% of all tumor samples. Consistent with the data in FIG. 13A, fewer cancer types are positive for TGFβ2 or TGFβ3, though several cancers show an equal or greater percentage of tumor samples that are TGFβ3 positive, including breast invasive carcinoma, mesothelioma, and sarcoma. These data suggest that cancer types may be stratified for TGFβ isoform expression, and that such stratification may be useful in identifying patients who are candidates for treatment with TGFβ isoform-specific inhibitors.

To further investigate this hypothesis, the log 2 (FPKM) RNAseq data from a subset of individual tumor samples was plotted in a heat map (FIG. 13C), setting the color threshold to reflect FPKM>30 as a minimum transcript level to be scored TGFβ isoform-positive.

Each sample is represented as a single row in the heat map, and samples are arranged by level of TGFβ1 expression (highest expression levels at top). Consistent with the analysis in FIG. 13B, a significant number of samples in each cancer type are positive for TGFβ1 expression. However, this representation also highlights the fact that many tumors express solely TGFβ1 transcripts, particularly in the esophageal carcinoma, bladder urothelial, lung adenocarcinoma, and cutaneous melanoma cancer types. Interestingly, such TGFβ1 skewing is not a feature of all cancers, as samples from breast invasive carcinoma show a much larger number of samples that are TGFβ3-positive than are TGFβ1 positive. Nonetheless, this analysis indicates that the $\beta_1$ isoform is the predominant, and in most cases, the only, TGFβ family member present in tumors from a large number of cancer patients. Taken together with data suggesting that TGFβ signaling plays a significant role in immunosuppression in the cancer microenvironment, these findings also point to the utility of TGFβ1-specific inhibition in treatment of these tumors.

Figures 1, 13D:
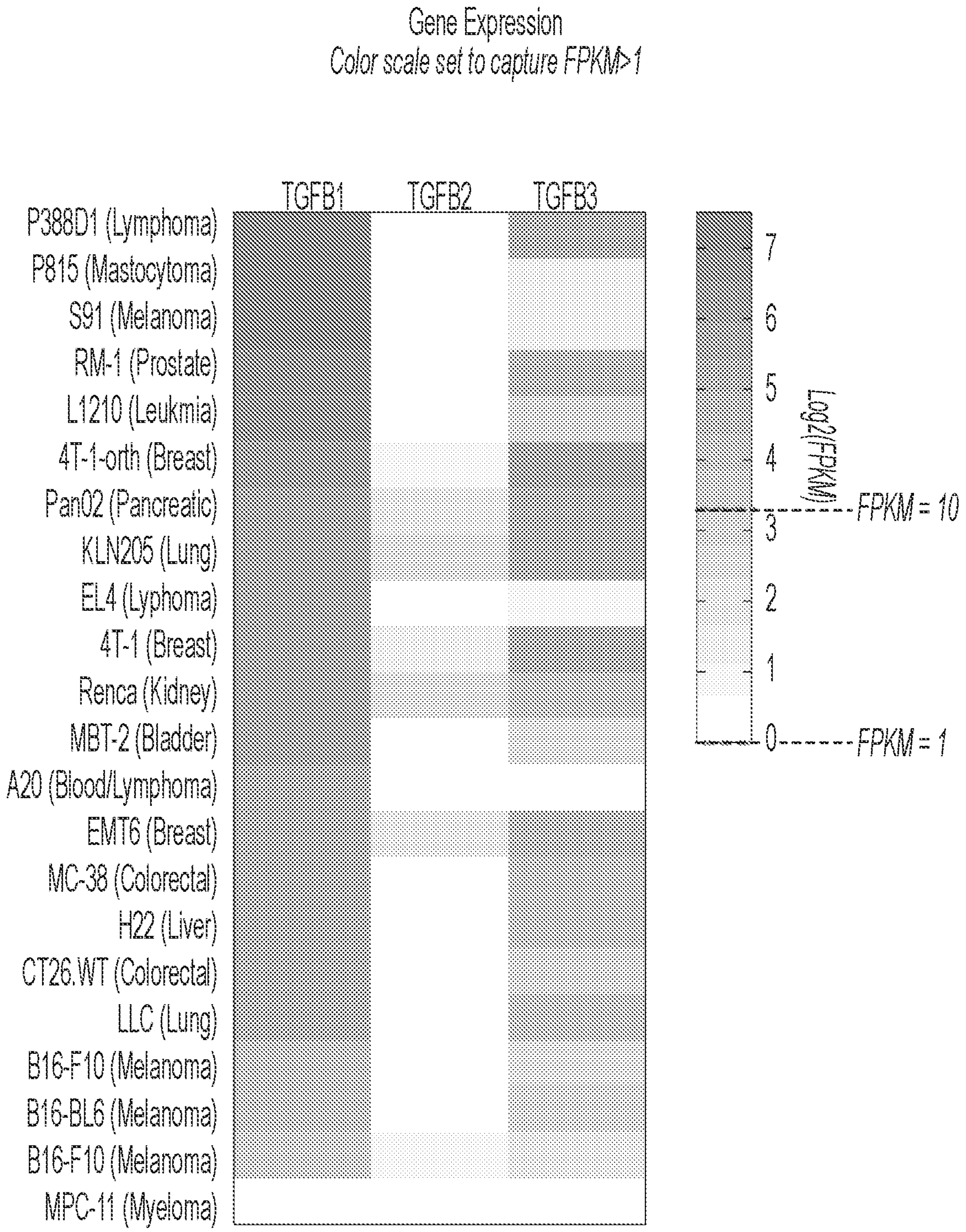
Figures 2, 13D:
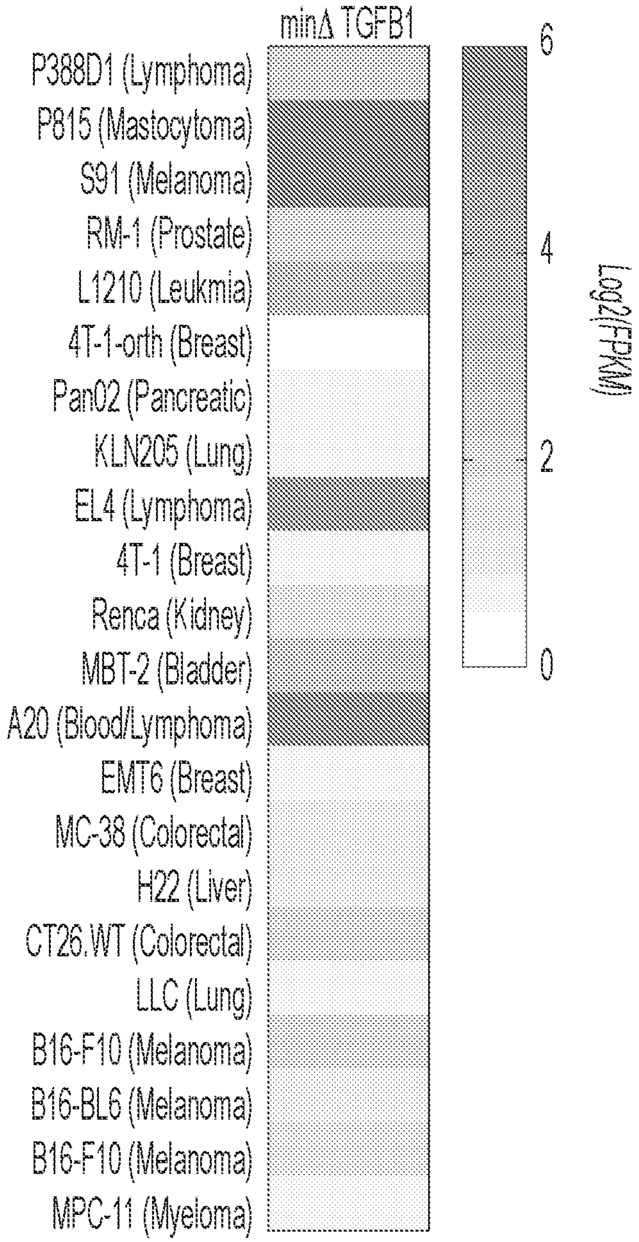

To identify mouse models in which to test the efficacy of TGFβ1-specific inhibition as a cancer therapeutic, TGFβ isoform expression in RNAseq data from a variety of cell lines used in mouse syngeneic tumor models was analyzed. For this analysis, two representations of the data were generated. First, similar to the data in FIG. 3, we generated a heat map of the log 2 (FPKM) values for tumors derived from each cell line (FIG. 13D, left). Because this analysis was used to identify syngeneic models expressing high TGFβ1 that are TGFβ2 and TGFβ3 negative, we were primarily concerned with avoiding false negatives, and we set our "positive" threshold at FPKM>1, well below that in the representations in FIGS. 13B and 13C.

As the data representation in FIG. 13D (left) makes clear, a number of syngeneic tumors commonly, including MC-38, 4T-1, and EMT6, express significant levels of both TGFβ1 and TGFβ3. In contrast, the A20 and EL4 models express TGFβ1 almost exclusively, and the S91 and P815 tumors show a strong bias for TGFβ1 expression.

To further evaluate the differential expression of TGFβ1 vs TGFβ2 and/or TGFβ3, the minΔTGFβ1 was calculated, defined as the smaller value of log 2 ($FPKM_{TGF\beta1}$)−log 2 ($FPKM_{TGF\beta2}$) or log2 ($FPKM_{TGF\beta1}$)−log 2 ($FPKM_{TGF\beta3}$). The minΔTGFβ1 for each model is shown as a heat map in FIG. 13D (right) and underscores the conclusion from FIG. 13D (left) that syngeneic tumors from the A20, EL4, S91, and/or P815 cell lines may represent excellent models in which to test the efficacy of TGFβ1-specific inhibitors.

Example 12. Effects of Ab3 and Ab2 in Combination with Anti-PD-1 Antibody on Tumor Progression in the MBT2 Syngeneic Bladder Cancer Mouse Model To evaluate the effects of Ab3 and Ab2 in combination with an anti-PD-1 antibody to decrease bladder carcinoma tumor progression, the MBT2 syngeneic bladder cancer mouse model was used. This is a very aggressive and fast-growing tumor model and is very difficult to overcome tumor progression with drug treatment.

Tumor Cell Culture

MBT-2 is a poorly differentiated murine bladder cancer cell line derived from a transplantable N-[4-(5-nitro-2-furyl)-2-thiazolyl] formamide-induced bladder cancer in a female C3H/He mouse. The cells were cultured in Roswell Park Memorial Institute (RPMI)-1600 medium with 10% fetal bovine serum and 100 μg/ml streptomycin in a 5% $CO_2$ atmosphere at 37 °C. The culture medium was replaced every other day, and subculture was performed when the cellular confluence reached 90%. Cells were harvested from subconfluent cultures by trypsinization and were washed in serum-free medium. Single cell suspensions with >90% cell viability were determined by Trypan blue exclusion. The cells were resuspended in phosphate-buffered saline (PBS) before injection.

In Vivo Implantation and Tumor Growth

The MBT2 cells used for implantation were harvested during log phase growth and resuspended in phosphate buffered saline (PBS). On the day of tumor implant, each test mouse was injected subcutaneously in the flank with $5\times10^5$ cells (0.1 mL cell suspension), and tumor growth was monitored. When tumors reached an average between 40-80 $mm^3$ and mice were randomized into groups of 15. Tumors were measured in two dimensions using calipers, and volume was calculated using the formula:

$$\text{Tumor Volume } (mm^3)=w^2\times l/2$$

where w=width and/=length, in mm, of the tumor. Tumor weight may be estimated with the assumption that 1 mg is equivalent to 1 $mm^3$ of tumor volume.

Treatment

Mice (n=15) bearing subcutaneous MBT2 tumors (40 to 80 $mm^3$) on Day 1 were administered intraperitoneally (i.p.) once a week for 29 days Ab3 at 10 mg/kg in a dosing volume of 10 mL/kg, Ab3 at 30 mg/kg in a dosing volume of 10 mL/kg, Ab2 at 3 mg/kg in a dosing volume of 10 mL/kg or Ab2 at 10 mg/kg in a dosing volume of 10 mL/kg. Rat anti mouse PD-1 antibody (RMP1-14-rIgG2a, BioXCell®) was administered i.p. twice a week at 10 mg/kg in a dosing volume of 10 mL/kg for 29 days.

Group 1 received anti-PD-1 antibody only. Group 2 received Ab3 (10 mg/kg) in combination with anti-PD-1 antibody. Group 3 received Ab3 (30 mg/kg) in combination with anti-PD-1 antibody. Group 4 received Ab2 (3 mg/kg) in combination with anti-PD-1 antibody. Group 5 received Ab2 (10 mg/kg) in combination with anti-PD-1 antibody. Treatment with isotype control was used as a control group (data not shown).

Endpoint and Tumor Growth Delay (TGD) Analysis

Tumors were measured using calipers twice per week, and each animal was euthanized when its tumor reached the endpoint volume of 1,200 $mm^3$. Mice that exited the study for tumor volume endpoint were documented as euthanized for tumor progression (TP), with the date of euthanasia.

Partial response (PR) due to treatment is defined as the tumor volume was 50% or less of its Day 1 volume for three consecutive measurements during the course of the study and equal to or greater than 13.5 $mm^3$ for one or more of these three measurements. In a complete response (CR) the tumor volume was less than 13.5 $mm^3$ for three consecutive measurements during the course of the study. Anti-PD-1/Ab3 at 10 mg/kg had 0 PR and 4 CR at end of study. Anti-PD-1/Ab3 at 30 mg/kg had 1 PR and 1 CR at end of study. Anti-PD-1/Ab2 at 3 mg/kg had 1 CR and no other responses at 10 mg/kg. Percent tumor growth delay (% TGD) is defined as the increase in the median time to endpoint in a treatment group compared to the untreated control, expressed as a percentage of the median time to endpoint (TTE) of the control:

T=median TTE for treatment

C=median TTE for control

% TGD=((T-C)/C)*100

Anti-PD-1/Ab2% TGD at 3 mg/kg was 11.4 and at 10 mg/kg was 13.6. Anti-PD-1/Ab3 at 10 mg/kg had 191% TGD and at 30 mg/kg was 196.

Figure 14:
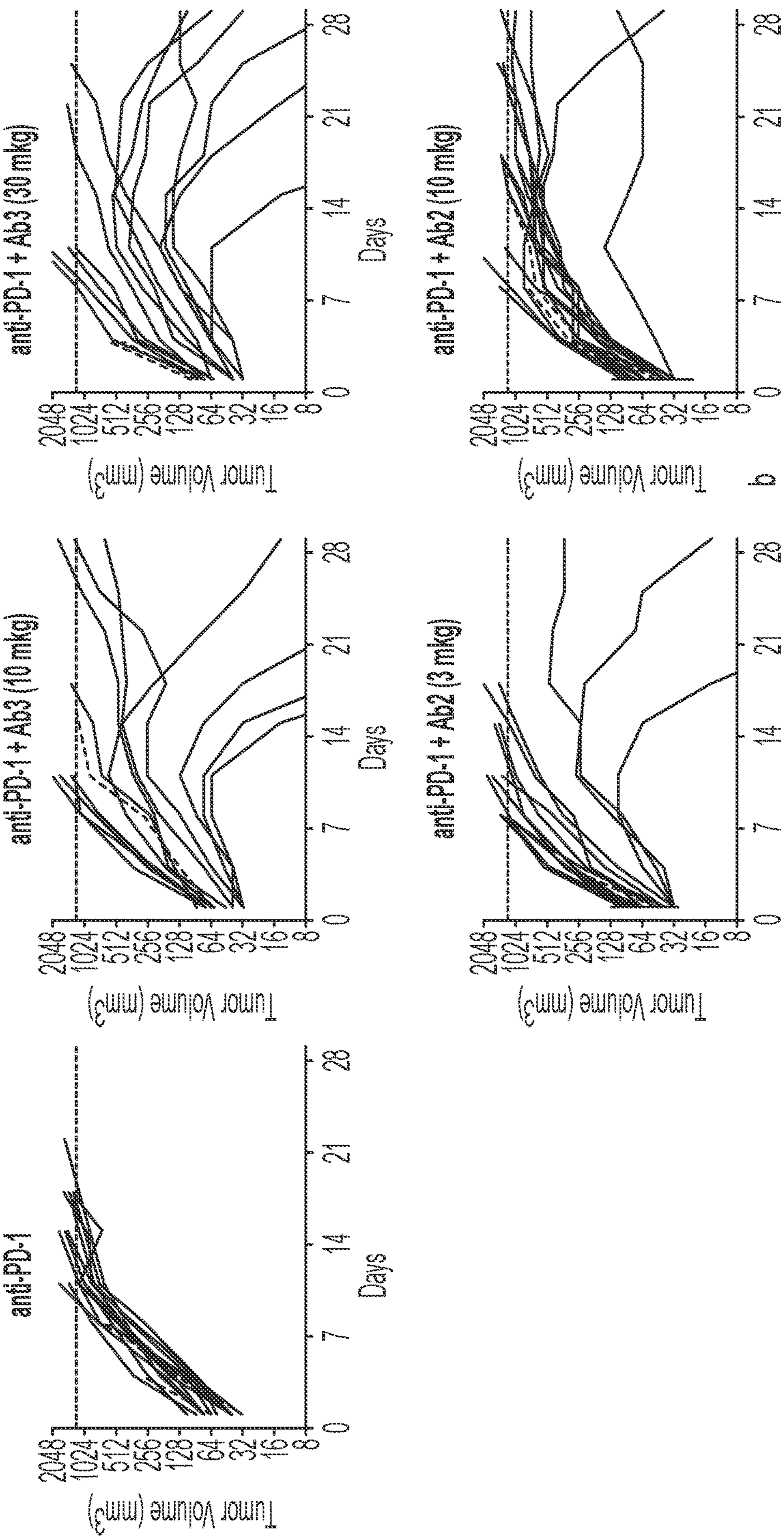
FIG. 14 provides a set of graphs that shows the change in tumor growth (tumor volume $mm^3$) measured over time (days) after administration of Ab3 at 30 mg/kg or 10 mg/kg or Ab2 at 3 mg/kg or 10 mg/kg, in combination with anti-PD-1 ($P<0.05$, Mann-Whitney U test) in MBT-2 tumor model. Anti-PD-1 alone was used as a control.

As shown in FIG. 14, administration of Ab3, at both the 10 mg/kg and 30 mg/kg doses, in combination with anti-PD-1, and Ab2 at both the 3 mg/kg and 10 mg/kg doses, in combination with anti-PD-1, delayed tumor growth as compared to treatment with anti-PD-1 alone. As shown in FIG. 14, most of the mice treated with anti-PD-1 alone reached a tumor volume of 1024 $mm^3$ (as indicated by the dotted line) between about day 8 and day 20, whereas mice treated with Ab3 at 10 mg/kg, Ab3 at 30 mg/kg, Ab2 at 3 mg/kg, or Ab2 at 10 mg/kg took up to about 28 days to reach a tumor volume of 1024 $mm^3$.

Figure 15:
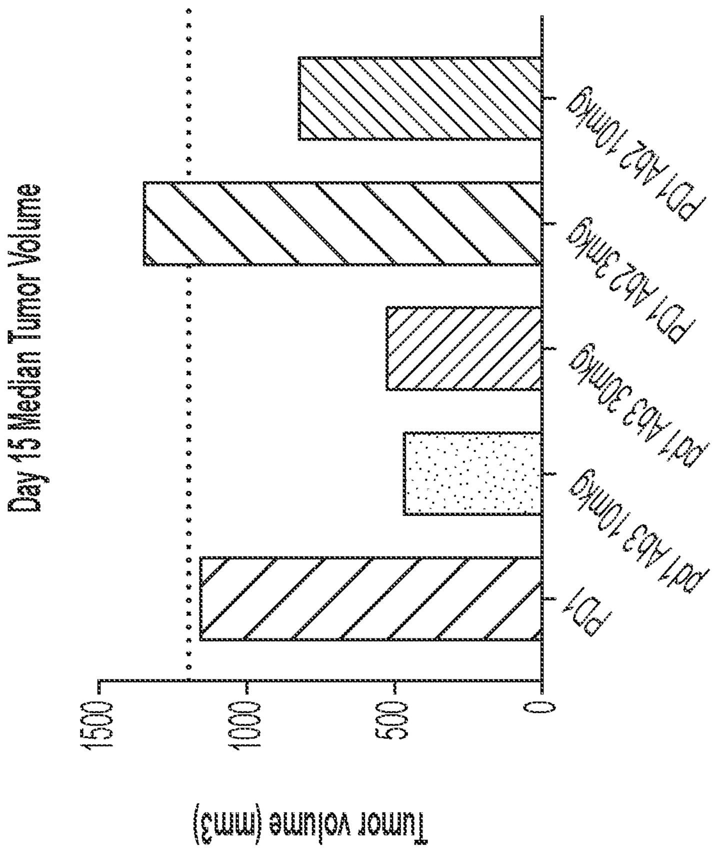
FIG. 15 is a graph that shows the median tumor volume ($mm^3$) at day 15 in mice administered Ab3 at 30 mg/kg or 10 mg/kg or Ab2 at 3 mg/kg or 10 mg/kg, in combination with anti-PD-1 ($P<0.05$, Mann-Whitney U test) in MBT-2 tumor model.

FIG. 15 is a graph that shows the median tumor volume ($mm^3$) at day 15 in mice administered Ab3 at 30 mg/kg or 10 mg/kg or Ab2 at 3 mg/kg or 10 mg/kg, in combination with anti-PD-1. As shown in FIG. 15, the median tumor volume at day 15 in mice treated with Ab3 at 10 mg/kg, Ab3 at 30 mg/kg, or Ab2 at 10 mg/kg was about 700 $mm^3$ or less, while the median tumor volume at day 15 in mice treated with Ab2 at 3 mg/kg or anti-PD-1 alone was 1000 $mm^3$ or more.

Example 13. Effects of Ab3 and Ab2 in Combination with Anti-PD-1 Antibody on Tumor Progression in the CloudmanS91 Melanoma Cancer Mouse Model To evaluate the effects of Ab3 and Ab2 in combination with an anti-PD-1 antibody to decrease melanoma tumor progression, the CloudmanS91 mouse melanoma model was used.

Tumor Cell Culture

Clone M3 [Cloudman S91 melanoma] (ATCCR CCL-53.1™) cells were obtained from the American Type Culture Collection (ATCC) and were maintained at CR Discovery Services as exponentially growing suspension cultures in Kaighn's modified Ham's F12 Medium supplemented with 2.5% fetal bovine serum, 15% horse serum, 2 mM glutamine, 100 units/mL penicillin G sodium, 100 μg/mL streptomycin sulfate and 25 μg/mL gentamicin. The tumor cells were grown in tissue culture flasks in a humidified incubator at 37 °C, in an atmosphere of 5% $CO_2$ and 95% air.

In Vivo Implantation and Tumor Growth

On the day of tumor implant, each female DBA/2 test mouse was injected subcutaneously in the flank with $5\times10^6$ CloudmanS91 cells in 50% Matrigel®, and tumor growth was monitored. When tumors reached a volume of 125-175 $mm^3$ mice were randomized into groups of 12 with identical mean tumor volumes and dosing began. Tumors were measured in two dimensions using calipers, and volume was calculated using the formula:

$$\text{Tumor Volume}(mm^3)=w^2\times1/2$$

where w=width and/=length, in mm, of the tumor. Tumor weight may be estimated with the assumption that 1 mg is equivalent to 1 $mm^3$ of tumor volume.

Treatment

Mice (n=12) bearing subcutaneous CloudmanS91 tumors (125-175 $mm^3$) on Day 1 were administered intraperitoneally (i.p.) once a week for 60 days Ab3 at 10 mg/kg in a dosing volume of 10 mL/kg; Ab3 at 30 mg/kg in a dosing volume of 10 ml/kg; Ab2 at 10 mg/kg in a dosing volume of 10 mL/kg; or Ab2 at 30 mg/kg in a dosing volume of 10 mL/kg. Rat anti mouse PD-1 antibody (RMP1-14-rIgG2a, BioXCell®) was administered i.p. twice a week at 10 mg/kg in a dosing volume of 10 mL/kg for 60 days.

Group 1 received anti-PD-1 antibody only. Group 2 received Ab3 (10 mg/kg) in combination with anti-PD-1 antibody. Group 3 received Ab3 (30 mg/kg) in combination with anti-PD-1 antibody. Group 4 received Ab2 (10 mg/kg) in combination with anti-PD-1 antibody. Group 5 received Ab2 (30 mg/kg) in combination with anti-PD-1 antibody. An untreated control was used, data not shown.

Endpoint and Tumor Growth Delay (TGD) Analysis

Tumors were measured using calipers twice per week, and each animal was euthanized when its tumor reached the endpoint volume of 2,000 $mm^3$ or at the end of the study (Day 60), whichever happened earlier. Mice that exited the study for tumor volume endpoint were documented as euthanized for tumor progression (TP), with the date of euthanasia. The time to endpoint (TTE) for analysis was calculated for each mouse according to the methods described in International Pat. Pub. No. WO 2018/129329, which is herein incorporated by reference in its entirety.

Figure 16:
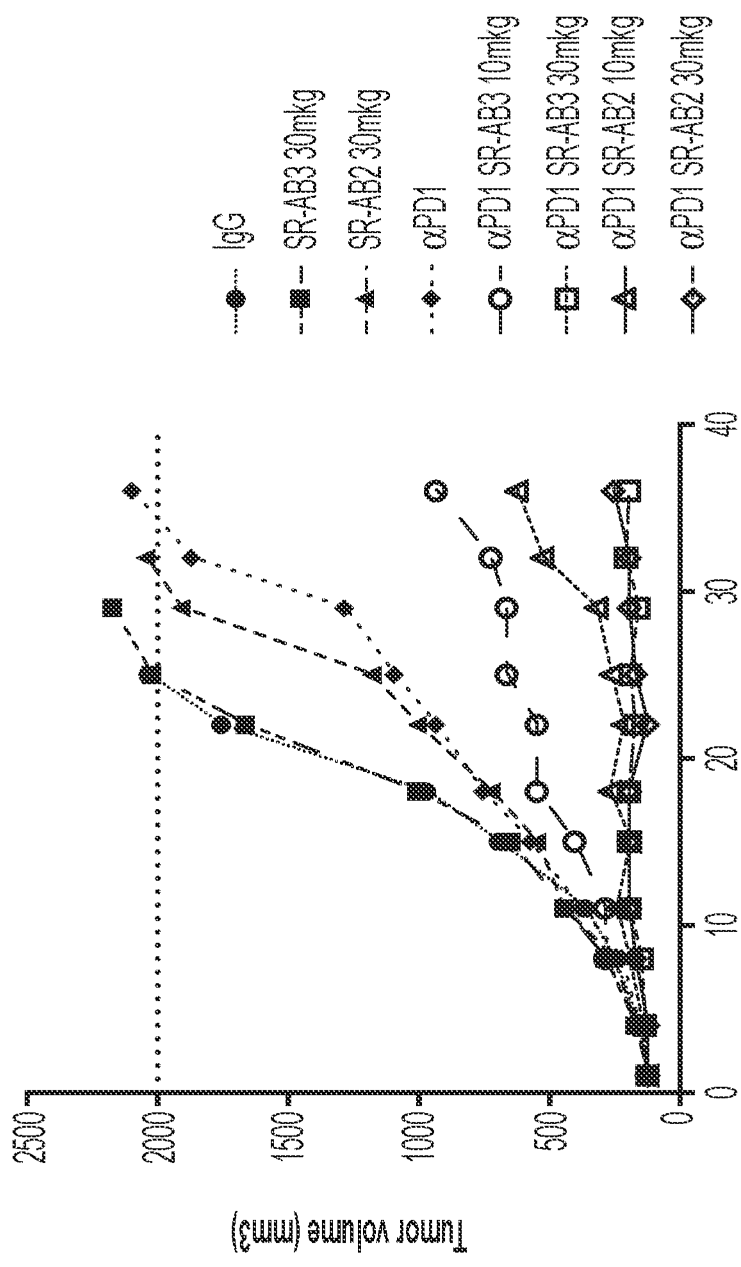
FIG. 16 provides a graph showing the S91 median tumor volumes as a function of time. The combination arms represent two different isoform-selective, TGFβ1 inhibitors (Ab3 and Ab2) at two dose levels, each in combination with anti-PD-1 treatment.
Figure 17A:
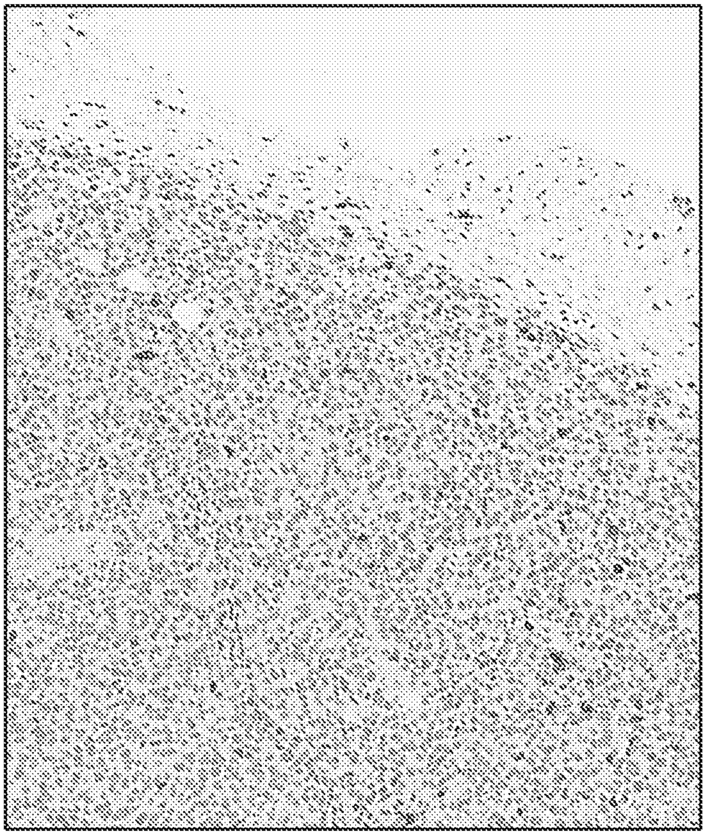
FIGS. 17A and 17B provide representative immunohistochemistry sections of S91 tumor model, stained with a CD8+ cell marker.
Figure 17B:
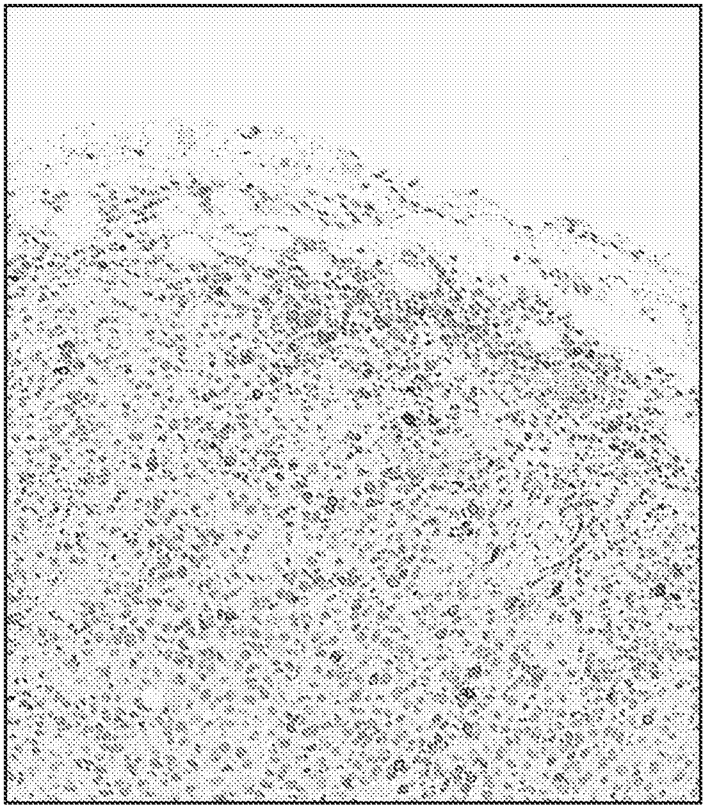
Figure 18A:
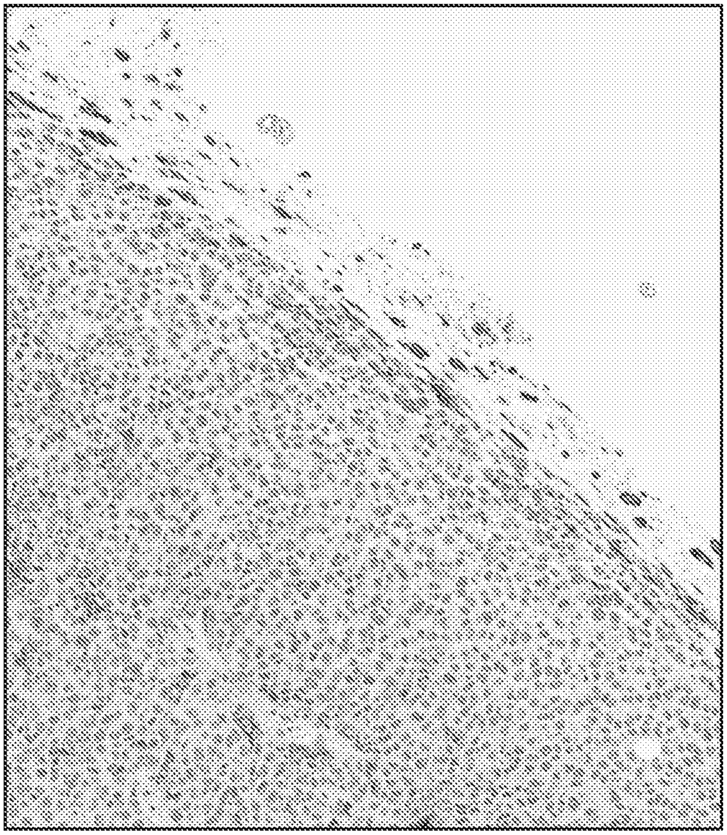
FIGS. 18A and 18B provide representative immunohistochemistry sections of S91 tumor, stained with a macrophage marker.
Figure 18B:
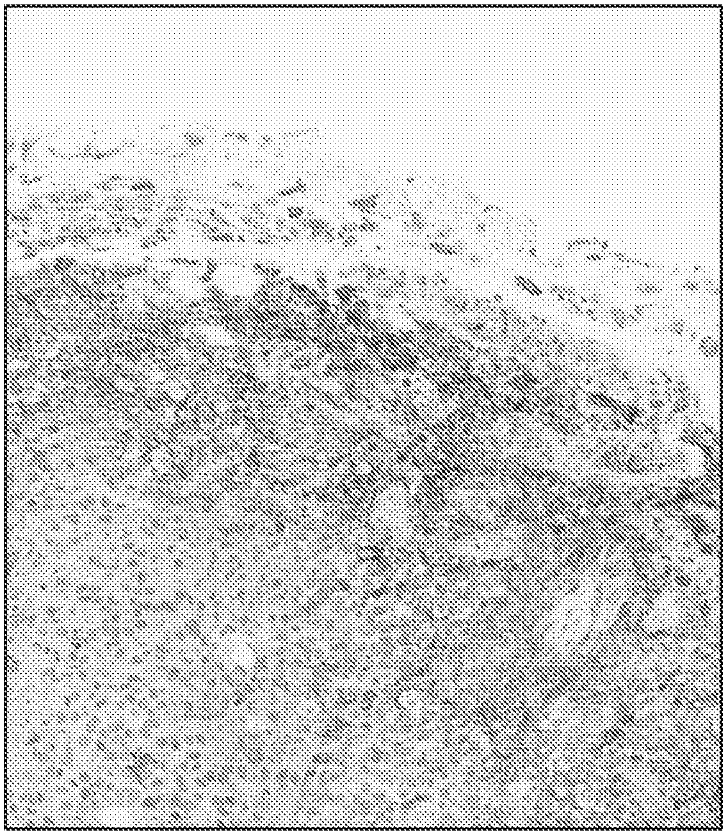

FIG. 16 shows the median tumor progression after treatment with Ab3 or Ab2 in combination with anti-PD-1 antibody. As shown in FIG. 16, administration of Ab3 or Ab2 at 10 mg/kg and 30 mg/kg, in combination with anti-PD-1, delayed tumor growth. FIGS. 17A and 17B provide representative immunohistochemistry sections of CloudmanS91 tumor model, stained with a CD8+ cell marker. FIGS. 18A and 18B provide representative immunohistochemistry sections of CloudmanS91 tumor, stained with the macrophage marker, F4/80. As shown in FIGS. 17B and 18B, treatment with an anti-PD-1 inhibitor and a isoform-specific TGFb1 inhibitor increased CD8+ T cell infiltration and macrophage infiltration in S91 tumors.

Example 14: Effect of pH on Ab2 Binding to proTGFb1 C4S

The FORTEBIOR OCTET® Red384 was used to test pH-sensitivity of Ab2 (human $IgG_4$) and a reference antibody as control ("R1") (human $IgG_4$), which is also an isoform-selective inhibitor of TGFβ1 that binds the latent complex in a pH-insensitive (pH-independent) matter. The antibodies were tested against sensor-immobilized human proTGFβ1 C4S, which contains a mutation in the prodomain to facilitate proTGFβ1 expression without disulfide linkage to a presentation molecule. Polystyrene 96-well black half area plates (Greiner BIO-ONE®) and amine reactive second-generation (AR2G) biosensors (ForteBio) were utilized for this experiment.

The amine reactive second-generation (AR2G) reagent kit (ForteBio part no. 18-5095) was utilized according to the manufacturer's specifications for the assessment of pH sensitivity of Ab2 and R1 binding to human proTGFβ1 C4S. AR2G biosensors were first allowed to hydrate in water offline for at least 10 minutes before the initiation of the experiment. Upon initiation of the experiment, AR2G tips were equilibrated in water for 1 minute. Then, the tips were moved into an activation solution for 5 minutes. The activation solution consists of 18 parts water, 1 part 400 mM EDC (1-Ethyl-3-[3-dimethylaminopropyl]carbodiimide hydrochloride), and 1 part 200 mM s-NHS (N-hydroxysulfosuccinimide). The activation solution is prepared immediately before use in the experiment. After tip activation, the tips were loaded for 3 minutes with a 10 μg/mL solution of human proTGFβ1 C4S in 10 mM sodium acetate buffer pH 5. After loading, the tips were quenched in ethanolamine pH 8.5 for 15 minutes. The tips were then baseline/blocked with a 20 minute incubation in 1× enhanced kinetics buffer. 1× enhanced kinetics buffer (1×EKB) is 1× kinetics buffer (FORTEBIO® part no 18-1105 diluted from 10× with PBS) with the addition of 2% BSA (Sigma A3059-100G), 0.5 M NaCl (Fisher S671-10), and 0.09% Tween™-20 (P7949-500M). Tips were then allowed to associate in a 10 μg/mL solution of Ab2 or R1 in 1×EKB (pH 7.3) for 10 minutes before the final 10 minute dissociation step. The dissociation was performed in 1×KB at pH 7 and pH 5.

Figure 19:
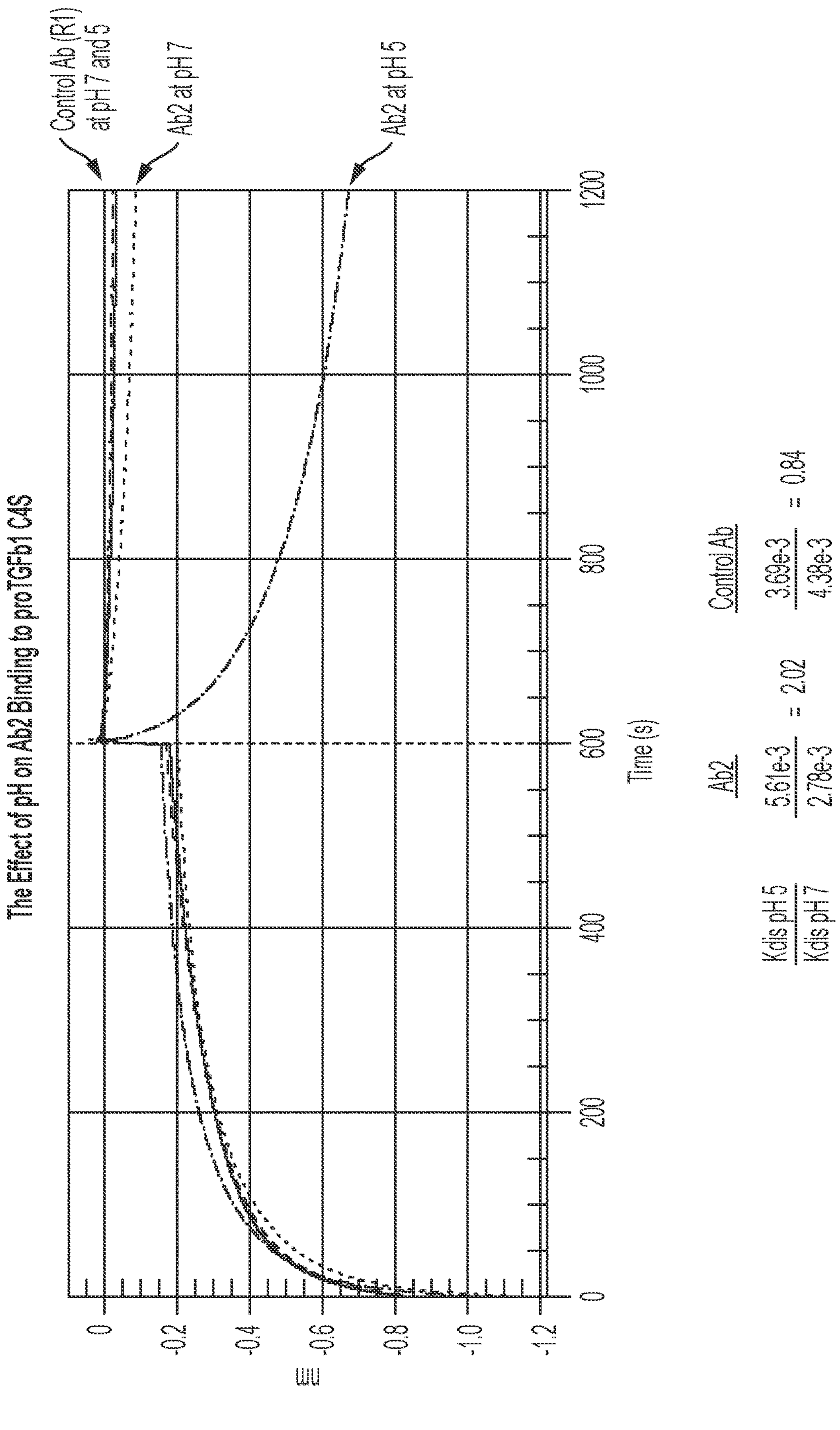
FIG. 19 provides a graph showing the association and dissociation of Ab2 to TGFβ1 C4S at different pHs.

FIG. 19 shows the binding kinetics of Ab2 and R[1] at different pHs. R1 showed minimal dissociation at pH 7 or pH 5 ($K_{dis}$=4.38e-3 and $K_{dis}$=3.69e3, respectively). Ab2 showed some dissociate at pH 7 ($K_{dis}$=2.78e-3). However, Ab2 showed a dramatic dissociation at pH 5 ($K_{dis}$=5.61e-3), indicating that Ab2 is pH-sensitive.

Figure 20:
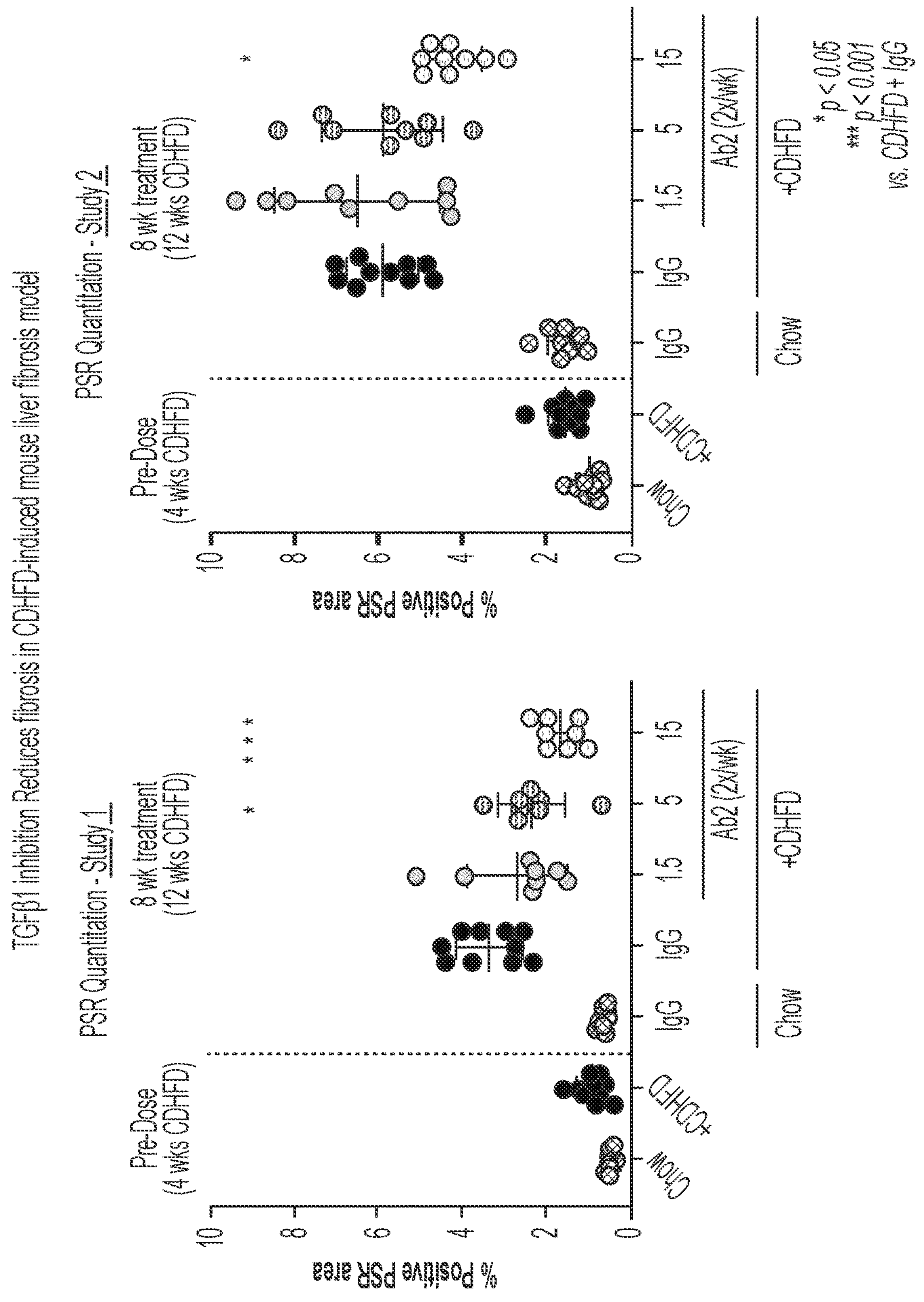
FIG. 20 provides 2 graphs showing picosirius red area (%) in liver sections of CDHFD mice treated with Ab2 or control.

Example 15: Anti-Fibrotic Effects of TGF61-Selective Activation Inhibitor in Mouse Fibrosis Models A choline-deficient high-fat diet (CDHFD)-induced liver fibrosis model, that recapitulates aspects of fatty liver conditions, was used in mice to examine effects of Ab2. Fibrosis was induced by feeding mice for 12 weeks on a choline-deficient high fat diet (CDHFD). Antibody treatment started after four weeks of fibrosis induction and was continued for eight weeks. The study was repeated twice, shown in FIG. 20 as (Study 1, left hand graph, and Study 2, right hand graph. FIG. 20 summarizes data from both studies.

Figure 21:
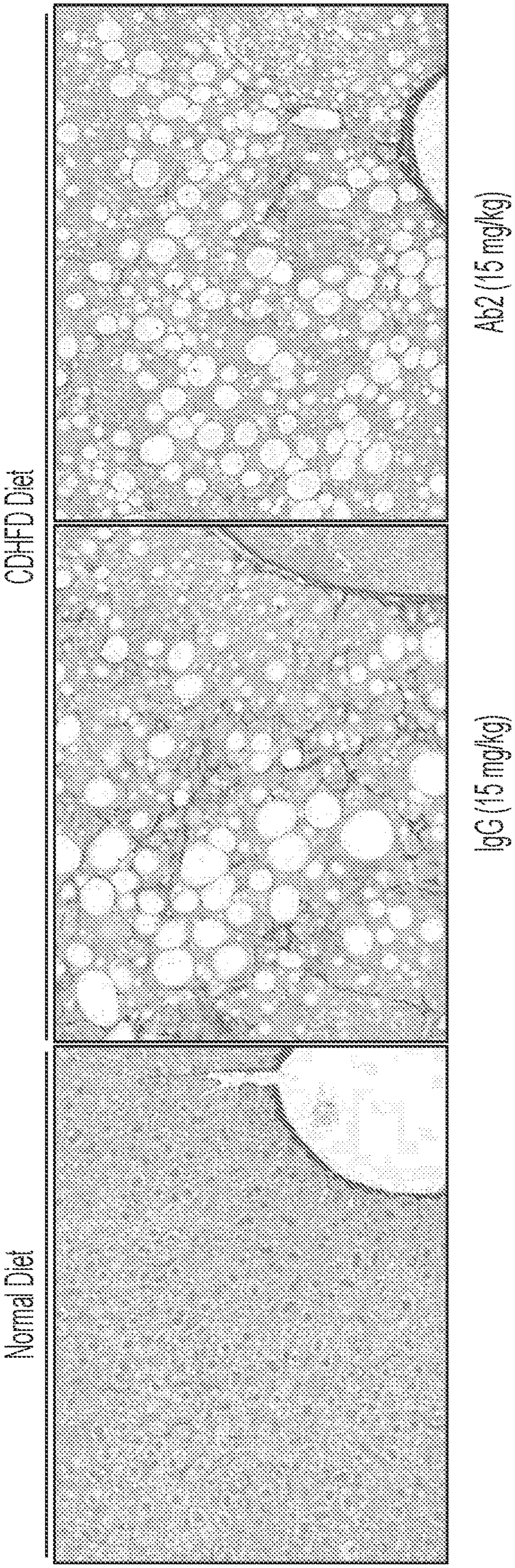
FIG. 21 provides 3 representative PSR-stained images from CDHFD mice treated with Ab2 or control.
Figure 22:
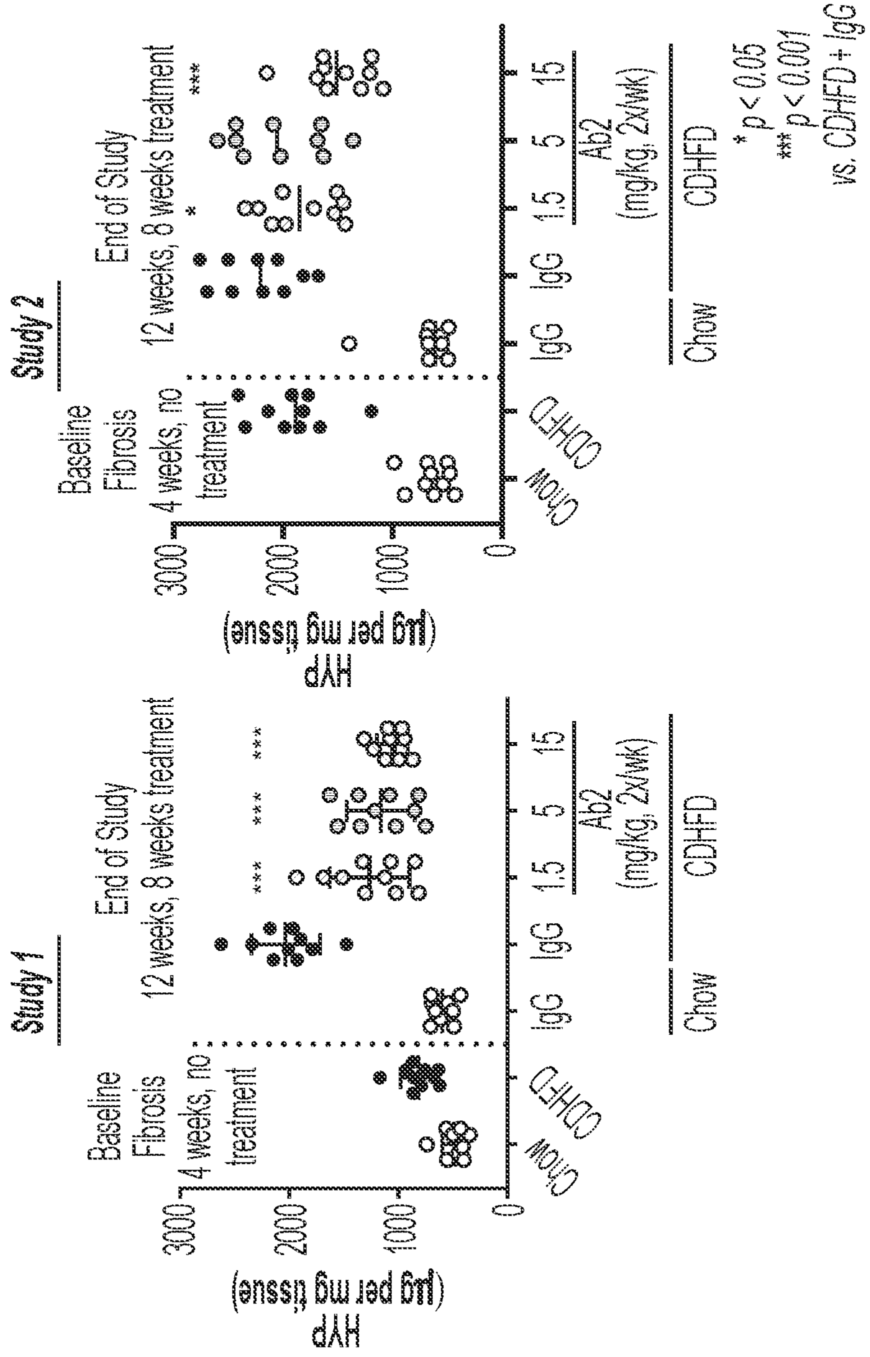
FIG. 22 provides two graphs showing hydroxyproline content (μg/mg tissue) in liver of CDHFD mice treated with Ab2 or control.
Figure 23:
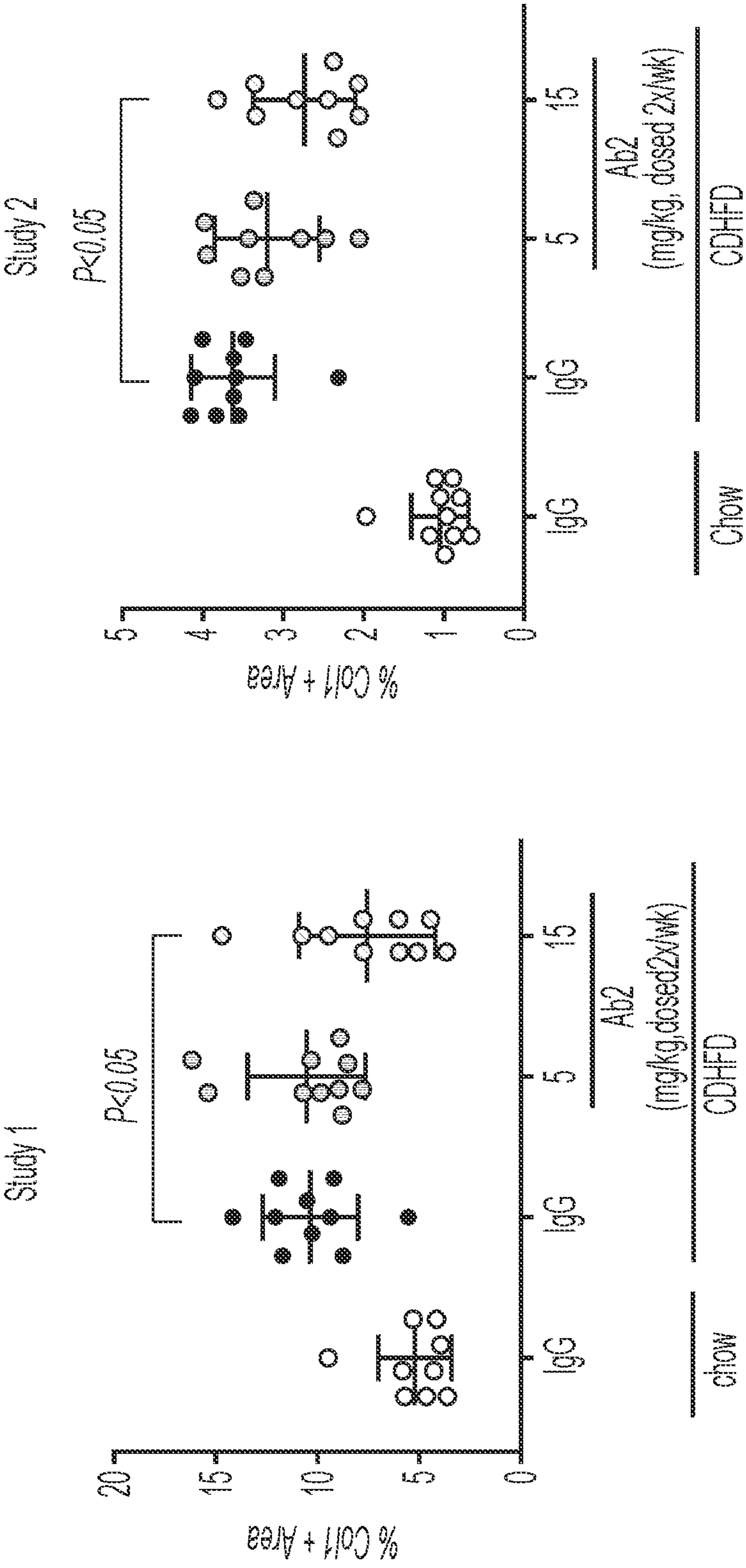
FIG. 23 provides two graphs showing type 1 collagen-positive area of liver sections of CDHFD mice treated with Ab2 or control.

Antifibrotic effect of Ab2 was observed in both studies, as evidenced by reduction of fibrotic tissue areas shown by Picrosirius red (PSR) staining (FIG. 21). The observed antifibrotic effect of Ab2 is consistent with other fibrotic parameters used to evaluate fibrosis, including reductions in Hydroxyproline ("HYP") content (FIG. 22) and reduction in type I collagen ("Col1") staining by quantitative IHC (FIG. 23). In addition, together with previous data (UUO, $CCl_4$, Alport) that demonstrated antifibrotic efficacy of Ab2, these results show reproducible in vivo activity of Ab2 in these preclinical mouse models of fibrosis.

Figure 28:
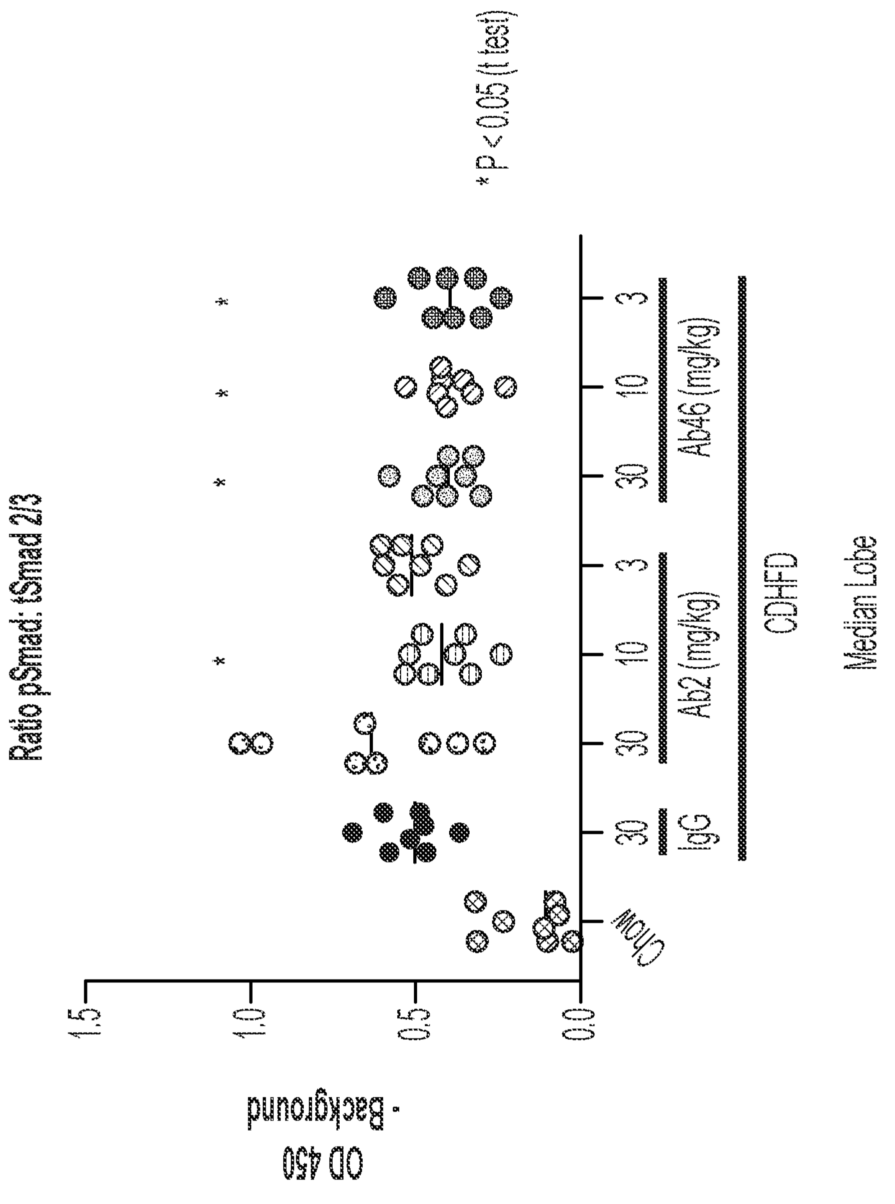
FIG. 28 provides a graph showing ratios of phosphorylated vs. total SMAD2/3 in the medial lobe of CDHFD mice liver. Significant reduction in pSMAD2/3 was seen at all doses tested of Ab46 in the medial lobe ($p<0.05$ (t test)).
Figure 29:
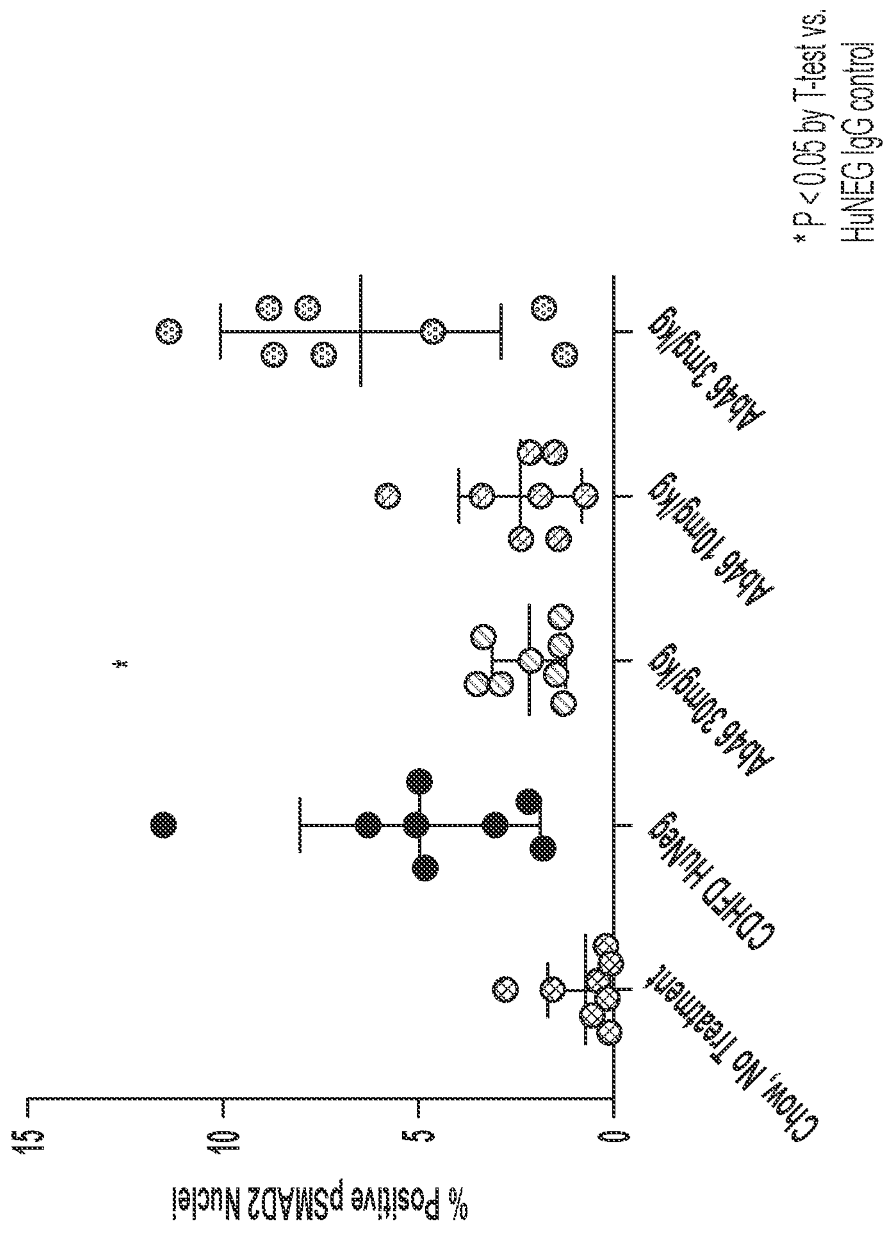
FIG. 29 provides a graph showing percent (%) positive phospho-SMAD2 (pSMAD2) nuclei in the liver of mice after 10 weeks of a choline-deficient high fat diet (CDHFD). Significant reduction in % positive pSMAD2 nuclei was seen in mice treated with 30 mg/kg dose of Ab46.

A mouse CDHFD target engagement study was performed to determine the in vivo activity of Ab46. Mice were fed on a CDHF diet for ten weeks. A first dose of Ab46 (3, 10, and 30 mg/kg) or the negative control ("HuNEG" $IgG_4$, 30 mg/kg) was given on Day 1 and Day 3. Tissue collection was performed on Day 5. FIG. 28 provides a graph showing ratios of phosphorylated versus total SMAD2/3 in the medial lobe of CDHFD mouse liver as measured by ELISA. Significant reduction in pSMAD2/3 was seen at all doses tested of Ab46 in the medial lobe ($p<0.05$ (t test)). The data show that Ab46 effectively reduces the activity of the TGFβ signaling pathway in animals in the CDHFD-induced liver fibrosis model. FIG. 29 provides a graph showing percent (%) positive phospho-SMAD2 (pSMAD2) nuclei in the left lateral lobe of the mice described above. Significant reduction in % positive pSMAD2 nuclei was seen in mice treated with the 30 mg/kg dose of Ab46. Thus, these results show that a substantial fraction of pSMAD2 signaling is driven by TGFβ1 isoform. Finally, reduction in % pSMAD2 nuclei was greater in the liver of mice after 10 weeks of CDHFD treated with Ab46 compared to comparable doses of Ab2 (data not shown), supporting the notion that isoform-selective inhibitors with slower off rates may provide enhanced in vivo potency, as compared to those with faster off rates.

Figure 30:
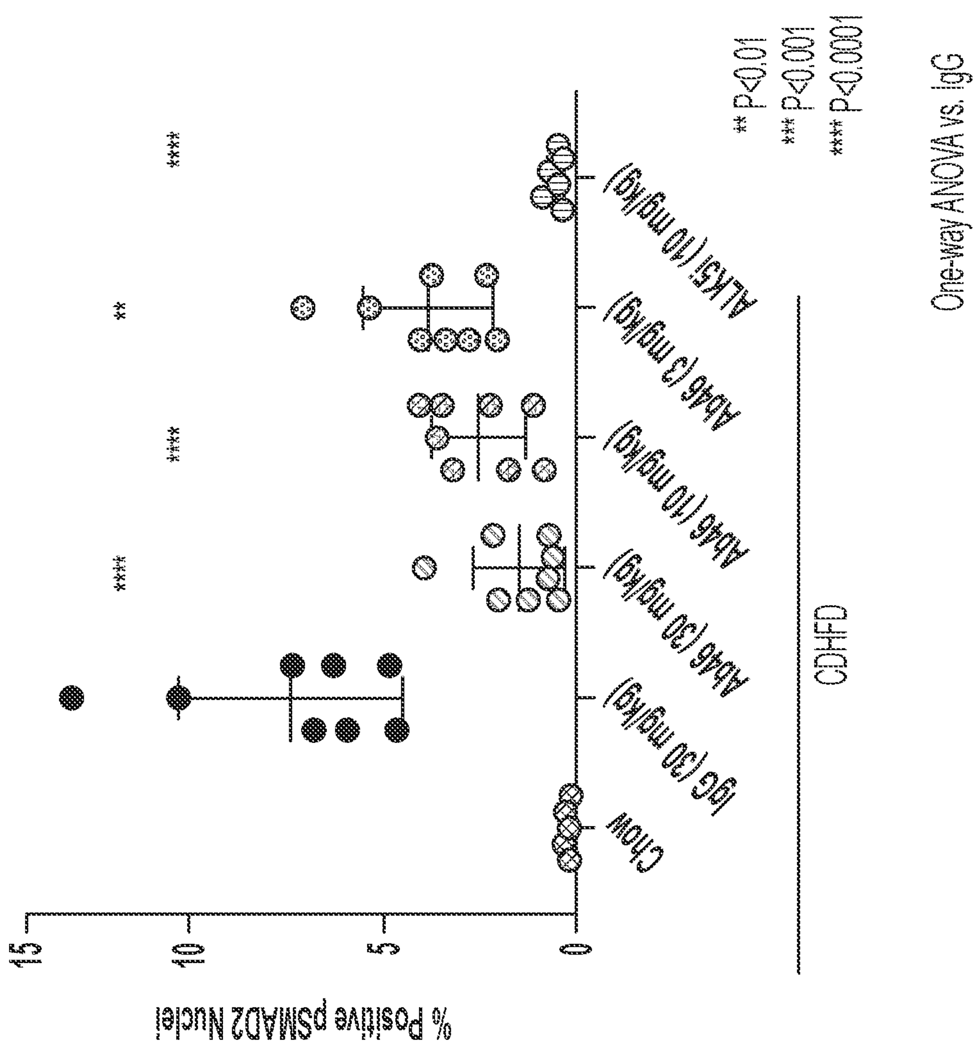
FIG. 30 provides a graph showing percent (%) positive phospho-SMAD2 (pSMAD2) nuclei in the liver of rats (eft lateral lobe) after 12 weeks of a CDHF diet. A human IgG (HuNeg; negative control) or Ab46 were administered on Day 1 and Day 3 after 12 weeks of CDHFD. An ALK5 inhibitor (ALK51; positive control) was given to a control group of rats two hours before rats were harvested. Treatment with all doses of Ab46 (3 mg/kg, 10 mg/kg, and 30 mg/kg) resulted in suppression of SMAD2 phosphorylation, as did treatment with the positive control (ALK5i).
Figure 31:
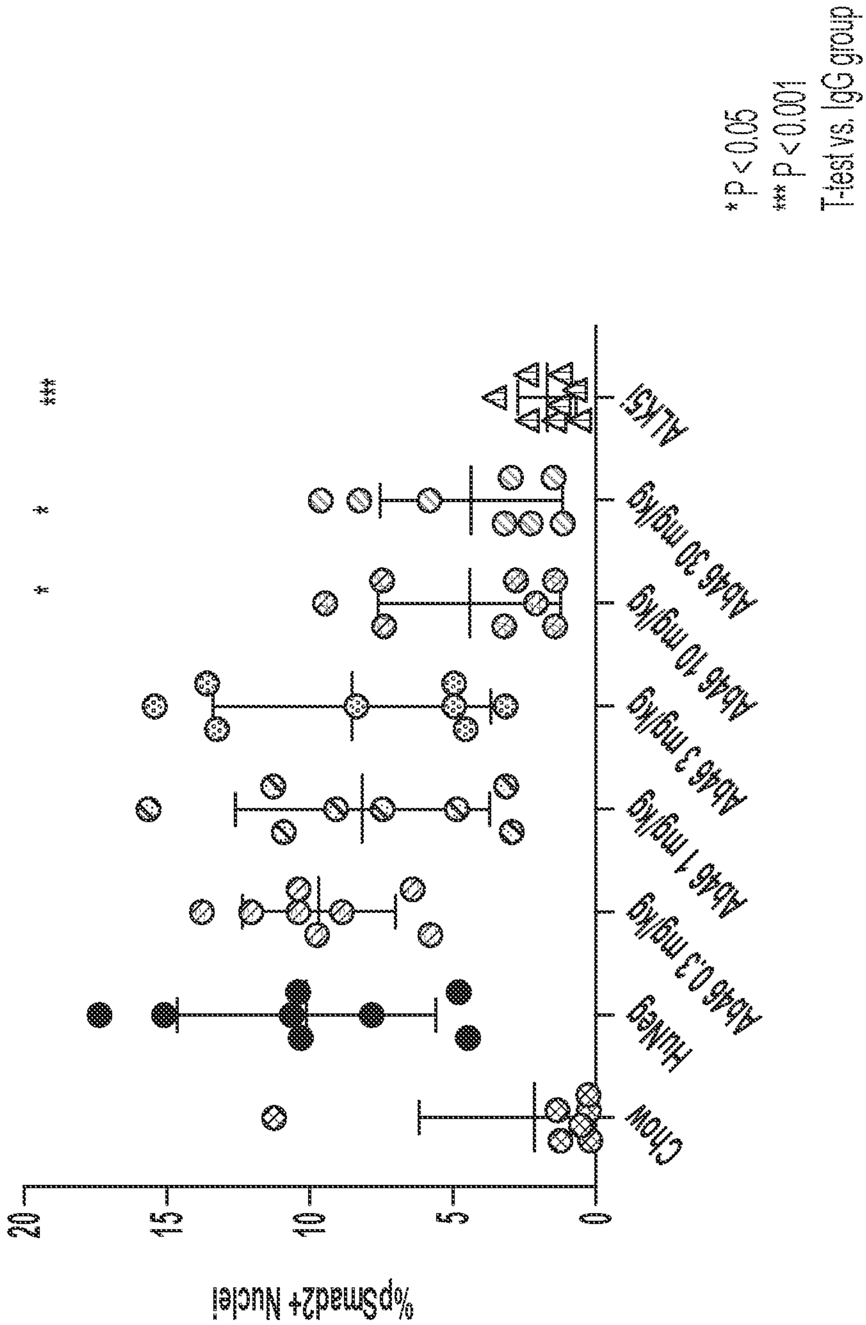
FIG. 31 provides a graph showing percent (%) positive phospho-SMAD2 (pSMAD2) nuclei in the liver of rats after 12 weeks of a CDHF diet. A human IgG (HuNeg; negative control) or Ab46 at doses of 0.3 mg/kg, 1 mg/kg, 3 mg/kg, 10 mg/kg, and 30 mg/kg were administered on Day 1 after 12 weeks of CDHFD. An ALK5 inhibitor (ALK5i; positive control) was given to a control group of rats two hours before rats were harvested. Treatment with doses of Ab46 10/mg/kg and 30 mg/kg appeared to fully suppress SMAD2 phosphorylation, as did treatment with the positive control (ALK5i).

A similar study was run in 10-12 week old male Wistar-Han rats as follows: rats were fed on a CDHF diet for 12 weeks and then randomized. A first dose of the negative control ("HuNEG" $IgG_4$, 30 mg/kg, n=6) or Ab46 (3, 10, and 30 mg/kg, n=8) was given on Day 1, and a second dose was given on Day 3. Treatment with a TGF-β type 1 receptor (ALK5) kinase inhibitor (ALK5i, 10 mg/kg) was used as a positive control. Tissue collection (left lateral lobe) was performed on Day 5. All rats had detectable serum antibody exposure. As shown in FIG. 30, all dose levels of Ab46 were able to suppress phosphorylation of SMAD2. As was observed in the mouse study, the reduction in percentage of pSMAD2-positive nuclei was greater for Ab46 than for Ab2. The study was repeated with a broader dose range: rats were fed on a CDHF diet for 12 weeks and then randomized. A single dose of 0.3 mg/kg, 1 mg/kg, 3 mg/kg, 10 mg/kg, or 30 mg/kg of Ab46 was given on Day 1, and tissue collection was performed after 48 hours. As shown in FIG. 31, significant reduction of pSMAD2-positive nuclei was observed for doses 10 mg/kg and 30 mg/kg, comparable to the suppression seen in the positive control (ALK5i).

Figure 24:
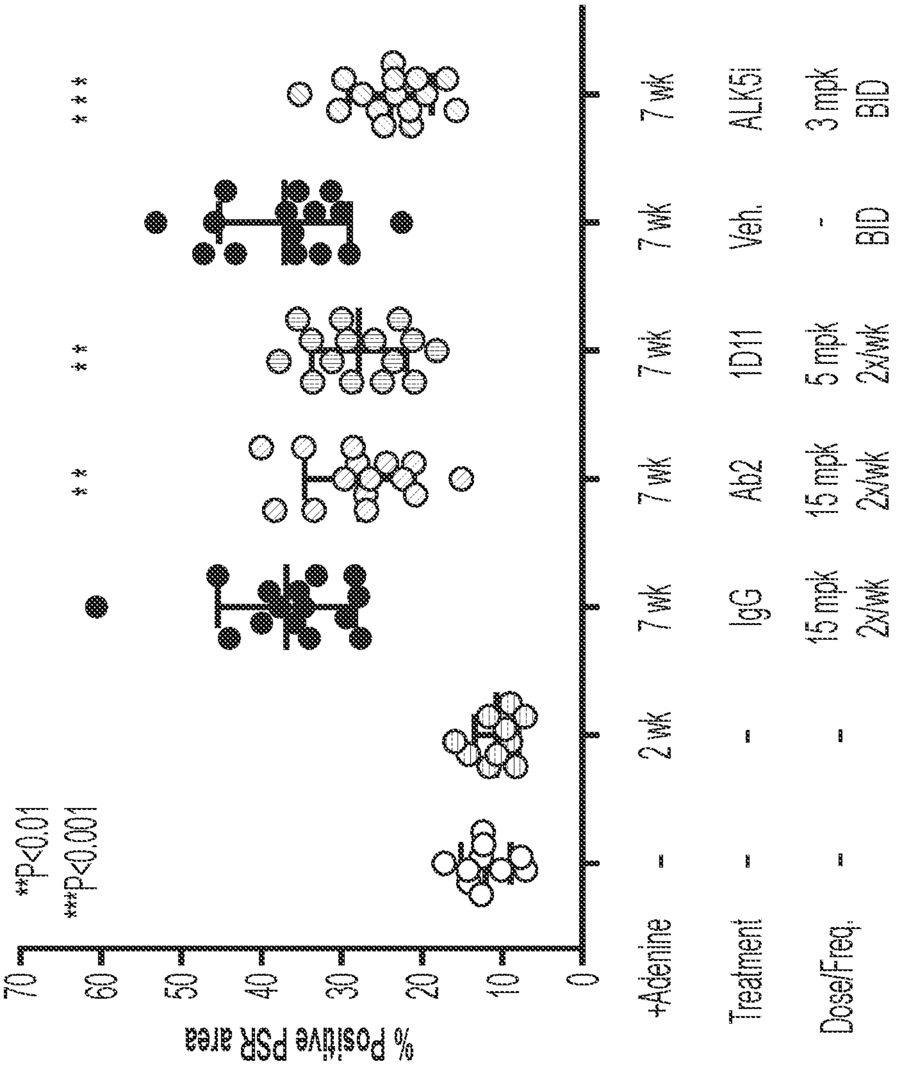
FIG. 24 provides a graph showing picosirius red area (%) in kidney sections of adenine-induced rat kidney fibrosis model.

Example 16: Anti-Fibrotic Effects of TGF61-Selective Activation Inhibitor in Rat Fibrosis Model To examine whether the antifibrotic effects observed with Ab2 can be reproduced in another species, a rat model of kidney fibrosis was used. Adenine treatment of rats induced rapid and aggressive fibrosis in the kidney. As shown in FIG. 24, Ab2, as well as the two positive controls (neutralizing antibody 1D11 and small molecule ALK5 antagonist) showed significant antifibrotic effects as measured by PSR.

Figure 25:
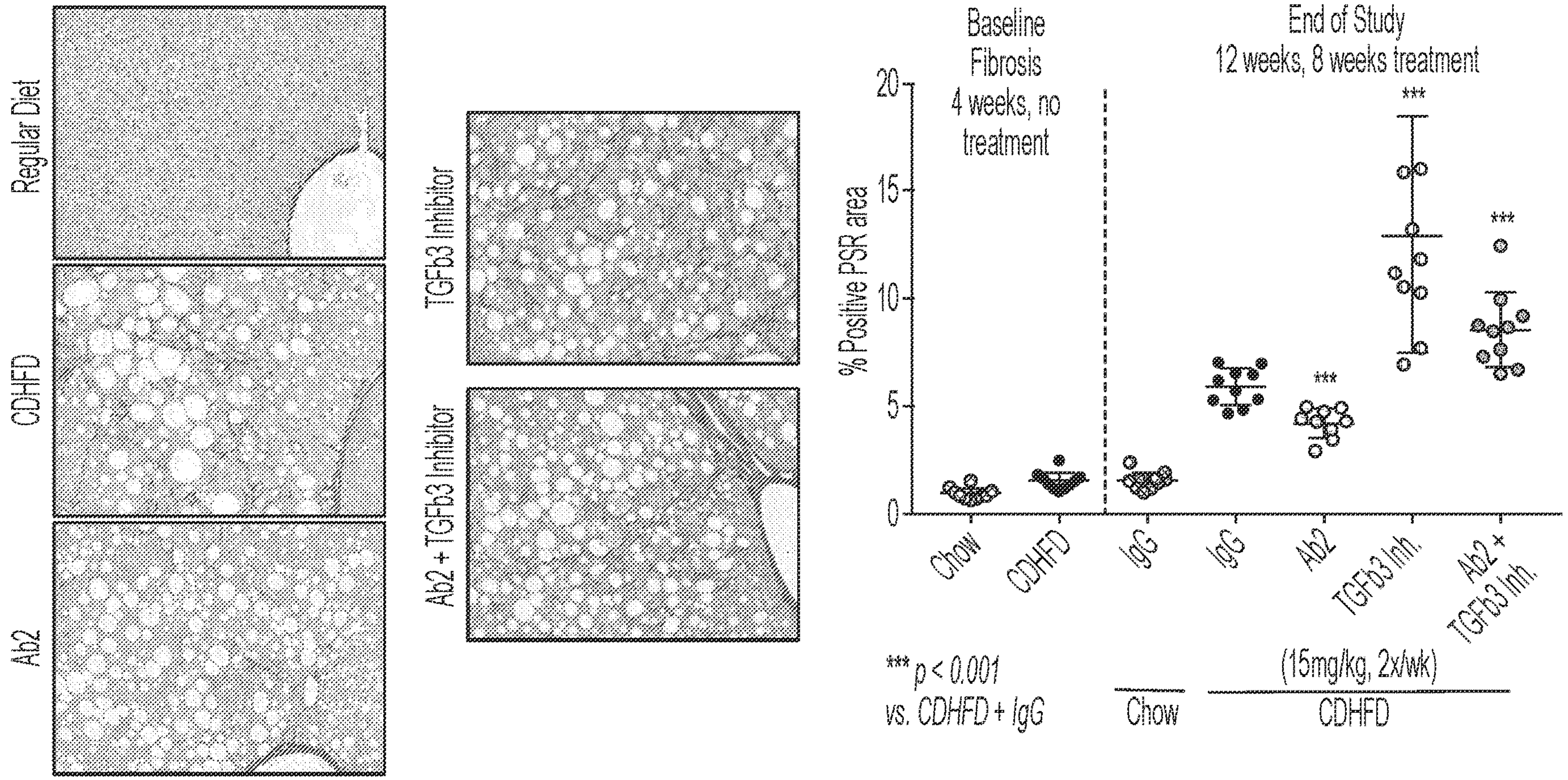
FIG. 25 provides 5 representative PSR-stained images from controls, CDHFD mice treated with Ab2, a TGFβ3 inhibitor, or both (left); A graph showing picosirius red area (%) in liver sections of CDHFD mice treated with Ab2, a TGFβ3 inhibitor, or both, as compared to control, is also provided (right).
Figure 26:
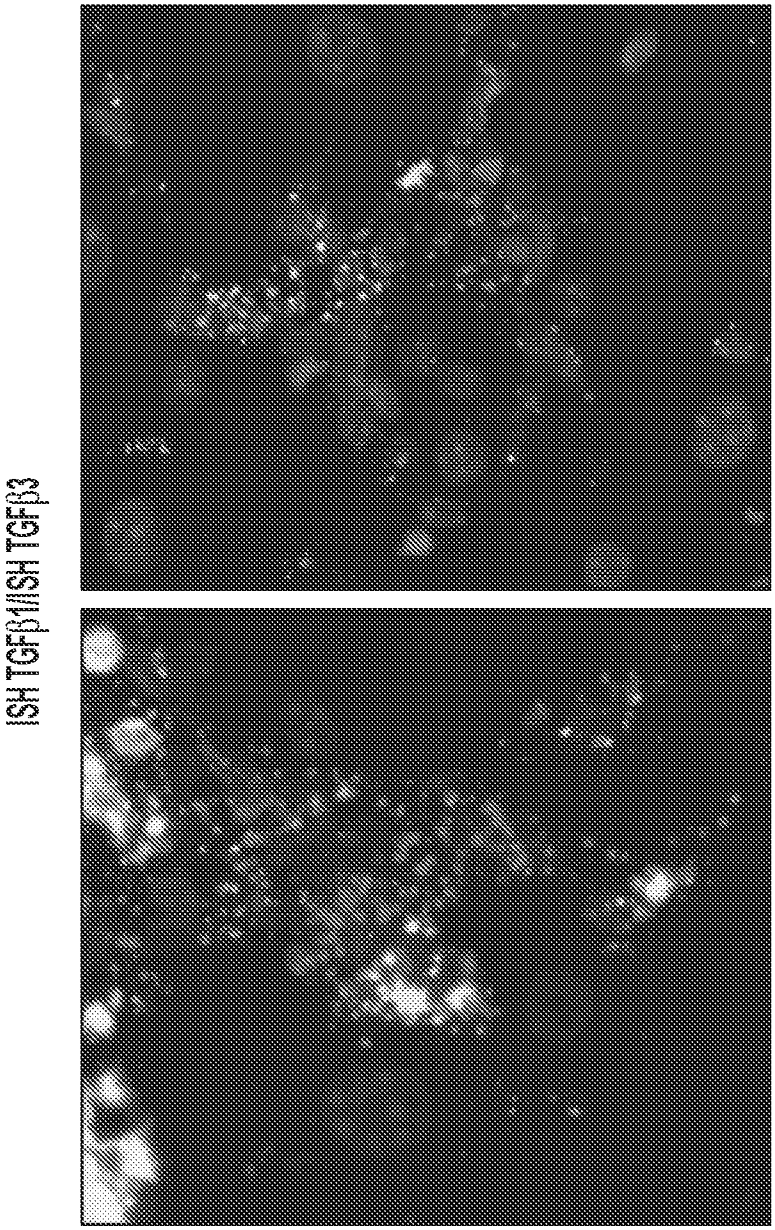
FIG. 26 provides immunocytochemistry images of mouse liver cells visualized with 2 fluorescent labels: green depicts TGFβ1 and red depicts TGFβ3.

Example 17: Pro-Fibrotic Effects of TGF63-Selective Activation Inhibitor in Liver Fibrosis Model Liver expresses both TGFβ1 and TGFβ3 isoforms. To investigate whether inhibition of both isoforms in the CDHFD model would further mitigate fibrosis of the liver, CDHFD mice were treated with Ab2 (TGFβ1-selective activation inhibitor) and a TGFβ3-selective activation inhibitor, either alone or in combination. In mice treated with TGFβ3 inhibitor, exacerbation of the disease was observed, as evidenced by PSR analysis and additional histopathology analyses (FIG. 25). Adenine treatment triggered fibrosis, as previously reported. At 12 weeks, e.g., end of the study, animals that received Ab2 showed significantly less fibrosis as compared to IgG-treated animals (negative control). By contrast, animals treated with TGFβ3-selective inhibitor showed significantly more fibrosis with approximately 12% PSR positive area. Animals that received a combination of both TGFβ3-selective inhibitor and TGFβ1-selective inhibitor (Ab2) showed an intermediate level of fibrosis, indicating that antifibrotic effects of Ab2 was mitigated by TGFβ3 inhibition.

The various features and embodiments of the present invention, referred to in individual sections above apply, as appropriate, to other sections, mutatis mutandis. Consequently, features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. An isoform-selective inhibitor of TGFβ1 activation, wherein the inhibitor is a monoclonal antibody or an antigen-binding fragment thereof, which selectively inhibits TGFβ1 activation;

wherein the monoclonal antibody or the antigen-binding fragment thereof binds each of human LTBP1-proTGFβ1 and/or human LTBP3-proTGFβ1 with a monovalent dissociation rate of 10.0e-4 (1/s) or less as measured by a surface plasmon resonance (SPR)-based assay, and with a $K_D$ of <1.0 nM; and, wherein the monoclonal antibody or the antigen-binding fragment thereof comprises the following six CDRs:

i) an H-CDR1 comprising GFTFADYA (SEQ ID NO: 276);

ii) an H-CDR2 comprising ISGSGAAT (SEQ ID NO: 282);

iii) an H-CDR3 comprising VSSGHWDYD (SEQ ID NO: 287);

iv) an L-CDR1 comprising QSISSY (SEQ ID NO: 279);

v) an L-CDR2 comprising AASGLES (SEQ ID NO: 284); and, vi) an L-CDR3 comprising QQTYGVPLT (SEQ ID NO: 285).

2. A pharmaceutical composition comprising the isoform-specific inhibitor of claim 1.

3. A method of treating of a disease involving extracellular matrix (ECM) dysregulation in a subject, the method comprising the steps of administering the isoform-selective inhibitor of claim 1 to the subject, optionally wherein the disease is a fibrosis.

4. An isolated monoclonal antibody or an antigen-binding fragment thereof, which binds human LTBP1-proTGFβ1 and/or human LTBP3-proTGFβ1, comprising:

a heavy chain complementary determining region 1 (CDRH1) comprising GFTFADYA (SEQ ID NO: 276);

a heavy chain complementary determining region 2 (CDRH2) comprising ISGSGAAT (SEQ ID NO: 282;

a heavy chain complementary determining region 3 (CDRH3) comprising VSSGHWDYD (SEQ ID NO: 287);

a light chain complementary determining region 1 (CDRL1) comprising QSISSY (SEQ ID NO: 279;

a light chain complementary determining region 2 (CDRL2) comprising AASGLES (SEQ ID NO: 284; and, a light chain complementary determining region 3 (CDRL3) comprising QQTYGVPLT (SEQ ID NO: 285).

5. The isolated monoclonal antibody or antigen-binding fragment thereof of claim 4, wherein, the VH comprises EVQLLESGGGLVQPGGSLRLSCAASGFTFADYA-MTWVRQAPGKGLEWVSAISGSGAATYFADSVK GRFTISRDNSKNTLYLQMNSLRAEDTAVYY-CARVSSGHWDYDYWGQGTLVTVSS (SEQ ID NO: 297), and wherein the VL comprises DIQLTQSPSSLSASVGDRVTITCRASQSISSYLNW-YQQKPGKAPKLLIYAASGLESGVPSRFSGSGSGT DFTLTISSLQPEDFATYYCQQTYGVPLTFGG-GTKVEIK (SEQ ID NO: 298).

* * * * *

SEQUENCE LISTING

<160> NUMBER OF SEQ ID NOS: 316

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24
<211> LENGTH: 361
<212> TYPE: PRT
<213> ORGANISM: Unknown
<220> FEATURE:
<221> NAME/KEY: source
<223> OTHER INFORMATION: /note="Description of Unknown: proTGFBETA1 sequence"

<400> SEQUENCE: 24

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335
```

Ile Val Tyr Tyr Val Gly Arg Lys Pro Lys Val Glu Gln Leu Ser Asn
340 345 350

Met Ile Val Arg Ser Cys Lys Cys Ser
355 360

<210> SEQ ID NO 25
<211> LENGTH: 361
<212> TYPE: PRT
<213> ORGANISM: Unknown
<220> FEATURE:
<221> NAME/KEY: source
<223> OTHER INFORMATION: /note="Description of Unknown: proTGFBETA1 C4S sequence"

<400> SEQUENCE: 25

Leu Ser Thr Ser Lys Thr Ile Asp Met Glu Leu Val Lys Arg Lys Arg
1 5 10 15

Ile Glu Ala Ile Arg Gly Gln Ile Leu Ser Lys Leu Arg Leu Ala Ser
20 25 30

Pro Pro Ser Gln Gly Glu Val Pro Pro Gly Pro Leu Pro Glu Ala Val
35 40 45

Leu Ala Leu Tyr Asn Ser Thr Arg Asp Arg Val Ala Gly Glu Ser Ala
50 55 60

Glu Pro Glu Pro Glu Pro Glu Ala Asp Tyr Tyr Ala Lys Glu Val Thr
65 70 75 80

Arg Val Leu Met Val Glu Thr His Asn Glu Ile Tyr Asp Lys Phe Lys
85 90 95

Gln Ser Thr His Ser Ile Tyr Met Phe Phe Asn Thr Ser Glu Leu Arg
100 105 110

Glu Ala Val Pro Glu Pro Val Leu Leu Ser Arg Ala Glu Leu Arg Leu
115 120 125

Leu Arg Leu Lys Leu Lys Val Glu Gln His Val Glu Leu Tyr Gln Lys
130 135 140

Tyr Ser Asn Asn Ser Trp Arg Tyr Leu Ser Asn Arg Leu Leu Ala Pro
145 150 155 160

Ser Asp Ser Pro Glu Trp Leu Ser Phe Asp Val Thr Gly Val Val Arg
165 170 175

Gln Trp Leu Ser Arg Gly Gly Glu Ile Glu Gly Phe Arg Leu Ser Ala
180 185 190

His Cys Ser Cys Asp Ser Arg Asp Asn Thr Leu Gln Val Asp Ile Asn
195 200 205

Gly Phe Thr Thr Gly Arg Arg Gly Asp Leu Ala Thr Ile His Gly Met
210 215 220

Asn Arg Pro Phe Leu Leu Leu Met Ala Thr Pro Leu Glu Arg Ala Gln
225 230 235 240

His Leu Gln Ser Ser Arg His Arg Arg Ala Leu Asp Thr Asn Tyr Cys
245 250 255

Phe Ser Ser Thr Glu Lys Asn Cys Cys Val Arg Gln Leu Tyr Ile Asp
260 265 270

Phe Arg Lys Asp Leu Gly Trp Lys Trp Ile His Glu Pro Lys Gly Tyr
275 280 285

His Ala Asn Phe Cys Leu Gly Pro Cys Pro Tyr Ile Trp Ser Leu Asp
290 295 300

Thr Gln Tyr Ser Lys Val Leu Ala Leu Tyr Asn Gln His Asn Pro Gly
305 310 315 320

Ala Ser Ala Ala Pro Cys Cys Val Pro Gln Ala Leu Glu Pro Leu Pro
325 330 335

Ile Val Tyr Tyr Val Gly Arg Lys Pro Lys Val Glu Gln Leu Ser Asn
340 345 350

Met Ile Val Arg Ser Cys Lys Cys Ser
355 360

<210> SEQ ID NO 26
<211> LENGTH: 360
<212> TYPE: PRT
<213> ORGANISM: Unknown
<220> FEATURE:
<221> NAME/KEY: source
<223> OTHER INFORMATION: /note="Description of Unknown: proTGFBETA1 D2G sequence"

<400> SEQUENCE: 26

Leu Ser Thr Cys Lys Thr Ile Asp Met Glu Leu Val Lys Arg Lys Arg
1 5 10 15

Ile Glu Ala Ile Arg Gly Gln Ile Leu Ser Lys Leu Arg Leu Ala Ser
20 25 30

Pro Pro Ser Gln Gly Glu Val Pro Pro Gly Pro Leu Pro Glu Ala Val
35 40 45

Leu Ala Leu Tyr Asn Ser Thr Arg Asp Arg Val Ala Gly Glu Ser Ala
50 55 60

Glu Pro Glu Pro Glu Pro Glu Ala Asp Tyr Tyr Ala Lys Glu Val Thr
65 70 75 80

Arg Val Leu Met Val Glu Thr His Asn Glu Ile Tyr Asp Lys Phe Lys
85 90 95

Gln Ser Thr His Ser Ile Tyr Met Phe Phe Asn Thr Ser Glu Leu Arg
100 105 110

Glu Ala Val Pro Glu Pro Val Leu Leu Ser Arg Ala Glu Leu Arg Leu
115 120 125

Leu Arg Leu Lys Leu Lys Val Glu Gln His Val Glu Leu Tyr Gln Lys
130 135 140

Tyr Ser Asn Asn Ser Trp Arg Tyr Leu Ser Asn Arg Leu Leu Ala Pro
145 150 155 160

Ser Asp Ser Pro Glu Trp Leu Ser Phe Asp Val Thr Gly Val Val Arg
165 170 175

Gln Trp Leu Ser Arg Gly Gly Glu Ile Glu Gly Phe Arg Leu Ser Ala
180 185 190

His Cys Ser Cys Asp Ser Arg Asp Asn Thr Leu Gln Val Asp Ile Asn
195 200 205

Gly Phe Thr Thr Gly Arg Arg Gly Asp Leu Ala Thr Ile His Gly Met
210 215 220

Asn Arg Pro Phe Leu Leu Leu Met Ala Thr Pro Leu Glu Arg Ala Gln
225 230 235 240

His Leu Gln Ser Ser Arg His Gly Ala Leu Asp Thr Asn Tyr Cys Phe
245 250 255

Ser Ser Thr Glu Lys Asn Cys Cys Val Arg Gln Leu Tyr Ile Asp Phe
260 265 270

Arg Lys Asp Leu Gly Trp Lys Trp Ile His Glu Pro Lys Gly Tyr His
275 280 285

Ala Asn Phe Cys Leu Gly Pro Cys Pro Tyr Ile Trp Ser Leu Asp Thr
290 295 300

Gln Tyr Ser Lys Val Leu Ala Leu Tyr Asn Gln His Asn Pro Gly Ala 305 310 315 320

Ser Ala Ala Pro Cys Cys Val Pro Gln Ala Leu Glu Pro Leu Pro Ile
325 330 335

Val Tyr Tyr Val Gly Arg Lys Pro Lys Val Glu Gln Leu Ser Asn Met
340 345 350

Ile Val Arg Ser Cys Lys Cys Ser
355 360

<210> SEQ ID NO 27
<211> LENGTH: 360
<212> TYPE: PRT
<213> ORGANISM: Unknown
<220> FEATURE:
<221> NAME/KEY: source
<223> OTHER INFORMATION: /note="Description of Unknown: proTGFBETA1 C4S D2G sequence"

<400> SEQUENCE: 27

Leu Ser Thr Ser Lys Thr Ile Asp Met Glu Leu Val Lys Arg Lys Arg
1 5 10 15

Ile Glu Ala Ile Arg Gly Gln Ile Leu Ser Lys Leu Arg Leu Ala Ser
20 25 30

Pro Pro Ser Gln Gly Glu Val Pro Pro Gly Pro Leu Pro Glu Ala Val
35 40 45

Leu Ala Leu Tyr Asn Ser Thr Arg Asp Arg Val Ala Gly Glu Ser Ala
50 55 60

Glu Pro Glu Pro Glu Pro Glu Ala Asp Tyr Tyr Ala Lys Glu Val Thr
65 70 75 80

Arg Val Leu Met Val Glu Thr His Asn Glu Ile Tyr Asp Lys Phe Lys
85 90 95

Gln Ser Thr His Ser Ile Tyr Met Phe Phe Asn Thr Ser Glu Leu Arg
100 105 110

Glu Ala Val Pro Glu Pro Val Leu Leu Ser Arg Ala Glu Leu Arg Leu
115 120 125

Leu Arg Leu Lys Leu Lys Val Glu Gln His Val Glu Leu Tyr Gln Lys
130 135 140

Tyr Ser Asn Asn Ser Trp Arg Tyr Leu Ser Asn Arg Leu Leu Ala Pro
145 150 155 160

Ser Asp Ser Pro Glu Trp Leu Ser Phe Asp Val Thr Gly Val Val Arg
165 170 175

Gln Trp Leu Ser Arg Gly Gly Glu Ile Glu Gly Phe Arg Leu Ser Ala
180 185 190

His Cys Ser Cys Asp Ser Arg Asp Asn Thr Leu Gln Val Asp Ile Asn
195 200 205

Gly Phe Thr Thr Gly Arg Arg Gly Asp Leu Ala Thr Ile His Gly Met
210 215 220

Asn Arg Pro Phe Leu Leu Leu Met Ala Thr Pro Leu Glu Arg Ala Gln
225 230 235 240

His Leu Gln Ser Ser Arg His Gly Ala Leu Asp Thr Asn Tyr Cys Phe
245 250 255

Ser Ser Thr Glu Lys Asn Cys Cys Val Arg Gln Leu Tyr Ile Asp Phe
260 265 270

Arg Lys Asp Leu Gly Trp Lys Trp Ile His Glu Pro Lys Gly Tyr His
275 280 285

Ala Asn Phe Cys Leu Gly Pro Cys Pro Tyr Ile Trp Ser Leu Asp Thr
290 295 300

```
Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360


<210> SEQ ID NO 28
<211> LENGTH: 395
<212> TYPE: PRT
<213> ORGANISM: Unknown
<220> FEATURE:
<221> NAME/KEY: source
<223> OTHER INFORMATION: /note="Description of Unknown:
      proTGFBETA2 sequence"

<400> SEQUENCE: 28

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285
```

```
Tyr Cys Phe Arg Asn Val Gln Asp Asn Cys Cys Leu Arg Pro Leu Tyr
    290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
        355                 360                 365

Leu Thr Ile Leu Tyr Tyr Ile Gly Lys Thr Pro Lys Ile Glu Gln Leu
    370                 375                 380

Ser Asn Met Ile Val Lys Ser Cys Lys Cys Ser
385                 390                 395


<210> SEQ ID NO 29
<211> LENGTH: 395
<212> TYPE: PRT
<213> ORGANISM: Unknown
<220> FEATURE:
<221> NAME/KEY: source
<223> OTHER INFORMATION: /note="Description of Unknown:
      proTGFBETA2 C5S sequence"

<400> SEQUENCE: 29

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
```

```
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
        275                 280                 285

Tyr Cys Phe Arg Asn Val Gln Asp Asn Cys Cys Leu Arg Pro Leu Tyr
    290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
        355                 360                 365

Leu Thr Ile Leu Tyr Tyr Ile Gly Lys Thr Pro Lys Ile Glu Gln Leu
    370                 375                 380

Ser Asn Met Ile Val Lys Ser Cys Lys Cys Ser
385                 390                 395


<210> SEQ ID NO 30
<211> LENGTH: 394
<212> TYPE: PRT
<213> ORGANISM: Unknown
<220> FEATURE:
<221> NAME/KEY: source
<223> OTHER INFORMATION: /note="Description of Unknown:
      proTGFBETA2 C5S D2G sequence"

<400> SEQUENCE: 30

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205
```

```
Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
    290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
    370                 375                 380

Asn Met Ile Val Lys Ser Cys Lys Cys Ser
385                 390


<210> SEQ ID NO 31
<211> LENGTH: 394
<212> TYPE: PRT
<213> ORGANISM: Unknown
<220> FEATURE:
<221> NAME/KEY: source
<223> OTHER INFORMATION: /note="Description of Unknown:
      proTGFBETA2 D2G sequence"

<400> SEQUENCE: 31

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
        35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
        115                 120                 125

Glu Phe Arg Val Phe Arg Leu Gln Asn Pro Lys Ala Arg Val Pro Glu
    130                 135                 140

Gln Arg Ile Glu Leu Tyr Gln Ile Leu Lys Ser Lys Asp Leu Thr Ser
145                 150                 155                 160
```

```
Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
        275                 280                 285

Cys Phe Arg Asn Val Gln Asp Asn Cys Cys Leu Arg Pro Leu Tyr Ile
    290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
    370                 375                 380

Asn Met Ile Val Lys Ser Cys Lys Cys Ser
385                 390


<210> SEQ ID NO 32
<211> LENGTH: 392
<212> TYPE: PRT
<213> ORGANISM: Unknown
<220> FEATURE:
<221> NAME/KEY: source
<223> OTHER INFORMATION: /note="Description of Unknown:
      proTGFBETA3 sequence"

<400> SEQUENCE: 32

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
```

```
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
        275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
        355                 360                 365

Leu Tyr Tyr Val Gly Arg Thr Pro Lys Val Glu Gln Leu Ser Asn Met
    370                 375                 380

Val Val Lys Ser Cys Lys Cys Ser
385                 390


<210> SEQ ID NO 33
<211> LENGTH: 392
<212> TYPE: PRT
<213> ORGANISM: Unknown
<220> FEATURE:
<221> NAME/KEY: source
<223> OTHER INFORMATION: /note="Description of Unknown:
      proTGFBETA3 C7S  sequence"

<400> SEQUENCE: 33

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80
```

Tyr Ala Lys Glu Ile His Lys Phe Asp Met Ile Gln Gly Leu Ala Glu
85 90 95

His Asn Glu Leu Ala Val Cys Pro Lys Gly Ile Thr Ser Lys Val Phe
100 105 110

Arg Phe Asn Val Ser Ser Val Glu Lys Asn Arg Thr Asn Leu Phe Arg
115 120 125

Ala Glu Phe Arg Val Leu Arg Val Pro Asn Pro Ser Ser Lys Arg Asn
130 135 140

Glu Gln Arg Ile Glu Leu Phe Gln Ile Leu Arg Pro Asp Glu His Ile
145 150 155 160

Ala Lys Gln Arg Tyr Ile Gly Gly Lys Asn Leu Pro Thr Arg Gly Thr
165 170 175

Ala Glu Trp Leu Ser Phe Asp Val Thr Asp Thr Val Arg Glu Trp Leu
180 185 190

Leu Arg Arg Glu Ser Asn Leu Gly Leu Glu Ile Ser Ile His Cys Pro
195 200 205

Cys His Thr Phe Gln Pro Asn Gly Asp Ile Leu Glu Asn Ile His Glu
210 215 220

Val Met Glu Ile Lys Phe Lys Gly Val Asp Asn Glu Asp Asp His Gly
225 230 235 240

Arg Gly Asp Leu Gly Arg Leu Lys Lys Gln Lys Asp His His Asn Pro
245 250 255

His Leu Ile Leu Met Met Ile Pro Pro His Arg Leu Asp Asn Pro Gly
260 265 270

Gln Gly Gly Gln Arg Lys Lys Arg Ala Leu Asp Thr Asn Tyr Cys Phe
275 280 285

Arg Asn Leu Glu Glu Asn Cys Cys Val Arg Pro Leu Tyr Ile Asp Phe
290 295 300

Arg Gln Asp Leu Gly Trp Lys Trp Val His Glu Pro Lys Gly Tyr Tyr
305 310 315 320

Ala Asn Phe Cys Ser Gly Pro Cys Pro Tyr Leu Arg Ser Ala Asp Thr
325 330 335

Thr His Ser Thr Val Leu Gly Leu Tyr Asn Thr Leu Asn Pro Glu Ala
340 345 350

Ser Ala Ser Pro Cys Cys Val Pro Gln Asp Leu Glu Pro Leu Thr Ile
355 360 365

Leu Tyr Tyr Val Gly Arg Thr Pro Lys Val Glu Gln Leu Ser Asn Met
370 375 380

Val Val Lys Ser Cys Lys Cys Ser
385 390

<210> SEQ ID NO 34
<211> LENGTH: 391
<212> TYPE: PRT
<213> ORGANISM: Unknown
<220> FEATURE:
<221> NAME/KEY: source
<223> OTHER INFORMATION: /note="Description of Unknown:
proTGFBETA3 C7S D2G sequence"

<400> SEQUENCE: 34

Ser Leu Ser Leu Ser Thr Ser Thr Thr Leu Asp Phe Gly His Ile Lys
1 5 10 15

Lys Lys Arg Val Glu Ala Ile Arg Gly Gln Ile Leu Ser Lys Leu Arg
20 25 30

```
Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
    370                 375                 380

Val Lys Ser Cys Lys Cys Ser
385                 390
```

```
<210> SEQ ID NO 35
<211> LENGTH: 391
<212> TYPE: PRT
<213> ORGANISM: Unknown
<220> FEATURE:
<221> NAME/KEY: source
<223> OTHER INFORMATION: /note="Description of Unknown:
      proTGFBETA3 D2G sequence"
```

<400> SEQUENCE: 35

```
Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
    370                 375                 380

Val Lys Ser Cys Lys Cys Ser
385                 390
```

<210> SEQ ID NO 36

<211> LENGTH: 361
<212> TYPE: PRT
<213> ORGANISM: Mus sp.

<400> SEQUENCE: 36

Leu Ser Thr Cys Lys Thr Ile Asp Met Glu Leu Val Lys Arg Lys Arg
1 5 10 15

Ile Glu Ala Ile Arg Gly Gln Ile Leu Ser Lys Leu Arg Leu Ala Ser
20 25 30

Pro Pro Ser Gln Gly Glu Val Pro Pro Gly Pro Leu Pro Glu Ala Val
35 40 45

Leu Ala Leu Tyr Asn Ser Thr Arg Asp Arg Val Ala Gly Glu Ser Ala
50 55 60

Asp Pro Glu Pro Glu Pro Glu Ala Asp Tyr Tyr Ala Lys Glu Val Thr
65 70 75 80

Arg Val Leu Met Val Asp Arg Asn Asn Ala Ile Tyr Glu Lys Thr Lys
85 90 95

Asp Ile Ser His Ser Ile Tyr Met Phe Phe Asn Thr Ser Asp Ile Arg
100 105 110

Glu Ala Val Pro Glu Pro Pro Leu Leu Ser Arg Ala Glu Leu Arg Leu
115 120 125

Gln Arg Leu Lys Ser Ser Val Glu Gln His Val Glu Leu Tyr Gln Lys
130 135 140

Tyr Ser Asn Asn Ser Trp Arg Tyr Leu Gly Asn Arg Leu Leu Thr Pro
145 150 155 160

Thr Asp Thr Pro Glu Trp Leu Ser Phe Asp Val Thr Gly Val Val Arg
165 170 175

Gln Trp Leu Asn Gln Gly Asp Gly Ile Gln Gly Phe Arg Phe Ser Ala
180 185 190

His Cys Ser Cys Asp Ser Lys Asp Asn Lys Leu His Val Glu Ile Asn
195 200 205

Gly Ile Ser Pro Lys Arg Arg Gly Asp Leu Gly Thr Ile His Asp Met
210 215 220

Asn Arg Pro Phe Leu Leu Leu Met Ala Thr Pro Leu Glu Arg Ala Gln
225 230 235 240

His Leu His Ser Ser Arg His Arg Arg Ala Leu Asp Thr Asn Tyr Cys
245 250 255

Phe Ser Ser Thr Glu Lys Asn Cys Cys Val Arg Gln Leu Tyr Ile Asp
260 265 270

Phe Arg Lys Asp Leu Gly Trp Lys Trp Ile His Glu Pro Lys Gly Tyr
275 280 285

His Ala Asn Phe Cys Leu Gly Pro Cys Pro Tyr Ile Trp Ser Leu Asp
290 295 300

Thr Gln Tyr Ser Lys Val Leu Ala Leu Tyr Asn Gln His Asn Pro Gly
305 310 315 320

Ala Ser Ala Ser Pro Cys Cys Val Pro Gln Ala Leu Glu Pro Leu Pro
325 330 335

Ile Val Tyr Tyr Val Gly Arg Lys Pro Lys Val Glu Gln Leu Ser Asn
340 345 350

Met Ile Val Arg Ser Cys Lys Cys Ser
355 360

<210> SEQ ID NO 37
<211> LENGTH: 361
<212> TYPE: PRT

<213> ORGANISM: Macaca fascicularis

<400> SEQUENCE: 37

Leu Ser Thr Cys Lys Thr Ile Asp Met Glu Leu Val Lys Arg Lys Arg
1 5 10 15

Ile Glu Ala Ile Arg Gly Gln Ile Leu Ser Lys Leu Arg Leu Ala Ser
20 25 30

Pro Pro Ser Gln Gly Glu Val Pro Pro Gly Pro Leu Pro Glu Ala Val
35 40 45

Leu Ala Leu Tyr Asn Ser Thr Arg Asp Arg Val Ala Gly Glu Ser Ala
50 55 60

Glu Pro Glu Pro Glu Pro Glu Ala Asp Tyr Tyr Ala Lys Glu Val Thr
65 70 75 80

Arg Val Leu Met Val Glu Thr His Asn Glu Ile Tyr Asp Lys Phe Lys
85 90 95

Gln Ser Thr His Ser Ile Tyr Met Phe Phe Asn Thr Ser Glu Leu Arg
100 105 110

Glu Ala Val Pro Glu Pro Val Leu Leu Ser Arg Ala Glu Leu Arg Leu
115 120 125

Leu Arg Leu Lys Leu Lys Val Glu Gln His Val Glu Leu Tyr Gln Lys
130 135 140

Tyr Ser Asn Asn Ser Trp Arg Tyr Leu Ser Asn Arg Leu Leu Ala Pro
145 150 155 160

Ser Asp Ser Pro Glu Trp Leu Ser Phe Asp Val Thr Gly Val Val Arg
165 170 175

Gln Trp Leu Ser Arg Gly Gly Glu Ile Glu Gly Phe Arg Leu Ser Ala
180 185 190

His Cys Ser Cys Asp Ser Lys Asp Asn Thr Leu Gln Val Asp Ile Asn
195 200 205

Gly Phe Thr Thr Gly Arg Arg Gly Asp Leu Ala Thr Ile His Gly Met
210 215 220

Asn Arg Pro Phe Leu Leu Leu Met Ala Thr Pro Leu Glu Arg Ala Gln
225 230 235 240

His Leu Gln Ser Ser Arg His Arg Arg Ala Leu Asp Thr Asn Tyr Cys
245 250 255

Phe Ser Ser Thr Glu Lys Asn Cys Cys Val Arg Gln Leu Tyr Ile Asp
260 265 270

Phe Arg Lys Asp Leu Gly Trp Lys Trp Ile His Glu Pro Lys Gly Tyr
275 280 285

His Ala Asn Phe Cys Leu Gly Pro Cys Pro Tyr Ile Trp Ser Leu Asp
290 295 300

Thr Gln Tyr Ser Lys Val Leu Ala Leu Tyr Asn Gln His Asn Pro Gly
305 310 315 320

Ala Ser Ala Ala Pro Cys Cys Val Pro Gln Ala Leu Glu Pro Leu Pro
325 330 335

Ile Val Tyr Tyr Val Gly Arg Lys Pro Lys Val Glu Gln Leu Ser Asn
340 345 350

Met Ile Val Arg Ser Cys Lys Cys Ser
355 360

<210> SEQ ID NO 38
<211> LENGTH: 249
<212> TYPE: PRT
<213> ORGANISM: Mus sp.

<400> SEQUENCE: 38

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245
```

<210> SEQ ID NO 39
<211> LENGTH: 249
<212> TYPE: PRT
<213> ORGANISM: Macaca fascicularis

<400> SEQUENCE: 39

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110
```

```
Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245


<210> SEQ ID NO 40
<211> LENGTH: 360
<212> TYPE: PRT
<213> ORGANISM: Mus sp.

<400> SEQUENCE: 40

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240
```

```
His Leu His Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ser Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360


<210> SEQ ID NO 41
<211> LENGTH: 361
<212> TYPE: PRT
<213> ORGANISM: Mus sp.

<400> SEQUENCE: 41

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
```

```
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360


<210> SEQ ID NO 42
<211> LENGTH: 361
<212> TYPE: PRT
<213> ORGANISM: Macaca fascicularis

<400> SEQUENCE: 42

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255
```

```
Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360


<210> SEQ ID NO 43
<211> LENGTH: 360
<212> TYPE: PRT
<213> ORGANISM: Macaca fascicularis

<400> SEQUENCE: 43

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270
```

Arg Lys Asp Leu Gly Trp Lys Trp Ile His Glu Pro Lys Gly Tyr His
275 280 285

Ala Asn Phe Cys Leu Gly Pro Cys Pro Tyr Ile Trp Ser Leu Asp Thr
290 295 300

Gln Tyr Ser Lys Val Leu Ala Leu Tyr Asn Gln His Asn Pro Gly Ala
305 310 315 320

Ser Ala Ala Pro Cys Cys Val Pro Gln Ala Leu Glu Pro Leu Pro Ile
325 330 335

Val Tyr Tyr Val Gly Arg Lys Pro Lys Val Glu Gln Leu Ser Asn Met
340 345 350

Ile Val Arg Ser Cys Lys Cys Ser
355 360

<210> SEQ ID NO 44
<211> LENGTH: 1260
<212> TYPE: PRT
<213> ORGANISM: Macaca fascicularis

<400> SEQUENCE: 44

Gly Pro Ala Gly Glu Arg Gly Ala Gly Gly Gly Gly Ala Leu Ala Arg
1 5 10 15

Glu Arg Phe Lys Val Val Phe Ala Pro Val Ile Cys Lys Arg Thr Cys
20 25 30

Leu Lys Gly Gln Cys Arg Asp Ser Cys Gln Gln Gly Ser Asn Met Thr
35 40 45

Leu Ile Gly Glu Asn Gly His Ser Thr Asp Thr Leu Thr Gly Ser Gly
50 55 60

Phe Arg Val Val Val Cys Pro Leu Pro Cys Met Asn Gly Gly Gln Cys
65 70 75 80

Ser Ser Arg Asn Gln Cys Leu Cys Pro Pro Asp Phe Thr Gly Arg Phe
85 90 95

Cys Gln Val Pro Ala Gly Gly Ala Gly Gly Gly Thr Gly Gly Ser Gly
100 105 110

Pro Gly Leu Ser Arg Ala Gly Ala Leu Ser Thr Gly Ala Leu Pro Pro
115 120 125

Leu Ala Pro Glu Gly Asp Ser Val Ala Ser Lys His Ala Ile Tyr Ala
130 135 140

Val Gln Val Ile Ala Asp Pro Pro Gly Pro Gly Glu Gly Pro Pro Ala
145 150 155 160

Gln His Ala Ala Phe Leu Val Pro Leu Gly Pro Gly Gln Ile Ser Ala
165 170 175

Glu Val Gln Ala Pro Pro Pro Val Val Asn Val Arg Val His His Pro
180 185 190

Pro Glu Ala Ser Val Gln Val His Arg Ile Glu Ser Ser Asn Ala Glu
195 200 205

Gly Ala Ala Pro Ser Gln His Leu Leu Pro His Pro Lys Pro Ser His
210 215 220

Pro Arg Pro Pro Thr Gln Lys Pro Leu Gly Arg Cys Phe Gln Asp Thr
225 230 235 240

Leu Pro Lys Gln Pro Cys Gly Ser Asn Pro Leu Pro Gly Leu Thr Lys
245 250 255

Gln Glu Asp Cys Cys Gly Ser Ile Gly Thr Ala Trp Gly Gln Ser Lys
260 265 270

Cys His Lys Cys Pro Gln Leu Gln Tyr Thr Gly Val Gln Lys Pro Gly

```
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile
            340                 345                 350

Ala Asp Lys Pro Glu Glu Lys Ser Leu Cys Phe Arg Leu Val Ser Pro
        355                 360                 365

Glu His Gln Cys Gln His Pro Leu Thr Thr Arg Leu Thr Arg Gln Leu
    370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Ala Gly Lys
                405                 410                 415

Gly Tyr His Ile Leu Thr Ser His Gln Thr Leu Thr Ile Gln Gly Glu
            420                 425                 430

Ser Asp Phe Ser Leu Phe Leu His Pro Asp Gly Pro Pro Lys Pro Gln
        435                 440                 445

Gln Leu Pro Glu Ser Pro Ser Gln Ala Pro Pro Pro Glu Asp Thr Glu
    450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Ser Pro Ala Arg Pro Tyr
                485                 490                 495

Pro Glu Leu Ile Ser Arg Pro Ser Pro Pro Thr Met Arg Trp Phe Leu
            500                 505                 510

Pro Asp Leu Pro Pro Ser Arg Ser Ala Val Glu Ile Ala Pro Thr Gln
        515                 520                 525

Val Thr Glu Thr Asp Glu Cys Arg Leu Asn Gln Asn Ile Cys Gly His
    530                 535                 540

Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
                565                 570                 575

Cys Glu Ala Glu Pro Cys Gly Pro Gly Arg Gly Ile Cys Met Asn Thr
            580                 585                 590

Gly Gly Ser Tyr Asn Cys His Cys Asn Arg Gly Tyr Arg Leu His Val
        595                 600                 605

Gly Ala Gly Gly Arg Ser Cys Val Asp Leu Asn Glu Cys Ala Lys Pro
    610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
        675                 680                 685

Pro Gly Tyr Arg Ser Gln Gly Gly Gly Ala Cys Arg Asp Val Asn Glu
    690                 695                 700
```

```
Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
                725                 730                 735

Gly Arg Ser Cys Val Asp Val Asp Glu Cys Glu Ala Gly Asp Val Cys
            740                 745                 750

Asp Asn Gly Ile Cys Thr Asn Thr Pro Gly Ser Phe Gln Cys Gln Cys
        755                 760                 765

Leu Ser Gly Tyr His Leu Ser Arg Asp Arg Ser His Cys Glu Asp Ile
    770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
                805                 810                 815

Gly Gly Arg Lys Cys Gln Asp Ile Asp Glu Cys Thr Gln Asp Pro Gly
            820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
    850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
        915                 920                 925

Pro Asp Gly Lys Gly Tyr Thr Gln Asp Asn Asn Ile Val Asn Tyr Gly
    930                 935                 940

Ile Pro Ala His Arg Asp Ile Asp Glu Cys Met Leu Phe Gly Ala Glu
945                 950                 955                 960

Ile Cys Lys Glu Gly Lys Cys Val Asn Thr Gln Pro Gly Tyr Glu Cys
                965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu  Ser Asn Cys Arg Asn  Gly Val Cys
        995                 1000                1005

Glu Asn  Thr Arg Gly Gly Tyr  Arg Cys Ala Cys Thr  Pro Pro Ala
    1010                1015                1020

Glu Tyr  Ser Pro Ala Gln Arg  Gln Cys Leu Ser Pro  Glu Glu Met
    1025                1030                1035

Asp Val  Asp Glu Cys Gln Asp  Pro Ala Ala Cys Arg  Pro Gly Arg
    1040                1045                1050

Cys Val  Asn Leu Pro Gly Ser  Tyr Arg Cys Glu Cys  Arg Pro Pro
    1055                1060                1065

Trp Val  Pro Gly Pro Ser Gly  Arg Asp Cys Gln Leu  Pro Glu Ser
    1070                1075                1080

Pro Ala  Glu Arg Ala Pro Glu  Arg Arg Asp Val Cys  Trp Ser Gln
    1085                1090                1095

Arg Gly  Glu Asp Gly Met Cys  Ala Gly Pro Gln Ala  Gly Pro Ala
    1100                1105                1110
```

```
Leu Thr  Phe Asp Asp Cys Cys  Cys Arg Gln Gly Arg  Gly Trp Gly
    1115                 1120                 1125

Ala Gln  Cys Arg Pro Cys Pro  Pro Arg Gly Ala Gly  Ser Gln Cys
    1130                 1135                 1140

Pro Thr  Ser Gln Ser Glu Ser  Asn Ser Phe Trp Asp  Thr Ser Pro
    1145                 1150                 1155

Leu Leu  Leu Gly Lys Pro Arg  Arg Asp Glu Asp Ser  Ser Glu Glu
    1160                 1165                 1170

Asp Ser  Asp Glu Cys Arg Cys  Val Ser Gly Arg Cys  Val Pro Arg
    1175                 1180                 1185

Pro Gly  Gly Ala Val Cys Glu  Cys Pro Gly Gly Phe  Gln Leu Asp
    1190                 1195                 1200

Ala Ser  Arg Ala Arg Cys Val  Asp Ile Asp Glu Cys  Arg Glu Leu
    1205                 1210                 1215

Asn Gln  Arg Gly Leu Leu Cys  Lys Ser Glu Arg Cys  Val Asn Thr
    1220                 1225                 1230

Ser Gly  Ser Phe Arg Cys Val  Cys Lys Ala Gly Phe  Ala Arg Ser
    1235                 1240                 1245

Arg Pro  His Gly Ala Cys Val  Pro Gln Arg Arg Arg
    1250                 1255                 1260


<210> SEQ ID NO 45
<211> LENGTH: 1228
<212> TYPE: PRT
<213> ORGANISM: Mus sp.

<400> SEQUENCE: 45

Gly Pro Ala Gly Glu Arg Gly Thr Gly Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
        35                  40                  45

Leu Ile Gly Glu Asn Gly His Ser Thr Asp Thr Leu Thr Gly Ser Ala
    50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Ala Gly Thr Gly Ala Gly Thr Gly Ser Ser Gly
            100                 105                 110

Pro Gly Leu Ala Arg Thr Gly Ala Met Ser Thr Gly Pro Leu Pro Pro
        115                 120                 125

Leu Ala Pro Glu Gly Glu Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Pro Val Val Asn Val Arg Val His His Pro
            180                 185                 190

Pro Glu Ala Ser Val Gln Val His Arg Ile Glu Gly Pro Asn Ala Glu
        195                 200                 205

Gly Pro Ala Ser Ser Gln His Leu Leu Pro His Pro Lys Pro Pro His
    210                 215                 220
```

```
Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Val
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Asn Val Cys His Gly Asp Cys Leu Asn Asn Pro Gly Ser Tyr Arg Cys
                325                 330                 335

Val Cys Pro Pro Gly His Ser Leu Gly Pro Leu Ala Ala Gln Cys Ile
            340                 345                 350

Ala Asp Lys Pro Glu Glu Lys Ser Leu Cys Phe Arg Leu Val Ser Thr
        355                 360                 365

Glu His Gln Cys Gln His Pro Leu Thr Thr Arg Leu Thr Arg Gln Leu
    370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Gly Lys Gly
                405                 410                 415

Tyr His Ile Leu Thr Ser His Gln Thr Leu Thr Ile Gln Gly Glu Ser
            420                 425                 430

Asp Phe Ser Leu Phe Leu His Pro Asp Gly Pro Pro Lys Pro Gln Gln
        435                 440                 445

Leu Pro Glu Ser Pro Ser Arg Ala Pro Pro Leu Glu Asp Thr Glu Glu
    450                 455                 460

Glu Arg Gly Val Thr Met Asp Pro Pro Val Ser Glu Glu Arg Ser Val
465                 470                 475                 480

Gln Gln Ser His Pro Thr Thr Thr Thr Ser Pro Pro Arg Pro Tyr Pro
                485                 490                 495

Glu Leu Ile Ser Arg Pro Ser Pro Pro Thr Phe His Arg Phe Leu Pro
            500                 505                 510

Asp Leu Pro Pro Ser Arg Ser Ala Val Glu Ile Ala Pro Thr Gln Val
        515                 520                 525

Thr Glu Thr Asp Glu Cys Arg Leu Asn Gln Asn Ile Cys Gly His Gly
    530                 535                 540

Gln Cys Val Pro Gly Pro Ser Asp Tyr Ser Cys His Cys Asn Ala Gly
545                 550                 555                 560

Tyr Arg Ser His Pro Gln His Arg Tyr Cys Val Asp Val Asn Glu Cys
                565                 570                 575

Glu Ala Glu Pro Cys Gly Pro Gly Lys Gly Ile Cys Met Asn Thr Gly
            580                 585                 590

Gly Ser Tyr Asn Cys His Cys Asn Arg Gly Tyr Arg Leu His Val Gly
        595                 600                 605

Ala Gly Gly Arg Ser Cys Val Asp Leu Asn Glu Cys Ala Lys Pro His
    610                 615                 620

Leu Cys Gly Asp Gly Gly Phe Cys Ile Asn Phe Pro Gly His Tyr Lys
625                 630                 635                 640
```

```
Cys Asn Cys Tyr Pro Gly Tyr Arg Leu Lys Ala Ser Arg Pro Pro Ile
                645                 650                 655

Cys Glu Asp Ile Asp Glu Cys Arg Asp Pro Ser Thr Cys Pro Asp Gly
            660                 665                 670

Lys Cys Glu Asn Lys Pro Gly Ser Phe Lys Cys Ile Ala Cys Gln Pro
        675                 680                 685

Gly Tyr Arg Ser Gln Gly Gly Gly Ala Cys Arg Asp Val Asn Glu Cys
    690                 695                 700

Ser Glu Gly Thr Pro Cys Ser Pro Gly Trp Cys Glu Asn Leu Pro Gly
705                 710                 715                 720

Ser Tyr Arg Cys Thr Cys Ala Gln Tyr Glu Pro Ala Gln Asp Gly Leu
                725                 730                 735

Ser Cys Ile Asp Val Asp Glu Cys Glu Ala Gly Lys Val Cys Gln Asp
            740                 745                 750

Gly Ile Cys Thr Asn Thr Pro Gly Ser Phe Gln Cys Gln Cys Leu Ser
        755                 760                 765

Gly Tyr His Leu Ser Arg Asp Arg Ser Arg Cys Glu Asp Ile Asp Glu
    770                 775                 780

Cys Asp Phe Pro Ala Ala Cys Ile Gly Gly Asp Cys Ile Asn Thr Asn
785                 790                 795                 800

Gly Ser Tyr Arg Cys Leu Cys Pro Leu Gly His Arg Leu Val Gly Gly
                805                 810                 815

Arg Lys Cys Lys Lys Asp Ile Asp Glu Cys Ser Gln Asp Pro Gly Leu
            820                 825                 830

Cys Leu Pro His Ala Cys Glu Asn Leu Gln Gly Ser Tyr Val Cys Val
        835                 840                 845

Cys Asp Glu Gly Phe Thr Leu Thr Gln Asp Gln His Gly Cys Glu Glu
    850                 855                 860

Val Glu Gln Pro His His Lys Lys Glu Cys Tyr Leu Asn Phe Asp Asp
865                 870                 875                 880

Thr Val Phe Cys Asp Ser Val Leu Ala Thr Asn Val Thr Gln Gln Glu
                885                 890                 895

Cys Cys Cys Ser Leu Gly Ala Gly Trp Gly Asp His Cys Glu Ile Tyr
            900                 905                 910

Pro Cys Pro Val Tyr Ser Ser Ala Glu Phe His Ser Leu Val Pro Asp
        915                 920                 925

Gly Lys Arg Leu His Ser Gly Gln Gln His Cys Glu Leu Cys Ile Pro
    930                 935                 940

Ala His Arg Asp Ile Asp Glu Cys Ile Leu Phe Gly Ala Glu Ile Cys
945                 950                 955                 960

Lys Glu Gly Lys Cys Val Asn Thr Gln Pro Gly Tyr Glu Cys Tyr Cys
                965                 970                 975

Lys Gln Gly Phe Tyr Tyr Asp Gly Asn Leu Leu Glu Cys Val Asp Val
            980                 985                 990

Asp Glu Cys Leu Asp Glu Ser Asn  Cys Arg Asn Gly Val  Cys Glu Asn
        995                 1000                 1005

Thr Arg  Gly Gly Tyr Arg Cys  Ala Cys Thr Pro Pro  Ala Glu Tyr
    1010                 1015                 1020

Ser Pro  Ala Gln Ala Gln Cys  Leu Ile Pro Glu Arg  Trp Ser Thr
    1025                 1030                 1035

Pro Gln  Arg Asp Val Lys Cys  Ala Gly Ala Ser Glu  Glu Arg Thr
    1040                 1045                 1050

Ala Cys  Val Trp Gly Pro Trp  Ala Gly Pro Ala Leu  Thr Phe Asp
```

```
    1055                1060                1065

Asp Cys  Cys Cys Arg Gln Pro  Arg Leu Gly Thr Gln  Cys Arg Pro
    1070                1075                1080

Cys Pro  Pro Arg Gly Thr Gly  Ser Gln Cys Pro Thr  Ser Gln Ser
    1085                1090                1095

Glu Ser  Asn Ser Phe Trp Asp  Thr Ser Pro Leu Leu  Leu Gly Lys
    1100                1105                1110

Ser Pro  Arg Asp Glu Asp Ser  Ser Glu Glu Asp Ser  Asp Glu Cys
    1115                1120                1125

Arg Cys  Val Ser Gly Arg Cys  Val Pro Arg Pro Gly  Gly Ala Val
    1130                1135                1140

Cys Glu  Cys Pro Gly Gly Phe  Gln Leu Asp Ala Ser  Arg Ala Arg
    1145                1150                1155

Cys Val  Asp Ile Asp Glu Cys  Arg Glu Leu Asn Gln  Arg Gly Leu
    1160                1165                1170

Leu Cys  Lys Ser Glu Arg Cys  Val Asn Thr Ser Gly  Ser Phe Arg
    1175                1180                1185

Cys Val  Cys Lys Ala Gly Phe  Thr Arg Ser Arg Pro  His Gly Pro
    1190                1195                1200

Ala Cys  Leu Ser Ala Ala Ala  Asp Asp Ala Ala Ile  Ala His Thr
    1205                1210                1215

Ser Val  Ile Asp His Arg Gly  Tyr Phe His
    1220                1225


<210> SEQ ID NO 46
<211> LENGTH: 1373
<212> TYPE: PRT
<213> ORGANISM: Macaca fascicularis

<400> SEQUENCE: 46

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Leu Cys His Leu Pro Cys Met Asn Gly
    50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
            100                 105                 110

His Ser Thr His Thr Leu Pro Leu Thr Val Thr Ser Gln Gln Gly Val
        115                 120                 125

Lys Val Lys Phe Pro Pro Asn Ile Val Asn Ile His Val Lys His Pro
    130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
            180                 185                 190
```

```
Ser His Gln Gln Val Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255

Tyr His Gly Tyr Asn Gln Met Met Glu Cys Leu Pro Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
    290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
            340                 345                 350

Lys Gln Leu Cys Cys Cys Ser Val Gly Lys Ala Trp Gly Pro His Cys
        355                 360                 365

Glu Lys Cys Pro Leu Pro Gly Thr Ala Ala Phe Lys Glu Ile Cys Pro
    370                 375                 380

Gly Gly Met Gly Tyr Thr Val Ser Gly Val His Arg Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Pro Leu Pro Ala Lys Glu
            420                 425                 430

Glu Pro Val Glu Ala Leu Thr Phe Ser Arg Glu His Gly Pro Gly Val
        435                 440                 445

Ala Glu Pro Glu Val Ala Thr Ala Pro Pro Glu Lys Glu Ile Pro Ser
    450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
                485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
        515                 520                 525

Asn Glu Cys Thr Val Asn Pro Asp Ile Cys Gly Ala Gly His Cys Ile
    530                 535                 540

Asn Leu Pro Val Arg Tyr Thr Cys Ile Cys Tyr Glu Gly Tyr Lys Phe
545                 550                 555                 560

Ser Glu Gln Gln Arg Lys Cys Val Asp Ile Asp Glu Cys Thr Gln Val
                565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
        595                 600                 605

Cys Ile Asp Val Asp Glu Cys Leu Arg Pro Asp Val Cys Gly Glu Gly
```

```
    610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Glu Pro Asn Val Cys Thr Asn
    690                 695                 700

Gly Asp Cys Ser Asn Leu Glu Gly Ser Tyr Met Cys Ser Cys His Lys
705                 710                 715                 720

Gly Tyr Thr Arg Thr Pro Asp His Lys His Cys Lys Asp Ile Asp Glu
                725                 730                 735

Cys Gln Gln Gly Asn Leu Cys Val Asn Gly Gln Cys Lys Asn Thr Glu
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Gln His His His Leu Cys
    770                 775                 780

Ala His Gly Gln Cys Arg Asn Thr Glu Gly Ser Phe Gln Cys Val Cys
785                 790                 795                 800

Asp Gln Gly Tyr Arg Ala Ser Gly Leu Gly Asp His Cys Glu Asp Ile
                805                 810                 815

Asn Glu Cys Leu Glu Asp Lys Ser Val Cys Gln Arg Gly Asp Cys Ile
            820                 825                 830

Asn Thr Ala Gly Ser Tyr Asp Cys Thr Cys Pro Asp Gly Phe Gln Leu
        835                 840                 845

Asp Asp Asn Lys Thr Cys Gln Asp Ile Asn Glu Cys Glu His Pro Gly
    850                 855                 860

Leu Cys Gly Pro Gln Gly Glu Cys Leu Asn Thr Glu Gly Ser Phe His
865                 870                 875                 880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
945                 950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Thr Ser Thr Asp Leu Asp Val Glu
            980                 985                 990

Gln Pro Lys Glu Glu Lys Lys Glu  Cys Tyr Tyr Asn Leu  Asn Asp Ala
        995                 1000                1005

Ser Leu  Cys Asp Asn Val Leu  Ala Pro Asn Val Thr  Lys Gln Glu
    1010                1015                1020

Cys Cys  Cys Thr Ser Gly Ala  Gly Trp Gly Asp Asn  Cys Glu Ile
    1025                1030                1035
```

Phe Pro Cys Pro Val Leu Gly Thr Ala Glu Phe Thr Glu Met Cys
1040 1045 1050

Pro Lys Gly Lys Gly Phe Val Pro Ala Gly Glu Ser Ser Ser Glu
1055 1060 1065

Ala Gly Gly Glu Asn Tyr Lys Asp Ala Asp Glu Cys Leu Leu Phe
1070 1075 1080

Gly Gln Glu Ile Cys Lys Asn Gly Phe Cys Leu Asn Thr Arg Pro
1085 1090 1095

Gly Tyr Glu Cys Tyr Cys Lys Gln Gly Thr Tyr Tyr Asp Pro Val
1100 1105 1110

Lys Leu Gln Cys Phe Asp Met Asp Glu Cys Gln Asp Pro Ser Ser
1115 1120 1125

Cys Ile Asp Gly Gln Cys Val Asn Thr Glu Gly Ser Tyr Asn Cys
1130 1135 1140

Phe Cys Thr His Pro Met Val Leu Asp Ala Ser Glu Lys Arg Cys
1145 1150 1155

Ile Arg Pro Ala Glu Ser Asn Glu Gln Ile Glu Glu Thr Asp Val
1160 1165 1170

Tyr Gln Asp Leu Cys Trp Glu His Leu Ser Asp Glu Tyr Val Cys
1175 1180 1185

Ser Arg Pro Leu Val Gly Lys Gln Thr Thr Tyr Thr Glu Cys Cys
1190 1195 1200

Cys Leu Tyr Gly Glu Ala Trp Gly Met Gln Cys Ala Leu Cys Pro
1205 1210 1215

Met Lys Asp Ser Asp Asp Tyr Ala Gln Leu Cys Asn Ile Pro Val
1220 1225 1230

Thr Gly Arg Arg Gln Pro Tyr Gly Arg Asp Ala Leu Val Asp Phe
1235 1240 1245

Ser Glu Gln Tyr Ala Pro Glu Ala Asp Pro Tyr Phe Ile Gln Asp
1250 1255 1260

Arg Phe Leu Asn Ser Phe Glu Glu Leu Gln Ala Glu Glu Cys Gly
1265 1270 1275

Ile Leu Asn Gly Cys Glu Asn Gly Arg Cys Val Arg Val Gln Glu
1280 1285 1290

Gly Tyr Thr Cys Asp Cys Phe Asp Gly Tyr His Leu Asp Thr Ala
1295 1300 1305

Lys Met Thr Cys Val Asp Val Asn Glu Cys Asp Glu Leu Asn Asn
1310 1315 1320

Arg Met Ser Leu Cys Lys Asn Ala Lys Cys Ile Asn Thr Glu Gly
1325 1330 1335

Ser Tyr Lys Cys Leu Cys Leu Pro Gly Tyr Val Pro Ser Asp Lys
1340 1345 1350

Pro Asn Tyr Cys Thr Pro Leu Asn Thr Ala Leu Asn Leu Glu Lys
1355 1360 1365

Asp Ser Asp Leu Glu
1370

<210> SEQ ID NO 47
<211> LENGTH: 1374
<212> TYPE: PRT
<213> ORGANISM: Mus sp.

<400> SEQUENCE: 47

Asn His Thr Gly Arg Ile Lys Val Val Phe Thr Pro Ser Ile Cys Lys

-continued

```
1               5                   10                  15

Val Thr Cys Thr Lys Gly Asn Cys Gln Asn Ser Cys Gln Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Ile Cys His Leu Pro Cys Met Asn Gly
    50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val Leu Gly Ala Ser Met Pro Lys Leu
                85                  90                  95

Tyr Gln His Ala Gln Gln Gln Gly Lys Ala Leu Gly Ser His Val Ile
            100                 105                 110

His Ser Thr His Thr Leu Pro Leu Thr Met Thr Ser Gln Gln Gly Val
        115                 120                 125

Lys Val Lys Phe Pro Pro Asn Ile Val Asn Ile His Val Lys His Pro
    130                 135                 140

Pro Glu Ala Ser Val Gln Ile His Gln Val Ser Arg Ile Asp Ser Pro
145                 150                 155                 160

Gly Gly Gln Lys Val Lys Glu Ala Gln Pro Gly Gln Ser Gln Val Ser
                165                 170                 175

Tyr Gln Gly Leu Pro Val Gln Lys Thr Gln Thr Val His Ser Thr Tyr
            180                 185                 190

Ser His Gln Gln Leu Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Gln Ser
                245                 250                 255

Tyr His Gly Tyr Thr Gln Met Met Glu Cys Leu Gln Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
    290                 295                 300

Ser Cys Lys Met Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Pro Gly Arg His Cys Met His Pro Leu Ser Val His Leu Thr
            340                 345                 350

Lys Gln Ile Cys Cys Cys Ser Val Gly Lys Ala Trp Gly Pro His Cys
        355                 360                 365

Glu Lys Cys Pro Leu Pro Gly Thr Ala Ala Phe Lys Glu Ile Cys Pro
    370                 375                 380

Gly Gly Met Gly Tyr Thr Val Ser Gly Val His Arg Arg Arg Pro Ile
385                 390                 395                 400

His Gln His Ile Gly Lys Glu Ala Val Tyr Val Lys Pro Lys Asn Thr
                405                 410                 415

Gln Pro Val Ala Lys Ser Thr His Pro Pro Pro Leu Pro Ala Lys Glu
            420                 425                 430
```

```
Glu Pro Val Glu Ala Leu Thr Ser Ser Trp Glu His Gly Pro Arg Gly
        435                 440                 445

Ala Glu Pro Glu Val Val Thr Ala Pro Pro Glu Lys Glu Ile Pro Ser
    450                 455                 460

Leu Asp Gln Glu Lys Thr Arg Leu Glu Pro Gly Gln Pro Gln Leu Ser
465                 470                 475                 480

Pro Gly Val Ser Thr Ile His Leu His Pro Gln Phe Pro Val Val Val
                485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
        515                 520                 525

Asn Glu Cys Thr Val Asn Pro Asp Ile Cys Gly Ala Gly His Cys Ile
    530                 535                 540

Asn Leu Pro Val Arg Tyr Thr Cys Ile Cys Tyr Glu Gly Tyr Lys Phe
545                 550                 555                 560

Ser Glu Gln Leu Arg Lys Cys Val Asp Ile Asp Glu Cys Ala Gln Val
                565                 570                 575

Arg His Leu Cys Ser Gln Gly Arg Cys Glu Asn Thr Glu Gly Ser Phe
            580                 585                 590

Leu Cys Val Cys Pro Ala Gly Phe Met Ala Ser Glu Glu Gly Thr Asn
        595                 600                 605

Cys Ile Asp Val Asp Glu Cys Leu Arg Pro Asp Met Cys Arg Asp Gly
    610                 615                 620

Arg Cys Ile Asn Thr Ala Gly Ala Phe Arg Cys Glu Tyr Cys Asp Ser
625                 630                 635                 640

Gly Tyr Arg Met Ser Arg Arg Gly Tyr Cys Glu Asp Ile Asp Glu Cys
                645                 650                 655

Leu Lys Pro Ser Thr Cys Pro Glu Glu Gln Cys Val Asn Thr Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Gln Pro Lys Val Cys Thr Asn
    690                 695                 700

Gly Ser Cys Thr Asn Leu Glu Gly Ser Tyr Met Cys Ser Cys His Arg
705                 710                 715                 720

Gly Tyr Ser Pro Thr Pro Asp His Arg His Cys Gln Asp Ile Asp Glu
                725                 730                 735

Cys Gln Gln Gly Asn Leu Cys Met Asn Gly Gln Cys Arg Asn Thr Asp
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Glu His His His Leu Cys
    770                 775                 780

Ser His Gly Gln Cys Arg Asn Thr Glu Gly Ser Phe Gln Cys Val Cys
785                 790                 795                 800

Asn Gln Gly Tyr Arg Ala Ser Val Leu Gly Asp His Cys Glu Asp Ile
                805                 810                 815

Asn Glu Cys Leu Glu Asp Ser Ser Val Cys Gln Gly Gly Asp Cys Ile
            820                 825                 830

Asn Thr Ala Gly Ser Tyr Asp Cys Thr Cys Pro Asp Gly Phe Gln Leu
        835                 840                 845
```

```
Asn Asp Asn Lys Gly Cys Gln Asp Ile Asn Glu Cys Ala Gln Pro Gly
    850                 855                 860

Leu Cys Gly Ser His Gly Glu Cys Leu Asn Thr Gln Gly Ser Phe His
865                 870                 875                 880

Cys Val Cys Glu Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
945                 950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Val Thr Glu Asp Ser Gly Val Asp
            980                 985                 990

Arg Gln Pro Arg Glu Glu Lys Lys  Glu Cys Tyr Tyr Asn  Leu Asn Asp
        995                 1000                1005

Ala Ser  Leu Cys Asp Asn Val  Leu Ala Pro Asn Val  Thr Lys Gln
    1010                1015                1020

Glu Cys  Cys Cys Thr Ser Gly  Ala Gly Trp Gly Asp  Asn Cys Glu
    1025                1030                1035

Ile Phe  Pro Cys Pro Val Gln  Gly Thr Ala Glu Phe  Thr Glu Met
    1040                1045                1050

Cys Pro  Arg Gly Lys Gly Leu  Val Pro Ala Gly Glu  Ser Ser Tyr
    1055                1060                1065

Asp Thr  Gly Gly Glu Asn Tyr  Lys Asp Ala Asp Glu  Cys Leu Leu
    1070                1075                1080

Phe Gly  Glu Glu Ile Cys Lys  Asn Gly Tyr Cys Leu  Asn Thr Gln
    1085                1090                1095

Pro Gly  Tyr Glu Cys Tyr Cys  Lys Gln Gly Thr Tyr  Tyr Asp Pro
    1100                1105                1110

Val Lys  Leu Gln Cys Phe Asp  Met Asp Glu Cys Gln  Asp Pro Asn
    1115                1120                1125

Ser Cys  Ile Asp Gly Gln Cys  Val Asn Thr Glu Gly  Ser Tyr Asn
    1130                1135                1140

Cys Phe  Cys Thr His Pro Met  Val Leu Asp Ala Ser  Glu Lys Arg
    1145                1150                1155

Cys Val  Gln Pro Thr Glu Ser  Asn Glu Gln Ile Glu  Glu Thr Asp
    1160                1165                1170

Val Tyr  Gln Asp Leu Cys Trp  Glu His Leu Ser Glu  Glu Tyr Val
    1175                1180                1185

Cys Ser  Arg Pro Leu Val Gly  Lys Gln Thr Thr Tyr  Thr Glu Cys
    1190                1195                1200

Cys Cys  Leu Tyr Gly Glu Ala  Trp Gly Met Gln Cys  Ala Leu Cys
    1205                1210                1215

Pro Met  Lys Asp Ser Asp Asp  Tyr Ala Gln Leu Cys  Asn Ile Pro
    1220                1225                1230

Val Thr  Gly Arg Arg Arg Pro  Tyr Gly Arg Asp Ala  Leu Val Asp
    1235                1240                1245

Phe Ser  Glu Gln Tyr Gly Pro  Glu Thr Asp Pro Tyr  Phe Ile Gln
```

```
    1250                1255                1260

Asp Arg  Phe Leu Asn Ser Phe  Glu Glu Leu Gln Ala  Glu Glu Cys
    1265                1270                1275

Gly Ile  Leu Asn Gly Cys Glu  Asn Gly Arg Cys Val  Arg Val Gln
    1280                1285                1290

Glu Gly  Tyr Thr Cys Asp Cys  Phe Asp Gly Tyr His  Leu Asp Met
    1295                1300                1305

Ala Lys  Met Thr Cys Val Asp  Val Asn Glu Cys Ser  Glu Leu Asn
    1310                1315                1320

Asn Arg  Met Ser Leu Cys Lys  Asn Ala Lys Cys Ile  Asn Thr Glu
    1325                1330                1335

Gly Ser  Tyr Lys Cys Leu Cys  Leu Pro Gly Tyr Ile  Pro Ser Asp
    1340                1345                1350

Lys Pro  Asn Tyr Cys Thr Pro  Leu Asn Ser Ala Leu  Asn Leu Asp
    1355                1360                1365

Lys Glu  Ser Asp Leu Glu
    1370


<210> SEQ ID NO 48
<211> LENGTH: 646
<212> TYPE: PRT
<213> ORGANISM: Mus sp.

<400> SEQUENCE: 48

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
            20                  25                  30

Leu Asp Ile Gln Ala Leu Tyr Leu Ser Gly Asn Gln Leu Gln Ser Ile
        35                  40                  45

Leu Val Ser Pro Leu Gly Phe Tyr Thr Ala Leu Arg His Leu Asp Leu
    50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
            100                 105                 110

Leu Asp Leu Ser Gly Asn Ser Leu His Gly Asn Leu Val Glu Arg Leu
        115                 120                 125

Leu Gly Glu Thr Pro Arg Leu Arg Thr Leu Ser Leu Ala Glu Asn Ser
    130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
            180                 185                 190

Leu Thr Cys Ile Ser Asp Phe Ser Leu Gln Gln Leu Gln Val Leu Asp
        195                 200                 205

Leu Ser Cys Asn Ser Ile Glu Ala Phe Gln Thr Ala Pro Glu Pro Gln
    210                 215                 220

Ala Gln Phe Gln Leu Ala Trp Leu Asp Leu Arg Glu Asn Lys Leu Leu
225                 230                 235                 240
```

```
His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
            260                 265                 270

Asp Leu His Ala Pro Ser Glu Gly Trp Ser Ala Ser Pro Leu Ser Asn
        275                 280                 285

Pro Ser Arg Asn Ala Ser Thr His Pro Leu Ser Gln Leu Leu Asn Leu
    290                 295                 300

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
                325                 330                 335

Ser Phe Glu Ala Arg Gln Val Asp Ser Leu Pro Cys Leu Val Leu Leu
            340                 345                 350

Asp Leu Ser His Asn Val Leu Glu Ala Leu Glu Leu Gly Thr Lys Val
        355                 360                 365

Leu Gly Ser Leu Gln Thr Leu Leu Leu Gln Asp Asn Ala Leu Gln Glu
    370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
                405                 410                 415

Pro Pro Gly Cys Val Asp Phe Ser Gly Ile Pro Thr Leu His Val Leu
            420                 425                 430

Asn Met Ala Gly Asn Ser Met Gly Met Leu Arg Ala Gly Ser Phe Leu
        435                 440                 445

His Thr Pro Leu Thr Glu Leu Asp Leu Ser Thr Asn Pro Gly Leu Asp
    450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
            500                 505                 510

Leu Pro Ala Trp Thr Arg Ala Val Ser Leu Glu Val Leu Asp Leu Arg
        515                 520                 525

Asn Asn Ser Phe Ser Leu Leu Pro Gly Asn Ala Met Gly Gly Leu Glu
    530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Glu Leu
            580                 585                 590

Ser Leu Ser Leu Val Arg Pro Glu Asp Cys Glu Lys Gly Gly Leu Lys
        595                 600                 605

Asn Val Asn Leu Ile Leu Leu Leu Ser Phe Thr Leu Val Ser Ala Ile
    610                 615                 620

Val Leu Thr Thr Leu Ala Thr Ile Cys Phe Leu Arg Arg Gln Lys Leu
625                 630                 635                 640

Ser Gln Gln Tyr Lys Ala
                645
```

<210> SEQ ID NO 49
<211> LENGTH: 611
<212> TYPE: PRT
<213> ORGANISM: Mus sp.

<400> SEQUENCE: 49

Ile Ser Gln Arg Arg Glu Gln Val Pro Cys Arg Thr Val Asn Lys Glu
1 5 10 15

Ala Leu Cys His Gly Leu Gly Leu Leu Gln Val Pro Ser Val Leu Ser
20 25 30

Leu Asp Ile Gln Ala Leu Tyr Leu Ser Gly Asn Gln Leu Gln Ser Ile
35 40 45

Leu Val Ser Pro Leu Gly Phe Tyr Thr Ala Leu Arg His Leu Asp Leu
50 55 60

Ser Asp Asn Gln Ile Ser Phe Leu Gln Ala Gly Val Phe Gln Ala Leu
65 70 75 80

Pro Tyr Leu Glu His Leu Asn Leu Ala His Asn Arg Leu Ala Thr Gly
85 90 95

Met Ala Leu Asn Ser Gly Gly Leu Gly Arg Leu Pro Leu Leu Val Ser
100 105 110

Leu Asp Leu Ser Gly Asn Ser Leu His Gly Asn Leu Val Glu Arg Leu
115 120 125

Leu Gly Glu Thr Pro Arg Leu Arg Thr Leu Ser Leu Ala Glu Asn Ser
130 135 140

Leu Thr Arg Leu Ala Arg His Thr Phe Trp Gly Met Pro Ala Val Glu
145 150 155 160

Gln Leu Asp Leu His Ser Asn Val Leu Met Asp Ile Glu Asp Gly Ala
165 170 175

Phe Glu Ala Leu Pro His Leu Thr His Leu Asn Leu Ser Arg Asn Ser
180 185 190

Leu Thr Cys Ile Ser Asp Phe Ser Leu Gln Gln Leu Gln Val Leu Asp
195 200 205

Leu Ser Cys Asn Ser Ile Glu Ala Phe Gln Thr Ala Pro Glu Pro Gln
210 215 220

Ala Gln Phe Gln Leu Ala Trp Leu Asp Leu Arg Glu Asn Lys Leu Leu
225 230 235 240

His Phe Pro Asp Leu Ala Val Phe Pro Arg Leu Ile Tyr Leu Asn Val
245 250 255

Ser Asn Asn Leu Ile Gln Leu Pro Ala Gly Leu Pro Arg Gly Ser Glu
260 265 270

Asp Leu His Ala Pro Ser Glu Gly Trp Ser Ala Ser Pro Leu Ser Asn
275 280 285

Pro Ser Arg Asn Ala Ser Thr His Pro Leu Ser Gln Leu Leu Asn Leu
290 295 300

Asp Leu Ser Tyr Asn Glu Ile Glu Leu Val Pro Ala Ser Phe Leu Glu
305 310 315 320

His Leu Thr Ser Leu Arg Phe Leu Asn Leu Ser Arg Asn Cys Leu Arg
325 330 335

Ser Phe Glu Ala Arg Gln Val Asp Ser Leu Pro Cys Leu Val Leu Leu
340 345 350

Asp Leu Ser His Asn Val Leu Glu Ala Leu Glu Leu Gly Thr Lys Val
355 360 365

Leu Gly Ser Leu Gln Thr Leu Leu Leu Gln Asp Asn Ala Leu Gln Glu
370 375 380

Leu Pro Pro Tyr Thr Phe Ala Ser Leu Ala Ser Leu Gln Arg Leu Asn
385 390 395 400

Leu Gln Gly Asn Gln Val Ser Pro Cys Gly Gly Pro Ala Glu Pro Gly
405 410 415

Pro Pro Gly Cys Val Asp Phe Ser Gly Ile Pro Thr Leu His Val Leu
420 425 430

Asn Met Ala Gly Asn Ser Met Gly Met Leu Arg Ala Gly Ser Phe Leu
435 440 445

His Thr Pro Leu Thr Glu Leu Asp Leu Ser Thr Asn Pro Gly Leu Asp
450 455 460

Val Ala Thr Gly Ala Leu Val Gly Leu Glu Ala Ser Leu Glu Val Leu
465 470 475 480

Glu Leu Gln Gly Asn Gly Leu Thr Val Leu Arg Val Asp Leu Pro Cys
485 490 495

Phe Leu Arg Leu Lys Arg Leu Asn Leu Ala Glu Asn Gln Leu Ser His
500 505 510

Leu Pro Ala Trp Thr Arg Ala Val Ser Leu Glu Val Leu Asp Leu Arg
515 520 525

Asn Asn Ser Phe Ser Leu Leu Pro Gly Asn Ala Met Gly Gly Leu Glu
530 535 540

Thr Ser Leu Arg Arg Leu Tyr Leu Gln Gly Asn Pro Leu Ser Cys Cys
545 550 555 560

Gly Asn Gly Trp Leu Ala Ala Gln Leu His Gln Gly Arg Val Asp Val
565 570 575

Asp Ala Thr Gln Asp Leu Ile Cys Arg Phe Gly Ser Gln Glu Glu Leu
580 585 590

Ser Leu Ser Leu Val Arg Pro Glu Asp Cys Glu Lys Gly Gly Leu Lys
595 600 605

Asn Val Asn
610

<210> SEQ ID NO 50
<211> LENGTH: 1375
<212> TYPE: PRT
<213> ORGANISM: Unknown
<220> FEATURE:
<221> NAME/KEY: source
<223> OTHER INFORMATION: /note="Description of Unknown:
LTBP1S sequence"

<400> SEQUENCE: 50

Asn His Thr Gly Arg Ile Lys Val Val Phe Thr Pro Ser Ile Cys Lys
1 5 10 15

Val Thr Cys Thr Lys Gly Ser Cys Gln Asn Ser Cys Glu Lys Gly Asn
20 25 30

Thr Thr Thr Leu Ile Ser Glu Asn Gly His Ala Ala Asp Thr Leu Thr
35 40 45

Ala Thr Asn Phe Arg Val Val Ile Cys His Leu Pro Cys Met Asn Gly
50 55 60

Gly Gln Cys Ser Ser Arg Asp Lys Cys Gln Cys Pro Pro Asn Phe Thr
65 70 75 80

Gly Lys Leu Cys Gln Ile Pro Val His Gly Ala Ser Val Pro Lys Leu
85 90 95

Tyr Gln His Ser Gln Gln Pro Gly Lys Ala Leu Gly Thr His Val Ile
100 105 110

His Ser Thr His Thr Leu Pro Leu Thr Val Thr Ser Gln Gln Gly Val

```
        115                 120                 125

Lys Val Lys Phe Pro Pro Asn Ile Val Asn Ile His Val Lys His Pro
    130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
            180                 185                 190

Ser His Gln Gln Val Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255

Tyr His Gly Tyr Asn Gln Met Met Glu Cys Leu Pro Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
    290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
            340                 345                 350

Lys Gln Leu Cys Cys Cys Ser Val Gly Lys Ala Trp Gly Pro His Cys
        355                 360                 365

Glu Lys Cys Pro Leu Pro Gly Thr Ala Ala Phe Lys Glu Ile Cys Pro
    370                 375                 380

Gly Gly Met Gly Tyr Thr Val Ser Gly Val His Arg Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Pro Leu Pro Ala Lys Glu
            420                 425                 430

Glu Pro Val Glu Ala Leu Thr Phe Ser Arg Glu His Gly Pro Gly Val
        435                 440                 445

Ala Glu Pro Glu Val Ala Thr Ala Pro Pro Glu Lys Glu Ile Pro Ser
    450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
                485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
        515                 520                 525

Asn Glu Cys Thr Val Asn Pro Asp Ile Cys Gly Ala Gly His Cys Ile
    530                 535                 540
```

```
Asn Leu Pro Val Arg Tyr Thr Cys Ile Cys Tyr Glu Gly Tyr Arg Phe
545                 550                 555                 560

Ser Glu Gln Gln Arg Lys Cys Val Asp Ile Asp Glu Cys Thr Gln Val
                565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
        595                 600                 605

Cys Ile Asp Val Asp Glu Cys Leu Arg Pro Asp Val Cys Gly Glu Gly
    610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Glu Pro Asn Val Cys Ala Asn
    690                 695                 700

Gly Asp Cys Ser Asn Leu Glu Gly Ser Tyr Met Cys Ser Cys His Lys
705                 710                 715                 720

Gly Tyr Thr Arg Thr Pro Asp His Lys His Cys Arg Asp Ile Asp Glu
                725                 730                 735

Cys Gln Gln Gly Asn Leu Cys Val Asn Gly Gln Cys Lys Asn Thr Glu
            740                 745                 750

Gly Ser Phe Arg Cys Thr Cys Gly Gln Gly Tyr Gln Leu Ser Ala Ala
        755                 760                 765

Lys Asp Gln Cys Glu Asp Ile Asp Glu Cys Gln His Arg His Leu Cys
    770                 775                 780

Ala His Gly Gln Cys Arg Asn Thr Glu Gly Ser Phe Gln Cys Val Cys
785                 790                 795                 800

Asp Gln Gly Tyr Arg Ala Ser Gly Leu Gly Asp His Cys Glu Asp Ile
                805                 810                 815

Asn Glu Cys Leu Glu Asp Lys Ser Val Cys Gln Arg Gly Asp Cys Ile
            820                 825                 830

Asn Thr Ala Gly Ser Tyr Asp Cys Thr Cys Pro Asp Gly Phe Gln Leu
        835                 840                 845

Asp Asp Asn Lys Thr Cys Gln Asp Ile Asn Glu Cys Glu His Pro Gly
    850                 855                 860

Leu Cys Gly Pro Gln Gly Glu Cys Leu Asn Thr Glu Gly Ser Phe His
865                 870                 875                 880

Cys Val Cys Gln Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
    930                 935                 940

Glu Leu Leu Ser Gly Val Cys Gly Glu Ala Phe Cys Glu Asn Val Glu
945                 950                 955                 960
```

-continued

```
Gly Ser Phe Leu Cys Val Cys Ala Asp Glu Asn Gln Glu Tyr Ser Pro
                965                 970                 975

Met Thr Gly Gln Cys Arg Ser Arg Thr Ser Thr Asp Leu Asp Val Asp
            980                 985                 990

Val Asp Gln Pro Lys Glu Glu Lys  Lys Glu Cys Tyr Tyr  Asn Leu Asn
        995                 1000                 1005

Asp Ala  Ser Leu Cys Asp Asn  Val Leu Ala Pro Asn  Val Thr Lys
    1010                 1015                 1020

Gln Glu  Cys Cys Cys Thr Ser  Gly Val Gly Trp Gly  Asp Asn Cys
    1025                 1030                 1035

Glu Ile  Phe Pro Cys Pro Val  Leu Gly Thr Ala Glu  Phe Thr Glu
    1040                 1045                 1050

Met Cys  Pro Lys Gly Lys Gly  Phe Val Pro Ala Gly  Glu Ser Ser
    1055                 1060                 1065

Ser Glu  Ala Gly Gly Glu Asn  Tyr Lys Asp Ala Asp  Glu Cys Leu
    1070                 1075                 1080

Leu Phe  Gly Gln Glu Ile Cys  Lys Asn Gly Phe Cys  Leu Asn Thr
    1085                 1090                 1095

Arg Pro  Gly Tyr Glu Cys Tyr  Cys Lys Gln Gly Thr  Tyr Tyr Asp
    1100                 1105                 1110

Pro Val  Lys Leu Gln Cys Phe  Asp Met Asp Glu Cys  Gln Asp Pro
    1115                 1120                 1125

Ser Ser  Cys Ile Asp Gly Gln  Cys Val Asn Thr Glu  Gly Ser Tyr
    1130                 1135                 1140

Asn Cys  Phe Cys Thr His Pro  Met Val Leu Asp Ala  Ser Glu Lys
    1145                 1150                 1155

Arg Cys  Ile Arg Pro Ala Glu  Ser Asn Glu Gln Ile  Glu Glu Thr
    1160                 1165                 1170

Asp Val  Tyr Gln Asp Leu Cys  Trp Glu His Leu Ser  Asp Glu Tyr
    1175                 1180                 1185

Val Cys  Ser Arg Pro Leu Val  Gly Lys Gln Thr Thr  Tyr Thr Glu
    1190                 1195                 1200

Cys Cys  Cys Leu Tyr Gly Glu  Ala Trp Gly Met Gln  Cys Ala Leu
    1205                 1210                 1215

Cys Pro  Leu Lys Asp Ser Asp  Asp Tyr Ala Gln Leu  Cys Asn Ile
    1220                 1225                 1230

Pro Val  Thr Gly Arg Arg Gln  Pro Tyr Gly Arg Asp  Ala Leu Val
    1235                 1240                 1245

Asp Phe  Ser Glu Gln Tyr Thr  Pro Glu Ala Asp Pro  Tyr Phe Ile
    1250                 1255                 1260

Gln Asp  Arg Phe Leu Asn Ser  Phe Glu Glu Leu Gln  Ala Glu Glu
    1265                 1270                 1275

Cys Gly  Ile Leu Asn Gly Cys  Glu Asn Gly Arg Cys  Val Arg Val
    1280                 1285                 1290

Gln Glu  Gly Tyr Thr Cys Asp  Cys Phe Asp Gly Tyr  His Leu Asp
    1295                 1300                 1305

Thr Ala  Lys Met Thr Cys Val  Asp Val Asn Glu Cys  Asp Glu Leu
    1310                 1315                 1320

Asn Asn  Arg Met Ser Leu Cys  Lys Asn Ala Lys Cys  Ile Asn Thr
    1325                 1330                 1335

Asp Gly  Ser Tyr Lys Cys Leu  Cys Leu Pro Gly Tyr  Val Pro Ser
    1340                 1345                 1350

Asp Lys  Pro Asn Tyr Cys Thr  Pro Leu Asn Thr Ala  Leu Asn Leu
```

```
    1355                1360                1365

Glu Lys  Asp Ser Asp Leu Glu
    1370                1375


<210> SEQ ID NO 51
<211> LENGTH: 1260
<212> TYPE: PRT
<213> ORGANISM: Unknown
<220> FEATURE:
<221> NAME/KEY: source
<223> OTHER INFORMATION: /note="Description of Unknown:
      LTBP3 sequence"

<400> SEQUENCE: 51

Gly Pro Ala Gly Glu Arg Gly Ala Gly Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
        35                  40                  45

Leu Ile Gly Glu Asn Gly His Ser Thr Asp Thr Leu Thr Gly Ser Gly
    50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Gly Thr Gly Gly Ser Gly
            100                 105                 110

Pro Gly Leu Ser Arg Thr Gly Ala Leu Ser Thr Gly Ala Leu Pro Pro
        115                 120                 125

Leu Ala Pro Glu Gly Asp Ser Val Ala Ser Lys His Ala Ile Tyr Ala
    130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Pro Val Val Asn Val Arg Val His His Pro
            180                 185                 190

Pro Glu Ala Ser Val Gln Val His Arg Ile Glu Ser Ser Asn Ala Glu
        195                 200                 205

Ser Ala Ala Pro Ser Gln His Leu Leu Pro His Pro Lys Pro Ser His
    210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Gly
        275                 280                 285

Pro Val Arg Gly Glu Val Gly Ala Asp Cys Pro Gln Gly Tyr Lys Arg
    290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335
```

```
Val Cys Pro Pro Gly His Ser Leu Gly Pro Ser Arg Thr Gln Cys Ile
            340                 345                 350

Ala Asp Lys Pro Glu Glu Lys Ser Leu Cys Phe Arg Leu Val Ser Pro
        355                 360                 365

Glu His Gln Cys Gln His Pro Leu Thr Thr Arg Leu Thr Arg Gln Leu
    370                 375                 380

Cys Cys Cys Ser Val Gly Lys Ala Trp Gly Ala Arg Cys Gln Arg Cys
385                 390                 395                 400

Pro Thr Asp Gly Thr Ala Ala Phe Lys Glu Ile Cys Pro Ala Gly Lys
                405                 410                 415

Gly Tyr His Ile Leu Thr Ser His Gln Thr Leu Thr Ile Gln Gly Glu
            420                 425                 430

Ser Asp Phe Ser Leu Phe Leu His Pro Asp Gly Pro Pro Lys Pro Gln
        435                 440                 445

Gln Leu Pro Glu Ser Pro Ser Gln Ala Pro Pro Pro Glu Asp Thr Glu
    450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Thr Pro Ala Arg Pro Tyr
                485                 490                 495

Pro Glu Leu Ile Ser Arg Pro Ser Pro Pro Thr Met Arg Trp Phe Leu
            500                 505                 510

Pro Asp Leu Pro Pro Ser Arg Ser Ala Val Glu Ile Ala Pro Thr Gln
        515                 520                 525

Val Thr Glu Thr Asp Glu Cys Arg Leu Asn Gln Asn Ile Cys Gly His
    530                 535                 540

Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
                565                 570                 575

Cys Glu Ala Glu Pro Cys Gly Pro Gly Arg Gly Ile Cys Met Asn Thr
            580                 585                 590

Gly Gly Ser Tyr Asn Cys His Cys Asn Arg Gly Tyr Arg Leu His Val
        595                 600                 605

Gly Ala Gly Gly Arg Ser Cys Val Asp Leu Asn Glu Cys Ala Lys Pro
    610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
        675                 680                 685

Pro Gly Tyr Arg Ser Gln Gly Gly Gly Ala Cys Arg Asp Val Asn Glu
    690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
                725                 730                 735

Gly Arg Ser Cys Leu Asp Val Asp Glu Cys Glu Ala Gly Asp Val Cys
            740                 745                 750
```

```
Asp Asn Gly Ile Cys Ser Asn Thr Pro Gly Ser Phe Gln Cys Gln Cys
        755                 760                 765

Leu Ser Gly Tyr His Leu Ser Arg Asp Arg Ser His Cys Glu Asp Ile
    770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Ser Gln Asp Pro Ser
            820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
    850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
            885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
        915                 920                 925

Pro Asp Gly Lys Gly Tyr Thr Gln Asp Asn Asn Ile Val Asn Tyr Gly
    930                 935                 940

Ile Pro Ala His Arg Asp Ile Asp Glu Cys Met Leu Phe Gly Ser Glu
945                 950                 955                 960

Ile Cys Lys Glu Gly Lys Cys Val Asn Thr Gln Pro Gly Tyr Glu Cys
            965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu  Ser Asn Cys Arg Asn  Gly Val Cys
        995                 1000                1005

Glu Asn  Thr Arg Gly Gly Tyr  Arg Cys Ala Cys Thr  Pro Pro Ala
    1010                1015                1020

Glu Tyr  Ser Pro Ala Gln Arg  Gln Cys Leu Ser Pro  Glu Glu Met
    1025                1030                1035

Asp Val  Asp Glu Cys Gln Asp  Pro Ala Ala Cys Arg  Pro Gly Arg
    1040                1045                1050

Cys Val  Asn Leu Pro Gly Ser  Tyr Arg Cys Glu Cys  Arg Pro Pro
    1055                1060                1065

Trp Val  Pro Gly Pro Ser Gly  Arg Asp Cys Gln Leu  Pro Glu Ser
    1070                1075                1080

Pro Ala  Glu Arg Ala Pro Glu  Arg Arg Asp Val Cys  Trp Ser Gln
    1085                1090                1095

Arg Gly  Glu Asp Gly Met Cys  Ala Gly Pro Leu Ala  Gly Pro Ala
    1100                1105                1110

Leu Thr  Phe Asp Asp Cys Cys  Cys Arg Gln Gly Arg  Gly Trp Gly
    1115                1120                1125

Ala Gln  Cys Arg Pro Cys Pro  Pro Arg Gly Ala Gly  Ser His Cys
    1130                1135                1140

Pro Thr  Ser Gln Ser Glu Ser  Asn Ser Phe Trp Asp  Thr Ser Pro
    1145                1150                1155

Leu Leu  Leu Gly Lys Pro Pro  Arg Asp Glu Asp Ser  Ser Glu Glu
```

```
    1160                1165                1170

Asp Ser  Asp Glu Cys Arg Cys  Val Ser Gly Arg Cys  Val Pro Arg
    1175                1180                1185

Pro Gly  Gly Ala Val Cys Glu  Cys Pro Gly Gly Phe  Gln Leu Asp
    1190                1195                1200

Ala Ser  Arg Ala Arg Cys Val  Asp Ile Asp Glu Cys  Arg Glu Leu
    1205                1210                1215

Asn Gln  Arg Gly Leu Leu Cys  Lys Ser Glu Arg Cys  Val Asn Thr
    1220                1225                1230

Ser Gly  Ser Phe Arg Cys Val  Cys Lys Ala Gly Phe  Ala Arg Ser
    1235                1240                1245

Arg Pro  His Gly Ala Cys Val  Pro Gln Arg Arg Arg
    1250                1255                1260


<210> SEQ ID NO 52
<211> LENGTH: 645
<212> TYPE: PRT
<213> ORGANISM: Unknown
<220> FEATURE:
<221> NAME/KEY: source
<223> OTHER INFORMATION: /note="Description of Unknown:
      GARP sequence"

<400> SEQUENCE: 52

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
            20                  25                  30

Asp Thr Glu Thr Leu Asp Leu Ser Gly Asn Gln Leu Arg Ser Ile Leu
        35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125

Gly Glu Ala Pro Ser Leu His Thr Leu Ser Leu Ala Glu Asn Ser Leu
    130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
    210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255
```

```
Asn Asn Leu Ile Arg Leu Pro Thr Gly Pro Pro Gln Asp Ser Lys Gly
            260                 265                 270

Ile His Ala Pro Ser Glu Gly Trp Ser Ala Leu Pro Leu Ser Ala Pro
        275                 280                 285

Ser Gly Asn Ala Ser Gly Arg Pro Leu Ser Gln Leu Leu Asn Leu Asp
    290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
        355                 360                 365

Gly Ser Leu Arg Thr Leu Leu Leu Gln Gly Asn Ala Leu Arg Asp Leu
    370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
        435                 440                 445

Thr Pro Leu Thr Glu Leu Asp Leu Ser Ser Asn Pro Gly Leu Glu Val
    450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
        515                 520                 525

Asn Ser Phe Ser Leu Leu Pro Gly Ser Ala Met Gly Gly Leu Glu Thr
    530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
        595                 600                 605

Ile Asn Leu Ile Ile Ile Leu Thr Phe Ile Leu Val Ser Ala Ile Leu
    610                 615                 620

Leu Thr Thr Leu Ala Ala Cys Cys Cys Val Arg Arg Gln Lys Phe Asn
625                 630                 635                 640

Gln Gln Tyr Lys Ala
                645
```

<210> SEQ ID NO 53
<211> LENGTH: 610

<212> TYPE: PRT
<213> ORGANISM: Unknown
<220> FEATURE:
<221> NAME/KEY: source
<223> OTHER INFORMATION: /note="Description of Unknown:
sGARP sequence"

<400> SEQUENCE: 53

Ala Gln His Gln Asp Lys Val Pro Cys Lys Met Val Asp Lys Lys Val
1 5 10 15

Ser Cys Gln Val Leu Gly Leu Leu Gln Val Pro Ser Val Leu Pro Pro
20 25 30

Asp Thr Glu Thr Leu Asp Leu Ser Gly Asn Gln Leu Arg Ser Ile Leu
35 40 45

Ala Ser Pro Leu Gly Phe Tyr Thr Ala Leu Arg His Leu Asp Leu Ser
50 55 60

Thr Asn Glu Ile Ser Phe Leu Gln Pro Gly Ala Phe Gln Ala Leu Thr
65 70 75 80

His Leu Glu His Leu Ser Leu Ala His Asn Arg Leu Ala Met Ala Thr
85 90 95

Ala Leu Ser Ala Gly Gly Leu Gly Pro Leu Pro Arg Val Thr Ser Leu
100 105 110

Asp Leu Ser Gly Asn Ser Leu Tyr Ser Gly Leu Leu Glu Arg Leu Leu
115 120 125

Gly Glu Ala Pro Ser Leu His Thr Leu Ser Leu Ala Glu Asn Ser Leu
130 135 140

Thr Arg Leu Thr Arg His Thr Phe Arg Asp Met Pro Ala Leu Glu Gln
145 150 155 160

Leu Asp Leu His Ser Asn Val Leu Met Asp Ile Glu Asp Gly Ala Phe
165 170 175

Glu Gly Leu Pro Arg Leu Thr His Leu Asn Leu Ser Arg Asn Ser Leu
180 185 190

Thr Cys Ile Ser Asp Phe Ser Leu Gln Gln Leu Arg Val Leu Asp Leu
195 200 205

Ser Cys Asn Ser Ile Glu Ala Phe Gln Thr Ala Ser Gln Pro Gln Ala
210 215 220

Glu Phe Gln Leu Thr Trp Leu Asp Leu Arg Glu Asn Lys Leu Leu His
225 230 235 240

Phe Pro Asp Leu Ala Ala Leu Pro Arg Leu Ile Tyr Leu Asn Leu Ser
245 250 255

Asn Asn Leu Ile Arg Leu Pro Thr Gly Pro Pro Gln Asp Ser Lys Gly
260 265 270

Ile His Ala Pro Ser Glu Gly Trp Ser Ala Leu Pro Leu Ser Ala Pro
275 280 285

Ser Gly Asn Ala Ser Gly Arg Pro Leu Ser Gln Leu Leu Asn Leu Asp
290 295 300

Leu Ser Tyr Asn Glu Ile Glu Leu Ile Pro Asp Ser Phe Leu Glu His
305 310 315 320

Leu Thr Ser Leu Cys Phe Leu Asn Leu Ser Arg Asn Cys Leu Arg Thr
325 330 335

Phe Glu Ala Arg Arg Leu Gly Ser Leu Pro Cys Leu Met Leu Leu Asp
340 345 350

Leu Ser His Asn Ala Leu Glu Thr Leu Glu Leu Gly Ala Arg Ala Leu
355 360 365

Gly Ser Leu Arg Thr Leu Leu Leu Gln Gly Asn Ala Leu Arg Asp Leu

```
    370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
        435                 440                 445

Thr Pro Leu Thr Glu Leu Asp Leu Ser Ser Asn Pro Gly Leu Glu Val
    450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
        515                 520                 525

Asn Ser Phe Ser Leu Leu Pro Gly Ser Ala Met Gly Gly Leu Glu Thr
    530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
        595                 600                 605

Ile Asn
    610


<210> SEQ ID NO 54
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Cys Pro Pro Cys Pro
1               5


<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ala Ser Thr Lys Gly Pro Ser Val Phe Pro Leu Ala Pro
1               5                   10


<210> SEQ ID NO 56
```

<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Ala Ser Thr Lys Gly Pro
1 5

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 57

Thr Val Ala Ala Pro Ser Val Phe Ile Phe Pro Pro
1 5 10

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

Thr Val Ala Ala Pro
1 5

<210> SEQ ID NO 59
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Ala Lys Thr Thr Pro Lys Leu Glu Glu Gly Glu Phe Ser Glu Ala Arg
1 5 10 15

<210> SEQ ID NO 60
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Ala Lys Thr Thr Pro Lys Leu Glu Glu Gly Glu Phe Ser Glu Ala Arg
1 5 10 15

Val

<210> SEQ ID NO 61
<211> LENGTH: 9
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 61

Ala Lys Thr Thr Pro Lys Leu Gly Gly
1 5

<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 62

Ser Ala Lys Thr Thr Pro Lys Leu Gly Gly
1 5 10

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 63

Ser Ala Lys Thr Thr Pro
1 5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 64

Arg Ala Asp Ala Ala Pro
1 5

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 65

Arg Ala Asp Ala Ala Pro Thr Val Ser
1 5

<210> SEQ ID NO 66
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 66

Arg Ala Asp Ala Ala Ala Ala Gly Gly Pro Gly Ser
1 5 10

<210> SEQ ID NO 67
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 67

Arg Ala Asp Ala Ala Ala Ala Gly Gly Gly Gly Ser Gly Gly Gly Gly
1 5 10 15

Ser Gly Gly Gly Gly Ser Gly Gly Gly Gly Ser
20 25

<210> SEQ ID NO 68
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 68

Ser Ala Lys Thr Thr Pro Lys Leu Glu Glu Gly Glu Phe Ser Glu Ala
1 5 10 15

Arg Val

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 69

Ala Asp Ala Ala Pro
1 5

<210> SEQ ID NO 70
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

Ala Asp Ala Ala Pro Thr Val Ser Ile Phe Pro Pro
1 5 10

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 71

Gln Pro Lys Ala Ala Pro
1 5

<210> SEQ ID NO 72
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 72

Gln Pro Lys Ala Ala Pro Ser Val Thr Leu Phe Pro Pro
1 5 10

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 73

Ala Lys Thr Thr Pro Pro
1 5

<210> SEQ ID NO 74
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 74

Ala Lys Thr Thr Pro Pro Ser Val Thr Pro Leu Ala Pro
1 5 10

<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 75

Ala Lys Thr Thr Ala Pro
1 5

<210> SEQ ID NO 76
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 76

```
Ala Lys Thr Thr Ala Pro Ser Val Tyr Pro Leu Ala Pro
1               5                   10


<210> SEQ ID NO 77
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gly Gly Gly Gly Ser Gly Gly Gly Gly Ser Gly Gly Gly Gly Ser
1               5                   10                  15


<210> SEQ ID NO 78
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Glu Asn Lys Val Glu Tyr Ala Pro Ala Leu Met Ala Leu Ser
1               5                   10                  15


<210> SEQ ID NO 79
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Pro Ala Lys Glu Leu Thr Pro Leu Lys Glu Ala Lys Val Ser
1               5                   10                  15


<210> SEQ ID NO 80
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly His Glu Ala Ala Ala Val Met Gln Val Gln Tyr Pro Ala Ser
1               5                   10                  15


<210> SEQ ID NO 81
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Thr Val Ala Ala Pro Ser Val Phe Ile Phe Pro Pro Thr Val Ala Ala
1               5                   10                  15
```

Pro Ser Val Phe Ile Phe Pro Pro
20

<210> SEQ ID NO 82
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Ala Ser Thr Lys Gly Pro Ser Val Phe Pro Leu Ala Pro Ala Ser Thr
1 5 10 15

Lys Gly Pro Ser Val Phe Pro Leu Ala Pro
20 25

<210> SEQ ID NO 83
<211> LENGTH: 692
<212> TYPE: PRT
<213> ORGANISM: Homo sapiens

<400> SEQUENCE: 83

Met Glu Leu Leu Pro Leu Trp Leu Cys Leu Gly Phe His Phe Leu Thr
1 5 10 15

Val Gly Trp Arg Asn Arg Ser Gly Thr Ala Thr Ala Ala Ser Gln Gly
20 25 30

Val Cys Lys Leu Val Gly Gly Ala Ala Asp Cys Arg Gly Gln Ser Leu
35 40 45

Ala Ser Val Pro Ser Ser Leu Pro Pro His Ala Arg Met Leu Thr Leu
50 55 60

Asp Ala Asn Pro Leu Lys Thr Leu Trp Asn His Ser Leu Gln Pro Tyr
65 70 75 80

Pro Leu Leu Glu Ser Leu Ser Leu His Ser Cys His Leu Glu Arg Ile
85 90 95

Ser Arg Gly Ala Phe Gln Glu Gln Gly His Leu Arg Ser Leu Val Leu
100 105 110

Gly Asp Asn Cys Leu Ser Glu Asn Tyr Glu Glu Thr Ala Ala Ala Leu
115 120 125

His Ala Leu Pro Gly Leu Arg Arg Leu Asp Leu Ser Gly Asn Ala Leu
130 135 140

Thr Glu Asp Met Ala Ala Leu Met Leu Gln Asn Leu Ser Ser Leu Arg
145 150 155 160

Ser Val Ser Leu Ala Gly Asn Thr Ile Met Arg Leu Asp Asp Ser Val
165 170 175

Phe Glu Gly Leu Glu Arg Leu Arg Glu Leu Asp Leu Gln Arg Asn Tyr
180 185 190

Ile Phe Glu Ile Glu Gly Gly Ala Phe Asp Gly Leu Ala Glu Leu Arg
195 200 205

His Leu Asn Leu Ala Phe Asn Asn Leu Pro Cys Ile Val Asp Phe Gly
210 215 220

Leu Thr Arg Leu Arg Val Leu Asn Val Ser Tyr Asn Val Leu Glu Trp
225 230 235 240

Phe Leu Ala Thr Gly Gly Glu Ala Ala Phe Glu Leu Glu Thr Leu Asp
245 250 255

Leu Ser His Asn Gln Leu Leu Phe Phe Pro Leu Leu Pro Gln Tyr Ser
260 265 270

```
Lys Leu Arg Thr Leu Leu Leu Arg Asp Asn Asn Met Gly Phe Tyr Arg
        275                 280                 285

Asp Leu Tyr Asn Thr Ser Ser Pro Arg Glu Met Val Ala Gln Phe Leu
    290                 295                 300

Leu Val Asp Gly Asn Val Thr Asn Ile Thr Thr Val Ser Leu Trp Glu
305                 310                 315                 320

Glu Phe Ser Ser Ser Asp Leu Ala Asp Leu Arg Phe Leu Asp Met Ser
                325                 330                 335

Gln Asn Gln Phe Gln Tyr Leu Pro Asp Gly Phe Leu Arg Lys Met Pro
            340                 345                 350

Ser Leu Ser His Leu Asn Leu His Gln Asn Cys Leu Met Thr Leu His
        355                 360                 365

Ile Arg Glu His Glu Pro Pro Gly Ala Leu Thr Glu Leu Asp Leu Ser
    370                 375                 380

His Asn Gln Leu Ser Glu Leu His Leu Ala Pro Gly Leu Ala Ser Cys
385                 390                 395                 400

Leu Gly Ser Leu Arg Leu Phe Asn Leu Ser Ser Asn Gln Leu Leu Gly
                405                 410                 415

Val Pro Pro Gly Leu Phe Ala Asn Ala Arg Asn Ile Thr Thr Leu Asp
            420                 425                 430

Met Ser His Asn Gln Ile Ser Leu Cys Pro Leu Pro Ala Ala Ser Asp
        435                 440                 445

Arg Val Gly Pro Pro Ser Cys Val Asp Phe Arg Asn Met Ala Ser Leu
    450                 455                 460

Arg Ser Leu Ser Leu Glu Gly Cys Gly Leu Gly Ala Leu Pro Asp Cys
465                 470                 475                 480

Pro Phe Gln Gly Thr Ser Leu Thr Tyr Leu Asp Leu Ser Ser Asn Trp
                485                 490                 495

Gly Val Leu Asn Gly Ser Leu Ala Pro Leu Gln Asp Val Ala Pro Met
            500                 505                 510

Leu Gln Val Leu Ser Leu Arg Asn Met Gly Leu His Ser Ser Phe Met
        515                 520                 525

Ala Leu Asp Phe Ser Gly Phe Gly Asn Leu Arg Asp Leu Asp Leu Ser
    530                 535                 540

Gly Asn Cys Leu Thr Thr Phe Pro Arg Phe Gly Gly Ser Leu Ala Leu
545                 550                 555                 560

Glu Thr Leu Asp Leu Arg Arg Asn Ser Leu Thr Ala Leu Pro Gln Lys
                565                 570                 575

Ala Val Ser Glu Gln Leu Ser Arg Gly Leu Arg Thr Ile Tyr Leu Ser
            580                 585                 590

Gln Asn Pro Tyr Asp Cys Cys Gly Val Asp Gly Trp Gly Ala Leu Gln
        595                 600                 605

His Gly Gln Thr Val Ala Asp Trp Ala Met Val Thr Cys Asn Leu Ser
    610                 615                 620

Ser Lys Ile Ile Arg Val Thr Glu Leu Pro Gly Gly Val Pro Arg Asp
625                 630                 635                 640

Cys Lys Trp Glu Arg Leu Asp Leu Gly Leu Leu Tyr Leu Val Leu Ile
                645                 650                 655

Leu Pro Ser Cys Leu Thr Leu Leu Val Ala Cys Thr Val Ile Val Leu
            660                 665                 670

Thr Phe Lys Lys Pro Leu Leu Gln Val Ile Lys Ser Arg Cys His Trp
        675                 680                 685
```

Ser Ser Val Tyr
690

<210> SEQ ID NO 84
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

Met Asp Met Arg Val Pro Ala Gln Leu Leu Gly Leu Leu Leu Leu Trp
1 5 10 15

Phe Ser Gly Val Leu Gly Trp Arg Asn Arg Ser Gly Thr Ala Thr Ala
20 25 30

Ala Ser Gln Gly Val Cys Lys Leu Val Gly Gly Ala Ala Asp Cys Arg
35 40 45

Gly Gln Ser Leu Ala Ser Val Pro Ser Ser Leu Pro Pro His Ala Arg
50 55 60

Met Leu Thr Leu Asp Ala Asn Pro Leu Lys Thr Leu Trp Asn His Ser
65 70 75 80

Leu Gln Pro Tyr Pro Leu Leu Glu Ser Leu Ser Leu His Ser Cys His
85 90 95

Leu Glu Arg Ile Ser Arg Gly Ala Phe Gln Glu Gln Gly His Leu Arg
100 105 110

Ser Leu Val Leu Gly Asp Asn Cys Leu Ser Glu Asn Tyr Glu Glu Thr
115 120 125

Ala Ala Ala Leu His Ala Leu Pro Gly Leu Arg Arg Leu Asp Leu Ser
130 135 140

Gly Asn Ala Leu Thr Glu Asp Met Ala Ala Leu Met Leu Gln Asn Leu
145 150 155 160

Ser Ser Leu Arg Ser Val Ser Leu Ala Gly Asn Thr Ile Met Arg Leu
165 170 175

Asp Asp Ser Val Phe Glu Gly Leu Glu Arg Leu Arg Glu Leu Asp Leu
180 185 190

Gln Arg Asn Tyr Ile Phe Glu Ile Glu Gly Gly Ala Phe Asp Gly Leu
195 200 205

Ala Glu Leu Arg His Leu Asn Leu Ala Phe Asn Asn Leu Pro Cys Ile
210 215 220

Val Asp Phe Gly Leu Thr Arg Leu Arg Val Leu Asn Val Ser Tyr Asn
225 230 235 240

Val Leu Glu Trp Phe Leu Ala Thr Gly Gly Glu Ala Ala Phe Glu Leu
245 250 255

Glu Thr Leu Asp Leu Ser His Asn Gln Leu Leu Phe Phe Pro Leu Leu
260 265 270

Pro Gln Tyr Ser Lys Leu Arg Thr Leu Leu Leu Arg Asp Asn Asn Met
275 280 285

Gly Phe Tyr Arg Asp Leu Tyr Asn Thr Ser Ser Pro Arg Glu Met Val
290 295 300

Ala Gln Phe Leu Leu Val Asp Gly Asn Val Thr Asn Ile Thr Thr Val
305 310 315 320

Ser Leu Trp Glu Glu Phe Ser Ser Ser Asp Leu Ala Asp Leu Arg Phe
325 330 335

Leu Asp Met Ser Gln Asn Gln Phe Gln Tyr Leu Pro Asp Gly Phe Leu

```
            340                 345                 350

Arg Lys Met Pro Ser Leu Ser His Leu Asn Leu His Gln Asn Cys Leu
        355                 360                 365

Met Thr Leu His Ile Arg Glu His Glu Pro Pro Gly Ala Leu Thr Glu
    370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
        435                 440                 445

Ala Ala Ser Asp Arg Val Gly Pro Pro Ser Cys Val Asp Phe Arg Asn
    450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
        515                 520                 525

Ser Ser Phe Met Ala Leu Asp Phe Ser Gly Phe Gly Asn Leu Arg Asp
    530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
        595                 600                 605

Gly Ala Leu Gln His Gly Gln Thr Val Ala Asp Trp Ala Met Val Thr
    610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu His His
                645                 650                 655

His His His His
            660


<210> SEQ ID NO 85

<400> SEQUENCE: 85

000


<210> SEQ ID NO 86

<400> SEQUENCE: 86

000


<210> SEQ ID NO 87
```

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 101

```
Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
            20                  25                  30

Ala Ser Gln Gly Val Cys Lys Leu Val Gly Gly Ala Ala Asp Cys Arg
        35                  40                  45

Gly Gln Ser Leu Ala Ser Val Pro Ser Ser Leu Pro Pro His Ala Arg
    50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
    210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
            260                 265                 270
```

```
Pro Gln Tyr Ser Lys Leu Arg Thr Leu Leu Leu Arg Asp Asn Asn Met
        275                 280                 285

Gly Phe Tyr Arg Asp Leu Tyr Asn Thr Ser Ser Pro Arg Glu Met Val
    290                 295                 300

Ala Gln Phe Leu Leu Val Asp Gly Asn Val Thr Asn Ile Thr Thr Val
305                 310                 315                 320

Ser Leu Trp Glu Glu Phe Ser Ser Ser Asp Leu Ala Asp Leu Arg Phe
                325                 330                 335

Leu Asp Met Ser Gln Asn Gln Phe Gln Tyr Leu Pro Asp Gly Phe Leu
            340                 345                 350

Arg Lys Met Pro Ser Leu Ser His Leu Asn Leu His Gln Asn Cys Leu
        355                 360                 365

Met Thr Leu His Ile Arg Glu His Glu Pro Pro Gly Ala Leu Thr Glu
    370                 375                 380

Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
                405                 410                 415

Gln Leu Leu Gly Val Pro Pro Gly Leu Phe Ala Asn Ala Arg Asn Ile
            420                 425                 430

Thr Thr Leu Asp Met Ser His Asn Gln Ile Ser Leu Cys Pro Leu Pro
        435                 440                 445

Ala Ala Ser Asp Arg Val Gly Pro Pro Ser Cys Val Asp Phe Arg Asn
    450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
        515                 520                 525

Ser Ser Phe Met Ala Leu Asp Phe Ser Gly Phe Gly Asn Leu Arg Asp
    530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
        595                 600                 605

Gly Ala Leu Gln His Gly Gln Thr Val Ala Asp Trp Ala Met Val Thr
    610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu Leu Ile
                645                 650                 655

Ile Ile Leu Thr Phe Ile Leu Val Ser Ala Ile Leu Leu Thr Thr Leu
            660                 665                 670

Ala Ala Cys Cys Cys Val Arg Arg Gln Lys Phe Asn Gln Gln Tyr Lys
        675                 680                 685

Ala
```

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258
<211> LENGTH: 21
<212> TYPE: PRT
<213> ORGANISM: Homo sapiens

<400> SEQUENCE: 258

Ser Gln Gly Glu Val Pro Pro Gly Pro Leu Pro Glu Ala Val Leu Ala
1               5                   10                  15

Leu Tyr Asn Ser Thr
            20

<210> SEQ ID NO 259
<211> LENGTH: 7
<212> TYPE: PRT
<213> ORGANISM: Homo sapiens

<400> SEQUENCE: 259

Leu Arg Glu Ala Val Pro Glu
1               5

<210> SEQ ID NO 260
<211> LENGTH: 8
<212> TYPE: PRT
<213> ORGANISM: Homo sapiens

<400> SEQUENCE: 260

Tyr His Ala Asn Phe Cys Leu Gly
1               5

<210> SEQ ID NO 261
<211> LENGTH: 24
<212> TYPE: PRT
<213> ORGANISM: Homo sapiens

<400> SEQUENCE: 261

Ser Pro Pro Ser Gln Gly Glu Val Pro Pro Gly Pro Leu Pro Glu Ala
1               5                   10                  15

Val Leu Ala Leu Tyr Asn Ser Thr
            20

<210> SEQ ID NO 262
<211> LENGTH: 17
<212> TYPE: PRT
<213> ORGANISM: Homo sapiens

<400> SEQUENCE: 262

Trp Lys Trp Ile His Glu Pro Lys Gly Tyr His Ala Asn Phe Cys Leu
1               5                   10                  15

Gly

<210> SEQ ID NO 263
<211> LENGTH: 249
<212> TYPE: PRT
<213> ORGANISM: Homo sapiens

<400> SEQUENCE: 263

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

```
Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245


<210> SEQ ID NO 264
<211> LENGTH: 45
<212> TYPE: PRT
<213> ORGANISM: Homo sapiens

<400> SEQUENCE: 264

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro
        35                  40                  45


<210> SEQ ID NO 265
<211> LENGTH: 112
<212> TYPE: PRT
<213> ORGANISM: Homo sapiens

<400> SEQUENCE: 265

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110


<210> SEQ ID NO 266
<211> LENGTH: 4
<212> TYPE: PRT
<213> ORGANISM: Homo sapiens
```

<400> SEQUENCE: 266

Arg His Arg Arg
1

<210> SEQ ID NO 267
<211> LENGTH: 204
<212> TYPE: PRT
<213> ORGANISM: Homo sapiens

<400> SEQUENCE: 267

Glu Ala Val Leu Ala Leu Tyr Asn Ser Thr Arg Asp Arg Val Ala Gly
1 5 10 15

Glu Ser Ala Glu Pro Glu Pro Glu Pro Glu Ala Asp Tyr Tyr Ala Lys
20 25 30

Glu Val Thr Arg Val Leu Met Val Glu Thr His Asn Glu Ile Tyr Asp
35 40 45

Lys Phe Lys Gln Ser Thr His Ser Ile Tyr Met Phe Phe Asn Thr Ser
50 55 60

Glu Leu Arg Glu Ala Val Pro Glu Pro Val Leu Leu Ser Arg Ala Glu
65 70 75 80

Leu Arg Leu Leu Arg Leu Lys Leu Lys Val Glu Gln His Val Glu Leu
85 90 95

Tyr Gln Lys Tyr Ser Asn Asn Ser Trp Arg Tyr Leu Ser Asn Arg Leu
100 105 110

Leu Ala Pro Ser Asp Ser Pro Glu Trp Leu Ser Phe Asp Val Thr Gly
115 120 125

Val Val Arg Gln Trp Leu Ser Arg Gly Gly Glu Ile Glu Gly Phe Arg
130 135 140

Leu Ser Ala His Cys Ser Cys Asp Ser Arg Asp Asn Thr Leu Gln Val
145 150 155 160

Asp Ile Asn Gly Phe Thr Thr Gly Arg Arg Gly Asp Leu Ala Thr Ile
165 170 175

His Gly Met Asn Arg Pro Phe Leu Leu Leu Met Ala Thr Pro Leu Glu
180 185 190

Arg Ala Gln His Leu Gln Ser Ser Arg His Arg Arg
195 200

<210> SEQ ID NO 268
<211> LENGTH: 29
<212> TYPE: PRT
<213> ORGANISM: Homo sapiens

<400> SEQUENCE: 268

Cys Val Arg Gln Leu Tyr Ile Asp Phe Arg Lys Asp Leu Gly Trp Lys
1 5 10 15

Trp Ile His Glu Pro Lys Gly Tyr His Ala Asn Phe Cys
20 25

<210> SEQ ID NO 269
<211> LENGTH: 35
<212> TYPE: PRT
<213> ORGANISM: Homo sapiens

<400> SEQUENCE: 269

Cys Val Pro Gln Ala Leu Glu Pro Leu Pro Ile Val Tyr Tyr Val Gly
1 5 10 15

Arg Lys Pro Lys Val Glu Gln Leu Ser Asn Met Ile Val Arg Ser Cys
20 25 30

Lys Cys Ser
35

<210> SEQ ID NO 270
<211> LENGTH: 15
<212> TYPE: PRT
<213> ORGANISM: Homo sapiens

<400> SEQUENCE: 270

Leu Ala Ser Pro Pro Ser Gln Gly Glu Val Pro Pro Gly Pro Leu
1 5 10 15

<210> SEQ ID NO 271
<211> LENGTH: 27
<212> TYPE: PRT
<213> ORGANISM: Homo sapiens

<400> SEQUENCE: 271

Leu Ala Ser Pro Pro Ser Gln Gly Glu Val Pro Pro Gly Pro Leu Pro
1 5 10 15

Glu Ala Val Leu Ala Leu Tyr Asn Ser Thr Arg
20 25

<210> SEQ ID NO 272
<211> LENGTH: 29
<212> TYPE: PRT
<213> ORGANISM: Homo sapiens

<400> SEQUENCE: 272

Leu Ser Thr Cys Lys Thr Ile Asp Met Glu Leu Val Lys Arg Lys Arg
1 5 10 15

Ile Glu Ala Ile Arg Gly Gln Ile Leu Ser Lys Leu Arg
20 25

<210> SEQ ID NO 273
<211> LENGTH: 10
<212> TYPE: PRT
<213> ORGANISM: Homo sapiens

<400> SEQUENCE: 273

Ala Val Leu Ala Leu Tyr Asn Ser Thr Arg
1 5 10

<210> SEQ ID NO 274
<211> LENGTH: 20
<212> TYPE: PRT
<213> ORGANISM: Homo sapiens

<400> SEQUENCE: 274

Asn Gly Phe Thr Thr Gly Arg Arg Gly Asp Leu Ala Thr Ile His Gly
1 5 10 15

Met Asn Arg Pro
20

<210> SEQ ID NO 275
<211> LENGTH: 13
<212> TYPE: PRT
<213> ORGANISM: Homo sapiens

<400> SEQUENCE: 275

Cys Ser Cys Asp Ser Arg Asp Asn Thr Leu Gln Val Asp
1 5 10

```
<210> SEQ ID NO 276
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Gly Phe Thr Phe Ala Asp Tyr Ala
1               5


<210> SEQ ID NO 277
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="K"
<220> FEATURE:
<221> NAME/KEY: SITE
<222> LOCATION: (1)..(8)
<223> OTHER INFORMATION: /note="Variant residues given in the sequence
      have no preference with respect to those in the annotations
      for variant positions"

<400> SEQUENCE: 277

Ile Ser Gly Ser Gly Ala Ala Thr
1               5


<210> SEQ ID NO 278
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="D" or "Q"
<220> FEATURE:
<221> NAME/KEY: VARIANT
<222> LOCATION: (8)..(8)
<223> OTHER INFORMATION: /replace="Y"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 278

Val Ser Ser Gly His Trp Asp Phe Asp
1               5


<210> SEQ ID NO 279
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 279

Gln Ser Ile Ser Ser Tyr
1 5

<210> SEQ ID NO 280
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="G" or "V"
<220> FEATURE:
<221> NAME/KEY: VARIANT
<222> LOCATION: (5)..(5)
<223> OTHER INFORMATION: /replace="N" or "E"
<220> FEATURE:
<221> NAME/KEY: VARIANT
<222> LOCATION: (6)..(6)
<223> OTHER INFORMATION: /replace="E"
<220> FEATURE:
<221> NAME/KEY: VARIANT
<222> LOCATION: (7)..(7)
<223> OTHER INFORMATION: /replace="T"
<220> FEATURE:
<221> NAME/KEY: SITE
<222> LOCATION: (1)..(7)
<223> OTHER INFORMATION: /note="Variant residues given in the sequence have no preference with respect to those in the annotations for variant positions"

<400> SEQUENCE: 280

Ala Ala Ser Asn Leu Gln Ser
1 5

<210> SEQ ID NO 281
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (5)..(5)
<223> OTHER INFORMATION: /replace="G"
<220> FEATURE:
<221> NAME/KEY: SITE
<222> LOCATION: (1)..(9)
<223> OTHER INFORMATION: /note="Variant residues given in the sequence have no preference with respect to those in the annotations for variant positions"

<400> SEQUENCE: 281

Gln Gln Thr Tyr Thr Val Pro Leu Thr
1 5

<210> SEQ ID NO 282
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 282

Ile Ser Gly Ser Gly Ala Ala Thr
1 5

<210> SEQ ID NO 283
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (5)..(5)
<223> OTHER INFORMATION: /replace="Q"
<220> FEATURE:
<221> NAME/KEY: VARIANT
<222> LOCATION: (8)..(8)
<223> OTHER INFORMATION: /replace="F"
<220> FEATURE:
<221> NAME/KEY: SITE
<222> LOCATION: (1)..(9)
<223> OTHER INFORMATION: /note="Variant residues given in the sequence have no preference with respect to those in the annotations for variant positions"

<400> SEQUENCE: 283

Val Ser Ser Gly His Trp Asp Tyr Asp
1 5

<210> SEQ ID NO 284
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 284

Ala Ala Ser Gly Leu Glu Ser
1 5

<210> SEQ ID NO 285
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 285

Gln Gln Thr Tyr Gly Val Pro Leu Thr
1 5

<210> SEQ ID NO 286
<211> LENGTH: 14
<212> TYPE: PRT
<213> ORGANISM: Homo sapiens

<400> SEQUENCE: 286

Ala Ser Pro Pro Ser Gln Gly Glu Val Pro Pro Gly Pro Leu
1 5 10

<210> SEQ ID NO 287
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 287

Val Ser Ser Gly His Trp Asp Tyr Asp
1 5

<210> SEQ ID NO 288
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 288

Ile Ser Gly Ser Gly Lys Ala Thr
1 5

<210> SEQ ID NO 289
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 289

Val Ser Ser Gly His Trp Asp Phe Asp
1 5

<210> SEQ ID NO 290
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 290

Val Ser Ser Gly Asp Trp Asp Tyr Asp
1 5

<210> SEQ ID NO 291
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 291

Val Ser Ser Gly Gln Trp Asp Tyr Asp
1 5

<210> SEQ ID NO 292
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 292

Ala Ala Ser Asn Leu Glu Ser
1 5

<210> SEQ ID NO 293
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 293

Ala Ala Ser Val Asn Glu Ser
1 5

<210> SEQ ID NO 294
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 294

Ala Ala Ser Asn Glu Glu Thr
1 5

<210> SEQ ID NO 295
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 295

Ala Ala Ser Asn Leu Gln Ser
1 5

<210> SEQ ID NO 296
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 296

Gln Gln Thr Tyr Thr Val Pro Leu Thr
1 5

<210> SEQ ID NO 297
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 297

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Asp Tyr
20 25 30

Ala Met Thr Trp Val Arg Gln Ala Pro Gly Lys Gly Leu Glu Trp Val
35 40 45

Ser Ala Ile Ser Gly Ser Gly Ala Ala Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Ser Ser Gly His Trp Asp Tyr Asp Tyr Trp Gly Gln Gly
100 105 110

Thr Leu Val Thr Val Ser Ser
115

<210> SEQ ID NO 298
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 298

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Gly Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Gly Val Pro Leu
85 90 95

Thr Phe Gly Gly Gly Thr Lys Val Glu Ile Lys
100 105

<210> SEQ ID NO 299
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 299

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Asp Tyr
20 25 30

Ala Met Thr Trp Val Arg Gln Ala Pro Gly Lys Gly Leu Glu Trp Val
35 40 45

Ser Ala Ile Ser Gly Ser Gly Ala Ala Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Ser Ser Gly His Trp Asp Phe Asp Tyr Trp Gly Gln Gly
100 105 110

Thr Leu Val Thr Val Ser Ser
115

<210> SEQ ID NO 300
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 300

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Thr Val Pro Leu
85 90 95

Thr Phe Gly Gly Gly Thr Lys Val Glu Ile Lys
100 105

<210> SEQ ID NO 301
<211> LENGTH: 6
<212> TYPE: PRT
<213> ORGANISM: Unknown
<220> FEATURE:
<221> NAME/KEY: source
<223> OTHER INFORMATION: /note="Description of Unknown:
TGFBETA1 sequence"

<400> SEQUENCE: 301

Leu Ser Lys Leu Arg Leu
1 5

<210> SEQ ID NO 302
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic 6xHis tag"

<400> SEQUENCE: 302

His His His His His His
1 5

<210> SEQ ID NO 303
<211> LENGTH: 7
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="N"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 303

Ala Ala Ser Gly Leu Glu Ser
1               5

<210> SEQ ID NO 304
<211> LENGTH: 20
<212> TYPE: PRT
<213> ORGANISM: Homo sapiens

<400> SEQUENCE: 304

Glu Asp Tyr Pro Glu Pro Glu Glu Val Pro Pro Glu Val Ile Ser Ile
1               5                   10                  15

Tyr Asn Ser Thr
            20

<210> SEQ ID NO 305
<211> LENGTH: 4
<212> TYPE: PRT
<213> ORGANISM: Homo sapiens

<400> SEQUENCE: 305

Met Glu Lys Asn
1

<210> SEQ ID NO 306
<211> LENGTH: 8
<212> TYPE: PRT
<213> ORGANISM: Homo sapiens

<400> SEQUENCE: 306

Tyr Asn Ala Asn Phe Cys Ala Gly
1               5

<210> SEQ ID NO 307
<211> LENGTH: 19
<212> TYPE: PRT
<213> ORGANISM: Homo sapiens

<400> SEQUENCE: 307

Glu Pro Thr Val Met Thr His Val Pro Tyr Gln Val Leu Ala Leu Tyr
1               5                   10                  15

Asn Ser Thr

<210> SEQ ID NO 308
<211> LENGTH: 4
<212> TYPE: PRT
<213> ORGANISM: Homo sapiens

<400> SEQUENCE: 308

Val Glu Lys Asn

1

<210> SEQ ID NO 309
<211> LENGTH: 8
<212> TYPE: PRT
<213> ORGANISM: Homo sapiens

<400> SEQUENCE: 309

Tyr Tyr Ala Asn Phe Cys Ser Gly
1               5

<210> SEQ ID NO 310
<211> LENGTH: 23
<212> TYPE: PRT
<213> ORGANISM: Homo sapiens

<400> SEQUENCE: 310

Ser Pro Pro Glu Asp Tyr Pro Glu Pro Glu Glu Val Pro Pro Glu Val
1               5                   10                  15

Ile Ser Ile Tyr Asn Ser Thr
            20

<210> SEQ ID NO 311
<211> LENGTH: 17
<212> TYPE: PRT
<213> ORGANISM: Homo sapiens

<400> SEQUENCE: 311

Trp Lys Trp Ile His Glu Pro Lys Gly Tyr Asn Ala Asn Phe Cys Ala
1               5                   10                  15

Gly

<210> SEQ ID NO 312
<211> LENGTH: 22
<212> TYPE: PRT
<213> ORGANISM: Homo sapiens

<400> SEQUENCE: 312

Ser Pro Pro Glu Pro Thr Val Met Thr His Val Pro Tyr Gln Val Leu
1               5                   10                  15

Ala Leu Tyr Asn Ser Thr
            20

<210> SEQ ID NO 313
<211> LENGTH: 17
<212> TYPE: PRT
<213> ORGANISM: Homo sapiens

<400> SEQUENCE: 313

Trp Lys Trp Val His Glu Pro Lys Gly Tyr Tyr Ala Asn Phe Cys Ser
1               5                   10                  15

Gly

<210> SEQ ID NO 314
<211> LENGTH: 23
<212> TYPE: PRT
<213> ORGANISM: Homo sapiens

<400> SEQUENCE: 314

Lys Leu Arg Leu Ala Ser Pro Pro Ser Gln Gly Glu Val Pro Pro Gly
1               5                   10                  15

Pro Leu Pro Glu Ala Val Leu

-continued

```
            20


<210> SEQ ID NO 315
<211> LENGTH: 22
<212> TYPE: PRT
<213> ORGANISM: Homo sapiens

<400> SEQUENCE: 315

Lys Leu Lys Leu Thr Ser Pro Pro Glu Asp Tyr Pro Glu Pro Glu Glu
1               5                   10                  15

Val Pro Pro Glu Val Ile
            20


<210> SEQ ID NO 316
<211> LENGTH: 21
<212> TYPE: PRT
<213> ORGANISM: Homo sapiens

<400> SEQUENCE: 316

Lys Leu Arg Leu Thr Ser Pro Pro Glu Pro Thr Val Met Thr His Val
1               5                   10                  15

Pro Tyr Gln Val Leu
            20
```